United States Patent
Woodard, Jr. et al.

(10) Patent No.: US 8,757,465 B2
(45) Date of Patent: Jun. 24, 2014

(54) FASTENER SYSTEM COMPRISING A RETENTION MATRIX AND AN ALIGNMENT MATRIX

(75) Inventors: James A. Woodard, Jr., Mason, OH (US); Charles J. Scheib, Loveland, OH (US); Chad P. Boudreaux, Cincinnati, OH (US); Dean B. Bruewer, Fairfield, OH (US); Richard F. Schwemberger, Cincinnati, OH (US); Christopher J. Schall, Cincinnati, OH (US); Jerome R. Morgan, Cincinnati, OH (US); Robert J. Simms, Liberty Township, OH (US); Jeffrey S. Swayze, Hamilton, OH (US); John N. Ouwerkerk, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 609 days.

(21) Appl. No.: 12/894,330

(22) Filed: Sep. 30, 2010

(65) Prior Publication Data

US 2012/0080503 A1 Apr. 5, 2012

(51) Int. Cl.
*A61B 17/072* (2006.01)

(52) U.S. Cl.
USPC ............... 227/176.1; 227/175.1; 606/219

(58) Field of Classification Search
USPC .............. 227/175.1, 176.1, 179.1, 180.1; 206/339; 411/921, 520, 525; 606/219, 606/220
See application file for complete search history.

(56) References Cited

U.S. PATENT DOCUMENTS

| | | | |
|---|---|---|---|
| 662,587 A | 11/1900 | Blake | |
| 951,393 A | 3/1910 | Hahn | |
| 1,306,107 A | 6/1919 | Elliott | |
| 2,132,295 A | 10/1938 | Hawkins | |
| 2,161,632 A | 6/1939 | Nattenheimer | |
| 2,211,117 A | 8/1940 | Hess | |
| 2,674,149 A | 4/1954 | Benson | |
| 2,853,074 A | 9/1958 | Olson | |
| 3,032,769 A | 5/1962 | Palmer | |
| 3,166,072 A * | 1/1965 | Sullivan, Jr. | 606/153 |
| 3,357,296 A | 12/1967 | Lefever | |
| 3,490,675 A | 1/1970 | Green et al. | |
| 3,551,987 A | 1/1971 | Wilkinson | |
| 3,643,851 A | 2/1972 | Green et al. | |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

U.S. Appl. No. 12/775,809, filed May 7, 2010.

(Continued)

*Primary Examiner* — Thanh Truong
*Assistant Examiner* — Nathaniel Chukwurah

(57) ABSTRACT

A surgical fastener system can comprise a plurality of fasteners which can be connected to each other by, one, a retention matrix which is assembled to the fasteners in order to capture tissue within the fasteners and, two, an alignment matrix configured to hold the fasteners together before the retention matrix is assembled thereto. In various embodiments, the retention matrix and the alignment matrix can each comprise a tissue-contacting surface configured to compress tissue therebetween.

24 Claims, 139 Drawing Sheets

(56) References Cited

U.S. PATENT DOCUMENTS

| | | | |
|---|---|---|---|
| 3,662,939 A | 5/1972 | Bryan | |
| 3,717,294 A | 2/1973 | Green | |
| 3,744,495 A * | 7/1973 | Johnson | 606/142 |
| 3,746,002 A | 7/1973 | Haller | |
| 3,819,100 A | 6/1974 | Noiles et al. | |
| 3,885,491 A | 5/1975 | Curtis | |
| RE28,932 E | 8/1976 | Noiles et al. | |
| 4,060,089 A | 11/1977 | Noiles | |
| 4,275,813 A | 6/1981 | Noiles | |
| 4,321,002 A | 3/1982 | Froehlich | |
| 4,331,277 A | 5/1982 | Green | |
| 4,340,331 A | 7/1982 | Savino | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,434,796 A * | 3/1984 | Karapetian et al. | 606/75 |
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |
| 4,522,327 A | 6/1985 | Korthoff et al. | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,589,416 A | 5/1986 | Green | |
| 4,610,383 A | 9/1986 | Rothfuss et al. | |
| 4,619,262 A | 10/1986 | Taylor | |
| 4,629,107 A | 12/1986 | Fedotov et al. | |
| 4,632,290 A | 12/1986 | Green et al. | |
| 4,655,222 A | 4/1987 | Florez et al. | |
| 4,664,305 A | 5/1987 | Blake, III et al. | |
| 4,671,445 A | 6/1987 | Barker et al. | |
| 4,715,520 A | 12/1987 | Roehr, Jr. et al. | |
| 4,728,020 A | 3/1988 | Green et al. | |
| 4,752,024 A | 6/1988 | Green et al. | |
| 4,754,909 A | 7/1988 | Barker et al. | |
| 4,767,044 A | 8/1988 | Green | |
| 4,805,617 A | 2/1989 | Bedi et al. | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,844,068 A | 7/1989 | Arata et al. | |
| 4,869,414 A | 9/1989 | Green et al. | |
| 4,869,415 A | 9/1989 | Fox | |
| 4,890,613 A | 1/1990 | Golden et al. | |
| 4,932,960 A | 6/1990 | Green et al. | |
| 4,941,623 A | 7/1990 | Pruitt | |
| 4,944,443 A | 7/1990 | Oddsen et al. | |
| 5,065,929 A | 11/1991 | Schulze et al. | |
| 5,071,430 A | 12/1991 | de Salis et al. | |
| 5,074,454 A | 12/1991 | Peters | |
| 5,116,349 A | 5/1992 | Aranyi | |
| 5,129,570 A | 7/1992 | Schulze et al. | |
| 5,137,198 A | 8/1992 | Nobis et al. | |
| 5,139,513 A | 8/1992 | Segato | |
| 5,141,144 A | 8/1992 | Foslien et al. | |
| 5,156,614 A | 10/1992 | Green et al. | |
| 5,158,567 A | 10/1992 | Green | |
| D330,699 S | 11/1992 | Gill | |
| 5,171,253 A | 12/1992 | Klieman et al. | |
| 5,211,649 A | 5/1993 | Kohler et al. | |
| 5,221,036 A | 6/1993 | Takase | |
| 5,222,963 A | 6/1993 | Brinkerhoff et al. | |
| 5,222,975 A | 6/1993 | Crainich | |
| 5,234,447 A | 8/1993 | Kaster et al. | |
| 5,236,440 A | 8/1993 | Hlavacek | |
| 5,258,009 A | 11/1993 | Conners | |
| 5,258,012 A | 11/1993 | Luscombe et al. | |
| 5,263,973 A | 11/1993 | Cook | |
| 5,275,608 A | 1/1994 | Forman et al. | |
| 5,282,806 A | 2/1994 | Haber et al. | |
| 5,282,829 A | 2/1994 | Hermes | |
| 5,285,945 A | 2/1994 | Brinkerhoff et al. | |
| 5,304,204 A | 4/1994 | Bregen | |
| 5,336,232 A | 8/1994 | Green et al. | |
| 5,342,395 A | 8/1994 | Jarrett et al. | |
| 5,342,396 A | 8/1994 | Cook | |
| 5,350,400 A | 9/1994 | Esposito et al. | |
| 5,352,238 A | 10/1994 | Green et al. | |
| 5,358,510 A | 10/1994 | Luscombe et al. | |
| 5,366,479 A | 11/1994 | McGarry et al. | |
| 5,397,324 A | 3/1995 | Carroll et al. | |
| 5,405,072 A | 4/1995 | Zlock et al. | |
| 5,411,508 A | 5/1995 | Bessler et al. | |
| 5,413,272 A | 5/1995 | Green et al. | |
| 5,415,334 A | 5/1995 | Williamson, IV et al. | |
| 5,417,361 A | 5/1995 | Williamson, IV | |
| 5,425,745 A | 6/1995 | Green et al. | |
| 5,439,479 A | 8/1995 | Shichman et al. | |
| 5,445,644 A | 8/1995 | Pietrafitta et al. | |
| 5,452,837 A | 9/1995 | Williamson, IV et al. | |
| 5,468,253 A | 11/1995 | Bezwada et al. | |
| 5,474,566 A | 12/1995 | Alesi et al. | |
| 5,478,354 A | 12/1995 | Tovey et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,503,635 A | 4/1996 | Sauer et al. | |
| 5,505,363 A | 4/1996 | Green et al. | |
| 5,507,426 A | 4/1996 | Young et al. | |
| 5,509,596 A | 4/1996 | Green et al. | |
| 5,520,700 A | 5/1996 | Beyar et al. | |
| 5,529,235 A | 6/1996 | Boiarski et al. | |
| 5,533,661 A | 7/1996 | Main et al. | |
| 5,535,934 A | 7/1996 | Boiarski et al. | |
| 5,540,375 A | 7/1996 | Bolanos et al. | |
| 5,542,594 A | 8/1996 | McKean et al. | |
| 5,549,621 A | 8/1996 | Bessler et al. | |
| 5,549,628 A | 8/1996 | Cooper et al. | |
| 5,553,765 A | 9/1996 | Knodel et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,571,116 A | 11/1996 | Bolanos et al. | |
| 5,575,799 A | 11/1996 | Bolanos et al. | |
| 5,575,803 A | 11/1996 | Cooper et al. | |
| 5,577,654 A | 11/1996 | Bishop | |
| 5,580,067 A | 12/1996 | Hamblin et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,601,224 A | 2/1997 | Bishop et al. | |
| 5,603,443 A | 2/1997 | Clark et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |
| 5,620,452 A | 4/1997 | Yoon | |
| 5,624,452 A | 4/1997 | Yates | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,632,433 A | 5/1997 | Grant et al. | |
| 5,634,584 A | 6/1997 | Okorocha et al. | |

(56) References Cited

U.S. PATENT DOCUMENTS

| | | |
|---|---|---|
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,690,269 A | 11/1997 | Bolanos et al. |
| 5,692,668 A | 12/1997 | Schulze et al. |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,702,408 A | 12/1997 | Wales et al. |
| 5,702,409 A | 12/1997 | Rayburn et al. |
| 5,704,534 A | 1/1998 | Huitema et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,733,308 A | 3/1998 | Daugherty et al. |
| 5,738,474 A | 4/1998 | Blewett |
| 5,743,456 A | 4/1998 | Jones et al. |
| 5,752,644 A | 5/1998 | Bolanos et al. |
| 5,752,965 A | 5/1998 | Francis et al. |
| 5,758,814 A | 6/1998 | Gallagher et al. |
| 5,762,256 A | 6/1998 | Mastri et al. |
| 5,766,188 A | 6/1998 | Igaki |
| 5,772,379 A | 6/1998 | Evensen |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,806,676 A | 9/1998 | Wasgien |
| 5,810,855 A | 9/1998 | Rayburn et al. |
| 5,814,057 A | 9/1998 | Oi et al. |
| 5,820,009 A | 10/1998 | Melling et al. |
| 5,826,776 A | 10/1998 | Schulze et al. |
| 5,829,662 A | 11/1998 | Allen et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,855,583 A | 1/1999 | Wang et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,915,616 A | 6/1999 | Viola et al. |
| 5,919,198 A | 7/1999 | Graves, Jr. et al. |
| 5,937,951 A | 8/1999 | Izuchukwu et al. |
| 5,941,442 A | 8/1999 | Geiste et al. |
| 5,954,259 A | 9/1999 | Viola et al. |
| 5,964,774 A | 10/1999 | McKean et al. |
| 6,010,054 A | 1/2000 | Johnson et al. |
| 6,024,748 A | 2/2000 | Manzo et al. |
| 6,032,849 A | 3/2000 | Mastri et al. |
| 6,042,601 A | 3/2000 | Smith |
| 6,045,560 A | 4/2000 | McKean et al. |
| 6,053,390 A | 4/2000 | Green et al. |
| 6,053,922 A | 4/2000 | Krause et al. |
| 6,063,097 A | 5/2000 | Oi et al. |
| 6,083,234 A | 7/2000 | Nicholas et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,156,056 A | 12/2000 | Kearns et al. |
| 6,171,330 B1 | 1/2001 | Benchetrit |
| 6,193,129 B1 | 2/2001 | Bittner et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,258,107 B1 | 7/2001 | Balázs et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,797 B2 | 6/2002 | Bombard et al. |
| RE37,814 E | 8/2002 | Allgeyer |
| 6,436,107 B1 | 8/2002 | Wang et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,488,196 B1 | 12/2002 | Fenton, Jr. |
| 6,488,197 B1 | 12/2002 | Whitman |
| 6,491,201 B1 | 12/2002 | Whitman |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,517,565 B1 | 2/2003 | Whitman et al. |
| 6,517,566 B1 | 2/2003 | Hovland et al. |
| 6,551,333 B2 | 4/2003 | Kuhns et al. |
| 6,578,751 B2 | 6/2003 | Hartwick |
| 6,588,643 B2 | 7/2003 | Bolduc et al. |
| 6,592,597 B2 | 7/2003 | Grant et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,638,285 B2 | 10/2003 | Gabbay |
| 6,644,532 B2 | 11/2003 | Green et al. |
| 6,656,193 B2 | 12/2003 | Grant et al. |
| 6,671,185 B2 | 12/2003 | Duval |
| 6,681,978 B2 | 1/2004 | Geiste et al. |
| 6,681,979 B2 | 1/2004 | Whitman |
| 6,692,507 B2 * | 2/2004 | Pugsley et al. ................. 606/153 |
| 6,695,199 B2 | 2/2004 | Whitman |
| 6,698,643 B2 | 3/2004 | Whitman |
| 6,716,232 B1 | 4/2004 | Vidal et al. |
| 6,716,233 B1 | 4/2004 | Whitman |
| 6,722,552 B2 | 4/2004 | Fenton, Jr. |
| 6,726,697 B2 | 4/2004 | Nicholas et al. |
| 6,736,854 B2 | 5/2004 | Vadurro et al. |
| 6,747,121 B2 | 6/2004 | Gogolewski |
| 6,755,338 B2 | 6/2004 | Hahnen et al. |

(56) References Cited

U.S. PATENT DOCUMENTS

| | | |
|---|---|---|
| 6,769,594 B2 | 8/2004 | Orban, III |
| 6,773,438 B1 | 8/2004 | Knodel et al. |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,821,284 B2 | 11/2004 | Sturtz et al. |
| 6,830,174 B2 | 12/2004 | Hillstead et al. |
| 6,837,846 B2 | 1/2005 | Jaffe et al. |
| 6,843,403 B2 | 1/2005 | Whitman |
| RE38,708 E | 3/2005 | Bolanos et al. |
| 6,863,694 B1 | 3/2005 | Boyce et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,877,647 B2 | 4/2005 | Ratcliff et al. |
| 6,905,057 B2 | 6/2005 | Swayze et al. |
| 6,913,608 B2 | 7/2005 | Liddicoat et al. |
| 6,939,358 B2 | 9/2005 | Palacios et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,220 B2 | 11/2005 | Marino et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,978 B2 | 1/2006 | Gannoe |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,041,868 B2 | 5/2006 | Greene et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,063,712 B2 | 6/2006 | Vargas et al. |
| 7,066,944 B2 | 6/2006 | Laufer et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,637 B2 | 8/2006 | Danitz et al. |
| 7,090,684 B2 | 8/2006 | McGuckin, Jr. et al. |
| 7,094,247 B2 | 8/2006 | Monassevitch et al. |
| 7,104,741 B2 | 9/2006 | Krohn |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,140,527 B2 | 11/2006 | Ehrenfels et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,179,267 B2 | 2/2007 | Nolan et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et |
| 7,213,736 B2 | 5/2007 | Wales et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,679 B2 | 9/2007 | McGuckin, Jr. et al. |
| 7,278,562 B2 | 10/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |

(56) References Cited

U.S. PATENT DOCUMENTS

| | | |
|---|---|---|
| 7,611,038 B2 | 11/2009 | Racenet et al. |
| 7,624,902 B2 | 12/2009 | Marczyk et al. |
| 7,631,793 B2 | 12/2009 | Rethy et al. |
| 7,637,409 B2 | 12/2009 | Marczyk |
| 7,644,848 B2 | 1/2010 | Swayze et al. |
| 7,651,498 B2 | 1/2010 | Shifrin et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,682,307 B2 | 3/2010 | Danitz et al. |
| 7,699,204 B2 | 4/2010 | Viola |
| 7,699,859 B2 | 4/2010 | Bombard et al. |
| 7,708,180 B2 | 5/2010 | Murray et al. |
| 7,708,758 B2 | 5/2010 | Lee et al. |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,748,587 B2 | 7/2010 | Haramiishi et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,770,775 B2 | 8/2010 | Shelton, IV et al. |
| 7,776,060 B2 | 8/2010 | Mooradian et al. |
| 7,780,054 B2 | 8/2010 | Wales |
| 7,780,663 B2 | 8/2010 | Yates et al. |
| 7,780,685 B2 | 8/2010 | Hunt et al. |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,914,543 B2 | 3/2011 | Roth et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,938,307 B2 | 5/2011 | Bettuchi |
| 7,942,890 B2 | 5/2011 | D'Agostino et al. |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,967,180 B2 | 6/2011 | Scirica |
| 7,980,443 B2 | 7/2011 | Scheib et al. |
| 8,002,795 B2 | 8/2011 | Beetel |
| 8,011,551 B2 | 9/2011 | Marczyk et al. |
| 8,011,555 B2 | 9/2011 | Tarinelli et al. |
| 8,028,883 B2 | 10/2011 | Stopek |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,062,330 B2 | 11/2011 | Prommersberger et al. |
| D650,074 S | 12/2011 | Hunt et al. |
| 8,091,756 B2 | 1/2012 | Viola |
| 8,097,017 B2 | 1/2012 | Viola |
| 8,123,103 B2 | 2/2012 | Milliman |
| 8,152,041 B2 | 4/2012 | Kostrzewski |
| 8,157,152 B2 | 4/2012 | Holsten et al. |
| 8,162,138 B2 | 4/2012 | Bettenhausen et al. |
| 8,167,895 B2 | 5/2012 | D'Agostino et al. |
| 8,205,781 B2 | 6/2012 | Baxter, III et al. |
| 8,211,125 B2 | 7/2012 | Spivey |
| 8,225,799 B2 | 7/2012 | Bettuchi |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,292,155 B2 | 10/2012 | Shelton, Iv et al. |
| 2002/0117534 A1 | 8/2002 | Green et al. |
| 2003/0023316 A1 | 1/2003 | Brown et al. |
| 2003/0220660 A1 | 11/2003 | Kortenbach et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0097987 A1 | 5/2004 | Pugsley et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0193189 A1 | 9/2004 | Kortenbach et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0070929 A1 | 3/2005 | Dalessandro et al. |
| 2005/0080454 A1 | 4/2005 | Drews et al. |
| 2005/0090817 A1 | 4/2005 | Phan |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0145675 A1 | 7/2005 | Hartwick et al. |
| 2005/0177181 A1 | 8/2005 | Kagan et al. |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0240222 A1 | 10/2005 | Shipp |
| 2005/0245965 A1 | 11/2005 | Orban, III et al. |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0020336 A1 | 1/2006 | Liddicoat |
| 2006/0025811 A1 | 2/2006 | Shelton, IV |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |

(56) References Cited

U.S. PATENT DOCUMENTS

| | | |
|---|---|---|
| 2006/0100643 A1 | 5/2006 | Laufer et al. |
| 2006/0108393 A1 | 5/2006 | Heinrich et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0073341 A1 | 3/2007 | Smith et al. |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0243227 A1 | 10/2007 | Gertner |
| 2007/0246505 A1 | 10/2007 | Pace-Floridia et al. |
| 2007/0260278 A1 | 11/2007 | Wheeler et al. |
| 2007/0270884 A1 | 11/2007 | Smith et al. |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0185419 A1 | 8/2008 | Smith et al. |
| 2008/0197167 A1 | 8/2008 | Viola et al. |
| 2008/0237296 A1 | 10/2008 | Boudreaux et al. |
| 2008/0251568 A1 | 10/2008 | Zemlok et al. |
| 2008/0251569 A1 | 10/2008 | Smith et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2010/0012704 A1 | 1/2010 | Tarinelli Racenet et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072254 A1 | 3/2010 | Aranyi et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0237132 A1 | 9/2010 | Measamer et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |

(56) References Cited

U.S. PATENT DOCUMENTS

| | | |
|---|---|---|
| 2010/0308100 A1 | 12/2010 | Boudreaux |
| 2010/0312261 A1 | 12/2010 | Suzuki et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174861 A1 | 7/2011 | Shelton, IV et al. |
| 2011/0174863 A1 | 7/2011 | Shelton, IV et al. |
| 2011/0178536 A1 | 7/2011 | Kostrzewski |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0233258 A1 | 9/2011 | Boudreaux |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0061448 A1 | 3/2012 | Zingman |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |

(56) References Cited

U.S. PATENT DOCUMENTS

| | | |
|---|---|---|
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |

FOREIGN PATENT DOCUMENTS

| | | |
|---|---|---|
| CA | 2514274 A1 | 1/2006 |
| CN | 1634601 A | 7/2005 |
| CN | 1868411 A | 11/2006 |
| CN | 1915180 A | 2/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 31 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |

(56) References Cited

FOREIGN PATENT DOCUMENTS

| | | |
|---|---|---|
| EP | 0959786 B1 | 9/2004 |
| EP | 1459695 A1 | 9/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1897502 A1 | 3/2008 |
| EP | 1330201 B1 | 6/2008 |
| EP | 1702568 B1 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1693008 B1 | 12/2008 |
| EP | 1759640 B1 | 12/2008 |
| EP | 2000102 A2 | 12/2008 |
| EP | 2008595 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550413 B1 | 6/2009 |
| EP | 1745748 B1 | 8/2009 |
| EP | 2090237 A1 | 8/2009 |
| EP | 2090244 A2 | 8/2009 |
| EP | 2090256 A2 | 8/2009 |
| EP | 2095777 A2 | 9/2009 |
| EP | 2110082 A1 | 10/2009 |
| EP | 1813208 B1 | 11/2009 |
| EP | 2116195 A1 | 11/2009 |
| EP | 1607050 B1 | 12/2009 |
| EP | 1815804 B1 | 12/2009 |
| EP | 1566150 B1 | 4/2010 |
| EP | 1813206 B1 | 4/2010 |
| EP | 1769754 B1 | 6/2010 |
| EP | 1535565 B1 | 10/2010 |
| EP | 1702570 B1 | 10/2010 |
| EP | 1785098 B1 | 10/2010 |
| EP | 2030578 B1 | 11/2010 |
| EP | 1627605 B1 | 12/2010 |
| EP | 1813205 B1 | 6/2011 |
| EP | 1785102 B1 | 1/2012 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | S 58500053 A | 1/1983 |
| JP | 61-98249 A | 5/1986 |
| JP | 63-203149 | 8/1988 |
| JP | 3-12126 A | 1/1991 |
| JP | 5-212039 A | 8/1993 |
| JP | 6007357 A | 1/1994 |
| JP | 7051273 A | 2/1995 |
| JP | 8033641 A | 2/1996 |
| JP | 8229050 A | 9/1996 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001286477 A | 10/2001 |
| JP | 2002143078 A | 5/2002 |
| JP | 2002369820 A | 12/2002 |
| JP | 2004-344663 | 12/2004 |
| JP | 2005-028149 A | 2/2005 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |

(56) References Cited

FOREIGN PATENT DOCUMENTS

| | | |
|---|---|---|
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-281405 A | 10/2006 |
| RU | 2008830 C1 | 3/1994 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A1 | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1722476 A1 | 3/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 12 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |

(56) References Cited

FOREIGN PATENT DOCUMENTS

| | | |
|---|---|---|
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2010/063795 A1 | 6/2010 |
| WO | WO 2012/044844 A2 | 4/2012 |

OTHER PUBLICATIONS

U.S. Appl. No. 12/775,699, filed May 7, 2010.
U.S. Appl. No, 12/894,306, filed Sep. 30, 2010.
U.S. Appl. No. 12/894,360, filed Sep. 30, 2010.
U.S. Appl. No, 12/894,322, filed Sep. 30, 2010.
U.S. Appl. No. 12/894,351, filed Sep. 30, 2010.
U.S. Appl. No. 12/894,339, filed Sep. 30, 2010.
U.S. Appl. No. 12/894,327, filed Sep. 30, 2010.
U.S. Appl. No. 12/894,311, filed Sep. 30, 2010.
U.S. Appl. No. 12/894,340, filed Sep. 30, 2010.
U.S. Appl. No. 12/894,350, filed Sep. 30, 2010.
U.S. Appl. No. 12/894,338, filed Sep. 30, 2010.
U.S. Appl. No. 12/894,369, filed Sep. 30, 2010.
U.S. Appl. No. 12/894,312, filed Sep. 30, 2010.
U.S. Appl. No. 12/894,377, filed Sep. 30, 2010.
U.S. Appl. No. 12/894,383, filed Sep. 30, 2010.
U.S. Appl. No. 12/894,389, filed Sep. 30, 2010.
U.S. Appl. No. 12/894,345, filed Sep. 30, 2010.
U.S. Appl. No. 12/894,318, filed Sep. 30, 2010.
U.S. Appl. No. 12/894,361, filed Sep. 30, 2010.
U.S. Appl. No. 12/894,367, filed Sep. 30, 2010.
U.S. Appl. No. 12/894,388, filed Sep. 30, 2010.
U.S. Appl. No. 12/894,376, filed Sep. 30, 2010.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.
2000,7539?cookieSet=1&journalCode?vsu which redirects to http://www3.interscience.wiley.com/journal/119040681/
abstract?CRETRY?1&SRETRY=0; [online] accessed: Sep. 22, 2008 (2 pages).
The Sodem Aseptic Battery Transfer Kit, Sodern Systems, 2000, 3 pages.
"Biomedical Coatings," Fort Wayne Metals, Research Products Corporation. obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: htttp://electronicdesign.com/Articles/Print.cfm?ArticleID=17465, accessed Jan. 15, 2008 (5 pages).
Datasheet for Panasonic TK Relays Ultra Low Profile 2 a Polarized Relay, Copyright Matsushita Electric Works, Ltd, (Known of at least as early as Aug. 17, 2010), 5 pages.
International Search Report and Written Opinion for PCT/US2011/054048, dated May 14, 2012 (11 pages).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
U.S. Appl. No. 13/242,086, filed Sep. 23, 2011.
U.S. Appl. No. 13/241,912, filed Sep. 23, 2011.
U.S. Appl. No. 13/241,922, filed Sep. 23, 2011.
U.S. Appl. No. 13/433,115, filed Mar. 28, 2012.
U.S. Appl. No. 13/433,118, filed Mar. 28, 2012.
U.S. Appl. No. 13/433,135, filed Mar. 28, 2012.

(56) References Cited

OTHER PUBLICATIONS

U.S. Appl. No. 13/433,129, filed Mar. 28, 2012.
U.S. Appl. No. 13/433,140, filed Mar. 28, 2012.
U.S. Appl. No. 13/433,147, filed Mar. 28, 2012.
U.S. Appl. No. 13/433,126, filed Mar. 28, 2012.
U.S. Appl. No. 13/433,132, filed Mar. 28, 2012.

* cited by examiner

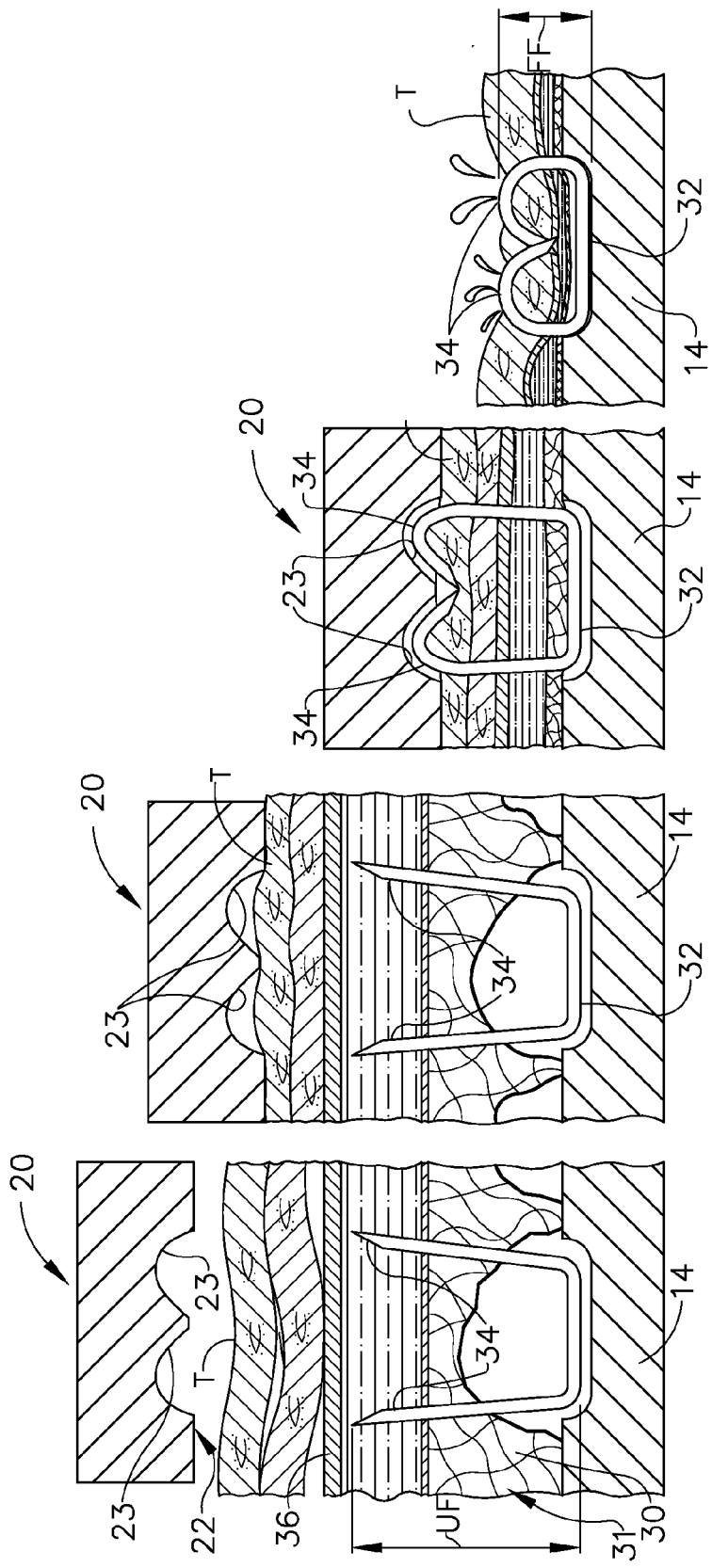

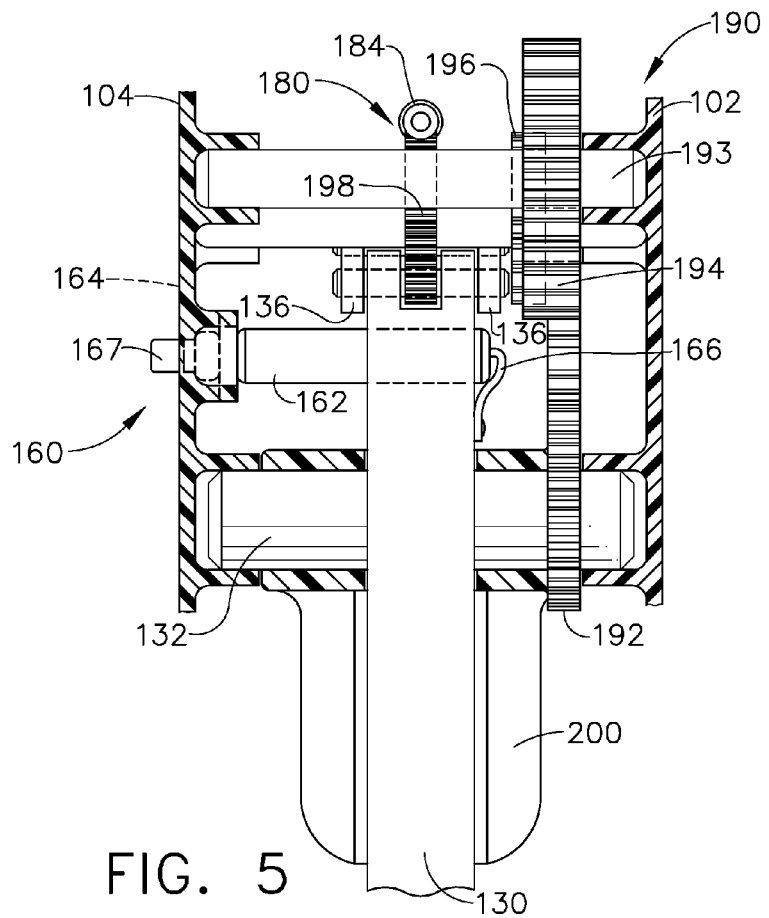
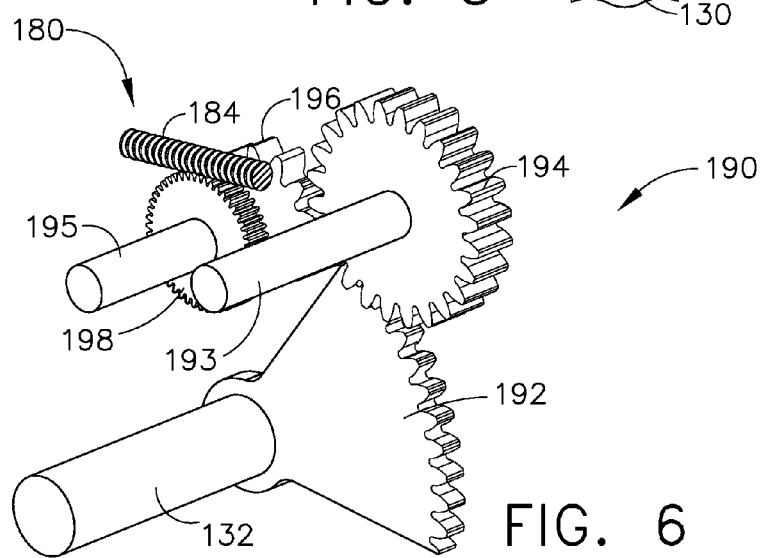
FIG. 5
FIG. 6

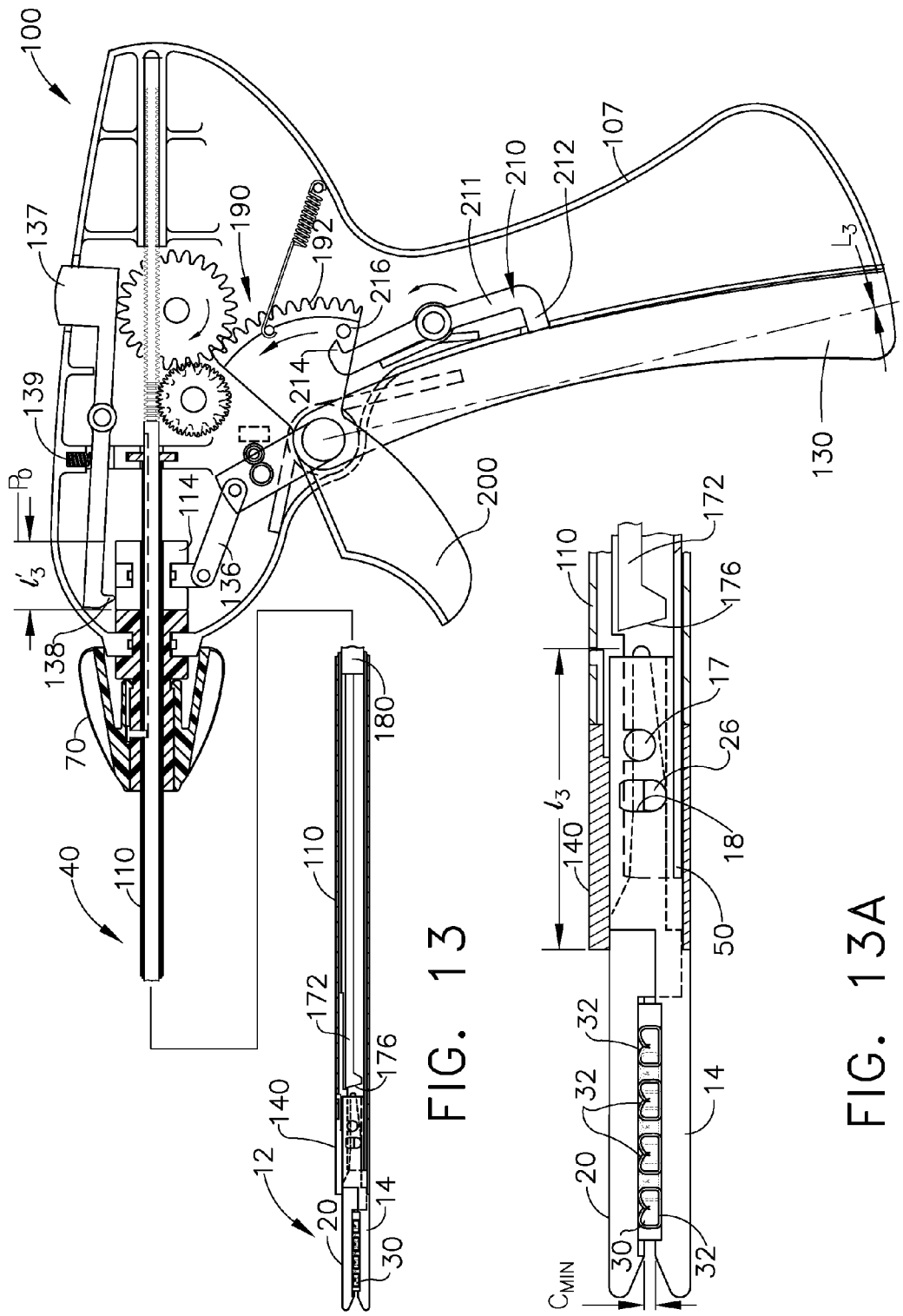

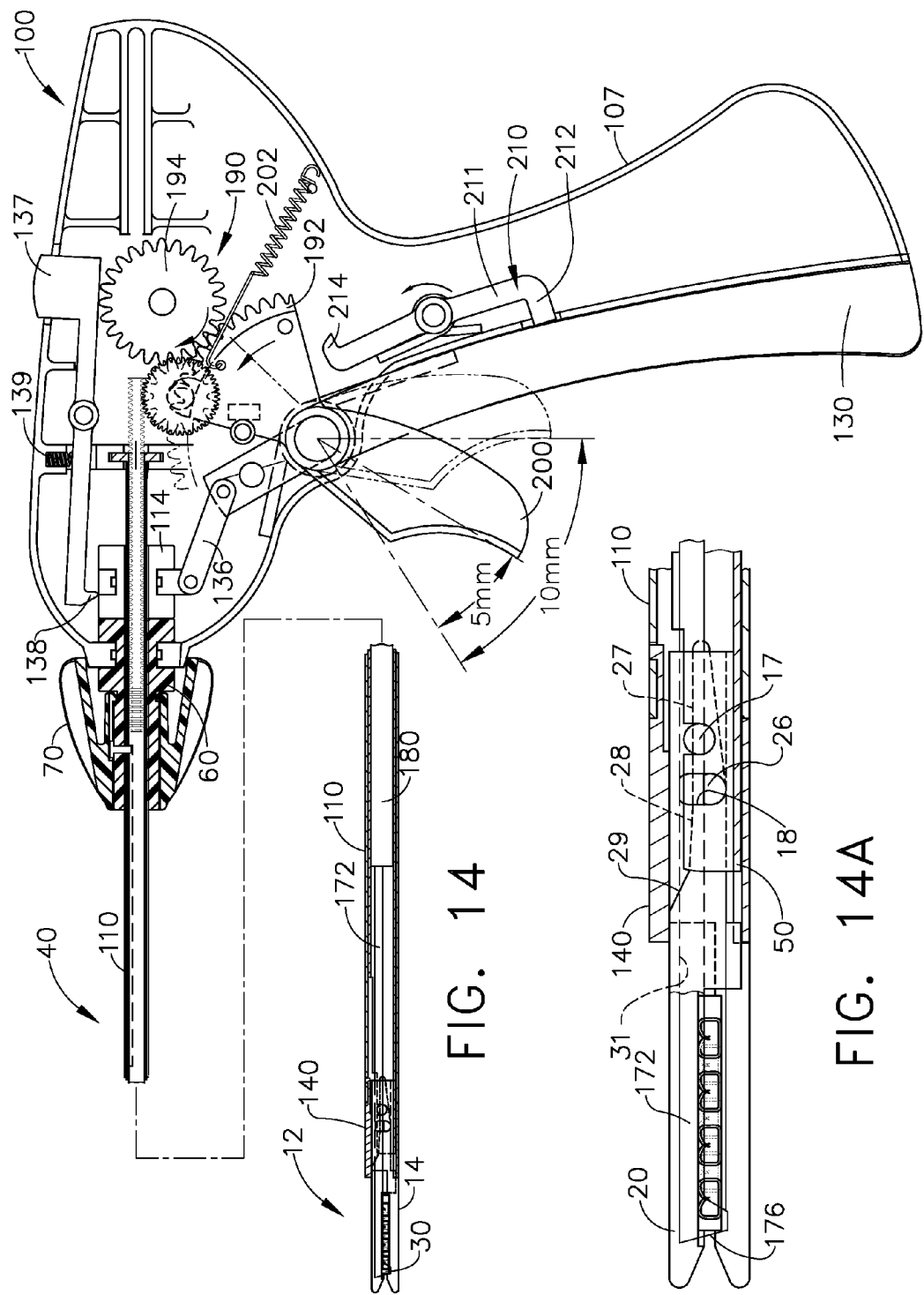

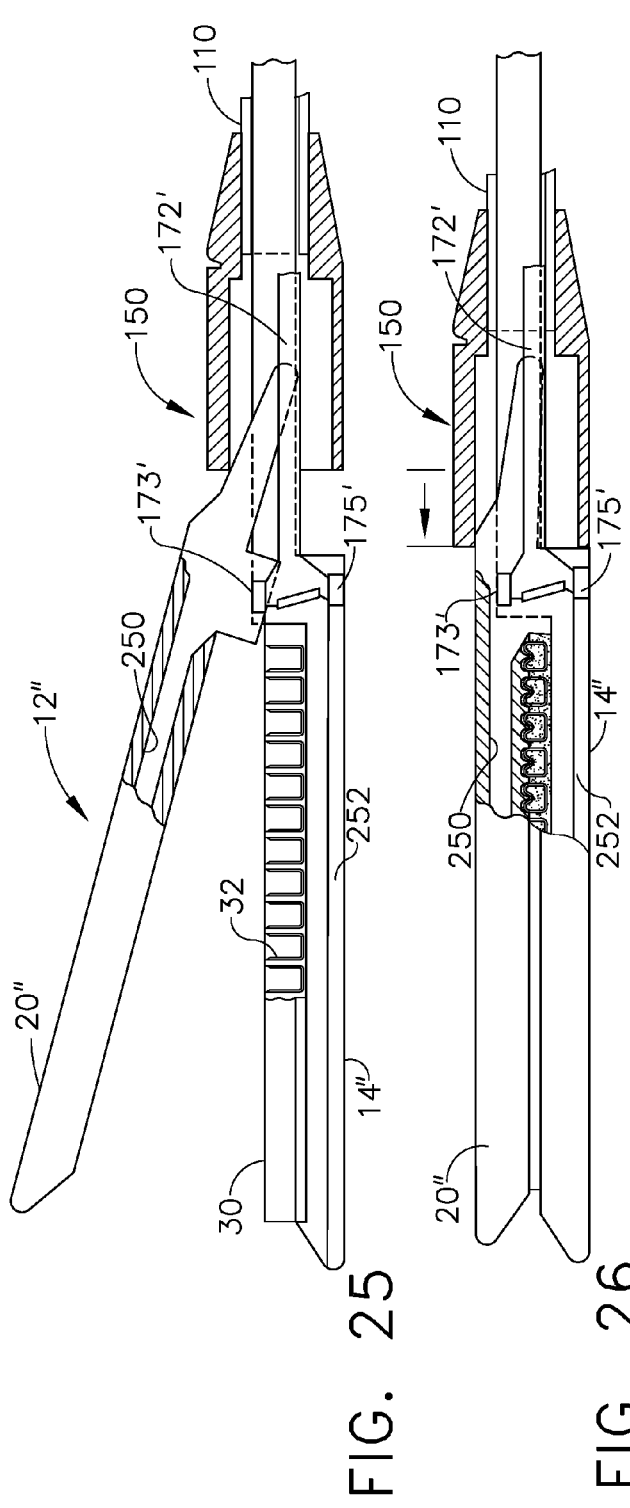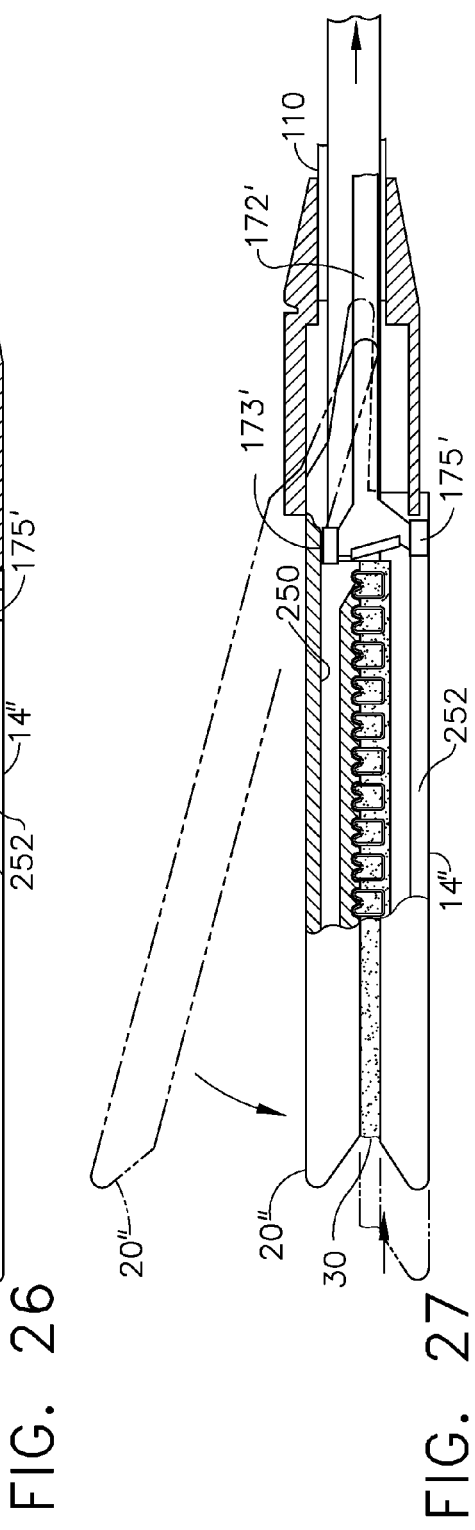
FIG. 25
FIG. 26
FIG. 27

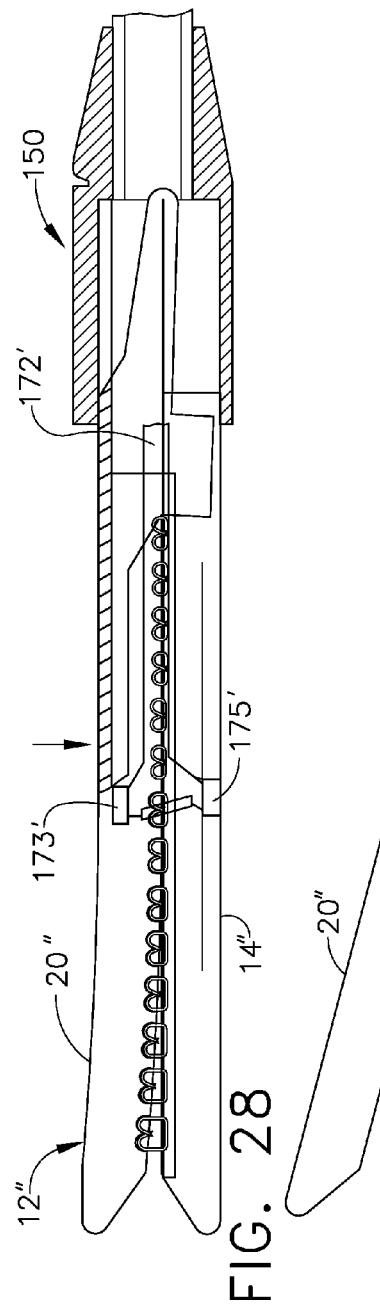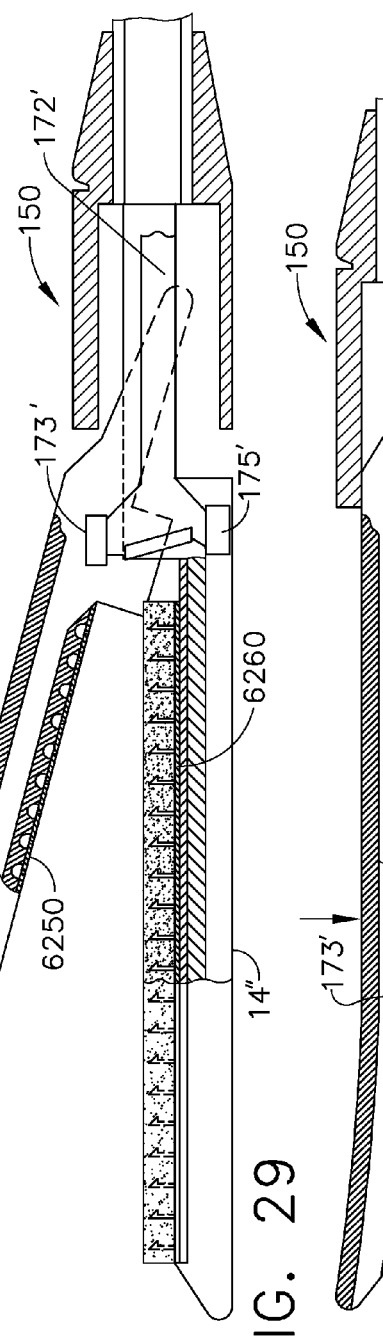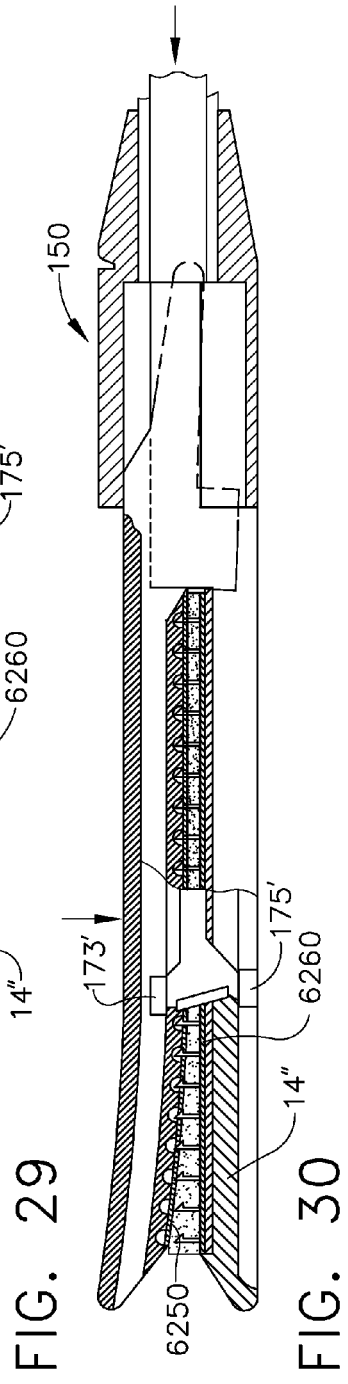

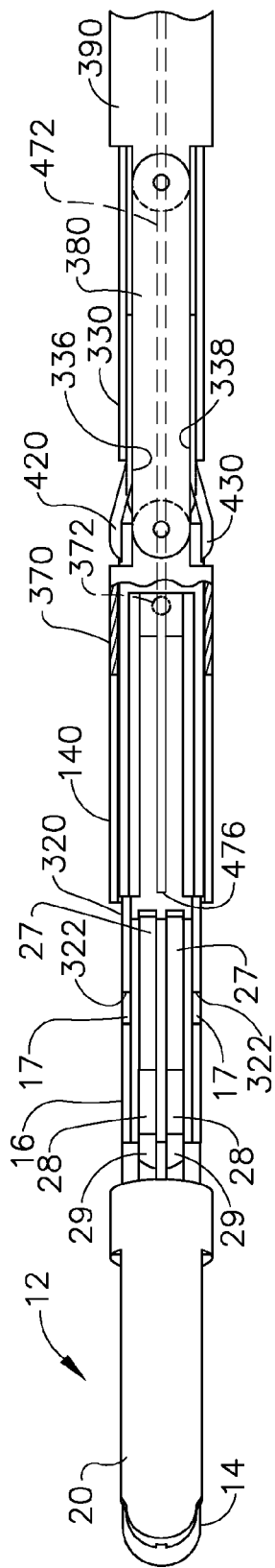
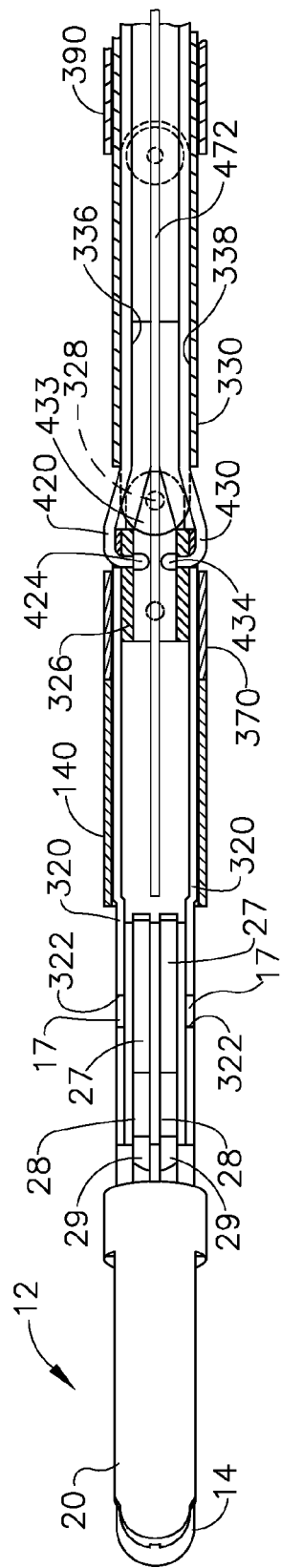
FIG. 33
FIG. 34

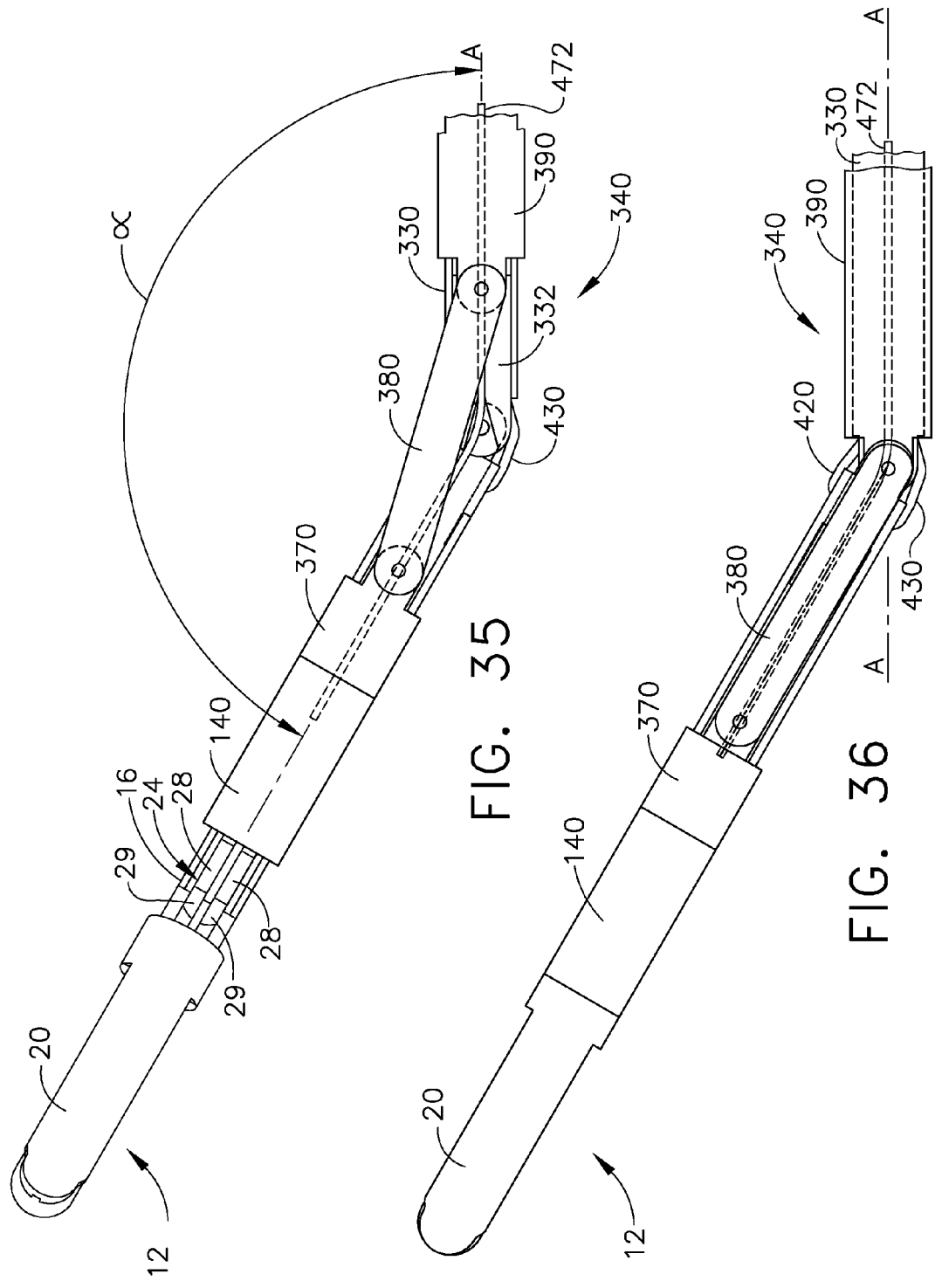

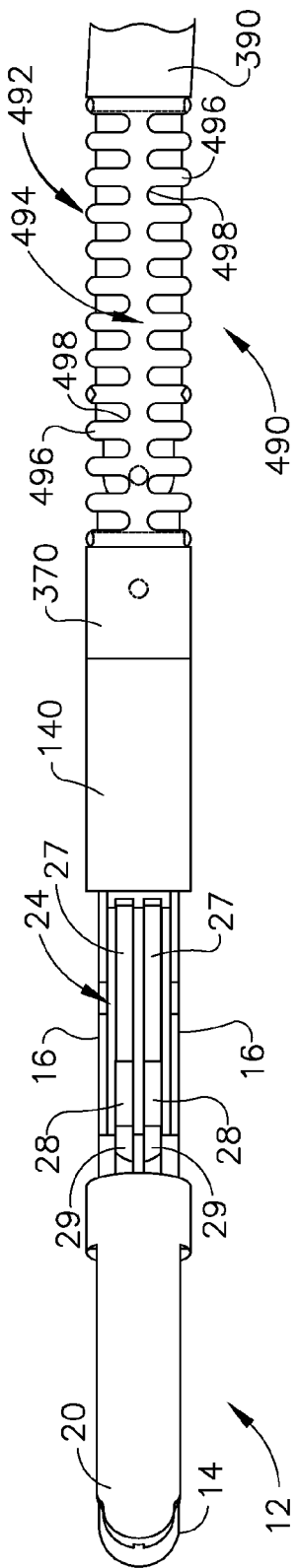
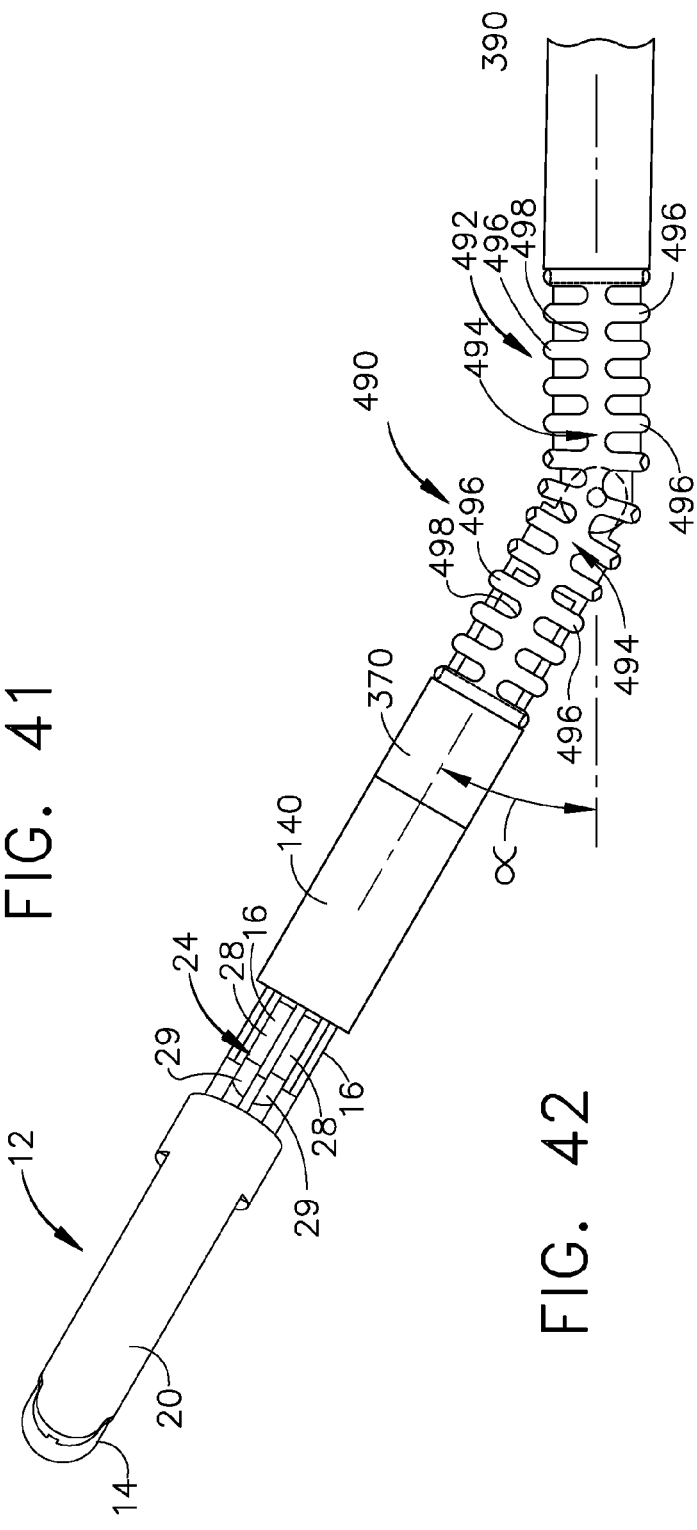
FIG. 41
FIG. 42

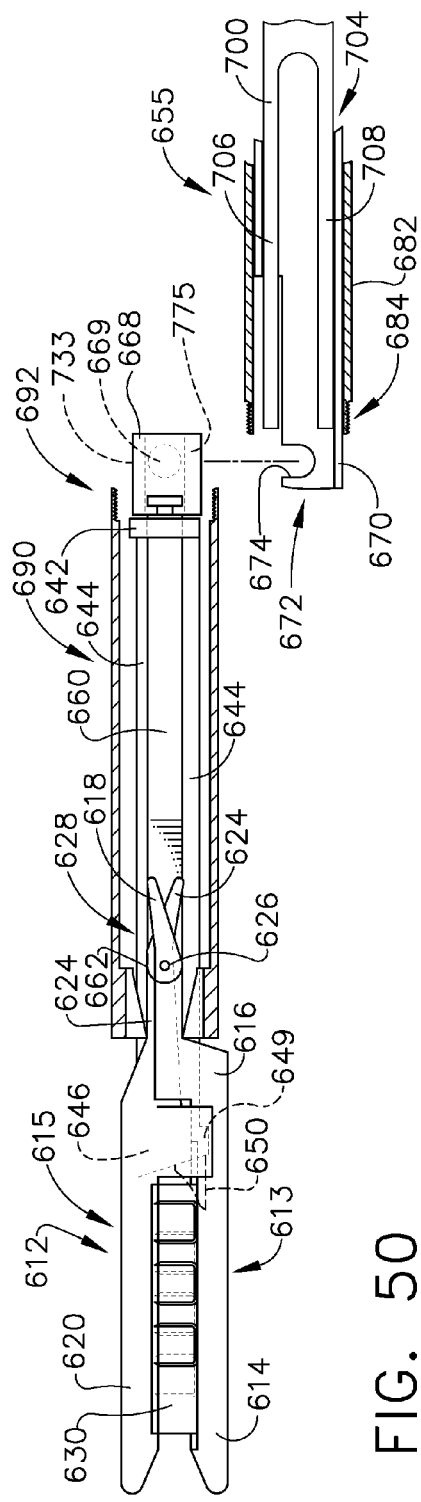
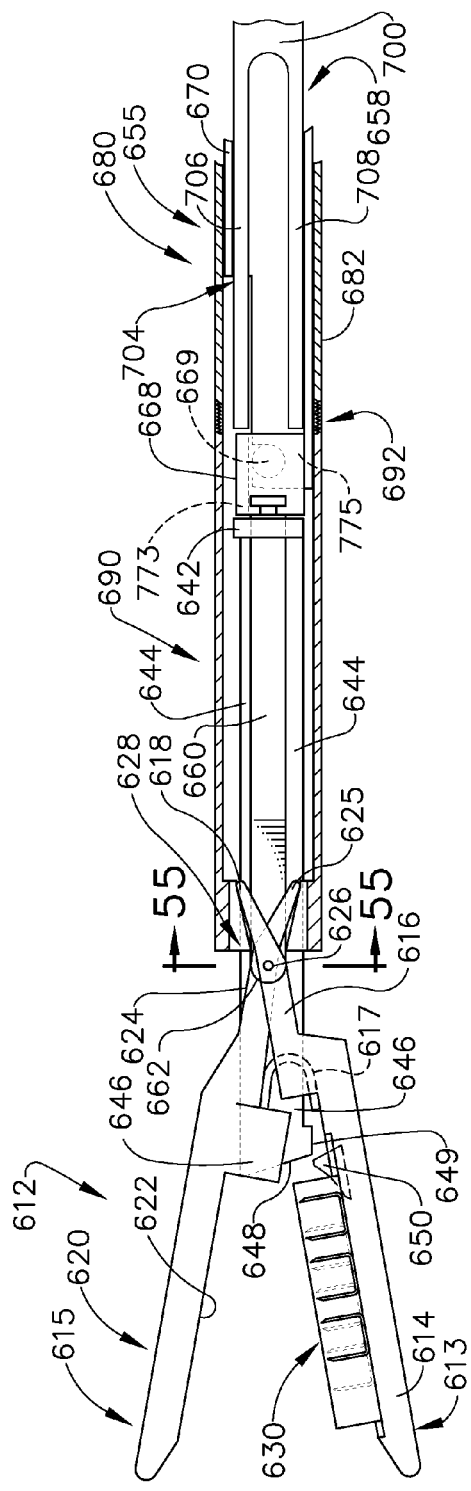

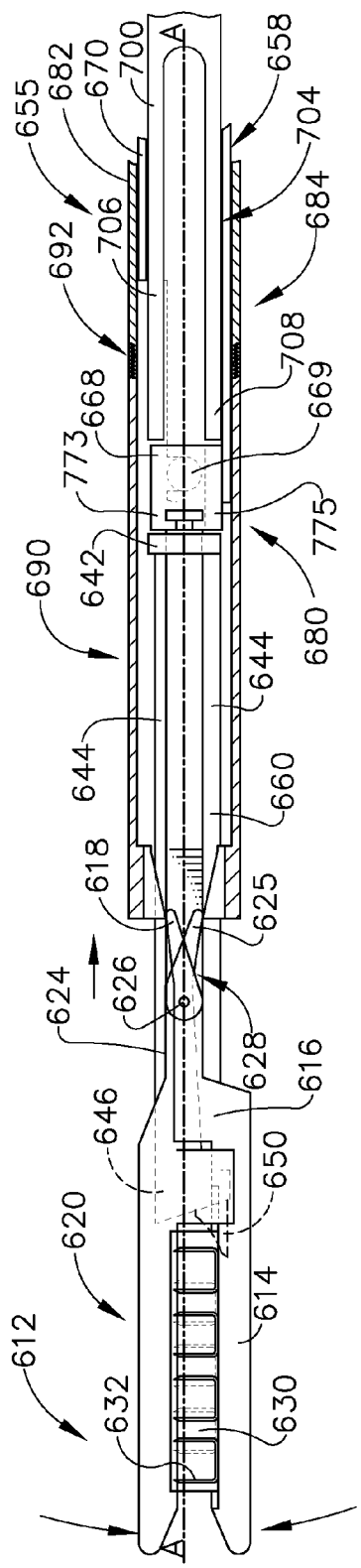

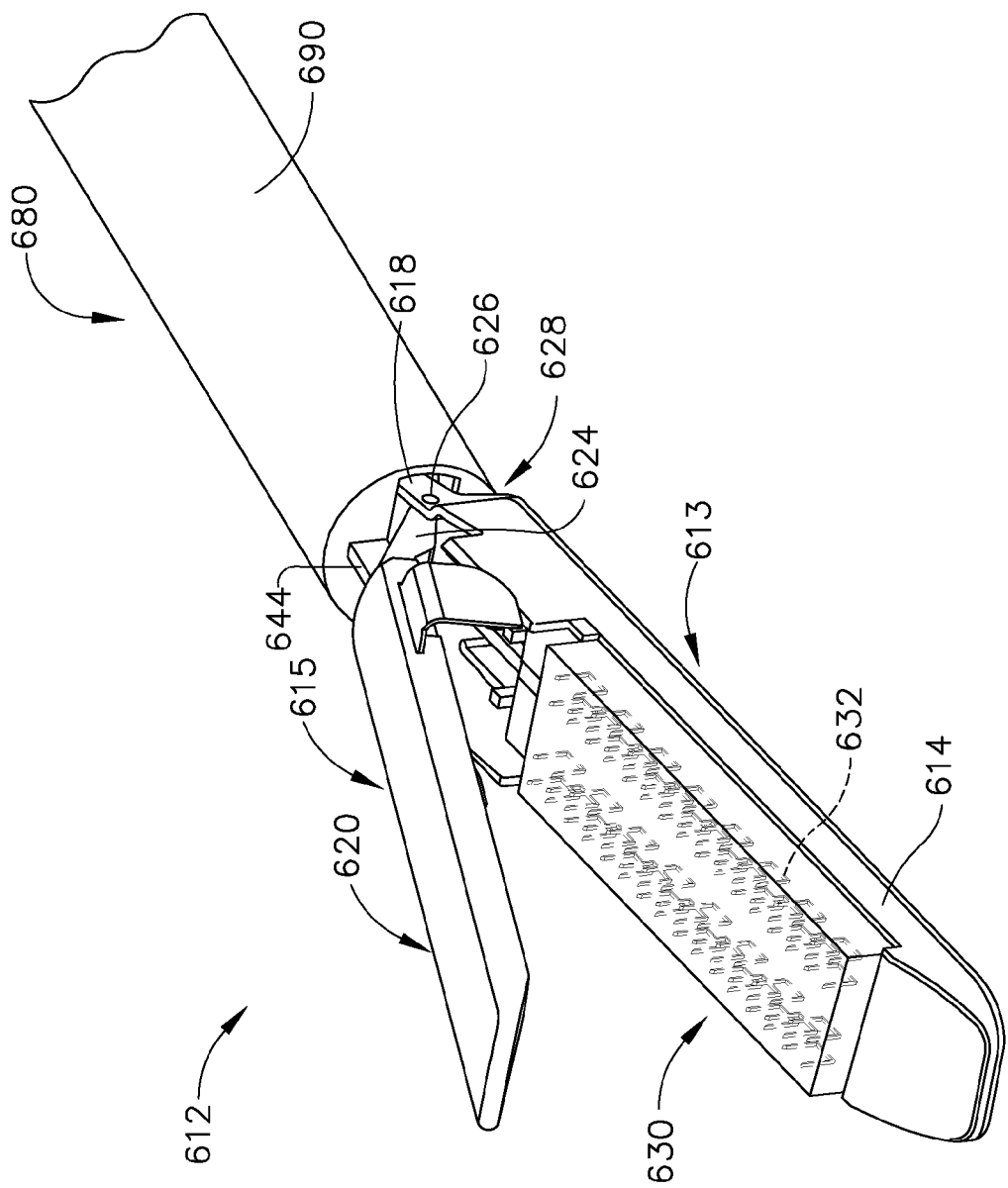

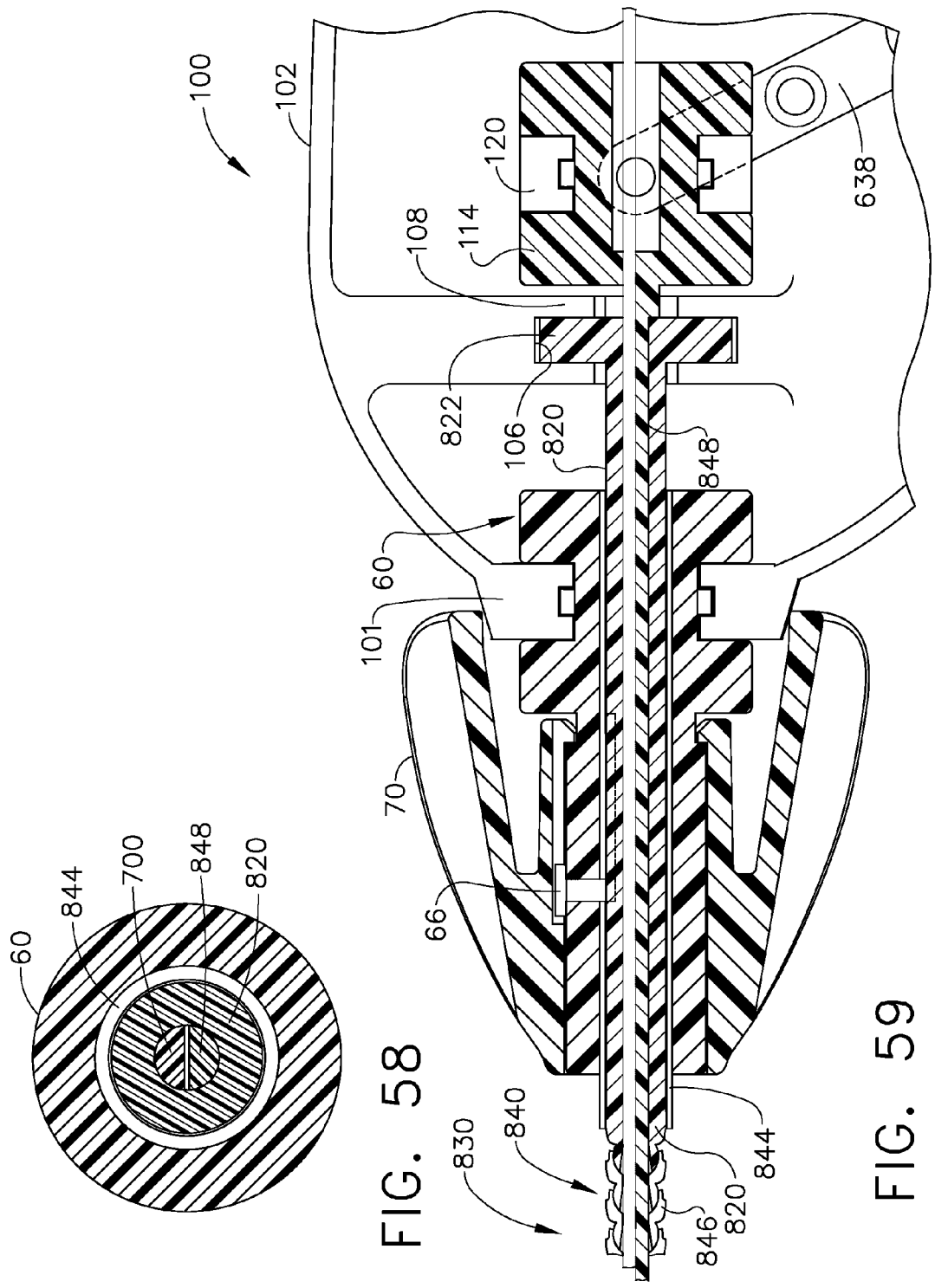

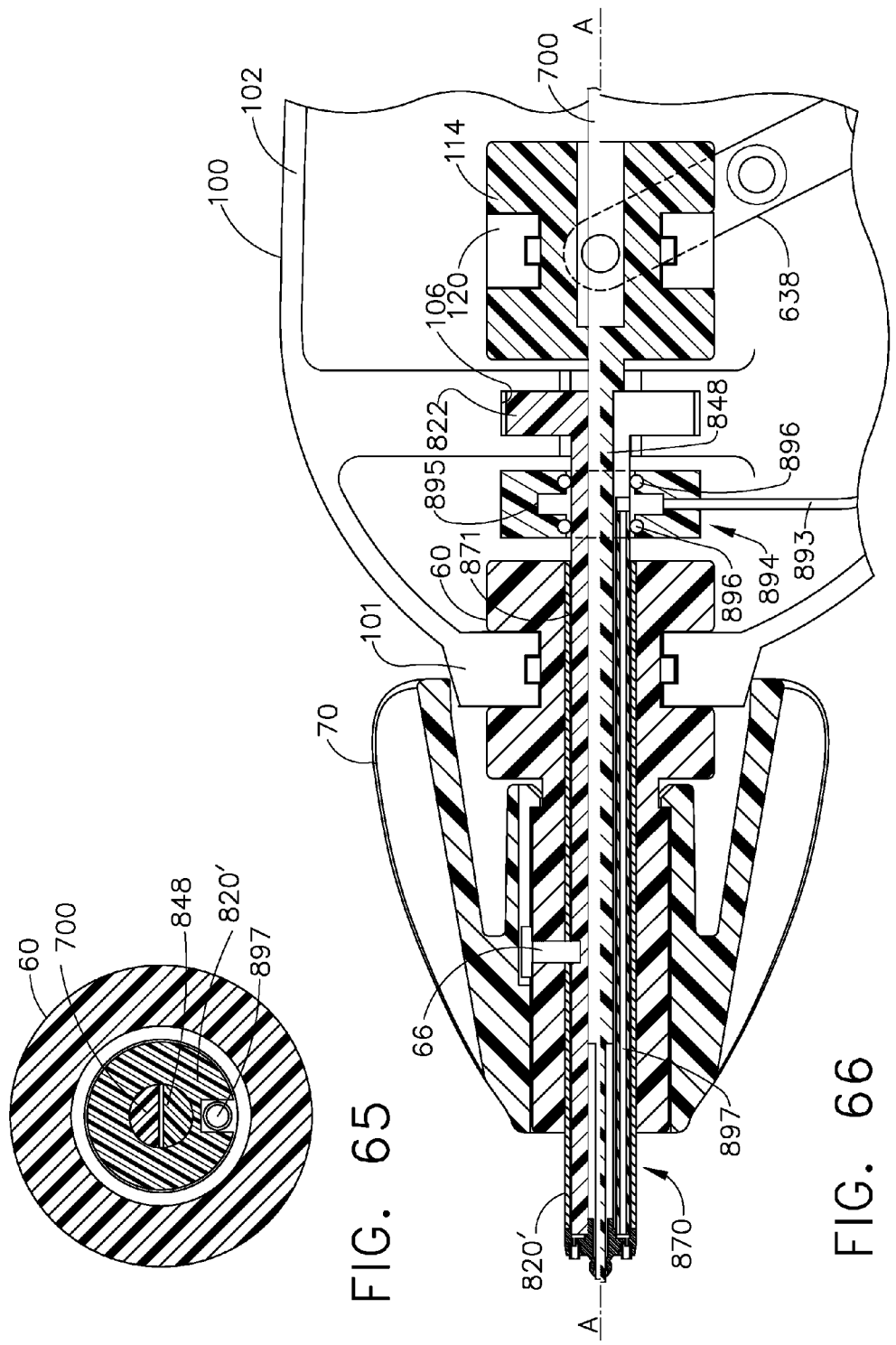

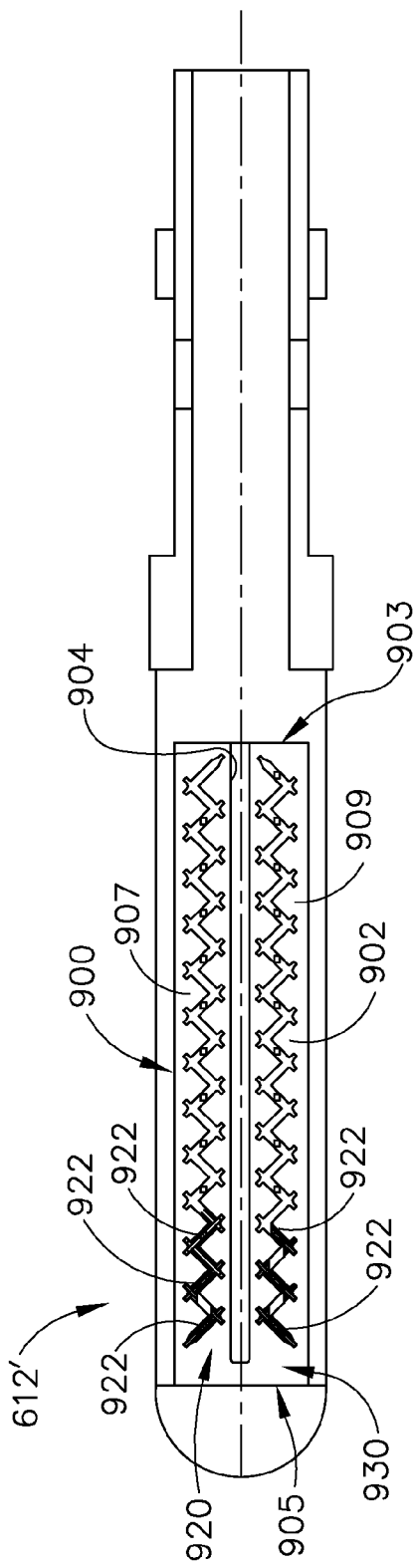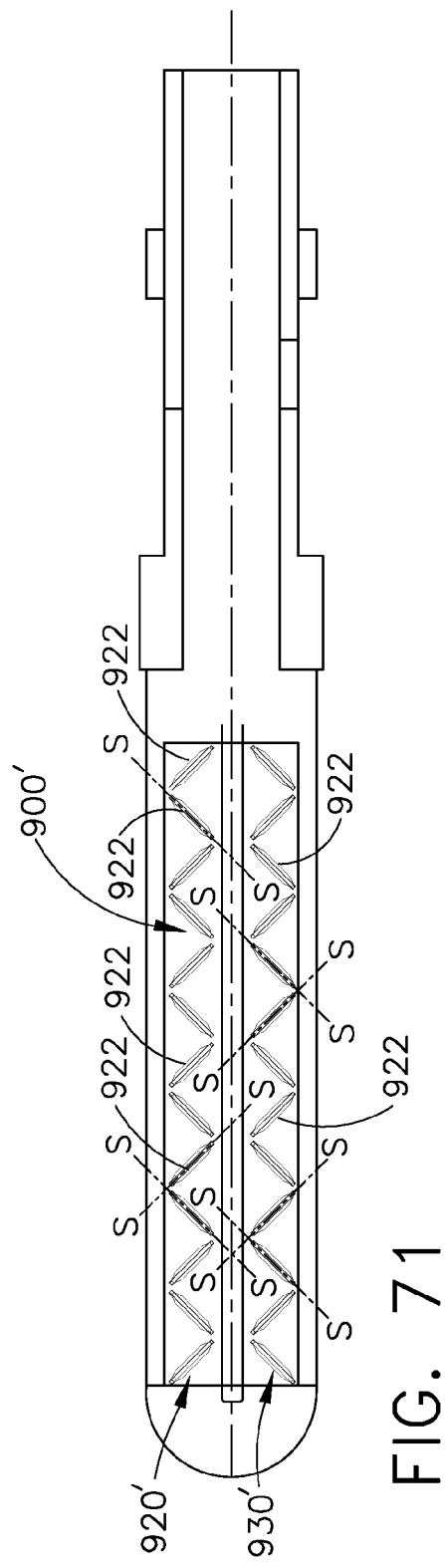

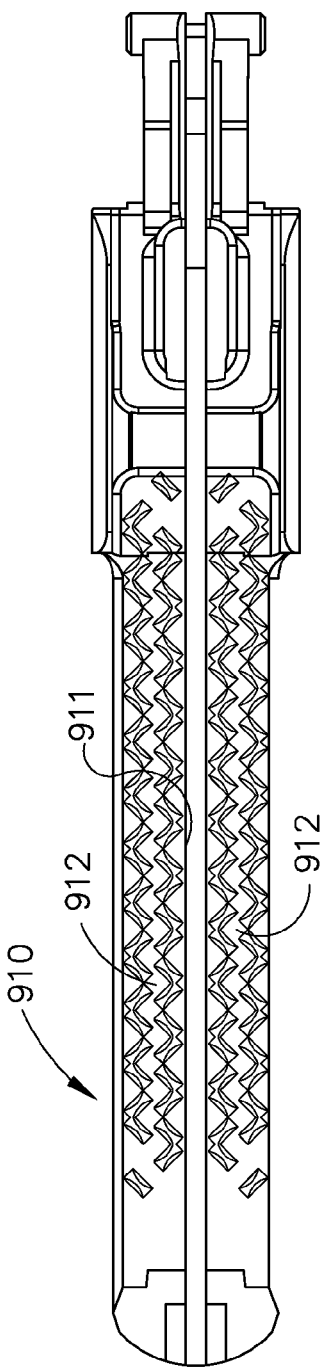
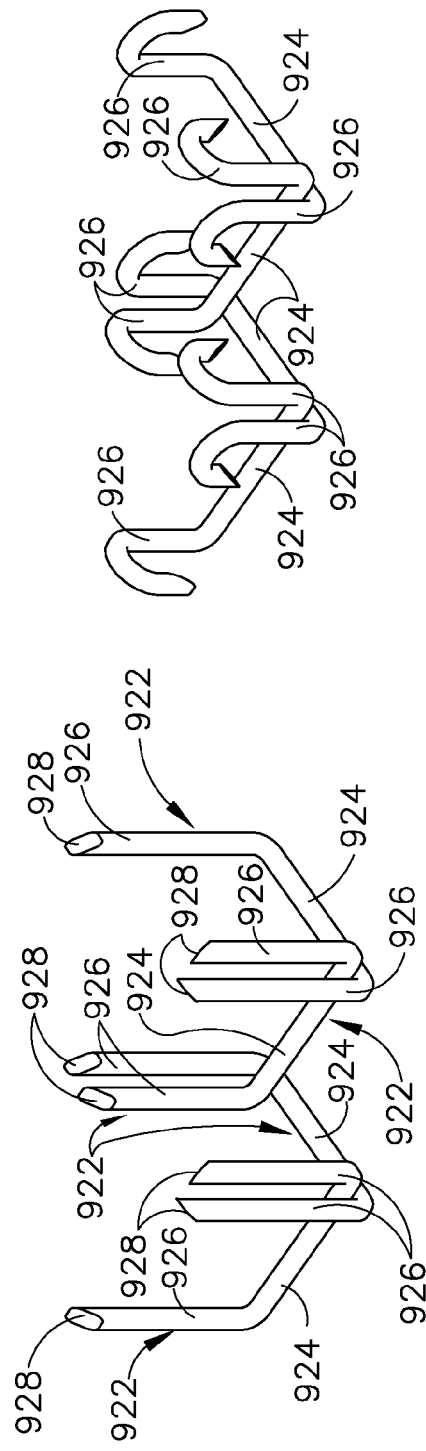
FIG. 72
FIG. 73
FIG. 74

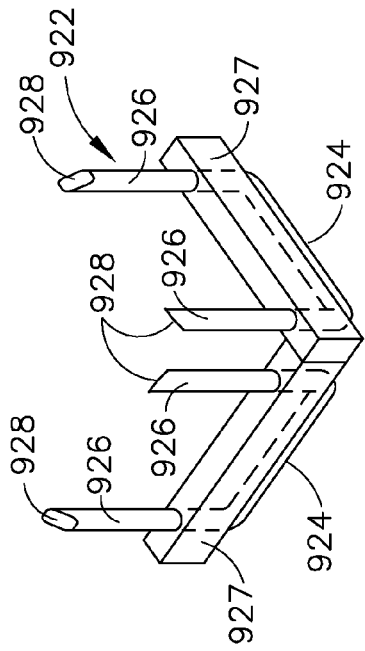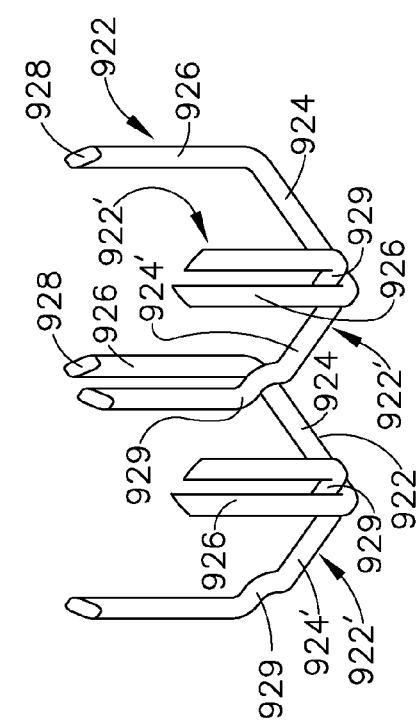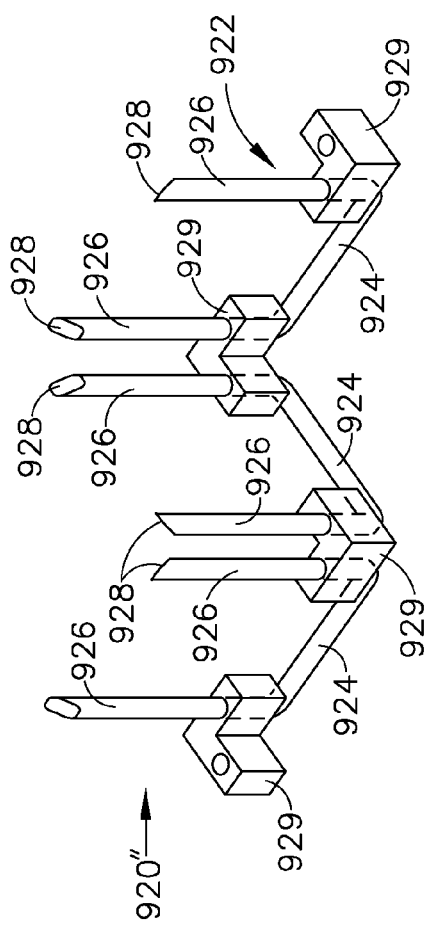

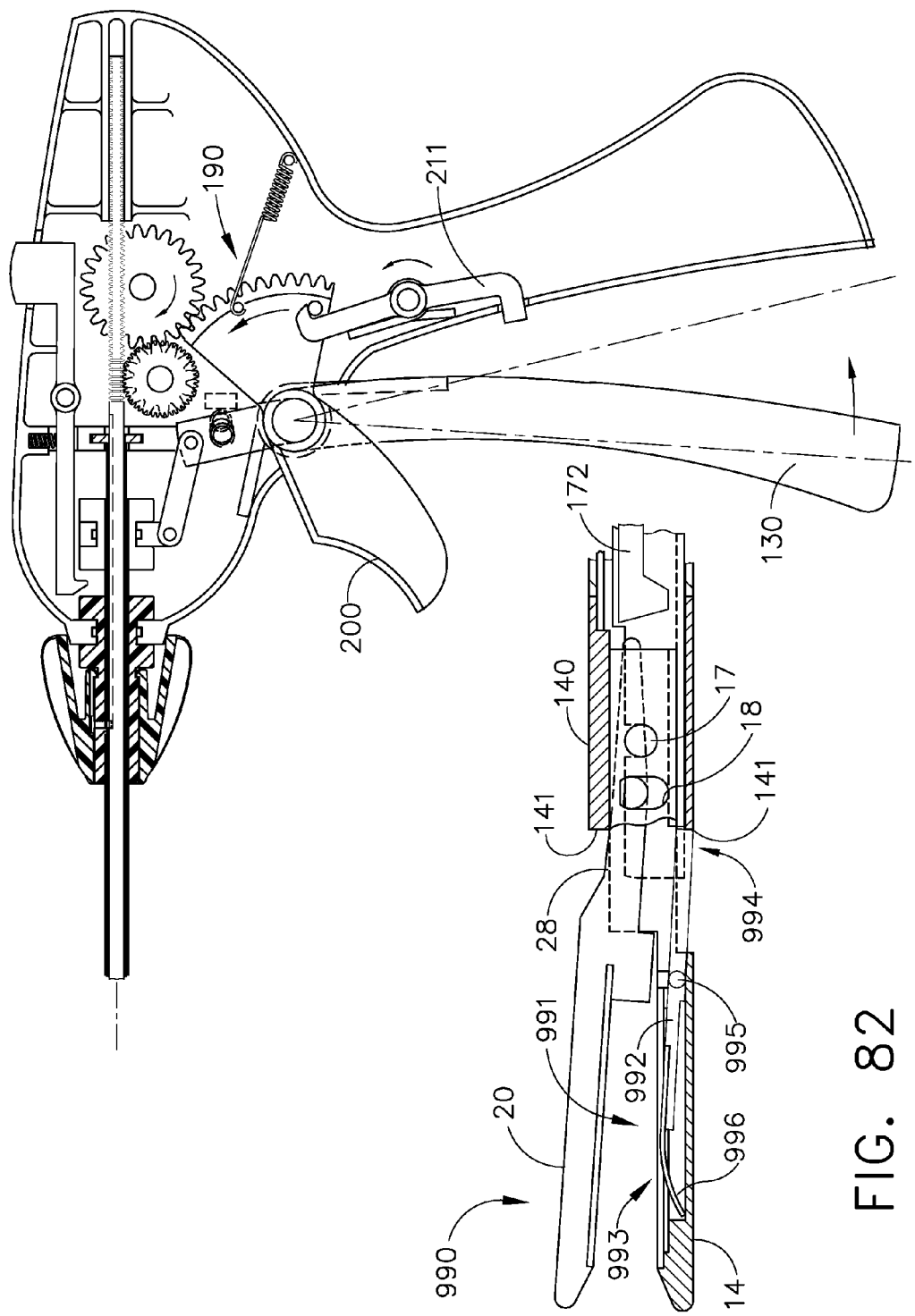

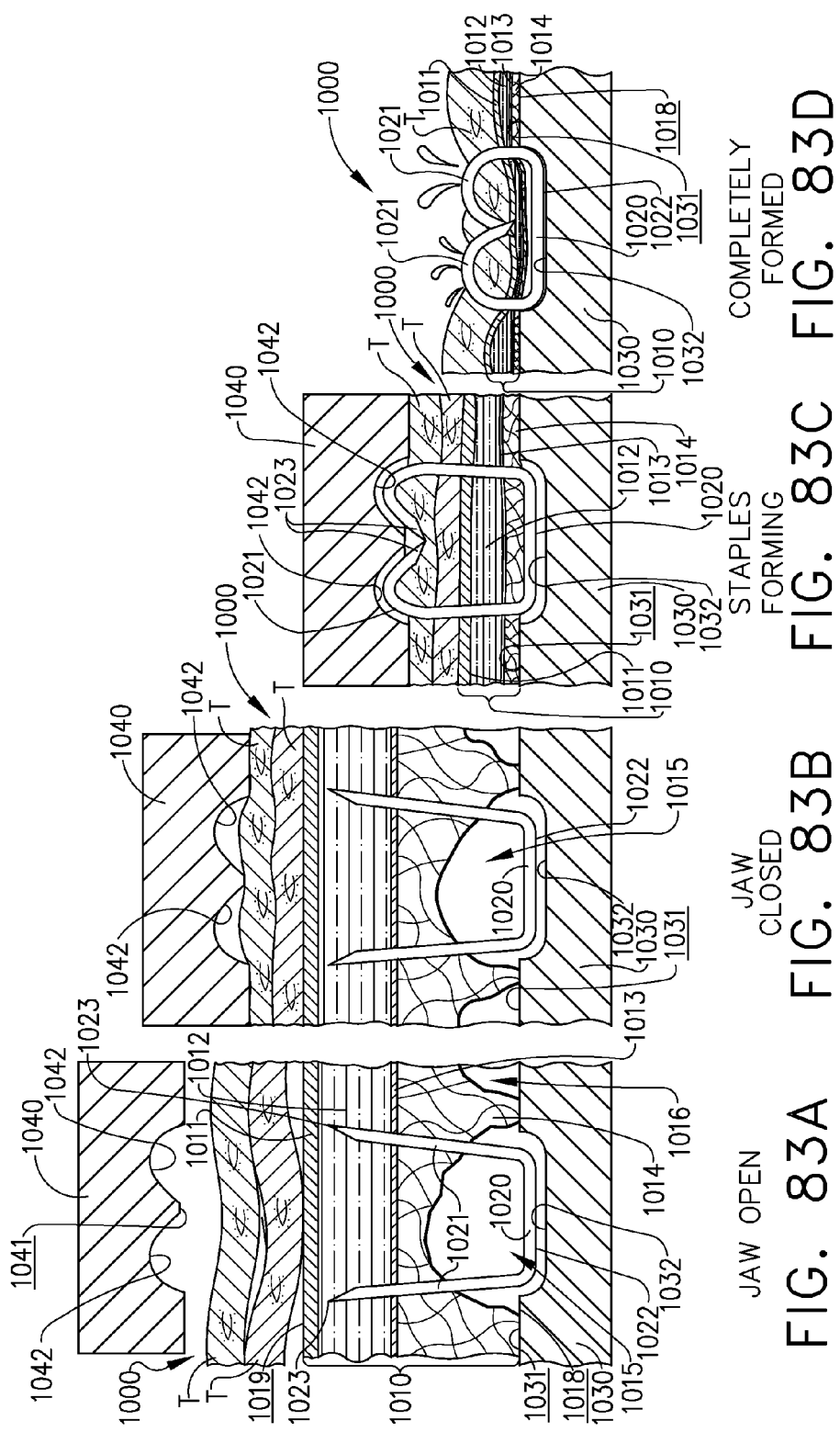

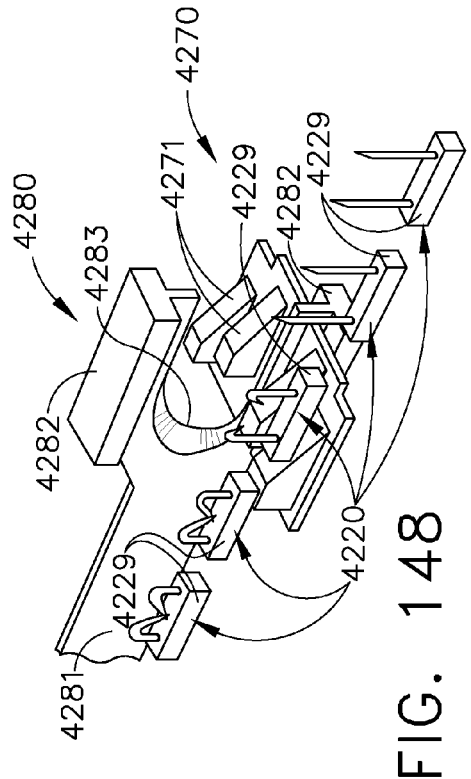
FIG. 147
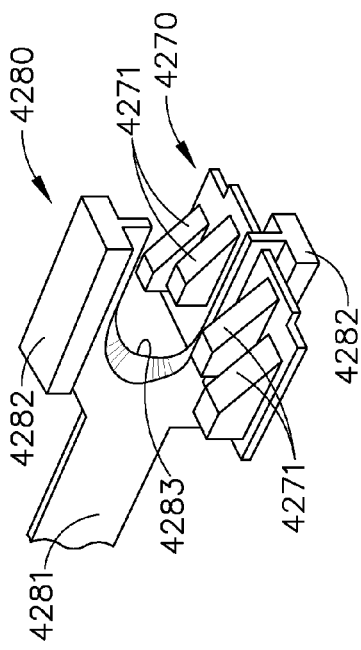
FIG. 148
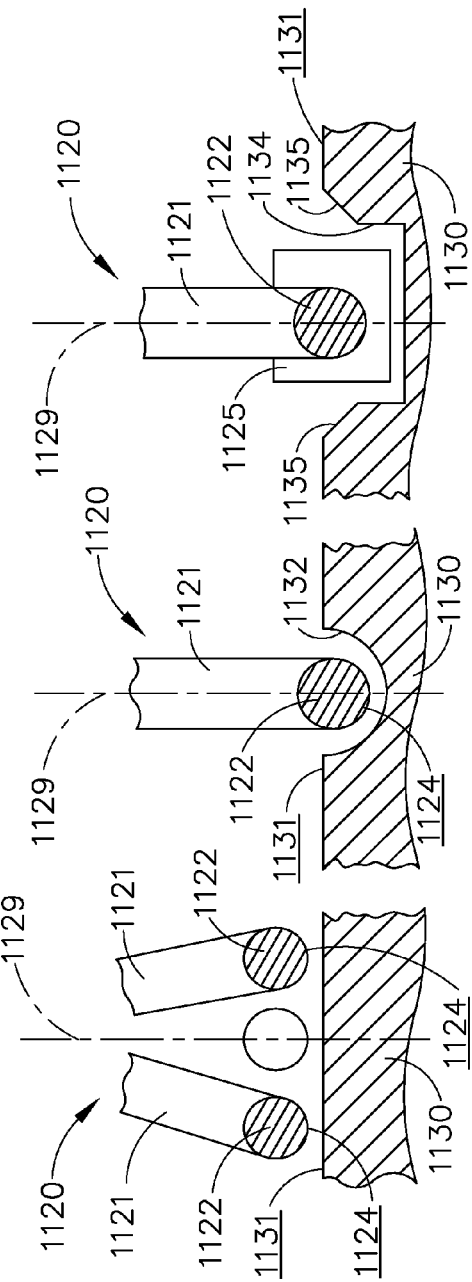
FIG. 85
FIG. 86
FIG. 87

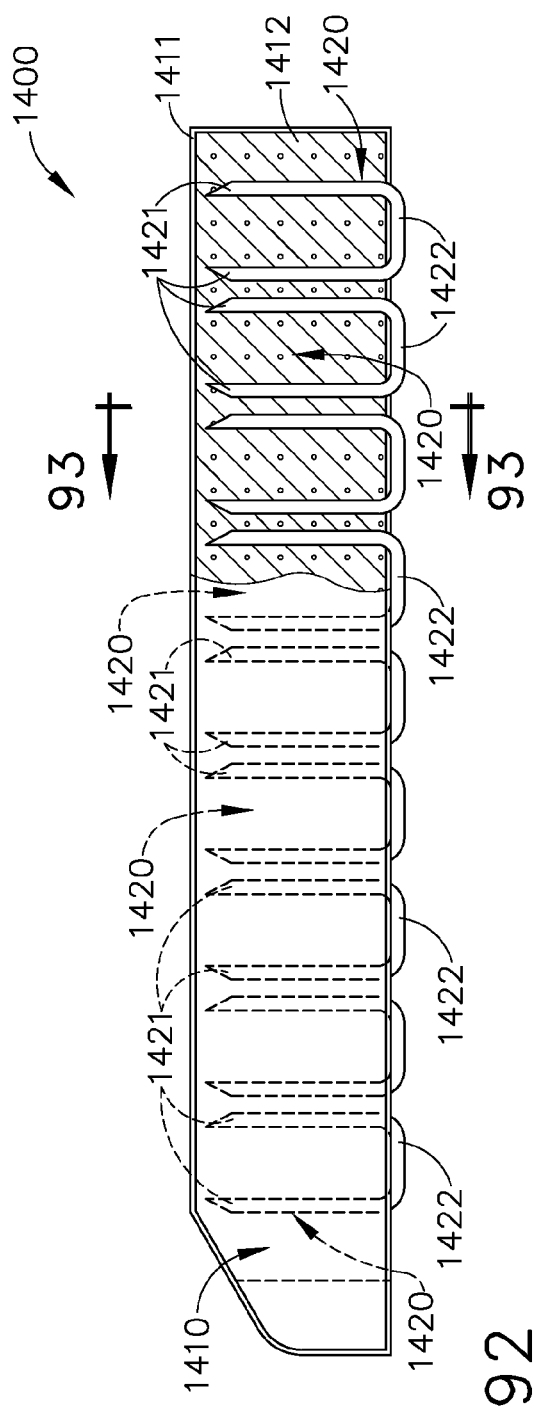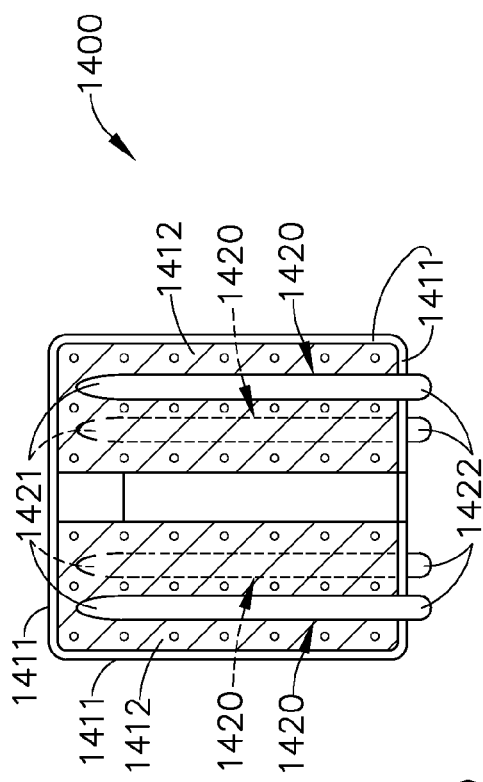
FIG. 92
FIG. 93

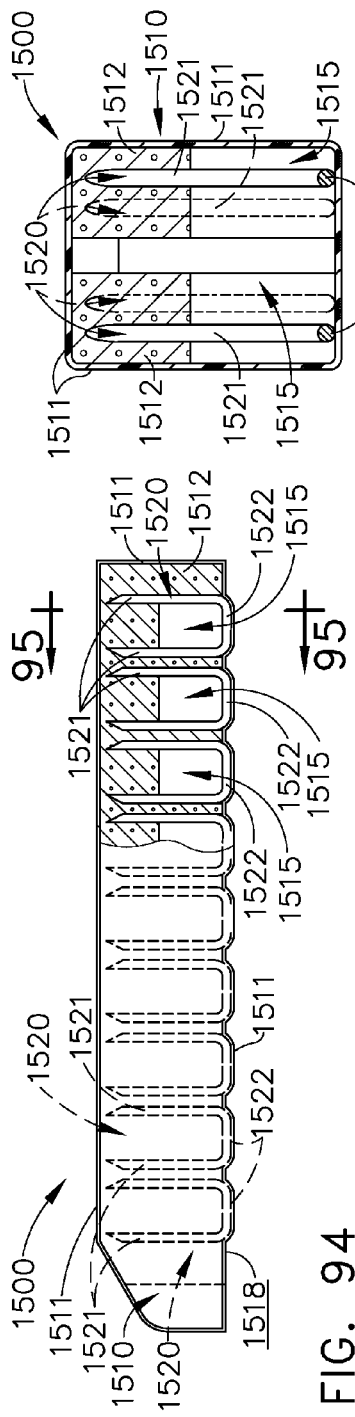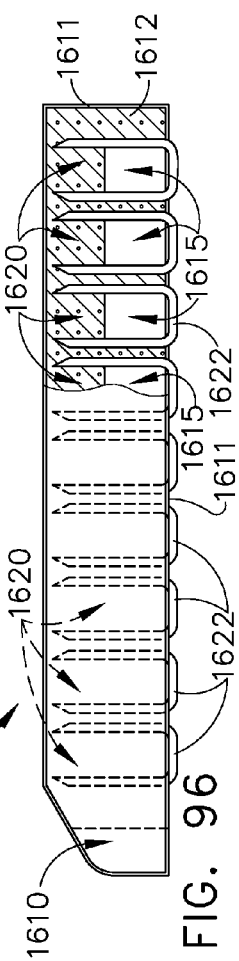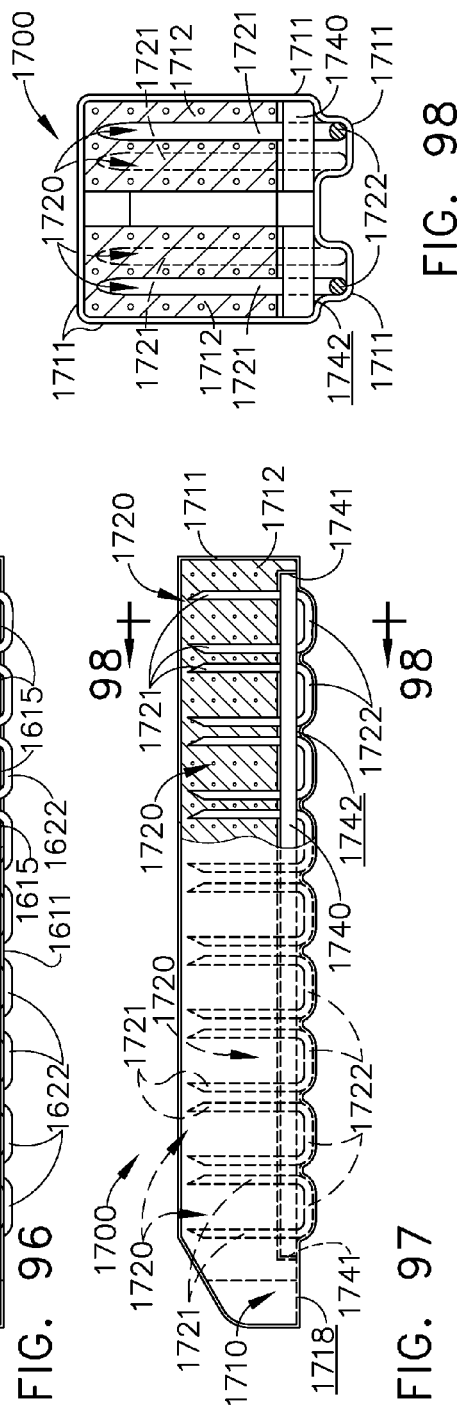

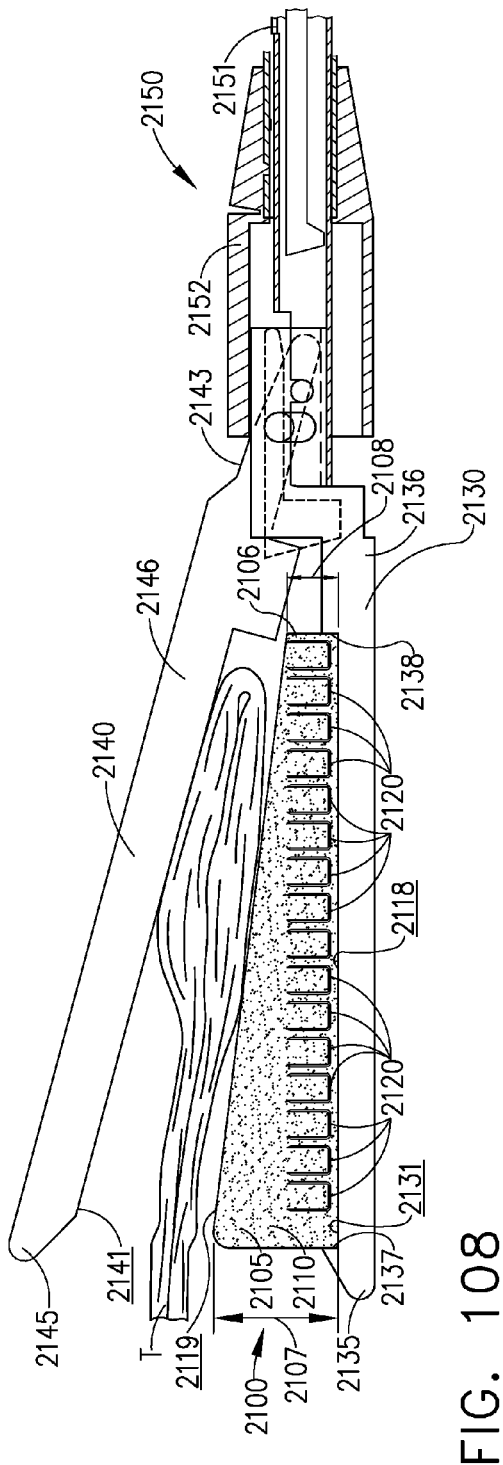
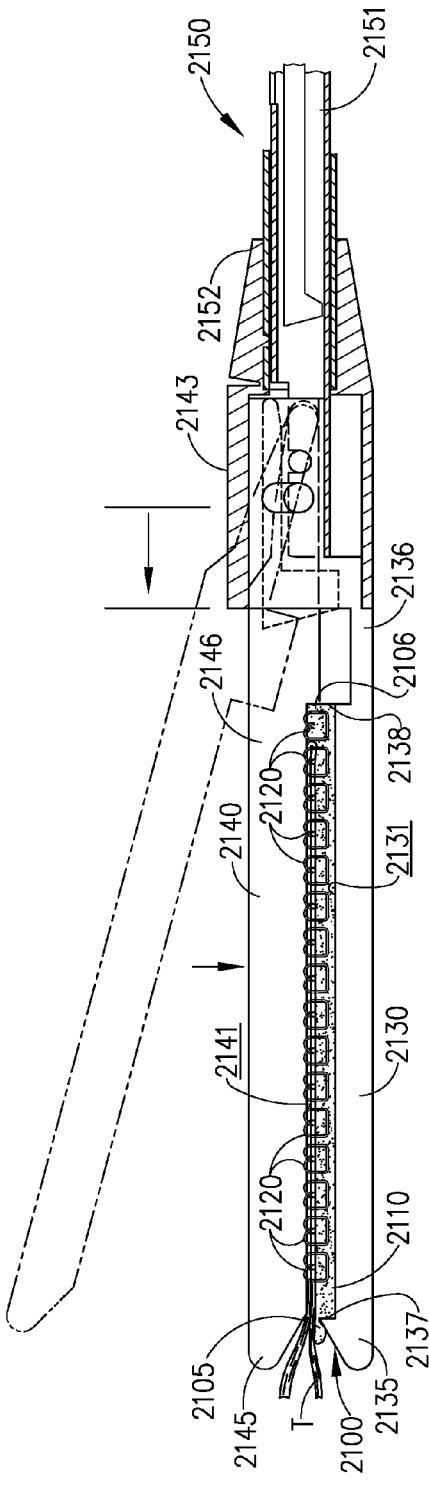
FIG. 108
FIG. 109

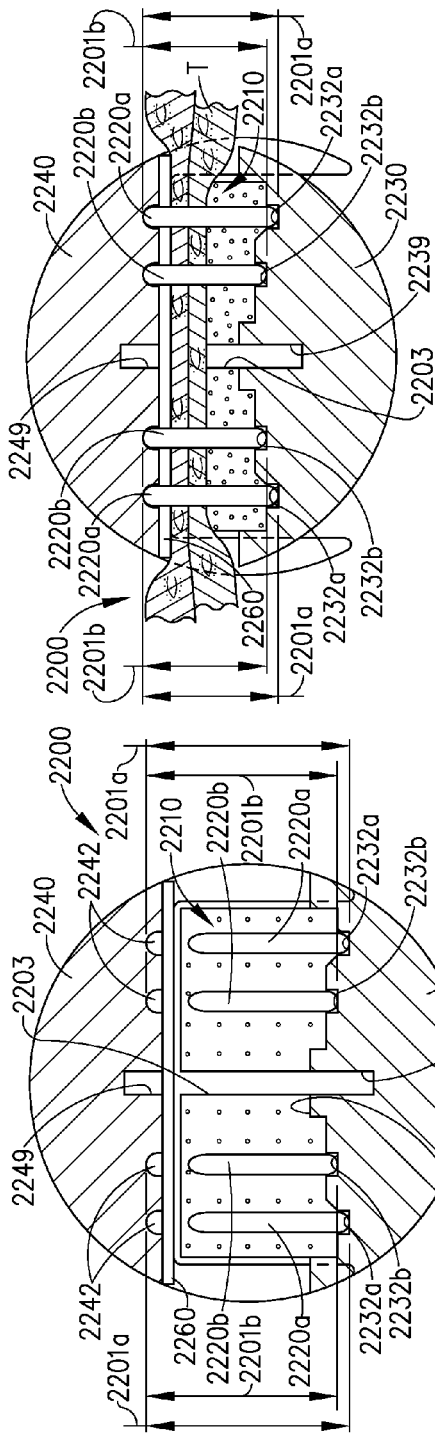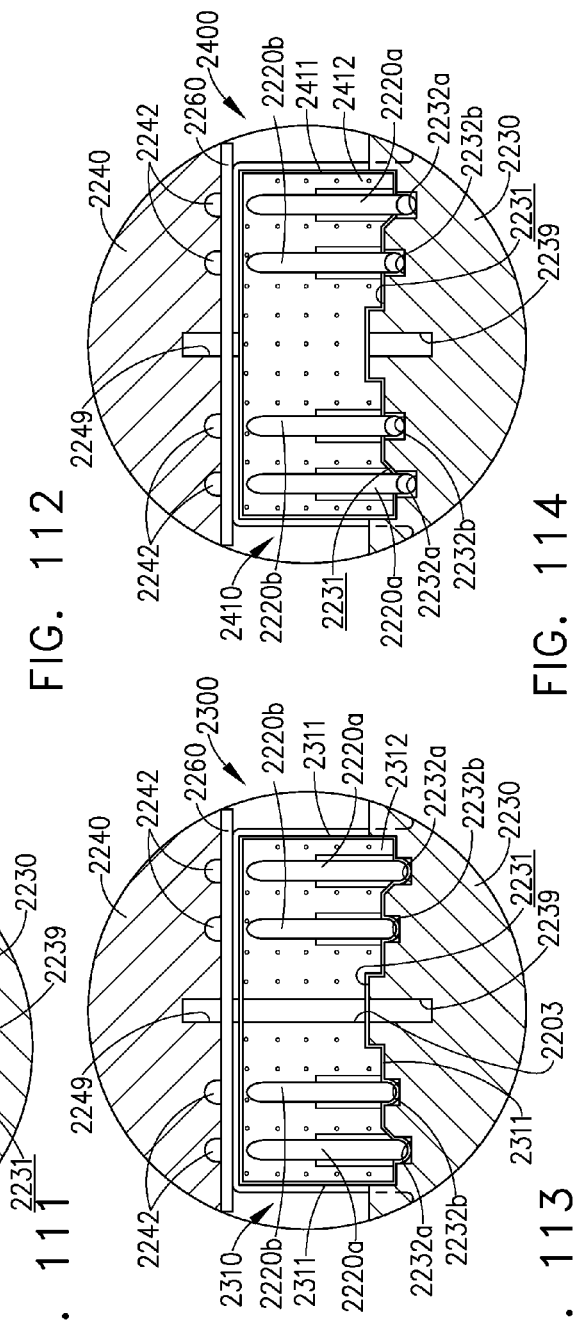

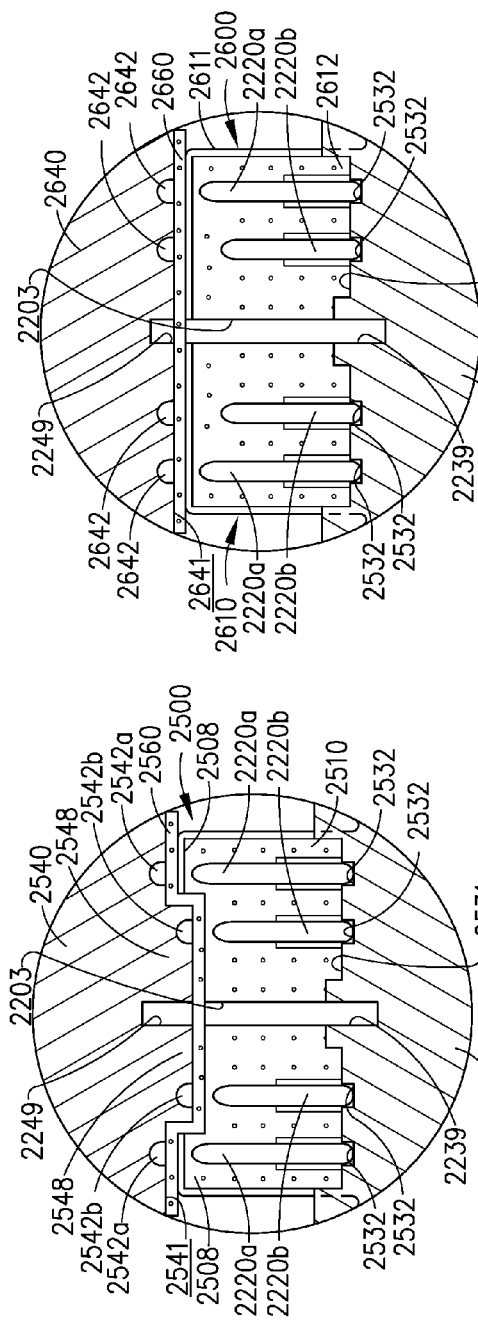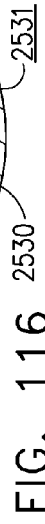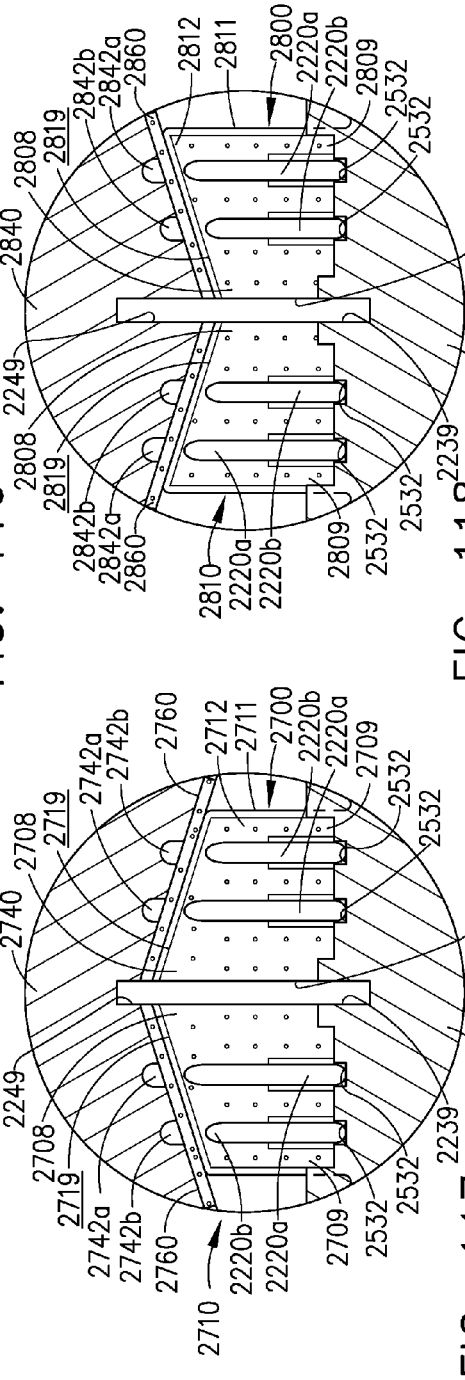

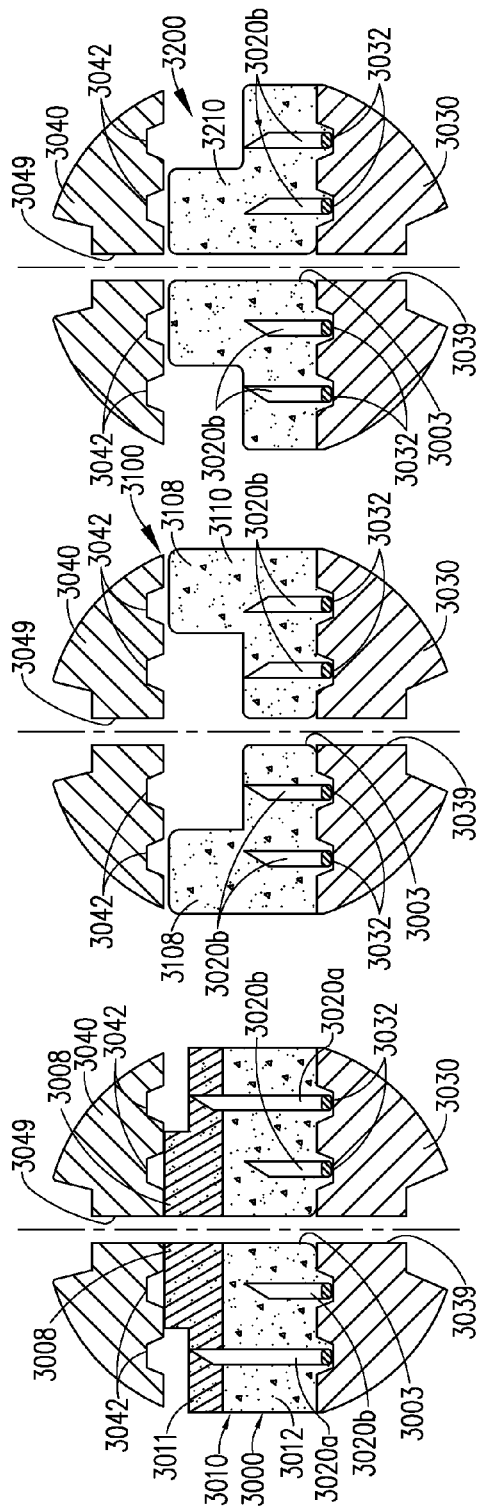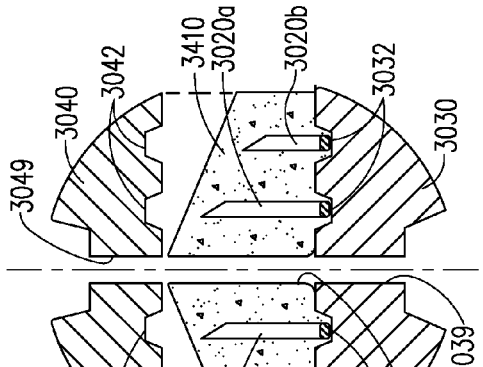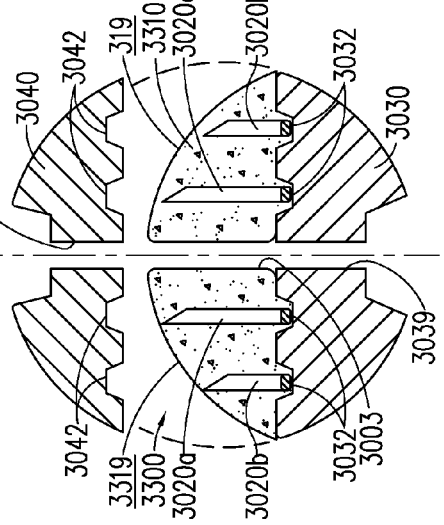

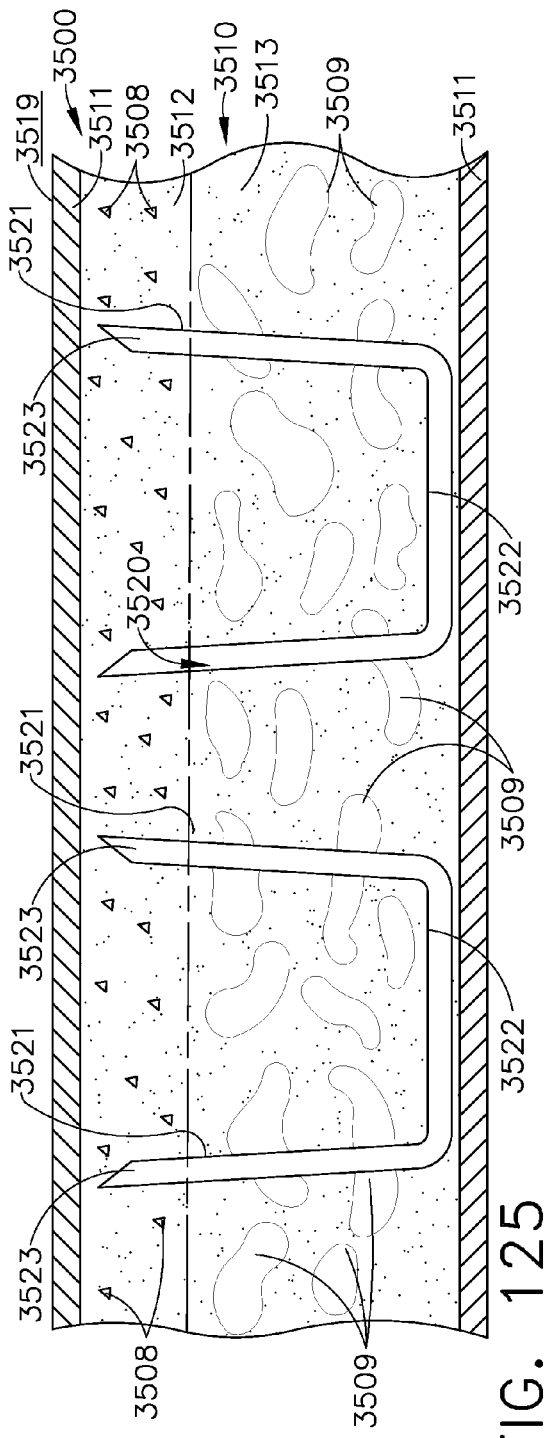
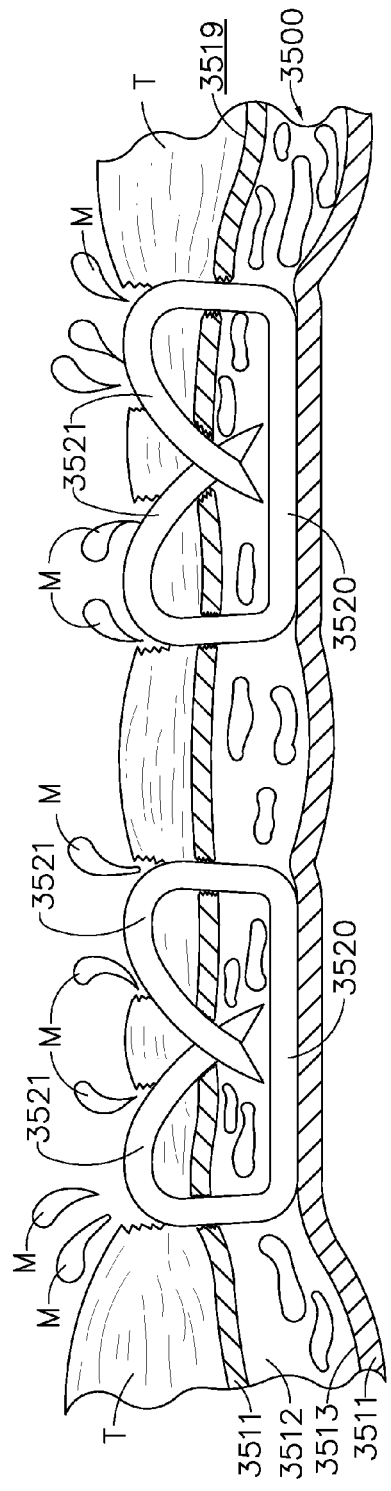
FIG. 125
FIG. 126

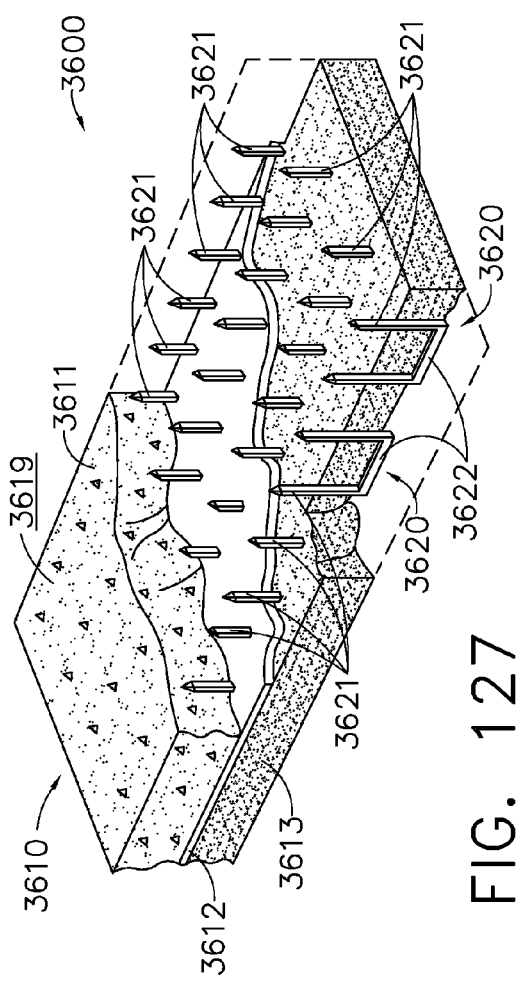
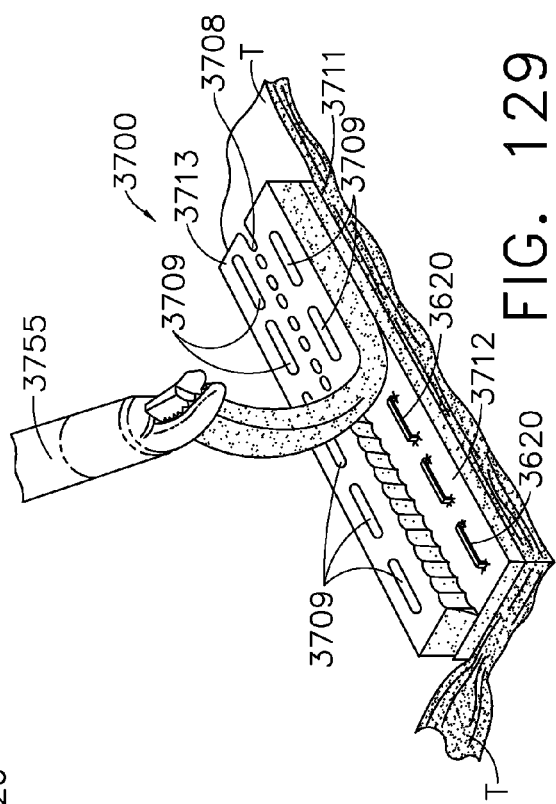
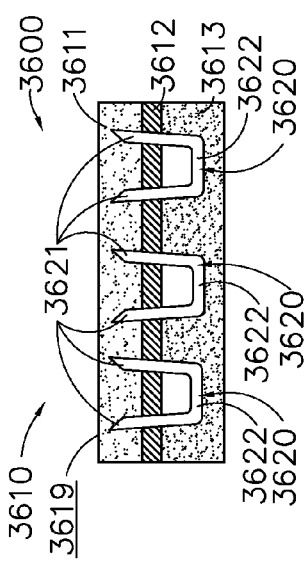
FIG. 127
FIG. 128
FIG. 129

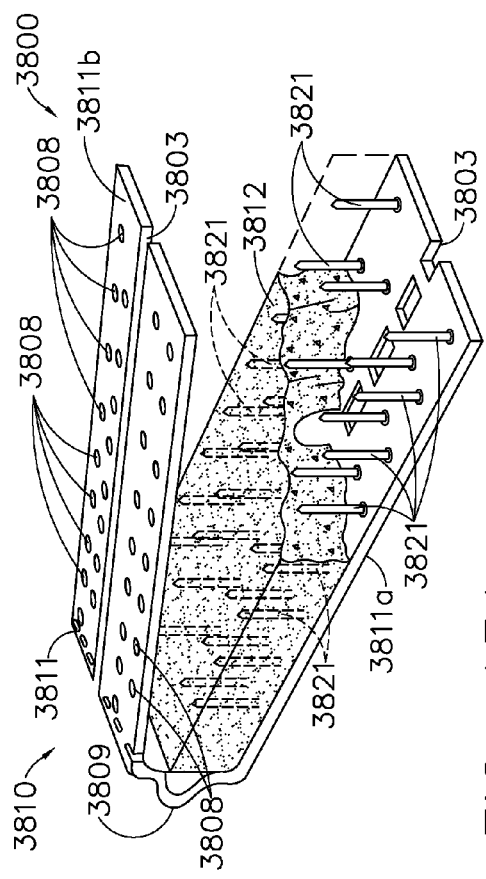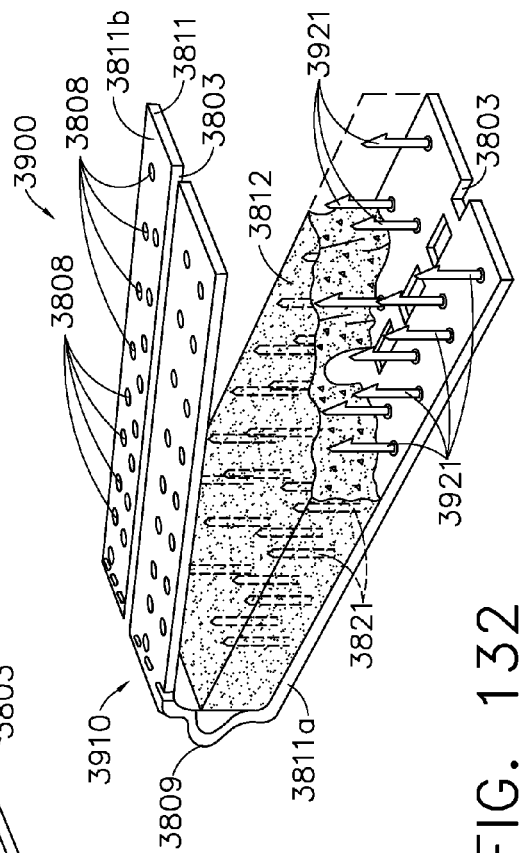
FIG. 131
FIG. 132

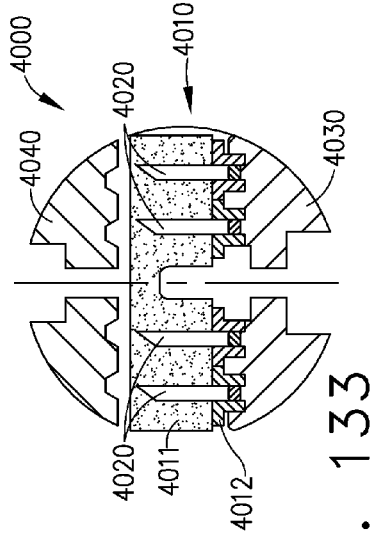
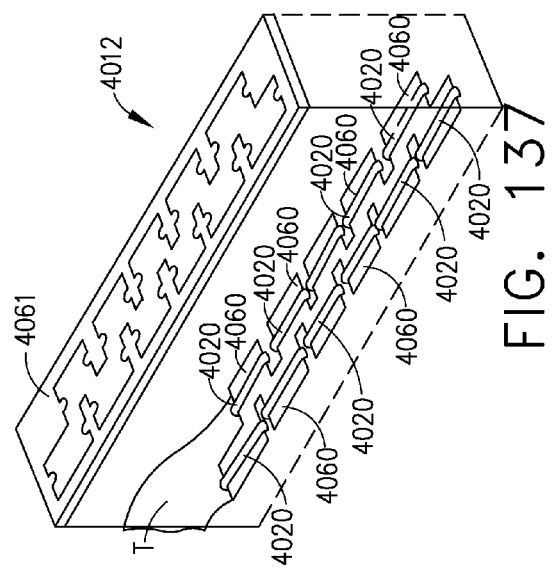
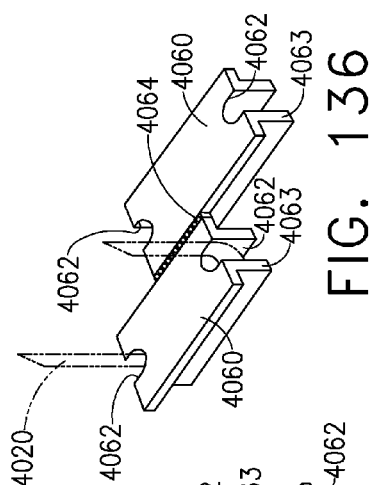
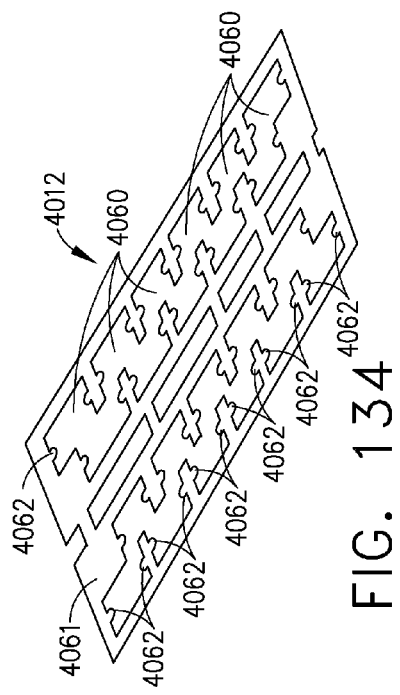

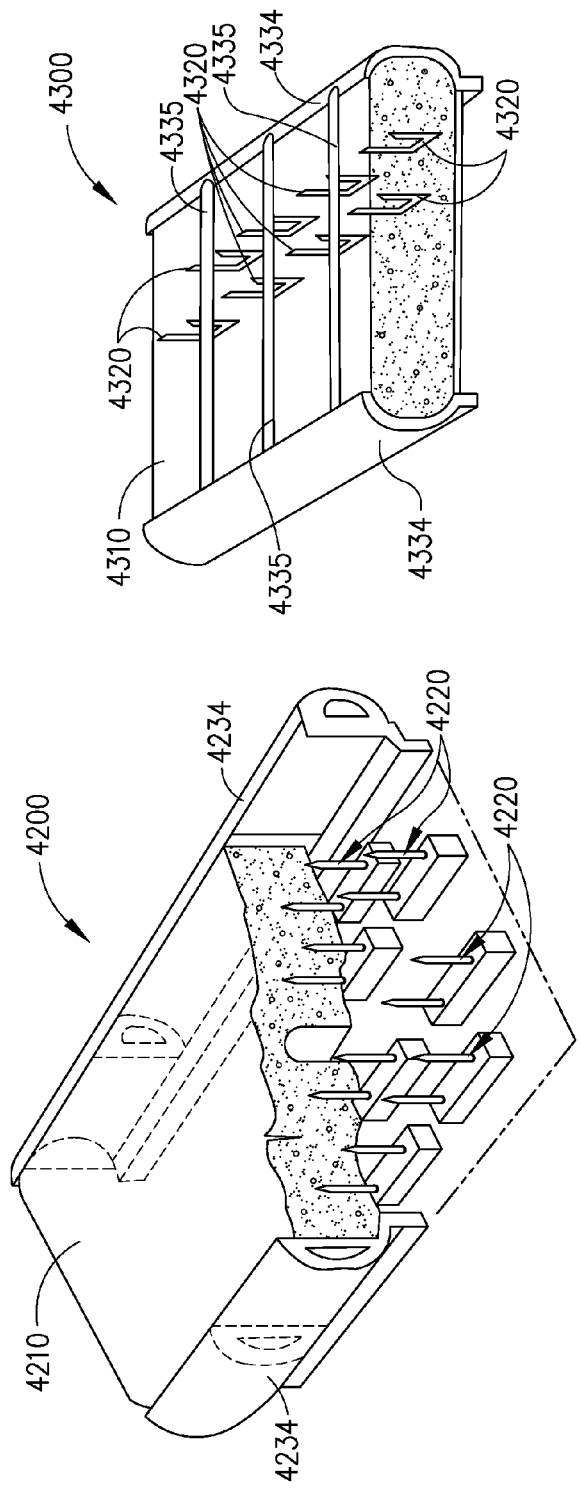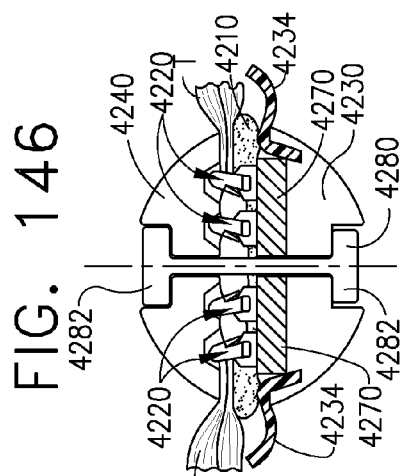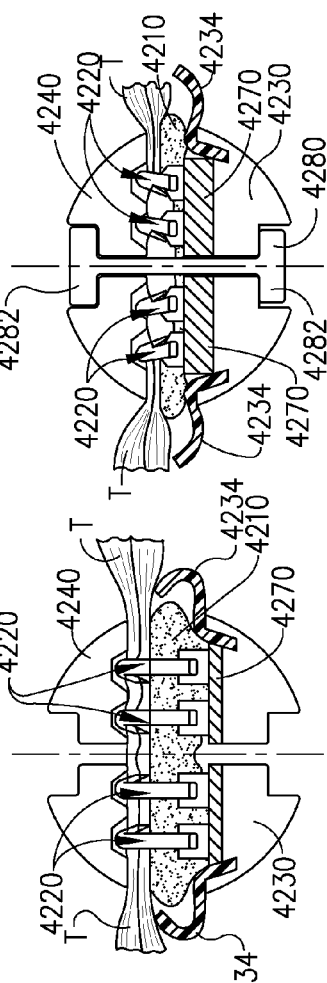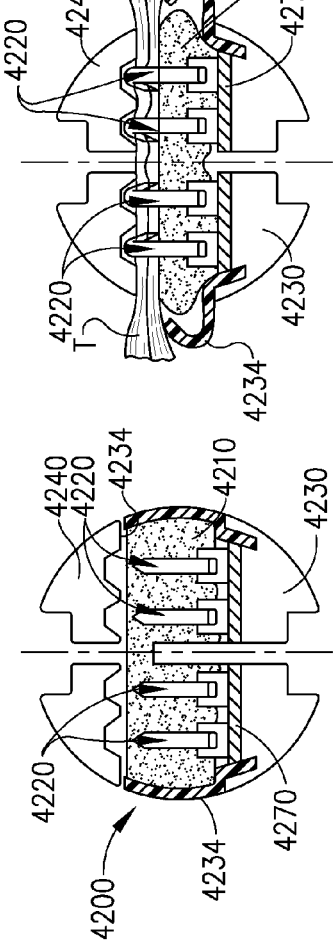
FIG. 142
FIG. 143
FIG. 144
FIG. 145
FIG. 146

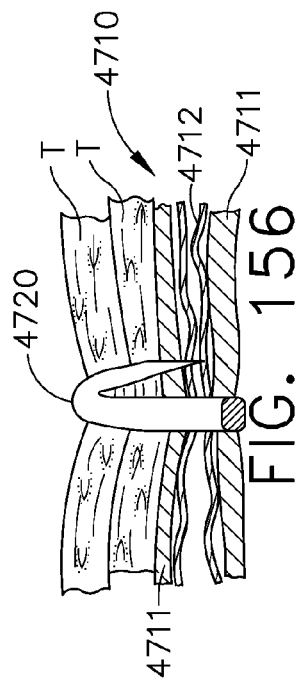
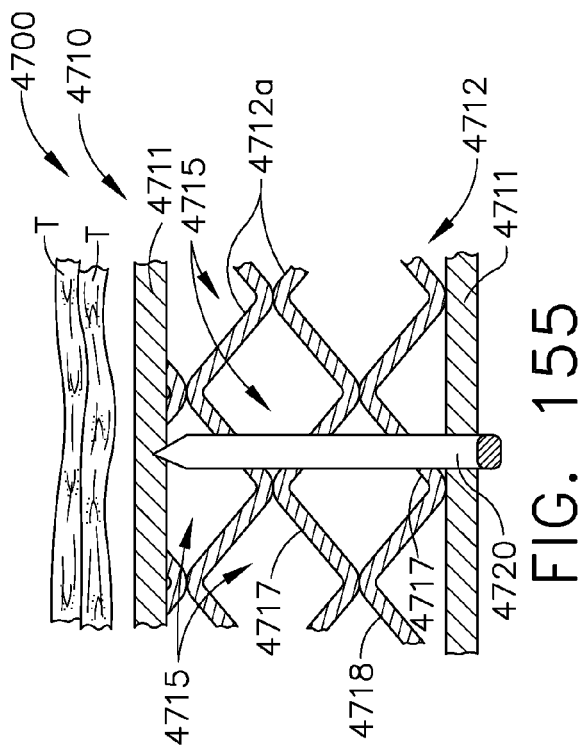
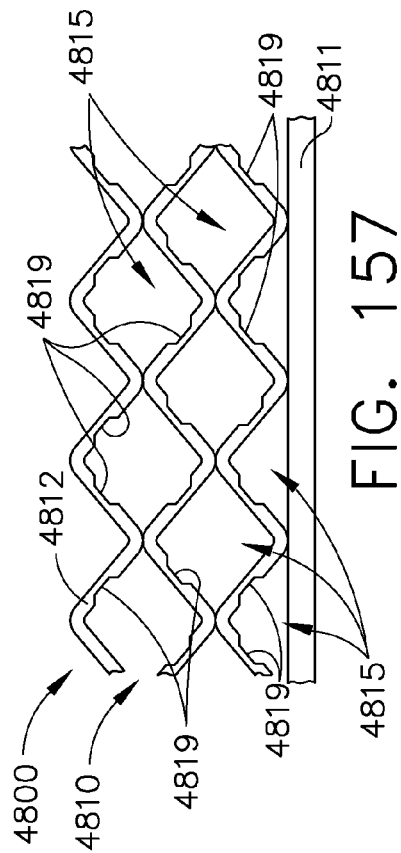

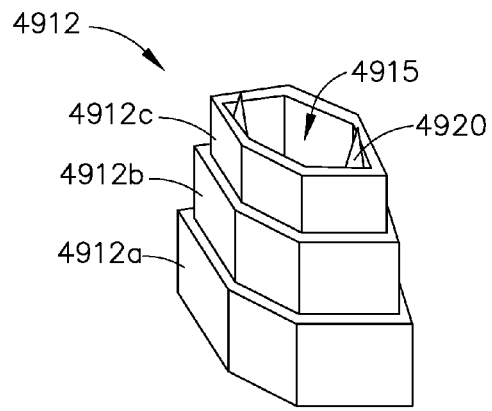
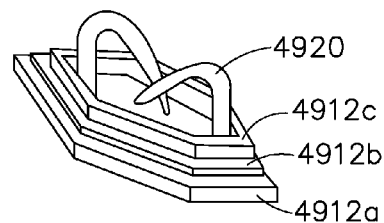
FIG. 159
FIG. 160
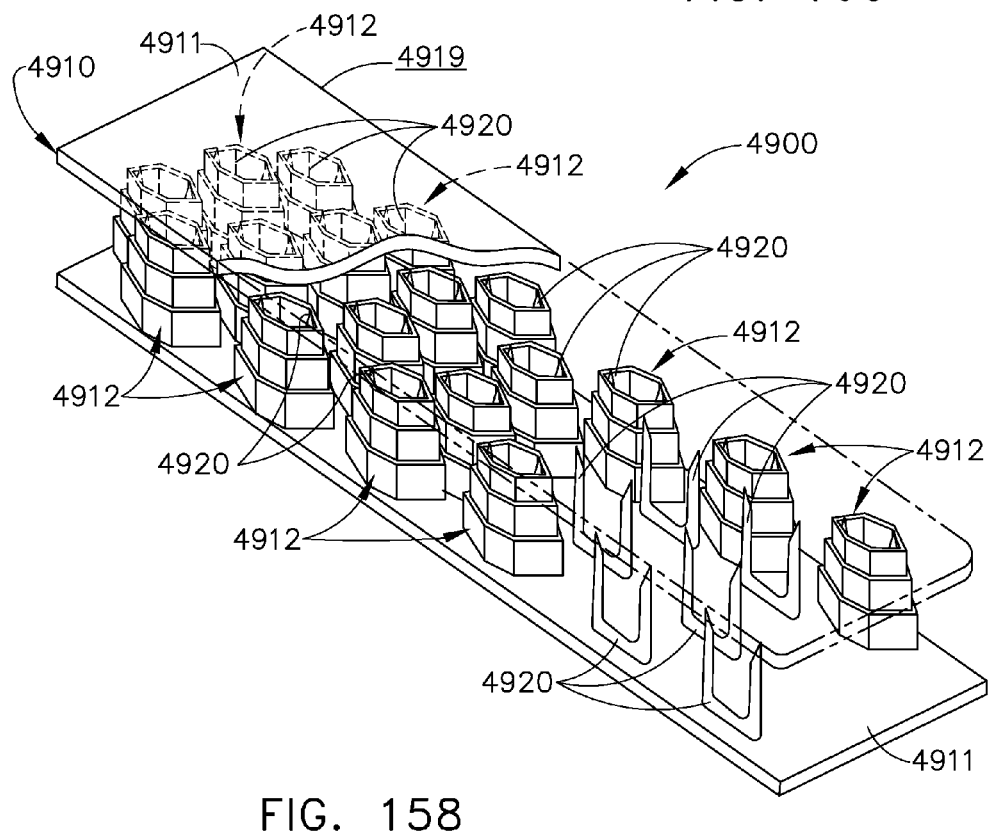
FIG. 158

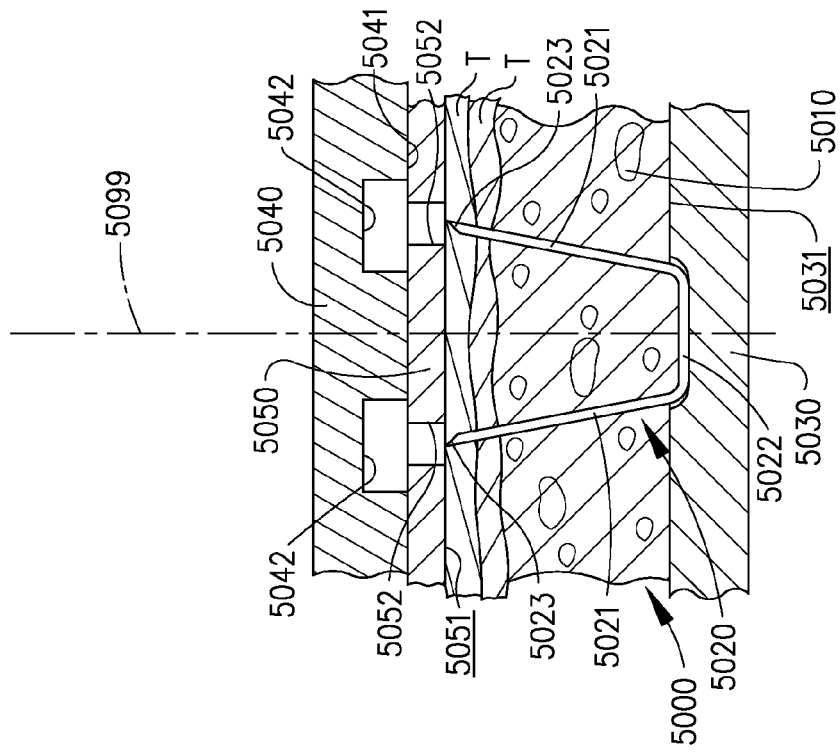
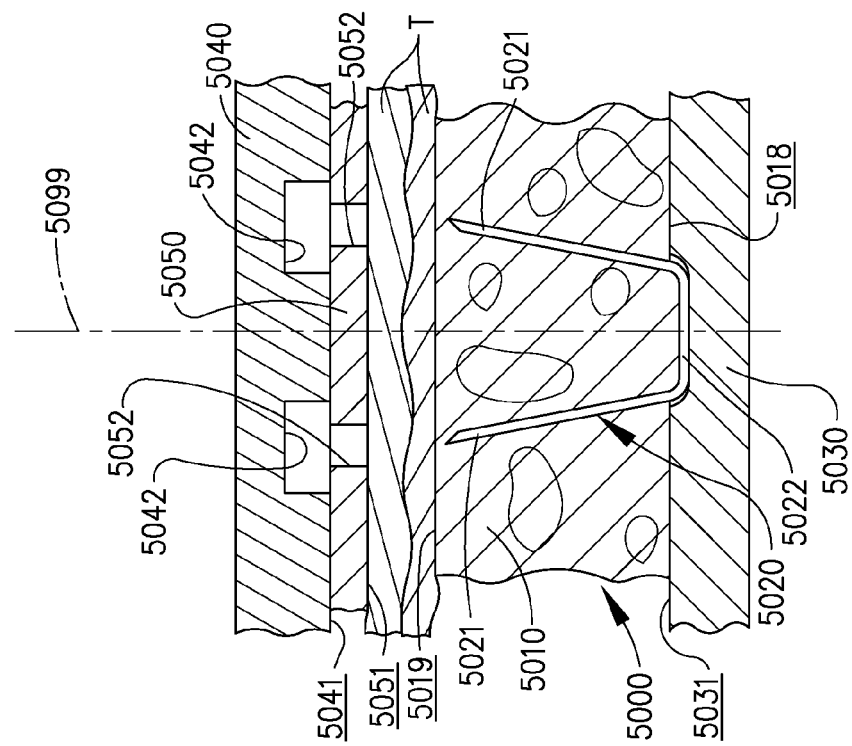

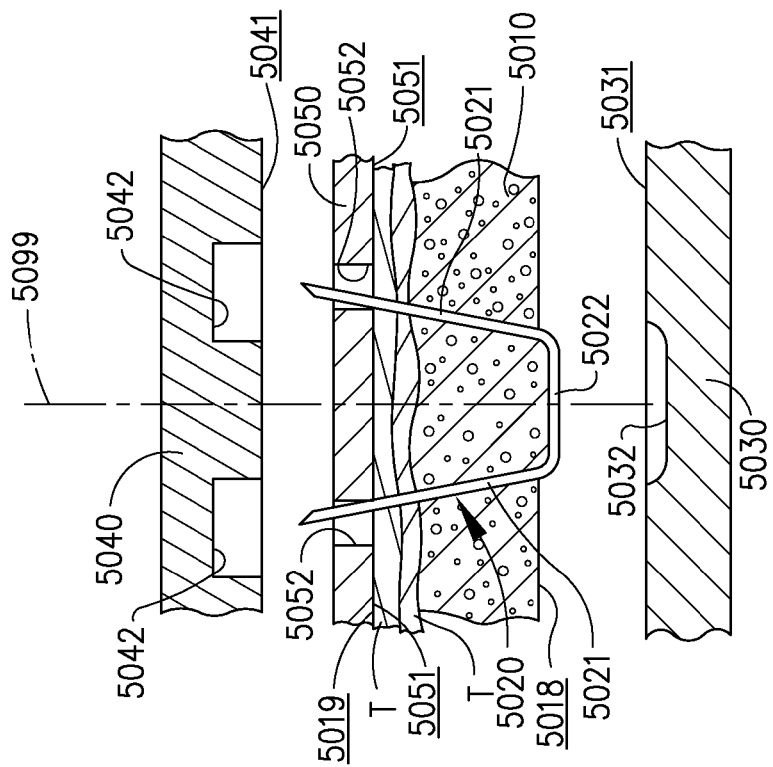
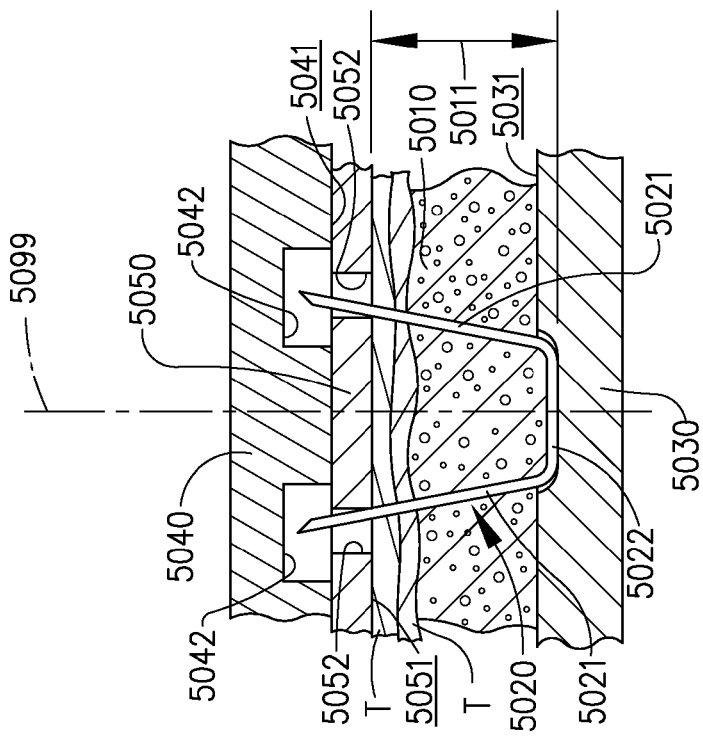
FIG. 161C
FIG. 161D

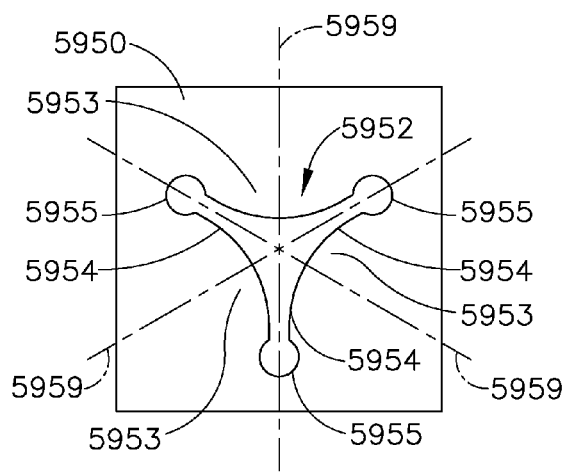
FIG. 174
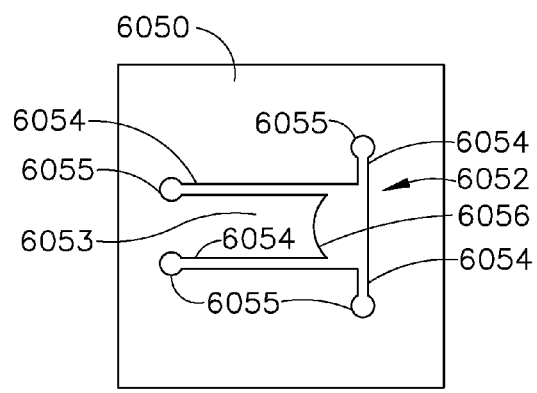 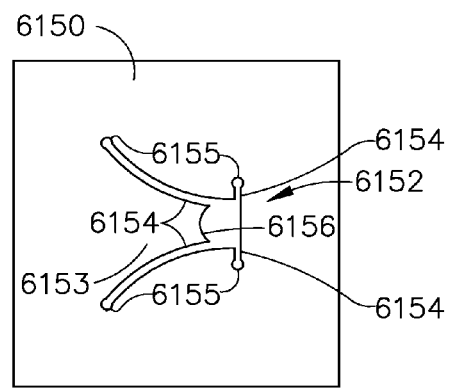
FIG. 175  FIG. 176

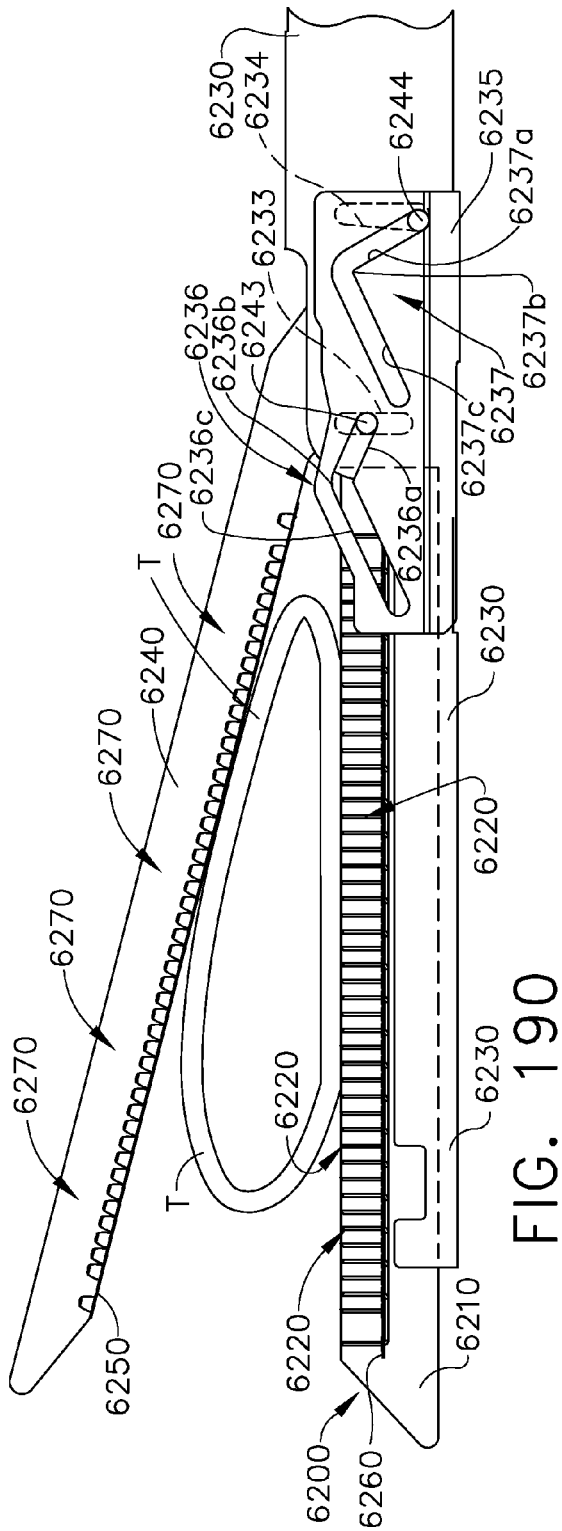
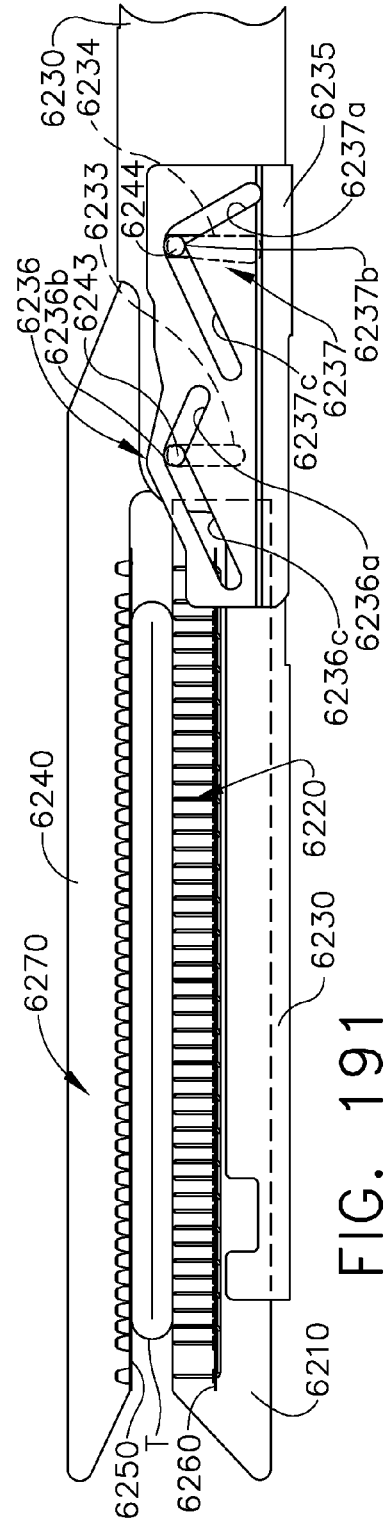
FIG. 190
FIG. 191

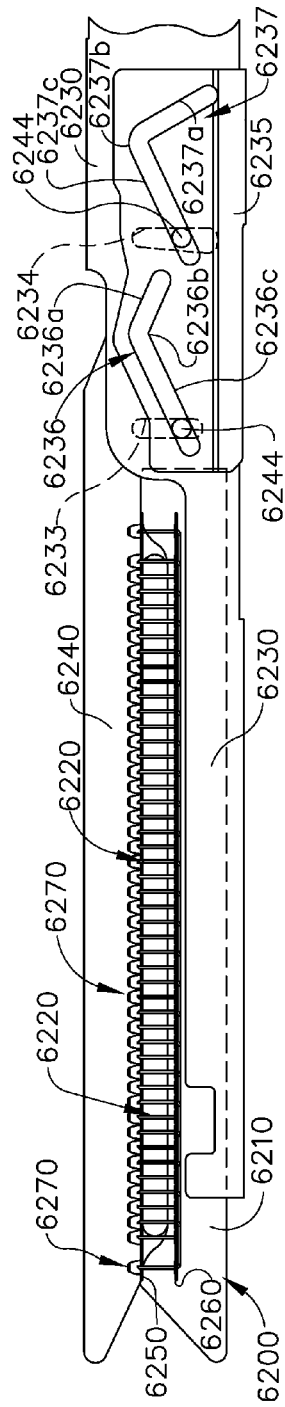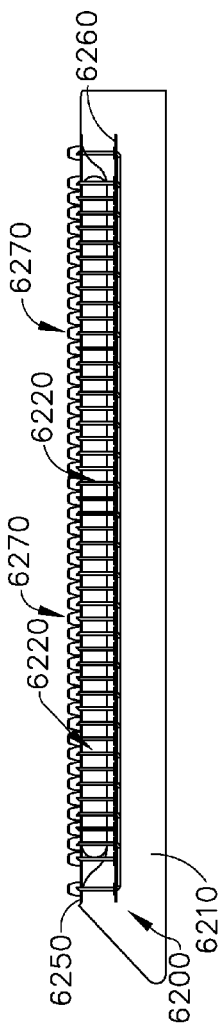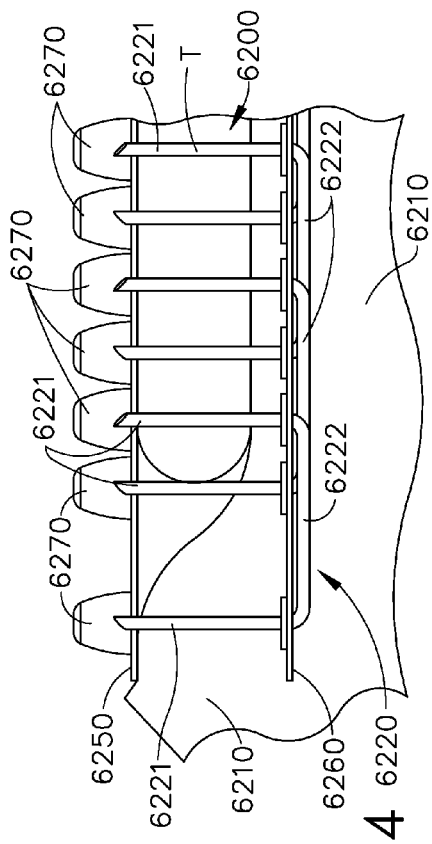
FIG. 192
FIG. 193
FIG. 194

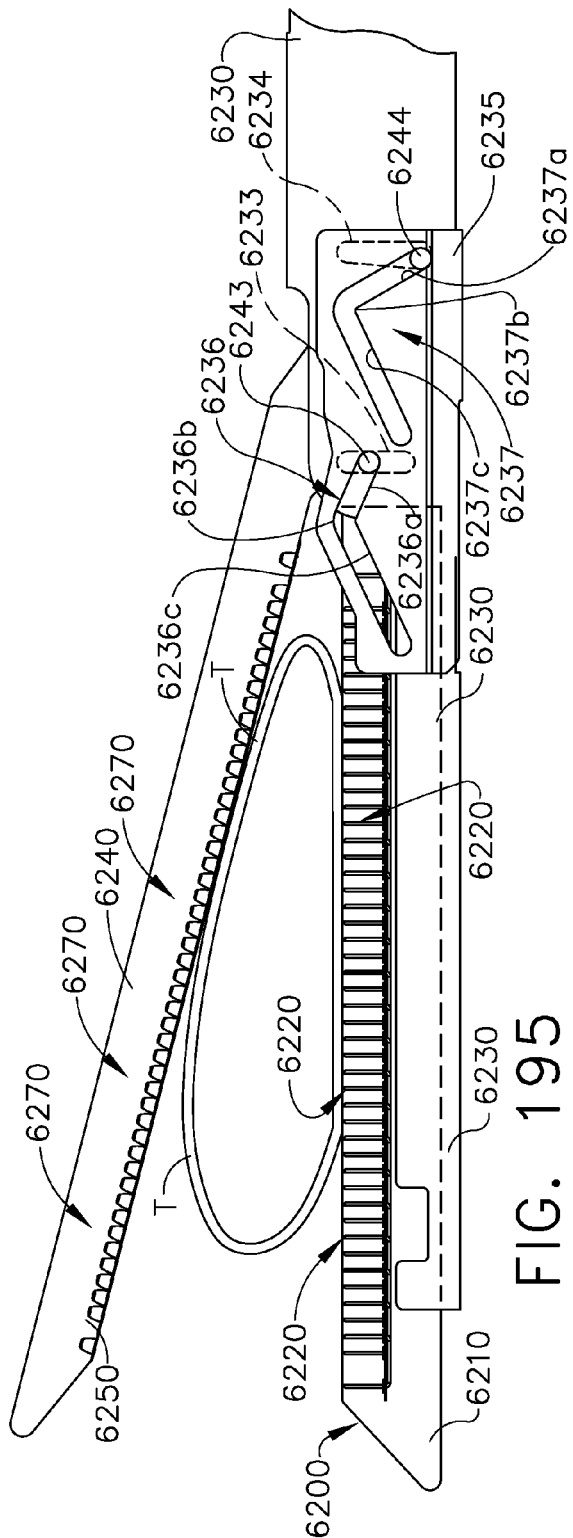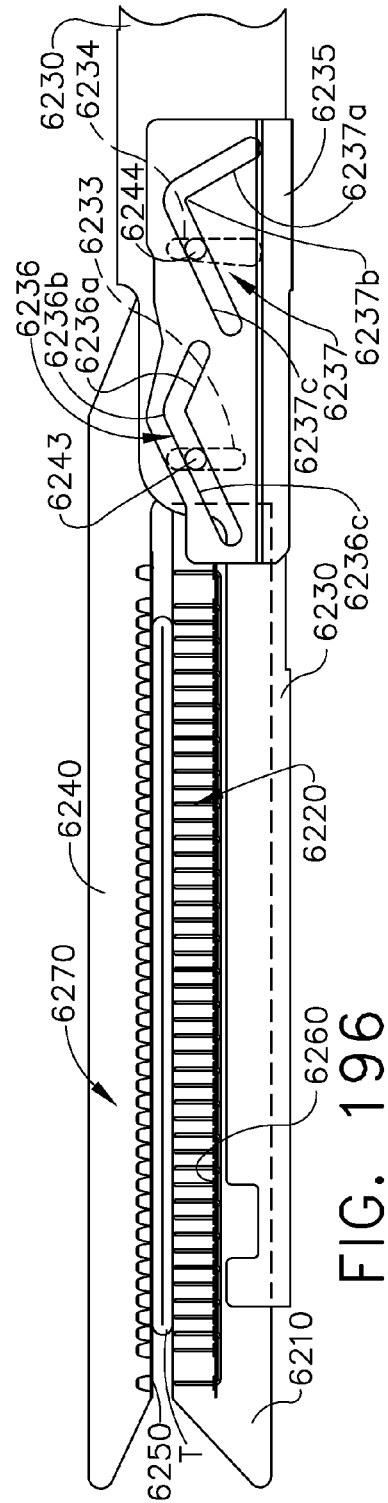

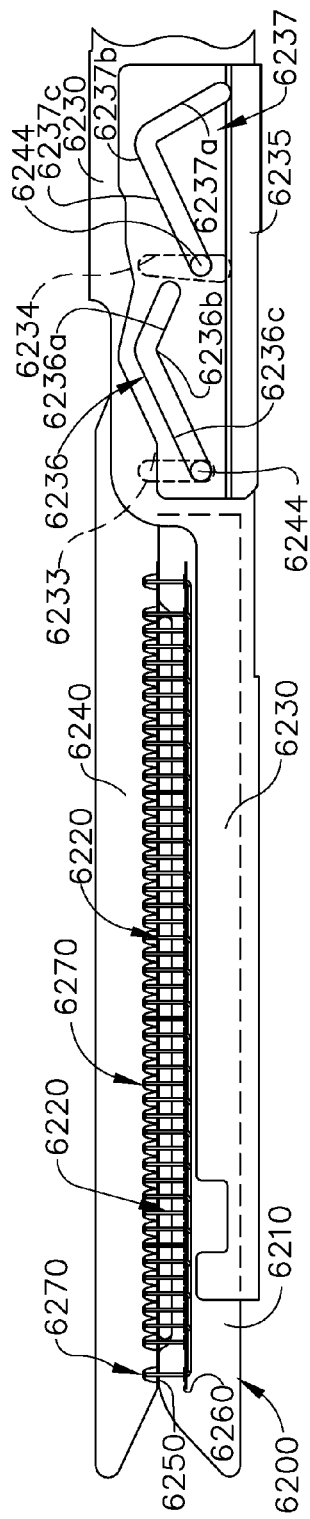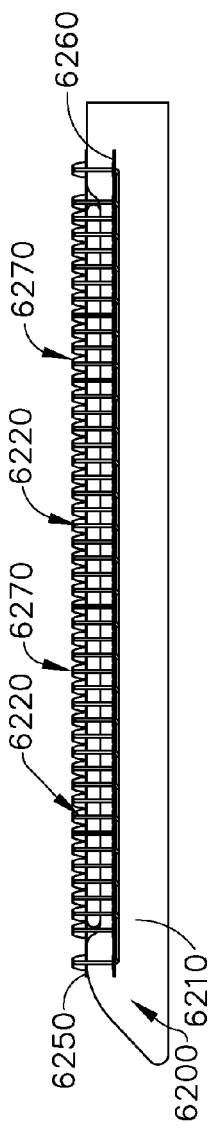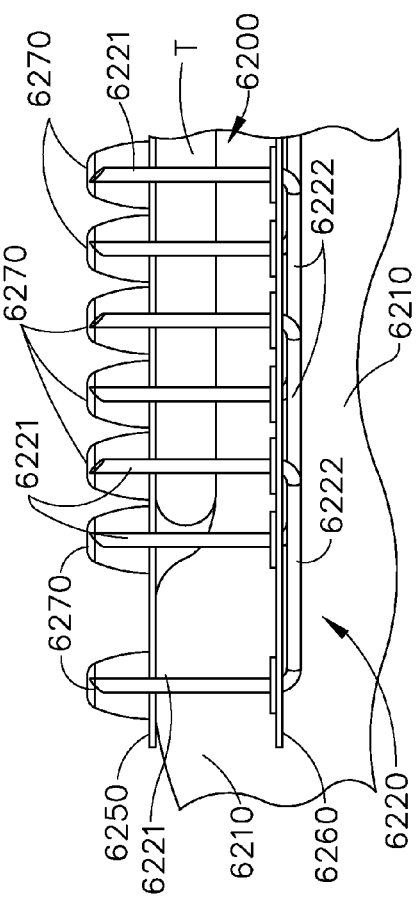

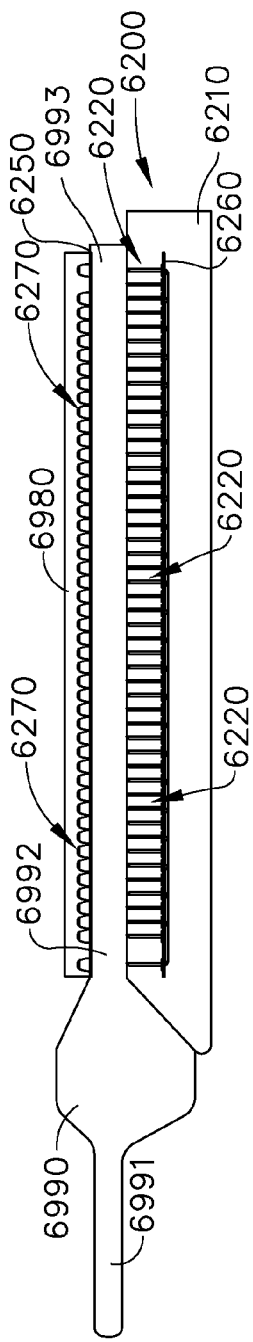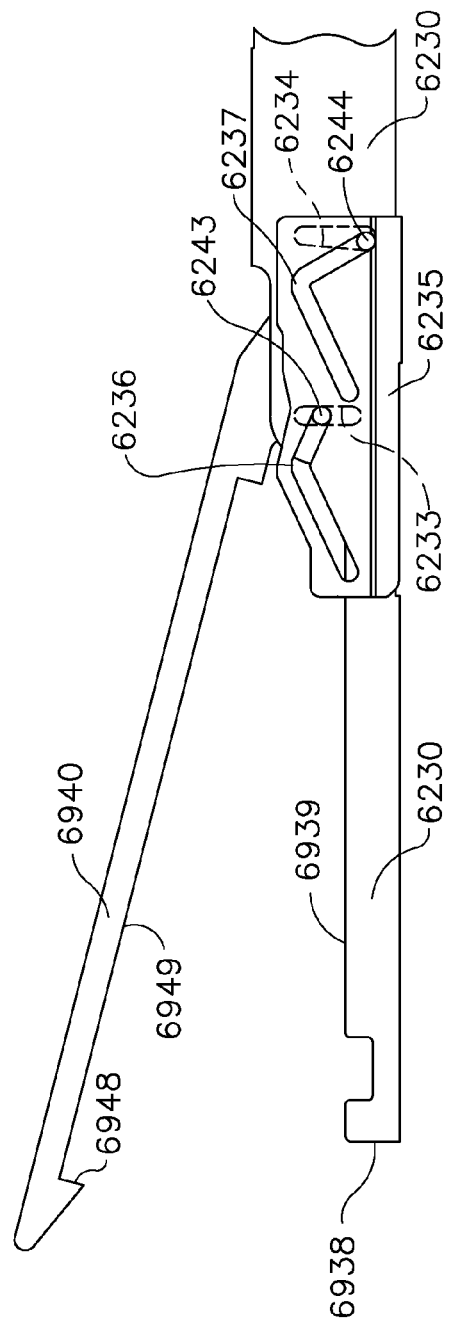

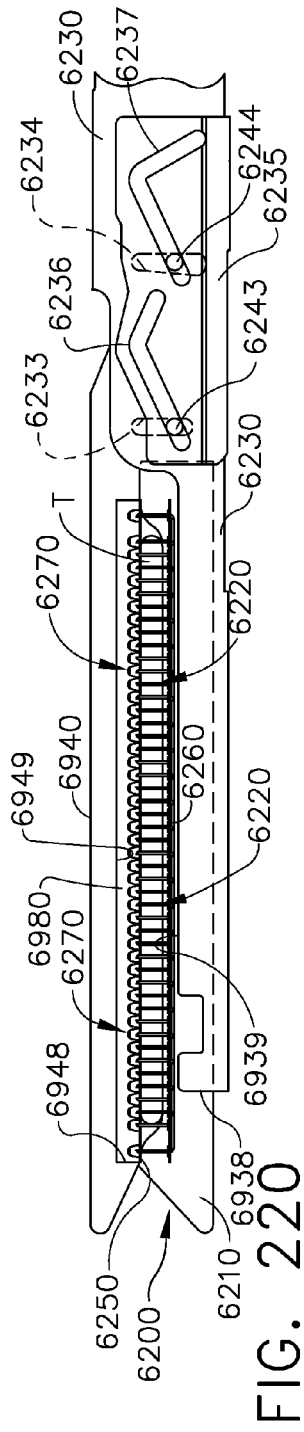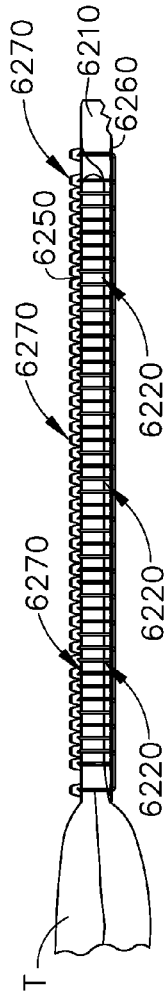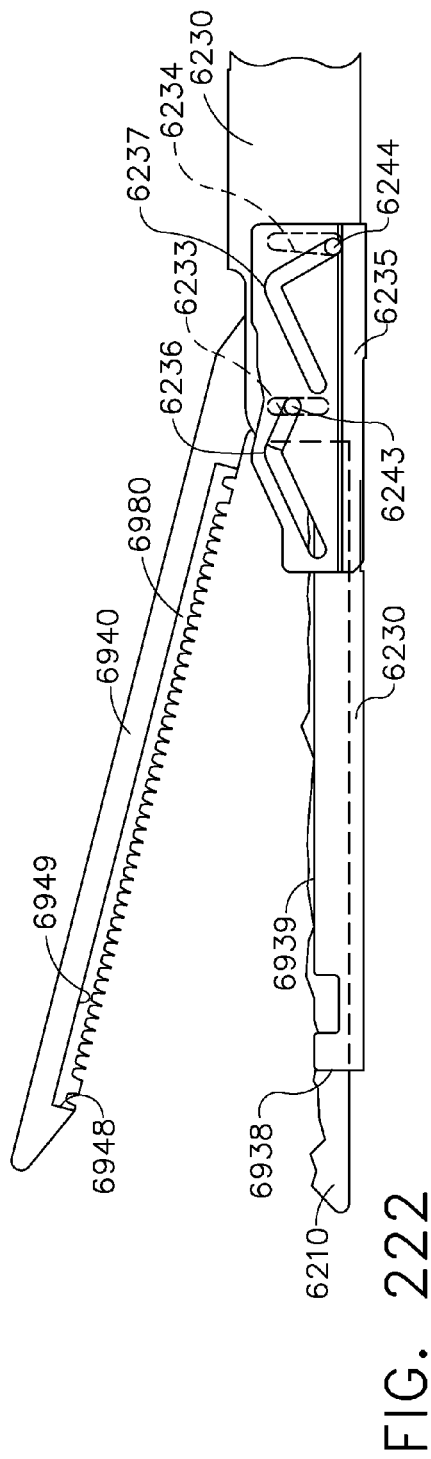

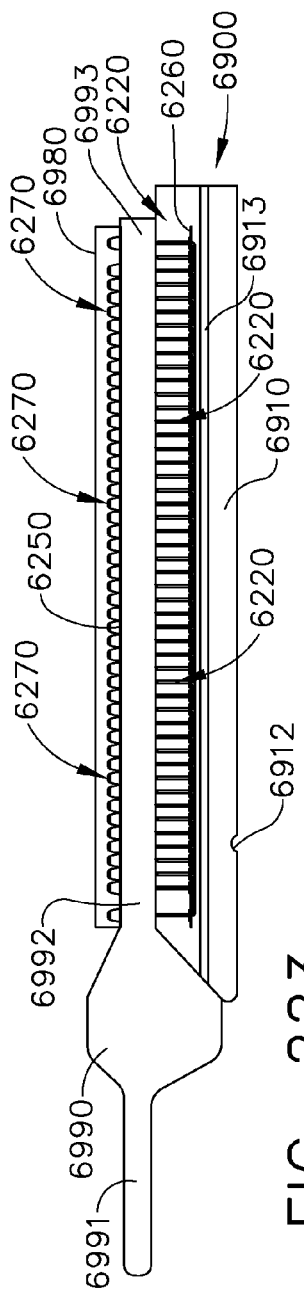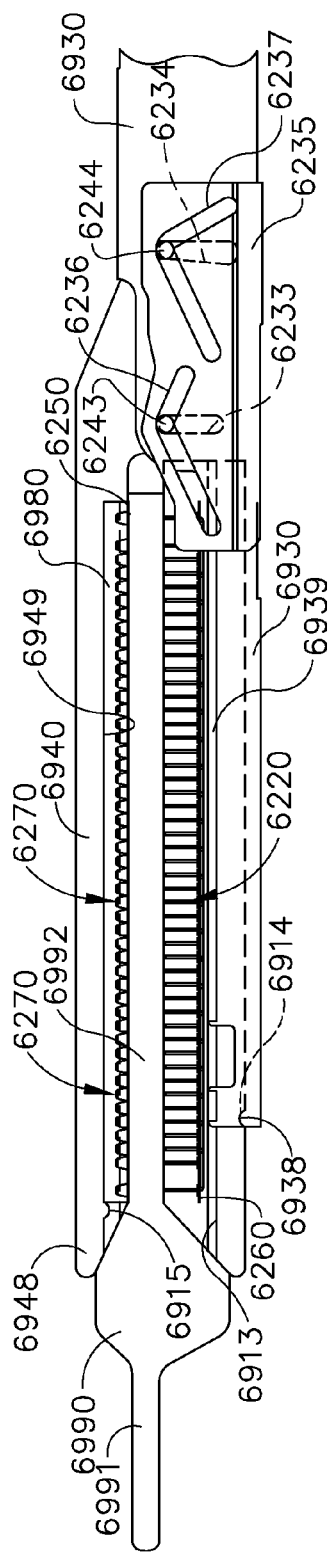

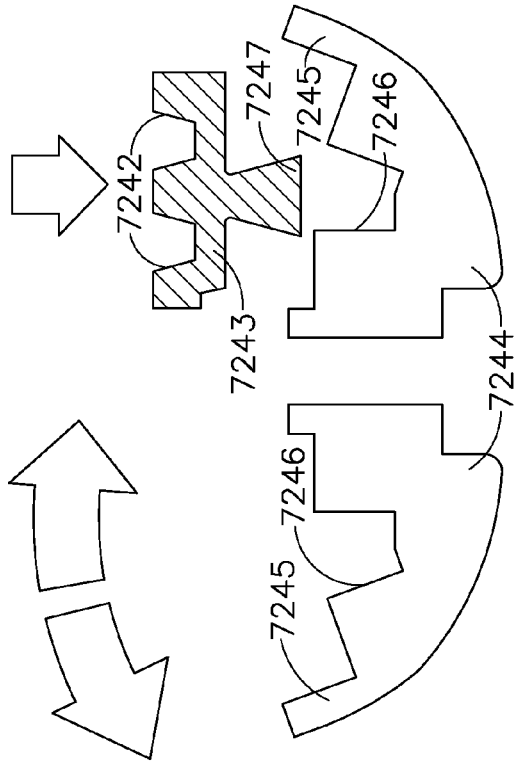
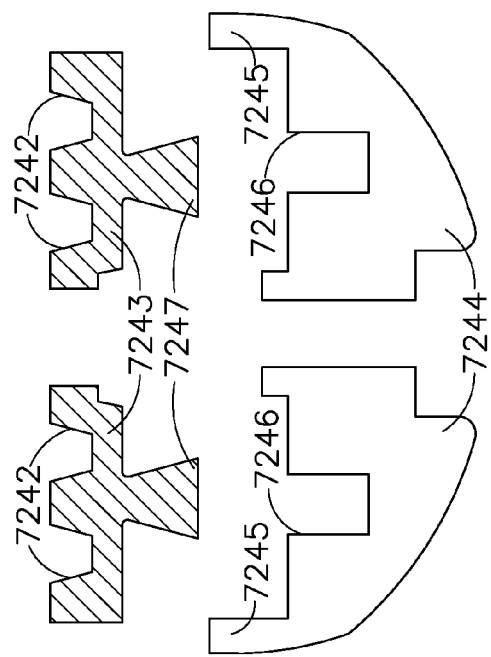
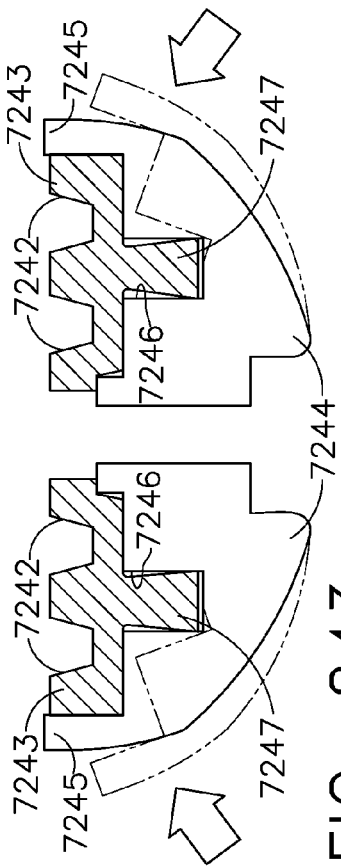
FIG. 241
FIG. 242
FIG. 243

FASTENER SYSTEM COMPRISING A RETENTION MATRIX AND AN ALIGNMENT MATRIX

BACKGROUND

1. Technical Field

The present invention relates to surgical instruments and, in various embodiments, to surgical cutting and stapling instruments and staple cartridges therefor that are designed to cut and staple tissue.

2. Background

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

In many endoscopic surgical applications, it is desirable to employ end effectors that are only as large as necessary to complete a particular surgical procedure. Smaller end effectors provide better visualization of the surgical site. Smaller end effectors also allow for better access and manipulation in tight spaces. Designers of such end effectors face many challenges when trying to develop small end effectors. The ability to manufacture small end effectors and, more particularly, small endocutters that are designed to cut and staple tissue is hampered by the magnitude of the actuation forces that are generally required to form lines of staples and cut tissue. Such actuation forces can also vary with the thickness and composition of the tissue being treated. For example, larger actuation forces are commonly required to cut and staple thick tissues. Whereas, the magnitude of the actuation forces required to cut and staple thinner tissues in general are smaller. Thus, many existing endocutters typically employ robust anvil closure systems and staple driving systems that are configured to accommodate a specific range of tissue thicknesses. Such devices, however, are often not well-suited for treating thinner tissues.

Prior endocutter devices also generally cut the tissue as the staples are driven and formed in the tissue on each side of the cut. While such devices are very effective for those procedures that require the tissue to be cut and fastened, they do not provide the surgeon with the option of installing fasteners without cutting tissue. Likewise, while various forms of articulating endocutters have been developed to improve access, the components generally employed in such devices must be substantial enough to accommodate structures that can generate and transmit sufficient firing and closure forces to the end effector from the handle of the device. Thus, such end effectors are often too large to effectively access tight spaces in the body.

Accordingly, there is a need for surgical cutting and stapling instruments and staple cartridge arrangements that address many of the challenges discussed above.

The foregoing discussion is intended only to illustrate some of the shortcomings present in the field of the invention at the time, and should not be taken as a disavowal of claim scope.

SUMMARY

In at least one embodiment, a surgical stapling system can comprise a first staple comprised of a wire, wherein the first staple comprises a first base and a first leg extending from the first base, a second staple comprised of a wire, wherein the second staple comprises a second base and a second leg extending from the second base, and a retention matrix. The retention matrix comprises a first matrix element comprising a first aperture configured to receive the first leg, a first alignment pocket at least partially surrounding the first aperture, wherein the first alignment pocket is configured to guide the first leg into the first aperture, and a first retention member configured to engage the first leg, a second matrix element comprising a second aperture configured to receive the second leg, a second alignment pocket at least partially surrounding the second aperture, wherein the second alignment pocket is configured to guide the second leg into the second aperture, and a second retention member configured to engage the second leg, and a connecting link connecting the first matrix element and the second matrix element. The stapling system can further comprise an alignment matrix comprising a first alignment guide operably engaged with the first leg and a second alignment guide operably engaged with the second leg, wherein the alignment matrix is configured to align the first leg with the second leg.

In at least one form, a surgical stapling system can comprise a first fastener comprising a first base and a first leg extending from the first base, a second fastener comprising a second base and a second leg extending from the second base, and a retention matrix. The retention matrix comprises a first matrix element comprising a first aperture configured to receive the first leg, a first pocket surrounding the first aperture, and a first retention tab configured to engage the first leg, a second matrix element comprising a second aperture configured to receive the second leg, a second pocket surrounding the second aperture, and a second retention tab configured to engage the second leg, and a flexible connector attached to the first matrix element and the second matrix element. The stapling system can further comprise an alignment matrix comprising a first alignment guide operably engaged with the first leg and a second alignment guide operably engaged with the second leg, wherein the alignment matrix is configured to align the first leg with the second leg.

In at least one form, a surgical stapling system can comprise a first staple comprised of a wire, wherein the first staple comprises a first base and a first leg extending from the first base, a second staple comprised of a wire, wherein the second staple comprises a second base and a second leg extending from the second base, and a retention matrix. The retention matrix can comprise a first matrix element comprising first receiving means for receiving the first leg, first alignment means for aligning the first leg with the first receiving means, and first retention means for engaging the first leg, a second matrix element comprising second receiving means for receiving the second leg, second alignment means for aligning the second leg with the second receiving means, and second retention means for engaging the second leg, and flexible connecting means for connecting the first matrix element and the second matrix element.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1B-1E illustrate portions of an end effector of various embodiments of the present invention clamping and stapling tissue with an implantable staple cartridge embodiment of the present invention;

FIG. 5 is a partial cross-sectional view of the handle assembly of FIG. 1 taken along line 5-5 in FIG. 1;

FIG. 6 is a perspective view of a portion of firing transmission embodiment of the present invention;

FIG. 9A is an enlarged view of the end effector and a portion of the surgical instrument of FIG. 10;

FIG. 10A is an enlarged view of the end effector and a portion of the surgical instrument of FIG. 10;

FIG. 11A is an enlarged view of the end effector and a portion of the surgical instrument of FIG. 11 with tissue received between the anvil and staple cartridge thereof;

FIG. 13 is a cross-sectional view of the surgical instrument of FIGS. 9-12 after the first firing adapter has been advanced over the staple forming ramp to fully form the staples within the implantable staple cartridge;

FIG. 13A is an enlarged view of the end effector and a portion of the surgical instrument of FIG. 13;

FIG. 14 is a cross-sectional view of the surgical instrument of FIGS. 9-13 after the first firing adapter has been advanced over the staple forming ramp to fully form the staples within the implantable staple cartridge and after the knife bar has been longitudinally advanced through the end effector;

FIG. 14A is an enlarged view of the end effector and a portion of the surgical instrument of FIG. 14;

FIG. 25 is a partial cross-sectional side view of another end effector embodiment of the present invention coupled to a portion of a surgical instrument embodiment of the present invention with the end effector supporting a surgical staple cartridge embodiment of the present invention and with the anvil thereof in an open position;

FIG. 26 is another partial cross-sectional side view of the end effector of FIG. 25 in a closed position;

FIG. 27 is another partial cross-sectional side view of the end effector of FIGS. 25 and 26 as the knife bar is starting to advance through the end effector;

FIG. 28 is another partial cross-sectional side view of the end effector of FIGS. 25-27 with the knife bar partially advanced therethrough;

FIG. 29 is a partial cross-sectional side view of another end effector embodiment of the present invention coupled to a portion of a surgical instrument embodiment of the present invention with the end effector supporting another surgical staple cartridge embodiment of the present invention and with the anvil thereof in an open position;

FIG. 30 is another partial cross-sectional side view of the end effector of FIG. 29 with the knife bar partially advanced therethrough;

FIG. 33 is a top view of the end effector and a portion of the elongated shaft assembly of the surgical instrument of FIG. 31 with portions thereof shown in cross-section taken along line 33-33 in FIG. 31;

FIG. 34 is a top view of the end effector and a portion of the elongated shaft assembly of the surgical instrument of FIG. 31 with portions thereof shown in cross-section;

FIG. 35 is another top view of the end effector and a portion of the elongated shaft assembly of the surgical instrument of FIG. 31 with the end effector in articulated orientation and with the end effector in an open position;

FIG. 36 is another top view of the end effector of FIG. 35 with the end effector in a closed or clamped position;

FIG. 41 is a top view of an end effector and a portion of an elongated shaft assembly of another surgical instrument embodiment of the present invention in an unarticulated orientation;

FIG. 42 is another top view of the end effector and portion of elongated shaft assembly of FIG. 41 in an articulated position;

FIG. 44A is a cross-sectional view of a portion of the articulated shaft assembly of FIG. 44;

FIG. 44B is another cross-sectional view of another portion of the articulated shaft assembly of FIG. 44;

FIG. 44C is another cross-sectional view of another portion of the articulated shaft assembly of FIG. 44;

FIG. 44D is another cross-sectional view of another portion of the articulated shaft assembly of FIG. 44;

FIG. 44E is another cross-sectional view of another portion of the articulated shaft assembly of FIG. 44;

FIG. 44F is another cross-sectional view of another portion of the articulated shaft assembly of FIG. 44;

FIG. 50 is a cross-sectional exploded assembly view of an end effector and the distal end of the elongated shaft assembly of FIG. 49;

FIG. 51 is another cross-sectional view of the end effector and portion of elongated shaft assembly of FIG. 50 with the end effector in an open position;

FIG. 52 is another cross-sectional view of the end effector and portion of the elongated shaft assembly with the end effector in a closed position;

FIG. 53 is another cross-sectional view of the end effector and portion of the elongated shaft of FIGS. 49-52 with the knife member in a fully fired position;

FIG. 54 is a perspective view of the end effector of FIGS. 51-53 in an open position;

FIG. 58 is a cross-sectional view of a portion of the elongated shaft assembly of FIGS. 56 and 57 taken along line 58-58 in FIG. 57;

FIG. 59 is an enlarged view of a portion of the handle assembly of FIG. 57;

FIG. 65 is a cross-sectional view of a portion of the elongated shaft assembly of FIGS. 63 and 64 taken along line 65-65 in FIG. 64;

FIG. 66 is an enlarged view of a portion of the handle assembly of FIG. 64;

FIG. 70 is a top view of the surgical staple cartridge and elongated channel of the device depicted in FIG. 69;

FIG. 71 is a top view of another surgical staple cartridge embodiment of the present invention installed in an elongated channel of an end effector embodiment of the present invention;

FIG. 72 is a bottom view of an anvil embodiment of the present invention;

FIG. 73 is a partial perspective view of a plurality of staples forming a portion of a staple line embodiment of the present invention;

FIG. 74 is another partial perspective view of the staple line embodiment of FIG. 73 with the staples thereof after being formed by being contacted by the anvil of the surgical cutting and stapling device;

FIG. 75 is a partial perspective view of alternative staples forming a portion of another staple line embodiment of the present invention;

FIG. 76 is a partial perspective view of alternative staples forming a portion of another staple line embodiment of the present invention;

FIG. 77 is a partial perspective view of alternative staples forming a portion of another staple line embodiment of the present invention;

FIG. 82 is another partial cross-sectional view of the surgical stapling instrument of FIG. 81 with the staple cartridge being removed from the end effector and the cartridge locking system in a locked position;

FIGS. 83A-83D diagram the deformation of a surgical staple positioned within a collapsible staple cartridge body in accordance with at least one embodiment;

FIG. 85 is a diagram depicting a staple positioned against a staple cartridge support surface and illustrating potential relative movement therebetween;

FIG. 86 is a cross-sectional view of a staple cartridge support surface comprising a slot, or trough, configured to stabilize the base of the staple of FIG. 85;

FIG. 87 is a cross-sectional view of a staple comprising an overmolded crown and a slot, or trough, configured to receive a portion of the crown in accordance with at least one alternative embodiment;

FIG. 92 is an elevational view of a staple cartridge in accordance with at least one embodiment comprising staples at least partially extending outside of a collapsible staple cartridge body and a protective layer surrounding the staple cartridge body;

FIG. 93 is a cross-sectional view of the staple cartridge of FIG. 92 taken along line 93-93 in FIG. 92;

FIG. 94 is a partial break-away view of a staple cartridge in accordance with at least one embodiment comprising staples at least partially embedded in a collapsible staple cartridge body, the staples being at least partially positioned in a staple cavity void in the staple cartridge body;

FIG. 95 is a cross-sectional view of the staple cartridge of FIG. 94 taken along line 95-95 in FIG. 94;

FIG. 96 is a partial break-away view of a staple cartridge in accordance with at least one embodiment;

FIG. 97 is a partial break-away view of a staple cartridge in accordance with at least one embodiment comprising staples at least partially embedded within a collapsible staple cartridge body and an alignment matrix connecting the staples and aligning the staples with respect to each other;

FIG. 98 is a cross-sectional view of the staple cartridge of FIG. 97 taken along line 98-98 in FIG. 97;

FIG. 102 is a diagram of the support plate of FIG. 100 being removed away from the inner layer;

FIG. 103 is a diagram of a subassembly comprising the inner layer of FIG. 99 and the staples of FIG. 101 being inserted into an outer layer;

FIG. 104 is a diagram illustrating the outer layer of FIG. 103 being sealed to form a sealed staple cartridge;

FIG. 105 is a cross-sectional view of the sealed staple cartridge of FIG. 104;

FIG. 106 is a cross-sectional view of a staple cartridge and staple cartridge channel in accordance with at least one embodiment;

FIG. 107 is a diagram illustrating a portion of the staple cartridge of FIG. 106 in a deformed state;

FIG. 108 is an elevational view of an end effector of a surgical stapler comprising an anvil in an open position and a staple cartridge positioned within a staple cartridge channel;

FIG. 109 is an elevational view of the end effector of FIG. 108 illustrating the anvil in a closed position and the staple cartridge compressed between the anvil and the staple cartridge channel;

FIG. 110 is an elevational view of the end effector of FIG. 108 illustrating the staple cartridge of FIG. 108 positioned within the staple cartridge channel in an alternative manner;

FIG. 111 is a cross-sectional view of an end effector of a surgical stapler comprising a compressible staple cartridge positioned within a staple cartridge channel and a piece of buttress material attached to an anvil;

FIG. 112 is a cross-sectional view of the end effector of FIG. 111 illustrating the anvil in a closed position;

FIG. 113 is a cross-sectional view of an alternative embodiment of an end effector of a surgical stapler comprising a staple cartridge comprising a water impermeable layer;

Figure 119:
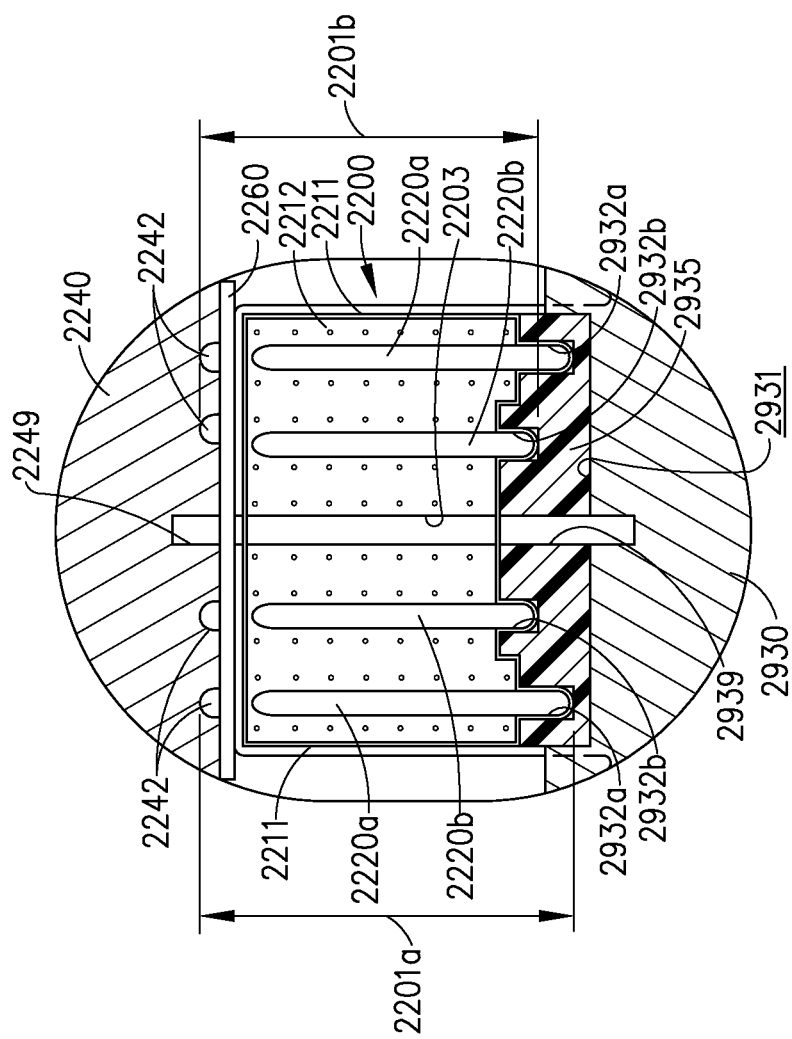
Figure 130:
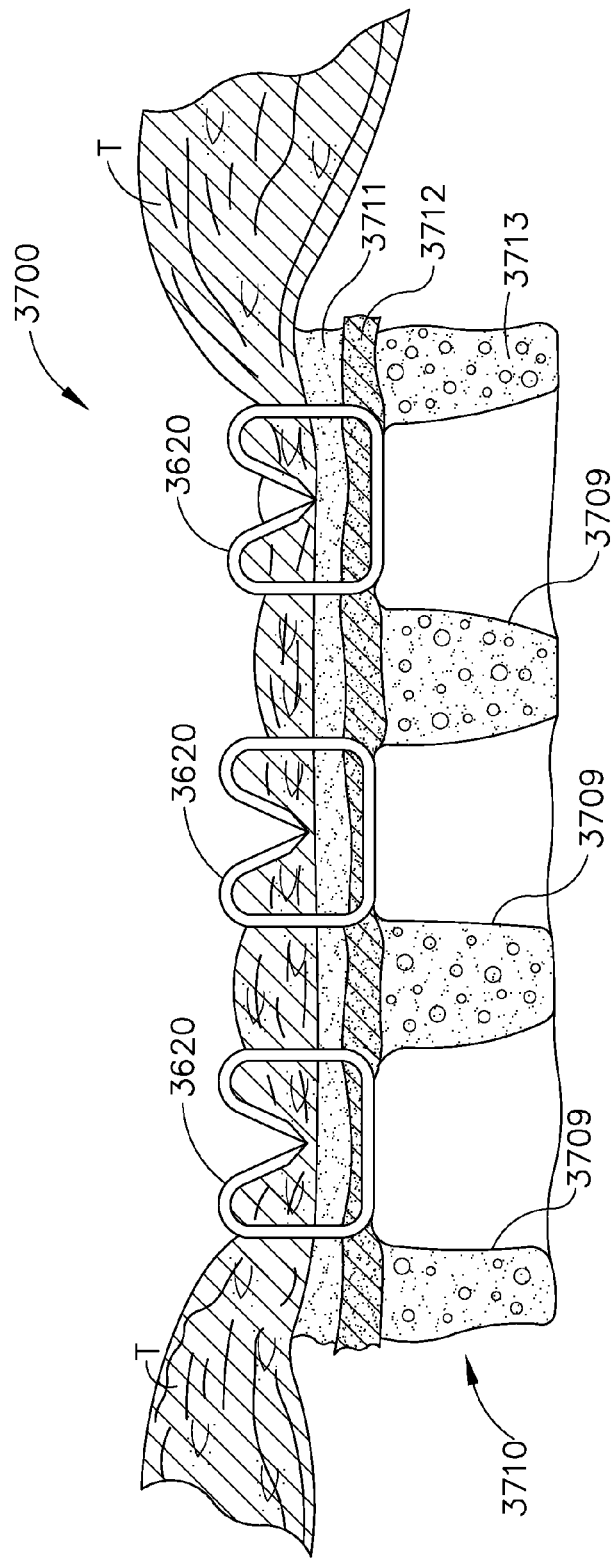
Figure 138:
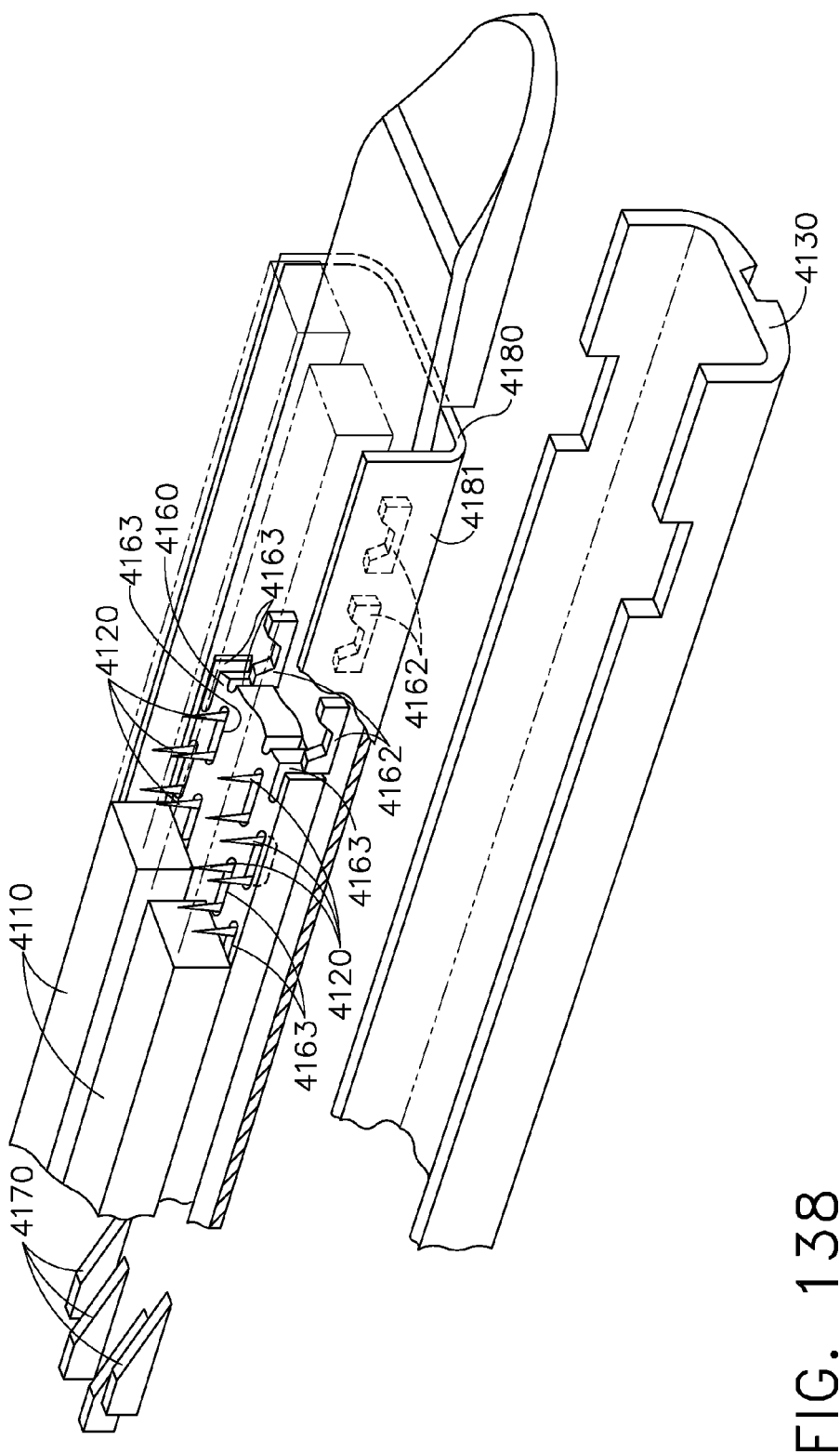
Figure 138A:
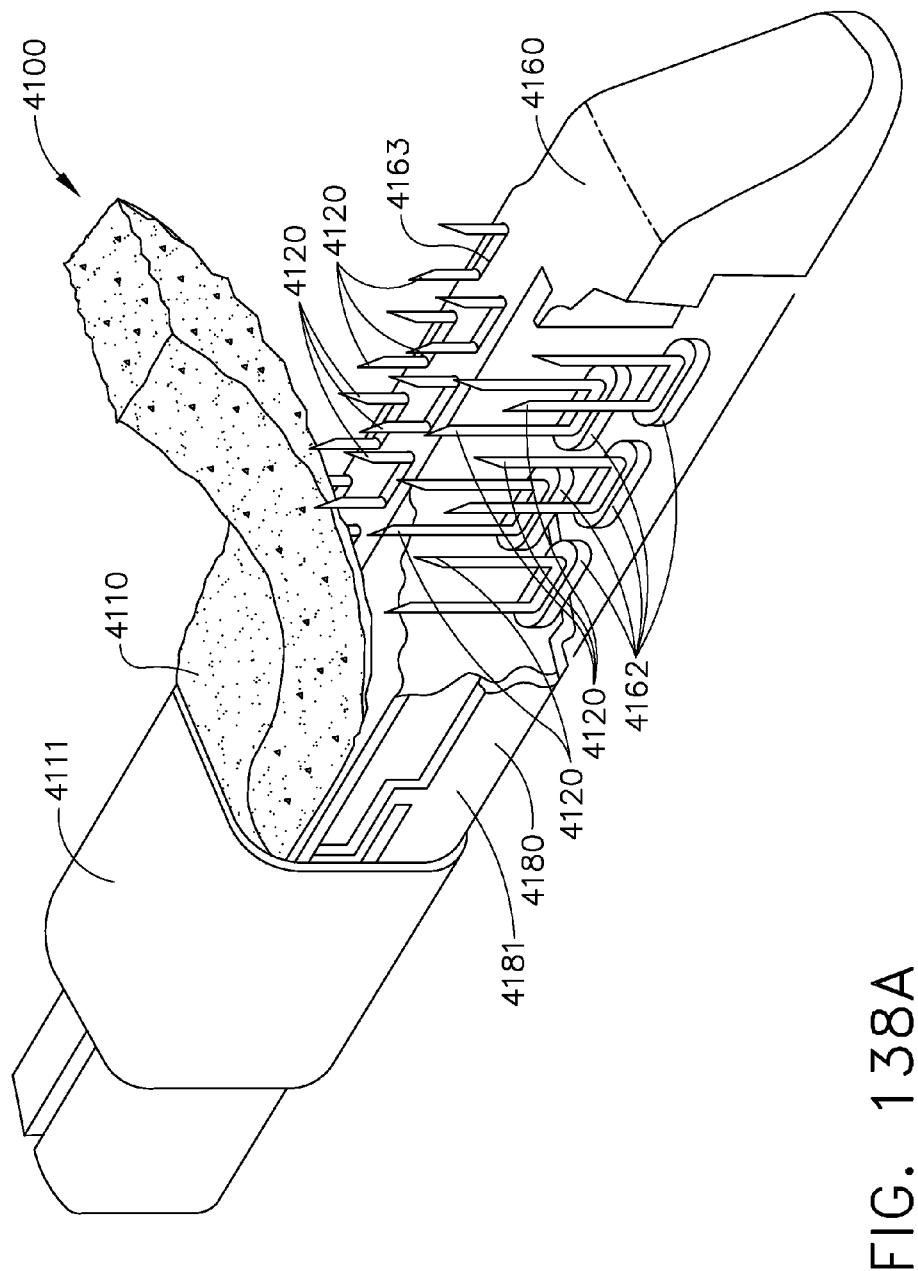
Figure 139:
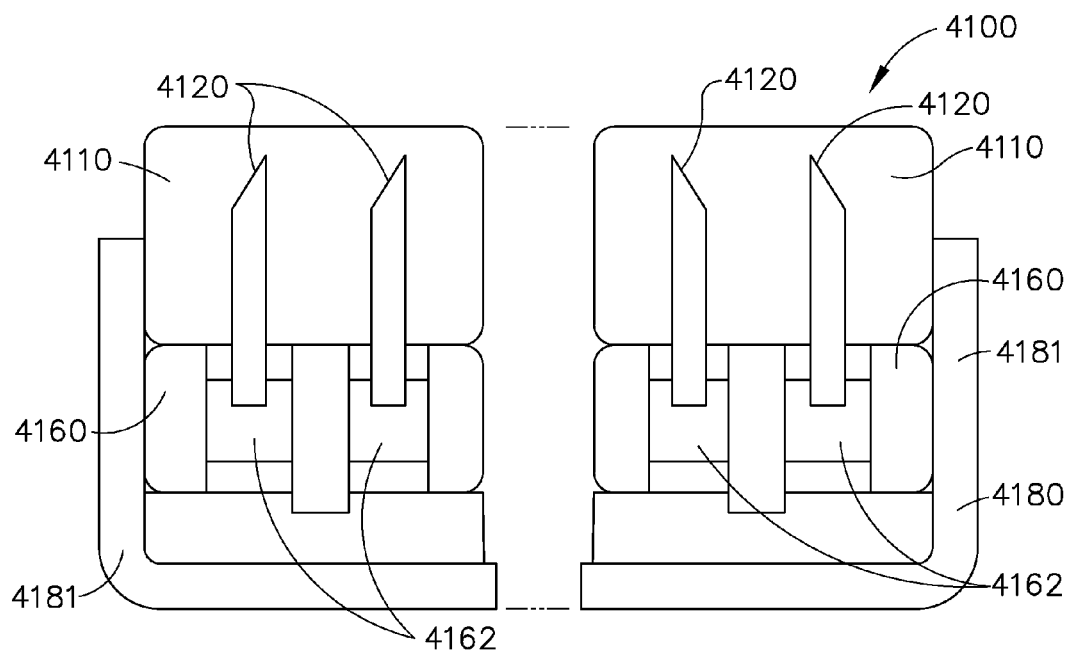
Figure 140:
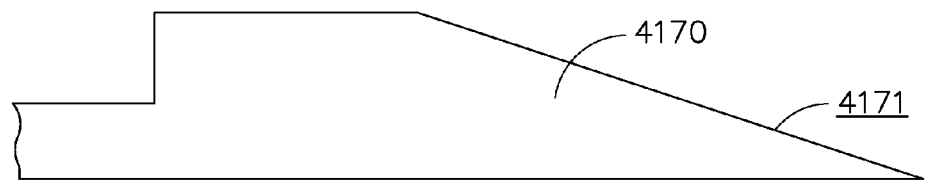
Figure 141:
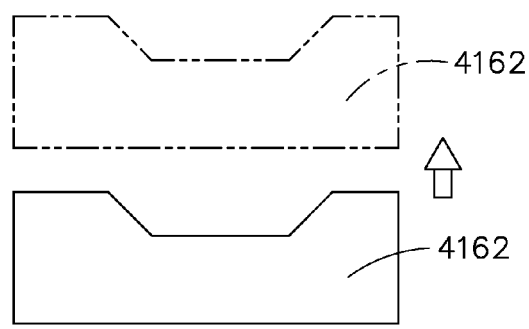
Figures 149, 150:
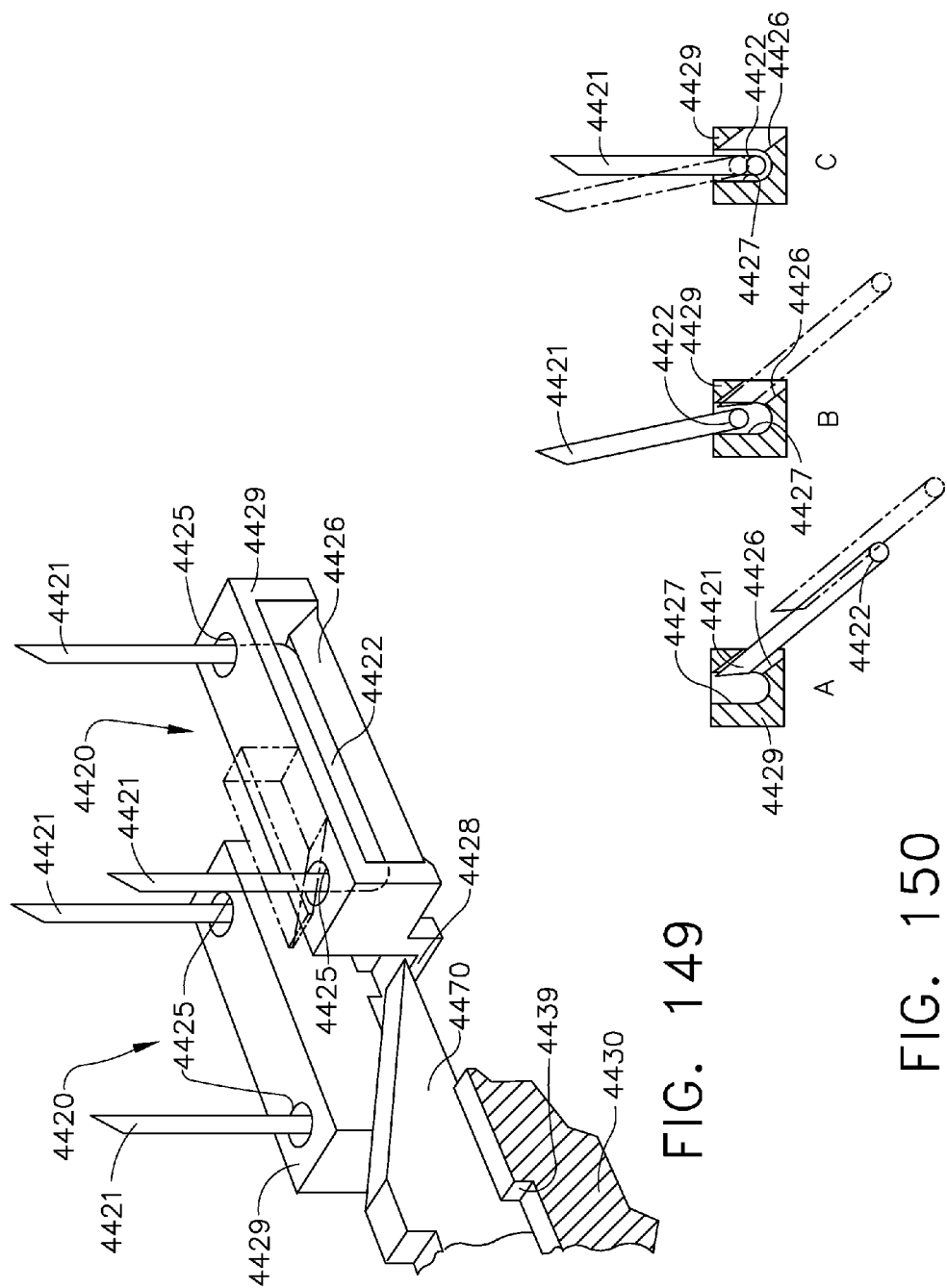
Figure 151:
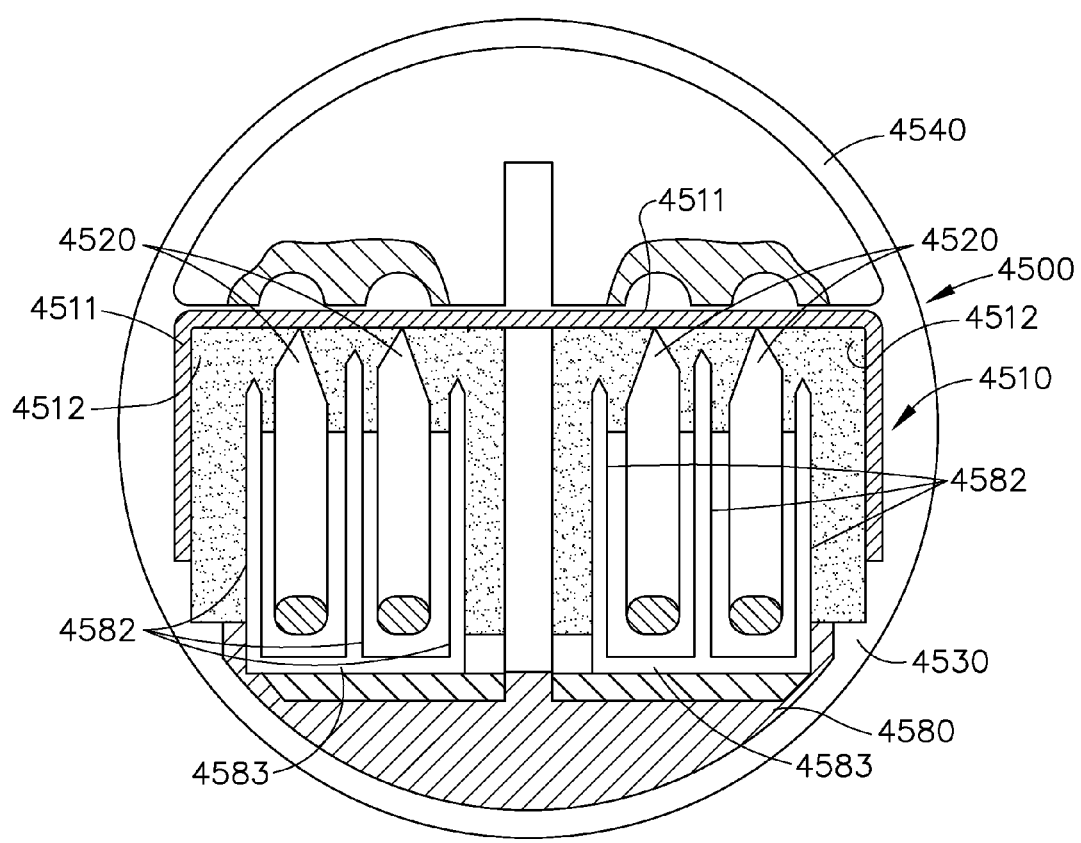
Figure 153:
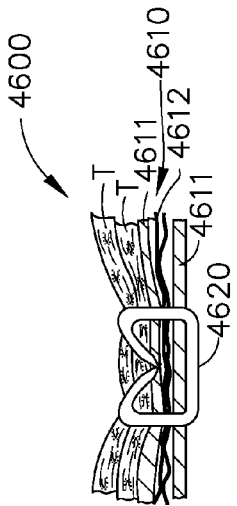
Figure 152:
Figure 154:
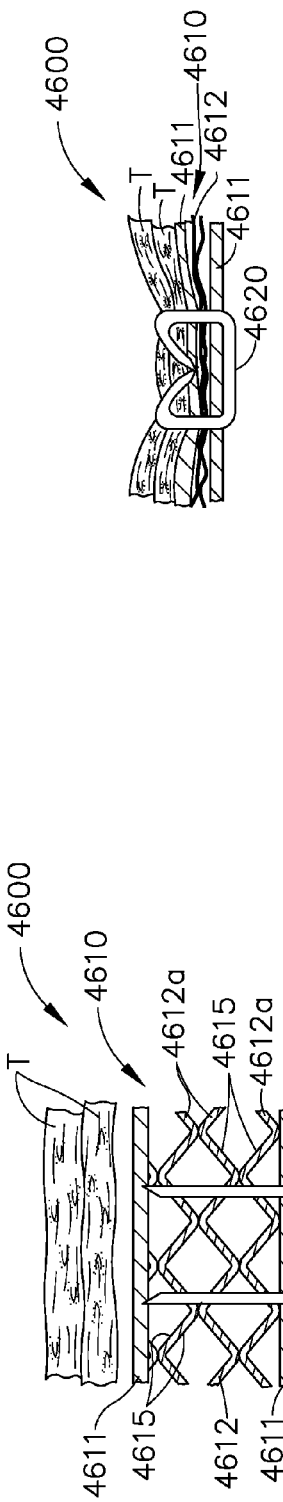
Figure 162:
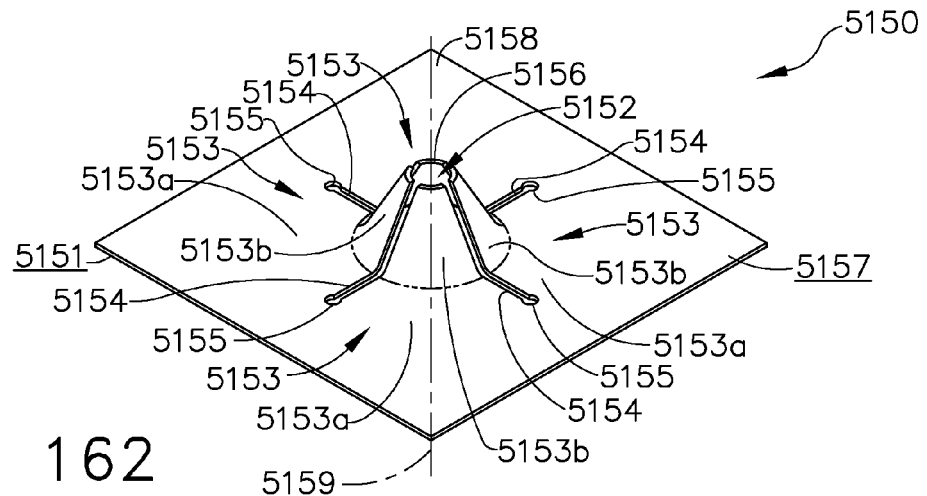
Figure 163:
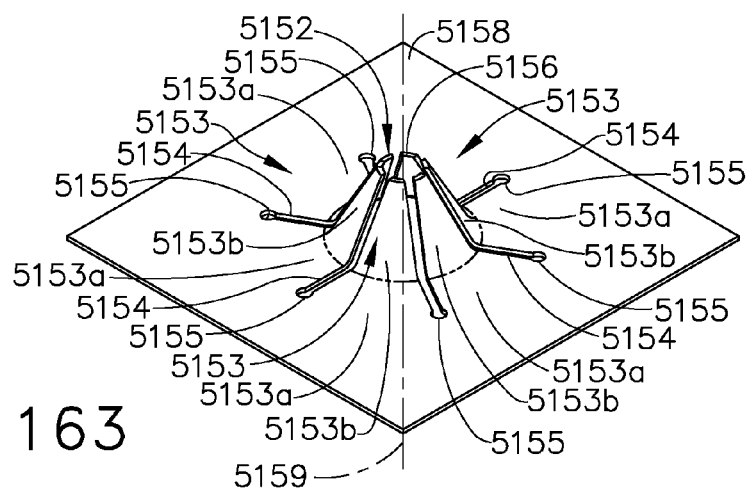
Figure 164:
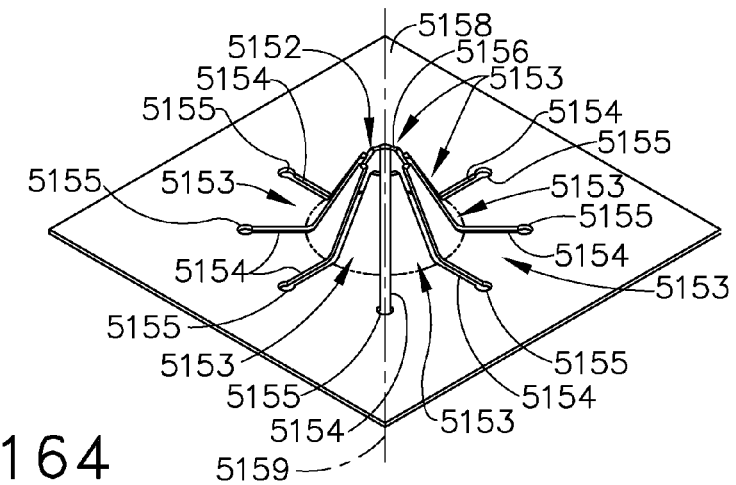
Figure 165:
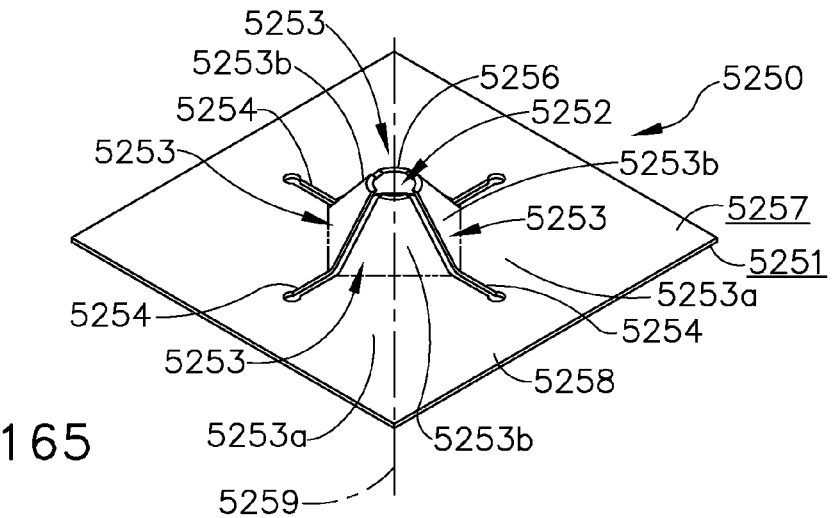
Figure 166:
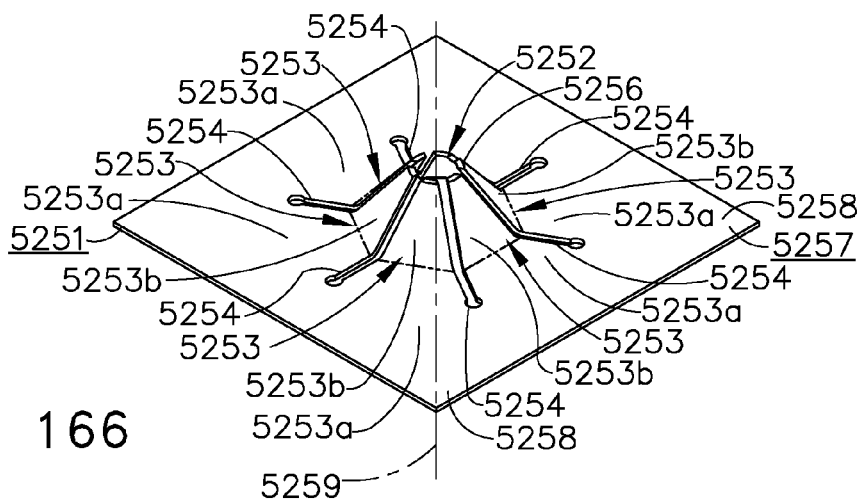
Figure 167:
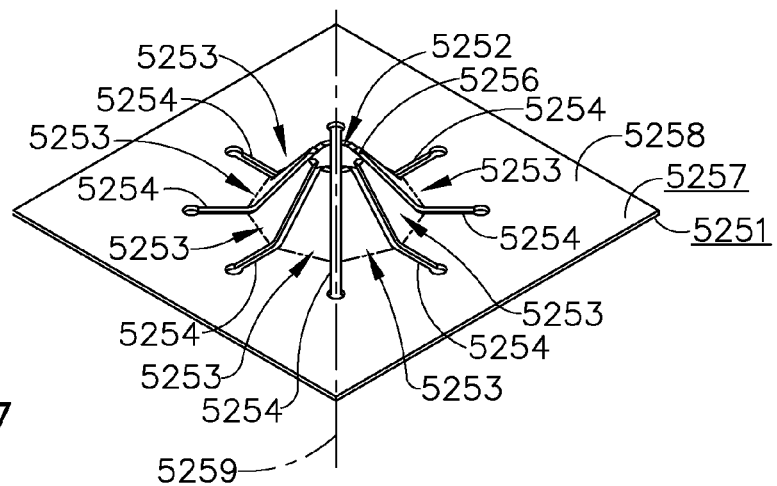
Figure 168:
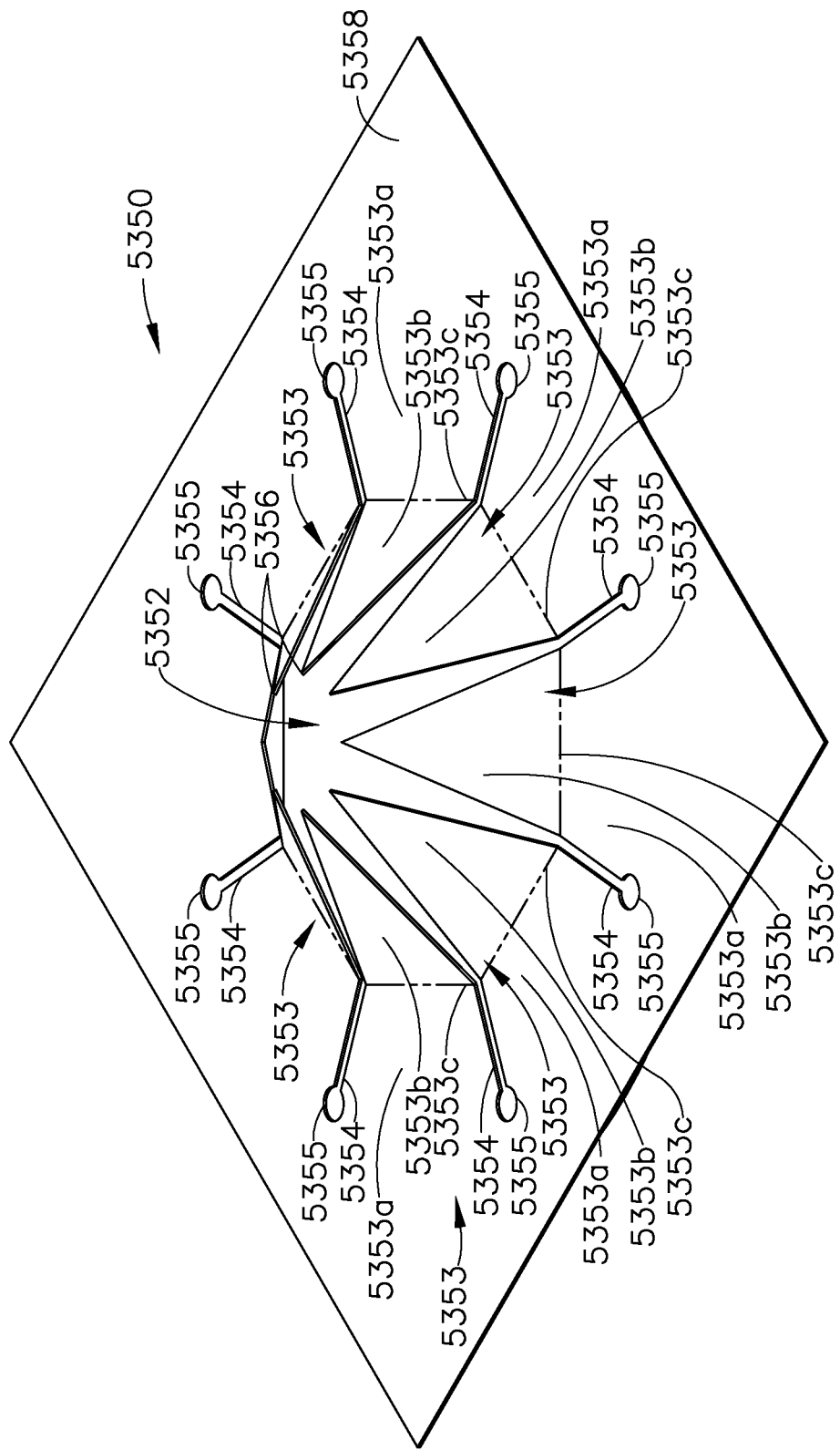
Figure 169:
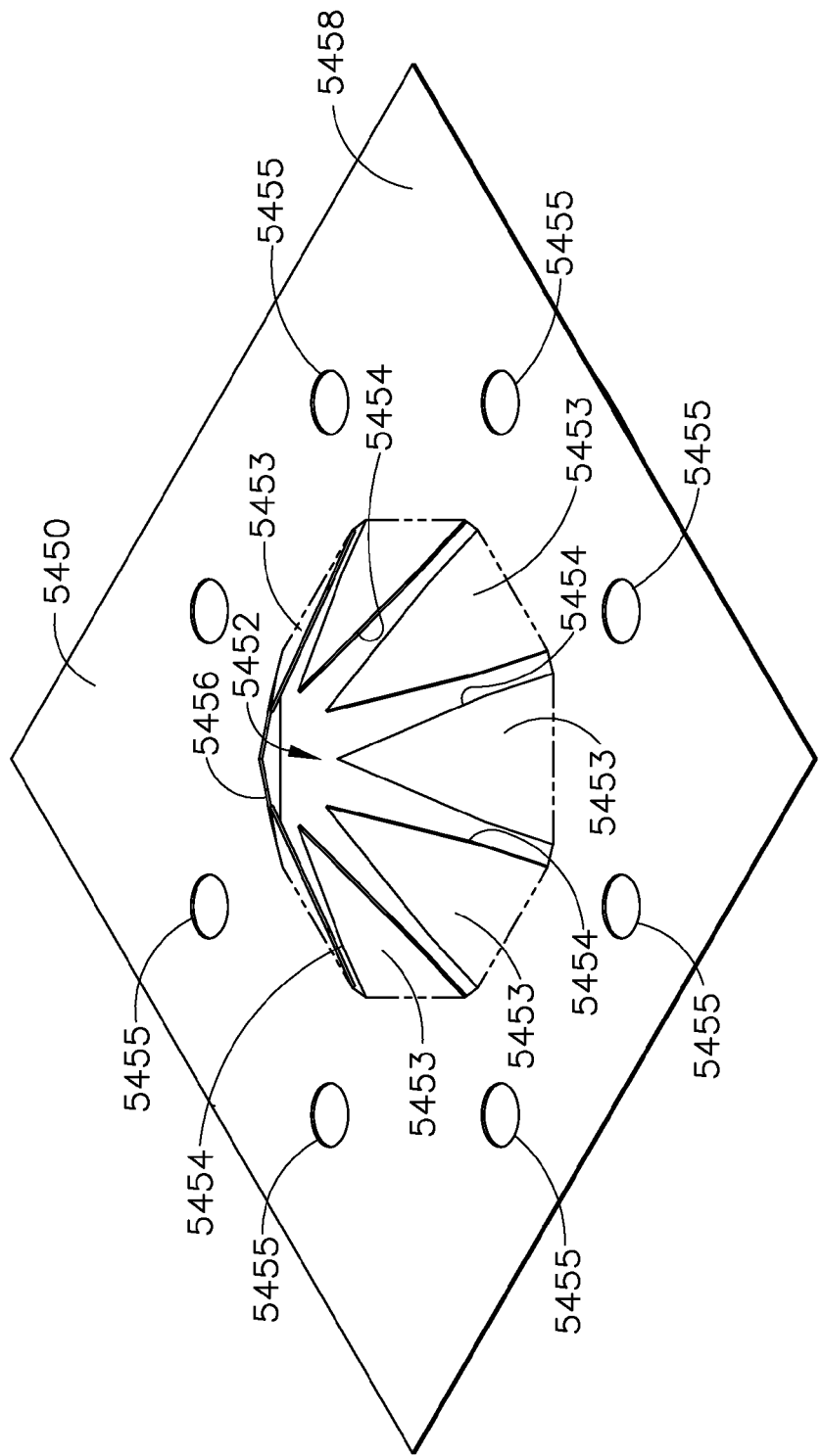
Figure 170:
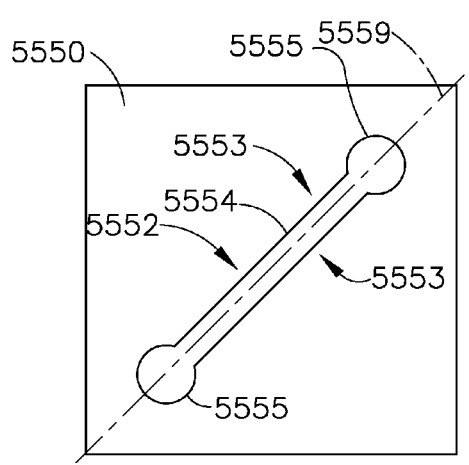
Figure 172:
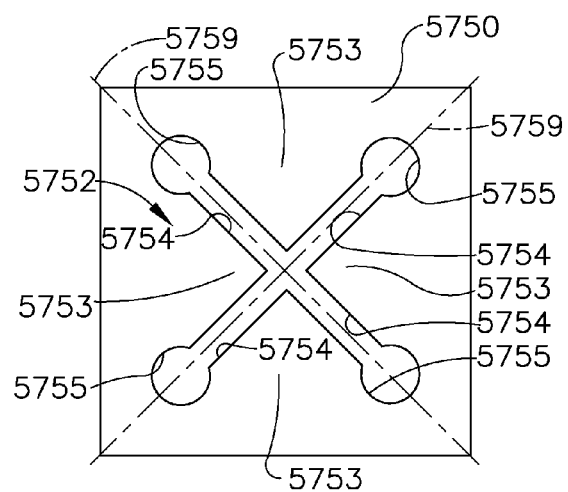
Figure 171:
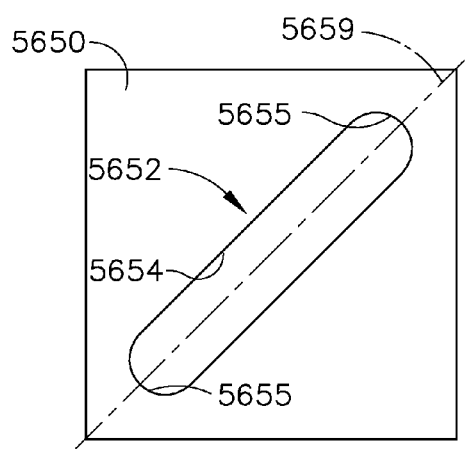
Figure 173:
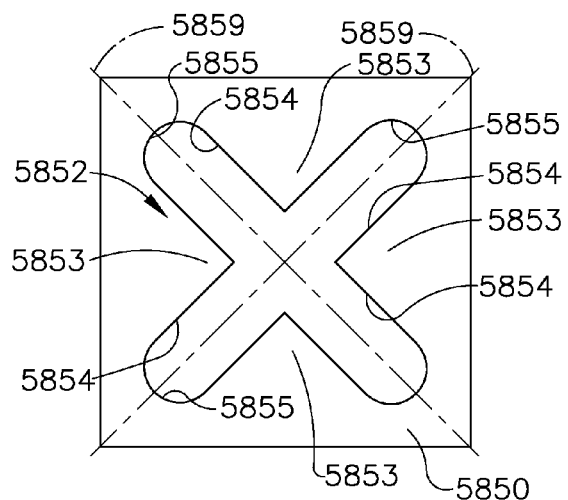
Figure 177:
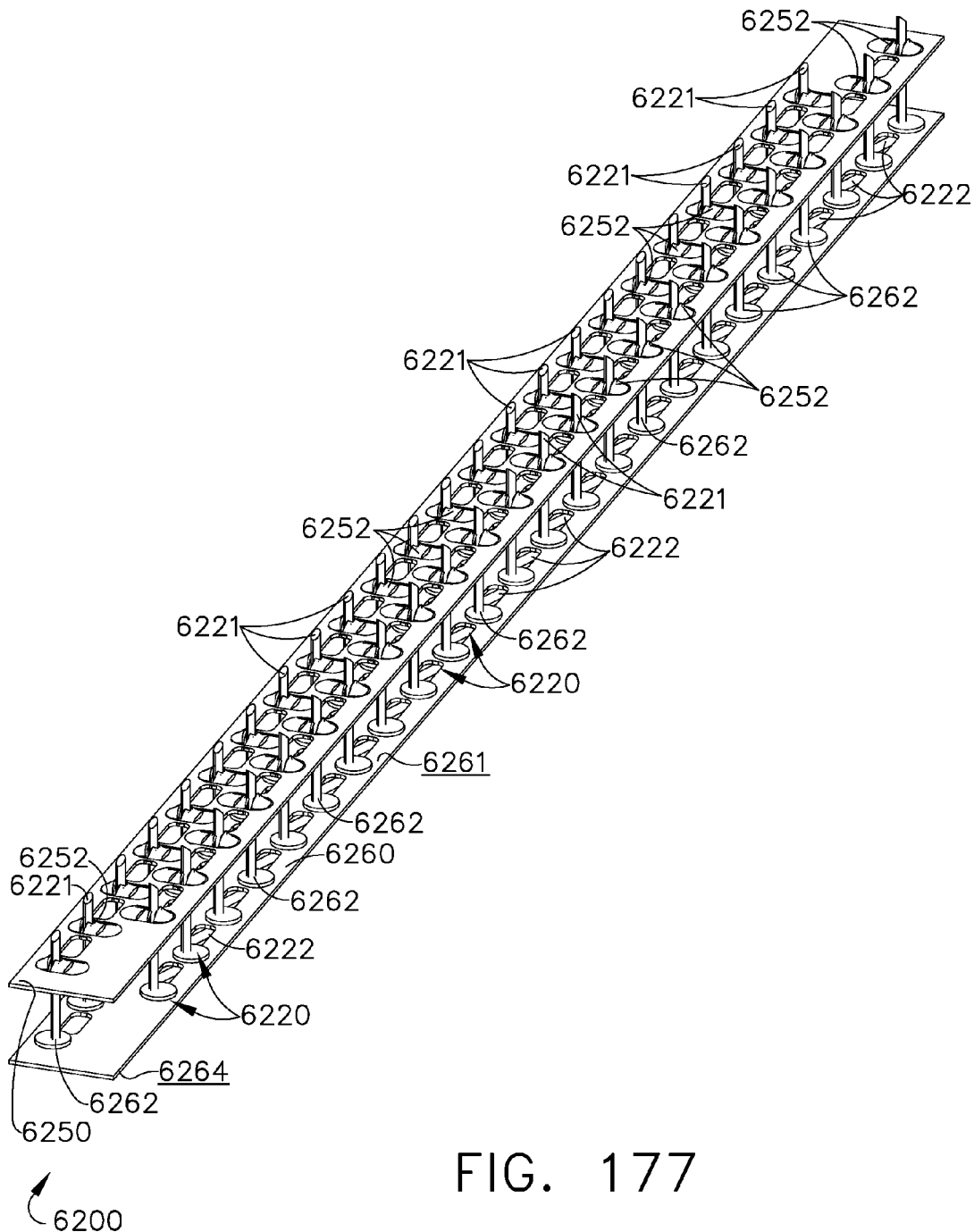
Figure 178:
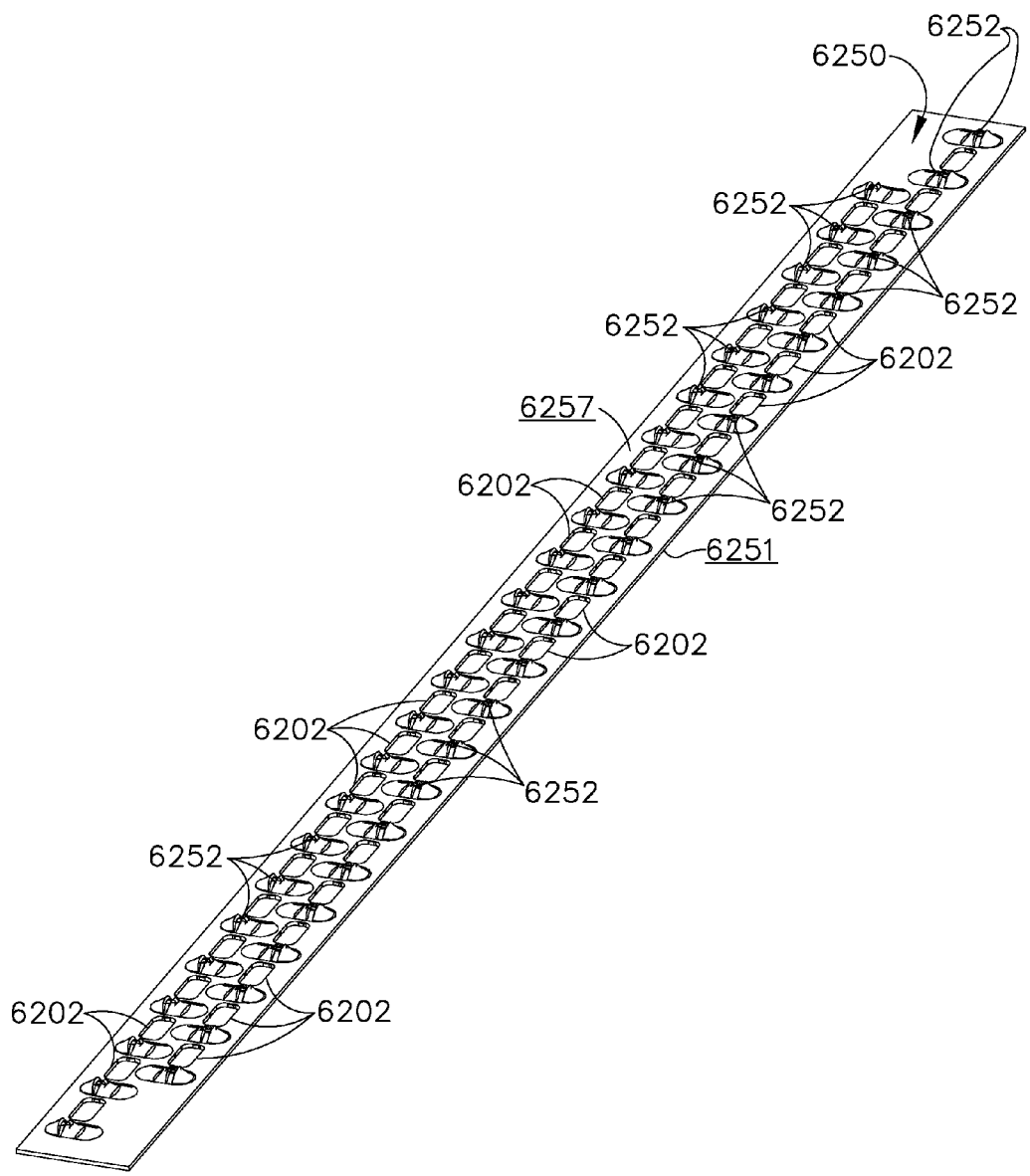
Figure 179:
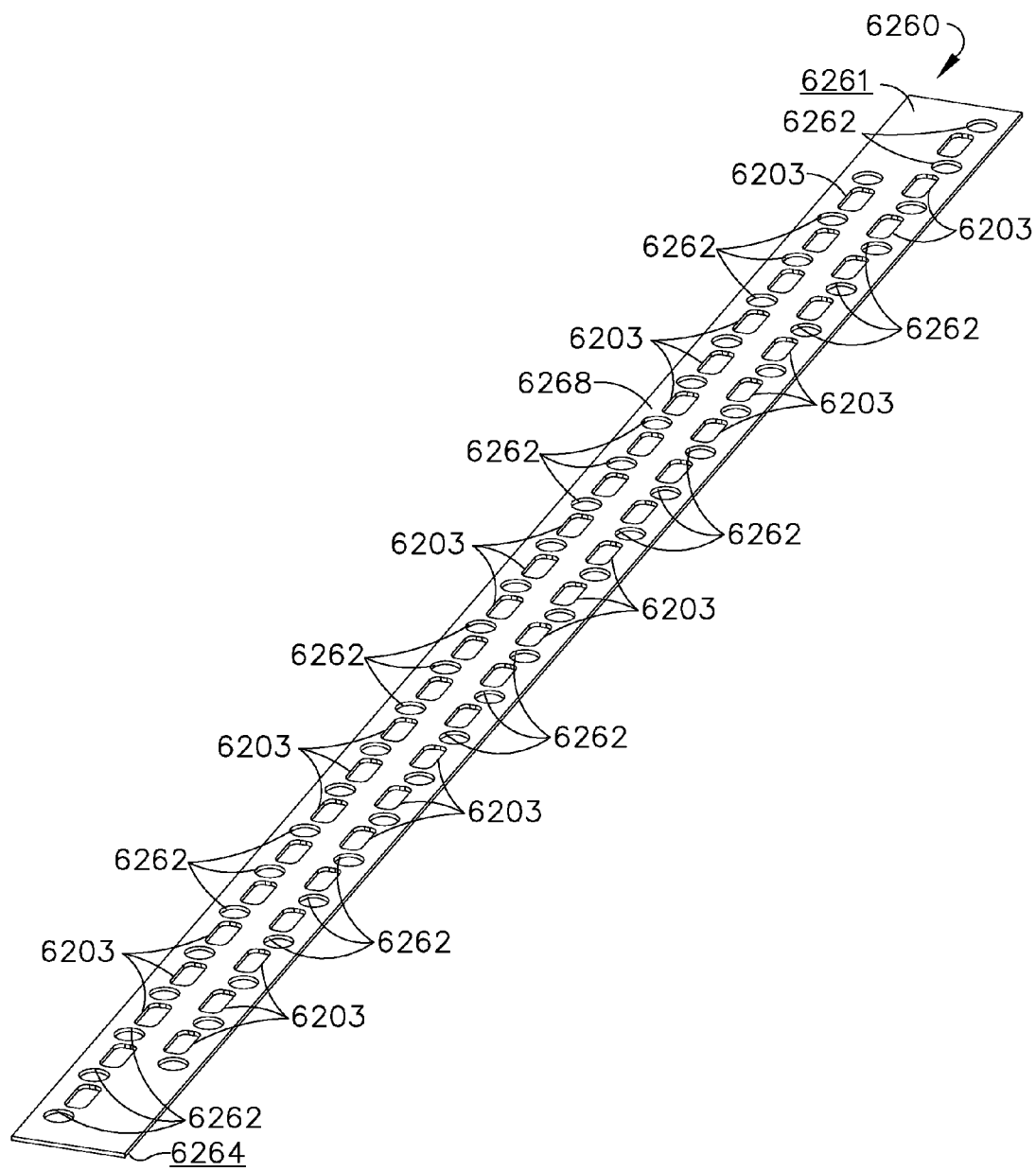
Figure 180:
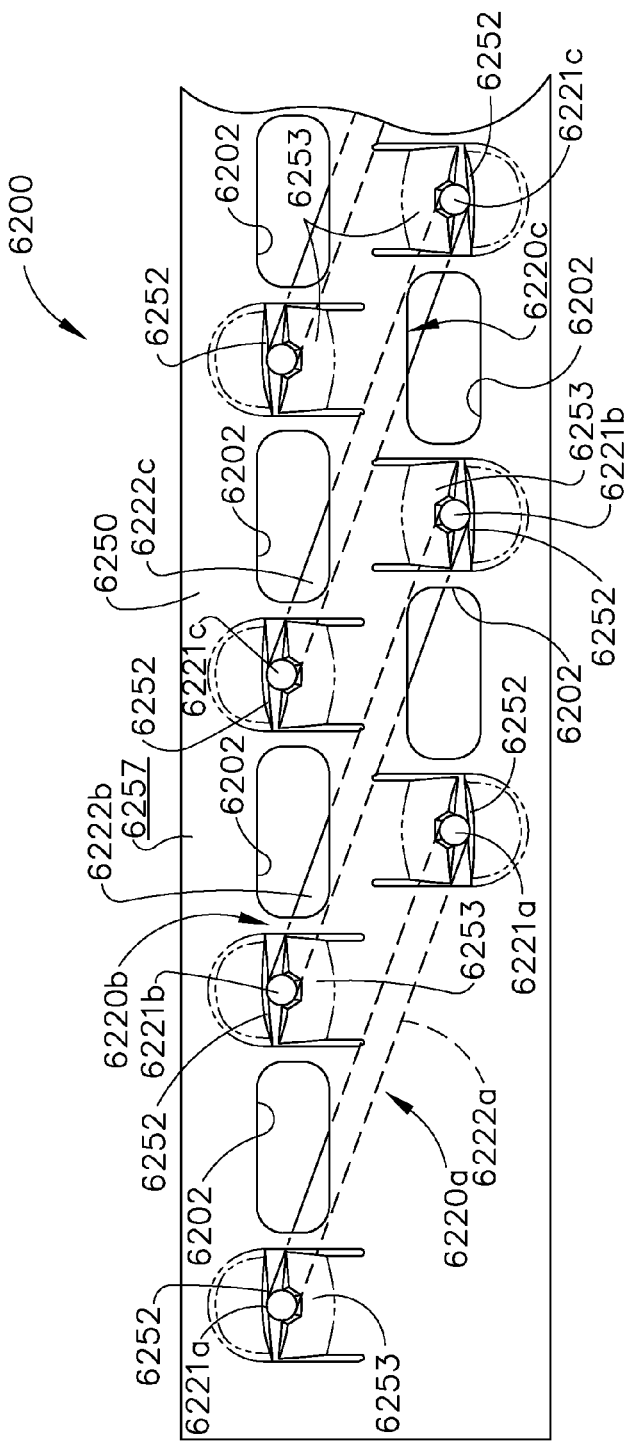
Figure 181:
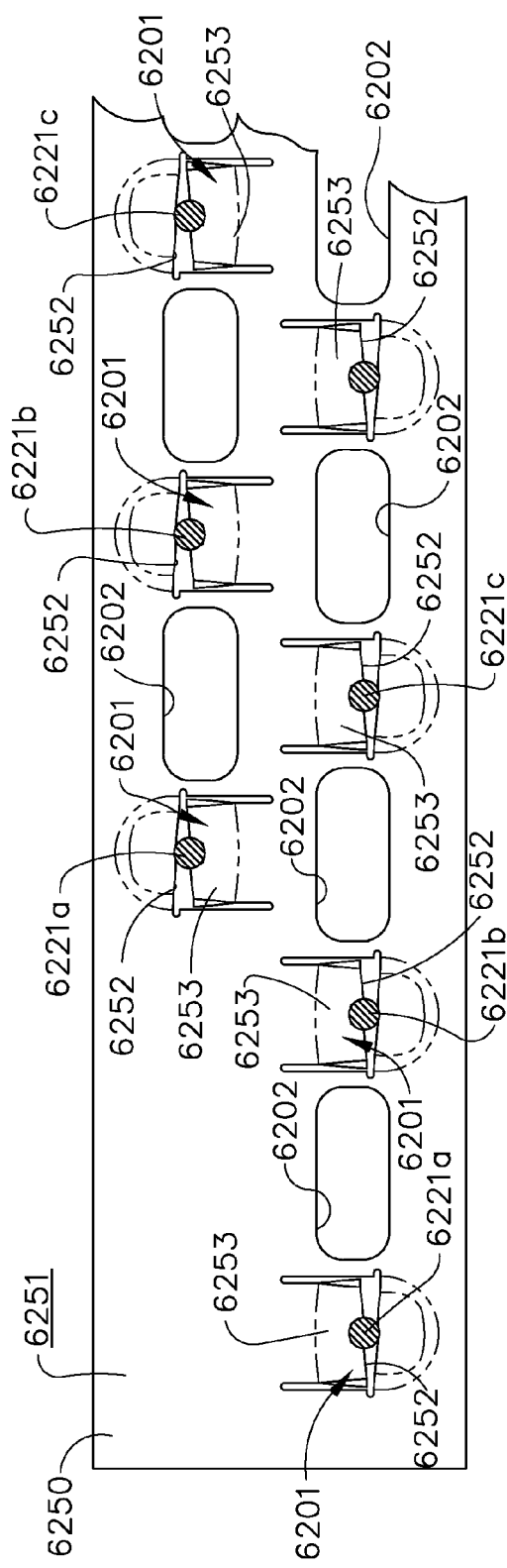
Figure 182:
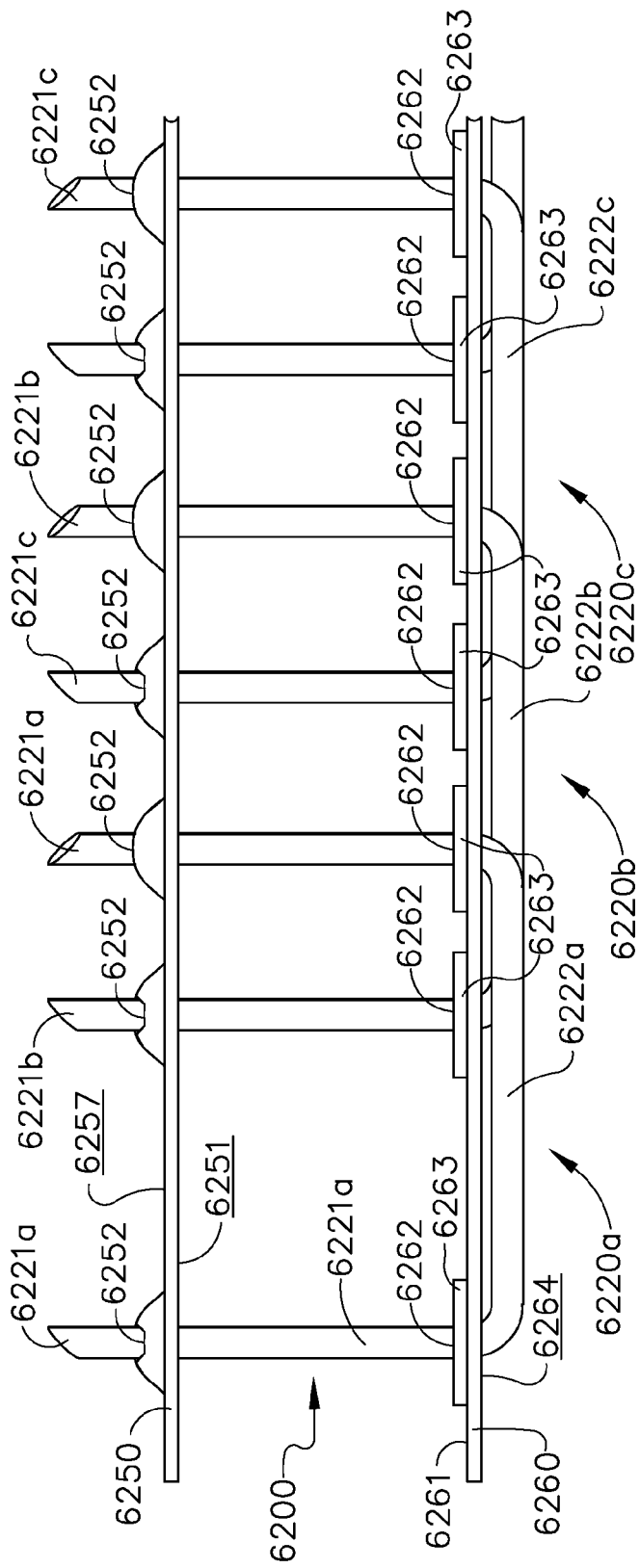
Figure 183:
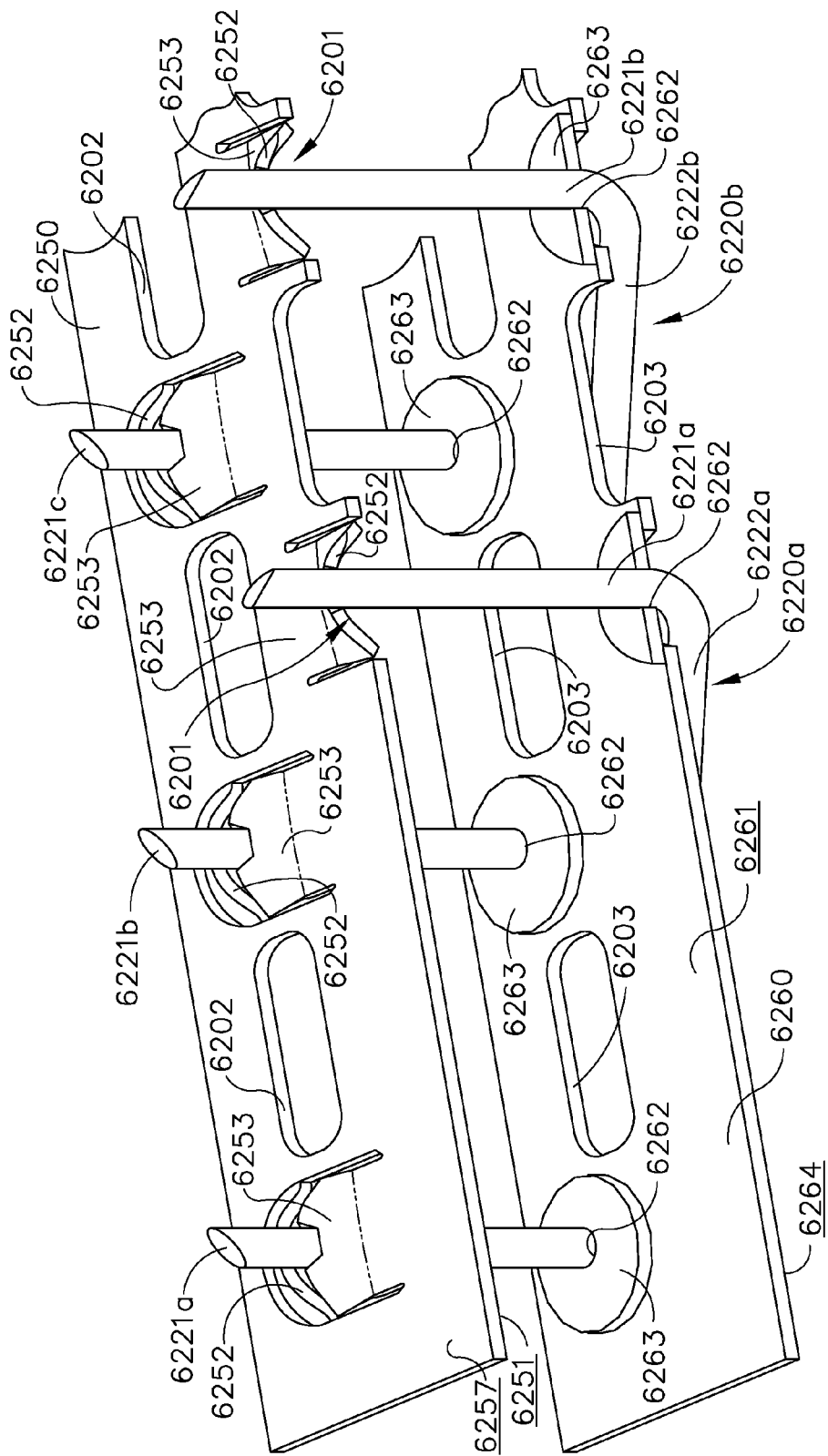
Figure 184:
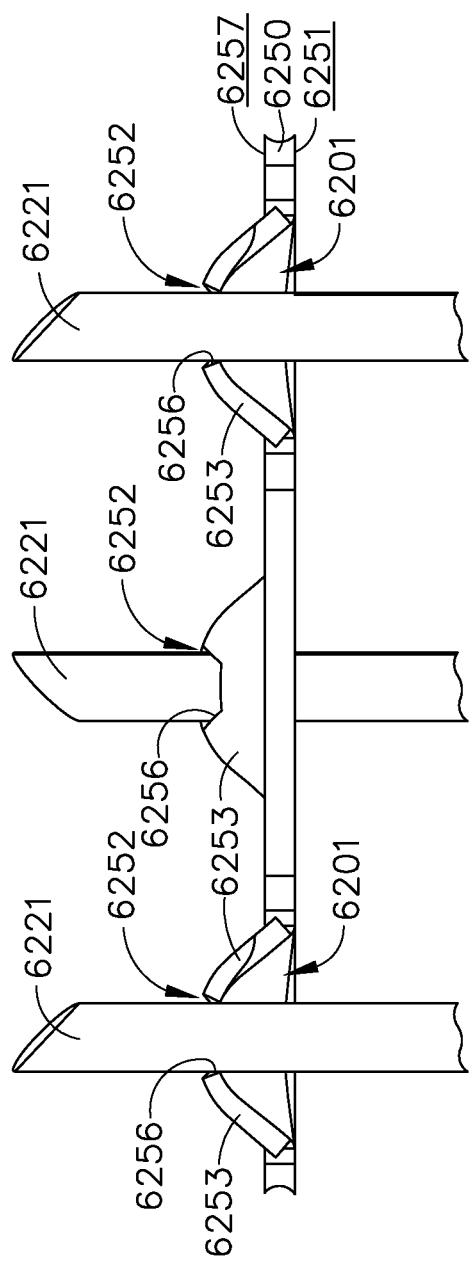
Figure 185:
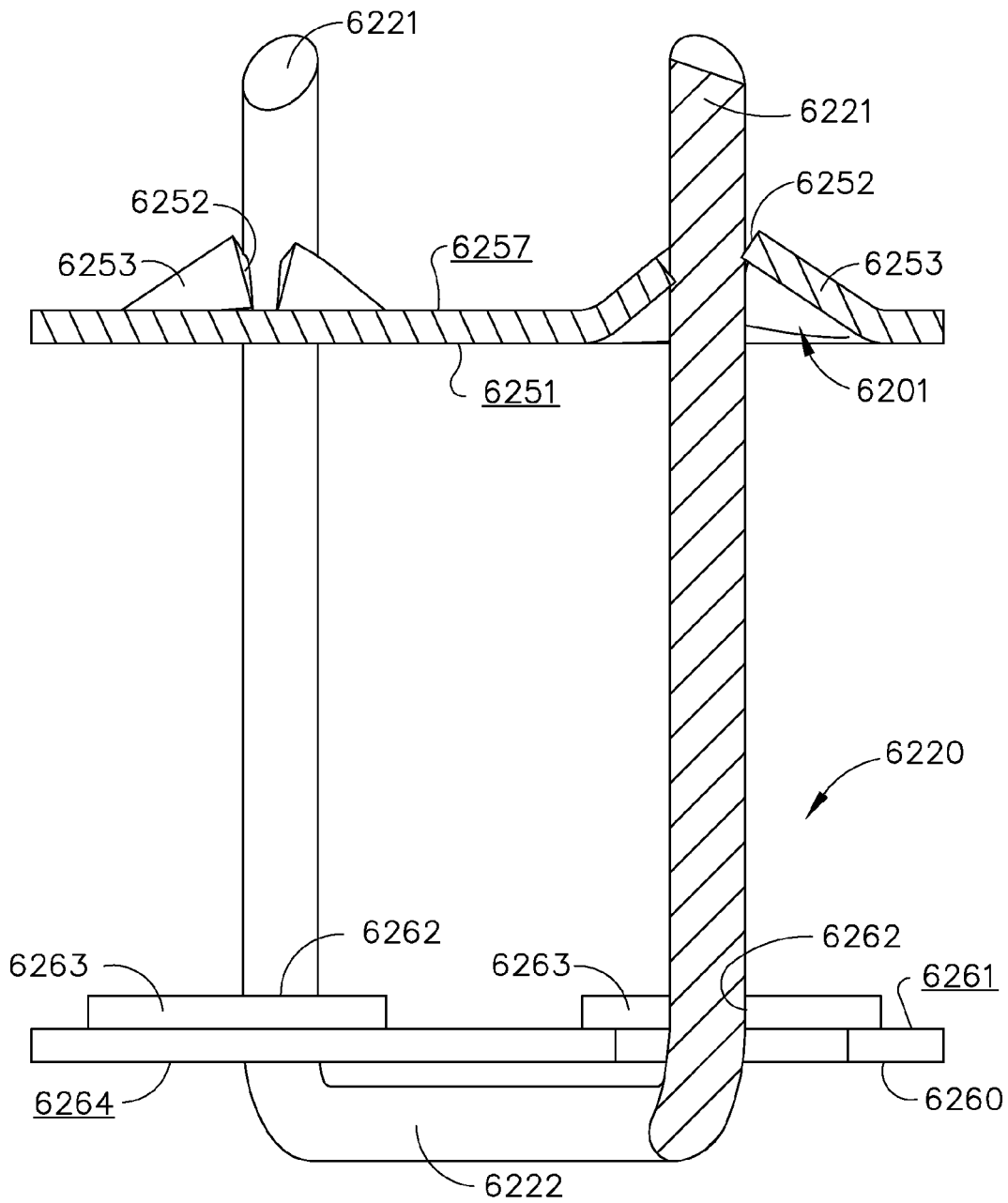
Figure 186:
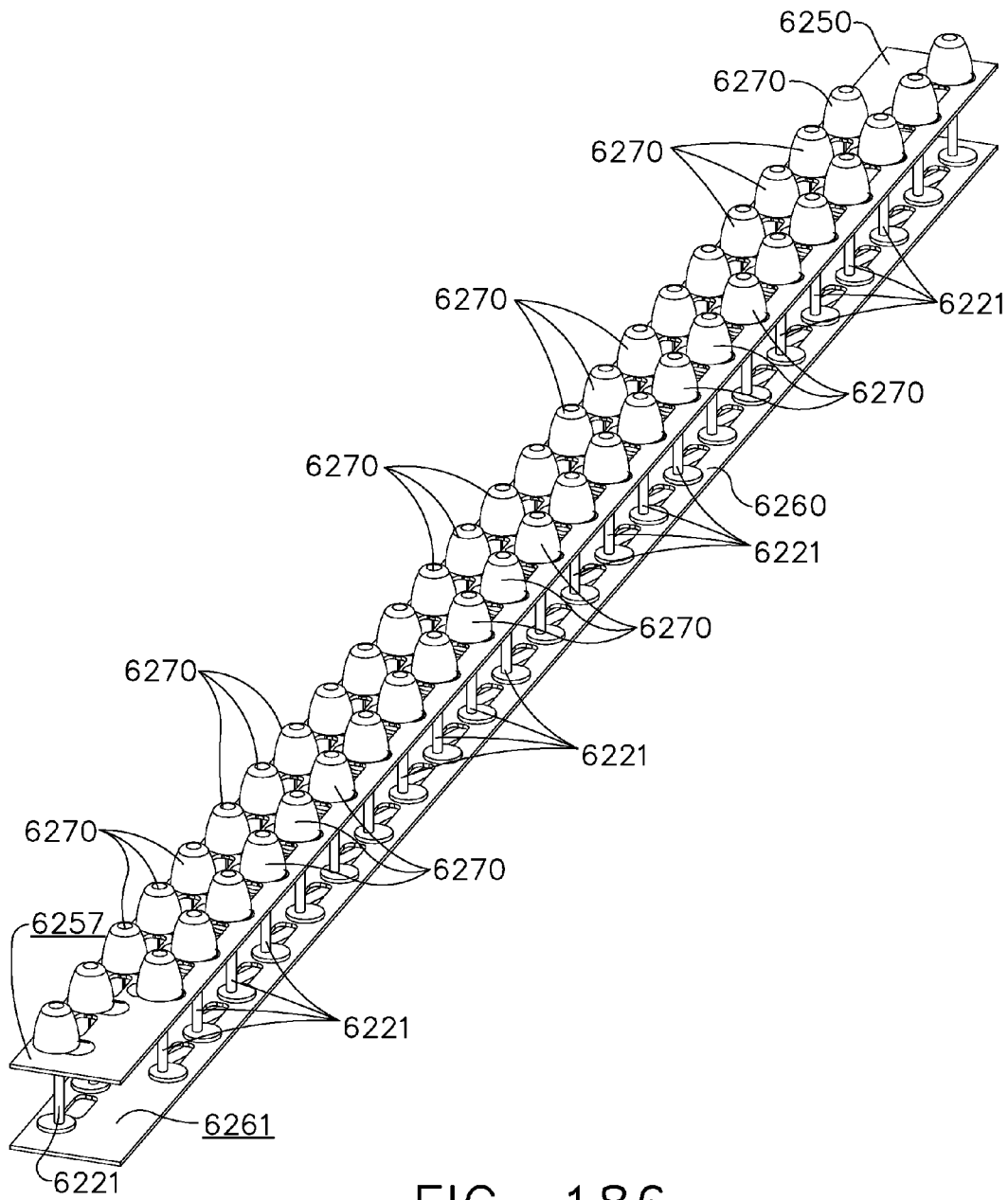
Figure 187:
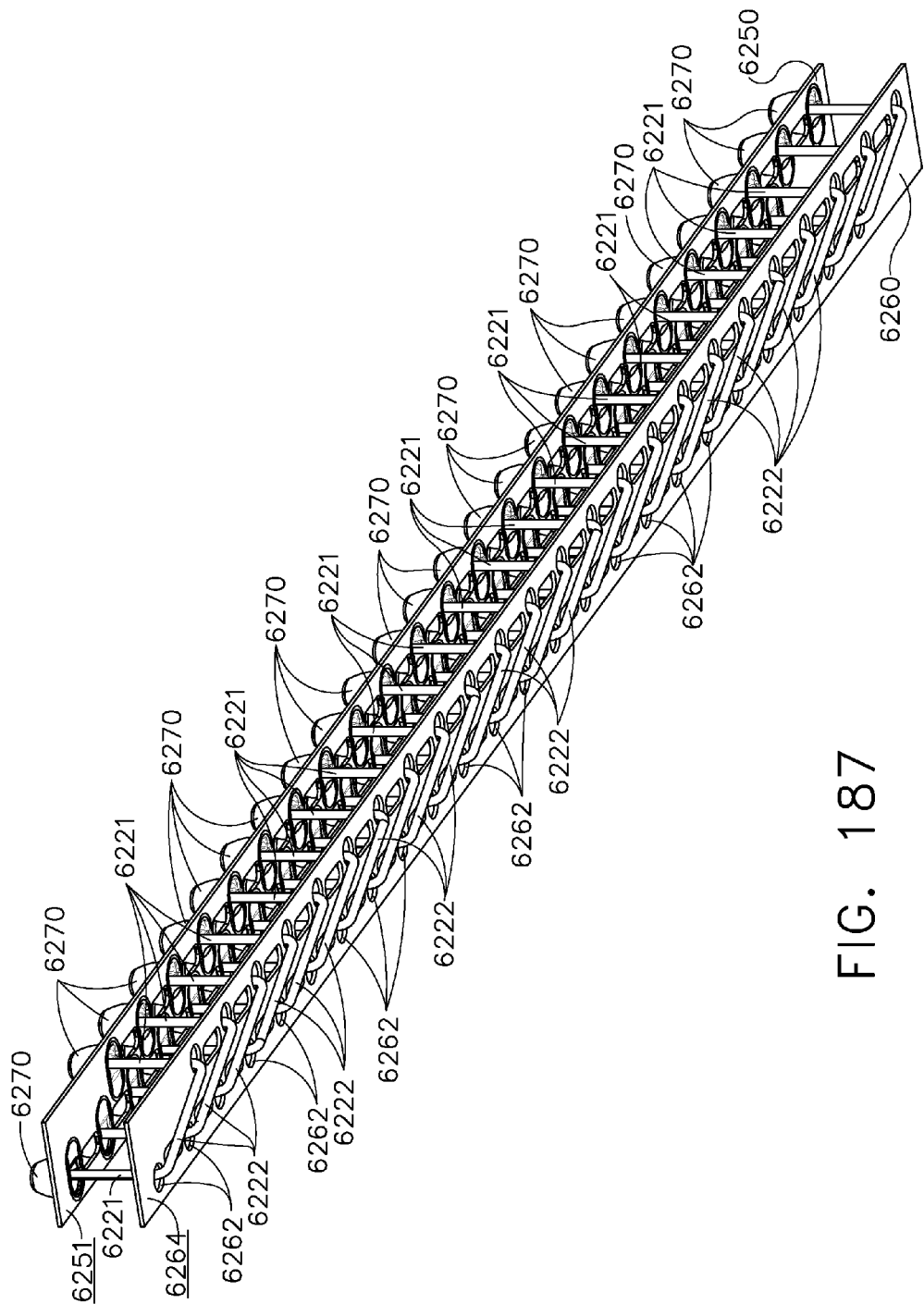
Figure 188:
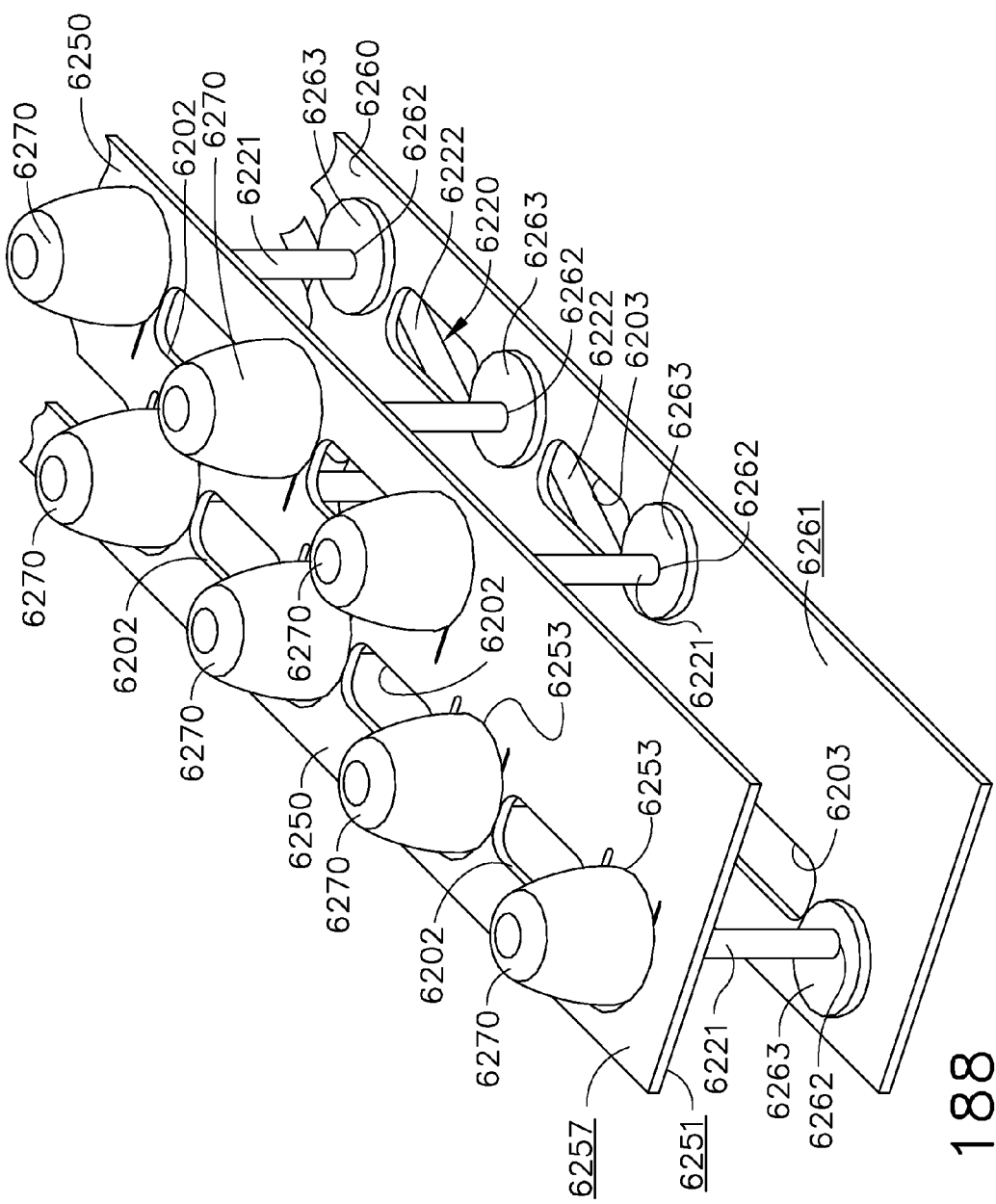
Figure 189:
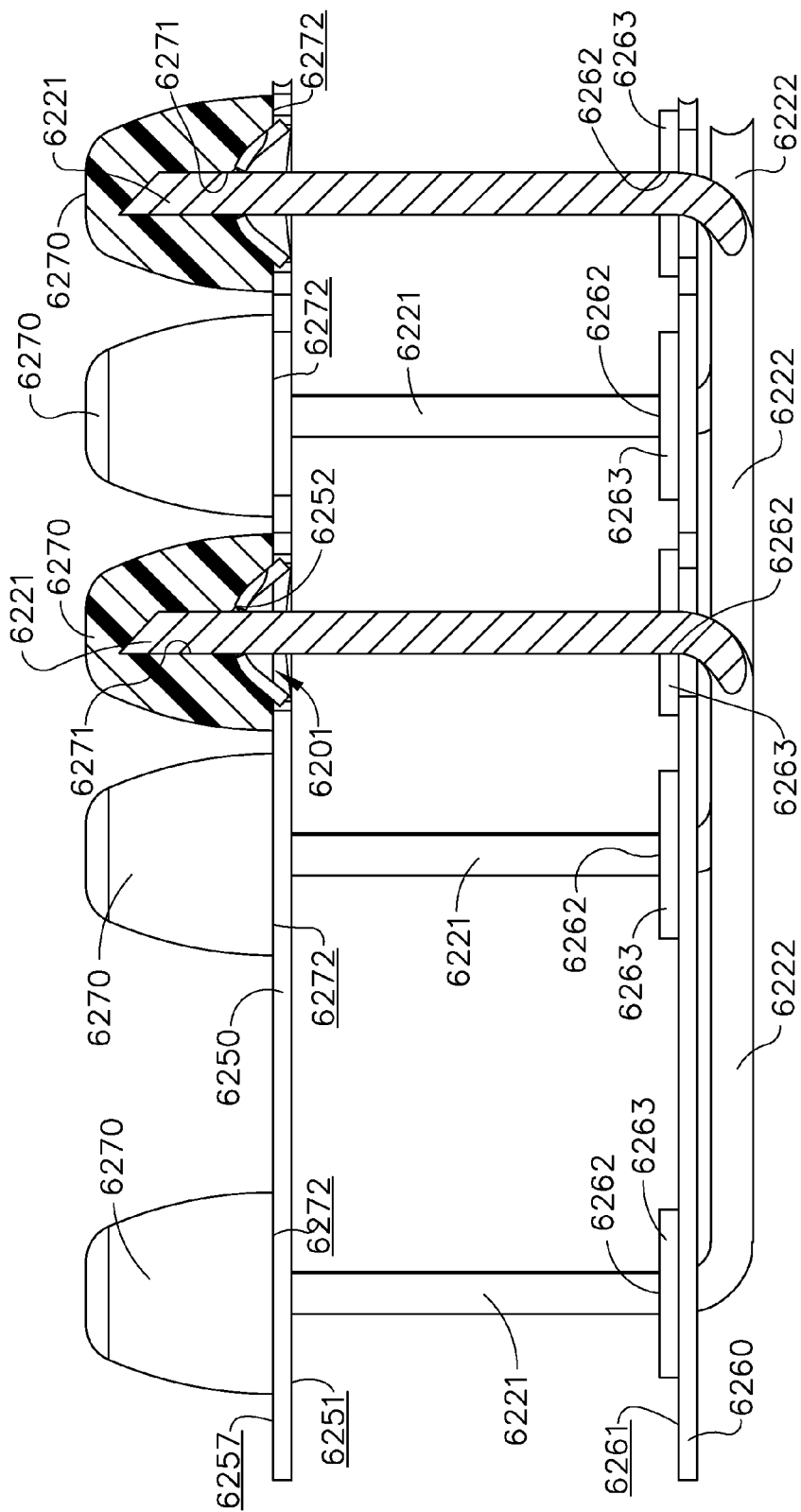
Figure 200:
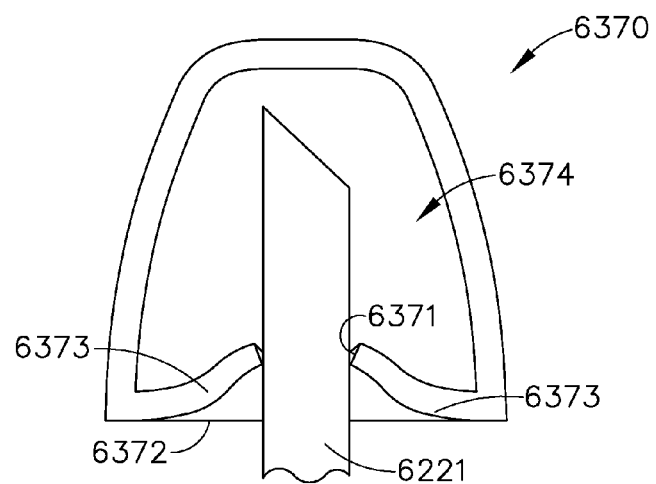
Figure 201:
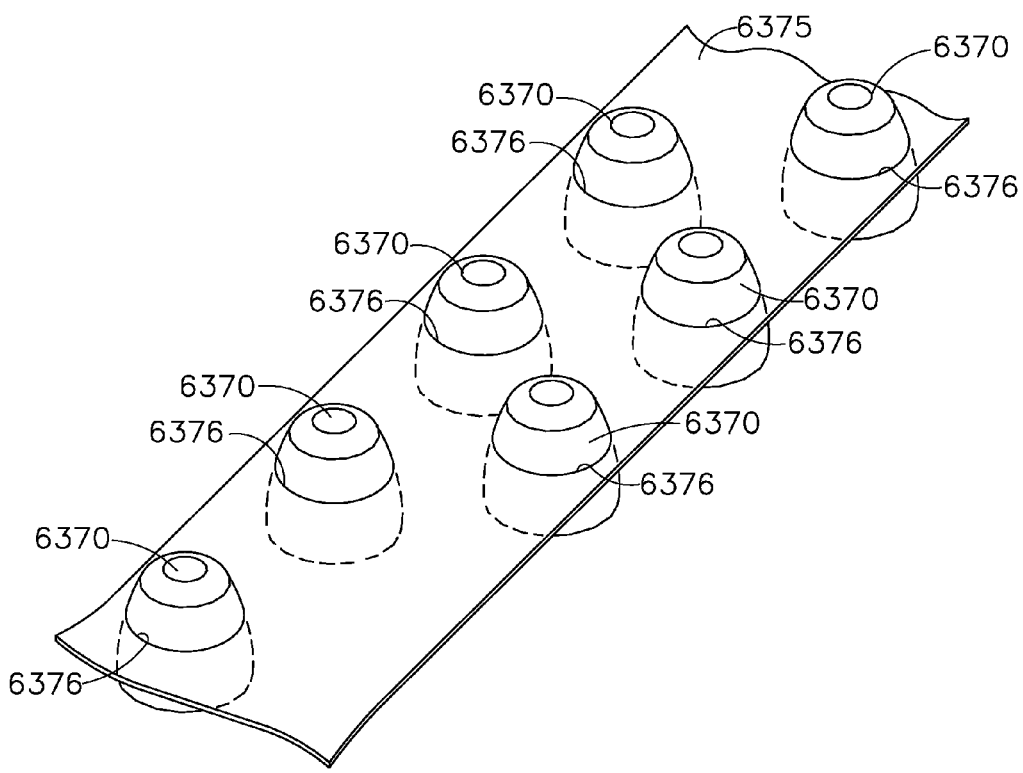
Figure 202:
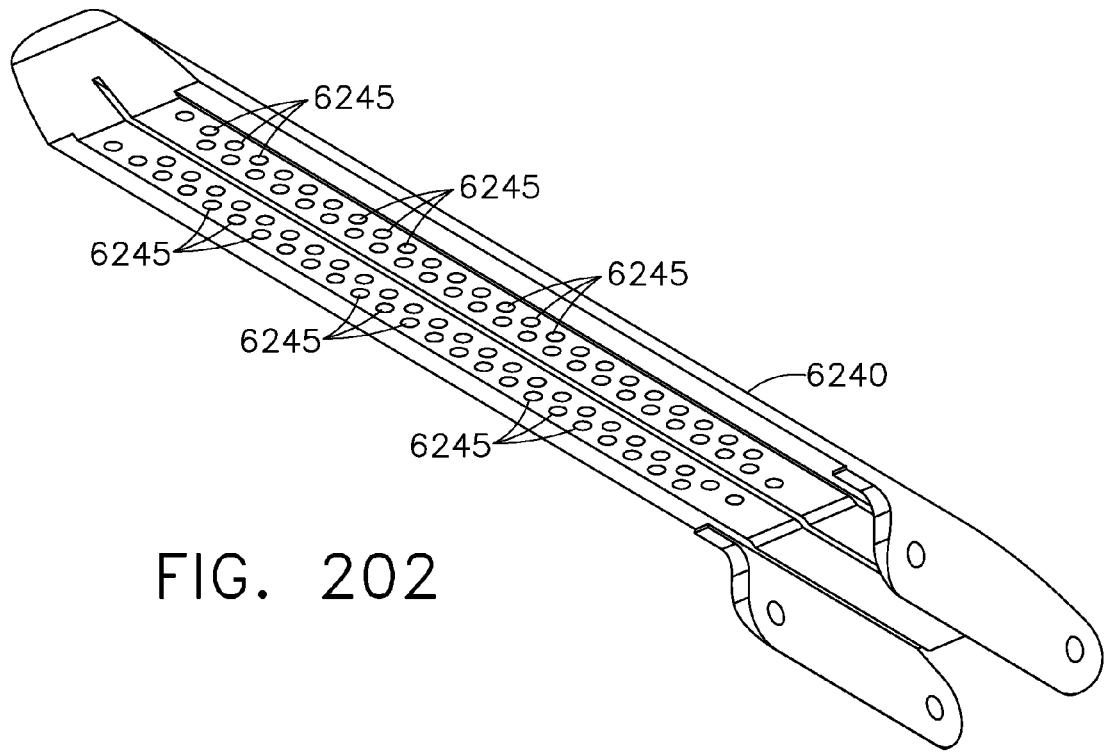
Figure 203:
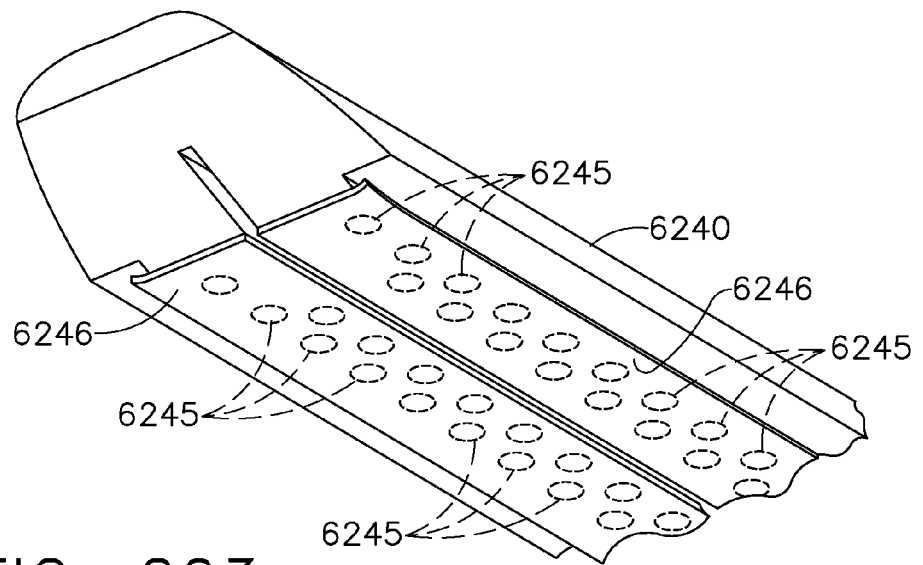
Figure 204:
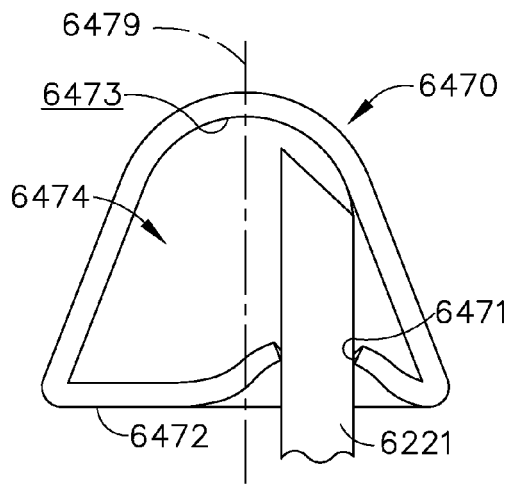
Figure 205:
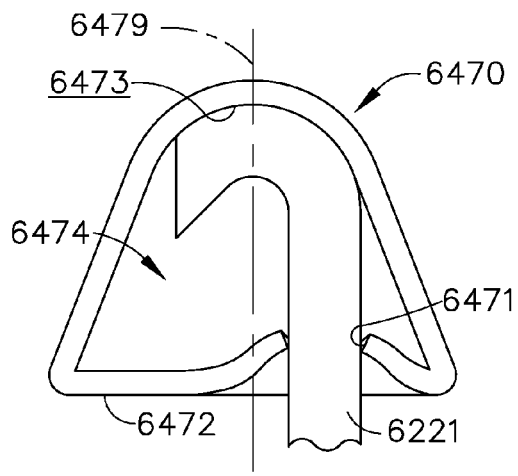
Figure 206:
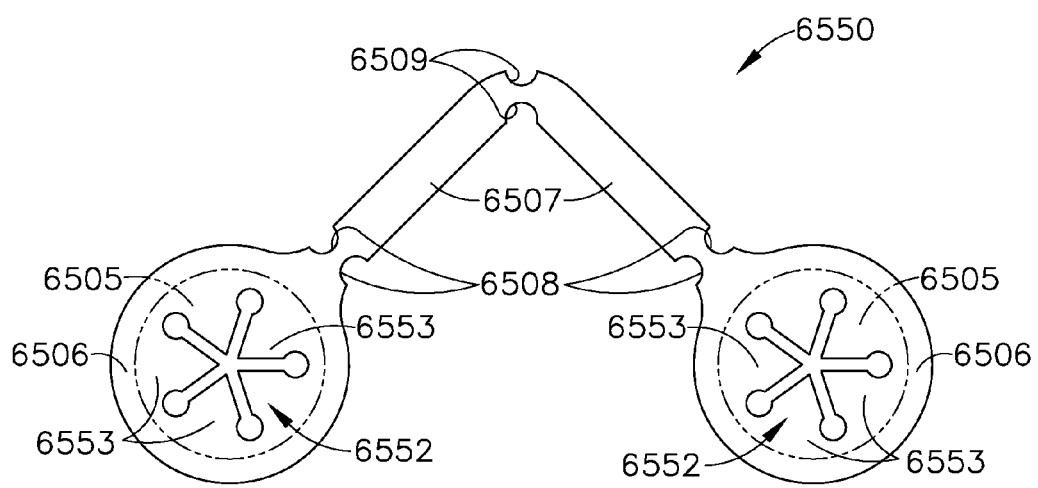
Figure 207:
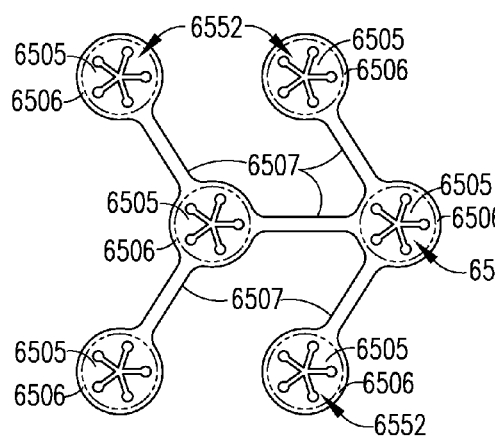
Figure 208:
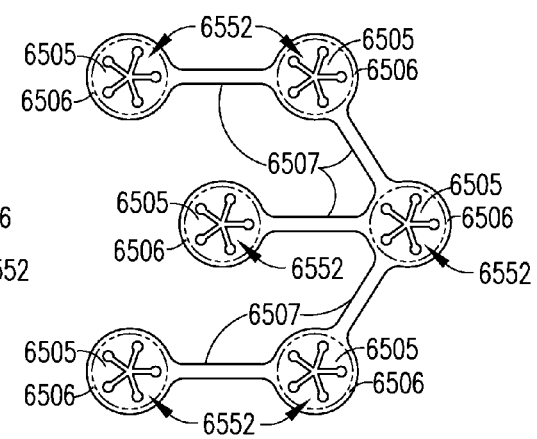
Figure 209:
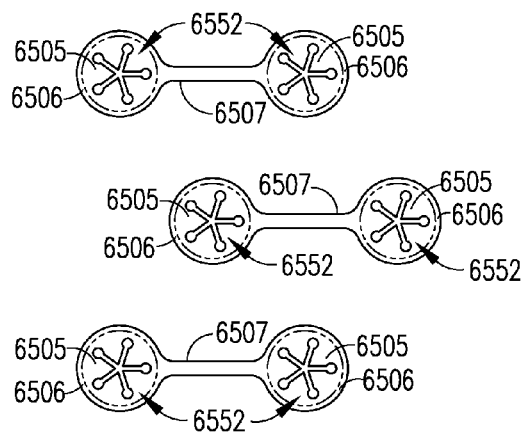
Figure 210:
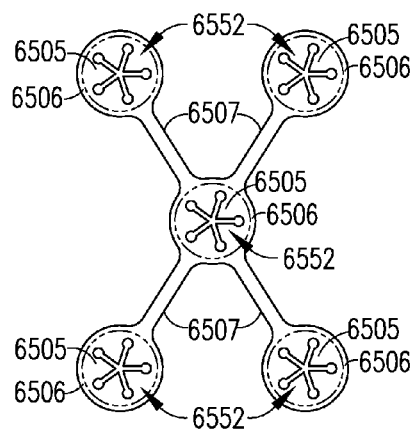
Figure 211:
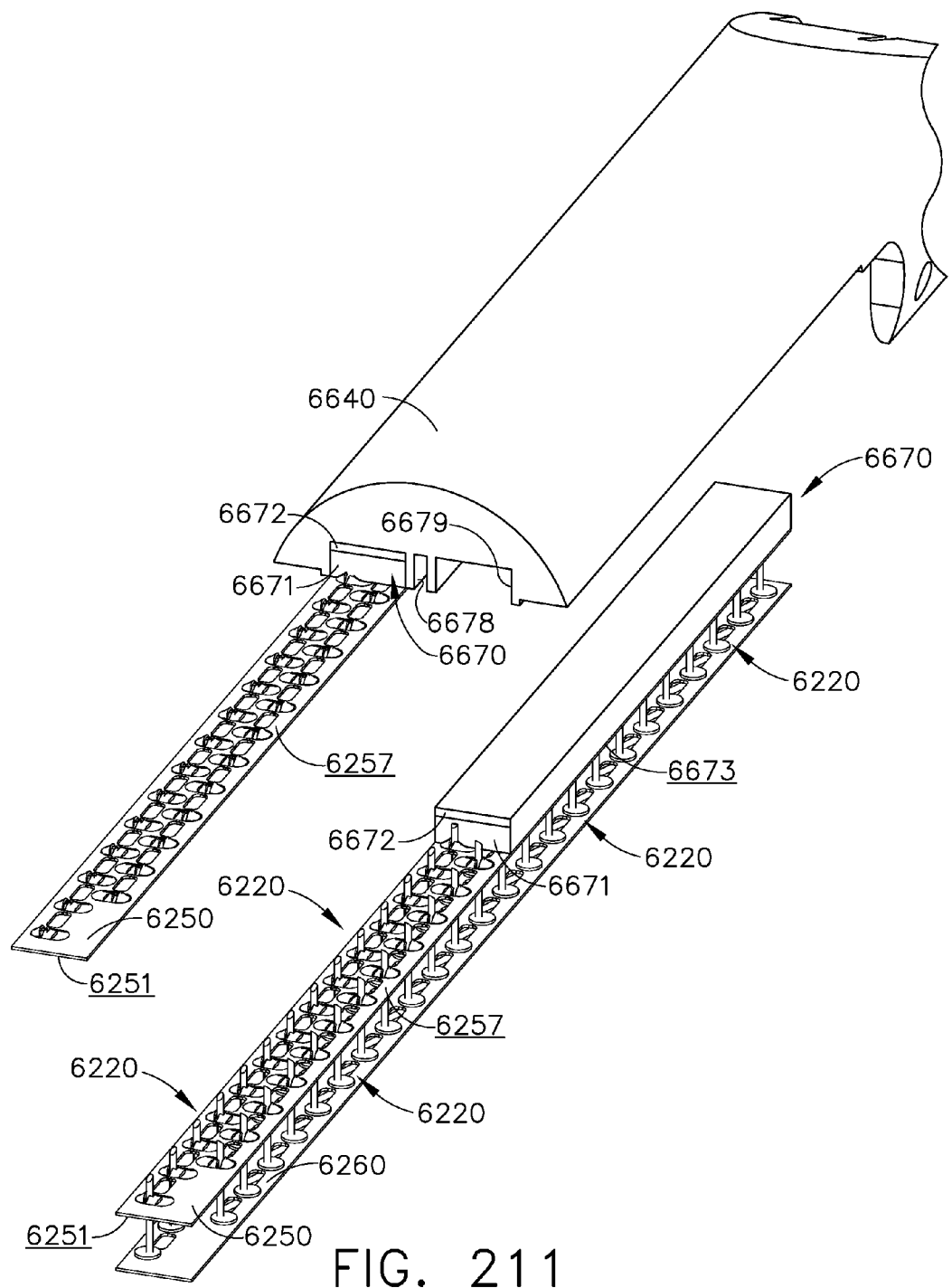
Figure 212:
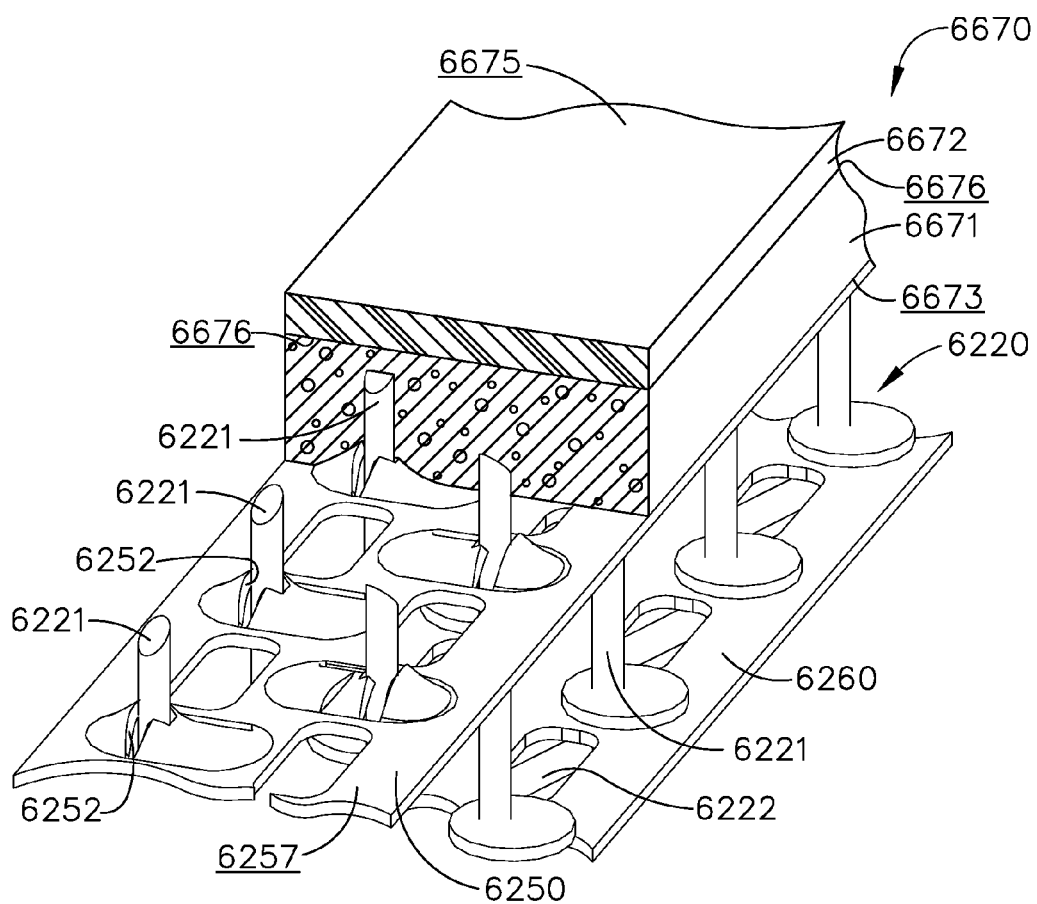
Figure 213:
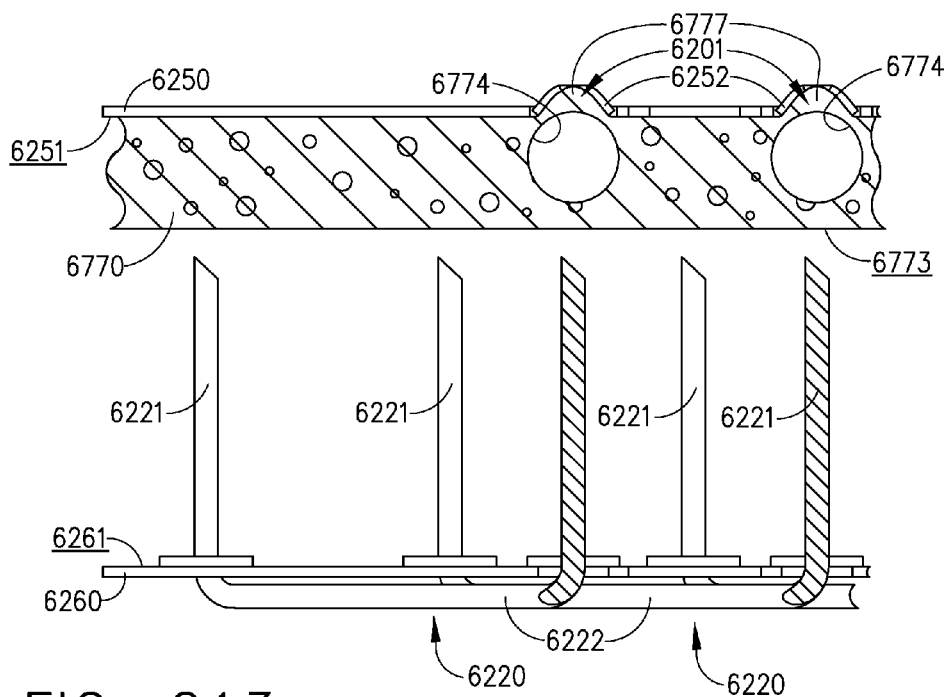
Figure 214:
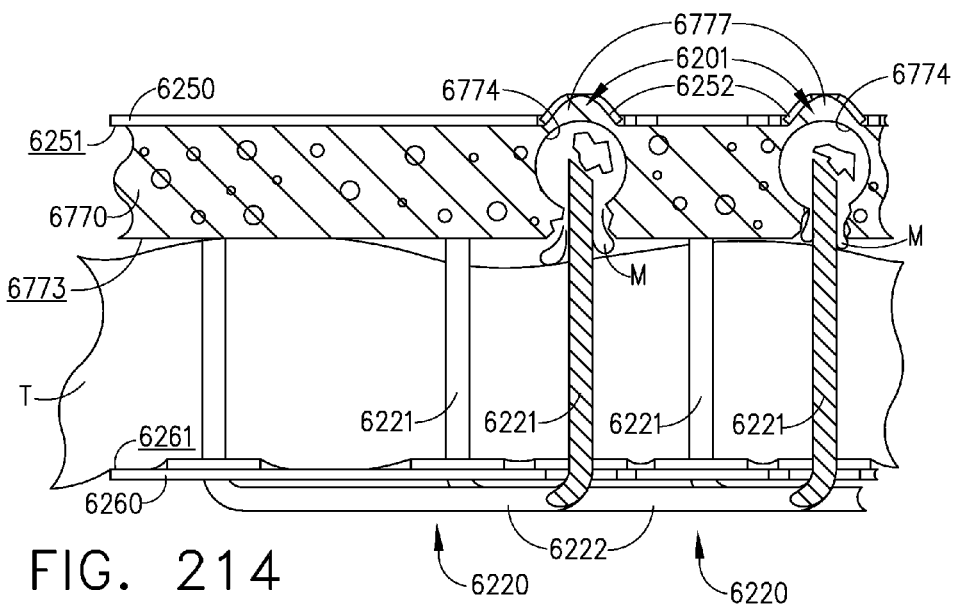
Figure 215:
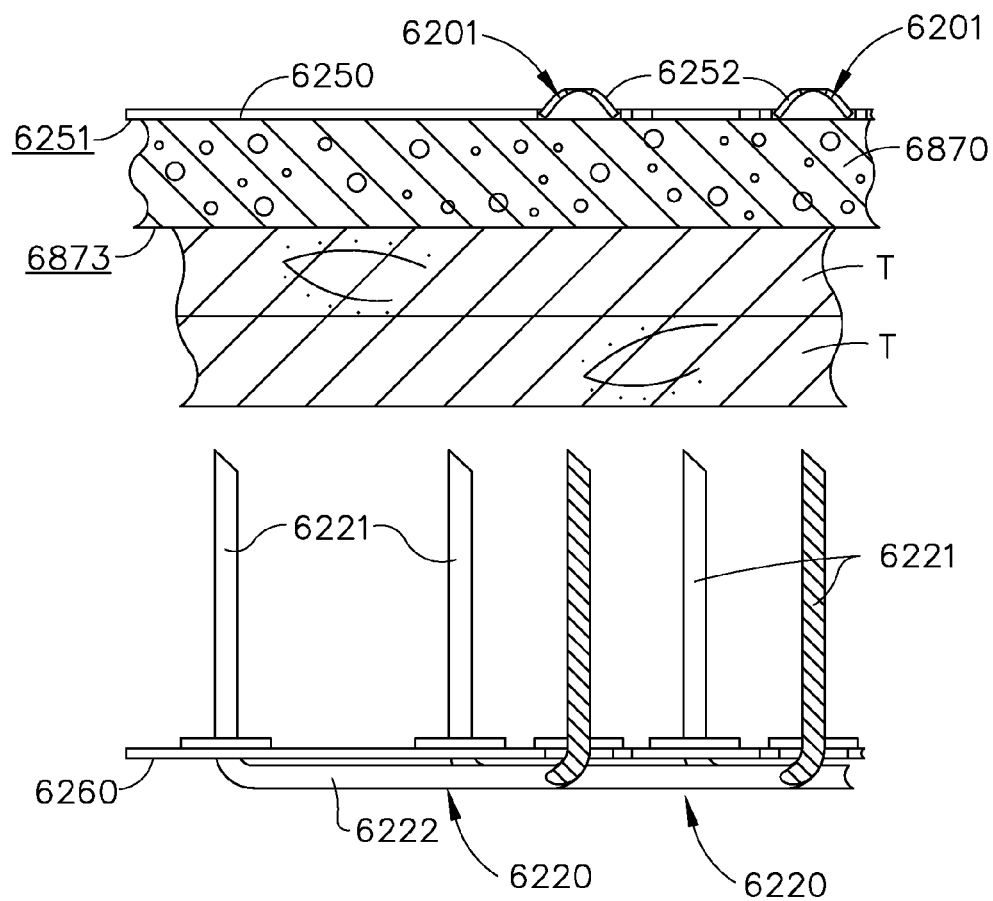
Figure 218:
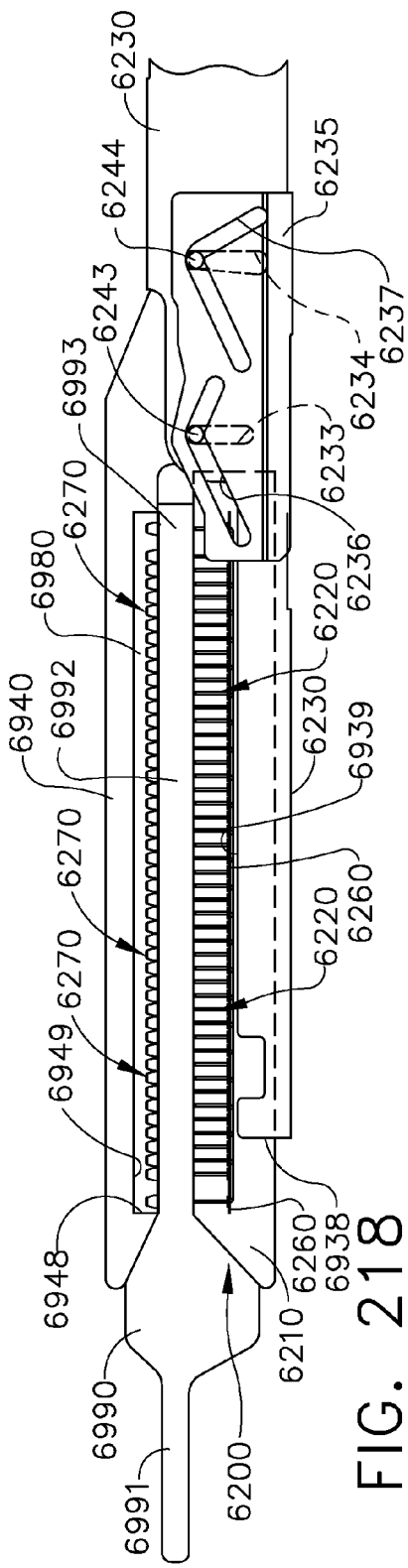
Figure 219:
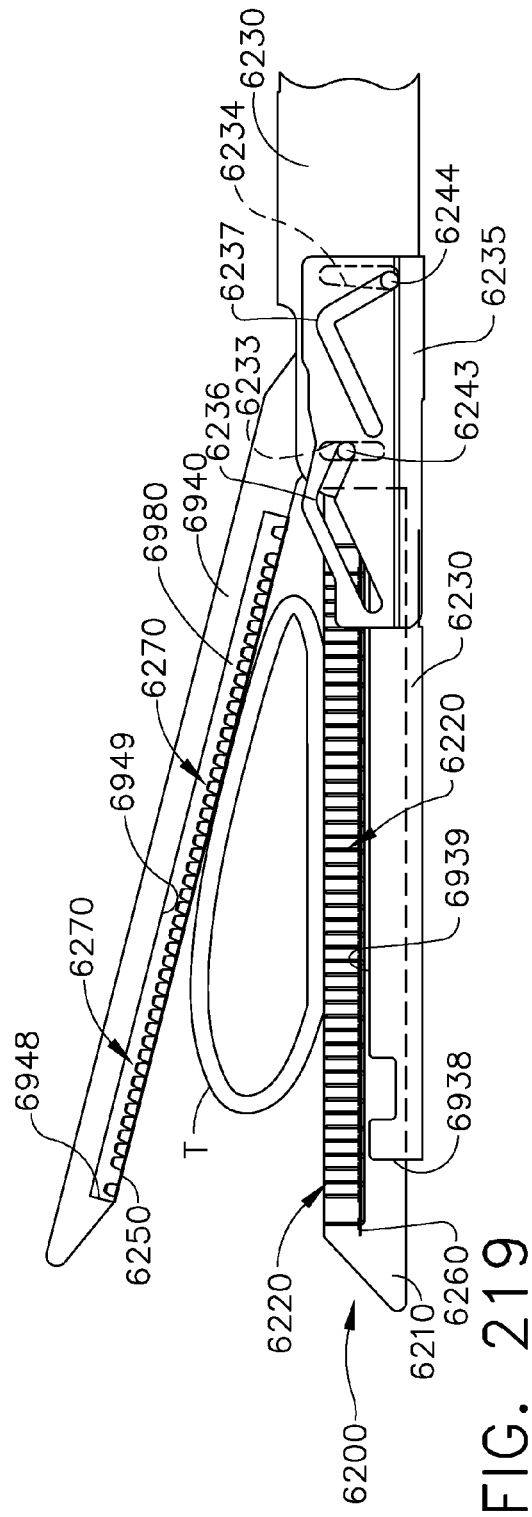
Figure 225:
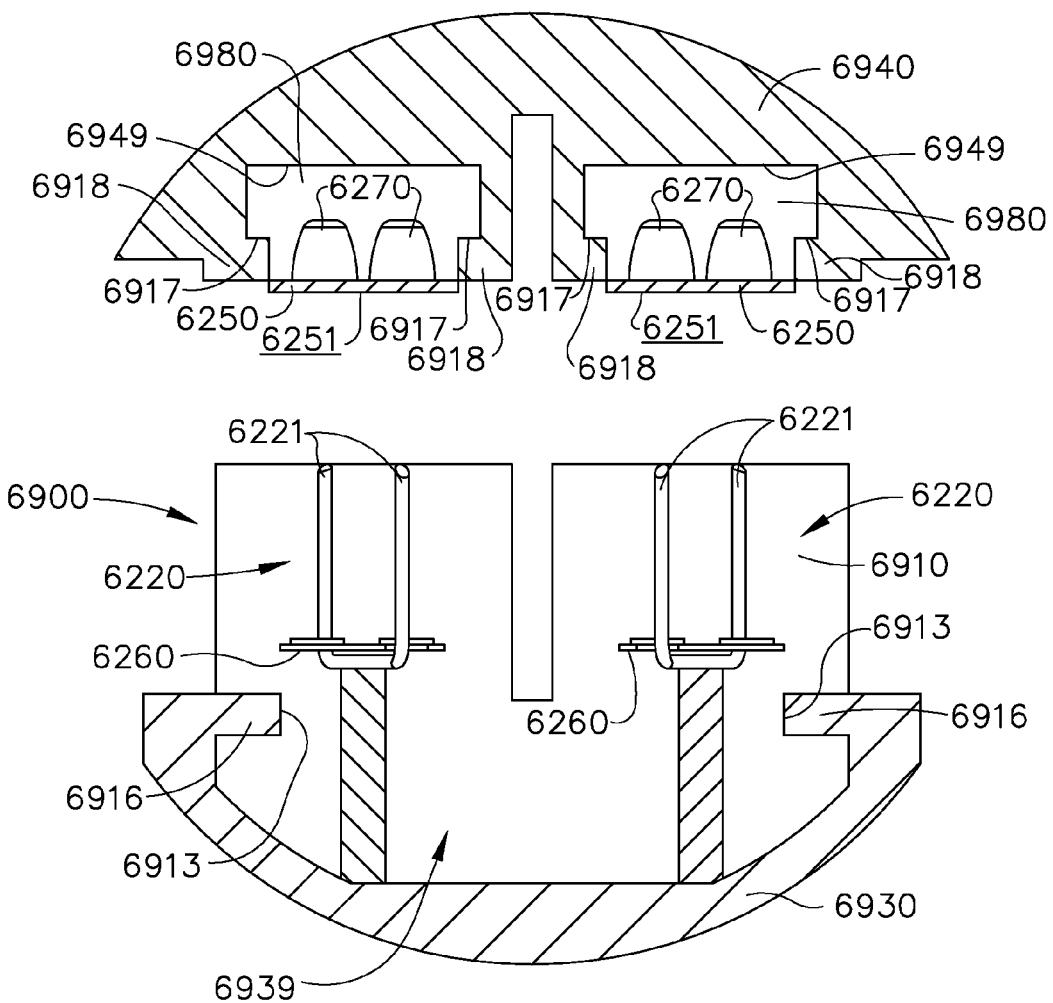
Figure 226:
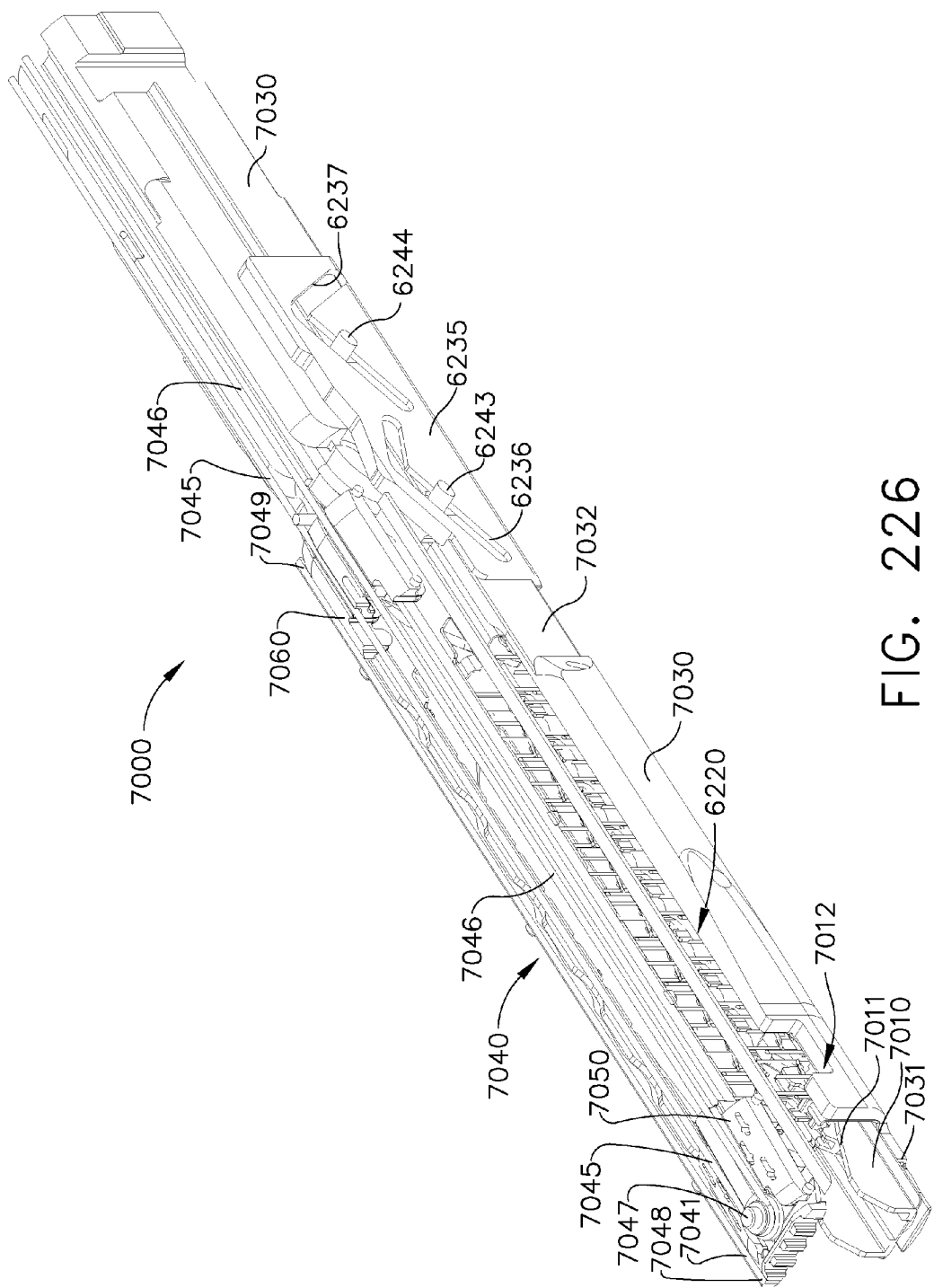
Figure 227:
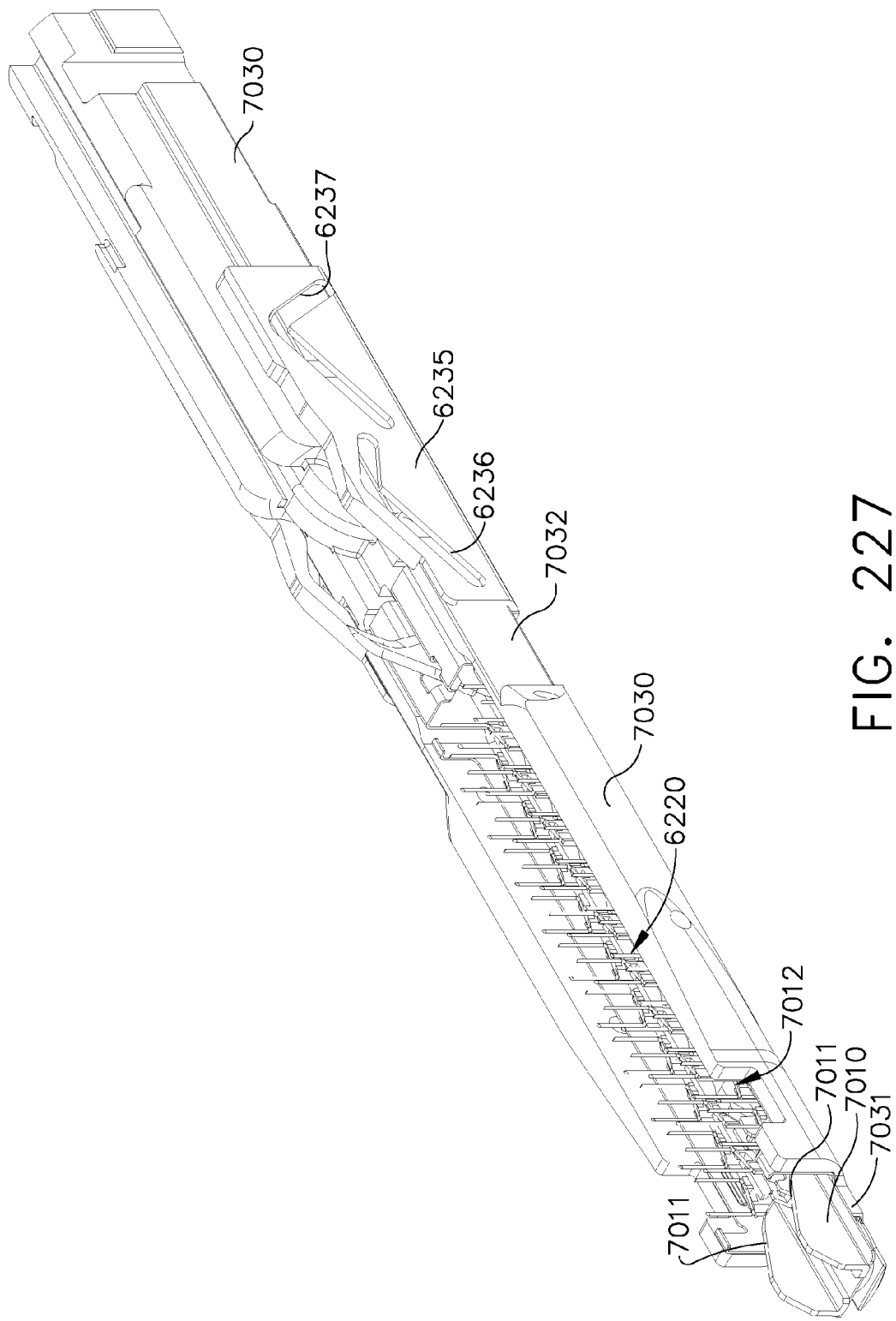
Figure 228:
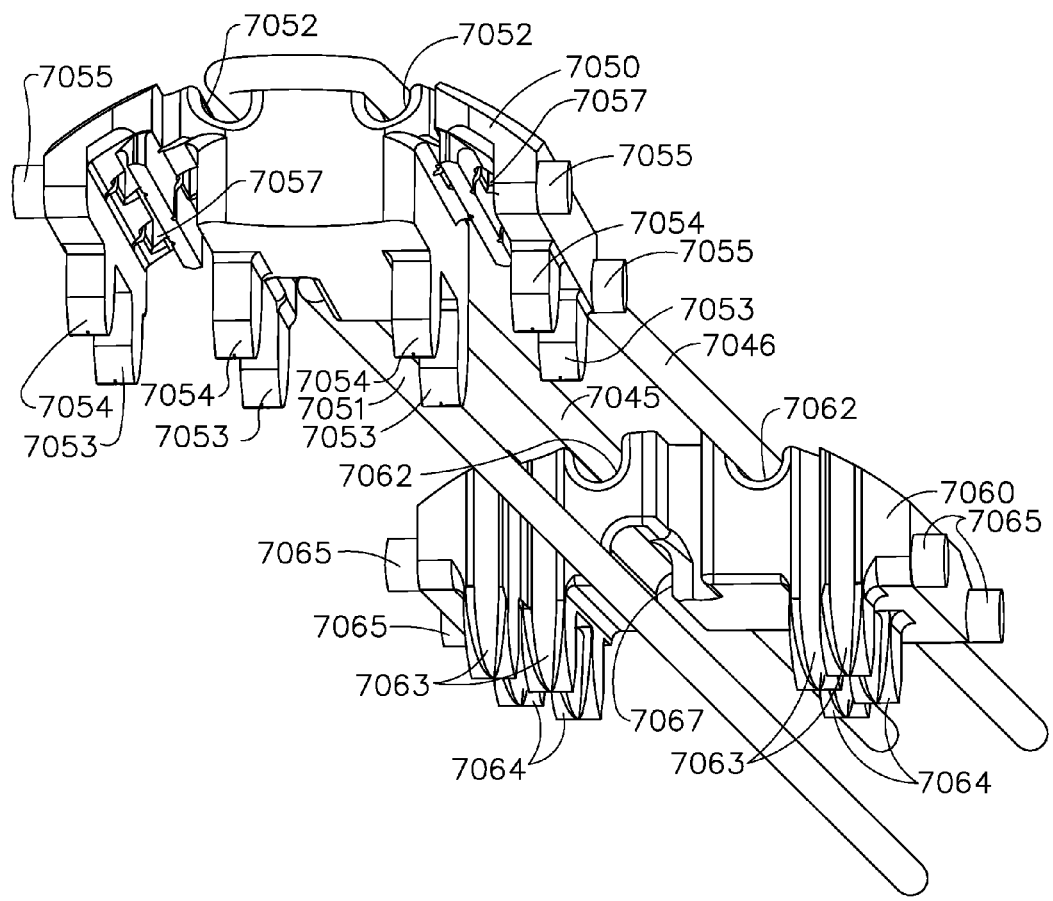
Figure 229:
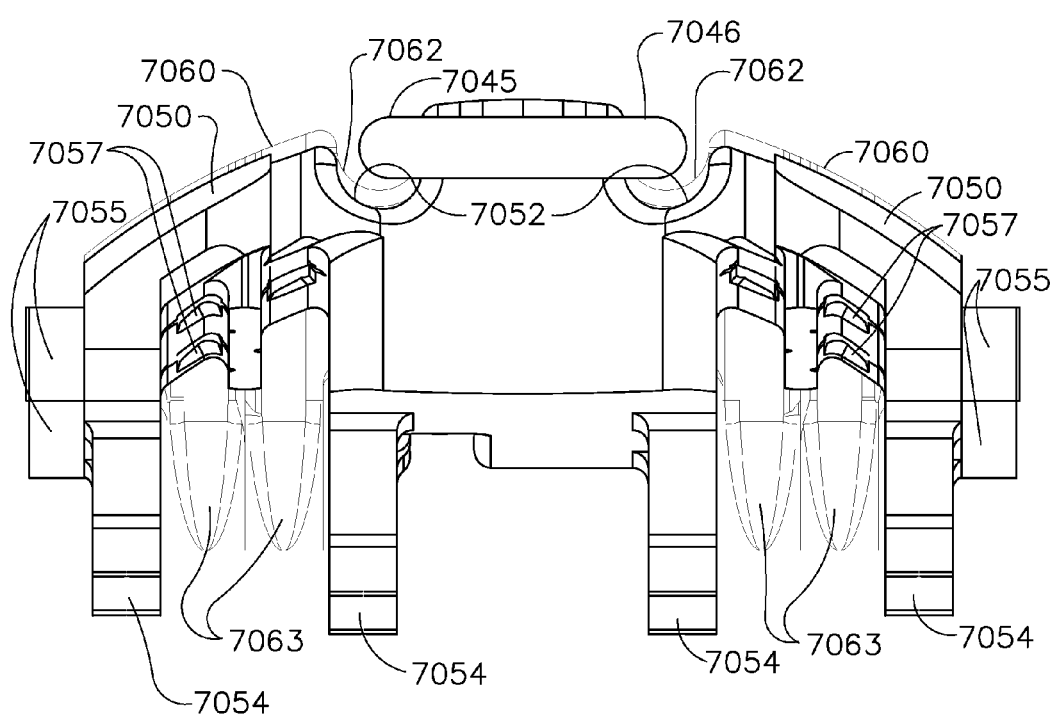
Figure 230:
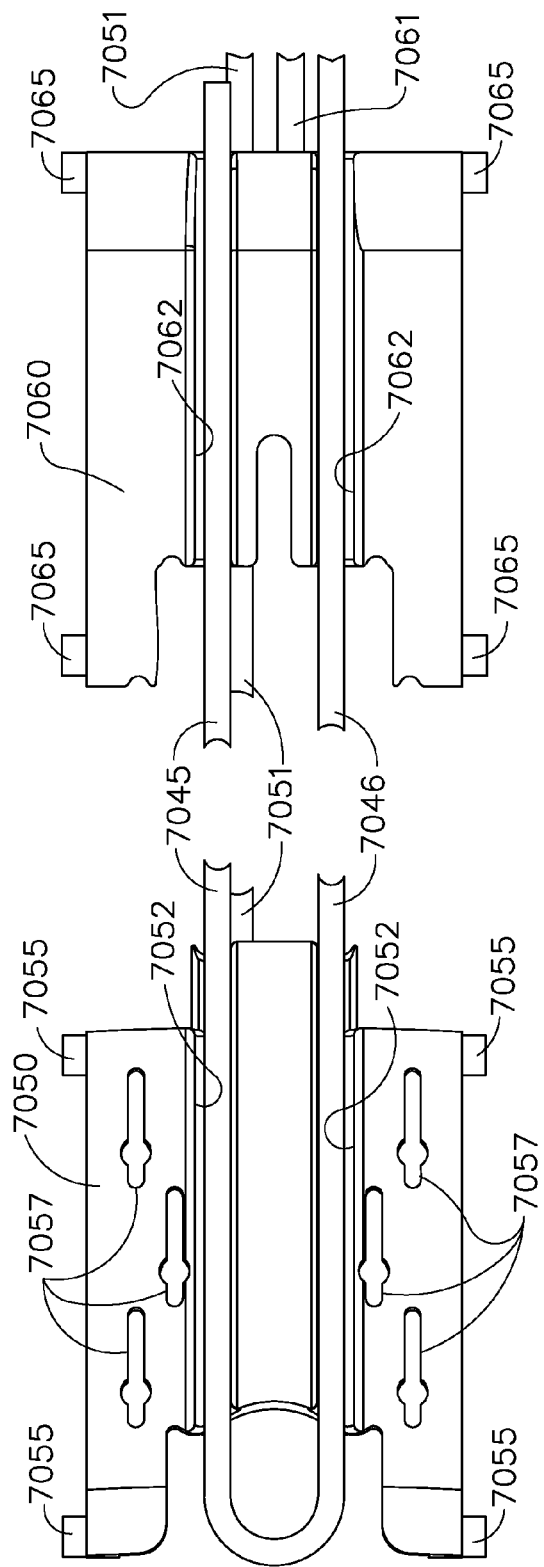
Figure 231:
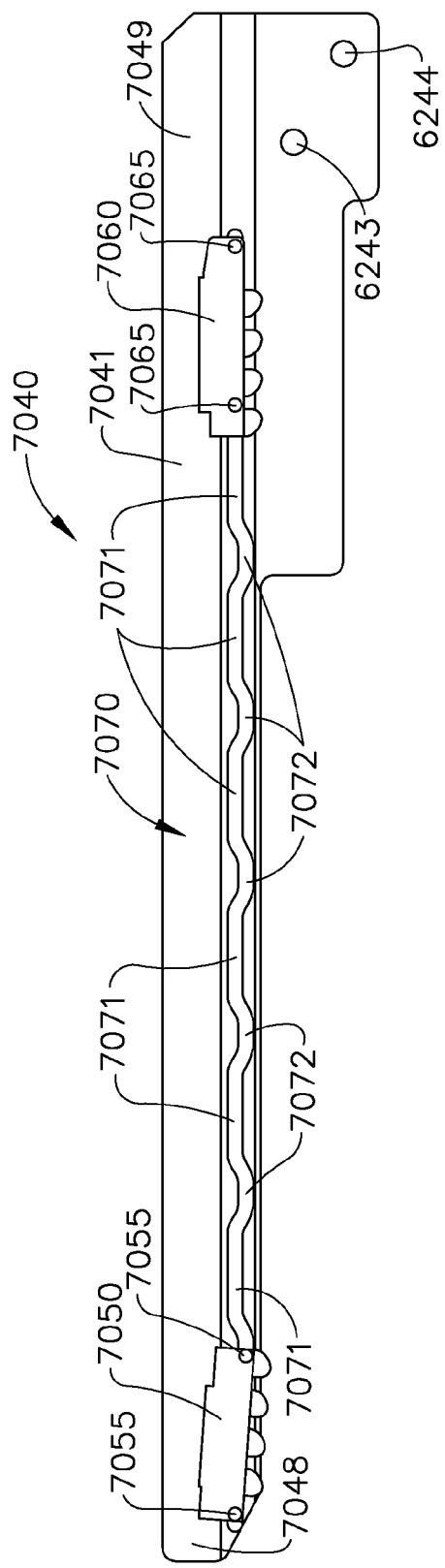
Figure 232:
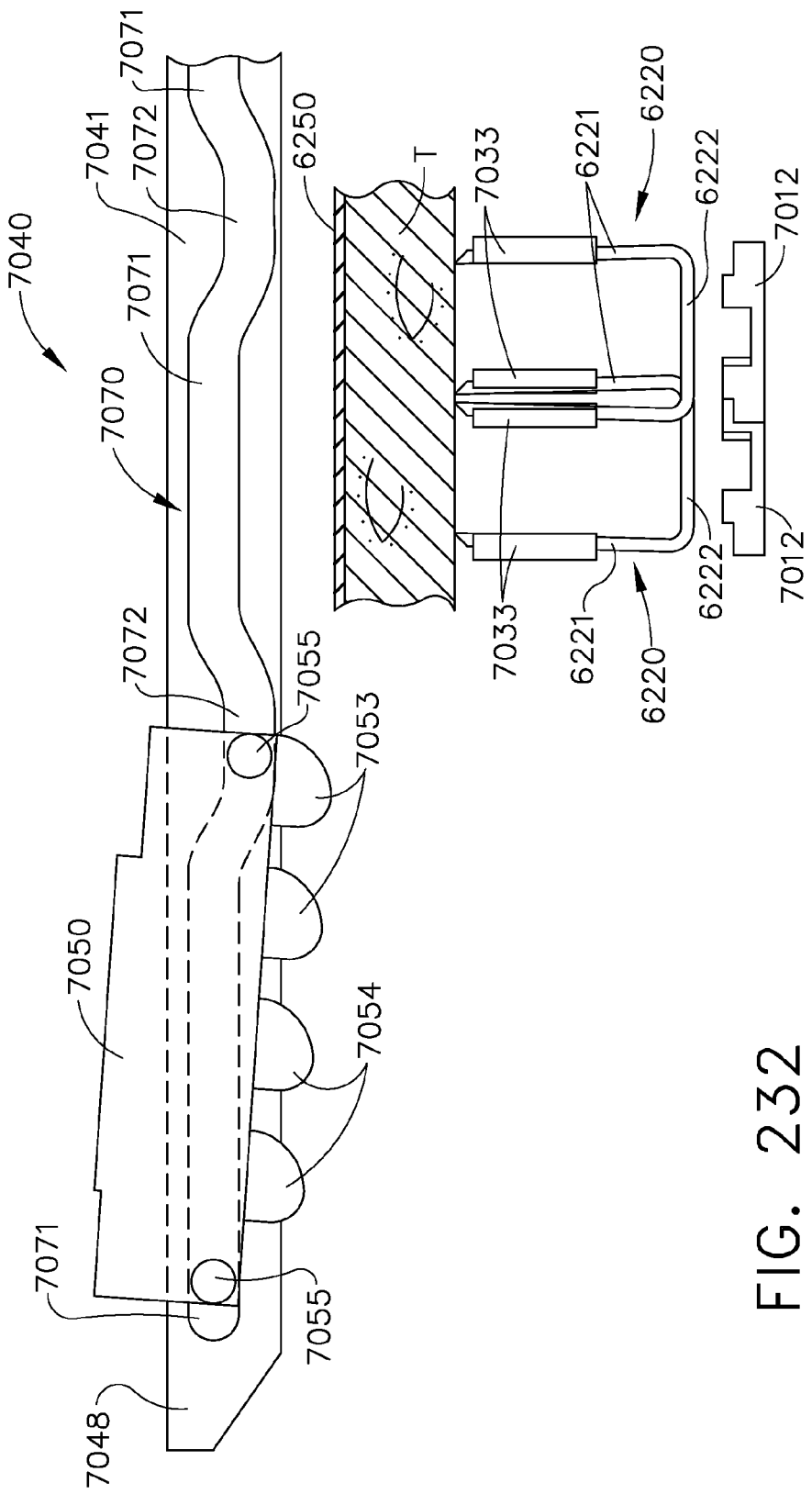
Figure 233:
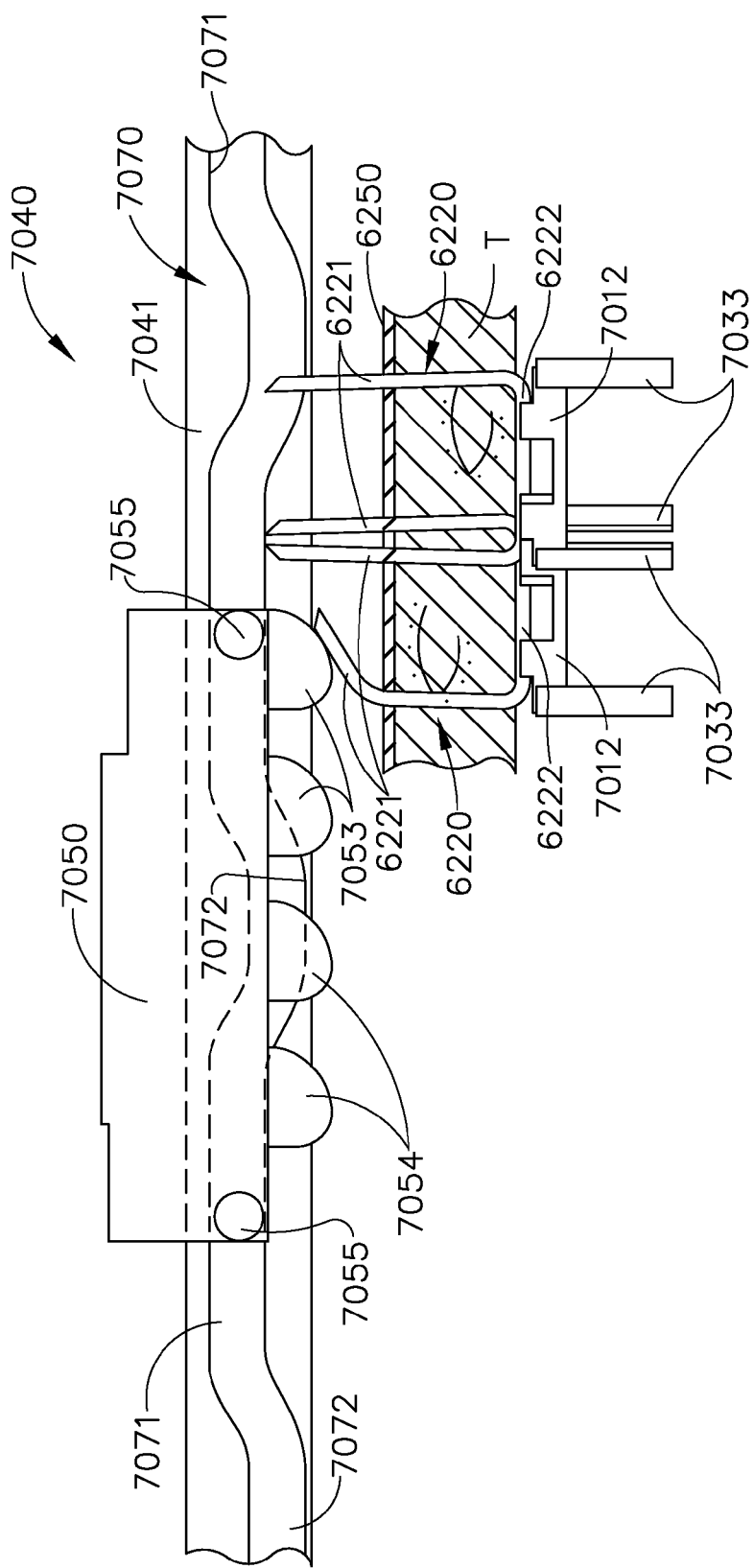
Figure 234:
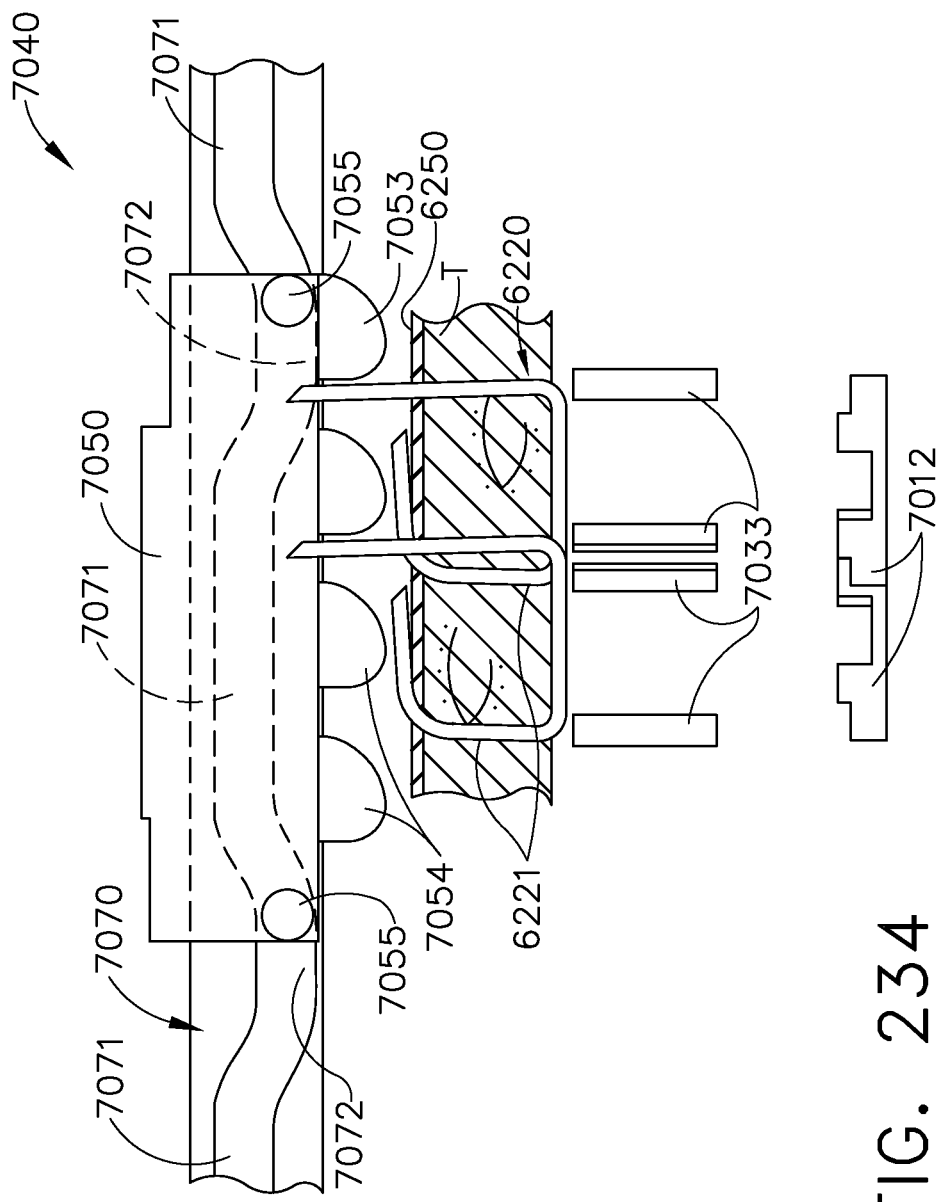
Figure 235:
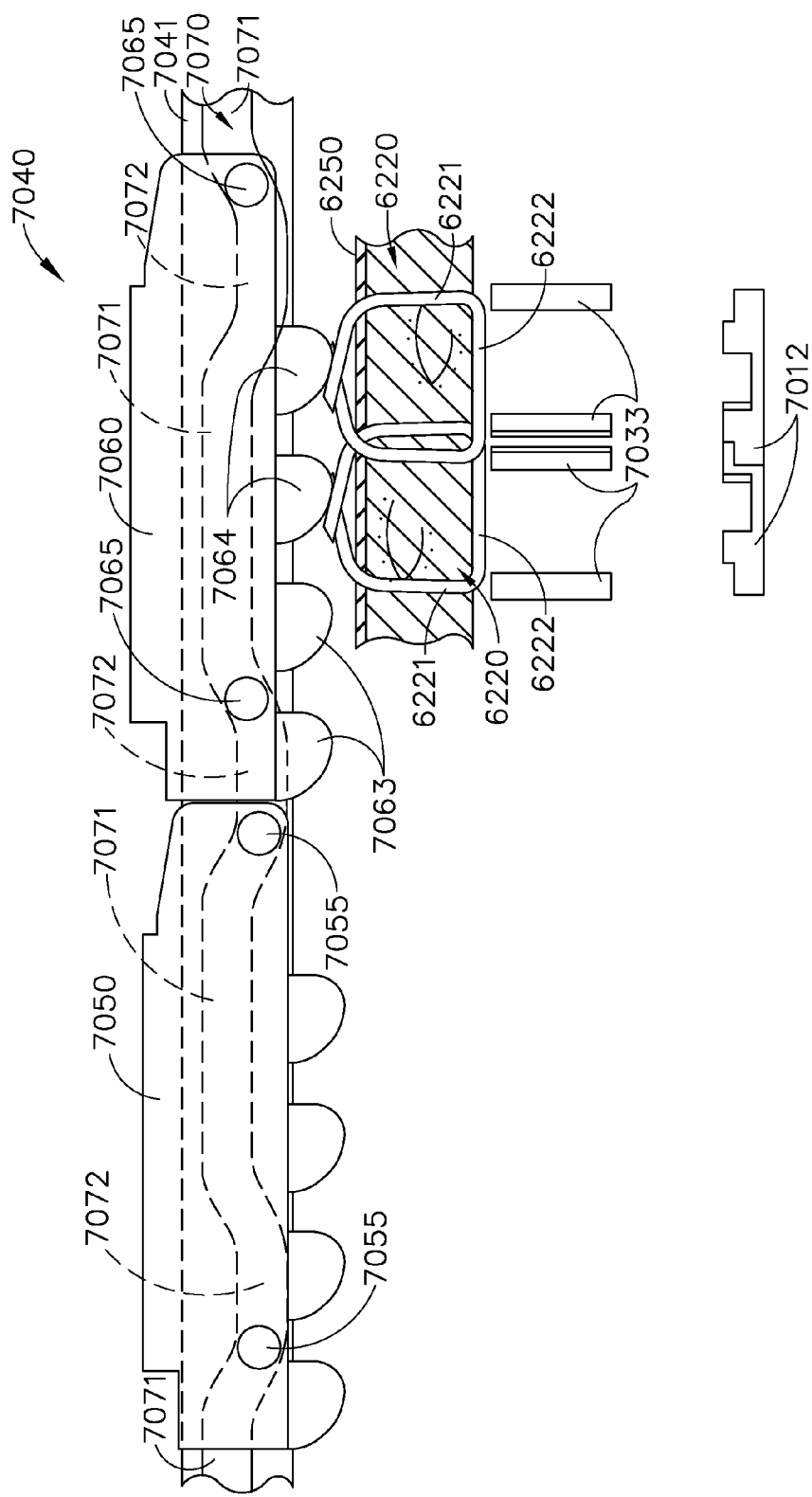
Figure 237:
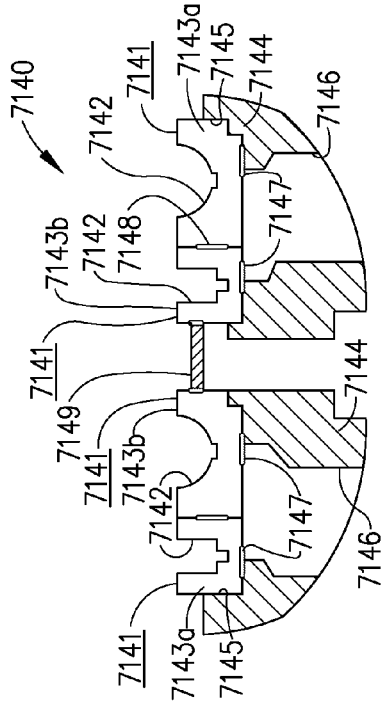
Figure 240:
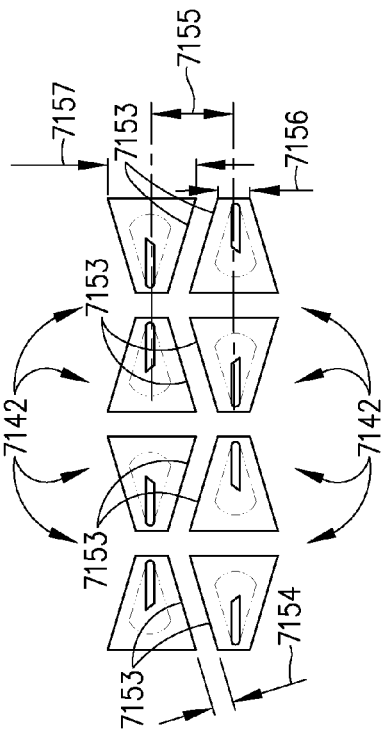
Figure 236:
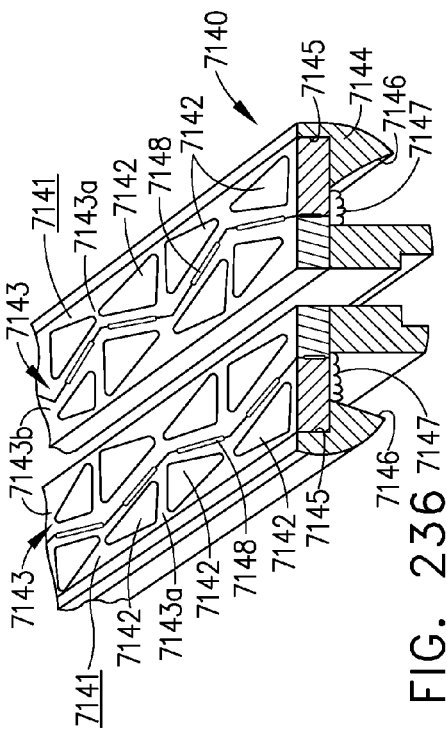
Figure 238:
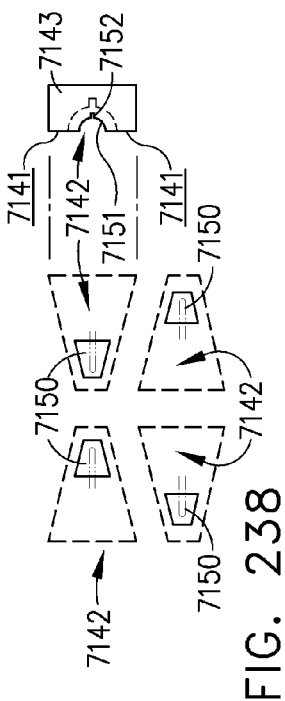
Figure 239:
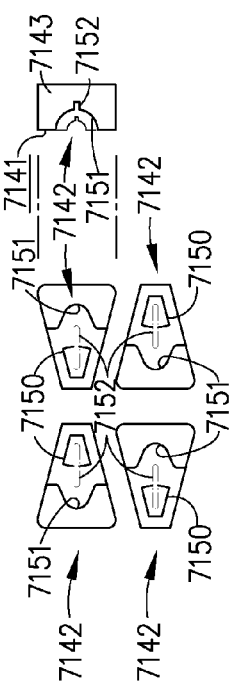

FIG. 114 is a cross-sectional view of another alternative embodiment of an end effector of a surgical stapler;

FIG. 115 is a cross-sectional view of an alternative embodiment of an end effector of a surgical stapler comprising a stepped anvil and a staple cartridge comprising a stepped cartridge body;

FIG. 116 is a cross-sectional view of another alternative embodiment of an end effector of a surgical stapler;

FIG. 117 is a cross-sectional view of an alternative embodiment of an end effector of a surgical stapler comprising inclined tissue-contacting surfaces;

FIG. 118 is a cross-sectional view of another alternative embodiment of an end effector of a surgical stapler comprising inclined tissue-contacting surfaces;

FIG. 119 is a cross-sectional view of an alternative embodiment of an end effector of a surgical stapler comprising a support insert configured to support a staple cartridge;

FIG. 120 is a cross-sectional view of an alternative embodiment of an end effector of a surgical stapler comprising a staple cartridge comprising a plurality of compressible layers;

FIG. 121 is a cross-sectional view of an alternative embodiment of an end effector of a surgical stapler comprising a staple cartridge comprising a stepped compressible cartridge body;

FIG. 122 is a cross-sectional view of another alternative embodiment of an end effector of a surgical stapler comprising a staple cartridge comprising a stepped compressible cartridge body;

FIG. 123 is a cross-sectional view of an alternative embodiment of an end effector of a surgical stapler comprising a staple cartridge comprising a curved tissue-contacting surface;

FIG. 124 is a cross-sectional view of an alternative embodiment of an end effector of a surgical stapler comprising a staple cartridge having an inclined tissue-contacting surface;

FIG. 125 is a cross-sectional view of a compressible staple cartridge comprising staples and at least one medicament stored therein;

FIG. 126 is a diagram illustrating the compressible staple cartridge of FIG. 125 after it has been compressed and the staples contained therein have been deformed;

FIG. 127 is a partial cut-away view of a staple cartridge in accordance with at least one embodiment;

FIG. 128 is a cross-sectional view of the staple cartridge of FIG. 127;

FIG. 129 is a perspective view of an implanted staple cartridge in accordance with at least one alternative embodiment;

FIG. 130 is a cross-sectional view of the implanted staple cartridge of FIG. 129;

FIG. 131 is a perspective view of an alternative embodiment of a staple cartridge comprising deformable members extending from an outer layer of the staple cartridge;

FIG. 132 is a perspective view of an alternative embodiment of a staple cartridge comprising an outer layer of the staple cartridge being assembled to an inner layer;

FIG. 133 is a cross-sectional view of an alternative embodiment of a staple cartridge comprising a plurality of staples, a compressible layer, and a pledget layer;

FIG. 134 is a perspective view of the pledget layer of FIG. 133;

FIG. 135 is a perspective view of a pledget singulated from the pledget layer of FIG. 133 and a staple aligned with a groove in the pledget;

FIG. 136 is a perspective view of two connected pledgets from the pledget layer of FIG. 133;

FIG. 137 is a perspective view of a pledget support frame of the pledget layer of FIG. 133 being removed from the singulated pledgets;

FIG. 138 is an exploded perspective view of an alternative embodiment of a compressible staple cartridge comprising staples therein and a system for driving the staples against an anvil;

FIG. 138A is a partial cut-away view of an alternative embodiment of the staple cartridge of FIG. 138;

FIG. 139 is a cross-sectional view of the staple cartridge of FIG. 138;

FIG. 140 is an elevational view of a sled configured to traverse the staple cartridge of FIG. 138 and move the staples to toward the anvil;

FIG. 141 is a diagram of a staple driver which can be lifted toward the anvil by the sled of FIG. 140;

FIG. 142 is a break-away view of a staple cartridge in accordance with at least one alternative embodiment comprising staples positioned within staple drivers;

FIG. 143 is a cross-sectional view of the staple cartridge of FIG. 142 positioned within a staple cartridge channel;

FIG. 144 is a cross-sectional view of the staple cartridge of FIG. 142 illustrating an anvil moved into a closed position and staples contained within the staple cartridge deformed by the anvil;

FIG. 145 is a cross-sectional view of the staple cartridge of FIG. 142 illustrating the staples moved upwardly toward the anvil;

FIG. 146 is a perspective view of an alternative embodiment of a staple cartridge comprising straps connecting the flexible sides of the staple cartridge;

FIG. 147 is a perspective view of a sled and cutting member assembly;

FIG. 148 is a diagram of the sled and cutting member assembly of FIG. 147 being used to lift the staples of the staple cartridge of FIG. 142;

FIG. 149 is a diagram illustrating a sled configured to engage and lift staples toward an anvil and a lock-out system configured to selectively permit the sled to move distally;

FIGS. 150A-150C illustrate the progression of a staple being inserted into a staple crown;

FIG. 151 is a cross-sectional view of a staple cartridge comprising a support pan or retainer;

FIG. 152 is a partial cross-sectional view of a compressible staple cartridge in accordance with at least one alternative embodiment;

FIG. 153 is a diagram illustrating the staple cartridge of FIG. 152 in an implanted condition;

FIG. 154 is a partial cut-away view of a compressible staple cartridge in accordance with at least one alternative embodiment;

FIG. 155 is a partial cross-sectional view of the staple cartridge of FIG. 154;

FIG. 156 is a diagram illustrating the staple cartridge of FIG. 154 in an implanted condition;

FIG. 157 is a partial cross-sectional view of a crushable staple cartridge in accordance with at least one alternative embodiment;

FIG. 158 is a partial cut-away view of a collapsible staple cartridge in accordance with at least one embodiment comprising a plurality of collapsible elements;

FIG. 159 is a perspective view of a collapsible element of FIG. 158 in an uncollapsed state;

FIG. 160 is a perspective view of the collapsible element of FIG. 159 in a collapsed state;

FIG. 161A is a partial cross-sectional view of an end effector of a surgical stapling instrument comprising a jaw, a staple cartridge channel positioned opposite the jaw, and a staple cartridge positioned within the staple cartridge channel, wherein the jaw comprises a retention matrix attached thereto;

FIG. 161B is a partial cross-sectional view of the end effector of FIG. 161A illustrating the jaw being moved toward the staple cartridge channel, the staple cartridge being compressed by the anvil and the retention matrix, and a staple at least partially extending through tissue positioned intermediate the retention matrix and the staple cartridge;

FIG. 161C is a partial cross-sectional view of the end effector of FIG. 161A illustrating the jaw in a final position and the retention matrix engaged with the staple of FIG. 161B;

FIG. 161D is a partial cross-sectional view of the end effector of FIG. 161A illustrating the jaw and the staple cartridge channel being moved away from the implanted staple cartridge and retention matrix;

FIG. 162 is a perspective view of a retention aperture of a retention matrix in accordance with at least one alternative embodiment comprising a plurality of retention members configured to engage a fastener leg extending therethrough;

FIG. 163 is a perspective view of a retention aperture of a retention matrix in accordance with at least one alternative embodiment comprising six retention members;

FIG. 164 is a perspective view of a retention aperture of a retention matrix in accordance with at least one alternative embodiment comprising eight retention members;

FIG. 165 is a perspective view of a retention aperture of a retention matrix in accordance with at least one alternative embodiment comprising a plurality of retention members configured to engage a fastener leg extending therethrough;

FIG. 166 is a perspective view of a retention aperture of a retention matrix in accordance with at least one alternative embodiment comprising six retention members;

FIG. 167 is a perspective view of a retention aperture of a retention matrix in accordance with at least one alternative embodiment comprising eight retention members;

FIG. 168 is a perspective view of a retention aperture of a retention matrix in accordance with at least one alternative embodiment comprising a plurality of retention members that have been stamped from a sheet of metal;

FIG. 169 is a perspective view of a retention aperture of a retention matrix in accordance with at least one alternative embodiment comprising a plurality of apertures extending around the perimeter of the retention aperture;

FIG. 170 is a top view of a retention aperture of a retention matrix in accordance with at least one alternative embodiment;

FIG. 171 is a top view of a retention aperture of a retention matrix in accordance with at least one alternative embodiment;

FIG. 172 is a top view of a retention aperture of a retention matrix in accordance with at least one alternative embodiment;

FIG. 173 is a top view of a retention aperture of a retention matrix in accordance with at least one alternative embodiment;

FIG. 174 is a top view of a retention aperture of a retention matrix in accordance with at least one alternative embodiment;

FIG. 175 is a top view of a retention aperture of a retention matrix comprising a retention tab extending into the retention aperture in accordance with at least one embodiment;

FIG. 176 is a top view of a retention aperture of a retention matrix comprising a retention tab extending into the retention aperture in accordance with at least one alternative embodiment;

FIG. 177 is a perspective view of a fastening system comprising a plurality of staples, a retention matrix engaged with the staples, and an alignment matrix configured to align the staples;

FIG. 178 is a perspective view of the retention matrix of FIG. 177;

FIG. 179 is a perspective view of the alignment matrix of FIG. 177;

FIG. 180 is a partial top view of the retention matrix of FIG. 177 engaged with the staples of FIG. 177;

FIG. 181 is a partial bottom view of the retention matrix of FIG. 177 engaged with the staples of FIG. 177;

FIG. 182 is a partial elevational view of the fastening system of FIG. 177;

FIG. 183 is a partial perspective view of the fastening system of FIG. 177;

FIG. 184 is a partial cross-sectional view of the retention matrix of FIG. 177 engaged with the staples of FIG. 177;

FIG. 185 is a partial cross-sectional view of the fastening system of FIG. 177;

FIG. 186 is a perspective view of the fastening system of FIG. 177 further comprising protective caps assembled to the legs of the staples;

FIG. 187 is a bottom perspective view of the fastening system arrangement of FIG. 186;

FIG. 188 is a partial perspective view of the fastening system arrangement of FIG. 186;

FIG. 189 is a partial cross-sectional view of the fastening system arrangement of FIG. 186;

FIG. 190 is an elevational view of an end effector in accordance with at least one embodiment comprising a jaw in an open position, a retention matrix and a plurality of protective caps positioned in the jaw, and a staple cartridge positioned in a staple cartridge channel;

FIG. 191 is an elevational view of the end effector of FIG. 190 in a closed position;

FIG. 192 is an elevational view of the end effector of FIG. 190 in a fired position;

FIG. 193 is an elevational view of the retention matrix and protective caps of FIG. 190 assembled to the staple cartridge of FIG. 190;

FIG. 194 is a detail view of the arrangement of FIG. 193;

FIG. 195 is an elevational view of the end effector of FIG. 190 illustrating the jaw in an open position with thinner tissue positioned between the retention matrix and the staple cartridge;

FIG. 196 is an elevational view of the end effector of FIG. 190 illustrating the jaw in a closed position against the thinner tissue of FIG. 195;

FIG. 197 is an elevational view of the end effector of FIG. 190 illustrating the jaw in a fired position to capture the thinner tissue of FIG. 195 between the retention matrix and the staple cartridge;

FIG. 198 is an elevational view of the retention matrix and the protective caps of FIG. 190 assembled to the staple cartridge of FIG. 190 with the thin tissue of FIG. 195 positioned therebetween;

FIG. 199 is a detail view of the arrangement of FIG. 198;

FIG. 200 is a cross-sectional view of a protective cap positioned on the tip of a staple leg in accordance with at least one alternative embodiment;

FIG. 201 is a perspective view of a plurality of protective caps embedded within a sheet of material;

FIG. 202 is a perspective view of a jaw comprising a plurality of recesses configured to receive a plurality of protective caps therein;

FIG. 203 is a detail view of a portion of a jaw comprising a sheet covering the protective caps positioned within the jaw of FIG. 202;

FIG. 204 is a cross-sectional view of a protective cap positioned on a tip of a staple leg in accordance with at least one alternative embodiment wherein the protective cap comprises an interior forming surface;

FIG. 205 is another cross-sectional view of the protective cap of FIG. 204 illustrating the staple leg being deformed against the forming surface;

FIG. 206 is a top view of an alternative embodiment of a retention matrix comprising a plurality of connected matrix elements;

FIG. 207 is a top view of an alternative embodiment of a retention matrix comprising a plurality of connected matrix elements;

FIG. 208 is a top view of an alternative embodiment of a retention matrix comprising a plurality of connected matrix elements;

FIG. 209 is a top view of an alternative embodiment of an array of retention matrices comprising a plurality of connected matrix elements;

FIG. 210 is a top view of an alternative embodiment of a retention matrix comprising a plurality of connected matrix elements;

FIG. 211 is a partial exploded view of a jaw comprising a retention matrix including a compressible cover;

FIG. 212 is a detail view of the retention matrix of FIG. 211;

FIG. 213 is a partial cross-sectional view of a fastening system comprising a retention matrix including a compressible layer and a plurality of cells encapsulating one or more medicaments;

FIG. 214 is a diagram illustrating staple legs which have pierced the cells of FIG. 213 as they are being engaged with the retention matrix;

FIG. 215 is a partial cross-sectional view of a fastening system comprising a retention matrix including a compressible layer;

FIG. 216 is an elevational view of a fastener cartridge insertion assembly comprising a holder, a first fastener cartridge, and a second fastener cartridge;

FIG. 217 is an elevational view of an end effector of a surgical stapler comprising a first jaw and a second jaw, the second jaw being illustrated in an open configuration;

FIG. 218 is an elevational view of the end effector of FIG. 217 illustrating the second jaw in a closed configuration and the fastener cartridge insertion assembly of FIG. 216 being used to load the first jaw with the first cartridge and the second jaw with the second cartridge;

FIG. 219 is an elevational view of the loaded end effector of FIG. 218 illustrating the cartridge insertion assembly removed from the end effector, the second jaw in an open configuration once again, and tissue positioned intermediate the first jaw and the second jaw;

FIG. 220 is an elevational view of the loaded end effector of FIG. 219 in a fired configuration;

FIG. 221 is an elevational view of the first cartridge and the second cartridge in an implanted condition;

FIG. 222 is an elevational view of the end effector of FIG. 217 illustrating a portion of the first cartridge still engaged with the first jaw in accordance with at least one embodiment;

FIG. 223 is an elevational view of an alternative embodiment of a fastener cartridge insertion assembly comprising a holder, a first fastener cartridge, and a second fastener cartridge;

FIG. 224 is an elevational view of the fastener cartridge insertion assembly of FIG. 223 being used to load a first jaw of an end effector with the first cartridge and a second jaw with the second cartridge;

FIG. 225 is a cross-sectional view of the loaded end effector of FIG. 224;

FIG. 226 is a perspective view of a surgical stapler comprising a bottom jaw and a top jaw in accordance with at least one embodiment illustrated with portions of the surgical stapler removed;

FIG. 227 is a perspective view of the surgical stapler of FIG. 226 with the top jaw removed;

FIG. 228 is a perspective view of a slidable anvil system of the top jaw of the surgical stapler of FIG. 226 comprising a first slidable anvil and a second slidable anvil;

FIG. 229 is an end view of the slidable anvil system of FIG. 228;

FIG. 230 is a top view of the slidable anvil system of FIG. 228;

FIG. 231 is a diagram illustrating the slidable anvil system of FIG. 228 in an unfired condition;

FIG. 232 is a diagram illustrating the first slidable anvil of the slidable anvil system of FIG. 228 in an unfired position and staples positioned within the bottom jaw in an undeployed position;

FIG. 233 is a diagram illustrating the staples in the bottom jaw in a deployed configuration and the first slidable anvil of FIG. 232 being pulled proximally to deform a first group of staple legs of the staples;

FIG. 234 is a diagram illustrating the first group of staples of FIG. 233 deformed to a fully deformed state;

FIG. 235 is a diagram illustrating the second slidable anvil of the slidable anvil system of FIG. 228 being pushed distally to deform a second group of staple legs;

FIG. 236 is a partial perspective view of an anvil comprising a plurality of forming pockets in at least one embodiment;

FIG. 237 is a cross-sectional end view of the anvil of FIG. 236;

FIG. 238 is a diagram illustrating a first step in manufacturing the forming pockets of FIG. 236;

FIG. 239 is a diagram illustrating a second step in manufacturing the forming pockets of FIG. 236;

FIG. 240 is a top view of the forming pocket arrangement of the anvil of FIG. 236;

FIG. 241 is a diagram illustrating a first step of a manufacturing process for producing an anvil;

FIG. 242 is a diagram illustrating a second step in the manufacturing process of FIG. 241; and FIG. 243 is a diagram illustrating a third step in the manufacturing process of FIG. 241.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

The Applicant of the present application also owns the U.S. patent applications identified below which were filed on even date herewith and which are each herein incorporated by reference in their respective entirety:

U.S. patent application Ser. No. 12/894,360, now U.S. Patent Publication No. 2012/0080484 A1, entitled "Surgical Stapling Instrument With a Variable Staple Forming System";

U.S. patent application Ser. No. 12/894,322, now U.S. Patent Publication No. 2012/0080501 A1, entitled "Surgical Stapling Instrument With Interchangeable Staple Cartridge Arrangements";

U.S. patent application Ser. No. 12/894,351, now U.S. Patent Publication No. 2012/0080502 A1, entitled "Surgical Cutting and Fastening Instruments With Separate and Distinct Fastener Deployment and Tissue Cutting Systems";

U.S. patent application Ser. No. 12/894,339, now U.S. Patent Publication No. 2012/0080500 A1, entitled "Surgical Stapling Instrument With Compact Articulation Control Arrangement";

U.S. patent application Ser. No. 12/894,327, now U.S. Patent Publication No. 2012/0080499 A1, entitled "Jaw Closure Arrangements For Surgical Instruments";

U.S. patent application Ser. No. 12/894,311, now U.S. Patent Publication No. 2012/0080496 A1, entitled "Surgical Instruments With Reconfigurable Shaft Segments";

U.S. patent application Ser. No. 12/894,340, now U.S. Patent Publication No. 2012/0080482 A1, entitled "Surgical Staple Cartridges Supporting Non-Linearly Arranged Staples and Surgical Stapling Instruments With Common Staple-Forming Pockets";

U.S. patent application Ser. No. 12/894,350, now U.S. Patent Publication No. 2012/0080478 A1, entitled "Surgical Staple Cartridges With Detachable Support Structures and Surgical Stapling Instruments With Systems For Preventing Actuation Motions When a Cartridge is Not Present";

U.S. patent application Ser. No. 12/894,338, now U.S. Patent Publication No. 2012/0080481 A1, entitled "Implantable Fastener Cartridge Having a Non-Uniform Arrangement";

U.S. patent application Ser. No. 12/894,369, now U.S. Patent Publication No. 2012/0080344 A1, entitled "Implantable Fastener Cartridge Comprising a Support Retainer";

U.S. patent application Ser. No. 12/894,312, now U.S. Patent Publication No. 2012/0080479 A1, entitled "Implantable Fastener Cartridge Comprising Multiple Layers";

U.S. patent application Ser. No. 12/894,377, now U.S. Patent Publication No. 2012/0080334 A1, entitled "Selectively Orientable Implantable Fastener Cartridge";

U.S. patent application Ser. No. 12/894,383, now U.S. Patent Publication No. 2012/0080345 A1, entitled "Implantable Fastener Cartridge Comprising Bioabsorbable Layers";

U.S. patent application Ser. No. 12/894,389, now U.S. Patent Publication No. 2012/0080335 A1, entitled "Compressible Fastener Cartridge";

U.S. patent application Ser. No. 12/894,345, now U.S. Patent Publication No. 2012/0080483 A1, entitled "Fasteners Supported By a Fastener Cartridge Support";

U.S. patent application Ser. No. 12/894,306, now U.S. Patent Publication No. 2012/0080332 A1 entitled "Collapsible Fastener Cartridge";

U.S. patent application Ser. No. 12/894,318, now U.S. Patent Publication No. 2012/0080480 A1, entitled "Fastener System Comprising a Plurality of Connected Retention Matrix Elements";

U.S. patent application Ser. No. 12/894,361, now U.S. Patent Publication No. 2012/0080333 A1, entitled "Fastener System Comprising a Retention Matrix";

U.S. patent application Ser. No. 12/894,367, now U.S. Patent Publication No. 2012/0080485 A1, entitled "Fastening Instrument For Deploying a Fastener System Comprising a Retention Matrix";

U.S. patent application Ser. No. 12/894,388, now U.S. Patent Publication No. 2012/0080487 A1, entitled "Fastener System Comprising a Retention Matrix and a Cover"; and U.S. patent application Ser. No. 12/894,376, now U.S. Patent Publication No. 2012/0080486 A1, entitled "Fastener System Comprising a Plurality of Fastener Cartridges".

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
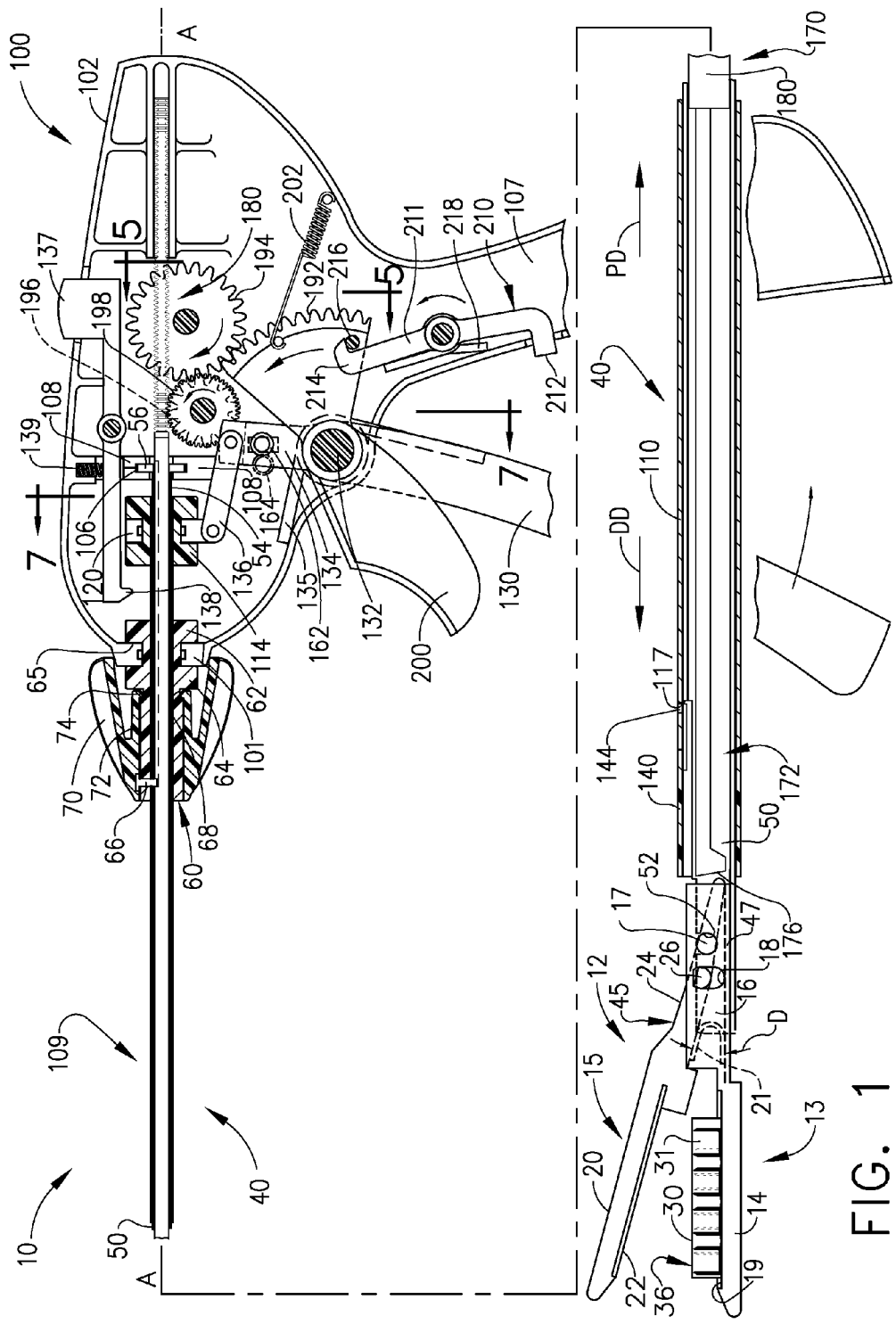
FIG. 1 is a cross-sectional view of a surgical instrument embodiment of the present invention.
Figure 1A:
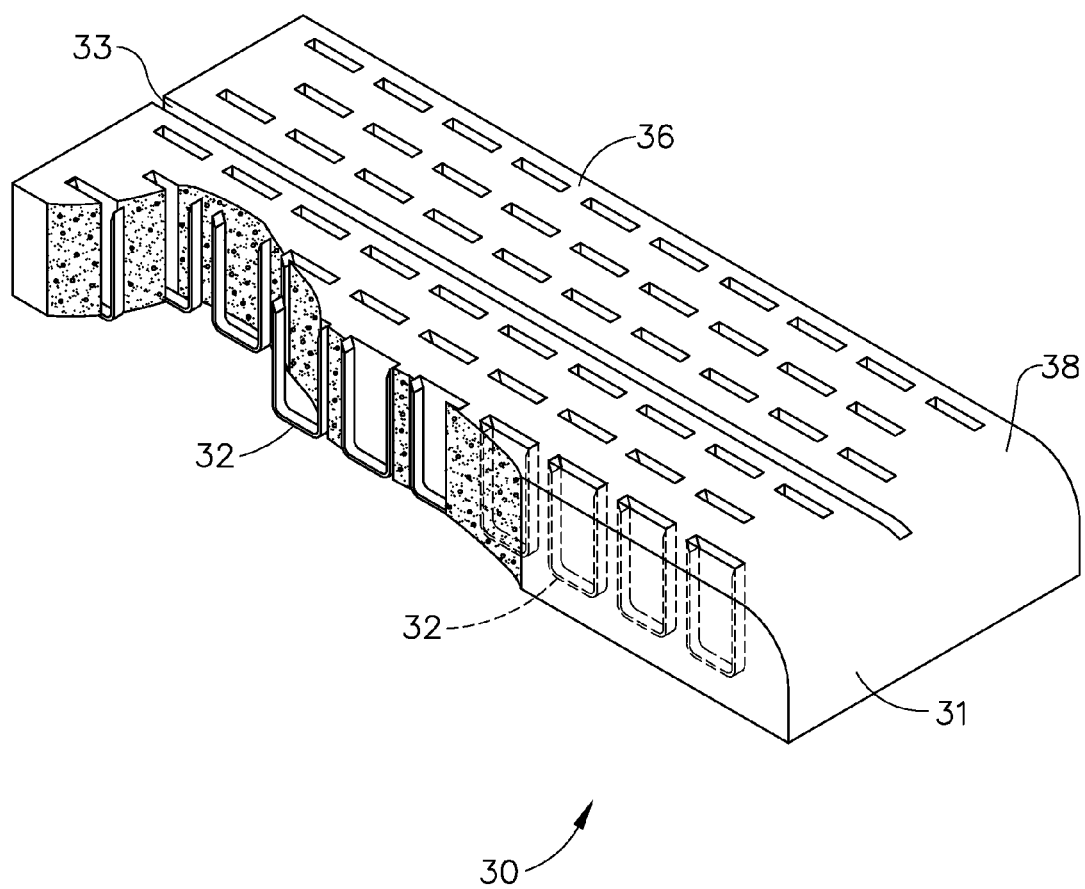
FIG. 1A is a perspective view of one embodiment of an implantable staple cartridge of the present invention.

Turning to the Drawings wherein like numerals denote like components throughout the several views, FIG. 1 depicts a surgical instrument 10 that is capable of practicing several unique benefits of the present invention. The surgical stapling instrument 10 is designed to manipulate and/or actuate various forms and sizes of end effectors 12 that are operably attached thereto. In the embodiment depicted in FIGS. 1 and 2, for example, the end effector 12 includes an elongated channel 14 that forms a lower jaw 13 of the end effector 12. The elongated channel 14 is configured to support an "implantable" staple cartridge 30 and also movably support an anvil 20 that functions as an upper jaw 15 of the end effector 12.

In various embodiments, the elongated channel 14 may be fabricated from, for example, 300 & 400 Series, 17-4 & 17-7 stainless steel, titanium, etc. and be formed with spaced side walls 16. The anvil 20 may be fabricated from, for example, 300 & 400 Series, 17-4 & 17-7 stainless steel, titanium, etc. and have a staple forming undersurface, generally labeled as 22 that has a plurality of staple forming pockets 23 formed therein. See FIGS. 1B-1E. In addition, the anvil 20 has a bifurcated ramp assembly 24 that protrudes proximally therefrom. An anvil pin 26 protrudes from each lateral side of the ramp assembly 24 to be received within a corresponding slot or opening 18 in the side walls 16 of the elongated channel 14 to facilitate its movable or pivotable attachment thereto.

Various forms of implantable staple cartridges may be employed with the various embodiments of the surgical instruments disclosed herein. Specific staple cartridge configurations and constructions will be discussed in further detail below. However, in the embodiment depicted in FIGS. 1A and 9-14, an implantable staple cartridge 30 is shown. In at least one embodiment, the staple cartridge 30 has a body portion 31 that consists of a compressible hemostat material such as, for example, oxidized regenerated cellulose ("ORC") or a bio-absorbable foam in which lines of unformed metal staples 32 are supported. In at least some embodiments, in order to prevent the staple from being affected and the hemostat material from being activated during the introduction and positioning process, the entire cartridge may be coated or wrapped in a biodegradable film 38 such as a polydioxanon film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The body 31 of staple cartridge 30 is sized to be removably supported within the elongated channel 14 as shown such that each staple 32 therein is aligned with corresponding staple forming pockets 23 in the anvil when the anvil 20 is driven into forming contact with the staple cartridge 30.

In use, once the end effector 12 has been positioned adjacent the target tissue, the end effector 12 is manipulated to capture or clamp the target tissue between an upper face 36 of the staple cartridge 30 and the staple forming surface 22 of the anvil 20. The staples 32 are formed by moving the anvil 20 in a path that is substantially parallel to the elongated channel 14 to bring the staple forming surface 22 and, more particularly, the staple forming pockets 23 therein into substantially simultaneous contact with the upper face 36 of the staple cartridge 30. As the anvil 20 continues to move into the staple cartridge 30, the legs 34 of the staples 32 contact a corresponding staple forming pocket 23 in anvil 20 which serves to bend the staple legs 34 over to form the staples 32 into a "B shape". Further movement of the anvil 20 toward the elongated channel 14 will further compress and form the staples 32 to a desired final formed height "FH".

The above-described staple forming process is generally depicted in FIGS. 1B-1E. For example, FIG. 1B illustrates the end effector 12 with target tissue "T" between the anvil 20 and the upper face 36 of the implantable staple cartridge 30. FIG. 1C illustrates the initial clamping position of the anvil 20 wherein the anvil has 20 been closed onto the target tissue "T" to clamp the target tissue "T" between the anvil 20 and the upper face 36 of the staple cartridge 30. FIG. 1D illustrates the initial staple formation wherein the anvil 20 has started to compress the staple cartridge 30 such that the legs 34 of the staples 32 are starting to be formed by the staple forming pockets 23 in the anvil 20. FIG. 1E illustrates the staple 32 in its final formed condition through the target tissue "T" with the anvil 20 removed for clarity purposes. Once the staples 32 have been formed and fastened to the target tissue "T", the surgeon will move the anvil 20 to the open position to enable the cartridge body 31 and the staples 32 to remain affixed to the target tissue while the end effector 12 is being withdrawn from the patient. The end effector 12 forms all of the staples simultaneously as the two jaws 13, 15 are clamped together. The remaining "crushed" body materials 31 act as both a hemostat (the ORC) and a staple line reinforcement (PGA, PDS or any of the other film compositions mentioned above 38). Also, since the staples 32 never have to leave the cartridge body 31 during forming, the likelihood of the staples 32 being malformed during forming is minimized. As used herein the term "implantable" means that, in addition to the staples, the cartridge body materials that support the staples will also remain in the patient and eventually be absorbed by the patient's body. Such implantable staple cartridges are distinguishable from prior cartridge arrangements that remain with the end effector and are removed therewith. Those "removable" staple cartridges typically include staple driver components and therefore may be much larger than the end effectors of the present invention that are designed to be employed in connection with certain unique and novel implantable staple cartridge embodiments of the present invention.

In various implementations, the end effector 12 is configured to be coupled to an elongated shaft assembly 40 that protrudes from a handle assembly 100. The end effector 12 (when closed) and the elongated shaft assembly 40 may have similar cross-sectional shapes and be sized to operably pass through a trocar tube or working channel in another form of access instrument. As used herein, the term "operably pass" means that the end effector and at least a portion of the elongated shaft assembly may be inserted through or passed through the channel or tube opening and can be manipulated therein as needed to complete the surgical stapling procedure. In some embodiments, when in a closed position, the jaws 13 and 15 of the end effector 12 may provide the end effector with a roughly circular cross-sectional shape that facilitates its passage through a circular passage/opening. However, the end effectors of various embodiments of the present invention, as well as the elongated shaft assembly embodiments, could conceivably be provided with other cross-sectional shapes that could otherwise pass through access passages and openings that have non-circular cross-sectional shapes. Thus, an overall size of a cross-section of a closed end effector will be related to the size of the passage or opening through which it is intended to pass. Thus, one end effector for example, may be referred to as a "5 mm" end effector which means it can operably pass through an opening that is at least approximately 5 mm in diameter.

In various embodiments of the present invention, the elongated shaft assembly 40 may have an outer diameter that is substantially the same as the outer diameter of the end effector 12 when in a closed position. For example, a 5 mm end effector may be coupled to an elongated shaft assembly 40 that has 5 mm cross-sectional diameter. However, as the present Detailed Description proceeds, it will become apparent that various embodiments of the present may be effectively used in connection with different sizes of end effectors. For example, a 10 mm end effector may be attached to an elongated shaft that has a 5 mm cross-sectional diameter. Conversely, for those applications wherein a 10 mm or larger access opening or passage is provided, the elongated shaft assembly 40 may have a 10 mm (or larger) cross-sectional diameter, but may also be able to actuate a 5 mm or 10 mm end effector. Accordingly, the outer shaft 40 may have an outer diameter that is the same as or is different from the outer diameter of a closed end effector 12 attached thereto.

As depicted, the elongated shaft assembly 40 extends distally from the handle assembly 100 in a generally straight line to define a longitudinal axis A-A. In various embodiments, for example, the elongated shaft assembly 40 may be approximately 9-16 inches (229-406 mm) long. However, the elongated shaft assembly 40 may be provided in other lengths and, in other embodiments, may have joints therein or be otherwise configured to facilitate articulation of the end effector 12 relative to other portions of the shaft or handle assembly as will be discussed in further detail below. In various embodiments, the elongated shaft assembly 40 includes a spine member 50 that extends from the handle assembly 100 to the end effector 12. The proximal end of the elongated channel 14 of the end effector 12 has a pair of retention trunions 17 protruding therefrom that are sized to be received within corresponding trunion openings or cradles 52 that are provided in a distal end of the spine member 50 to enable the end effector 12 to be removably coupled the elongated shaft assembly 40. The spine member 50 may be fabricated from, for example, 6061 or 7075 aluminum, stainless steel, titanium, etc.

In various embodiments, the handle assembly 100 comprises a pistol grip-type housing that may be fabricated in two or more pieces for assembly purposes. For example, the handle assembly 100 as shown comprises a right hand case member 102 and a left hand case member 104 (FIGS. 5, 7, and 8) that are molded or otherwise fabricated from a polymer or plastic material and are designed to mate together. Such case members 102 and 104 may be attached together by snap features, pegs and sockets molded or otherwise formed therein and/or by adhesive, screws, etc. The spine member 50 has a proximal end 54 that has a flange 56 formed thereon. The flange 56 is configured to be rotatably supported within a groove 106 formed by mating ribs 108 that protrude inwardly from each of the case members 102, 104. Such arrangement facilitates the attachment of the spine member 50 to the handle assembly 100 while enabling the spine member 50 to be rotated relative to the handle assembly 100 about the longitudinal axis A-A in a 360° path.

Figure 4:
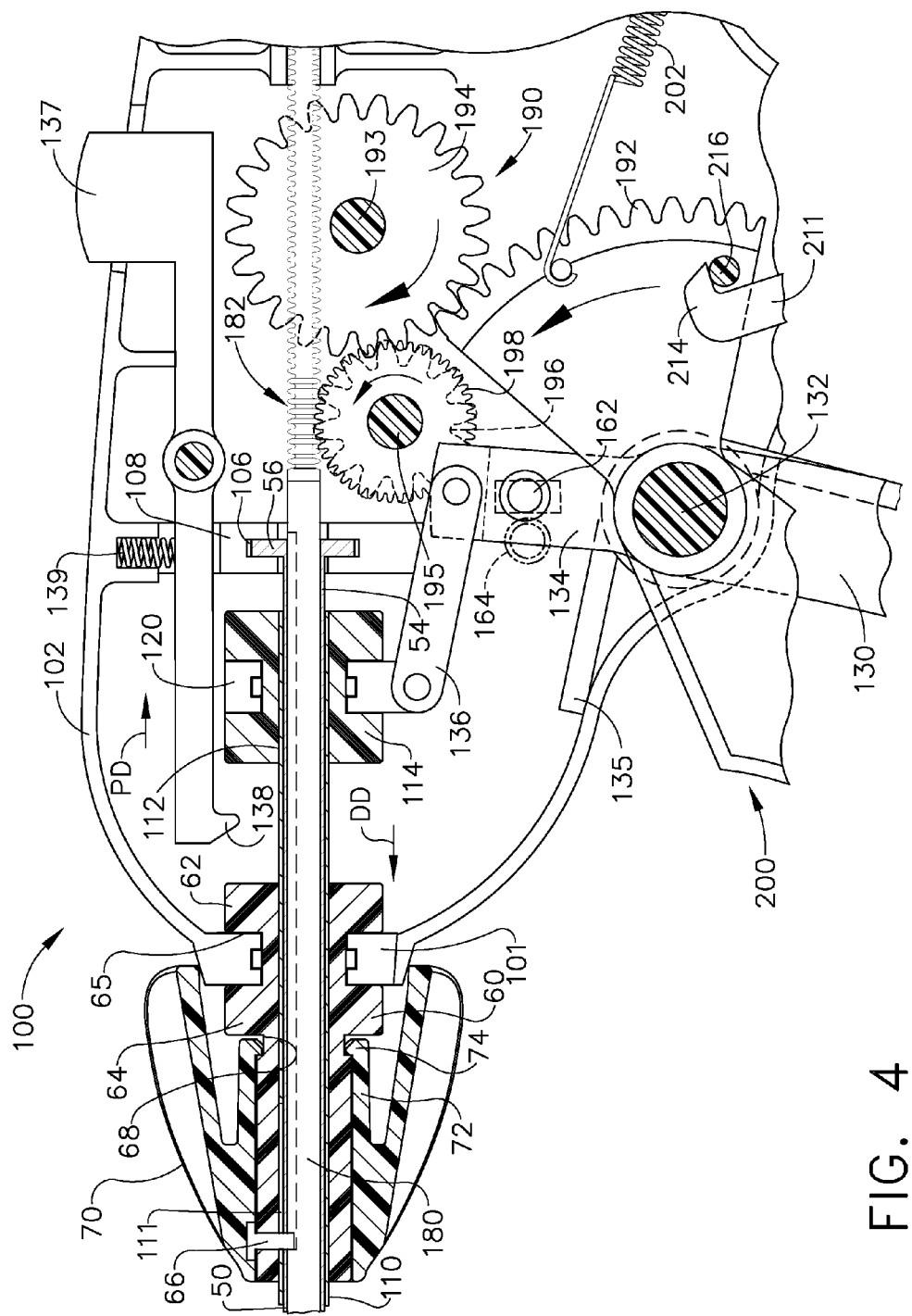
FIG. 4 is a is a cross-sectional view of a portion of the handle assembly depicted in FIG. 1.

As can be further seen in FIGS. 1 and 4, the spine member 50 passes through and is supported by a mounting bushing 60 that is rotatably affixed to the handle assembly 100. The mounting bushing 60 has a proximal flange 62 and a distal flange 64 that define a rotational groove 65 that is configured to rotatably receive a nose portion 101 of the handle assembly 100 therebetween. Such arrangement enables the mounting bushing 60 to rotate about longitudinal axis A-A relative to the handle assembly 100. The spine member 50 is non-rotatably pinned to the mounting bushing 60 by a spine pin 66. In addition, a rotation knob 70 is attached to the mounting bushing 60. In one embodiment, for example, the rotation knob 70 has a hollow mounting flange portion 72 that is sized to receive a portion of the mounting bushing 60 therein. In various embodiments, the rotation knob 70 may be fabricated from, for example, glass or carbon filled Nylon, polycarbonate, Ultem®, etc. and is affixed to the mounting bushing 60 by the spine pin 66 as well. In addition, an inwardly protruding retention flange 74 is formed on the mounting flange portion 72 and is configured to extend into a radial groove 68 formed in the mounting bushing 60. Thus, the surgeon may rotate the spine member 50 (and the end effector 12 attached thereto) about longitudinal axis A-A in a 360° path by grasping the rotation knob 70 and rotating it relative to the handle assembly 100.

In various embodiments, the anvil 20 is retained in an open position by an anvil spring 21 or other biasing arrangement as depicted in FIGS. 1, 9A, 10A, and 11A. The anvil 20 is selectively movable from the open position to various closed or clamping and firing positions by a firing system, generally designated as 109. The firing system 109 includes a "firing member" 110 which, in various embodiments, comprises a hollow firing tube 110. The hollow firing tube 110 is axially movable on the spine member 50 and thus forms the outer portion of the elongated shaft assembly 40. The firing tube 110 may be fabricated from a polymer or other suitable material and have a proximal end 112 that is attached to a firing yoke 114 of the firing system 109. See FIG. 4. In various embodiments for example, the firing yoke 114 may be overmolded to the proximal end 112 of the firing tube 110. However, other fastener arrangements may be employed.

As can be seen in FIGS. 1 and 4, the firing yoke 114 may be rotatably supported within a support collar 120 that is configured to move axially within the handle assembly 100. In various embodiments, the support collar 120 has a pair of laterally extending fins 122 that are sized to be slidably received within fin slots 103 and 105 formed in the right and left hand case members 102, 104, respectively. See FIG. 7. Thus, the support collar 120 may slide axially within the handle housing 100 while enabling the firing yoke 114 and firing tube 110 to rotate relative thereto about the longitudinal axis A-A. As can be seen in FIG. 4, a longitudinal slot 111 is provided through the firing tube 110 to enable the spine pin 66 to extend therethrough into the spine member 50 while facilitating the axial travel of the firing tube 110 on the spine member 50.

The firing system 109 further comprises a firing trigger 130 which serves to control the axial travel of the firing tube 110 on the spine member 50. See FIG. 1. Such axial movement in the distal direction of the firing tube 110 into firing interaction with the anvil 20 is referred to herein as "firing motion". As can be seen in FIG. 1, the firing trigger 130 is movably or pivotally coupled to the handle assembly 100 by a pivot pin 132. A torsion spring 135 is employed to bias the firing trigger 130 away from the pistol grip portion 107 of the handle assembly 100 to an un-actuated "open" or starting position. As can be seen in FIGS. 1 and 4, the firing trigger 130 has an upper portion 134 that is movably attached to (pinned) firing links 136 that are movably attached to (pinned) the support collar 120. Thus, movement of the firing trigger 130 from the starting position (FIGS. 1 and 9) toward an ending position adjacent the pistol grip portion 107 of the handle assembly 100 (FIG. 14) will cause the firing yoke 114 and the firing tube 110 to move in the distal direction "DD". Movement of the firing trigger 130 away from the pistol grip portion 107 of the handle assembly 100 (under the bias of the torsion spring 135) will cause the firing yoke 114 and firing tube 110 to move in the proximal direction "PD" on the spine member 50.

Various embodiments of the present invention may be employed with different sizes and configurations of implantable staple cartridges. For example, the surgical instrument 10, when used in connection with a first firing adapter 140, may be used with a 5 mm end effector 12 that is approximately 20 mm long (or in other lengths) which supports an implantable staple cartridge 30. Such end effector size may be particularly well-suited, for example, to complete relatively fine dissection and vascular transactions. However, as will be discussed in further detail below, the surgical instrument 10 may also be employed, for example, in connection with other sizes of end effectors and staple cartridges by replacing the first firing adapter 140 with a second firing adapter 150. In still other embodiments, the elongated shaft assembly 40 may configured to be attached to only one form or size of end effector. In such embodiments, for example, the pressure surfaces 146 or 158 (normally provided on the firing adapters 140, 150, respectively) would be integrally formed in the distal end of the firing tube 110—depending upon the particular size of end effector with which it is to be used.

Figure 2:
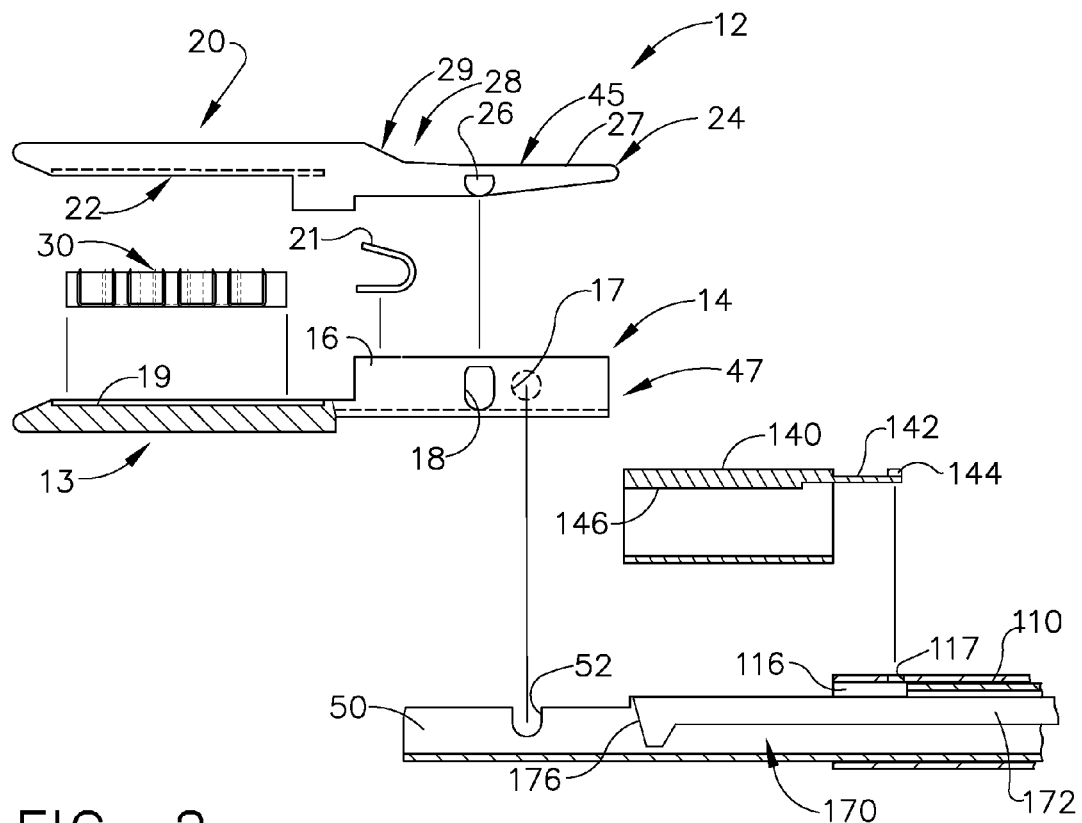
FIG. 2 is an exploded assembly view of an end effector embodiment and a portion of a surgical stapling instrument embodiment of the present invention shown in cross-section.

As can be seen in FIG. 2, the first firing adapter 140 is substantially hollow and has a first spring portion 142 that is configured to extend into an open distal end 116 of the firing tube 110. A first retainer button 144 is formed on the first spring portion 142 and is sized to be received within a retaining hole 117 provided in the distal end portion of the firing tube 110. See FIGS. 1 and 2. Thus, to detach the first firing adapter 140 from the firing tube 110, the user simply depresses the retainer button 144 out of the retaining hole 117 and withdraws the first firing adapter 140 out of the firing tube 110. As can also be seen in FIG. 2, the first firing adapter 140 has an interior pressure surface 146 that is configured to interface with the bifurcated ramp assembly 24 of the anvil 20.

Figure 3:
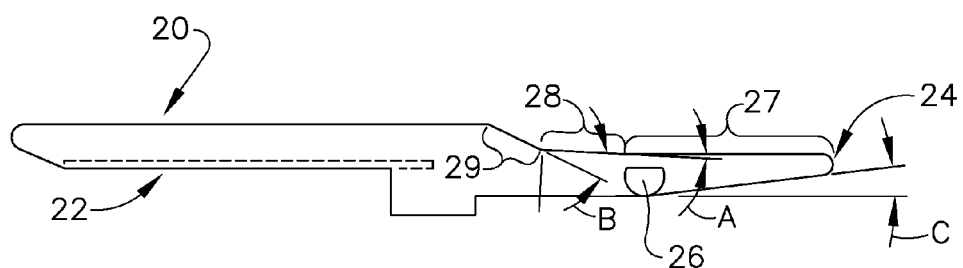
FIG. 3 is a side elevational view of an anvil embodiment of the present invention.

In various implementations, the bifurcated ramp assembly 24 on the anvil 20 comprises a pair of tines 45 that are separated by a blade-receiving groove (not shown). Each tine 45 has a proximal surface 27 that is substantially parallel to the bottom of the elongated channel 14 when the anvil 20 is in a closed position. The proximal surface 27 then transitions into a clamping ramp 28 that is distal to the proximal surface 27. See FIG. 3. The clamping ramp 28 is oriented at a clamping angle "A" with respect to the proximal surface 27. In various embodiments, for example, clamping angle "A" may be approximately 15 to 30 degrees. As will be discussed in further detail below, when the first pressure surface 146 of the first firing adapter 140 contacts the clamping ramp 28, the anvil 20 will be moved toward the elongated channel 14 and more specifically toward the staple cartridge 30 therein. As the first firing adapter 140 is further moved distally, the first pressure surface 146 contacts a staple forming ramp 29 on each of the anvil tines 45 to further drive the anvil 20 into the staple cartridge 30 to form the staples 32 therein. As is also shown in FIG. 3, the staple forming ramp 29 is oriented at a forming angle "B" relative to the clamping ramp 27. In various embodiments, for example, forming angle "B" may be approximately 5 to 20 degrees. The ramp assembly 24 of the anvil 20 may further have a sloped under surface 25 thereon (e.g., angle "C" is approximately 5 to 40 degrees) such that when the anvil 20 is in an open position, the sloped undersurface 25 surface enables the anvil 20 to pivot to a 15° open limit (angle "β" in FIG. 11A).

One method of removably coupling the end effector 12 to the spine member 50 will now be explained. The coupling process is commenced by inserting the retention trunions 17 on the elongated channel 14 into the trunion cradles 52 in the spine member 50. Thereafter, the surgeon advances the firing trigger 130 toward the pistol grip 107 of the housing assembly 100 to distally advance the firing tube 110 and the first firing adapter 140 over a proximal end portion 47 of the elongated channel 14 to thereby retain the trunions 17 in their respective cradles 52. See FIGS. 10 and 10A. Such position of the first firing adapter 140 over the trunions 17 is referred to herein as the "coupled position". Various embodiments of the present invention may also have an end effector locking assembly 160 for locking the firing trigger 130 in position after an end effector 12 has been attached to the spine member 50.

Figure 7:
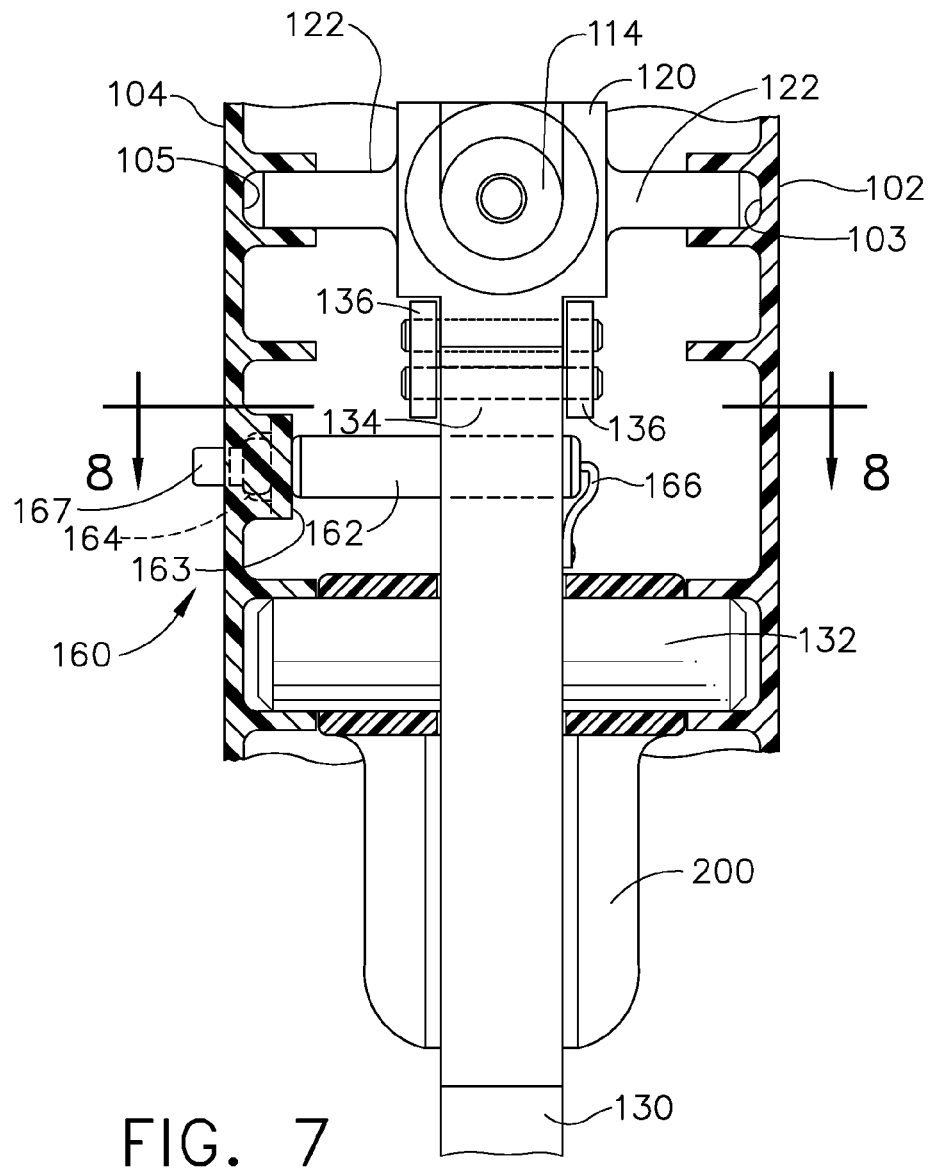
FIG. 7 is a partial cross-sectional view of the handle assembly of FIG. 1 taken along line 7-7 in FIG. 1.
Figure 8:
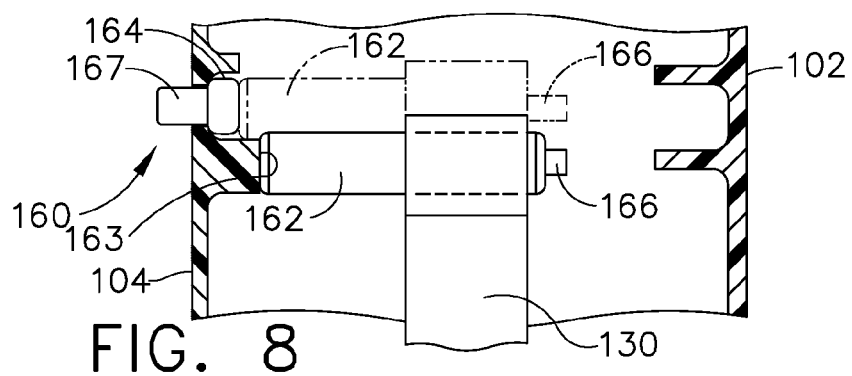
FIG. 8 is a partial cross-sectional view of a portion of the handle assembly of FIG. 7 taken along line 8-8 in FIG. 7.

More specifically and with reference to FIGS. 5, 7, and 8, one embodiment of the end effector locking assembly 160 includes a retention pin 162 that is movably supported in the upper portion 134 of the firing trigger 130. The retention pin 162 is spring-biased toward the left hand case member 104 by a retention spring 166. When the firing trigger 130 is in an un-actuated (starting) position, the retention pin 162 is biased into abutting contact with a start detent 163 that protrudes inwardly from the left hand case member 104. See FIGS. 7 and 8. As discussed above, the firing tube 110 must initially be advanced distally to the coupled position wherein the first firing adapter 140 retains the retention trunions 17 of the end effector 12 in the trunion cradles 52 in the spine member 50. The surgeon advances the firing adapter 140 distally to the coupled position by pulling the firing trigger 130 from the starting position toward the pistol grip 107. As the firing trigger 130 is initially actuated, the retention pin 162 slides in abutting contact with the start detent 163 until the firing tube 110 has advanced the first firing adapter 140 to the coupled position at which point the retention pin 162 is biased into a locking cavity 164 formed in the left hand case member 104. See FIG. 8. In various embodiments, when the retention pin 162 enters into the locking cavity 164, the pin 162 may make an audible "click" or other sound, as well as provide a tactile indication to the surgeon that the end effector 12 has been "locked" onto the spine member 50. In addition, the surgeon cannot inadvertently continue to actuate the firing trigger 130 to start to form staples 32 in the end effector 12 without intentionally biasing the retention pin 162 out of the locking cavity 164. Similarly, if the surgeon releases the firing trigger 130 when in the coupled position, it is retained in that position by the retention pin 162 to prevent the firing trigger 130 from returning to the starting position and thereby releasing the end effector 12 from the spine member 50.

In various implementations, a firing trigger release button 167 is mounted within the left hand case member 104 of the handle assembly 100 to enable the surgeon to intentionally release the retention pin 162 to enable the firing trigger 130 to be further actuated or returned to the starting position. See FIGS. 5, 7, and 8. The firing trigger release button 167 is movably mounted within the locking cavity 164 and is spring-biased to an un-activated position (FIG. 8). When the firing trigger release button 167 is pressed inwardly, it contacts the retention pin 162 and moves it out of the locking cavity 163 to enable the firing trigger 130 to be further activated.

As thus far described, the surgical instrument 10 may be used as a grasping device to manipulate/position tissue. Further movement of the firing trigger 130 toward the pistol grip portion 107 after the trigger 130 has been unlocked (by depressing the retention release button 167) will cause the firing adapter 140 to contact the clamping ramp 28 on the anvil 20. As the pressure surface portion 146 of the first firing adapter rides up the clamping ramp 28, the anvil will move towards the staple cartridge 30 in the elongated channel 14. Thus, the surgeon may manipulate the anvil 20 toward and away from the staple cartridge 30 to grasp and release tissue therebetween without forming the staples.

Figure 11:
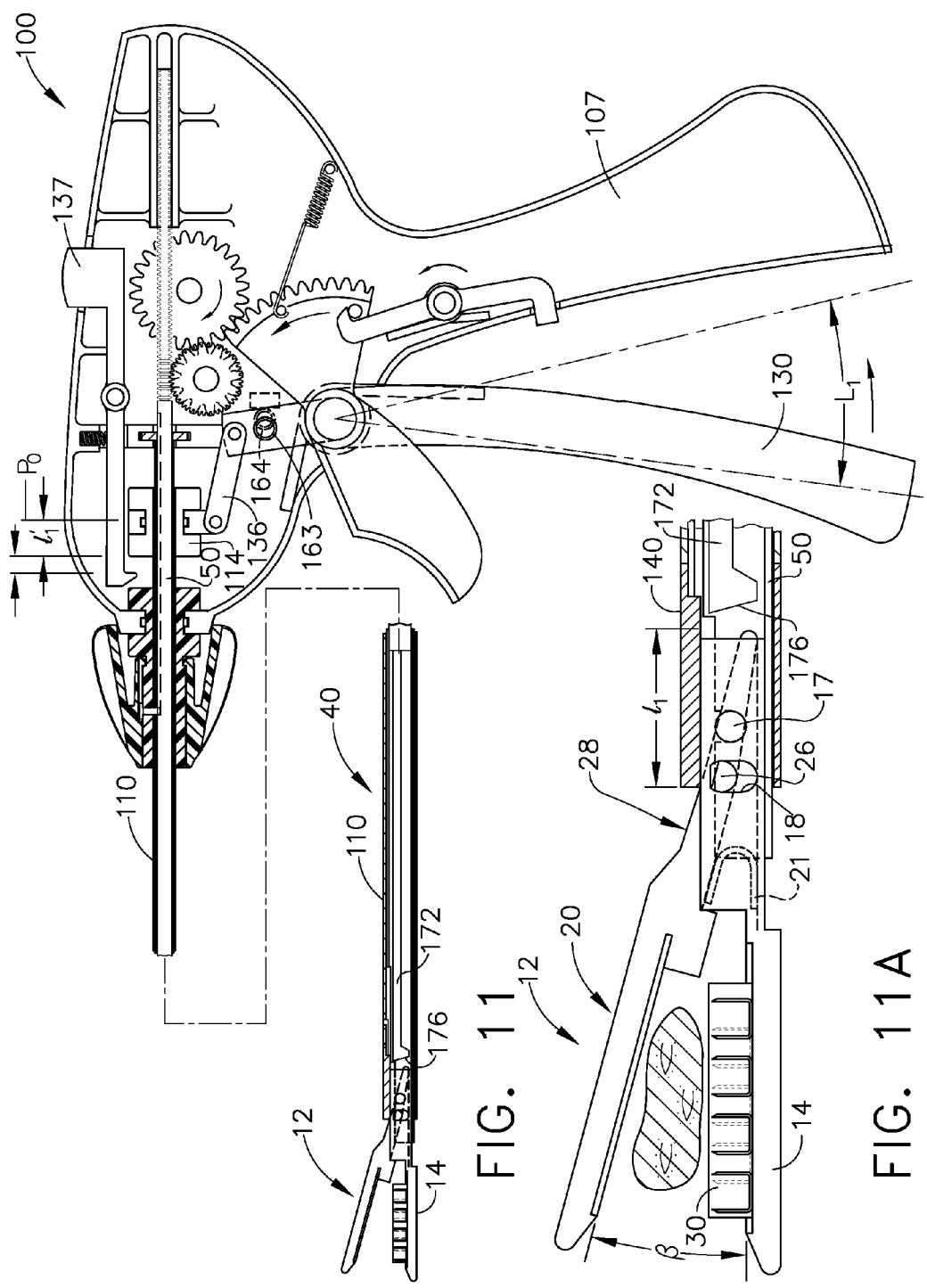
FIG. 11 is a cross-sectional view of the surgical instrument of FIGS. 9 and 10 after the first firing adapter has been advanced to the beginning of the clamping ramp portions of the anvil.
Figures 12, 12A:
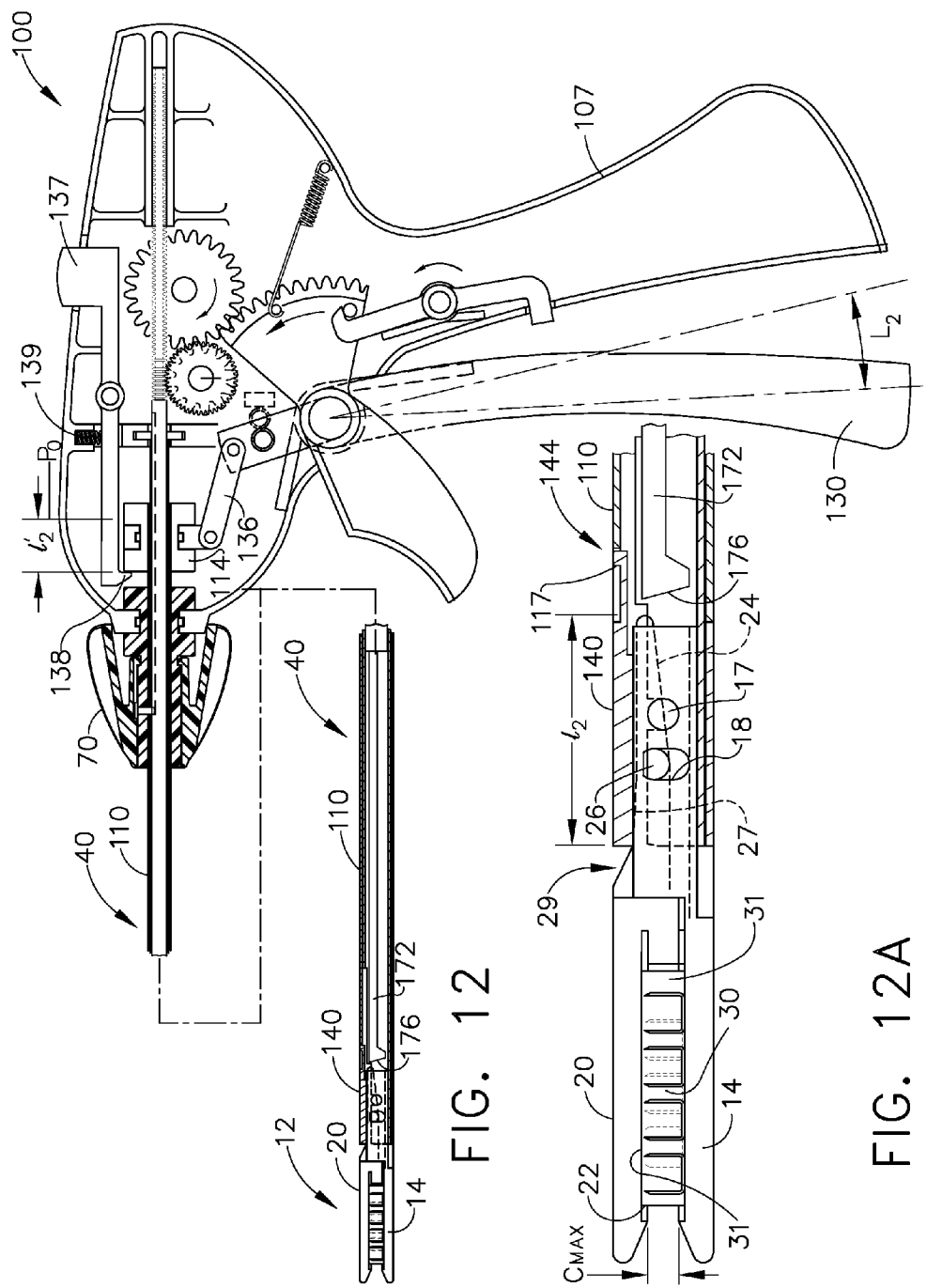
FIG. 12 is a is a cross-sectional view of the surgical instrument of FIGS. 9-11 after the first firing adapter has been advanced over the clamping ramp portions of the anvil.
FIG. 12A is an enlarged view of the end effector and a portion of the surgical instrument of FIG. 12.

Various embodiments of the present invention may further include a firing system lock button 137 that is pivotally attached to the handle assembly 100. See FIGS. 1 and 4. In one form, the firing system lock button 137 has a latch 138 formed on a distal end thereof that is oriented to engage the firing yoke 114 when the firing release button is in a first latching position. As can be seen in FIGS. 1 and 4, a latch spring 139 serves to bias the firing system lock button 137 to the first latching position (FIGS. 11 and 12). As will be explained in further detail below, the latch 138 serves to engage the firing yoke 114 at a point where the position of the firing yoke 114 on the spine member 50 corresponds to a point wherein the pressure surface 146 of the first firing adapter 140 is about to distally advance up the clamping ramp 28 on the anvil 20. It will be understood that, as the first firing adapter 140 advances axially up the clamping ramp 28, the anvil 20 will move in a path such that its staple forming surface portion 22 is substantially parallel to the upper face 36 of the staple cartridge 30.

After the end effector 12 has been coupled to the spine member 50, the staple forming process is commenced by first depressing the firing system lock button 137 to enable the firing yoke 114 to be further moved distally on the spine member 50 and ultimately compress the anvil 20 into the staple cartridge 30. See FIG. 13. After depressing the firing system lock button 137, the surgeon continues to actuate the firing trigger 130 towards the pistol grip 107 thereby driving the pressure surface 146 of the first staple collar 140 up the corresponding staple forming ramp 29 to force the anvil 20 into forming contact with the staples 32 in the staple cartridge 30. The firing system lock button 137 prevents the inadvertent forming of the staples 32 until the surgeon is ready to start that process. In this embodiment, the surgeon must depress the firing system lock button 137 before the firing trigger 130 may be further actuated to begin the staple forming process.

The surgical instrument 10 may be solely used as a tissue stapling device if so desired. However, various embodiments of the present invention may also include a tissue cutting system, generally designated as 170. In at least one form, the tissue cutting system 170 comprises a knife member 172 that may be selectively advanced from an un-actuated position adjacent the proximal end of the end effector 12 (FIGS. 1 and 9-13) to an actuated position (FIG. 14) by actuating a knife advancement trigger 200. The knife member 172 is movably supported within the spine member 50 and is attached or otherwise protrudes from a knife rod 180. The knife member 172 may be fabricated from, for example, 420 or 440 stainless steel with a hardness of greater than 38HRC (Rockwell Hardness C-scale) and have a tissue cutting edge 176 formed on the distal end 174 thereof and be configured to slidably extend through a slot 31 in the anvil 20 and a centrally disposed slot 33 in the staple cartridge 30 to cut through tissue that is clamped in the end effector 12. See FIG. 14A. As can be seen in FIG. 4, the knife rod 180 extends through the spine member 50 and has a proximal end portion 182. The proximal end portion 182 drivingly interfaces with a knife transmission 190 that is operably attached to the knife advance trigger 200. In various embodiments, the knife advance trigger 200 is attached to pivot pin 132 such that it may be pivoted or otherwise actuated without actuating the firing trigger 130. In various embodiments, a first knife gear 192 is also attached to the pivot pin 132 such that actuation of the knife advance trigger 200 also pivots the first knife gear 192. A firing return spring 202 is attached between the first knife gear 192 and the handle housing 100 to bias the knife advancement trigger 200 to a starting or un-actuated position. See FIGS. 1 and 4.

Turning to FIGS. 5 and 6, various embodiments of the knife transmission 190 also include a second knife gear 194 that is rotatably supported on a second gear spindle 193 and in meshing engagement with the first knife gear 192. The second knife gear 194 is in meshing engagement with a third knife gear 196 that is supported on a third gear spindle 195. Also supported on the third gear spindle 195 is a fourth knife gear 198. The fourth knife gear 198 is adapted to drivingly engage a series of annular gear teeth or rings 184 on a proximal end of the knife rod 180. Thus, such arrangement enables the fourth knife gear 198 to axially drive the knife rod 180 in the distal direction "DD" or proximal direction "PD" while enabling the firing rod 180 to rotate about longitudinal axis A-A with respect to the fourth knife gear 198. Accordingly, the surgeon may axially advance the firing rod 180 and ultimately the knife member 172 distally by pulling the knife advancement trigger 200 towards the pistol grip 107 of the handle assembly 100.

Various embodiments of the present invention further include a knife lockout system 210 that prevents the advancement of the knife member 72 unless the firing trigger 130 has been pulled to the fully fired position (FIGS. 13 and 14). Such feature will therefore prevent the activation of the knife advancement system 170 unless the staples have first been fired or formed into the tissue. As can be seen in FIG. 1, various implementations of the knife lockout system 210 comprise a knife lockout bar 211 that is pivotally supported within the pistol grip portion 107 of the handle assembly 100. The knife lockout bar 211 has an activation end 212 that is adapted to be engaged by the firing trigger 130 when the firing trigger 130 is in the fully fired position. In addition, the knife lockout bar 211 has a retaining hook 214 on its other end that is adapted to hookingly engage a latch rod 216 on the first cut gear 192. A knife lock spring 218 is employed to bias the knife lockout bar 211 to a "locked" position wherein the retaining hook 214 is retained in engagement with the latch rod 216 to thereby prevent actuation of the knife advancement trigger 200 unless the firing trigger 130 is in the fully fired position. See FIG. 9.

Various methods of operating at least one of the surgical instrument embodiments of the present invention will now be explained with reference to FIGS. 9, 9A, 10, 10A, 11, 11A, 12, 12A, 13, 13A, 14, and 14A. As can be appreciated from reference to FIGS. 1, 9 and 9A, when the knife bar 172 is in the depicted "starting" or un-actuated position, the tissue cutting edge 176 is proximal to the distal end of the first firing adapter 140 such that the sharp tissue cutting edge 176 is not exposed to the user. In alternative embodiments, wherein the elongated shaft assembly is manufactured for use with a single form or size of end effector (e.g., wherein the firing adapters 140, 150 are not employed), the cutting edge 176 of the knife bar 172 would be located proximal to the distal end of the firing tube to prevent the tissue cutting edge 176 from being exposed to the user in those embodiments as well.

Figure 9:
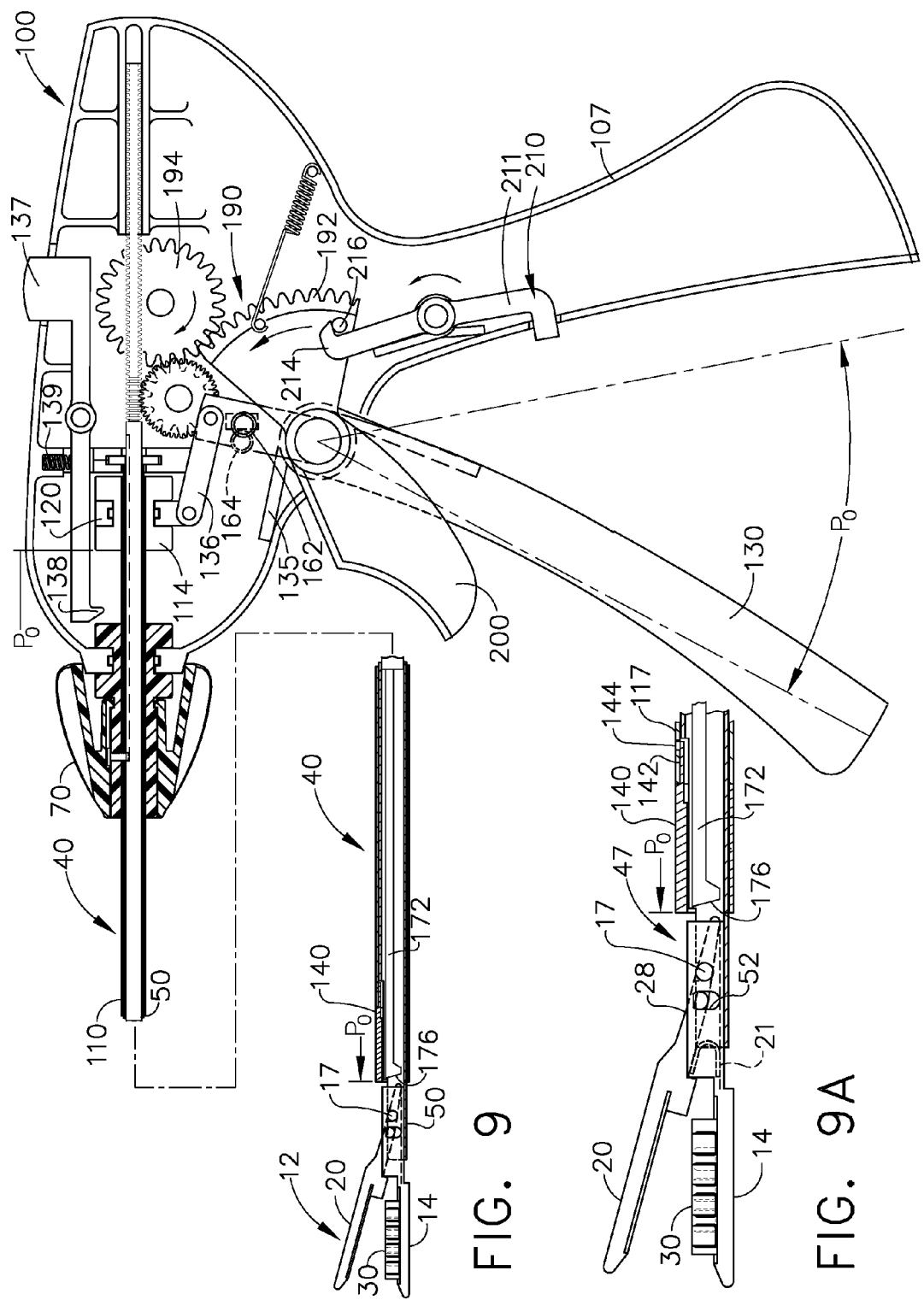
FIG. 9 is a cross-sectional view of a surgical instrument embodiment of the present invention after an end effector has been coupled to a spine portion of the surgical instrument and prior to being locked thereto.

FIGS. 9 and 9A illustrate the end effector 12 after it has been attached to the spine member 50 by inserting the retention trunions 17 on the end effector 12 into the trunion cradles 52 in the spine member 50. As illustrated in FIG. 9, the firing trigger 130 is in an un-actuated or starting position and the end effector 12 has not yet been locked to the spine member 50 by the first firing adapter 140. "$P_O$" represents the distance that the firing trigger 130 can travel before the first firing adapter 140 starts to travel up the clamping ramp portion 28 of the anvil 20. The knife advancement trigger 200 is also in a locked un-actuated position.

Figure 10:
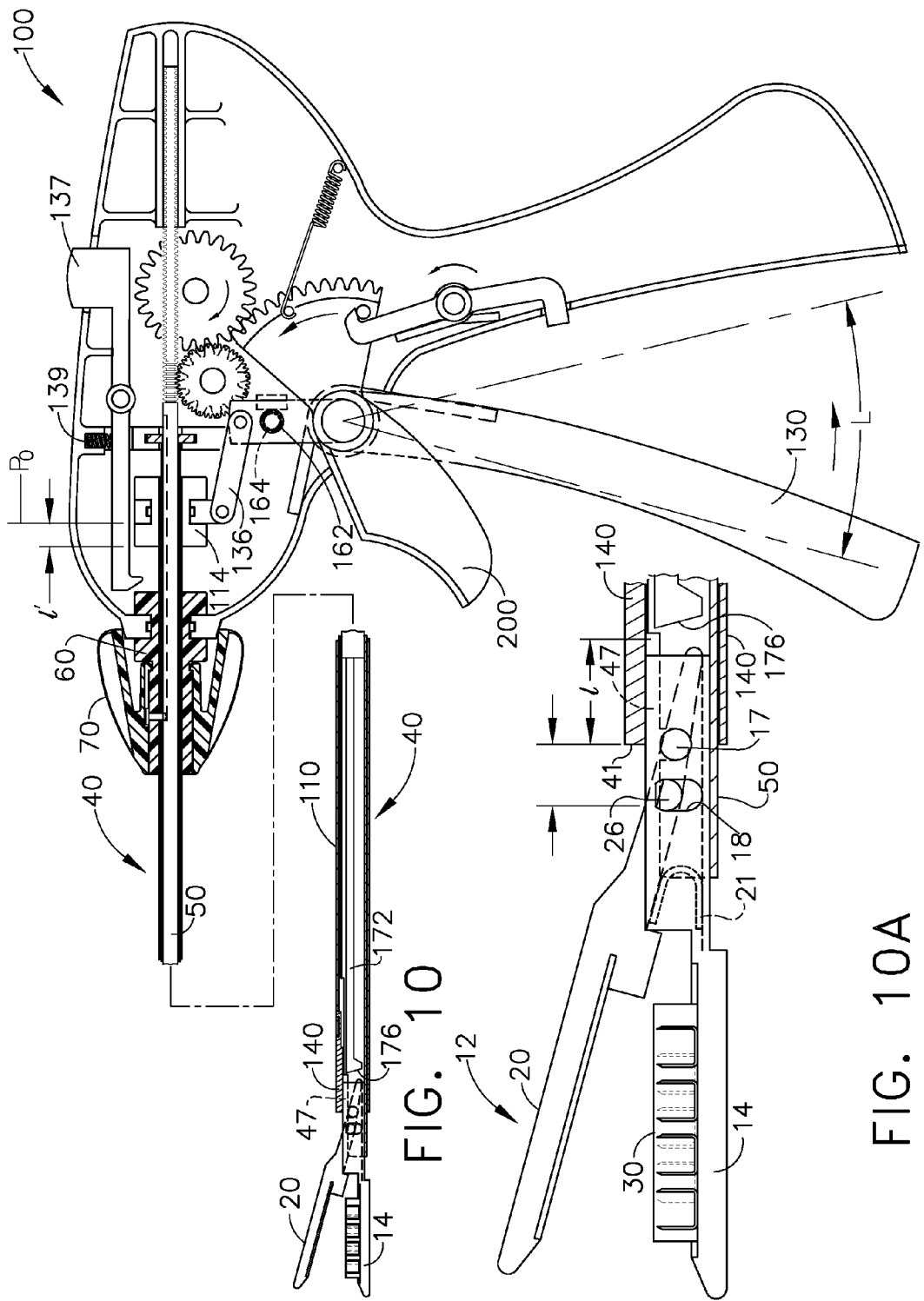
FIG. 10 is a cross-sectional view of the surgical instrument of FIG. 9 after the end effector has been locked to the spine portion of the surgical instrument.

FIGS. 10 and 10A illustrate the position of the firing trigger 130 after it has been advanced to a position wherein the end effector 12 is been locked to the spine member 50 by the first firing adapter 40. This position is referred to herein as the "coupled" position. When in the coupled position, the retention pin 162 has snapped into the locking cavity 164 (FIG. 8) to thereby provide the surgeon with an audible and tactile indication that the end effector 12 is now locked to the spine member 50. The firing trigger 130 cannot be actuated further until the surgeon intentionally depresses the firing trigger release button 167 (FIGS. 5, 7, and 8) to bias the retention pin 62 out of the locking cavity 164. The distance that the distal end 141 of the first firing adapter 140 has traveled is represented as distance "l" (FIG. 10A) and the corresponding distance that the firing yoke 114 has traveled on the spine member 50 is represented as distance "l". FIGS. 11 and 11A illustrate a position of the firing trigger 130 after the release button (not shown) has been depressed and the surgeon has activated the firing trigger 130 to move the first firing adapter 140 to the beginning of the clamping ramps 28 on the anvil 20. As can be seen in those Figures, the anvil spring 21 has biased the anvil 20 to an open position. The travel of the distal end of the first firing adapter 140 is represented as distance "$l_1$" and the corresponding distance that the firing yoke 114 has traveled on the spine member 50 is represented as distance "$l'_1$". FIGS. 12 and 12A illustrate the position of the first firing adapter 140 after it has been advanced to the start of the staple forming ramp 29 of the anvil 20. This position represents the maximum amount of clamping that can be attained before staple formation begins. This position is referred to herein as a "maximum clamped position". As can be seen in FIG. 12, the firing yoke 114 has contacted the latch 138 on the firing trigger release button 137 and therefore cannot be further advanced distally until the firing trigger release button 137 has been depressed. As can be seen in FIG. 12A, the staple forming surface 22 of the anvil 20 is substantially parallel to the upper face 31 of the staple cartridge 30. The distance between the staple forming portion 22 of the anvil 20 and the top retaining surface of the elongated channel 14 has been represented as "$C_{max}$". In various embodiments, $C_{max}$ may be, for example, 0.085 to 0.144 inches (approximately 2.15 to 3.65 mm) for staple cartridges 30 with body portions 31 that have a substantially equivalent thickness. In at least one embodiment, for example, the cartridge thickness may be as much as approximately 0.01 to 0.03 inches (approximately 0.25 mm to 0.76 mm) larger than the staple size. The total distance that the first firing adapter 140 has traveled from the starting position to this maximum clamped position is represented as "$l_2$" and the corresponding distance that the firing yoke 114 has traveled on the spine member 50 is represented as "$l'_2$". FIGS. 13 and 13A illustrate the position of the firing yoke 114 in a fully fired position wherein the staples 32 in the staple cartridge 30 have been fully formed. When in that position, the distance between the staple forming portion 22 of the anvil 20 and the top retaining surface of the elongated channel 14 is represented as "$C_{min}$". In various embodiments, "$C_{min}$" may be, for example, approximately 0.015 to 0.030 inches (approximately 0.38 mm to 0.76 mm) for staple cartridges that support staples that, when unformed, have legs that are approximately 0.075 to 0.134 inches (approximately 1.90 mm to 3.40 mm) long (distance "UF" in FIG. 1A) and when fully formed have a fully formed height of, for example, approximately 0.025 inches to 0.04 inches (approximately 0.63 mm to 1.01 mm) which comprises distance "FF" in FIG. 1D. The total distance that the first firing adapter 140 has traveled from the starting position to this fully fired position is represented as "$l_3$" and the corresponding distance that the firing yoke 114 has traveled on the spine member 50 is represented as "$l'_3$". As can also be seen in FIG. 13, the firing trigger 130 is in the fully fired position and has contacted the activation end 212 of the knife lockout bar 211 to bias the retaining hook 214 out of engagement with the latch rod 216 on the first cut gear 192.

Transection, especially of vessels may be one of the highest stress steps of any surgical procedure. In the laparoscopic environment, it is even more stressful because if something fails, the entire procedure may need to be converted to an open procedure almost immediately in order to prevent catastrophic events from occurring. Thus, it may be desirable to employ a surgical stapling instrument that has the ability to optionally cut tissue after the staples have been deployed. Various embodiments of the present invention meet such needs.

After the staples have been "fired" (formed) into the target tissue, the surgeon may depress the firing trigger release button 167 to enable the firing trigger 130 to return to the starting position under the bias of the torsion spring 135 which enables the anvil 20 to be biased to an open position under the bias of spring 21. When in the open position, the surgeon may withdraw the end effector 12 leaving the implantable staple cartridge 30 and staples 32 behind. In applications wherein the end effector was inserted through a passage, working channel, etc. the surgeon will return the anvil 20 to the closed position by activating the firing trigger 130 to enable the end effector 12 to be withdrawn out through the passage or working channel. If, however, the surgeon desires to cut the target tissue after firing the staples, the surgeon activates the knife advancement trigger 200 in the above-described manner to drive the knife bar 72 through the target tissue to the end of the end effector as shown in FIGS. 14, 14A. FIG. 14 illustrates the amount of travel of the knife advancement trigger 200 in various embodiments for different lengths of end effectors/staple cartridges wherein the knife bar 72 has been advanced to the fully fired position within the end effector 12. Thereafter, the surgeon may release the knife advancement trigger 200 to enable the firing return spring 202 to cause the firing transmission to return the knife bar 72 to the starting (un-actuated) position (FIGS. 13, 13A). Once the knife bar 72 has been returned to the starting position, the surgeon may open the end effector jaws 13, 15 to release the implantable cartridge 30 within the patient and then withdraw the end effector 12 from the patient. Thus, such surgical instruments of the present invention facilitate the use of small implantable staple cartridges that may be inserted through relatively smaller working channels and passages, while providing the surgeon with the option to fire the staples without cutting tissue or if desired to also cut tissue after the staples have been fired.

Figure 15:
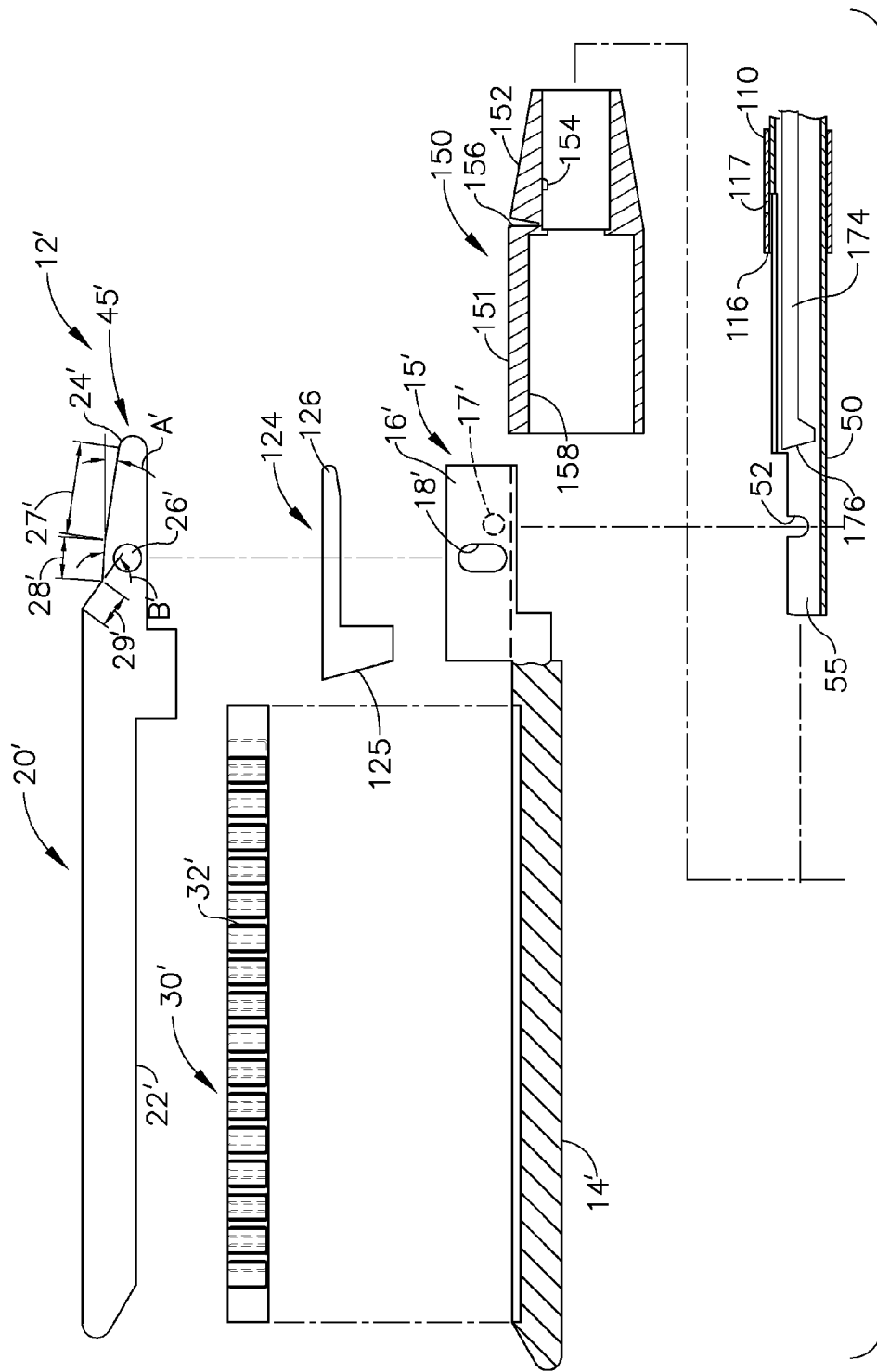
FIG. 15 is an exploded view of another end effector embodiment of the present invention with a portion of the spine member of a surgical instrument embodiment of the present invention shown in cross-section.

As indicated above, the surgical instrument 10 can be employed in connection with other end effectors that support other sizes of staple cartridges that contain other sizes and numbers of staples. FIGS. 15-19 illustrate use of an end effector 12' which operably supports a staple cartridge 30' that has staples 32' that are larger than the staples 32 in the staple cartridge 30. For example, the staples 32 in a staple cartridge 30 may be approximately 0.080-0.085 inches (approximately 2.03 to 2.15 mm staples, whereas the staples 32' in the staple cartridge 30' may be approximately 0.075 inches (approximately 1.90 mm). In various embodiments, the staple cartridge 30' is longer than the staple cartridge 30. For example, the staple cartridge 30 may be approximately 0.78 inches (approximately 20 mm) long; whereas the staple cartridge 30' may be approximately 1.57 inches (approximately 40 mm) long. FIG. 15 is an exploded view of an end effector 12', a second firing adapter 150 and the distal end 55 of the spine member 50. As can be seen in FIG. 15, the elongated channel 14' has a pair of spaced side walls 16' that each has a slot or opening 18' therein that is sized to receive a corresponding anvil pin 26'. The anvil 20' and the elongated channel 14' may together form an end effector 12' that has an overall diameter that would permit the end effector 12' to pass through an opening that has a diameter of at least approximately 0.20 inches (approximately 5.0 mm). The anvil 20' also has a staple forming portion 22' that has a plurality of staple forming pockets formed therein and a bifurcated ramp assembly 24' that protrudes proximally therefrom. The proximal end 15' of the elongated channel 14' has a pair of retention trunions 17' protruding therefrom that are sized to be received within corresponding trunion cradles 52 that are provided in the spine member 50.

As can be seen in FIG. 15, the second firing adapter 150 has a substantially hollow body portion 151 and a proximal collar portion 152 that has an inwardly extending retaining protrusion 154 therein. A slot 156 is provided between the body portion 151 and the proximal collar portion 152 to enable the collar portion 152 to be biased relative to the body portion 151 to facilitate the insertion of the retaining protrusion 154 into the retaining hole 117 in the firing tube 110. To detach the second firing adapter 150 from the firing tube 110, the surgeon depresses the proximal collar portion 152 to move the retaining protrusion 154 out of the retaining hole 117 to thereby enable the second firing adapter 150 to be pulled distally off of the firing tube 110.

In various embodiments, the anvil 20' has a bifurcated ramp assembly 24' that comprises a pair of tines 45' that each has a proximal surface 27' that transitions into a clamping ramp 28' that is distal to the proximal surface 27'. See FIG. 15. The clamping ramp 28' is oriented at an angle "A'" with respect to the proximal surface 27'. In various embodiments, for example, angle "A'" may be approximately 50 to 30 degrees. As will be discussed in further detail below, when a second pressure surface 158 of the second firing adapter 150 contacts the clamping ramps 28', the anvil 20' will be moved toward the elongated channel 14' and more specifically toward the staple cartridge 30' therein. See FIG. 17. As the second firing adapter 150 is further moved distally, the second pressure surface 158 contacts staple forming ramps 29' on the anvil tines 45 to further drive the anvil 20' toward the staple cartridge 30' to form the staples 32' therein. See FIG. 18. The staple forming ramp 29' is oriented at an angle "B" relative to the clamping ramp 27'. In various embodiments, for example, angle "B" may be approximately 5 to 20 degrees. A spring (not shown) may be provided between the ramp assembly 24' and the bottom of the elongated channel 14' to bias the anvil 20' to that open position.

Figure 16:
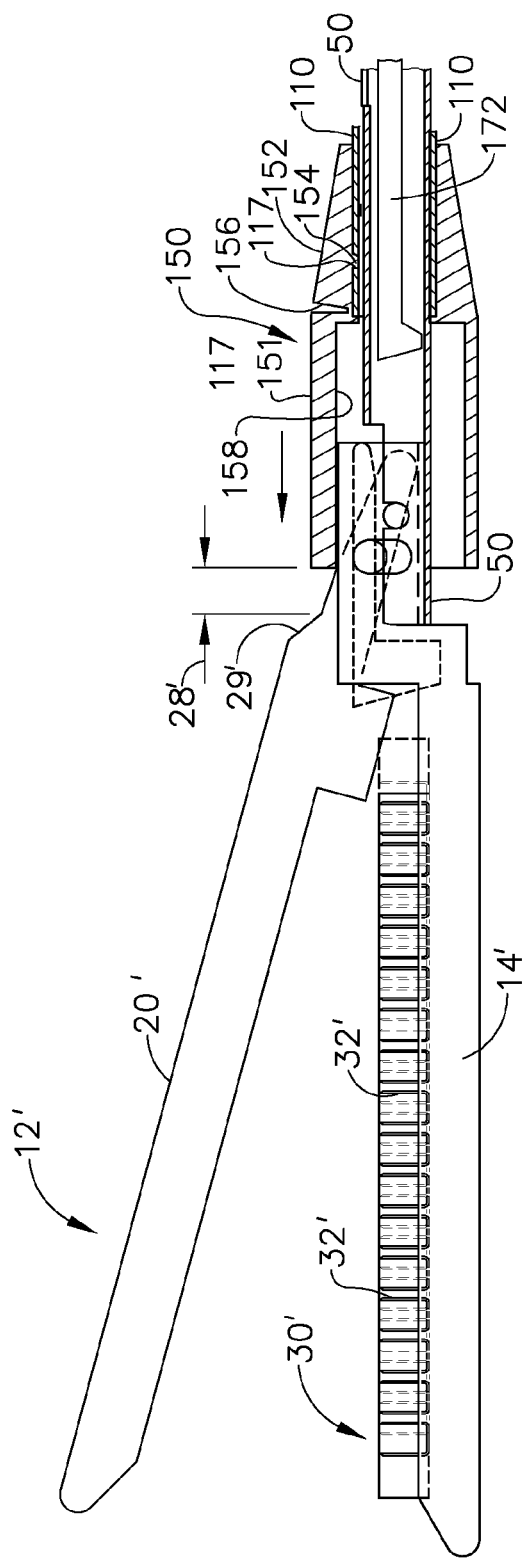
FIG. 16 is a partial cross-sectional view of the end effector embodiment of FIG. 15 in the open position and attached to the surgical instrument embodiment.
Figure 17:
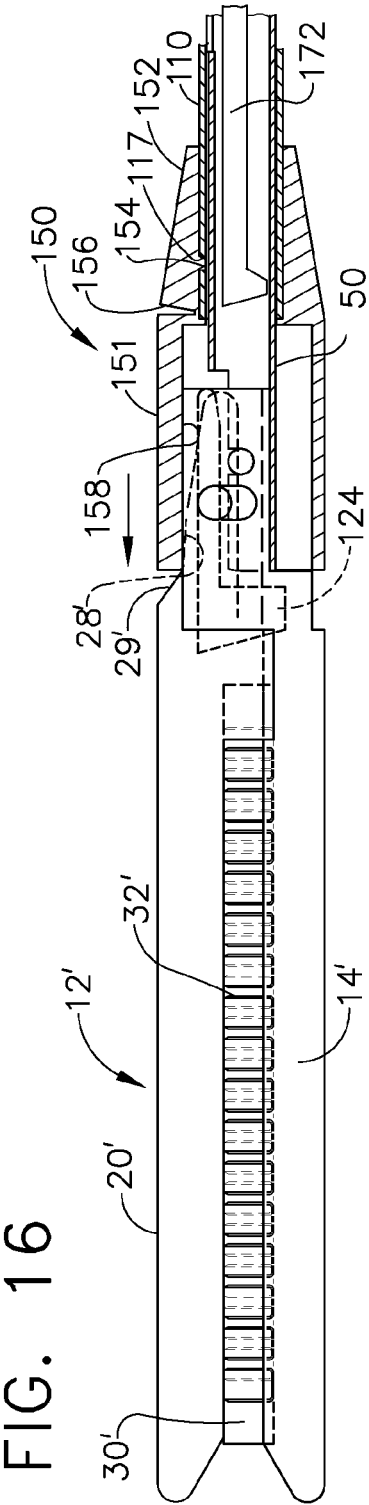
FIG. 17 is another partial cross-sectional view of the end effector embodiment of FIGS. 15 and 16 in the fully clamped position.
Figure 18:
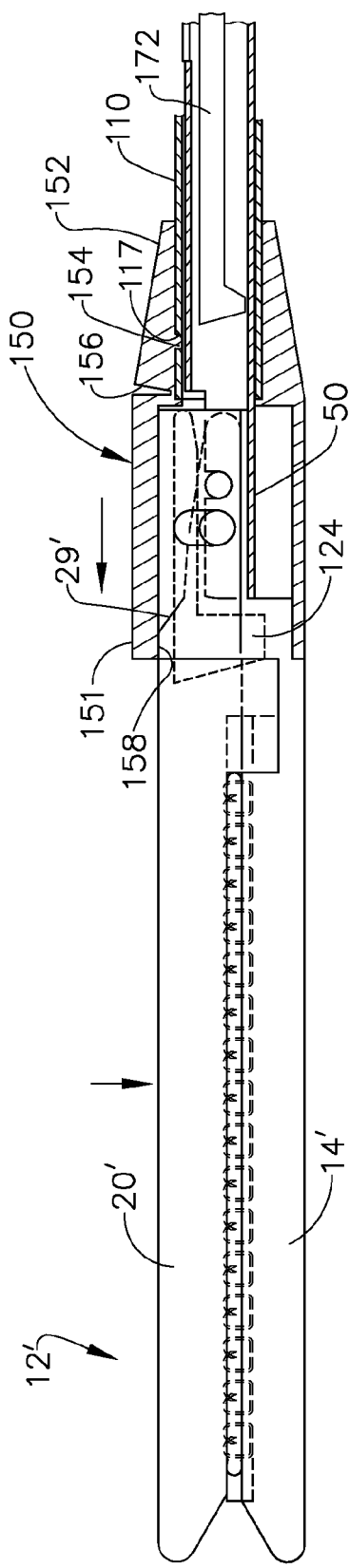
FIG. 18 is another partial cross-sectional view of the end effector embodiment of FIGS. 15-17 in the fully fired position and prior to advancement of the distal knife member.

FIG. 16 shows the position of the second firing adapter 150 after the surgeon has distally advanced the second firing adapter 150 to the start of the clamping ramp portions 28'. Operation of the second firing adapter 150 is controlled by the firing trigger 130 in the manner described above with respect to the first firing adapter 140. FIG. 17 illustrates the position of the second firing adapter 150 in a fully clamped position. FIG. 18 illustrates the position of the second firing adapter 150 in the fully fired position wherein the staples 32' in the staple cartridge 30' have been formed through the clamped tissue (not shown).

Figure 19:
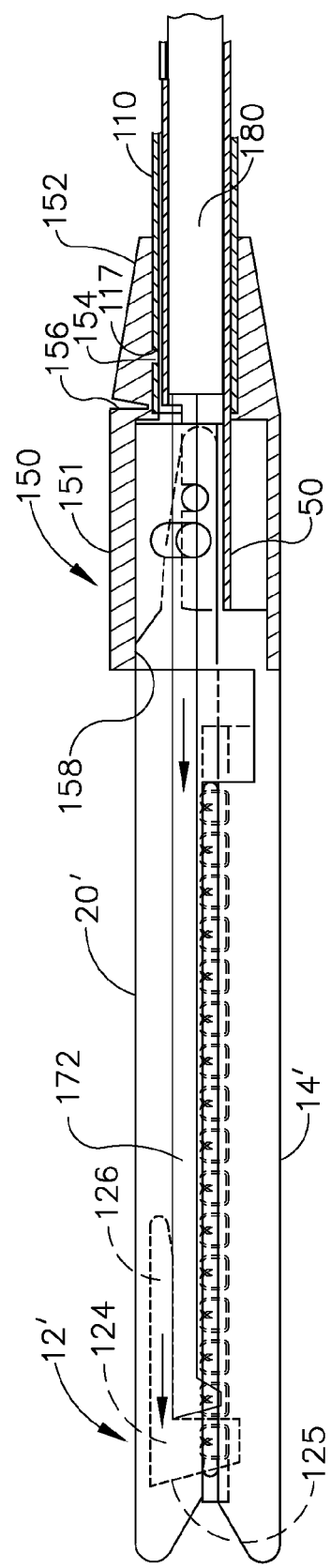
FIG. 19 is another partial cross-sectional view of the end effector embodiment of FIGS. 15-18 in the fully fired position and after complete advancement of the distal knife member.
Figure 20:
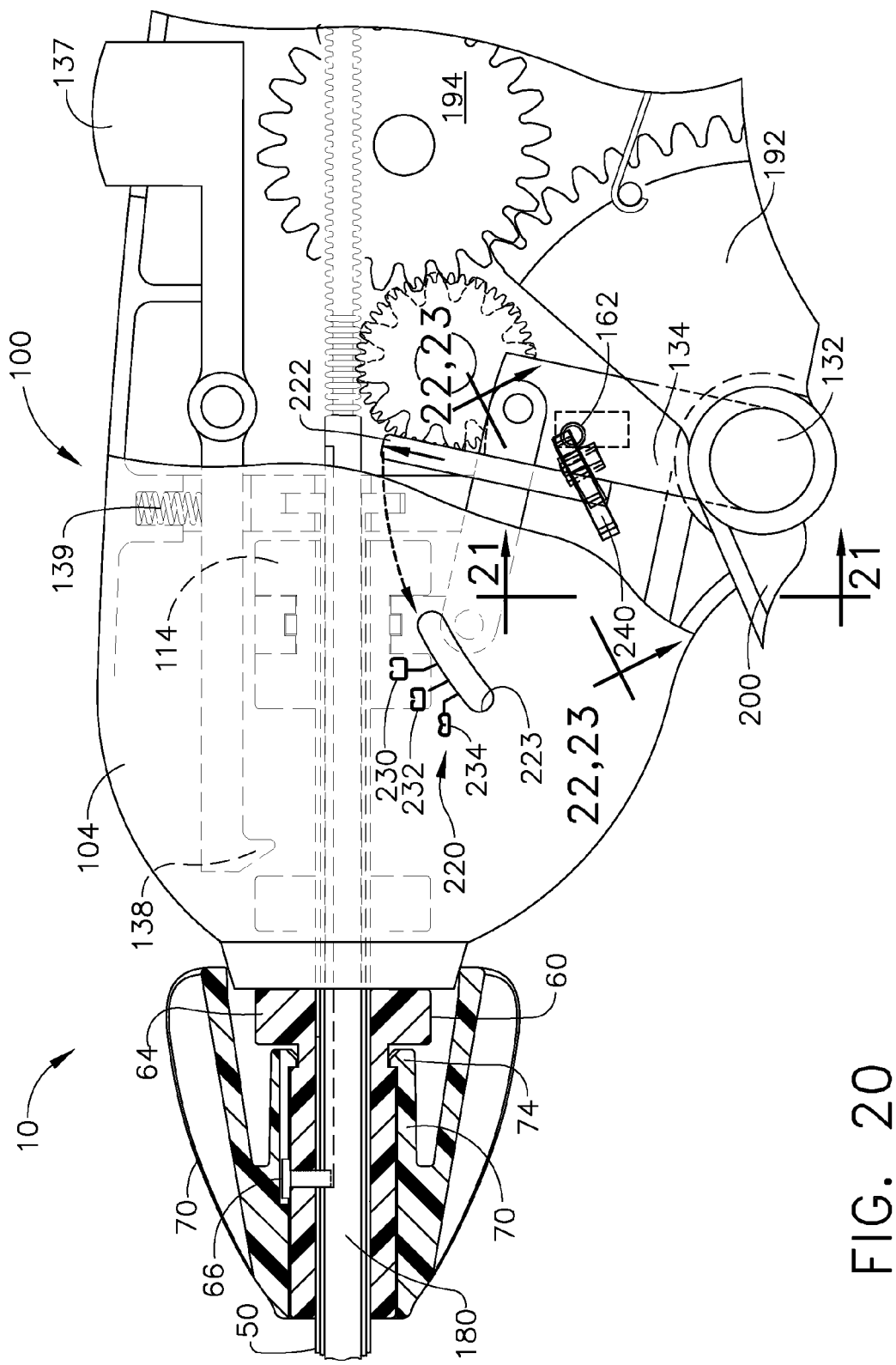
FIG. 20 is a cross-sectional view of a portion of another handle assembly embodiment of the present invention.
Figure 21:
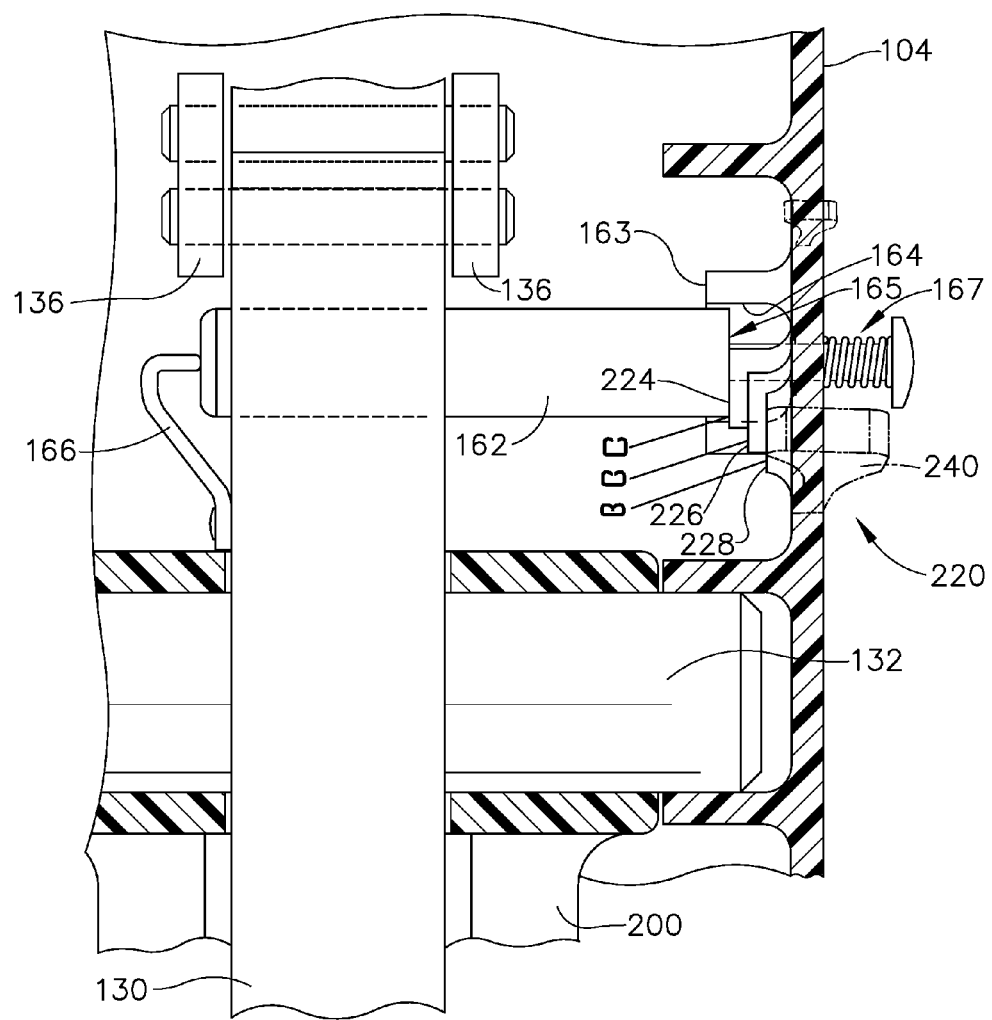
FIG. 21 is a partial cross-sectional view of a portion of the handle assembly of FIG. 20 taken along line 21-21 in FIG. 20.
Figure 22:
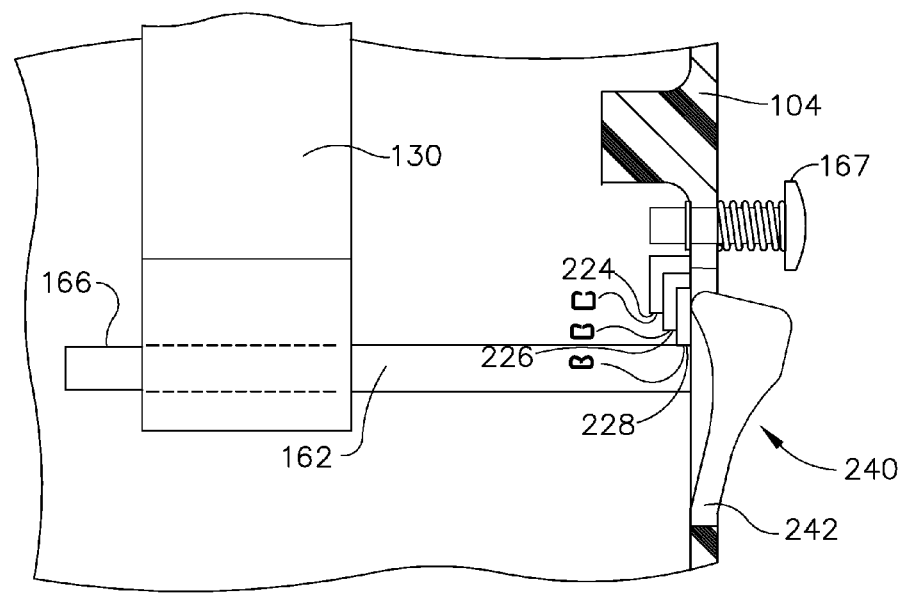
FIG. 22 is a partial cross-sectional view of a portion of the handle assembly of FIG. 20 taken along line 22-22 in FIG. 20.
Figure 23:
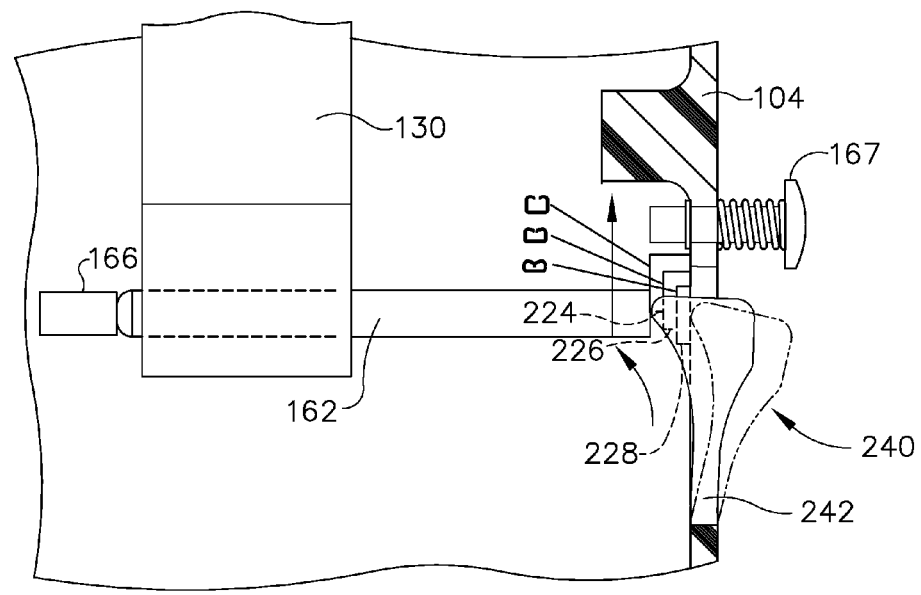
FIG. 23 is a partial cross-sectional view of a portion of the handle assembly of FIG. 20 taken along line 23-23 in FIG. 20.

As indicated above, the implantable staple cartridge 30' is longer than the implantable staple cartridge 30. Thus, as shown in FIG. 15, the end effector 12' also includes a distal knife member 124 that is movably supported in the elongated channel 14'. The distal knife member 124 has a tissue cutting edge 125 and a proximal portion 126 that is configured for engagement by the knife bar 72. Thus, if the surgeon desires to cut the tissue after the staples have been fired, the surgeon activates the firing trigger 200 as described above to drive the knife bar 172 distally into contact with the distal knife member 124 to drive the distal knife member 124 through the tissue as illustrated in FIG. 19. The distal knife member 124 may have at least one retainer portion thereon that is adapted to slide through a correspondingly shaped slot (not shown) in the elongated channel 14'. Such arrangement enables the end effector 12' to be opened after the staples have been formed and the tissue has been cut. The distal knife member 124 remains in the anvil 20' and is removed with the end effector 12' when it is withdrawn from the patient.

Thus, various embodiments of the surgical instrument 10 have separate stapling and tissue cutting mechanisms such that the surgeon may staple the tissue without cutting the tissue. The various embodiments of the stapling instrument of the present invention can be successfully employed with different sizes of end effectors that are adapted to fire different sizes and numbers of staples. The surgical instruments may be provided in the form of a kit that includes an instrument 10 and a first firing adapter 140 and a second firing adapter 150 that enables the instrument to be employed to fire different sizes of implantable staple cartridges.

Various unique and novel embodiments of the present invention employ a compressible staple cartridge that supports staples in a substantially stationary position for forming contact by the anvil. Unlike prior surgical stapling arrangements that employ staple driving elements, the staples in the cartridges of various embodiments of the present invention are not driven into the anvil. In the various embodiments of the present invention, the anvil is driven into the unformed staples. The degree of staple formation attained is dependent upon how far the anvil is driven into the staples. Such arrangement provides the surgeon with the ability to adjust the amount of forming or firing pressure applied to the staples and thereby alter the final formed height of the staples.

In various embodiments, the amount of firing motion that is applied to the movable anvil is dependent upon the degree of actuation of the firing trigger. For example, if the surgeon desires to attain only partially formed staples, then the firing trigger is only partially depressed inward towards the pistol grip 107. To attain more staple formation, the surgeon simply compresses the firing trigger further which results in the anvil being further driven into forming contact with the staples. As used herein, the term "forming contact" means that the staple forming surface or staple forming pockets have contacted the ends of the staple legs and have started to form or bend the legs over into a formed position. The degree of staple formation refers to how far the staple legs have been folded over and ultimately relates to the forming height of the staple as referenced above. Those of ordinary skill in the art will further understand that, because the anvil 20 moves in a substantially parallel relationship with respect to the staple cartridge as the firing motions are applied thereto, the staples are formed substantially simultaneously with substantially the same formed heights.

FIGS. 20-23 illustrate an alternative surgical instrument 10 that employs a staple height indicator assembly 220. In various embodiments, the staple height indicator assembly 220 comprises an indicator bar 222 that is attached to the upper portion 134 of the firing trigger 130 for pivotal travel therewith. As the firing trigger 130 is pivoted toward the pistol portion 107 of the handle assembly 100 to compress the anvil 20 into the staple cartridge 30 as described above, the indicator bar 222 is viewable through a window 223 in the left hand case member 104. In this embodiment, the staple height indicator assembly 220 also includes a series of detents 24, 26, 28 that are formed in the left hand case member 104 and which correspond to three stages of staple formation. In particular, once the firing trigger 130 is initially actuated, the retention pin 162 slides in abutting contact with the start detent 163 until the firing tube 110 has advanced the firing adapter 140 or 150 to the above-described locking position at which point the retention pin 162 is biased into a locking cavity 164 formed in the left hand case member 104. When the surgeon desires to start to close the jaws 13, 35 of the end effector 12, the retention release button 167 is depressed to enable the firing trigger 130 to be further actuated. When the firing trigger release button 167 is pressed inwardly, it contacts the retention pin 162 and moves it out of the locking cavity 163 to enable the firing trigger 130 to be activated. As described above, the surgeon may now use the bottom and top jaws 13, 15, respectively of the end effector 12 to grasp and manipulate tissue. When the surgeon desires to commence the staple forming process, the firing trigger release button 167 is depressed which enables the firing yoke 114 to be advanced distally as the surgeon continues to depress the firing trigger 130.

Further advancement of the firing trigger 130 moves the anvil 20 into forming contact with the staples 32 in the staple cartridge 30. As the firing trigger 130 is further depressed, the flat end 165 of the retention pin 162 will slide off of starting detent 163 and contact the first detent 224 that corresponds to a first amount of staple formation that is represented by a first staple height symbol 230 on the left hand case member 104. See FIG. 20. As shown, the first staple height symbol 230 comprises a picture of a staple that has just started to form. Other symbols/indicia could be used to designate this stage of staple formation. As the retention pin 162 engages the first detent 224 and audible click may be heard by the surgeon. The engagement of the retention pin 162 with the first detent 224 may also provide some tactile feedback to the surgeon through the firing trigger 130. In addition, the staple height indicator bar 222 may be viewed through the viewing window 223 adjacent to the first height staple symbol 230. If the surgeon desires to further form the staples 32 in the staple cartridge, the retention pin 162 is pressed out of engagement with the first detent 224 by a release button 240 that is formed into the second hand case member 104. In various embodiments for example, the release button 240 may be integrally formed into the left hand case member 104 with a hinge portion 242 that is part of the left hand case member 104. Such arrangement enables the release button 240 to be pressed into the end 165 of the retention pin 162 to move it out of engagement with any of the first, second and third detents 224, 226, 228. Once the retention pin 162 has been pressed out of the first detent 224, the firing trigger 130 may be further depressed until the retention pin 162 engages the second staple formation detention 226. Such position of the firing trigger 130 has resulted in further movement of the anvil 20 into staple forming contact with the staples 32 in the staple cartridge 30. Again, the retention pin 162 snaps into the second staple formation detent 226 providing the surgeon with audible and tactile feedback that the firing trigger 130 is in the second staple formation position. When in that position, the staple height indicator bar 222 may be viewed through the viewing window 223 and is adjacent to the second staple height symbol 232. If the surgeon desires to further form the staples 32 in the staple cartridge 30, the retention pin 162 is pressed out of engagement with the second detent 226 by depressing the release button 240. Thereafter, the firing trigger 130 may be depressed further until the retention pin 162 engages the third staple formation detent 228 corresponding to the final stage of staple formation. Again, the retention pin 162 snaps into the third staple formation detent 228 providing the surgeon with audible and tactile feedback that the firing trigger 130 is in the third staple formation position. When in that position, the staple height indicator bar 222 may be viewed through the viewing window 223 and is adjacent to the staple height symbol 234. After the staples have been formed a desired amount, the surgeon may bias the retention pin 162 out of the third staple height detent 228 to enable the firing trigger 130 to return to the starting position. Or, if desired, the surgeon may then commence the tissue cutting procedure as described above before returning the firing trigger 130 to the starting position.

Figure 24:
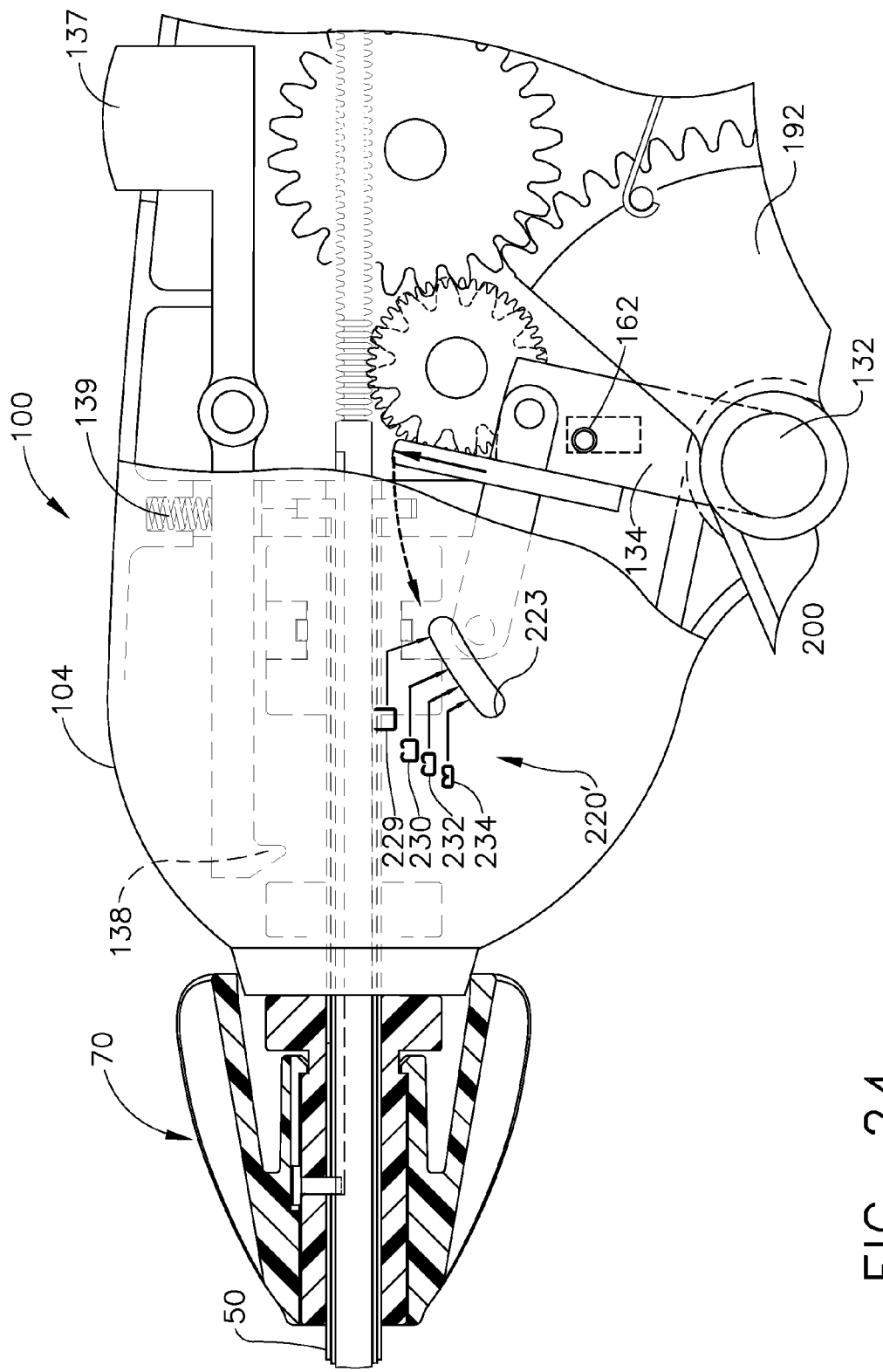
FIG. 24 is a cross-sectional view of a portion of another handle assembly embodiment of the present invention.

FIG. 24 illustrates an alternative embodiment wherein the staple height indicator assembly, generally designated as 220', does not include the series of detents that correspond to the various staple formations. This embodiment, however, does include the staple height indicator bar 222 and viewing window 223. Thus, the surgeon may monitor the amount of staple formation being achieved by monitoring the position of the staple height indicator bar 222 through the viewing window 223. This embodiment does include the staple height indicator symbols 230, 232, 234 as described above. In addition, this embodiment may also include an unformed staple symbol 229 that corresponds to the starting position wherein the staples 32 have not yet started to be formed by the anvil 20. This embodiment would otherwise operate in the same manners described above.

FIGS. 25 and 26 illustrate an alternative end effector 12" that is similar to the end effector 12' described above, except with the following differences that are configured to accommodate a knife bar 172'. The knife bar 172' is coupled to or protrudes from a knife rod 180 and is otherwise operated in the above described manner with respect to the knife bar 172. However, in this embodiment, the knife bar 172' is long enough to traverse the entire length of the end effector 12" and therefore, a separate distal knife member is not employed in the end effector 12". The knife bar 172' has an upper transverse member 173' and a lower transverse member 175' formed thereon. The upper transverse member 173' is oriented to slidably transverse a corresponding elongated slot 250 in anvil 20" and the lower transverse member 175' is oriented to traverse an elongated slot 252 in the elongated channel 14" of the end effector 12". A disengagement slot (not shown) is also provide din the anvil 20" such that when the knife bar 172' has been driven to an ending position with thin end effector 12", the upper transverse member 173' drops through the corresponding slot to enable the anvil 20" to move to the open position to disengage the stapled and cut tissue. The anvil 20" may be otherwise identical to anvil 20 described above and the elongated channel 14" may be otherwise identical to elongated channel 14 described above.

In these embodiments, the anvil 20" is biased to a fully open position (FIG. 25) by a spring or other opening arrangement (not shown). The anvil 20" is moved between the open and fully clamped positions by the axial travel of the firing adapter 150 in the manner described above. Once the firing adapter 150 has been advanced to the fully clamped position (FIG. 26), the surgeon may then advance the knife bar 172" distally in the manner described above. If the surgeon desires to use the end effector as a grasping device to manipulate tissue, the firing adapter may be moved proximally to allow the anvil 20" to move away from the elongated channel 14" as represented in FIG. 27 in broken lines. In this embodiment, as the knife bar 172" moves distally, the upper transverse member 173' and the lower transverse member 175' draw the anvil 20" and elongated channel 14" together to achieve the desired staple formation as the knife bar 172" is advanced distally through the end effector 12". See FIG. 28. Thus, in this embodiment, staple formation occurs simultaneously with tissue cutting, but the staples themselves may be sequentially formed as the knife bar 172" is driven distally.

FIGS. 29 and 30 illustrate use of an end effector 12" that has an anvil 20" that is fabricated from, for example, stainless steel, titanium, PGA (Polyglycolic acid) or other absorbable plastic and is somewhat flexible. These Figures also illustrate use of a retention matrix 6250 and an alignment matrix 6206 which will be discussed in further detail below. As can be seen in FIG. 29, the anvil 20" flexes into the fully formed position as the knife bar 172" is driven distally therethrough.

In many surgical applications, it is desirable or advantageous to employ a surgical cutting and stapling instrument that has an end effector that may be articulated relative to the elongated shaft assembly. The ability to access tight areas with prior articulatable instruments, however, was often times limited due to the size and construction of the members used to effect articulation of the end effector. FIGS. 31-40 illustrate another surgical instrument embodiment of the present invention that is capable of articulating the end effector relative to the elongated shaft and which employs a relatively compact articulation control arrangement in the handle assembly.

Figure 31:
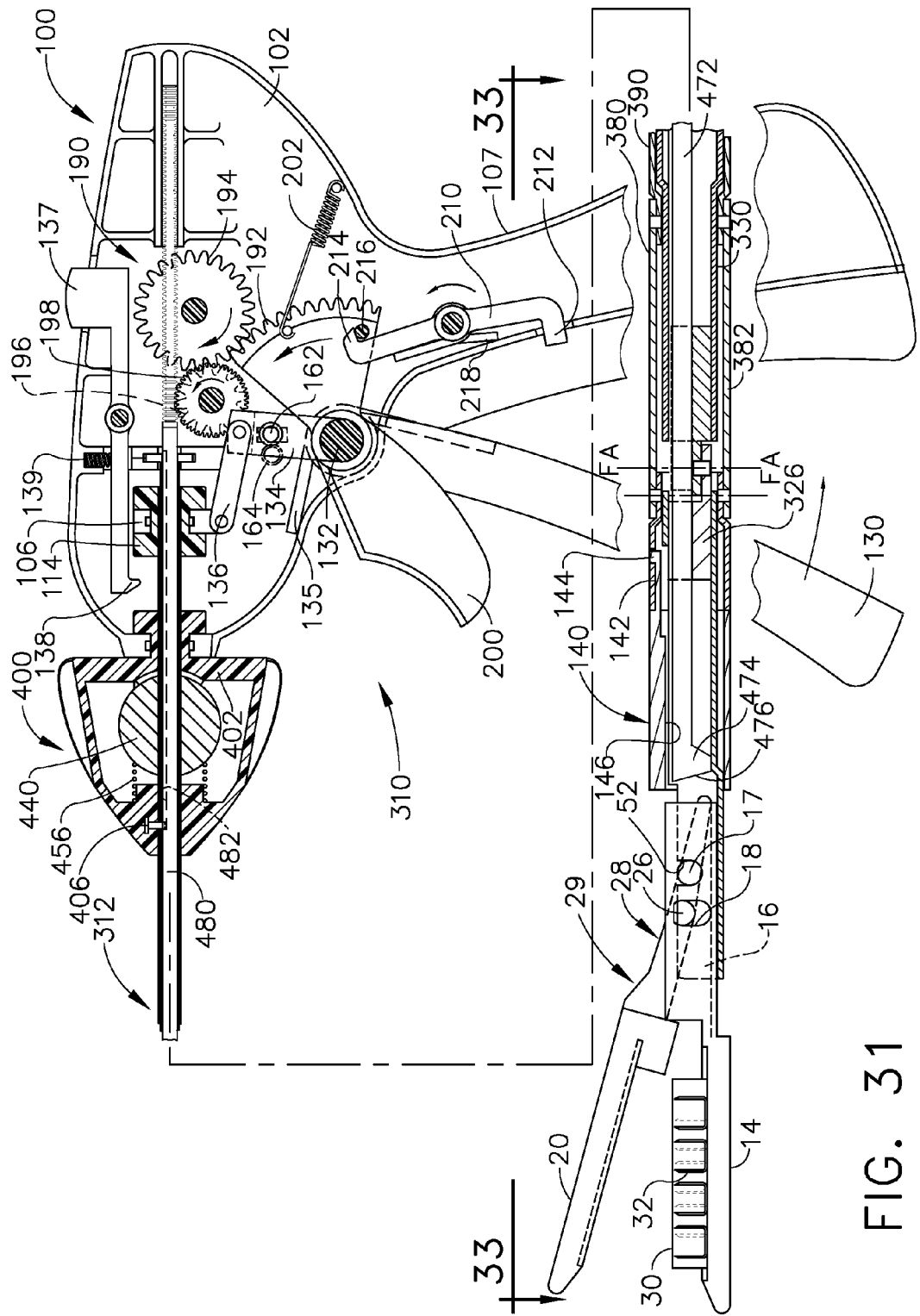
FIG. 31 is a cross-sectional view of another surgical instrument embodiment of the present invention with the anvil of the end effector thereof in an open position.
Figure 32:
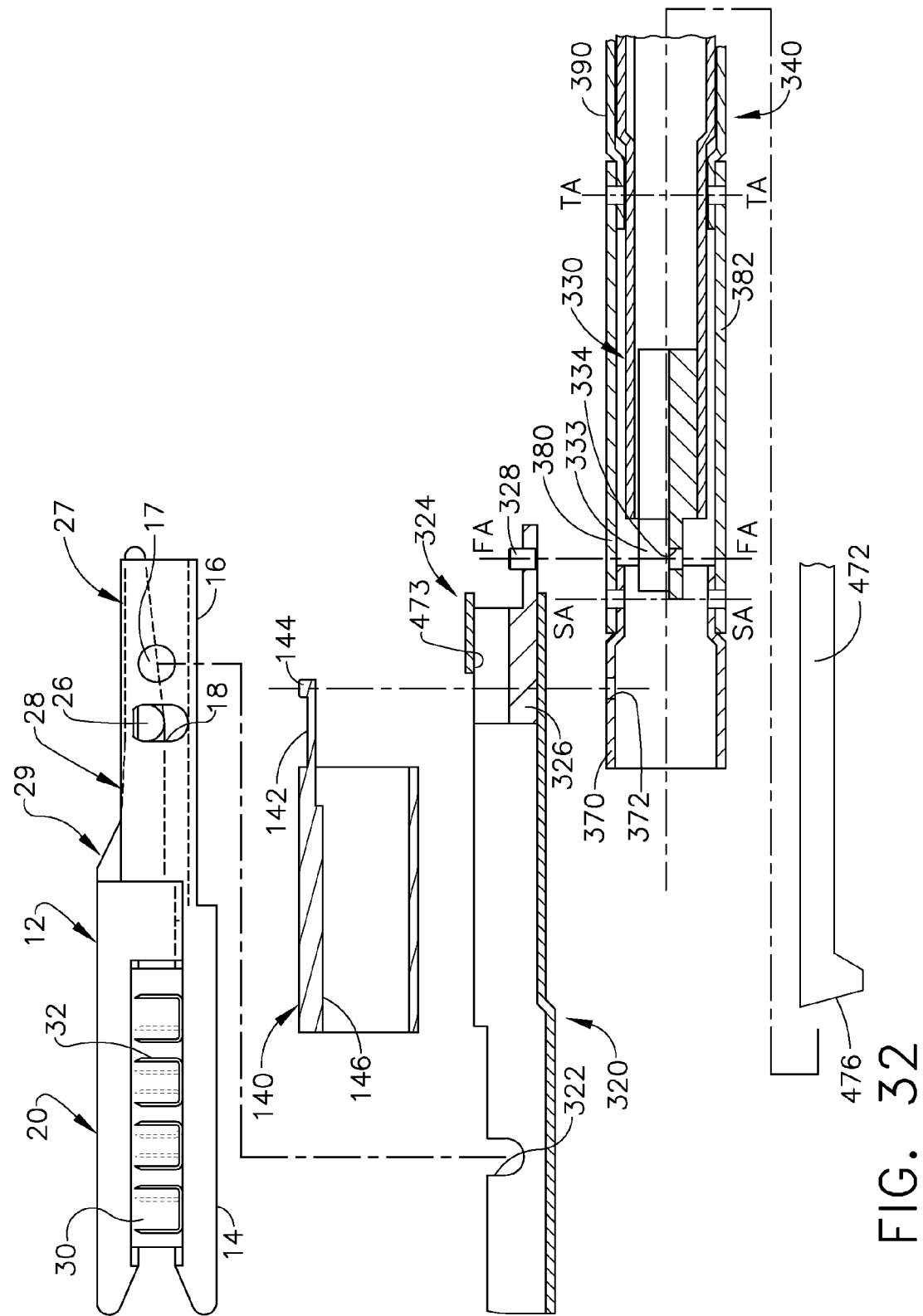
FIG. 32 is an exploded assembly view of the end effector embodiment and a portion of the surgical stapling instrument embodiment of FIG. 31 shown in cross-section.

The surgical instrument 310 of this embodiment is substantially similar to the various surgical instrument embodiments 10 described above, except that this embodiment employs an articulated shaft assembly 312 to facilitate selective positioning of the end effector 12 relative to the elongated longitudinal axis A-A. While the surgical instrument 310 will be described herein for use in connection with an end effector 12 of the type described above, those of ordinary skill in the art will appreciate that the surgical instrument 310 may also be employed in connection with a second firing adapter 150 to actuate an end effector 12' or other end effector arrangements. As can be seen in FIGS. 31 and 32, the articulated shaft assembly 312 includes a distal shaft assembly portion 314 that is pivotally coupled to a proximal shaft assembly portion 316 that is operably coupled to the handle assembly 100. In various embodiments, for example, the distal shaft assembly 314 includes a distal spine member 320 that has a pair of trunion cradles 322 therein for receiving the trunions 17 therein. See FIG. 32. The distal spine member 320 has a proximal end 324 that includes a pivot base 326 that has a pivot pin 328 protruding therefrom.

As can be seen in FIG. 32, the proximal shaft assembly portion 316 includes a proximal spine segment 330 that has a proximal pivot base and knife guide 332 attached thereto. The knife guide 332 may, for example, be welded or attached to the proximal spine segment 330 with adhesive or other fastener arrangements. A pivot hole 334 is provided in the proximal pivot base knife guide 332 to rotatably receive the pivot pin 328 therein to enable the distal spine segment 320 to pivot relative to the proximal spine segment 330 about a first pivot axis FA-FA that is substantially transverse to the longitudinal axis A-A. The surgical instrument 310 further includes a distal firing tube segment 370 that is pivotally coupled to a pair of firing tube links 380, 382 for pivotal travel about a second axis SA-SA. The distal firing tube segment 370 has a retainer hole 372 for receiving the retainer button 144 of the first firing adapter 140 therein. The pair of firing tube links 380, 382 are pivotally coupled to a proximal firing tube 390 for pivotal travel relative thereto about a third pivot axis TA-TA. See FIG. 32.

Figure 38:
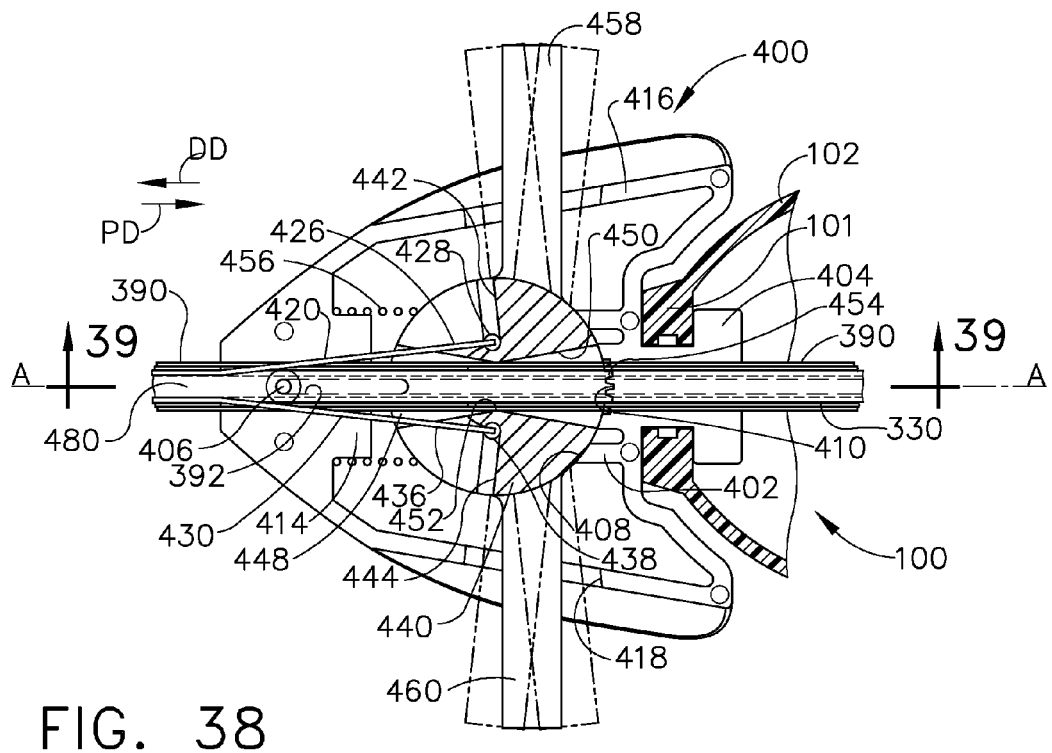
FIG. 38 is a cross-sectional view of a portion of the handle assembly of the surgical instrument of FIG. 31.
Figure 39:
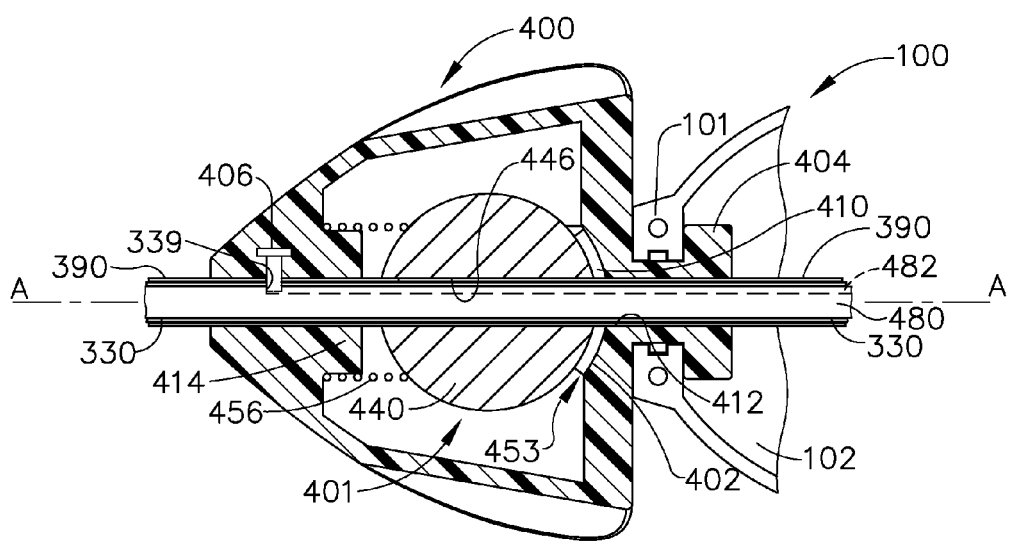
FIG. 39 is another cross-sectional view of the portion of the handle assembly of FIG. 38 taken along line 39-39 in FIG. 38.

In various embodiments, the proximal firing tube 390 is attached to a rotation knob 400 that is rotatably attached to the handle assembly 100. See FIGS. 31, 38 and 39. The rotation knob 400 may be molded from a polymer or plastic material and include a hub portion 402 and flange portion 404 that is spaced from the hub portion 402. A nose portion 101 of the handle assembly 100 is received between the hub portion 402 and the flange portion 404 to enable the rotation knob 400 to be rotatable relative to the handle assembly 100 about longitudinal axis A-A. In other embodiments, the rotation knob 400 may be fabricated from other suitable materials. In the depicted embodiment, the proximal firing tube 390 and the proximal spine segment 330 are each non-movably attached to the rotation knob 400. As can be seen in FIGS. 38 and 39, the proximal spine segment 330 and the proximal firing tube 390 are pinned to the rotation knob 400 by a pin 406. Thus, the surgeon may rotate the end effector 12 relative to the handle housing 100 in a 360° path about the longitudinal axis A-A by rotating the rotation knob 400.

Figure 37:
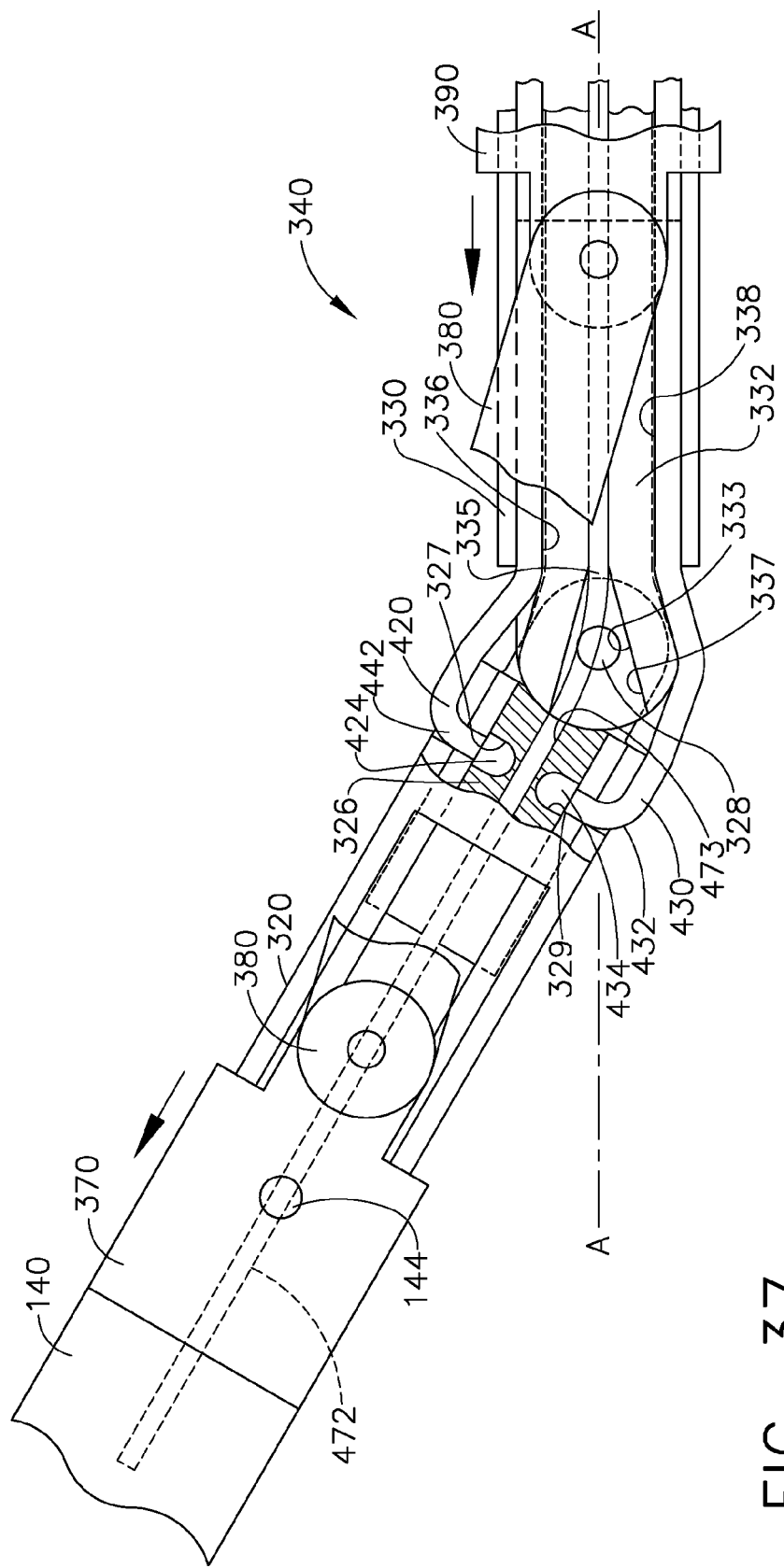
FIG. 37 is an enlarged view of a portion of the end effector and surgical instrument embodiment depicted in FIG. 36.
Figure 40:
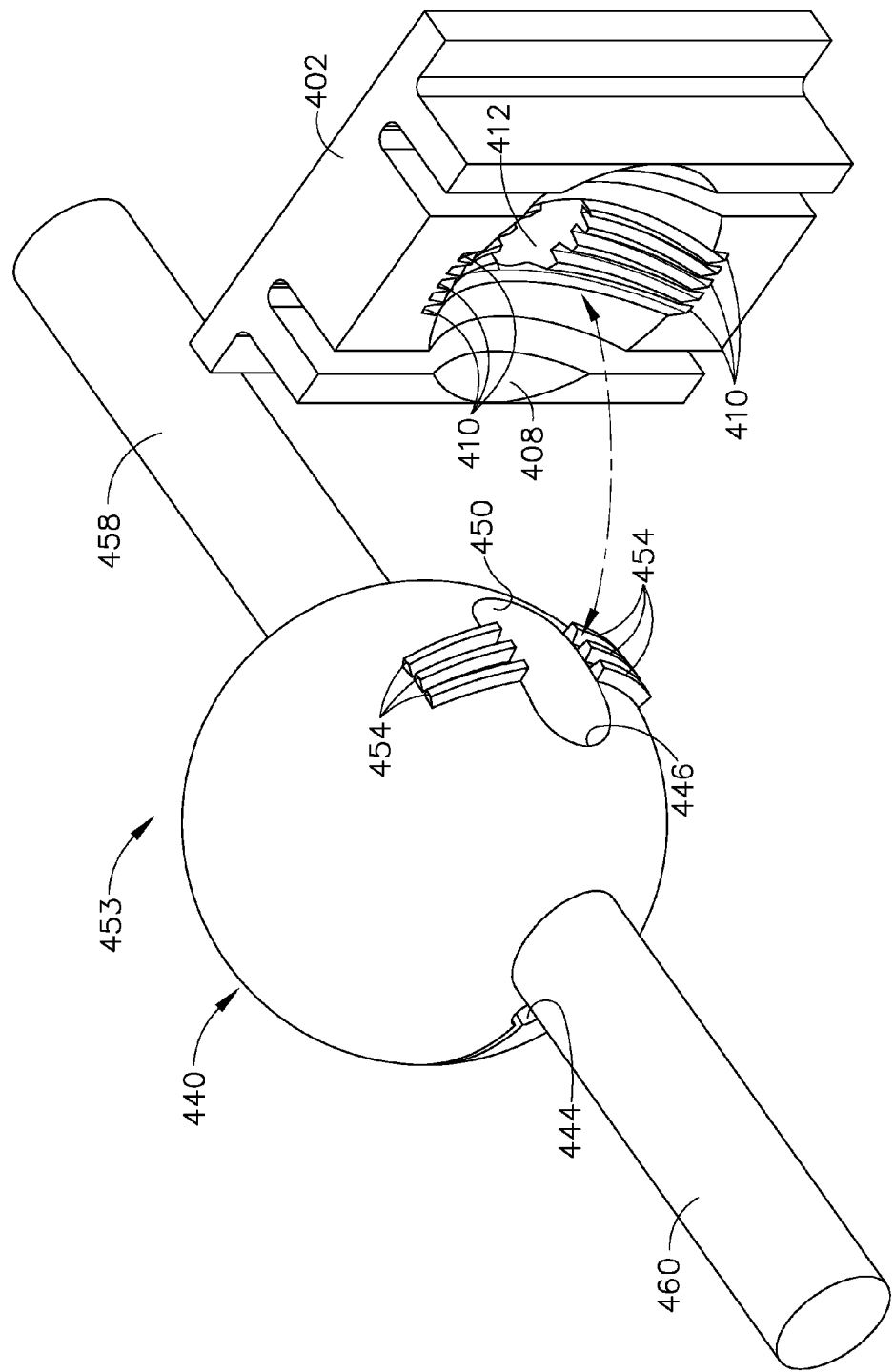
FIG. 40 is a partial perspective exploded view of an articulation ball and socket arrangement of various embodiments of the present invention.

Referring to FIGS. 37, 38 and 40, in various embodiments, the end effector 12 may be selectively articulated relative to the longitudinal axis A-A by a pair of articulation members 420, 430 that are attached to the distal pivot base 326 and an articulation ball 440 that is rotatably supported within a socket 408 in the rotation knob 400. In various embodiments, the articulation members 420, 430 may comprise, for example, cables that are fabricated from multiwire cable, Nitinol, titanium, etc. The first or right articulation member 420 has a distal end 422 that has a lug 424 formed thereon that is sized to be press-fit into a first cable attachment hole 327 that is provided in the distal pivot base 326. Likewise, the second or left articulation member 430 has a distal end 432 that has a lug 434 formed thereon that is sized to be press-fit into a second cable attachment hole 329 that is provided in the distal pivot base 326. See FIG. 37. Thus, the end effector 12 may be pivoted to the right about first axis FA-FA (FIGS. 35 and 36) by pulling on the first or right articulation member 420 and the end effector 12 may be pivoted to the left about first axis FA-FA by pulling the second or left articulation member 430. In various embodiments, the right articulation member 420 may be slidably received within a right cable channel 336 formed in the proximal spine segment 330 and the left articulation member 430 may be slidably received within a left cable channel 338 in the proximal spine segment 330.

Turning to FIGS. 38-40, the first articulation member 420 has a proximal end 426 that has a retaining ball 428 swaged thereon or otherwise attached thereto that is adapted to be received within a first retaining slot 442 in the articulation ball 440 that is rotatably supported within a socket 401 in the rotation knob 400. Likewise, the second articulation member 430 has a proximal end 436 that has a retaining ball 438 swaged thereon or otherwise attached thereto that is adapted to be received within a second retaining slot 444 in the articulation ball 440. As can be most particularly seen in FIG. 40, the articulation ball 440 further has an actuator slot 446 therethrough that facilitates the unimpeded passage of the proximal firing tube segment 390 therein. As shown in FIG. 38, the actuator slot 446 may taper from wider opening portions 448, 450 to a passage 452 in the center of the articulation ball 440 that permits sliding passage of the proximal firing tube segment 390. As will be discussed further below, the articulation ball 440 is rotatably or pivotally supported within the socket 401 and is selectively movable from a neutral position (shown in FIG. 38 in solid lines) to first and second articulation control positions (shown in FIG. 38 in broken lines). The articulation ball 440 is also axially movable within the socket 401.

As can be seen in FIG. 40, the surgical instrument 310 may include a locking arrangement, generally designated as 453 for locking the articulation ball 440 in any one of the neutral, first and second articulation control positions. In various embodiments, the locking arrangement 453 comprises a series of locking detent segments 454 that are provided on the articulation ball 440 and are adapted to mate with locking ribs 410 that are formed within a recessed 408 formed in a hub portion 402 oriented within the socket area 401 of the rotation knob 400. An actuator passage 412 extends through the hub portion 402 and aligns with the actuator slot 446 in the articulation ball 440 to accommodate the proximal firing tube segment 390 therethrough. As can be seen in FIGS. 38 and 39, an actuator ball spring 456 is journaled on a spring retention hub 414 portion of the rotation knob 400 to it bias the articulation ball 440 proximally such that the locking detents 454 are brought into retaining engagement with the locking ribs 410 in the hub portion 402.

To facilitate application of articulation motions to the articulation ball 440, a pair of laterally extending articulation handles 458, 460 protrude from the articulation ball 440 in diametrically opposite directions. In various embodiments, the articulation ball 440 may be fabricated from, for example, polycarbonate, Nylon, Ultem®, with no fill, glass fill, carbon fill, mineral fill, etc. and have the locking detents 454 machined or molded thereon. The articulation handles 458, 460 may be attached to the articulation ball 440 by press fits, welds, etc. Such locking arrangement enables the articulation ball 440 to be locked in any of the neutral or first or second articulation positions. Once the surgeon has moved the articulation ball 440 to achieve the desired articulated position of the end effector, the surgeon may release the articulation ball 440 to enable the actuator ball spring 456 to bias the articulation ball 440 proximally such that the locking detents 454 are brought into retaining engagement with the locking ribs 410 in the hub portion 402. In various embodiments, the actuator ball spring 456 may be sized such that the articulation ball 440 may spring back to the neutral position when the articulated end effector is forcibly pulled back through a trocar or similar opening. Furthermore, use of the articulation handles 458, 460 enable the degree of articulation to be "tuned" to the particular surgical application.

As can be seen in FIG. 38, the first or right articulation handle 458 protrudes through a right slot 416 in the rotation knob 400 and the second or left articulation handle 460 protrudes through a left slot 418 in the rotation knob 400. To articulate the end effector 12 relative to the longitudinal axis A-A, the surgeon first moves the right and left articulation handles 458, 460 axially in the distal direction "DD" to disengage the locking detents 454 from the locking ribs 410 in the hub portion 402 of the rotation knob 400. Thereafter, the surgeon may pivot the articulation ball 440 by moving the articulation handles 458, 460 in the desired directions to apply articulation motions to the articulation members 420, 430. For example, the end effector 12 may be pivoted to the right by moving the right articulation handle 458 in the proximal direction "PD" and the left articulation handle 460 in the distal direction "DD" to apply a pulling motion (articulation motion) to the right articulation member 420 and a pushing motion to the left articulation member 430. Similarly, the end effector 12 may be pivoted to the left by moving the left articulation handle 460 in the proximal direction "PD" and the right articulation handle 458 in the distal direction "DD" to apply a pulling motion (articulation motion) to the left articulation member 430 and a pushing motion to the right articulation member 420. The various ranges of motions of the right and left articulation handles 458, 460 are illustrated in broken lines in FIG. 38. In this way, the end effector 12 can be optimally positioned in a variety of angular positions, e.g., by angling clockwise or counterclockwise, without requiring rotation or other movement of the elongated shaft assembly 40. FIG. 35 shows the angle α which in various embodiments can be from 0° to 45°.

Various embodiments of the surgical instrument 310 include a knife bar 472 that is movably supported within the hollow proximal spine segment 330 and through a knife support slot 333 that tapers from a narrow proximal portion 335 to a wide distal portion 337 to enable the knife bar 472 to flex therearound to accommodate the articulation of the end effector 12 about the longitudinal axis A-A. See FIG. 37. In various embodiments, the knife bar 472 may be fabricated from, for example, 300 or 400 Series stainless steel and have a tissue cutting edge 476 formed on the distal end thereof. As can be further seen in FIG. 37, the knife bar 472 slidably passes through a knife slot 473 in the distal pivot base 326. A proximal end 478 of the knife bar 472 is attached to a knife rod 480 that extends through the proximal spine segment 330 to drivingly engage the firing transmission 190 as was described above. See FIG. 31. The retention pin 406 extends into a longitudinal slot 392 (FIG. 38) in the proximal firing tube segment 390 and through a hole 339 in the proximal spine segment 330 (FIG. 39) and into a longitudinal slot 482 in the knife rod 480 to enable the proximal firing tube segment 390 and the knife rod 480 to move axially relative to the proximal spine segment 330 and handle assembly 100. Thus, the surgeon may selectively operate the knife bar 472 to cut tissue by operating the knife advancement trigger 200 in the manner described above.

Various articulation arrangements are disclosed in U.S. patent application Ser. No. 12/775,809, entitled "Laparoscopic Devices With Articulating End Effectors", to Frederick E. Shelton IV, filed May 7, 2010 and U.S. patent application Ser. No. 12/775,699, entitled "Bendable Shaft For Handle Positioning" to Frederick E. Shelton IV, et al., filed May 7, 2010, the disclosures of each being herein incorporated by reference in their respective entireties. FIGS. 41 and 42 illustrate an alternative articulated shaft assembly 490 that is substantially identical to the articulated shaft assembly 340 and is operated in substantially the same way except for the intermediate firing tube segment 492 which replaces the firing tube link 380 employed in the articulated shaft assembly 340. As can be seen in FIGS. 41 and 42, the intermediate firing tube segment 492 extends from the distal firing tube segment 370 to the proximal firing tube segment 390. In various embodiments, the intermediate firing tube segment 492 may be fabricated from Nylon, Isoplast®, or other flexible plastic. In various embodiments, the intermediate firing tube segment 492 has two longitudinally extending compression spine portions 494 from which a plurality of spaced rib segments 496 that are separated by spaces 498 extend to form a substantially hollow tube segment through which the other components of the spine assembly and knife bar may operably pass. The spine portions 494 are configured to transmit the compression motions from the proximal firing tube segment 390 to the distal firing tube segment 370 which are of sufficient magnitude to actuate the anvil 20 to a fully fired position while enabling the end effector 12 to be selectively articulated relative to the longitudinal axis A-A. The intermediate firing tube segment 492 has a distal end portion 491 that is attached to the distal firing tube segment by, for example, pins, slotted bosses, snap features, etc. as well as proximal portion 493 that is attached to the proximal firing tube segment 390 by the same or similar means. In this embodiment, the end effector 12 can be optimally positioned in a variety of angular positions, e.g., by angling clockwise or counterclockwise, without requiring rotation or other movement of the elongated shaft assembly 490. FIG. 42 shows the angle α which in various embodiments can be from 0° to 45°.

Figure 43:
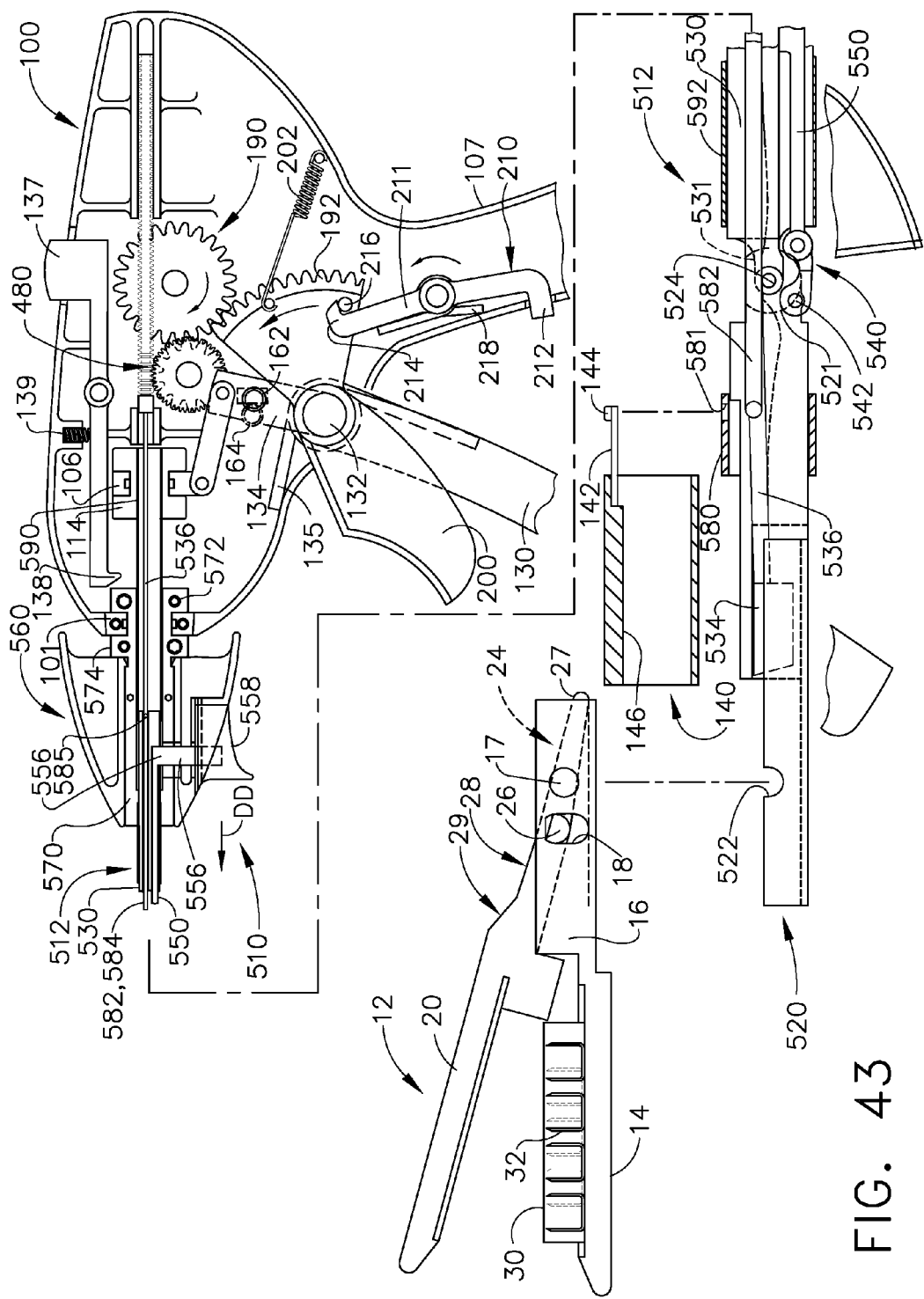
FIG. 43 is cross-sectional view of another surgical instrument embodiment of the present invention.
Figure 44:
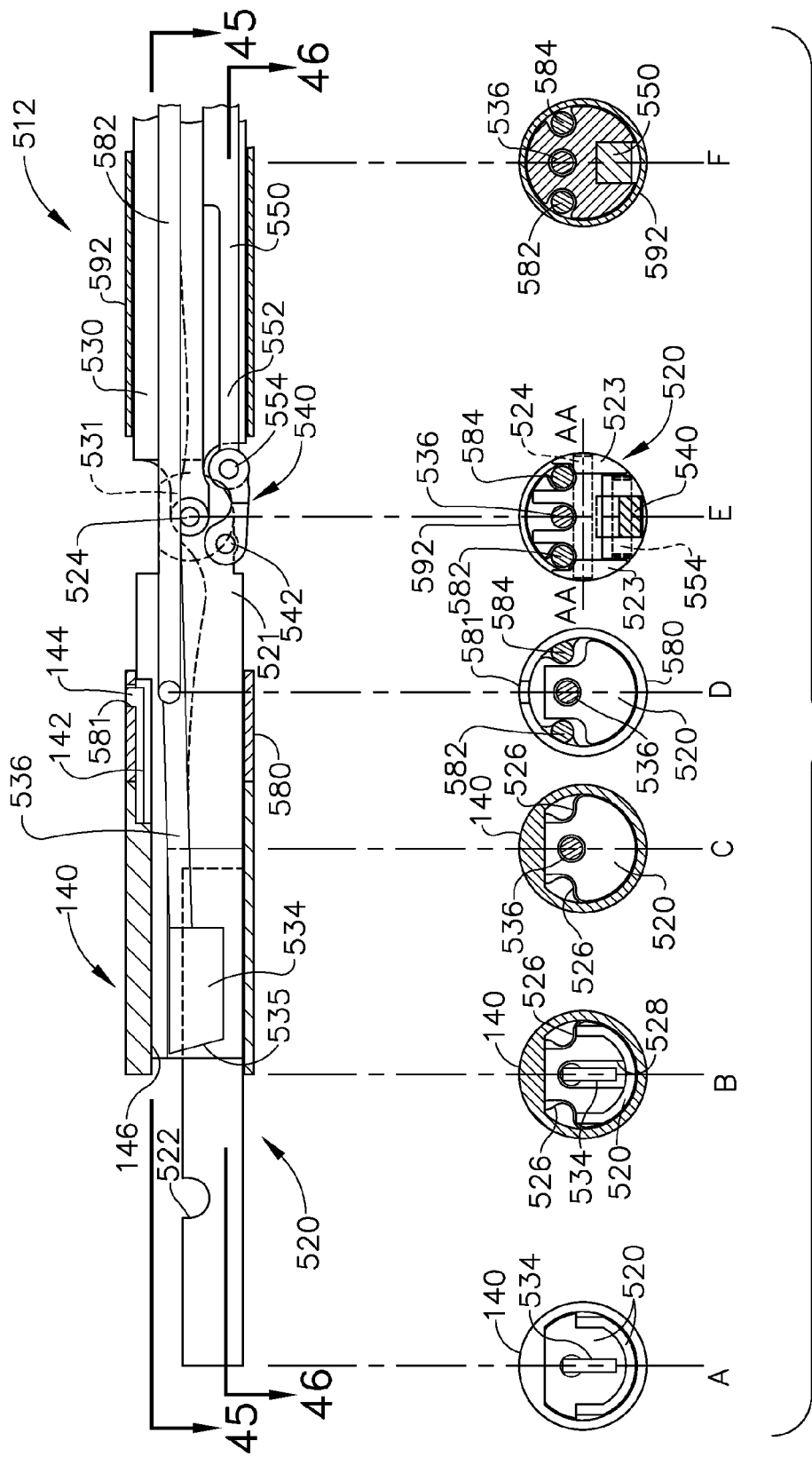
FIG. 44 is partial cross-sectional view of a portion of the articulated shaft assembly of the surgical instrument embodiment of FIG. 43.
Figure 45:
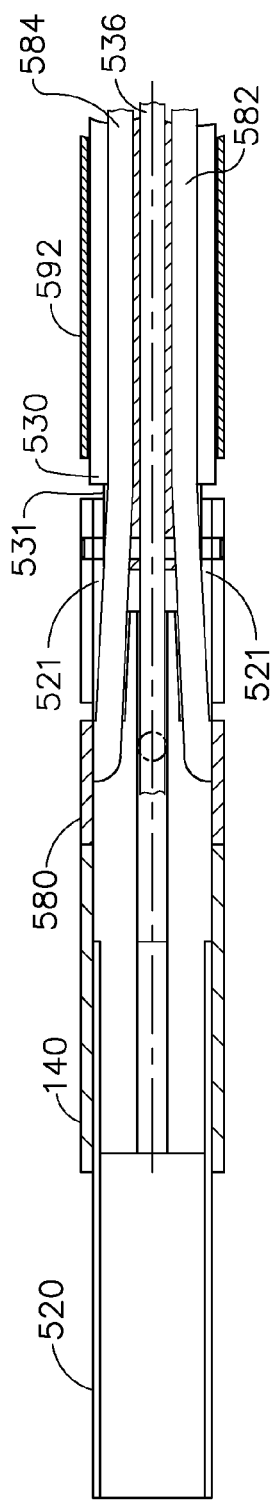
FIG. 45 is a partial cross-sectional view of the articulated shaft assembly of FIG. 44 taken along line 45-45 in FIG. 44.

FIGS. 43-47 illustrate another surgical instrument embodiment of the present invention. The surgical instrument 510 of this embodiment is substantially similar to the surgical instrument embodiment 310 described above, except for the various differences discussed below. While the surgical instrument 510 will be described herein for use in connection with an end effector 12 of the type described above, those of ordinary skill in the art will appreciate that the surgical instrument may also be employed in connection with a second firing adapter 150 to actuate an end effector 12' or it may be used in connection with other end effector arrangements. Various embodiments of the surgical instrument 510 include an articulated shaft assembly 512 to facilitate selective positioning of the end effector 12 relative to the longitudinal axis A-A. As can be seen in FIGS. 43 and 44, the articulated shaft assembly 512 includes a distal spine member 520 that has a pair of trunion cradles 522 therein for receiving the trunions 17 therein. The distal spine member 520 has a proximal end 521 that is pivotally coupled to a distal end 531 of a proximal spine segment 530. In particular, the proximal end 521 of the distal spine segment 520 has a pair of spaced distal spine tines 523 that support an articulation pin 524 that extends through the distal end 531 of the proximal spine segment 530 to define an articulation axis AA-AA that is substantially transverse to longitudinal axis A-A. See FIG. 46.

Figure 46:
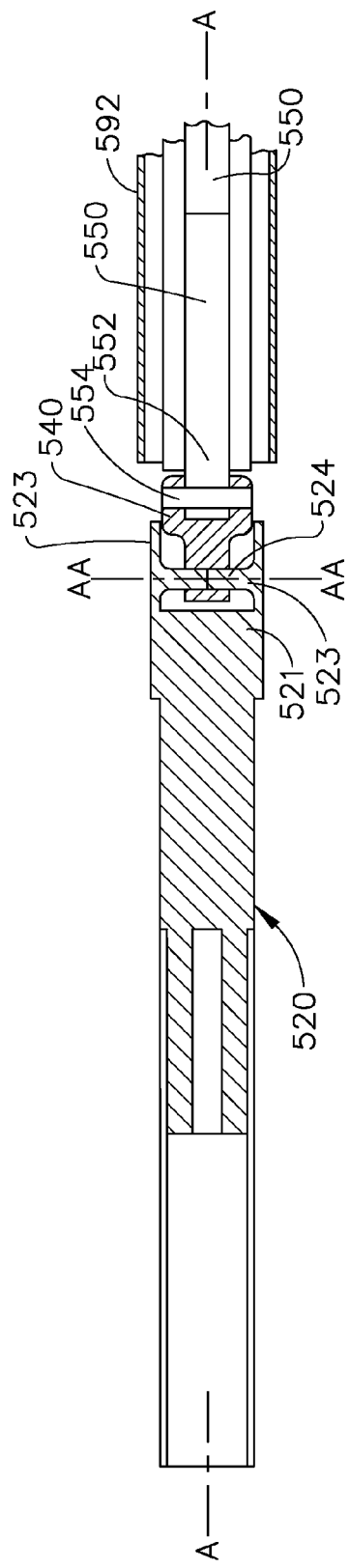
FIG. 46 is a partial cross-sectional view of the articulated shaft assembly of FIG. 44 taken along line 46-46 in FIG. 44.
Figure 47:
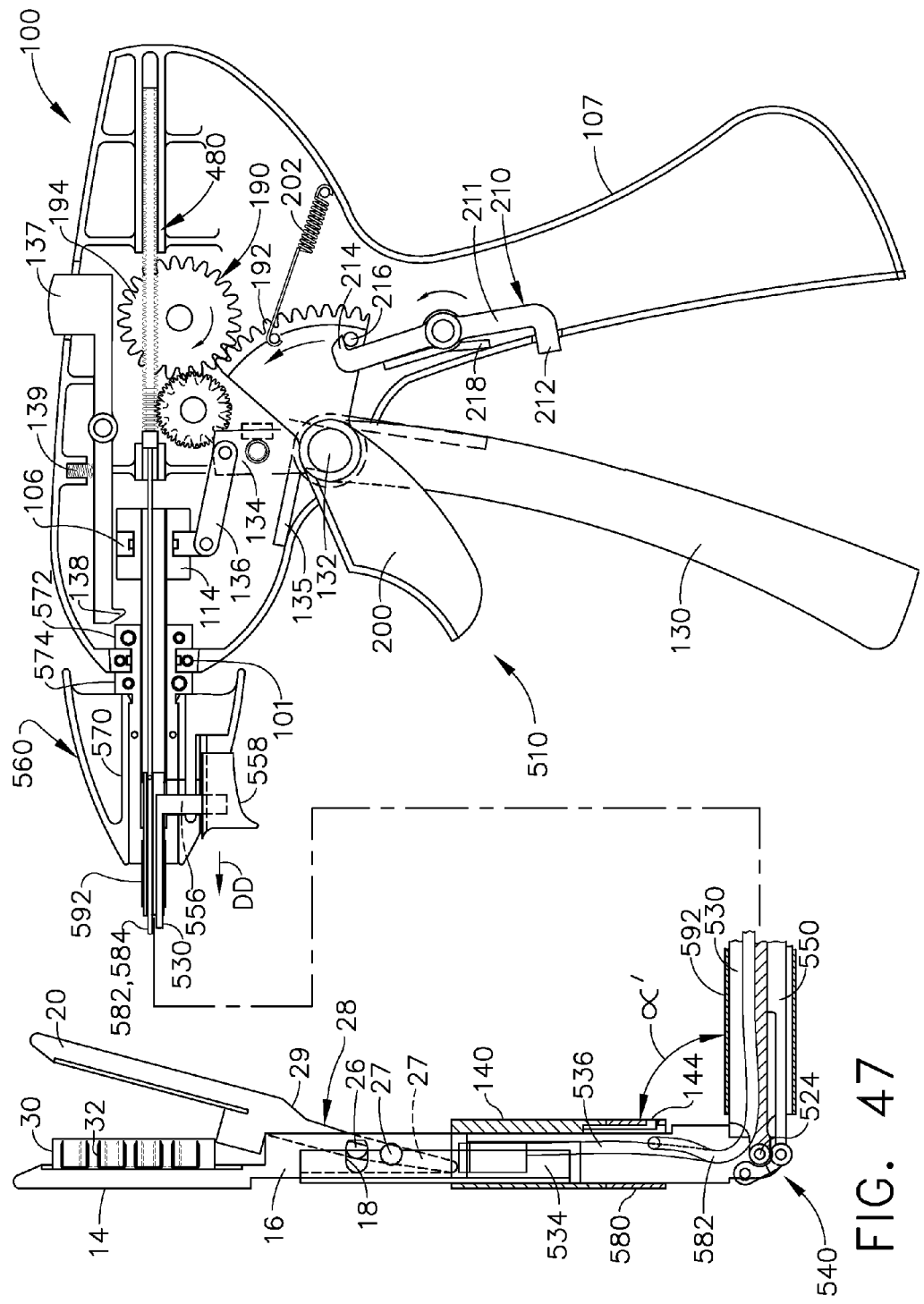
FIG. 47 is another cross-sectional view of the surgical instrument of FIG. 43 with the end effector thereof shown in a fully articulated position.

In various embodiments of the present invention, the end effector 12 is articulatable to a variety of different orientations about the longitudinal axis A-A. For example, angle α' in FIG. 47 can range from 180° to 90°. The end effector 12 is articulated by means of at least one articulation member 550 that is coupled to an articulation link 540. Articulation link 540 is pivotally coupled to the distal end 521 of the distal spine segment 520 by a distal pin 542. See FIG. 43. The articulation link 540 is pivotally coupled to the distal end 552 of the articulation rod 550 by an articulation rod pin 554 as shown in FIG. 46. As can be seen in FIG. 43, the articulation member 550 extends through the articulated shaft assembly 512 and has a proximal end 556 that extends into a rotation knob 560 that is rotatably coupled to the handle assembly 100. The proximal end 556 of the articulation member 550 is coupled to an articulation control member or button 558 that is slidably coupled to the rotation knob 560 for selective axial travel relative thereto. Thus, axially sliding the articulation button 558 in the distal direction "DD" will cause the end effector 12 to pivot about the longitudinal axis A-A in the manner illustrated in FIG. 47. To return the end effector to a starting unarticulated position wherein the end effector is coaxially aligned on the longitudinal axis A-A, the surgeon simply slides the actuator button 558 in the proximal direction "PD" on the rotation knob 560.

As with some of the embodiments described above, the rotation knob 560 is non-rotatably coupled to a mounting bushing 570 that is rotatably affixed to the handle assembly 100. See FIGS. 43 and 47. The mounting bushing 570 has a proximal flange 572 and a distal flange 574 that define a rotational groove 575 therebetween to rotatably receive a nose portion 101 of the handle assembly 100 therebetween. Such arrangement enables the mounting bushing 570 to rotate about longitudinal axis A-A relative to the handle assembly 100. The proximal spine segment 530 is non-rotatably pinned or otherwise attached (welded, adhesive, etc.) to the mounting bushing 570 such that rotation of the rotation knob 560 about longitudinal axis A-A causes the end effector 12 to rotate about longitudinal axis A-A. It will be understood that such arrangement may facilitate rotation of the end effector 12 in a 360° path about the longitudinal axis A-A.

This embodiment also has a distal firing tube segment 580 that is coupled to the first firing adapter 140 and axially movable on the distal spine segment 520. In particular, the retainer button 144 on the first firing adapter 140 is received within a retainer hole 581 in the distal firing tube segment 580 in the manner described above. The distal firing tube segment 580 is actuated by at least one firing member that is attached thereto. In a preferred embodiment, the distal firing tube segment 580 is actuated by a pair of firing bands 582, 584 attached thereto. The firing bands 582, 584 are attached to a band mount 585 coupled to a proximal firing tube segment 590 that is attached to the firing yoke 114 in the above-described manner. Also journaled on the proximal spine segment 530 and coupled to the rotation knob 560 for rotation therewith is a cover tube 592. The proximal firing tube 590 and the band mount 585 are axially movable relative to the cover tube 592. The firing bands 582, 584 are slidably received within lateral band channels 526 in the distal spine member 520 as shown in FIG. 44C. In various embodiments, the firing bands 582, 584 each comprise a thin flexible member that may be fabricated from, for example, stainless steel and are each capable of pushing on the distal firing tube segment 580 to actuate or close the anvil 20 in the above-described manner to form the staples 32 in the implantable staple cartridge 30. Actuation of the firing cables 582, 584 is accomplished by pulling the firing trigger 130 in the above-described manners. Returning the firing trigger 130 to the starting position will pull on the firing cables 582, 584 and cause the first firing adapter 140 to either pull the anvil 20 to an open position or to move to a position wherein a spring (not shown) biases the anvil 20 to the open position.

Figure 48:
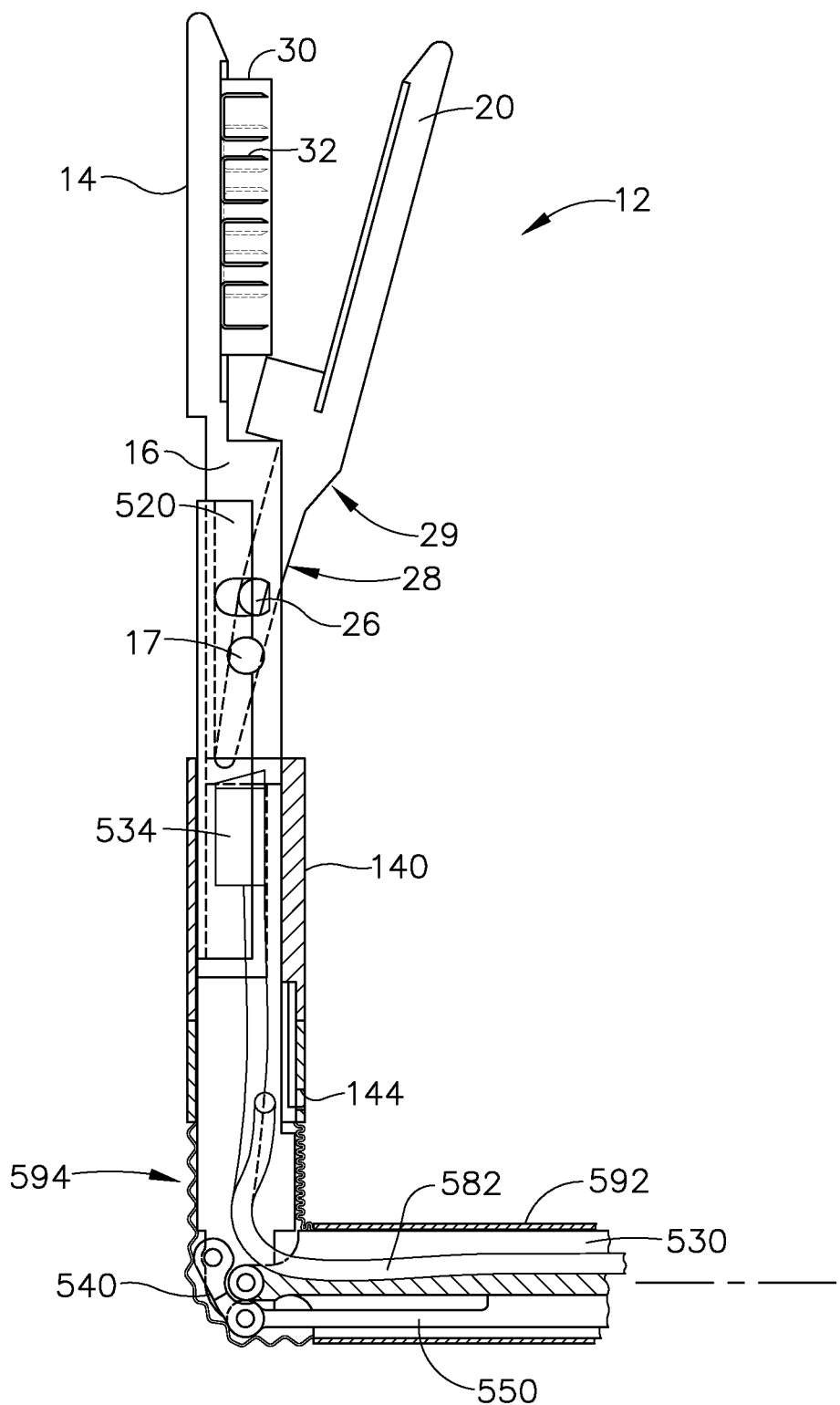
FIG. 48 is a cross-sectional view of the end effector of FIG. 47 with a bellows-like cover extending over the articulation joint.

The surgical instrument 510 may further include a knife 534 that is movably supported within a knife support slot 528 in the distal spine segment 520. See FIG. 44B. In various embodiments, the knife bar 534 may be fabricated from, for example, 300 or 400 stainless steel, etc. and have a tissue cutting edge 535 formed on the distal end thereof. The knife bar 534 is attached to a knife band 536 that may be fabricated from 300 or 400 series stainless steel. The knife band may, for example, comprise 0.007 to 0.012 inch thick stainless steel band material that is more hardened than the rod. The knife cable 536 extends through the distal spine member 520 and the proximal spine segment 530 and is attached to a knife rod 480 that drivingly engages the firing transmission 190 as was described above. Thus, the surgeon may selectively operate the knife bar 534 to cut tissue by operating the knife advancement trigger 200 in the manner described above. Various embodiments may also employ a bellows-like cover member 594 to prevent dirt, tissue, debris, etc. from fouling the articulation joint. See FIG. 48.

FIGS. 49-53 illustrate another surgical instrument embodiment of the present invention. The surgical instrument 610 of this embodiment is substantially similar to the surgical instrument embodiment 10 described above, except for the differences explained below. The surgical instrument 610 is configured to actuate an end effector 612 that has two movable jaws 613, 615. In various embodiments, the end effector 612 is coupled to an elongated shaft assembly 655 that protrudes from a handle assembly 100. See FIG. 49. The elongated shaft assembly 655 includes an elongated spine assembly 658 and an elongated closure tube assembly 680 that is axially movable on the spine assembly 658 in the proximal and distal directions. As shown, the elongated shaft assembly 655 extends distally from the handle assembly 100 in a generally straight line along a longitudinal axis A-A. In various embodiments, the elongated shaft assembly 655 may be approximately 9 to 16 inches (approximately 228.8 mm to 406.4 mm) long. However, the elongated shaft assembly 655 may be provided in other lengths.

Referring to FIGS. 50 and 51, in various embodiments, the lower jaw 613 of the end effector 612 comprises an elongated channel 614 and the upper jaw 615 comprises an anvil 620. The elongated channel 614 has a pair of spaced side walls 616 that each terminate in an upwardly protruding closure end or tip 618. The elongated channel 614 may be fabricated from, for example 17-4 or 400 series stainless steel and be sized to operably support a staple cartridge 630 or other form of staple cartridge therein. The anvil 620 may be fabricated from 416, 17-4, 17-7 stainless steel, etc. In at least one embodiment, for example, end effector 612 (when in a closed position) and the elongated shaft assembly 655 each have a maximum outer diameter that would permit the device to be operably passed through an opening that has a diameter of at least approximately 8-12 mm (approximately 0.31-0.47 inches). However, the end effector 612 and elongated shaft assembly 655 may have other diameters and shapes. The end effector 612 further includes a distal spine segment 660 that is adapted to be removably coupled to a distal end of a proximal spine segment 670 as will be further explained below.

Figure 55:
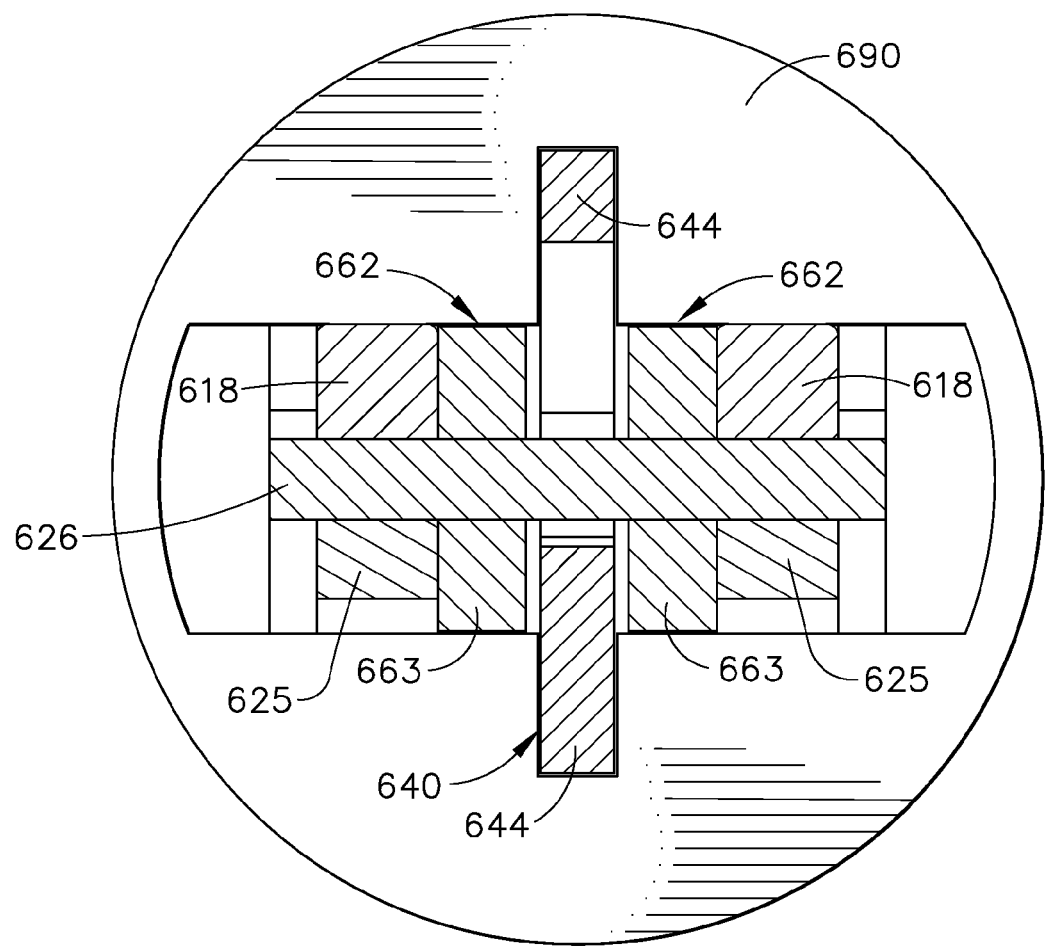
FIG. 55 is a cross-sectional view of the end effector of FIGS. 51-54 taken along line 55-55 in FIG. 51.

The anvil 620 has a staple forming portion 622 that has a plurality of staple forming pockets formed therein. In addition, the anvil 620 has a bifurcated closure portion 624 that includes at least one and preferably a pair of downwardly extending closure tips 625. As can be seen in FIGS. 50-53, in at least one embodiment, the closure tips 625 and the corresponding closure ends or tips 618 of the elongated channel 614 are pivotally pinned to spine lugs 663 of a bifurcated distal end 662 of a distal spine segment 660 (FIG. 55) of a spine assembly 658 by a pivot pin 626 such that, when viewed from the side, the closure tips 625 and closure tips 618 form a movable "scissors-like" closure structure generally designated as 628. In other embodiments, the anvil 620 may be movably coupled to the elongated channel 614.

Various embodiments of the end effector 612 also include an axially movable knife assembly 640 that includes a knife plate 642 that has a pair of spaced knife bars 644 protruding distally therefrom that are configured to slide axially between the spine lugs 663 of the distal spine segment 660. See FIG. 55. A knife member 646 is attached to, or otherwise formed on, the distal ends of the knife bars 644. In various embodiments, the knife bars 644 and the knife member 646 may be fabricated from, for example, 300 or 400 Series stainless steel. A tissue cutting edge 648 is formed on a distal end of the knife member 646. A lower portion 649 of the knife member 646 is configured to engage a staple driving sled 650 that is movably supported within the elongated shaft 614. The staple driving sled 650 may be retained in a slot or slot arrangements (not shown) in the elongated channel 614 to facilitate axial movement of the staple driving sled 650 from a starting position (FIGS. 50-52) to an end position (FIG. 53) while remaining connected to the elongated channel 614. The staple driving sled 650 has a staple driving surface or surfaces 652 thereon that are oriented to drivingly engage the staples 632 in the staple cartridge 630 and drive the staples 632 upward toward the staple forming portion 622 of the anvil 620 as the knife member 646 is distally advanced through the end effector 612.

Figure 49:
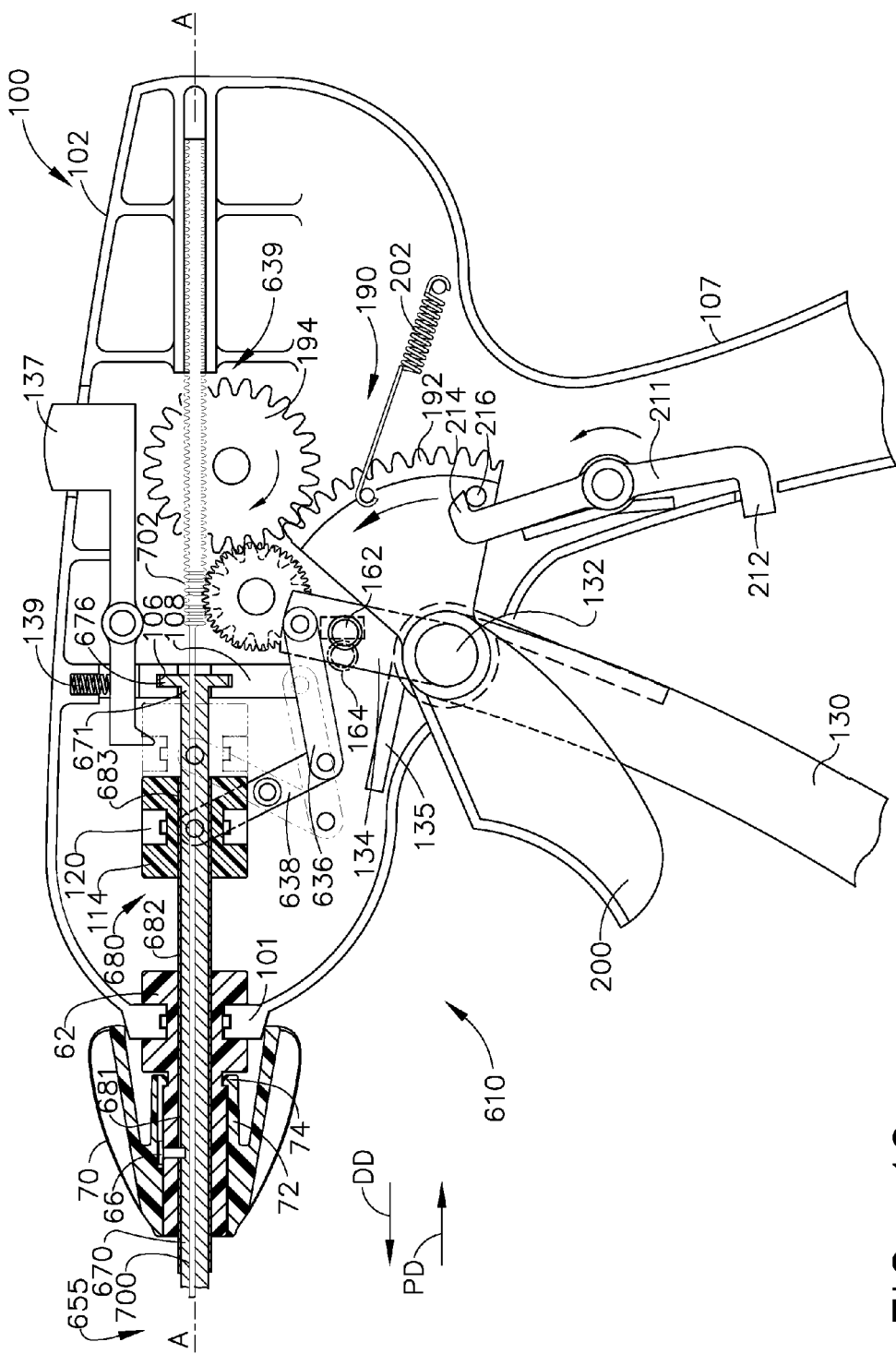
FIG. 49 is a cross-section view of a handle assembly of another surgical instrument embodiment of the present invention.

Also in various embodiments, a distal spine nut 668 is rotatably coupled to the proximal end 664 of the distal spine segment 660 for rotational travel relative thereto about the longitudinal axis A-A. The distal spine nut 668 has a pair of inwardly extending trunions 669 that are sized to be received in corresponding trunion slots 674 in a distal end 672 of a proximal spine segment 670 that protrudes from the handle assembly 100 to enable the distal spine segment 660 to rotate relative to the proximal spine segment 670. As can be seen in FIG. 49, the proximal spine segment 670 is pinned to the rotation knob 70 (by pin 66) that is rotatably mounted to the handle assembly 100 in the above-described manner to facilitate rotation of the end effector 612 about the longitudinal axis A-A in a 360° path.

As can also be seen in FIG. 49, a flange 676 is formed on a proximal end 671 of the proximal spine segment 670. The flange 676 is configured to be rotatably supported within a groove 106 formed by mating ribs 108 that protrude inwardly from each of the case members 102, 104. Such arrangement facilitates the attachment of the proximal spine segment 670 to the handle assembly 100 while enabling the proximal spine segment 670 to be rotated relative to the handle assembly 100 about the longitudinal axis A-A in a 360° path. The proximal closure tube segment 682 may be fabricated from a polymer or other suitable material and have a proximal end 683 that is attached to a firing yoke 114 that is constructed and movably mounted within the handle assembly 100 in the various manners described above. In various embodiments for example, the firing yoke 114 may be over-molded to the proximal end 683 of the proximal closure tube segment 682. However, other fastener arrangements may be employed. As described above, the firing yoke 114 may be rotatably supported within a support collar 120 that is configured to move axially within the handle assembly 100. As can be seen in FIG. 49, a longitudinal slot 681 is provided through the proximal closure tube segment 682 to enable the spine pin 66 to extend therethrough into the proximal spine segment 670 while facilitating the axial travel of the proximal closure tube segment 682 on the distal spine segment 670.

As can be seen in FIG. 49, the firing trigger 130 has an upper portion 134 that is pivotally (pinned) to firing links 636, 638 that are pivotally (pinned) to the support collar 120. Thus, movement of the firing trigger 130 toward the pistol grip portion 107 of the handle assembly 100 will cause the firing yoke 114 and the proximal closure tube segment 682 to move in the proximal direction "PD" (shown in broken lines in FIG. 49). Movement of the clamp and firing trigger 130 away from the pistol grip portion 107 of the handle assembly 100 will cause the firing yoke 114 and firing tube 110 to move in the proximal direction "DD" on the proximal spine segment 670.

As can be seen in FIGS. 50-53, the proximal closure tube segment 682 has a distal end 684 that is configured to be attached to a proximal end 692 of a distal closure tube segment 690. In the illustrated embodiment, the distal closure tube segment 690 is configured to be threadably attached to the distal end 684 of the proximal closure tube segment 682. The distal end 694 of the distal closure tube segment 690 has a tapered drive member 696 therein that is configured to interface with the scissors-like closure structure 628 such that when the distal closure tube segment 690 is in the position illustrated in FIG. 51, an end effector spring or springs 617 positioned between the elongated channel 614 and the anvil 620 serves to bias the anvil 620 to the open position illustrated in that Figure. However, when the distal closure tube segment 690 is pulled in the proximal direction "PD", the tapered drive member 696 contacts the scissors-like closure structure 628 to pivot the jaws 613 (elongated channel 614) and 615 (anvil 620) towards each other. See FIGS. 52 and 53.

The surgical instrument 610 may further include a knife advancement system 639 that includes knife rod 700 that extends through the proximal spine segment 670 and has a proximal end portion 702 that drivingly interfaces with a firing transmission 190 that is operably attached to a knife advance trigger 200 in the manner described above. Thus, the surgeon may advance the knife rod 700 distally by pulling the knife advancement trigger 200 as was described above. As can be seen in FIGS. 52 and 53, the knife rod 700 has a bifurcated distal end 704 that includes an upper knife rod segment 706 and a lower knife rod segment 708 that are configured to engage the knife plate 642. As can be seen in FIGS. 51-54, the upper knife rod segment 706 is configured to slide through an upper slot 773 in the spine nut 668 and the lower knife rod segment 708 is configured to slide through a lower slot 775 in the spine nut 668.

To use the surgical instrument 610, the end effector 612 is attached to the distal end 672 of the proximal spine segment 670 by inserting the trunions 669 on the spine nut 668 into their corresponding trunion cradles 674 in the proximal spine segment 670. See FIG. 50. Thereafter, the surgeon or clinician may rotate the end effector 612 relative to the elongated shaft assembly 655 to thread the distal closure tube segment 690 onto the proximal closure tube segment 682 to form the closure tube assembly 680. The end effector 612 may have the staple cartridge 630 therein or the clinician may install the staple cartridge into the elongated channel 614 at this or a later time. Once the end effector 612 has been attached to the elongated shaft assembly 655 of the surgical instrument 610, the surgeon may insert the end effector 612 and elongated shaft assembly 655 through an access passage extending into the patient (e.g., through a trocar or endoscope, etc. or through an incision—in the case of open surgery) to grasp the target tissue between the end effector jaws 613, 615. As with various embodiments described above, the jaws 613, 615 are closed by manipulating the firing trigger 130 relative to the pistol grip 107 of the handle assembly 100. Once the target tissue has been grasped between the end effector jaws 613, 615, the surgeon may "fire" or form the staples 632 into the target tissue by compressing the anvil 620 into the staple cartridge 630 in the manner described above. If the procedure does not require the target tissue to be cut, the surgeon may then release the firing trigger 130 to permit the anvil 620 to move to the open position (under biasing motion from spring 617) and thereby release the implantable staple cartridge 630 from the end effector 612. The surgeon may then re-close the end effector jaws 613, 615 to permit the end effector 612 to be withdrawn through an access passage or working channel. If, however, the surgeon desires to cut the target tissue between the lines of staples 632, the surgeon may fire the knife assembly 640 by operating the knife advancement trigger 200 in the manner described above to drive the knife member 648 distally through the target tissue. As the knife member 648 moves distally through the end effector 612, it contacts the staple driving sled 650 which serves to further drive the staples 632 into forming contact with the staple forming surface 622 of the anvil 620 to further form the staples 632. See FIG. 53. Thereafter, the surgeon may open the end effector 612 to release the cut/staple target tissue and implantable staple cartridge 630 therefrom.

Thus, the unique and novel closure tube arrangement which closes the jaws of the end effector by moving the closure tube distally enables smaller closure structures to be employed while still maintaining the ability to generate large closure forces required to form staples. In addition, this embodiment of the present invention provides the surgeon with the flexibility to staple tissue with out cutting it in applications not requiring the tissue to be cut.

FIGS. 56-60 illustrate an alternative surgical instrument embodiment 810 that is substantially identical to the surgical instrument 610 described above, except for the differences discussed below. The surgical instrument 810, for example, includes a flexible spine assembly 820 that has a proximal end with a flange 822 thereon that is rotatably received within a groove 106 formed by mating ribs 108 that protrude inwardly from each of the case members 102, 104 forming the handle assembly 100. See FIGS. 57 and 58. Such mounting arrangement facilitates rotational travel of the flexible spine assembly 820 relative to the handle assembly 100. In various embodiments, the flexible spine assembly 820 may be fabricated from, for example, Nylon, Acrylonitrile butadiene styrene (ABS), polycarbonate, liquid crystal polymer, stainless steel, titanium, etc. and may be configured for use with an end effector 612 of the type described above.

Figure 56:
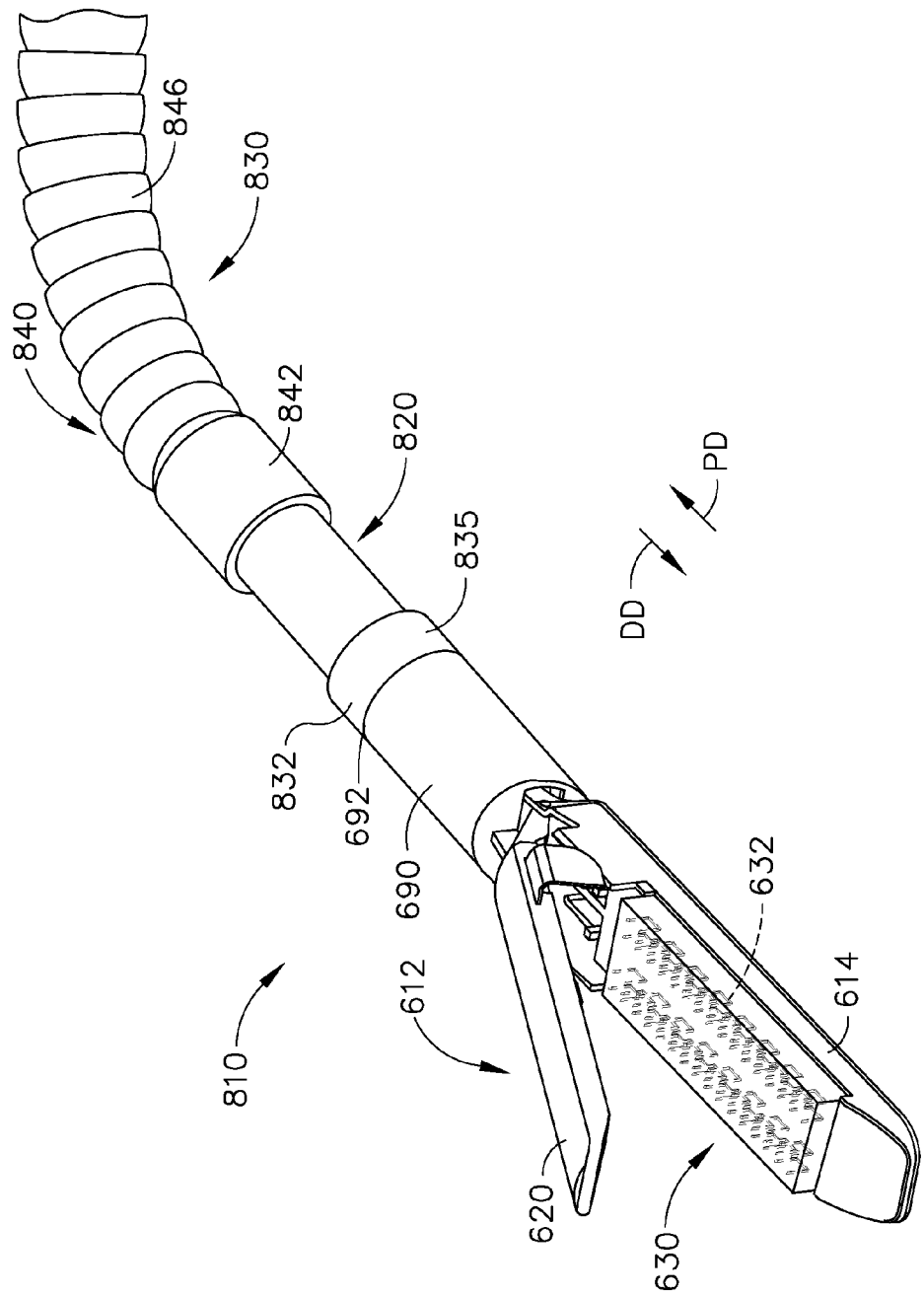
FIG. 56 is a partial perspective view of an elongated shaft assembly of another embodiment of the present invention attached to an end effector embodiment of the present invention.
Figure 57:
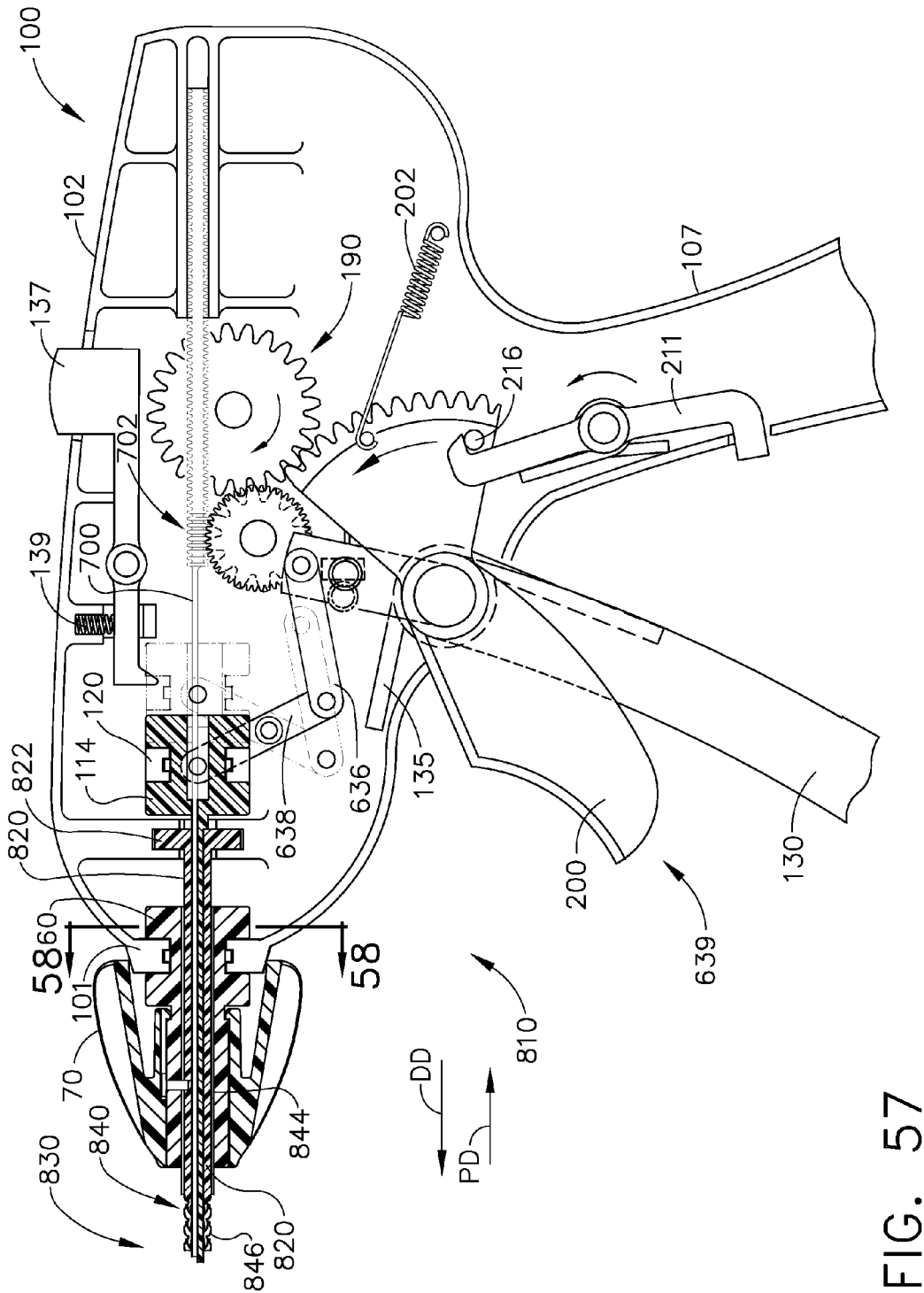
FIG. 57 is a partial cross-sectional view of a handle assembly of another surgical instrument embodiment of the present invention.

The surgical instrument 810 further includes an elongated shaft assembly generally represented by 830. In various embodiments, for example, the elongated shaft assembly 830 includes a reconfigurable shaft segment 840 and a proximal shaft segment 844. As can be seen in FIG. 56, for example, the reconfigurable shaft segment 840 may have a distal mounting collar 842 that is non-movably attached to a portion of the flexible spine assembly 820 by, for example, adhesive, welding, fasteners, etc. The reconfigurable shaft segment 840 is selectively reconfigurable between a linear configuration wherein all portions of the reconfigurable segment 840 are substantially coaxially aligned with each other (i.e., they form a substantially straight hollow tubular structure) and configurations wherein at least one of the portions is not coaxially or linearly aligned with another portion of the reconfigurable segment 840. In the embodiment depicted in FIG. 56, for example, the reconfigurable shaft segment 840 may be fabricated from Nylon, Acrylonitrile butadiene styrene (ABS), polycarbonate, etc. and have a plurality of ribs 846 that facilitate the reconfiguration of the segment 840 from a linear or coaxial alignment orientation to non-linear or non-coaxial orientations (e.g., serpentine, curved, etc.) and remain in such orientations until the user reconfigures the shaft segment 840 by hand or through the use of other surgical instruments such as grasping devices and the like. Thus, the reconfigurable shaft segment 840 is "passively articulatable" meaning that the device is not equipped with articulation means for actively controlling the articulation of the segment 840.

In various embodiments, the proximal shaft segment 844 is coupled to the reconfigurable shaft segment 840 by, for example, interlocking features or pins and serves to facilitate rotational attachment of the reconfigurable shaft segment 840 to the handle assembly 100. In at least one embodiment, for example, the proximal shaft segment 844 is coupled to the mounting bushing 60 that is rotatably affixed to the handle assembly 100 as described hereinabove. See FIGS. 57 and 59.

Figure 60:
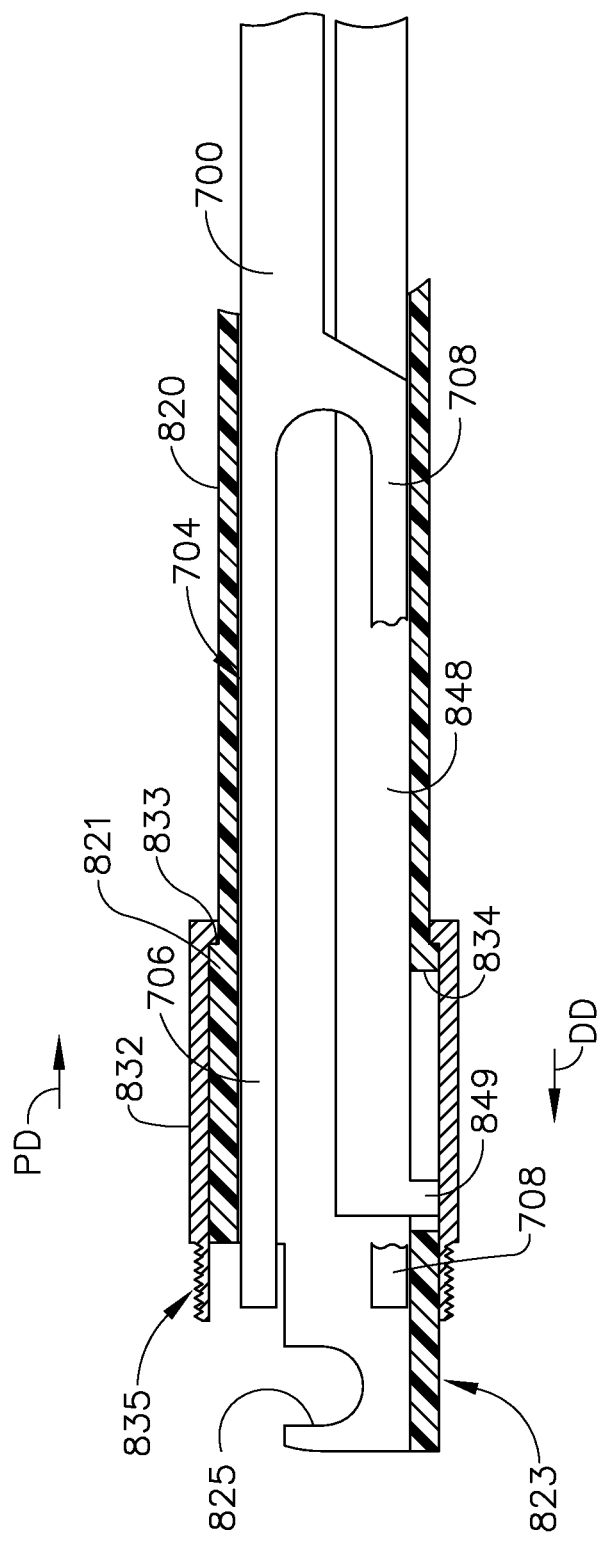
FIG. 60 is a cross-sectional view of a distal end portion of the elongated shaft assembly of FIGS. 56-59.

Also in various embodiments, a closure tube segment 832 is movably mounted on a portion of the flexible spine assembly 820 for selective movement thereon. See FIGS. 56 and 60. As can be seen in FIG. 60, in at least one embodiment, the closure tube segment 832 and the spine assembly 820 are formed with opposing flanged portions 833, 821 respectively, such that the closure tube segment 832 is prevented from sliding off of the spine assembly 820 while remaining movably mounted thereon. In various embodiments, a flexible closure member 848 is coupled to, or comprises a portion of, the firing yoke 114. See FIGS. 57 and 59. The flexible closure member 848 may be fabricated from, for example, stainless steel, etc. and have a distal end portion 849 that extends through an elongated slot 834 in the spine assembly 820 to be coupled to the closure tube segment 832. Such arrangement facilitates movement of the closure tube segment 832 in the distal direction "DD" and proximal direction "PD" on the spine assembly 820 by actuating the firing trigger 130 in the manners described above.

As can be seen in FIG. 56, the surgical instrument 810 may be employed with an end effector 612 which was described in detail above. In particular, the end effector 612 may be removably coupled to the flexible spine assembly 820 by inserting the trunions 669 on the spine nut 668 into corresponding trunion slots 825 in a distal end 825 of the spine assembly 820. See FIG. 60. A distal end 835 of the closure tube segment 832 is configured to be threadably attached to the proximal end 692 of the distal closure tube segment 690 in the above-described manner.

In at least one embodiment, the surgical instrument 810 further includes a knife advancement system 639 that includes knife rod 700 that extends through the spine assembly 820 and has a proximal end portion 702 that drivingly interfaces with a firing transmission 190 that is operably attached to a knife advance trigger 200 in the manner described above. Thus, the surgeon may advance the knife rod 700 distally by pulling the knife advancement trigger 200 as was described above. The knife rod 700 has a bifurcated distal end 704 that includes an upper knife rod segment 706 and a lower knife rod segment 708 that are configured to engage the knife plate 642 in the end effector 612. See FIG. 60.

To use the surgical instrument 810, the end effector 612 is attached to the distal end 823 of the spine assembly 820 by inserting the trunions 669 on the spine nut 668 into their corresponding trunion cradles 825. Thereafter, the surgeon or clinician may rotate the end effector 612 to thread the distal closure tube segment 690 onto the closure tube segment 832. The end effector 612 may have the staple cartridge 630 therein or the clinician may install the staple cartridge into the elongated channel 614 at this time. Once the end effector 612 has been attached to the elongated closure tube assembly 830 of the surgical instrument 810, the surgeon may configure the reconfigurable shaft segment 840 such that the elongated shaft assembly portions are coaxially aligned for insertion through an opening or working channel that extends into the patient (e.g., through a trocar or endoscope, etc. or through an incision—in the case of open surgery). Thereafter, the surgeon may reconfigure the reconfigurable shaft segment 840 such that portions thereof are not coaxially aligned with each other to orient the end effector 612 attached thereto in a desired position relative to the target tissue. As with various embodiments described above the jaws 613, 615 are closed by manipulating the firing trigger 130 relative to the pistol grip 107 of the handle assembly 100. Once the target tissue has been grasped between the end effector jaws 613, 615, the surgeon may "fire" or form the staples 632 into the target tissue by compressing the anvil 620 into the staple cartridge 630 in the manner described above. If the procedure does not require the target tissue to be cut, the surgeon may then release the firing trigger 130 to permit the anvil 620 to move to the open position (under biasing motion from spring 617) and thereby release the implantable staple cartridge 630 from the end effector 612. The surgeon may then re-close the end effector jaws 613, 615 and reconfigure the reconfigurable shaft segment 840 to permit the end effector 612 to be withdrawn through an access passage or working channel. If, however, the surgeon desires to cut the target tissue between the lines of staples 632, the surgeon may fire the knife assembly 640 by operating the knife advancement trigger 200 in the manner described above to drive the knife member 648 distally through the target tissue. As the knife member 648 moves distally through the end effector 612, it contacts the staple driving sled 650 which serves to further drive the staples 632 into forming contact with the staple forming surface 622 of the anvil 620 to further form the staples 632. Thereafter, the surgeon may open the end effector 612 to release the cut/staple target tissue and implantable staple cartridge 630 therefrom.

Figure 61:
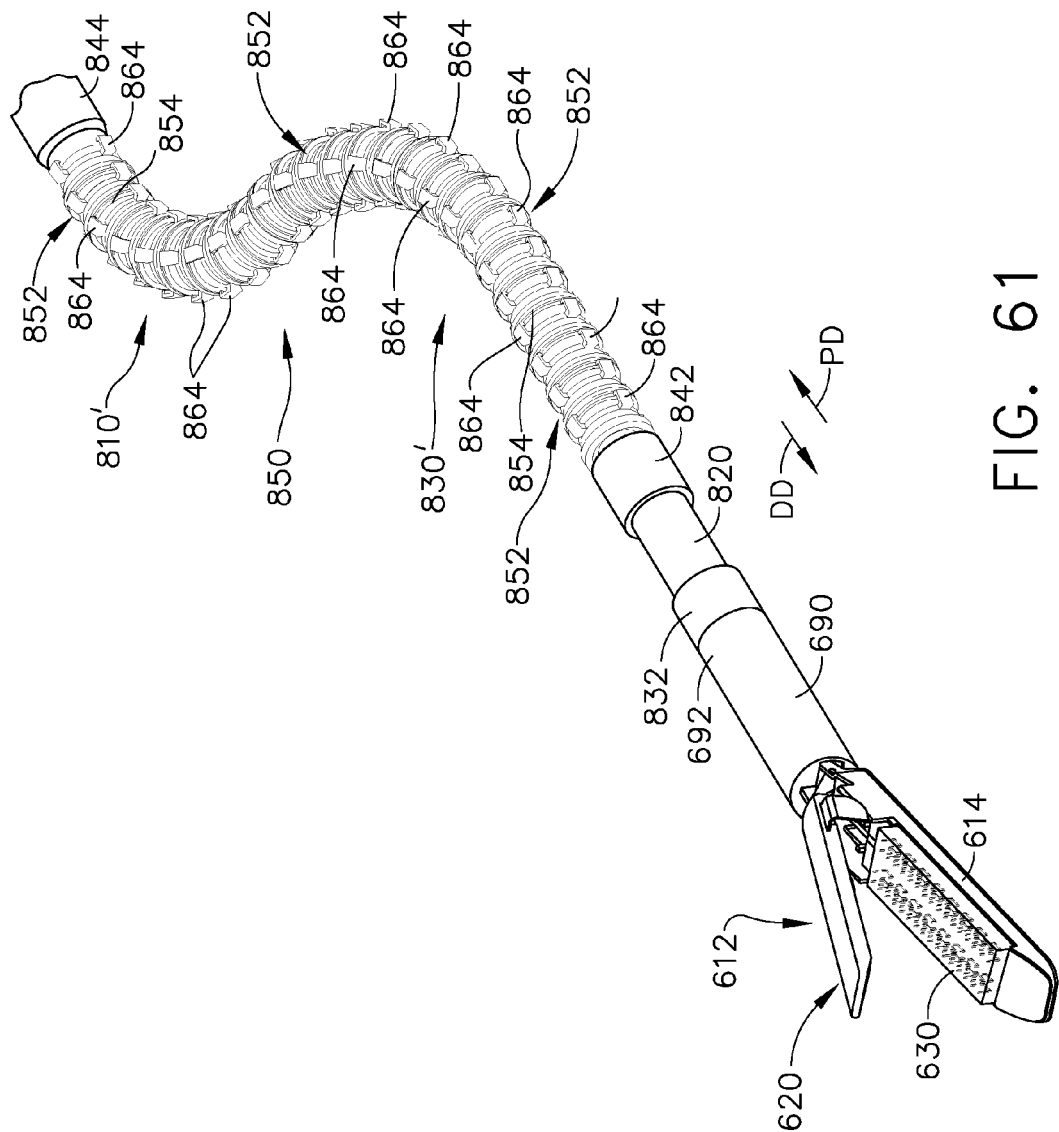
FIG. 61 is a partial perspective view of an elongated shaft assembly of another embodiment of the present invention attached to an end effector embodiment of the present invention.
Figure 62:
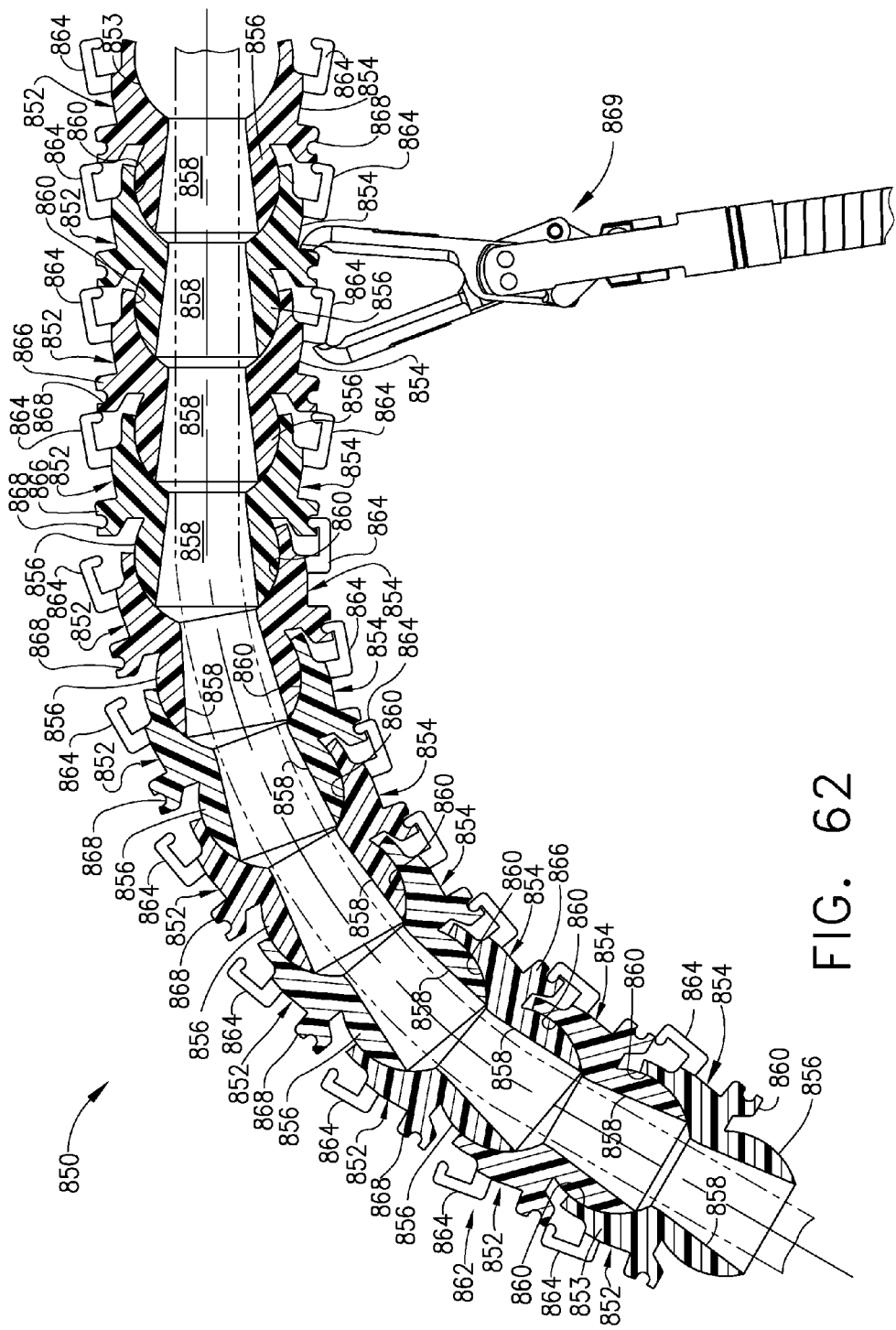
FIG. 62 is a cross-sectional view of a portion of a reconfigurable shaft segment of the elongated shaft of FIG. 61.
Figure 63:
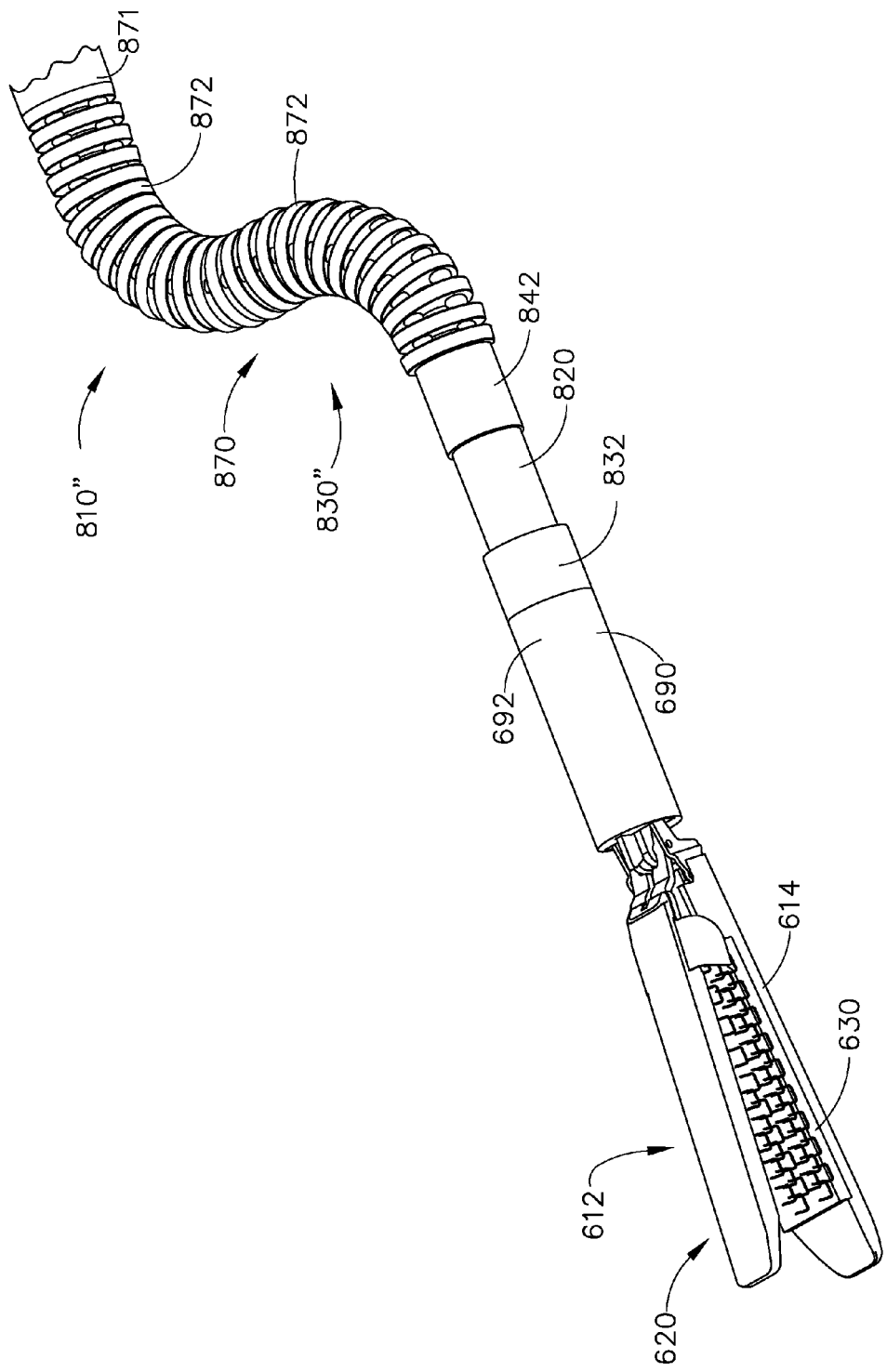
FIG. 63 is a partial perspective view of an elongated shaft assembly of another embodiment of the present invention attached to an end effector embodiment of the present invention.
Figure 64:
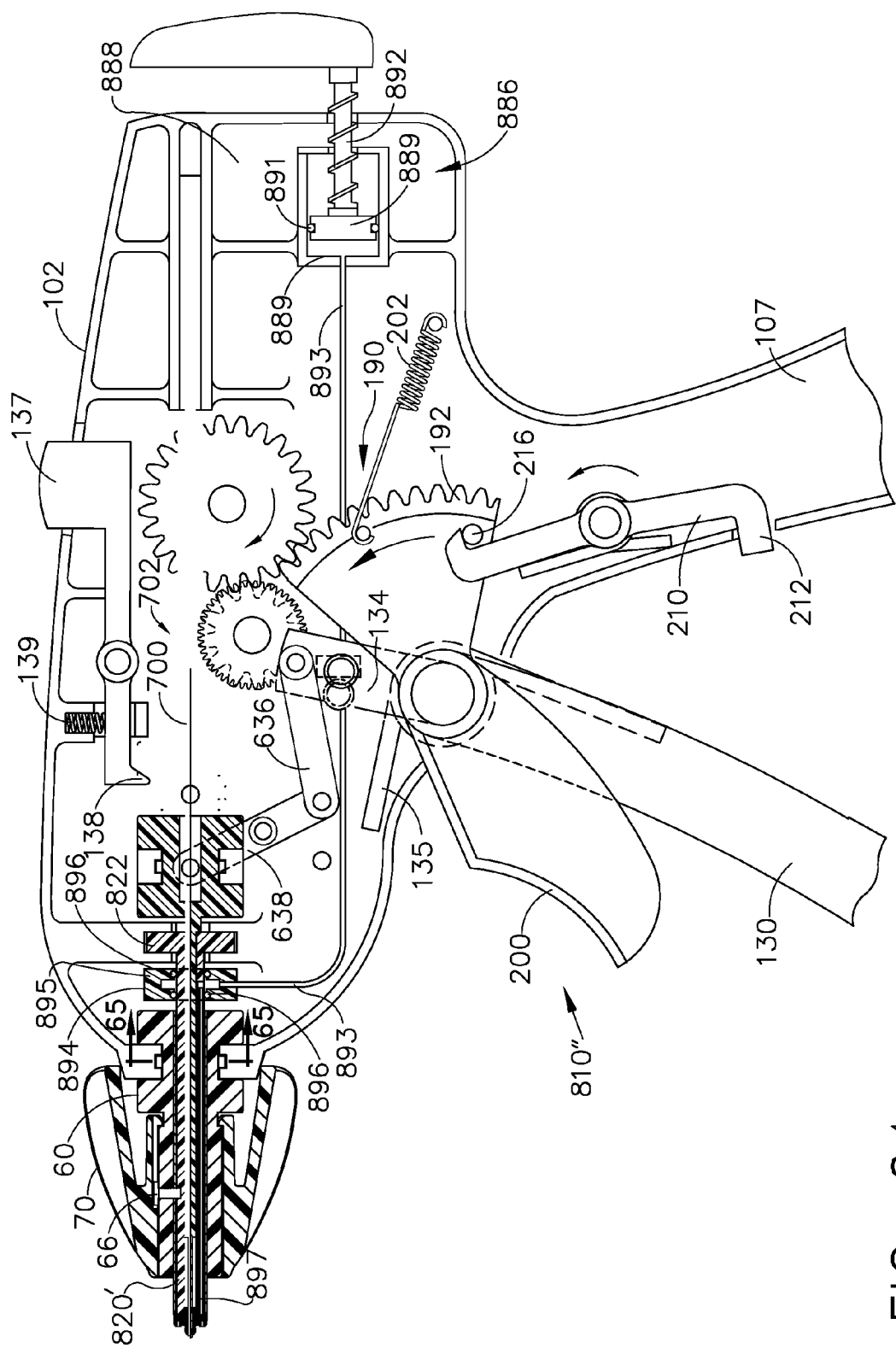
FIG. 64 is a cross-sectional view of a handle assembly of another surgical instrument embodiment of the present invention.

FIGS. 61 and 62 illustrate another surgical instrument embodiment 810' that is substantially identical to the surgical instrument 810 embodiment described above, except for the reconfigurable shaft segment 850 which comprises a portion of an elongated shaft assembly 830' that is operably coupled to handle assembly 100 for operating an end effector 612. In various embodiments, the reconfigurable shaft segment 850 comprises a plurality of movably interconnected tubular links 852. Each tubular link 852 may be fabricated from, for example, Nylon, Acrylonitrile butadiene styrene (ABS), polycarbonate with or without glass or carbon fill, etc. and have a tubular body portion 854. The tubular body portion 854 may have a sphere-like or ball-like coupler portion 856 formed thereon that has a spine-receiving passage 858 therethrough. In addition, the tubular spine-receiving passage 858 extends into a hollow socket 860 formed in the tubular body portion 854 that is sized to movably receive the ball-like coupler portion 856 of an adjacent tubular link 852. The ball-like coupler portions 856 are sized relative to the sockets 860 to permit the ball-like coupler portion 856 to be snapped therein and retained in a desired configuration wherein the shaft segment is in a substantially straight line to configurations wherein the shaft 850 may have a curved (FIG. 62) or serpentine-like configuration (FIG. 61).

While the ball-like coupler portions 856 and sockets 860 may be sized relative to each other to create a small amount of frictional force therebetween that can retain the segment 850 in a desired orientation until an external force is applied thereto, the embodiment depicted in FIGS. 60 and 61, employs a locking system 862 to releasably retain or immovably lock the tubular links 852 together in a desired configuration. As can be seen in those Figures, the locking means 862 comprises at least one, and preferably a plurality of, flexible latch nubs or members 864 formed on the perimeter of the tubular link 852 adjacent one end 853 thereof. In a preferred embodiment, four latch nubs 864 are employed. Other embodiments could have 1, 2, 3 or more than four latch nubs 864. Each tubular link 852 further comprises a locking member 866 that corresponds to each latch nub 864 adjacent the other end 865 of the link 852. Each locking member 866 has a latch-receiving notch 868 therein configured to releasably receive a portion of the corresponding latch nub 864 formed on an adjacent tubular link 852 therein.

To use the surgical instrument 810', the end effector 612 is attached to the distal end 823 of the spine assembly 820 in the manner described above. The distal closure tube segment 690 of the end effector 612 is threaded onto the closure tube segment 832. Once the end effector 612 has been attached to the elongated closure tube assembly 830 of the surgical instrument 810', the surgeon may configure the reconfigurable shaft segment 850 such that the elongated shaft assembly portions are coaxially aligned for insertion through an opening or working channel that extends into the patient (e.g., through a trocar or endoscope, etc. or through an incision—in the case of open surgery). Thereafter, the surgeon may employ, for example, a grasping instrument 869 to configure the movable links 852 of the reconfigurable shaft segment 850 to a desired orientation and then press the appropriate locking nubs 864 on each link 852 into their corresponding latch receiving notch 868 to lock the links 852 in the desired orientation. See FIG. 62. As with various embodiments described above, the jaws 613, 615 are closed by manipulating the firing trigger 130 relative to the pistol grip 107 of the handle assembly 100. Once the target tissue has been grasped between the end effector jaws 613, 615, the surgeon may "fire" or form the staples 632 into the target tissue by compressing the anvil 620 into the staple cartridge 630 in the manner described above. If the procedure does not require the target tissue to be cut, the surgeon may then release the firing trigger 130 to permit the anvil 620 to move to the open position (under biasing motion from spring 617) and thereby release the implantable staple cartridge 630 from the end effector 612. The surgeon may then re-close the end effector jaws 613, 615 and use the grasping instrument 869 to remove the locking nubs 864 from their corresponding latch receiving notches 868 to permit the links 852 to be aligned in such a manner to permit the device to be withdrawn through an access passage or working channel. If, however, the surgeon desires to cut the target tissue between the lines of staples 632, the surgeon may fire the knife assembly 640 by operating the knife advancement trigger 200 in the manner described above to drive the knife member 648 distally through the target tissue. As the knife member 648 moves distally through the end effector 612, it contacts the staple driving sled 650 which serves to further drive the staples 632 into forming contact with the staple forming surface 622 of the anvil 620 to further form the staples 632. Thereafter, the surgeon may open the end effector 612 to release the cut/stapled target tissue and implantable staple cartridge 630 therefrom.

FIGS. 63-68 illustrate another surgical instrument embodiment 810" that is substantially identical to the surgical instrument embodiments 810, 810' described above, except for the reconfigurable shaft segment 870 and related locking system 882 of the elongated shaft assembly. In various embodiments, the reconfigurable shaft segment 870 comprises a plurality of movably interconnected tubular links 872 and is coupled to a proximal shaft segment 871 that is coupled to the mounting bushing 60 rotatably supported within the handle assembly 100 as discussed in detail above. Each tubular link 872 may be fabricated from, for example, Nylon, Acrylonitrile butadiene styrene (ABS), polycarbonate, etc. and have a tubular body portion 874. See FIG. 67. The tubular body portion 874 may have a sphere-like or ball-like coupler portion 876 formed thereon that has a spine-receiving passage 878 extending therethrough. In addition, the tubular spine-receiving passage 878 extends into a hollow socket 880 formed in the tubular body portion 854 that is sized to movably receive the ball-like coupler portion 876 of an adjacent tubular link 872. The ball-like coupler portions 876 are sized relative to the sockets 880 to permit the ball-like coupler portion 876 to be snapped therein and retained in a desired configuration wherein the reconfigurable shaft segment 870 is in a substantially straight line (FIG. 67) to configurations wherein the shaft 870 may have a curved (FIG. 68) or serpentine-like configuration.

Figure 67:
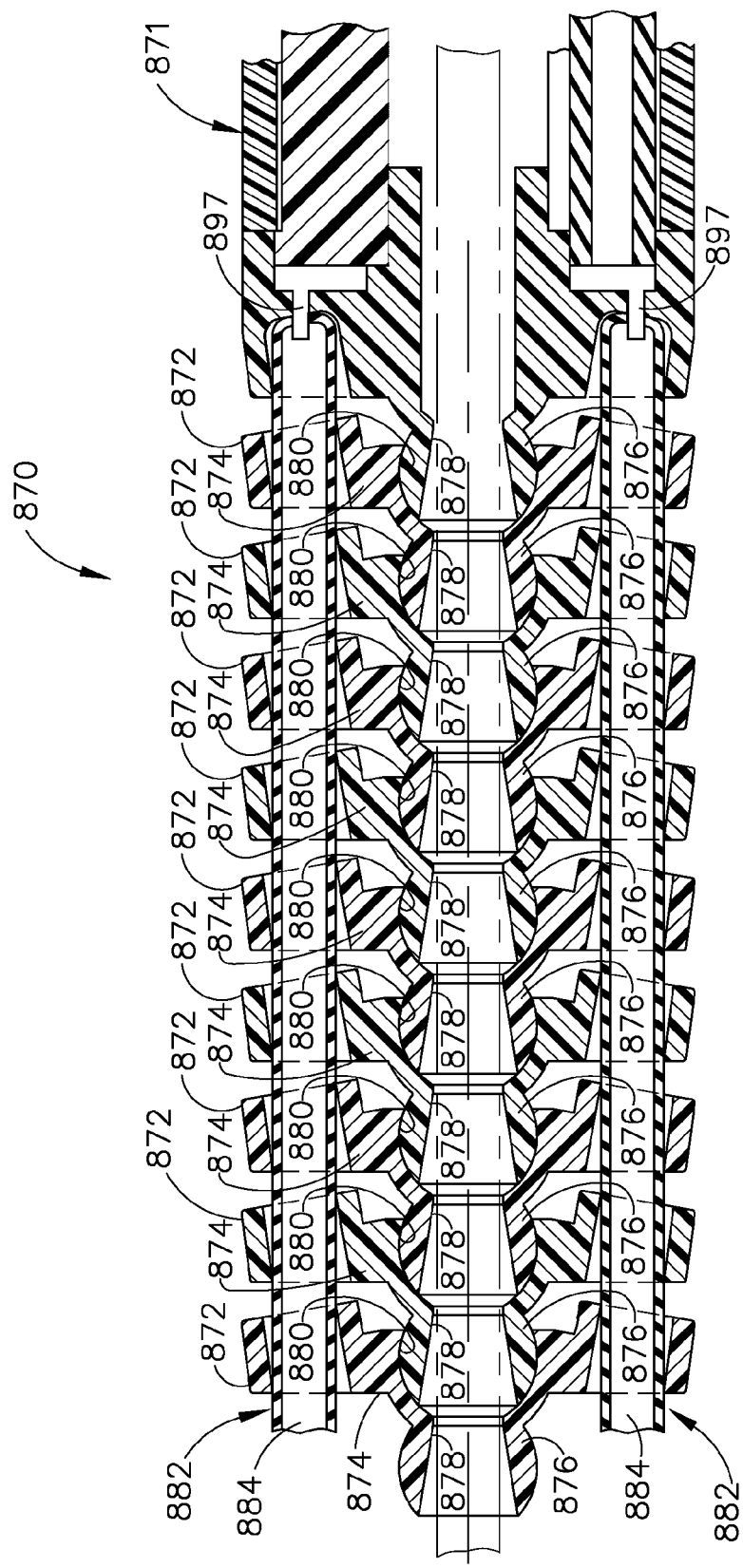
FIG. 67 is a cross-sectional view of a portion of the reconfigurable shaft segment depicted in FIG. 63 with the tubular link portions thereof aligned in a substantially straight line.
Figure 68:
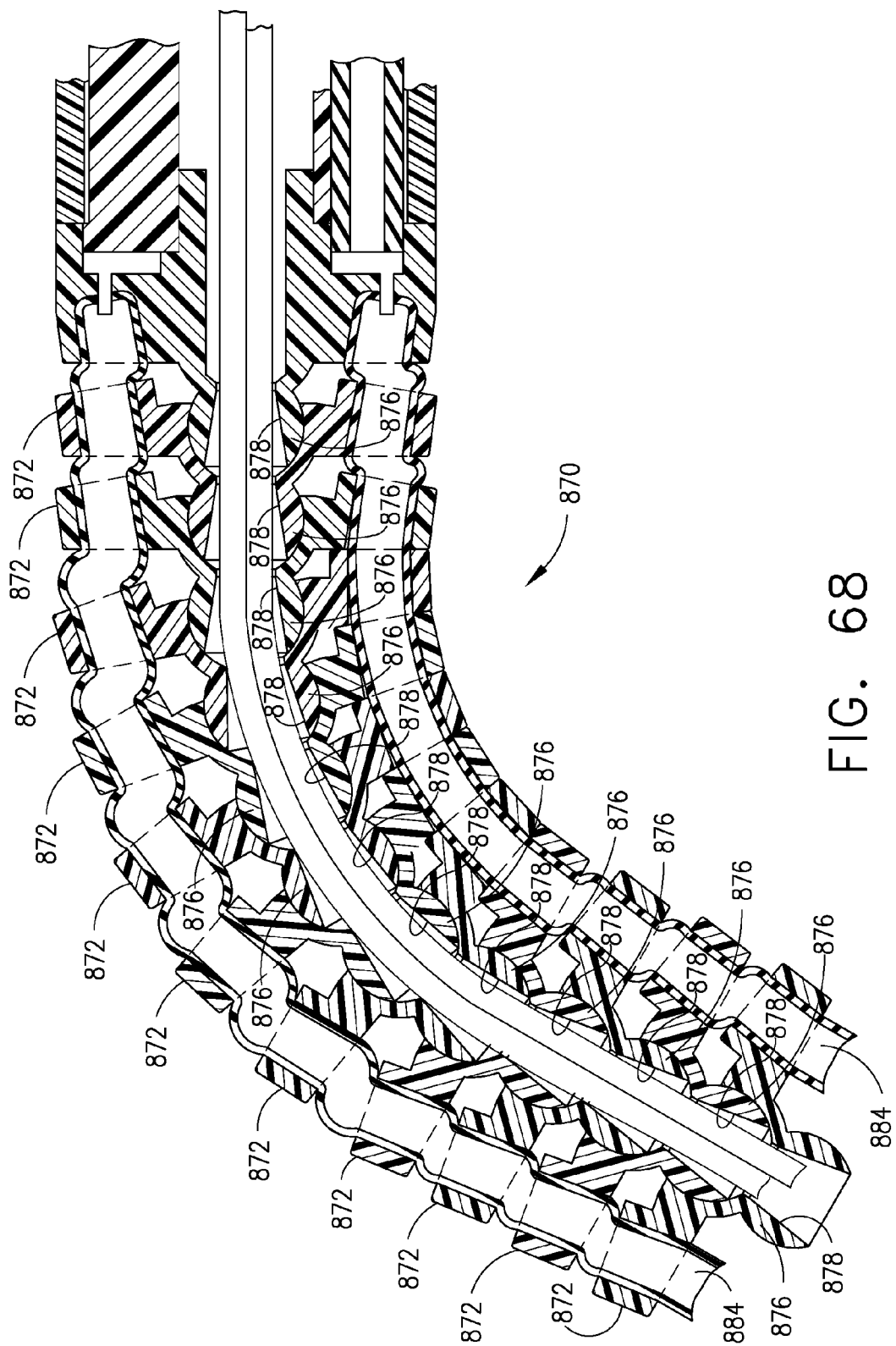
FIG. 68 is a cross-sectional view of a portion of the reconfigurable shaft segment depicted in FIGS. 63 and 67 with the tubular link portions thereof aligned in a substantially curved (non-coaxial) orientation.

While the ball-like coupler portions 876 and sockets 880 may be, in at least one embodiment, sized relative to each other to create a small amount of frictional force therebetween that can retain tubular links 872 of the reconfigurable shaft segment 870 in desired orientations until an external force is applied thereto, the embodiment depicted in FIGS. 63-68, employs a locking system 882 for releasably retaining or immovably locking the tubular links 872 together in a desired configuration. As can be seen in FIGS. 67 and 68, the locking means 882 comprises at least one, and preferably two, selectively expandable locking bladders 884 that extend through the tubular links 872 in diametrically opposed positions. In various embodiments, the locking bladders 884 may be fabricated from, for example, Nylon film, etc. and be adapted to receive pressurized fluid from a source of pressurized fluid 886. In the embodiment depicted in FIG. 64, the source of pressurized fluid 886 comprises fluid pump arrangement 888 that is adapted to supply air under pressure into the locking bladders 884. In particular, in at least one embodiment, the fluid pump arrangement 888 comprises a cylinder 889 that has a piston 890 therein. The piston 890 has an O-ring or other seal arrangement 891 around its perimeter and is attached to a threaded pump handle 892 that threadably engages a portion of the handle assembly 100. Thus, by screwing the pump handle 892 into the handle assembly 100, air in the cylinder 890 is pumped under pressure through a supply conduit 893 that extends from the cylinder 890 to a manifold assembly 894 that is received on the spine assembly 820. The air pressure may be relieved in the locking bladders 884 by screwing the pump handle 894 in an opposite direction.

As can be seen in FIG. 65, the manifold assembly 894 comprises an annular manifold area 895 that is sealed on each side by O-rings or other seals 896. The annular manifold area 895 communicates with a supply line 897 that extends through the proximal shaft segment 871 and which is coupled for discharge into the locking bladders 884. Such arrangement serves to supply pressurized air into the locking bladders 884 while facilitating the rotational travel of the spine assembly 820 about the longitudinal axis A-A relative to the handle assembly 100. As used herein, the term pressurized fluid may comprise, for example, air, saline or preferably glycerine. In alternative embodiments, the tubular members may be filled with a very low durometer rubber or elastomer. When a pressure is applied to the rubber material, it will deform filing the voids and locking the shaft in much the same way as the fluid embodiment does.

To use the surgical instrument 810", the end effector 612 is attached to the distal end 823 of the spine assembly 820' in the manner described above. The distal closure tube segment 690 of the end effector 612 is threaded onto the closure tube segment 832. Once the end effector 612 has been attached to the elongated shaft assembly 830" of the surgical instrument 810", the surgeon may configure the reconfigurable shaft segment 870 such that the elongated shaft assembly portions 830" are coaxially aligned for insertion through an opening or working channel that extends into the patient (e.g., through a trocar or endoscope, etc. or through an incision—in the case of open surgery). Thereafter, the surgeon may employ, for example, a grasping instrument to configure the movable links 872 of the reconfigurable shaft segment 870 to a desired orientation. Once the reconfigurable shaft segment 870 has been oriented in a desired orientation, the surgeon may then screw in the pump handle 892 into the handle housing 100 to pressurize the locking bladders 884 to lock the movable links 872 in position as shown in FIG. 68. As with various embodiments described above, the jaws 613, 615 are closed by manipulating the firing trigger 130 relative to the pistol grip 107 of the handle assembly 100. Once the target tissue has been grasped between the end effector jaws 613, 615, the surgeon may "fire" or form the staples 632 into the target tissue by compressing the anvil 620 into the staple cartridge 630 in the manner described above. If the procedure does not require the target tissue to be cut, the surgeon may then release the firing trigger 130 to permit the anvil 620 to move to the open position (under biasing motion from spring 617) and thereby release the implantable staple cartridge 630 from the end effector 612. The surgeon may then re-close the end effector jaws 613, 615 and release the pressure in the locking bladders 884 by screwing the pump handle 892 in an opposite direction. A grasping instrument may be employed to manipulate the movable links 872 to a substantially coaxially aligned orientation (FIG. 67) or other orientation required to enable the device to be withdrawn from the patient. If, however, the surgeon desires to cut the target tissue between the lines of staples 632, the surgeon may fire the knife assembly 640 by operating the knife advancement trigger 200 in the manner described above to drive the knife member 648 distally through the target tissue. As the knife member 648 moves distally through the end effector 612, it contacts the staple driving sled 650 which serves to further drive the staples 632 into forming contact with the staple forming surface 622 of the anvil 620 to further form the staples 632. Thereafter, the surgeon may open the end effector 612 to release the cut/stapled target tissue and implantable staple cartridge 630 therefrom.

The various embodiments disclosed herein that include a reconfigurable shaft segment represent a vast improvement over traditional articulatable surgical instrument arrangements that employ lockable articulation joints. Such surgical instruments are typically limited to 1 or 2 degrees of freedom for placement of the end effector at the transection site. The various embodiments of the present invention allow for a wider range of possible end effector positions and therefore provide the surgeon with much more flexibility when using the device through a single access port.

The unique and novel features of the various surgical staple cartridges and the surgical instruments of the present invention enable the staples in those cartridges to be arranged in one or more linear or non-linear lines. A plurality of such staple lines may be provided on each side of an elongated slot that is centrally disposed within the staple cartridge for receiving the tissue cutting member therethrough. In one arrangement, for example, the staples in one line may be substantially parallel with the staples in adjacent line(s) of staples, but offset therefrom. In still other embodiments, one or more lines of staples may be non-linear in nature. That is, the base of at least one staple in a line of staples may extend along an axis that is substantially transverse to the bases of other staples in the same staple line. For example, as will be discussed in further detail below, in alternative embodiments, the lines of staples on each side of the elongated slot may have a zigzag appearance. Such non-linear staple arrangements may be made possible due to the fact that the staples are not driven upwardly into the anvil. Instead in these various embodiments, the anvil is brought into forming contact with the tips of the non-moving staples. Such non-linear staple arrangements may attain better tissue fastening results with less staples than various linear staple arrangements employed in prior staple cartridges wherein the staples are actually driven upwardly into forming contact with the anvil.

Figure 69:
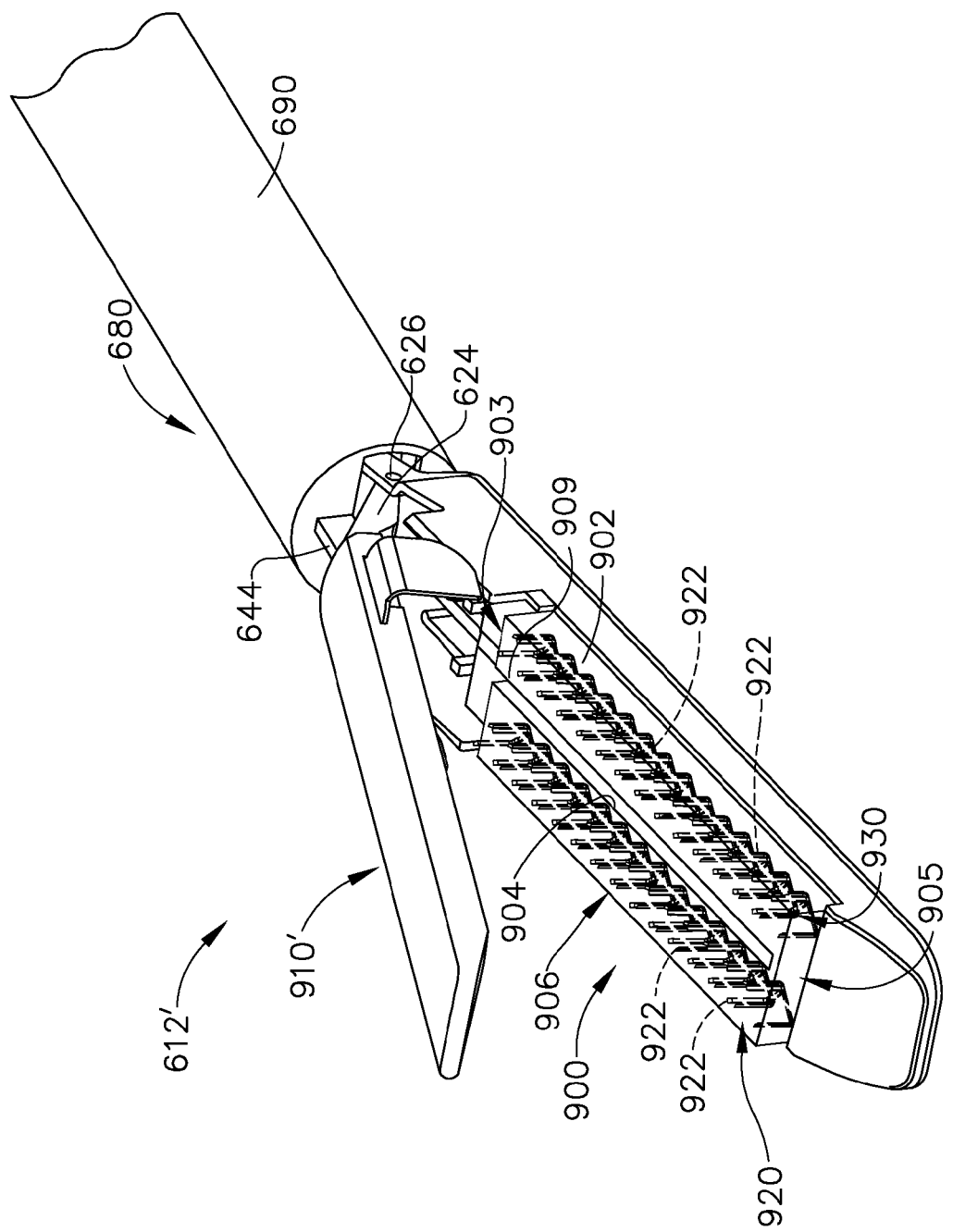
FIG. 69 is a perspective view of an alternative staple cartridge embodiment of the present invention installed in a surgical cutting and stapling device embodiment of the present invention.

FIG. 69 illustrates use of a surgical staple cartridge embodiment 900 in an end effector embodiment 612' of the present invention. The end effector 612' may be used in connection with the surgical instrument 610 in the various manners described above. The end effector 612' may be identical to end effector 612 as described above except for the differences described below. As can be seen in FIGS. 69 and 70, an embodiment of the surgical staple cartridge 900 has a cartridge body 902 that has a centrally disposed elongated slot 904 extending through a proximal end 903 to an area adjacent a distal end 605. The elongated slot 904 is configured to permit knife body 646 of the surgical instrument 610 to axially move therethrough during a tissue cutting operation in the manner described above. In at least one embodiment, the cartridge body 902 consists of a compressible hemostat material such as, for example, oxidized regenerated cellulose ("ORC") or a bio-absorbable foam fabricated from, for example, PGA (Polyglycolic acid, sold under the trademark Vicryl), PCL (polycaprolactone), PLA or PLLA (Polyactic acid), PDS, (Polydioxanone), PHA (polyhydroxyalkanoate), PGCL (poliglecaprone 25, sold under the trademark Monocryl) or a composite of PGA, PCL, PLA and PDS in which lines 920, 930 of unformed staples 922 are supported. However, the cartridge body 902 may be fabricated from other materials that serve to support the unformed staples 922 in a desired orientation such that they may be compressed as the anvil 910 is brought into contact therewith. As with various other embodiments described above, the staple cartridge 900 is implantable and is left attached to the stapled tissue after the stapling procedure has been completed. In at least some embodiments, in order to prevent the staples 922 from being affected and the hemostat material from being activated during the introduction and positioning process, the entire cartridge 900 may be coated or wrapped in a biodegradable film 906 such as a polydioxanon film sold under the trademark PDS® or with a Polyglycerol sebacate (PGS) film or other biodegradable films fabricated from, for example, PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured.

The cartridge body 902 of staple cartridge 900 is sized to be removably supported within the elongated channel 614 of the end effector 612'.

In the embodiment depicted in FIGS. 69, 73, and 74, the surgical staple cartridge 900 operably supports a first line 920 of staples 922 on one lateral side 907 of the elongated slot 904 and a second line 930 of staples 922 on the other lateral side 909 of the elongated slot 904. In various embodiments, the staples 922 may be fabricated from a metal material such as, for example, Titanium, Titanium alloys (e.g., 6AI-4V Titanium, 3al-2.5V Titanium), Stainless Steel, etc. and have a staple base 924 and two upstanding staple legs 926 protruding therefrom. Each staple leg 926 may have a tissue-piercing tip 928 formed thereon. In the first line 920 of staples 922, the staple base 924 of at least one staple 922 overlaps the staple base of another staple 922. In a preferred embodiment, the staple base 924 of each staple 922 overlaps the staple bases 924 of two adjacent staples 922, except for the base 924 of the last staple 922 on each end of the first staple line 920. See FIG. 73. Thus, the first staple line 920 has a substantially non-linear shape. More particularly, when viewed from above, the first staple line 920 has a substantially zigzag appearance.

As can be seen in FIG. 72, the anvil 90 has two sequential longitudinal staple forming pockets 912 that each has a substantial zigzag shape that corresponds to the shape of the first line 920 of staples 922 such that, when the anvil 910 is brought into forming contact with the staples 922, the legs 926 thereof are formed as shown in FIG. 74. Thus, the distal leg of one staple shares the same pocket as the proximal leg of the next staple longitudinally. Such arrangement allows for a denser pocket pattern, even to a point where the staples themselves interact (e.g., are folded over one another). In prior staple pocket arrangements, in general, there has to be between 0.005 and 0.015 inches of metal/space from one set of pockets to the next. This embodiment of the present invention, however, has a spacing arrangement from 0 to 0.02 inches of interference/overlap (essentially a −0.020") because one staple mates with the next staple, for example. Such arrangements allow for 15-30% more staples in the same space. Furthermore, when the staples interlock, there is less need for multiple lateral rows of staples. Prior arrangements commonly employ three rows on each side of the tissue cut line to prevent the existing of an open path through which blood may pass. Lines of interlocking staples are less likely to leave paths through which blood may pass. Another distinct advantage provided by the various interlocking staple arrangements of the present invention relates to improved "burst strength" which relates to the amount of force required to tear a staple line open.

Another staple forming pocket arrangement of the present invention may comprise a common staple forming pocket. As used herein, the term "common staple forming pocket" means that one forming pocket can form all of the staples in a single line of staples as opposed to prior anvil designs wherein a discrete forming pocket is provided for each leg of each staple to be formed.

FIG. 75 illustrates yet another staple embodiment 922' wherein the base 924' has an offset portion 928 to facilitate a tighter overlap of the bases 924'. As indicated above, the staple cartridge 900 has a second line 930 of staples 922 supported on a second lateral side 909 of the elongated slot 904. The second line 930 of staples 922 is substantially identical to the first line 920 of staples 922. Thus, the anvil 910 has a second common staple forming pocket 912 that corresponds to the second line of staples 930 for forming contact therewith. In alternative embodiments, however, the second line 930 of staples 922 may differ from the first line 920 of staples in shape and, perhaps, number of staples.

FIG. 71 illustrates a surgical staple cartridge 900' that is substantially identical to the staple cartridge 900 described above, with the exception of the lines 920', 930' of staples 922 supported therein. For example, in this embodiment, the line 920' of staples 922 are arranged relative to each other such that a base axis S-S of at least one staple base 924 is substantially transverse to the base axis S-S of the staple base 924 of at least one other adjacent staple 922. Such predetermined pattern of staples, when viewed from above, comprises a substantially zigzag arrangement. In the embodiment depicted in FIG. 76, the respective bases 924 of staples 922 may additionally have a base support member 927 overmolded thereon as shown. In various embodiments, the base support member 927 may be fabricated from, for example, non-absorbable plastic such as Polyether ether ketone "PEEK" or absorbable plastic such as, for example, Polyglycolic acid "PGA", Polylactic acid "PLA" or "PLLA", Polydioxanone "PDS", PCL (polycaprolactone), PHA (polyhydroxyalkanoate), PGCL (poliglecaprone 25, sold under the trademark Monocryl) or various composite mixes if PGS, PDS, PLA, PGA, and PCL. The base support members 927 facilitate interlocking between the staples without making the staples themselves overlap. Thus, such arrangements could form staples with "B" shapes or inverted "W" shapes without the legs of the staples themselves overlapping. However, the crowns are connected by the base support members so they act like overlapping staples. Such arrangement allow the combined pockets to have two discrete paths for each leg.

The embodiment depicted in FIG. 77 employs a staple line 920" wherein the legs 926 of adjacent staples 922 are coupled together by a coupler portion 929 molded or otherwise attached thereto. Each coupler portion 929 may be fabricated from, for example, Polyether ether ketone "PEEK" or absorbable plastic such as, for example, Polyglycolic acid "PGA", Polylactic acid "PLA" or "PLLA", Polydioxanone "PDS", PCL (polycaprolactone), PHA (polyhydroxyalkanoate), PGCL (poliglecaprone 25, sold under the trademark Monocryl) or various composite mixes if PGS, PDS, PLA, PGA, and PCL. Such staple line 920" has substantial zigzag appearance when viewed from above. While the various surgical staple cartridge embodiments 900, 900' have been explained with reference to use with the end effectors 612' and the surgical stapling instrument 610, it will be understood that the staple cartridges 900, 900' may be effectively employed with the various other end effectors and surgical instruments described hereinabove, with appropriate staple forming pocket arrangements being provided in the anvils of those instruments in order to achieved the desired amount of staple formation upon movement of the anvils into forming contact with the staples.

Figure 78:
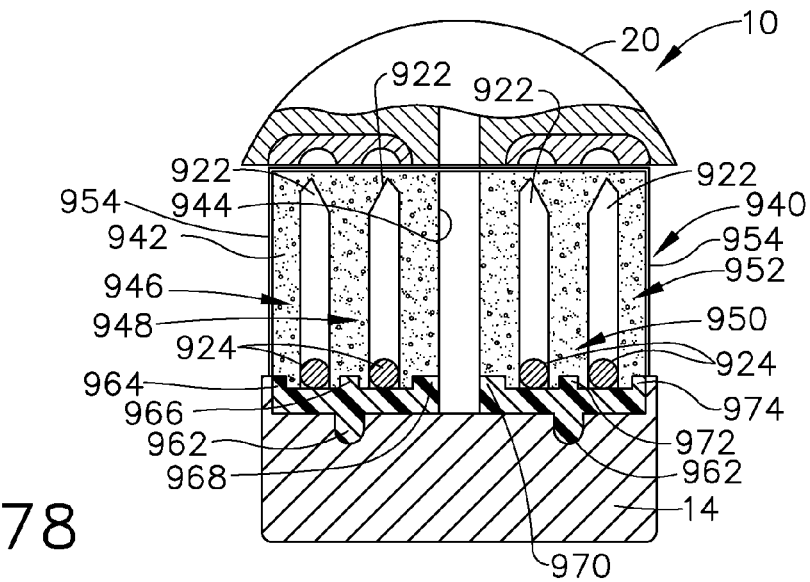
FIG. 78 is a cross-sectional view of an end effectors embodiment of the present invention supporting a staple cartridge embodiment of the present invention.
Figure 79:
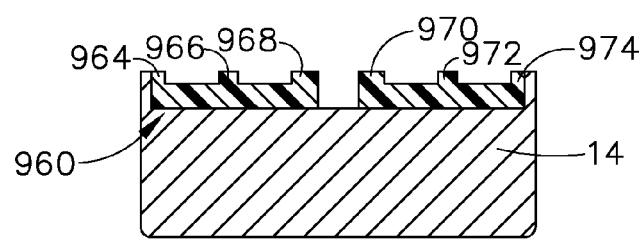
FIG. 79 is a cross-sectional view of the elongated channel portion of the end effector of FIG. 78 after the implantable staple cartridge body portion and staples have been removed therefrom.

FIGS. 78 and 79 illustrate another surgical staple cartridge 940 embodiment supported in an elongated channel 14 of a surgical instrument 10 of the present invention. In at least one embodiment, the surgical staple cartridge 940 includes a cartridge body 942 that has a centrally disposed elongated slot 944 extending at least partially therethrough. The elongated slot 944 is configured to permit a knife body of the surgical instrument 10 to axially move therethrough during a tissue cutting operation in the manner described above. In various embodiments, the cartridge body 942 consists of a compressible hemostat material such as, for example, oxidized regenerated cellulose ("ORC") or a bio-absorbable foam of the types described above or below in which lines 946, 948, 950, 952 of unformed staples 922 are supported. In at least some embodiments, in order to prevent the staples 922 from being affected and the hemostat material from being activated during the introduction and positioning process, the entire cartridge 940 may be coated or wrapped in a biodegradable film 954 such as a polydioxanon film sold under the trademark PDS® or with a Polyglycerol sebacate (PGS) film or other biodegradable films fabricated from, for example, PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured.

In the embodiment depicted in FIG. 78, the cartridge 940 further includes a cartridge support member 960 that is coupled to the cartridge body 942. In various embodiments, the cartridge support member 960 may be fabricated from a rigid material such as, for example, Titanium, Stainless Steel, Aluminum, any alloy of the foregoing, etc. and may be partially embedded within the cartridge body 942. In various embodiments, the cartridge support member 960 may be held in place by, for example, film 954. In still other embodiments wherein a limited bond is desired, sporadic use of cyanoacylate could be used to "glue" the two components together. In yet other embodiments, the cartridge body 942 may be heated and "welded" or "fused" to the cartridge support member 960. In various embodiments, the cartridge support member 960 forms at least a portion of the bottom surface of the cartridge body 942 for mating with the elongated channel 14. In a preferred embodiment, the cartridge support member 960 has one or more snap features 962 protruding therefrom for releasably coupling the cartridge support member 960 to the elongated channel 14. Other forms of snap features/fastener arrangements may be employed for releasably coupling the cartridge support member 960 to the elongated channel 14.

Figure 80:
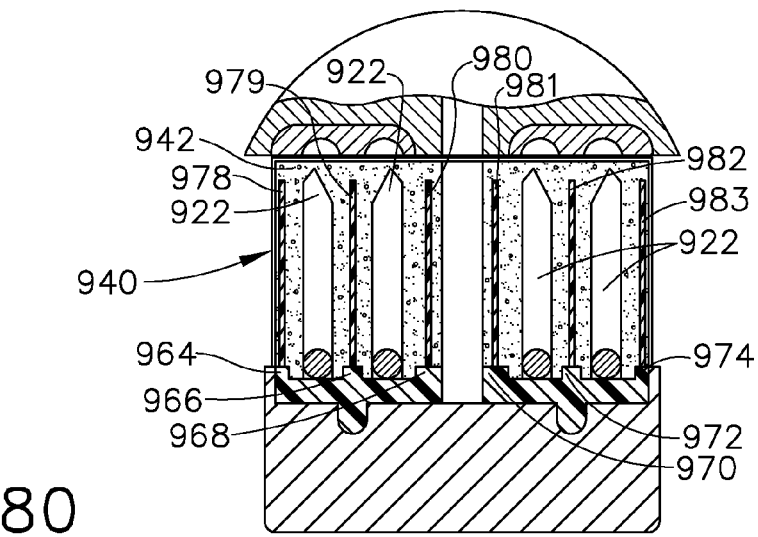
FIG. 80 is a cross-sectional view of an end effectors embodiment of the present invention supporting another staple cartridge embodiment of the present invention.

In various embodiments, the cartridge support member 960 has a series of support ridges 964, 966, 968, 970, 972, 974, 976 formed thereon to provide some lateral support to the bases 924 of the staples 922 in the staple lines 946, 948, 950, 952 as shown in FIG. 78. Thus, in at least some embodiments, the support ridges are substantially coextensive with the staple lines. FIG. 80 illustrates an alternative staple cartridge embodiment 940' that is substantially identical to cartridge 940, except for the inclusion of upstanding fin portions 978, 979, 980, 981, 982, 983 that protrude from the support ridges 964, 966, 968, 970, 972, 976, respectively to provide additional lateral support to the staples 922. In various embodiments, the fin portions may be integrally formed with the cartridge support member 960 and have a height that is about ½ or less of the height of the cartridge. Thus, in preferred embodiments, for example, any standing features supporting the foam cannot extend above the maximum compression height of the foam. Thus, if the cartridge is designed, for example, to compress to ⅓ of its original height when fired, the fins would between 66% of the uncompressed height, all the way down to 10% of uncompressed height.

In use, once the staples 922 have been formed through contact with the anvil 20 in the manner described above, the anvil 20 is opened and the end effector 12 is pulled away from the stapled tissue. As the end effector 12 is pulled away from the stapled tissue, the cartridge body 942 remains fastened to the stapled tissue and is then separated from the cartridge support member 960 which remains coupled to the elongated channel 14. In various embodiments, the cartridge support member 960 is provided with a color that differs from the color of the material comprising the cartridge body 942 as well as the color of the elongated channel 14. Such arrangement provides the surgeon with an easily recognizable indication that no staple cartridge is present within the end effector. Thus, the surgeon will not inadvertently attempt to reinsert/use the end effector without first installing a new staple cartridge therein. To do so, the surgeon simply disconnects the snap features of the cartridge support member 960 from the elongated channel 14 to enable the cartridge support member 960 of a new staple cartridge 940 to be placed therein. While the staple cartridges 940, 940' have been explained with reference to surgical instrument 10, it will be understood that those cartridges may be effectively employed with many of the other surgical instrument embodiments disclosed herein without departing from the spirit and scope of the present invention.

Figure 81:
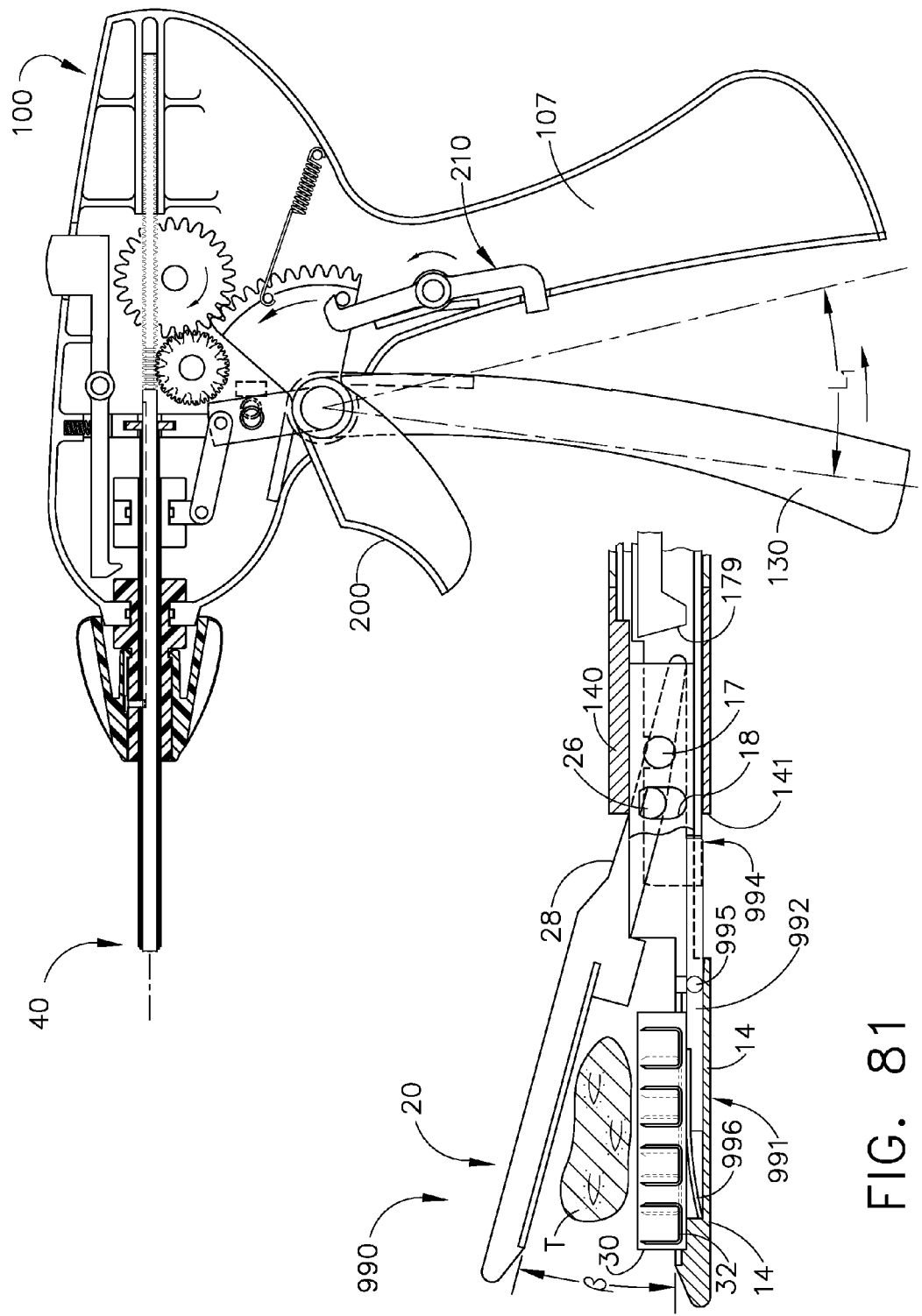
FIG. 81 is a partial cross-sectional view of a surgical stapling instrument embodiment of the present invention with a staple cartridge supported in the end effector thereof to move the cartridge locking system to an unlocked position.

FIGS. 81 and 82 illustrate use of a surgical instrument embodiment 10 in connection with an end effector 990 that is substantially identical to end effector 12 described above except for a closure lockout arrangement 991 that is movably coupled to or otherwise supported within the elongated channel 14. In various embodiments, the closure lockout arrangement 991 includes a lockout arm 992 that has a distal end 993 and a proximal end 994. The lockout arm 992 is pivotally coupled to the elongated channel about a pivot member or trunion 995. The distal end portion has a leaf spring 996 or other biasing member attached thereto to bias the lockout arm 992 into an actuated or locking position wherein the proximal end portion 994 engages the distal end 141 of the first firing collar 141 to prevent the first firing collar 140 to be distally advanced to a "fired" position. However, when a staple cartridge 30 is installed in the elongated channel 14, the staple cartridge 30 causes the lockout arm 992 to move into an unactuated or unlocked position such that the firing collar 140 may be advanced distally past the lockout arm 992 to complete the staple firing process. See FIG. 81.

When in the locked position, the firing collar 140 cannot be advanced distally to complete the firing process. In addition, the firing trigger 130 cannot be advanced to the fully fired position wherein the knife lockout bar 210 is moved to an unlocked position to thereby enable the surgeon to advance the knife bar 172. Thus, when there is no cartridge present within the end effector 990, the closure lockout arrangement 991 is in the locked position which ultimately prevents the knife bar 172 from being advanced. As such, the surgeon is unable to advance the knife bar 172 to cut tissue unless a cartridge 30 is present within the end effector 990. It will be understood that the closure lockout arrangement 991 as described above may be effectively incorporated into many of the surgical instrument embodiments disclosed herein without departing from the spirit and scope of the present invention.

In various embodiments, a staple cartridge can comprise a cartridge body and a plurality of staples stored within the cartridge body. In use, the staple cartridge can be introduced into a surgical site and positioned on a side of the tissue being treated. In addition, a staple-forming anvil can be positioned on the opposite side of the tissue. In various embodiments, the anvil can be carried by a first jaw and the staple cartridge can be carried by a second jaw, wherein the first jaw and/or the second jaw can be moved toward the other. Once the staple cartridge and the anvil have been positioned relative to the tissue, the staples can be ejected from the staple cartridge body such that the staples can pierce the tissue and contact the staple-forming anvil. Once the staples have been deployed from the staple cartridge body, the staple cartridge body can then be removed from the surgical site. In various embodiments disclosed herein, a staple cartridge, or at least a portion of a staple cartridge, can be implanted with the staples. In at least one such embodiment, as described in greater detail further below, a staple cartridge can comprise a cartridge body which can be compressed, crushed, and/or collapsed by the anvil when the anvil is moved from an open position into a closed position. When the cartridge body is compressed, crushed, and/or collapsed, the staples positioned within the cartridge body can be deformed by the anvil. Alternatively, the jaw supporting the staple cartridge can be moved toward the anvil into a closed position. In either event, in various embodiments, the staples can be deformed while they are at least partially positioned within the cartridge body. In certain embodiments, the staples may not be ejected from the staple cartridge while, in some embodiments, the staples can be ejected from the staple cartridge along with a portion of the cartridge body.

Referring now to FIGS. 83A-83D, a compressible staple cartridge, such as staple cartridge 1000, for example, can comprise a compressible, implantable cartridge body 1010 and, in addition, a plurality of staples 1020 positioned in the compressible cartridge body 1010, although only one staple 1020 is depicted in FIGS. 83A-83D. FIG. 83A illustrates the staple cartridge 1000 supported by a staple cartridge support, or staple cartridge channel, 1030, wherein the staple cartridge 1000 is illustrated in an uncompressed condition. In such an uncompressed condition, the anvil 1040 may or may not be in contact with the tissue T. In use, the anvil 1040 can be moved from an open position into contact with the tissue T as illustrated in FIG. 83B and position the tissue T against the cartridge body 1010. Even though the anvil 1040 can position the tissue T against a tissue-contacting surface 1019 of staple cartridge body 1010, referring again to FIG. 83B, the staple cartridge body 1010 may be subjected to little, if any, compressive force or pressure at such point and the staples 1020 may remain in an unformed, or unfired, condition. As illustrated in FIGS. 83A and 83B, the staple cartridge body 1010 can comprise one or more layers and the staple legs 1021 of staples 1020 can extend upwardly through these layers. In various embodiments, the cartridge body 1010 can comprise a first layer 1011, a second layer 1012, a third layer 1013, wherein the second layer 1012 can be positioned intermediate the first layer 1011 and the third layer 1013, and a fourth layer 1014, wherein the third layer 1013 can be positioned intermediate the second layer 1012 and the fourth layer 1014. In at least one embodiment, the bases 1022 of the staples 1020 can be positioned within cavities 1015 in the fourth layer 1014 and the staple legs 1021 can extend upwardly from the bases 1022 and through the fourth layer 1014, the third layer 1013, and the second layer 1012, for example. In various embodiments, each deformable leg 1021 can comprise a tip, such as sharp tip 1023, for example, which can be positioned in the second layer 1012, for example, when the staple cartridge 1000 is in an uncompressed condition. In at least one such embodiment, the tips 1023 may not extend into and/or through the first layer 1011, wherein, in at least one embodiment, the tips 1023 may not protrude through the tissue-contacting surface 1019 when the staple cartridge 1000 is in an uncompressed condition. In certain other embodiments, the sharp tips 1023 may be positioned in the third layer 1013, and/or any other suitable layer, when the staple cartridge is in an uncompressed condition. In various alternative embodiments, a cartridge body of a staple cartridge may have any suitable number of layers such as less than four layers or more than four layers, for example.

In various embodiments, as described in greater detail below, the first layer 1011 can be comprised of a buttress material and/or plastic material, such as polydioxanone (PDS) and/or polyglycolic acid (PGA), for example, and the second layer 1012 can be comprised of a bioabsorbable foam material and/or a compressible hemostatic material, such as oxidized regenerated cellulose (ORC), for example. In various embodiments, one or more of the first layer 1011, the second layer 1012, the third layer 1013, and the fourth layer 1014 may hold the staples 1020 within the staple cartridge body 1010 and, in addition, maintain the staples 1020 in alignment with one another. In various embodiments, the third layer 1013 can be comprised of a buttress material, or a fairly incompressible or inelastic material, which can be configured to hold the staple legs 1021 of the staples 1020 in position relative to one another. Furthermore, the second layer 1012 and the fourth layer 1014, which are positioned on opposite sides of the third layer 1013, can stabilize, or reduce the movement of, the staples 1020 even though the second layer 1012 and the fourth layer 1014 can be comprised of a compressible foam or elastic material. In certain embodiments, the staple tips 1023 of the staple legs 1021 can be at least partially embedded in the first layer 1011. In at least one such embodiment, the first layer 1011 and the third layer 1013 can be configured to co-operatively and firmly hold the staple legs 1021 in position. In at least one embodiment, the first layer 1011 and the third layer 1013 can each be comprised of a sheet of bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and the second layer 1012 and the fourth layer 1014 can each be comprised of at least one hemostatic material or agent.

Although the first layer 1011 can be compressible, the second layer 1012 can be substantially more compressible than the first layer 1011. For example, the second layer 1012 can be about twice as compressible, about three times as compressible, about four times as compressible, about five times as compressible, and/or about ten times as compressible, for example, as the first layer 1011. Stated another way, the second layer 1012 may compress about two times, about three times, about four times, about five times, and/or about ten times as much as first layer 1011, for a given force. In certain embodiments, the second layer 1012 can be between about twice as compressible and about ten times as compressible, for example, as the first layer 1011. In at least one embodiment, the second layer 1012 can comprise a plurality of air voids defined therein, wherein the amount and/or size of the air voids in the second layer 1012 can be controlled in order to provide a desired compressibility of the second layer 1012. Similar to the above, although the third layer 1013 can be compressible, the fourth layer 1014 can be substantially more compressible than the third layer 1013. For example, the fourth layer 1014 can be about twice as compressible, about three times as compressible, about four times as compressible, about five times as compressible, and/or about ten times as compressible, for example, as the third layer 1013. Stated another way, the fourth layer 1014 may compress about two times, about three times, about four times, about five times, and/or about ten times as much as third layer 1013, for a given force. In certain embodiments, the fourth layer 1014 can be between about twice as compressible and about ten times as compressible, for example, as the third layer 1013. In at least one embodiment, the fourth layer 1014 can comprise a plurality of air voids defined therein, wherein the amount and/or size of the air voids in the fourth layer 1014 can be controlled in order to provide a desired compressibility of the fourth layer 1014. In various circumstances, the compressibility of a cartridge body, or cartridge body layer, can be expressed in terms of a compression rate, i.e., a distance in which a layer is compressed for a given amount of force. For example, a layer having a high compression rate will compress a larger distance for a given amount of compressive force applied to the layer as compared to a layer having a lower compression rate. This being said, the second layer 1012 can have a higher compression rate than the first layer 1011 and, similarly, the fourth layer 1014 can have a higher compression rate than the third layer 1013. In various embodiments, the second layer 1012 and the fourth layer 1014 can be comprised of the same material and can comprise the same compression rate. In various embodiments, the second layer 1012 and the fourth layer 1014 can be comprised of materials having different compression rates. Similarly, the first layer 1011 and the third layer 1013 can be comprised of the same material and can comprise the same compression rate. In certain embodiments, the first layer 1011 and the third layer 1013 can be comprised of materials having different compression rates.

As the anvil 1040 is moved toward its closed position, the anvil 1040 can contact tissue T and apply a compressive force to the tissue T and the staple cartridge 1000, as illustrated in FIG. 83C. In such circumstances, the anvil 1040 can push the top surface, or tissue-contacting surface 1019, of the cartridge body 1010 downwardly toward the staple cartridge support 1030. In various embodiments, the staple cartridge support 1030 can comprise a cartridge support surface 1031 which can be configured to support the staple cartridge 1000 as the staple cartridge 1000 is compressed between the cartridge support surface 1031 and the tissue-contacting surface 1041 of anvil 1040. Owing to the pressure applied by the anvil 1040, the cartridge body 1010 can be compressed and the anvil 1040 can come into contact with the staples 1020. More particularly, in various embodiments, the compression of the cartridge body 1010 and the downward movement of the tissue-contacting surface 1019 can cause the tips 1023 of the staple legs 1021 to pierce the first layer 1011 of cartridge body 1010, pierce the tissue T, and enter into forming pockets 1042 in the anvil 1040. As the cartridge body 1010 is further compressed by the anvil 1040, the tips 1023 can contact the walls defining the forming pockets 1042 and, as a result, the legs 1021 can be deformed or curled inwardly, for example, as illustrated in FIG. 83C. As the staple legs 1021 are being deformed, as also illustrated in FIG. 83C, the bases 1022 of the staples 1020 can be in contact with or supported by the staple cartridge support 1030. In various embodiments, as described in greater detail below, the staple cartridge support 1030 can comprise a plurality of support features, such as staple support grooves, slots, or troughs 1032, for example, which can be configured to support the staples 1020, or at least the bases 1022 of the staples 1020, as the staples 1020 are being deformed. As also illustrated in FIG. 83C, the cavities 1015 in the fourth layer 1014 can collapse as a result of the compressive force applied to the staple cartridge body 1010. In addition to the cavities 1015, the staple cartridge body 1010 can further comprise one or more voids, such as voids 1016, for example, which may or may not comprise a portion of a staple positioned therein, that can be configured to allow the cartridge body 1010 to collapse. In various embodiments, the cavities 1015 and/or the voids 1016 can be configured to collapse such that the walls defining the cavities and/or walls deflect downwardly and contact the cartridge support surface 1031 and/or contact a layer of the cartridge body 1010 positioned underneath the cavities and/or voids.

Upon comparing FIG. 83B and FIG. 83C, it is evident that the second layer 1012 and the fourth layer 1014 have been substantially compressed by the compressive pressure applied by the anvil 1040. It may also be noted that the first layer 1011 and the third layer 1013 have been compressed as well. As the anvil 1040 is moved into its closed position, the anvil 1040 may continue to further compress the cartridge body 1010 by pushing the tissue-contacting surface 1019 downwardly toward the staple cartridge support 1030. As the cartridge body 1010 is further compressed, the anvil 1040 can deform the staples 1020 into their completely-formed shape as illustrated in FIG. 83D. Referring to FIG. 83D, the legs 1021 of each staple 1020 can be deformed downwardly toward the base 1022 of each staple 1020 in order to capture at least a portion of the tissue T, the first layer 1011, the second layer 1012, the third layer 1013, and the fourth layer 1014 between the deformable legs 1021 and the base 1022. Upon comparing FIGS. 83C and 83D, it is further evident that the second layer 1012 and the fourth layer 1014 have been further substantially compressed by the compressive pressure applied by the anvil 1040. It may also be noted upon comparing FIGS. 83C and 83D that the first layer 1011 and the third layer 1013 have been further compressed as well. After the staples 1020 have been completely, or at least sufficiently, formed, the anvil 1040 can be lifted away from the tissue T and the staple cartridge support 1030 can be moved away, and/or detached from, the staple cartridge 1000. As depicted in FIG. 83D, and as a result of the above, the cartridge body 1010 can be implanted with the staples 1020. In various circumstances, the implanted cartridge body 1010 can support the tissue along the staple line. In some circumstances, a hemostatic agent, and/or any other suitable therapeutic medicament, contained within the implanted cartridge body 1010 can treat the tissue over time. A hemostatic agent, as mentioned above, can reduce the bleeding of the stapled and/or incised tissue while a bonding agent or tissue adhesive can provide strength to the tissue over time. The implanted cartridge body 1010 can be comprised of materials such as ORC (oxidized regenerated cellulous), protein matrix, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain circumstances, the cartridge body 1010 can comprise an antibiotic and/or anti-microbial material, such as colloidal silver and/or triclosan, for example, which can reduce the possibility of infection in the surgical site.

In various embodiments, the layers of the cartridge body 1010 can be connected to one another. In at least one embodiment, the second layer 1012 can be adhered to the first layer 1011, the third layer 1013 can be adhered to the second layer 1012, and the fourth layer 1014 can be adhered to the third layer 1013 utilizing at least one adhesive, such as fibrin and/or protein hydrogel, for example. In certain embodiments, although not illustrated, the layers of the cartridge body 1010 can be connected together by interlocking mechanical features. In at least one such embodiment, the first layer 1011 and the second layer 1012 can each comprise corresponding interlocking features, such as a tongue and groove arrangement and/or a dovetail joint arrangement, for example. Similarly, the second layer 1012 and the third layer 1013 can each comprise corresponding interlocking features while the third layer 1013 and the fourth layer 1014 can each comprise corresponding interlocking features. In certain embodiments, although not illustrated, the staple cartridge 1000 can comprise one or more rivets, for example, which can extend through one or more layers of the cartridge body 1010. In at least one such embodiment, each rivet can comprise a first end, or head, positioned adjacent to the first layer 1011 and a second head positioned adjacent to the fourth layer 1014 which can be either assembled to or formed by a second end of the rivet. Owing to the compressible nature of the cartridge body 1010, in at least one embodiment, the rivets can compress the cartridge body 1010 such that the heads of the rivets can be recessed relative to the tissue-contacting surface 1019 and/or the bottom surface 1018 of the cartridge body 1010, for example. In at least one such embodiment, the rivets can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, the layers of the cartridge body 1010 may not be connected to one another other than by the staples 1020 contained therein. In at least one such embodiment, the frictional engagement between the staple legs 1021 and the cartridge body 1010, for example, can hold the layers of the cartridge body 1010 together and, once the staples have been formed, the layers can be captured within the staples 1020. In certain embodiments, at least a portion of the staple legs 1021 can comprise a roughened surface or rough coating which can increase the friction forces between the staples 1020 and the cartridge body 1010.

As described above, a surgical instrument can comprise a first jaw including the staple cartridge support 1030 and a second jaw including the anvil 1040. In various embodiments, as described in greater detail further below, the staple cartridge 1000 can comprise one or more retention features which can be configured to engage the staple cartridge support 1030 and, as a result, releasably retain the staple cartridge 1000 to the staple cartridge support 1030. In certain embodiments, the staple cartridge 1000 can be adhered to the staple cartridge support 1030 by at least one adhesive, such as fibrin and/or protein hydrogel, for example. In use, in at least one circumstance, especially in laparoscopic and/or endoscopic surgery, the second jaw can be moved into a closed position opposite the first jaw, for example, such that the first and second jaws can be inserted through a trocar into a surgical site. In at least one such embodiment, the trocar can define an approximately 5 mm aperture, or cannula, through which the first and second jaws can be inserted. In certain embodiments, the second jaw can be moved into a partially-closed position intermediate the open position and the closed position which can allow the first and second jaws to be inserted through the trocar without deforming the staples 1020 contained in the staple cartridge body 1010. In at least one such embodiment, the anvil 1040 may not apply a compressive force to the staple cartridge body 1010 when the second jaw is in its partially-closed intermediate position while, in certain other embodiments, the anvil 1040 can compress the staple cartridge body 1010 when the second jaw is in its partially-closed intermediate position. Even though the anvil 1040 can compress the staple cartridge body 1010 when it is in such an intermediate position, the anvil 1040 may not sufficiently compress the staple cartridge body 1010 such that the anvil 1040 comes into contact with the staples 1020 and/or such that the staples 1020 are deformed by the anvil 1040. Once the first and second jaws have been inserted through the trocar into the surgical site, the second jaw can be opened once again and the anvil 1040 and the staple cartridge 1000 can be positioned relative to the targeted tissue as described above.

Figure 84A:
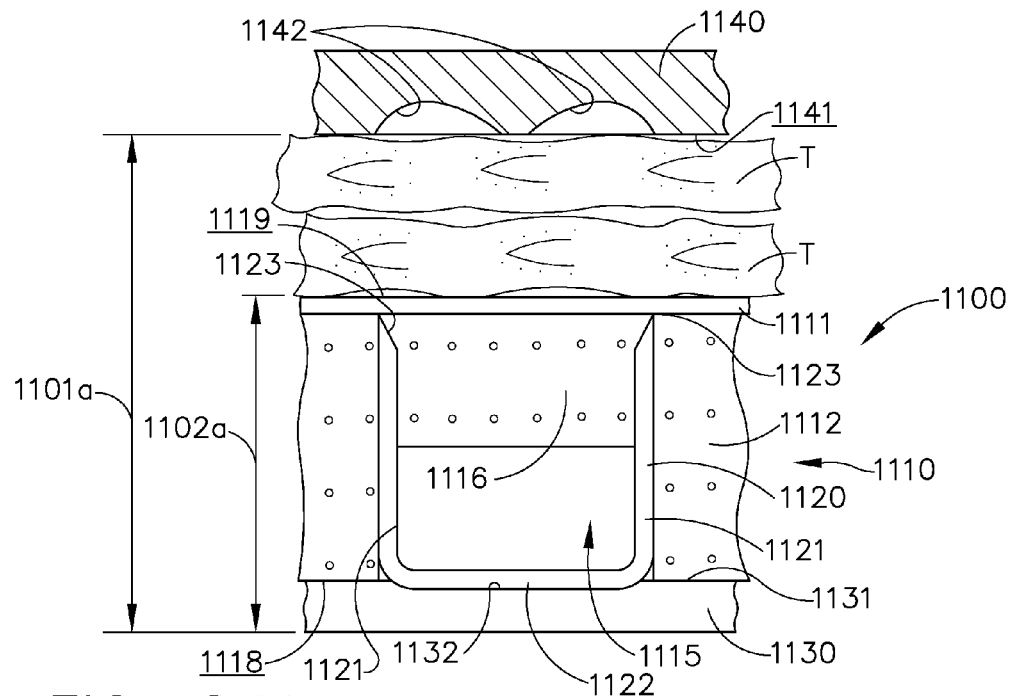
FIG. 84A is a diagram illustrating a staple positioned in a crushable staple cartridge body.
Figure 84B:
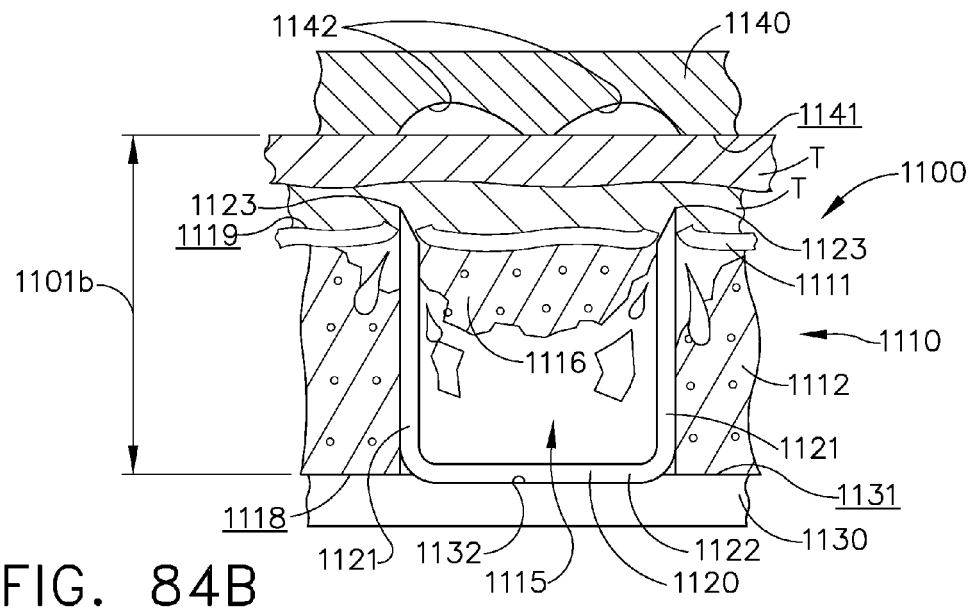
FIG. 84B is a diagram illustrating the crushable staple cartridge body of FIG. 84A being crushed by an anvil.
Figure 84C:
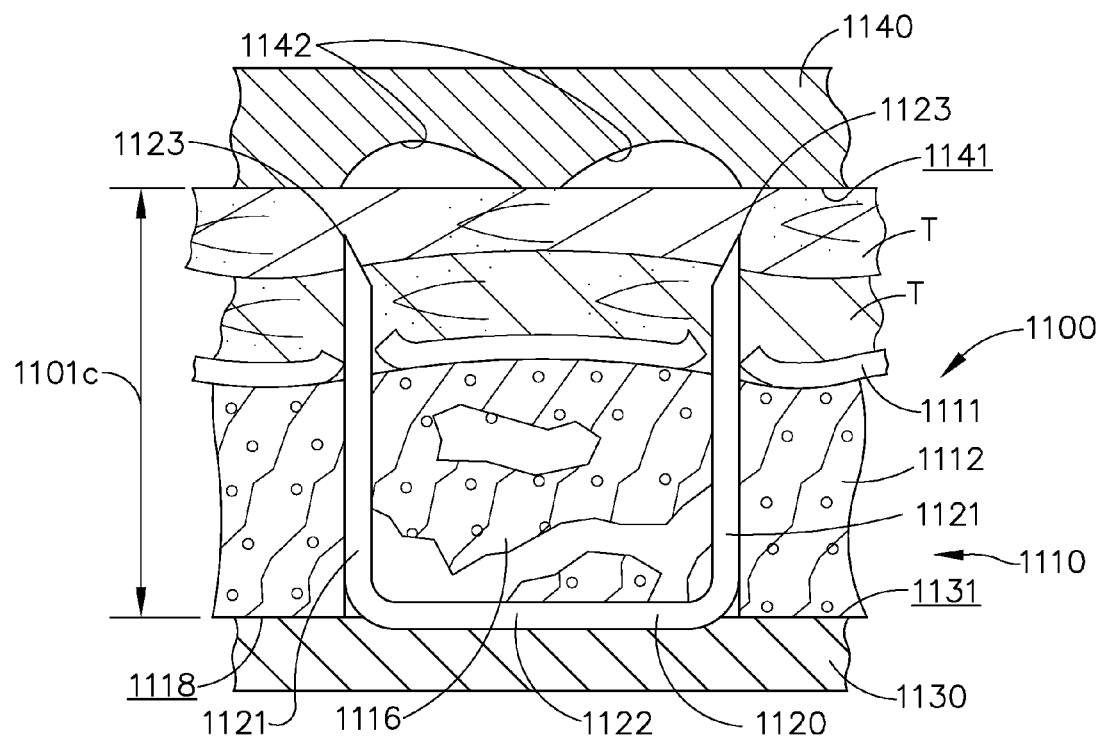
FIG. 84C is a diagram illustrating the crushable staple cartridge body of FIG. 84A being further crushed by the anvil.

In various embodiments, referring now to FIGS. 84A-84D, an end effector of a surgical stapler can comprise an implantable staple cartridge 1100 positioned intermediate an anvil 1140 and a staple cartridge support 1130. Similar to the above, the anvil 1140 can comprise a tissue-contacting surface 1141, the staple cartridge 1100 can comprise a tissue-contacting surface 1119, and the staple cartridge support 1130 can comprise a support surface 1131 which can be configured to support the staple cartridge 1100. Referring to FIG. 84A, the anvil 1140 can be utilized to position the tissue T against the tissue contacting surface 1119 of staple cartridge 1100 without deforming the staple cartridge 1100 and, when the anvil 1140 is in such a position, the tissue-contacting surface 1141 can be positioned a distance 1101a away from the staple cartridge support surface 1131 and the tissue-contacting surface 1119 can be positioned a distance 1102a away from the staple cartridge support surface 1131. Thereafter, as the anvil 1140 is moved toward the staple cartridge support 1130, referring now to FIG. 84B, the anvil 1140 can push the top surface, or tissue-contacting surface 1119, of staple cartridge 1100 downwardly and compress the first layer 1111 and the second layer 1112 of cartridge body 1110. As the layers 1111 and 1112 are compressed, referring again to FIG. 84B, the second layer 1112 can be crushed and the legs 1121 of staples 1120 can pierce the first layer 1111 and enter into the tissue T. In at least one such embodiment, the staples 1120 can be at least partially positioned within staple cavities, or voids, 1115 in the second layer 1112 and, when the second layer 1112 is compressed, the staple cavities 1115 can collapse and, as a result, allow the second layer 1112 to collapse around the staples 1120. In various embodiments, the second layer 1112 can comprise cover portions 1116 which can extend over the staple cavities 1115 and enclose, or at least partially enclose, the staple cavities 1115. FIG. 84B illustrates the cover portions 1116 being crushed downwardly into the staple cavities 1115. In certain embodiments, the second layer 1112 can comprise one or more weakened portions which can facilitate the collapse of the second layer 1112. In various embodiments, such weakened portions can comprise score marks, perforations, and/or thin cross-sections, for example, which can facilitate a controlled collapse of the cartridge body 1110. In at least one embodiment, the first layer 1111 can comprise one or more weakened portions which can facilitate the penetration of the staple legs 1121 through the first layer 1111. In various embodiments, such weakened portions can comprise score marks, perforations, and/or thin cross-sections, for example, which can be aligned, or at least substantially aligned, with the staple legs 1121.

Figure 84D:
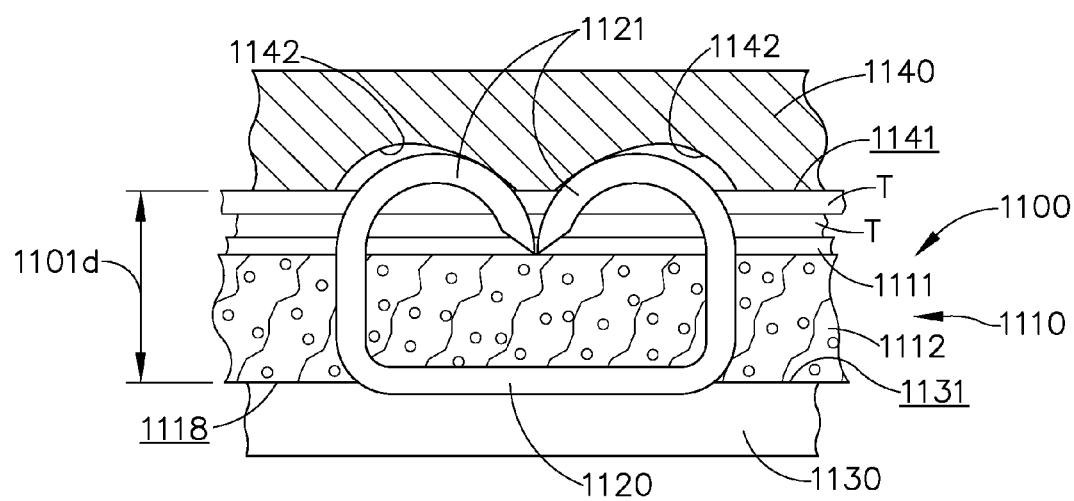
FIG. 84D is a diagram illustrating the staple of FIG. 84A in a fully formed configuration and the crushable staple cartridge of FIG. 84A in a fully crushed condition.

When the anvil 1140 is in a partially closed, unfired position, referring again to FIG. 84A, the anvil 1140 can be positioned a distance 1101a away from the cartridge support surface 1131 such that a gap is defined therebetween. This gap can be filled by the staple cartridge 1100, having a staple cartridge height 1102a, and the tissue T. As the anvil 1140 is moved downwardly to compress the staple cartridge 1100, referring again to FIG. 84B, the distance between the tissue contacting surface 1141 and the cartridge support surface 1131 can be defined by a distance 1101b which is shorter than the distance 1101a. In various circumstances, the gap between the tissue-contacting surface 1141 of anvil 1140 and the cartridge support surface 1131, defined by distance 1101b, may be larger than the original, undeformed staple cartridge height 1102a. As the anvil 1140 is moved closer to the cartridge support surface 1131, referring now to FIG. 84C, the second layer 1112 can continue to collapse and the distance between the staple legs 1121 and the forming pockets 1142 can decrease. Similarly, the distance between the tissue-contacting surface 1141 and the cartridge support surface 1131 can decrease to a distance 1101c which, in various embodiments, may be greater than, equal to, or less than the original, undeformed cartridge height 1102a. Referring now to FIG. 84D, the anvil 1140 can be moved into a final, fired position in which the staples 1120 have been fully formed, or at least formed to a desired height. In such a position, the tissue-contacting surface 1141 of anvil 1140 can be a distance 1101d away from the cartridge support surface 1131, wherein the distance 1101d can be shorter than the original, undeformed cartridge height 1102a. As also illustrated in FIG. 84D, the staple cavities 1115 may be fully, or at least substantially, collapsed and the staples 1120 may be completely, or at least substantially, surrounded by the collapsed second layer 1112. In various circumstances, the anvil 1140 can be thereafter moved away from the staple cartridge 1100. Once the anvil 1140 has been disengaged from the staple cartridge 1100, the cartridge body 1110 can at least partially re-expand in various locations, i.e., locations intermediate adjacent staples 1120, for example. In at least one embodiment, the crushed cartridge body 1110 may not resiliently re-expand. In various embodiments, the formed staples 1120 and, in addition, the cartridge body 1110 positioned intermediate adjacent staples 1120 may apply pressure, or compressive forces, to the tissue T which may provide various therapeutic benefits.

As discussed above, referring again to the embodiment illustrated in FIG. 84A, each staple 1120 can comprise staple legs 1121 extending therefrom. Although staples 1120 are depicted as comprising two staple legs 1121, various staples can be utilized which can comprise one staple leg or, alternatively, more than two staple legs, such as three staple legs or four staple legs, for example. As illustrated in FIG. 84A, each staple leg 1121 can be embedded in the second layer 1112 of the cartridge body 1110 such that the staples 1120 are secured within the second layer 1112. In various embodiments, the staples 1120 can be inserted into the staple cavities 1115 in cartridge body 1110 such that the tips 1123 of the staple legs 1121 enter into the cavities 1115 before the bases 1122. After the tips 1123 have been inserted into the cavities 1115, in various embodiments, the tips 1123 can be pressed into the cover portions 1116 and incise the second layer 1112. In various embodiments, the staples 1120 can be seated to a sufficient depth within the second layer 1112 such that the staples 1120 do not move, or at least substantially move, relative to the second layer 1112. In certain embodiments, the staples 1120 can be seated to a sufficient depth within the second layer 1112 such that the bases 1122 are positioned or embedded within the staple cavities 1115. In various other embodiments, the bases 1122 may not be positioned or embedded within the second layer 1112. In certain embodiments, referring again to FIG. 84A, the bases 1122 may extend below the bottom surface 1118 of the cartridge body 1110. In certain embodiments, the bases 1122 can rest on, or can be directly positioned against, the cartridge support surface 1130. In various embodiments, the cartridge support surface 1130 can comprise support features extending therefrom and/or defined therein wherein, in at least one such embodiment, the bases 1122 of the staples 1120 may be positioned within and supported by one or more support grooves, slots, or troughs, 1132, for example, in the staple cartridge support 1130, as described in greater detail further below.

Further to the above, referring now to FIG. 85, the bases 1122 of the staples 1120 can be positioned directly against the support surface 1131 of staple cartridge support 1130. In various embodiments, including embodiments where the staple bases 1122 comprise circular or arcuate bottom surfaces 1124, for example, the staple bases 1122 may move or slide along the staple cartridge support surface 1131. Such sliding can occur when the anvil 1140 is pressed against the tips 1123 of the staple legs 1121 during the staple forming process. In certain embodiments, as described above and referring now to FIG. 86, the staple cartridge support 1130 can comprise one or more support slots 1132 therein which can be configured to eliminate, or at least reduce, the relative movement between the staple bases 1122 and the cartridge support surface 1131. In at least one such embodiment, each support slot 1132 can be defined by a surface contour which matches, or at least substantially matches, the contour of the bottom surface of the staple positioned therein. For example, the bottom surface 1124 of the base 1122 depicted in FIG. 86 can comprise a circular, or at least substantially circular, surface and the support slot 1132 can also comprise a circular, or at least substantially circular, surface. In at least one such embodiment, the surface defining the slot 1132 can be defined by a radius of curvature which is greater than or equal to a radius of curvature which defines bottom surface 1124. Although the slots 1132 may assist in preventing or reducing relative sliding movement between the staples 1120 and the staple cartridge support 1130, the slots 1132 may also be configured to prevent or reduce relative rotational movement between the staples 1120 and the staple cartridge support 1130. More particularly, in at least one embodiment, the slots 1132 can be configured to closely receive the bases 1122 in order to prevent or reduce the rotation of the staples 1120 about axes 1129, for example, such that the staples 1120 do not rotate or twist when they are being deformed.

In various embodiments, further to the above, each staple 1120 can be formed from a round, or an at least substantially round, wire. In certain embodiments, the legs and the base of each staple can be formed from a wire having a non-circular cross-section, such as a rectangular cross-section, for example. In at least one such embodiment, the staple cartridge support 1130 can comprise corresponding non-circular slots, such as rectangular slots, for example, configured to receive the bases of such staples. In various embodiments, referring now to FIG. 87, each staple 1120 can comprise a crown, such as a crown 1125, for example, overmolded onto a base 1122 wherein each crown 1125 can be positioned within a support slot in the staple cartridge support 1130. In at least one such embodiment, each crown 1125 can comprise a square and/or rectangular cross-section, for example, which can be configured to be received within square and/or rectangular slots 1134, for example, in the staple cartridge support 1130. In various embodiments, the crowns 1125 can be comprised of a bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and can be formed around the bases 1122 of the staples 1120 by an injection molding process, for example. Various crowns and methods for forming various crowns are disclosed in U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, the entire disclosure of which is incorporated be reference herein. Referring again to FIG. 87, the slots 1134 can further comprise lead-ins, or bevels, 1135 which can be configured to facilitate the insertion of the crowns 1125 into the slots 1134. In various embodiments, the bases and/or crowns of the staples 1120 may be positioned within the slots 1134 when the staple cartridge 1100 is assembled to the staple cartridge support 1130. In certain embodiments, the crowns 1125 of the staples 1120 may be aligned with the slots 1134 when the staple cartridge 1100 is assembled to the staple cartridge support 1130. In at least one such embodiment, the crowns 1125 may not enter into the slots 1134 until a compressive force is applied to the staple legs 1121 and the bases and/or crowns of the staples 1120 are pushed downwardly into the slots 1134.

Figure 88:
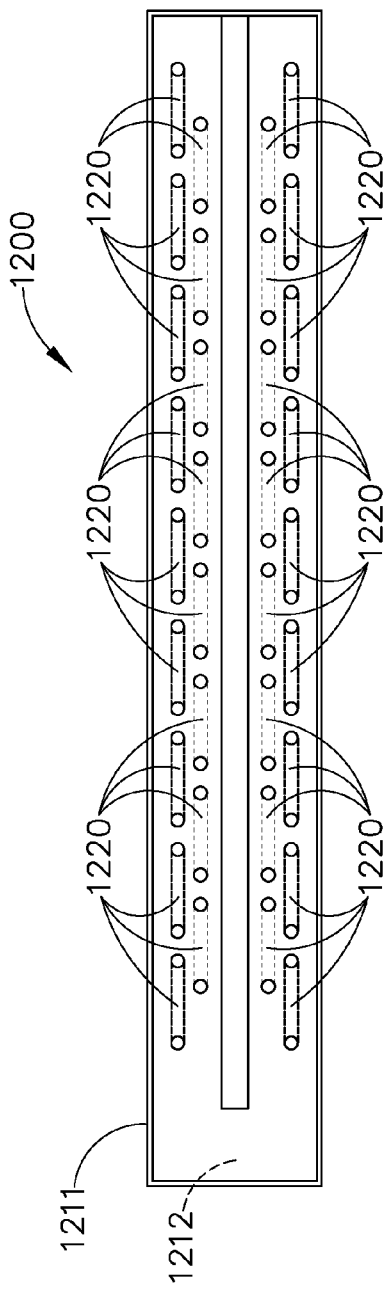
FIG. 88 is a top view of a staple cartridge in accordance with at least one embodiment comprising staples embedded in a collapsible staple cartridge body.
Figure 89:
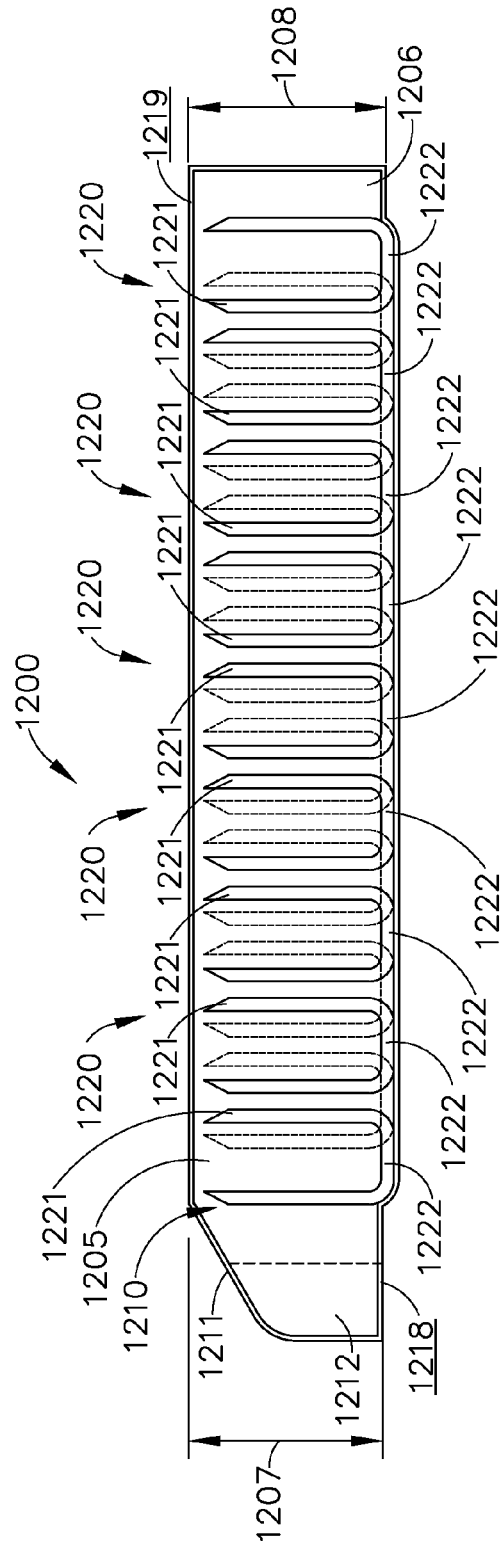
FIG. 89 is an elevational view of the staple cartridge of FIG. 88.

In various embodiments, referring now to FIGS. 88 and 89, a staple cartridge, such as staple cartridge 1200, for example, can comprise a compressible, implantable cartridge body 1210 comprising an outer layer 1211 and an inner layer 1212. Similar to the above, the staple cartridge 1200 can comprise a plurality of staples 1220 positioned within the cartridge body 1210. In various embodiments, each staple 1220 can comprise a base 1222 and one or more staple legs 1221 extending therefrom. In at least one such embodiment, the staple legs 1221 can be inserted into the inner layer 1212 and seated to a depth in which the bases 1222 of the staples 1220 abut and/or are positioned adjacent to the bottom surface 1218 of the inner layer 1212, for example. In the embodiment depicted in FIGS. 88 and 89, the inner layer 1212 does not comprise staple cavities configured to receive a portion of the staples 1220 while, in other embodiments, the inner layer 1212 can comprise such staple cavities. In various embodiments, further to the above, the inner layer 1212 can be comprised of a compressible material, such as bioabsorbable foam and/or oxidized regenerated cellulose (ORC), for example, which can be configured to allow the cartridge body 1210 to collapse when a compressive load is applied thereto. In various embodiments, the inner layer 1212 can be comprised of a lyophilized foam comprising polylactic acid (PLA) and/or polyglycolic acid (PGA), for example. The ORC may be commercially available under the trade name Surgicel and can comprise a loose woven fabric (like a surgical sponge), loose fibers (like a cotton ball), and/or a foam. In at least one embodiment, the inner layer 1212 can be comprised of a material including medicaments, such as freeze-dried thrombin and/or fibrin, for example, contained therein and/or coated thereon which can be water-activated and/or activated by fluids within the patient's body, for example. In at least one such embodiment, the freeze-dried thrombin and/or fibrin can be held on a Vicryl (PGA) matrix, for example. In certain circumstances, however, the activatable medicaments can be unintentionally activated when the staple cartridge 1200 is inserted into a surgical site within the patient, for example. In various embodiments, referring again to FIGS. 88 and 89, the outer layer 1211 can be comprised of a water impermeable, or at least substantially water impermeable, material such that liquids do not come into contact with, or at least substantially contact, the inner layer 1212 until after the cartridge body 1210 has been compressed and the staple legs have penetrated the outer layer 1211 and/or after the outer layer 1211 has been incised in some fashion. In various embodiments, the outer layer 1211 can be comprised of a buttress material and/or plastic material, such as polydioxanone (PDS) and/or polyglycolic acid (PGA), for example. In certain embodiments, the outer layer 1211 can comprise a wrap which surrounds the inner layer 1212 and the staples 1220. More particularly, in at least one embodiment, the staples 1220 can be inserted into the inner layer 1212 and the outer layer 1211 can be wrapped around the sub-assembly comprising the inner layer 1212 and the staples 1220 and then sealed.

Figure 90:
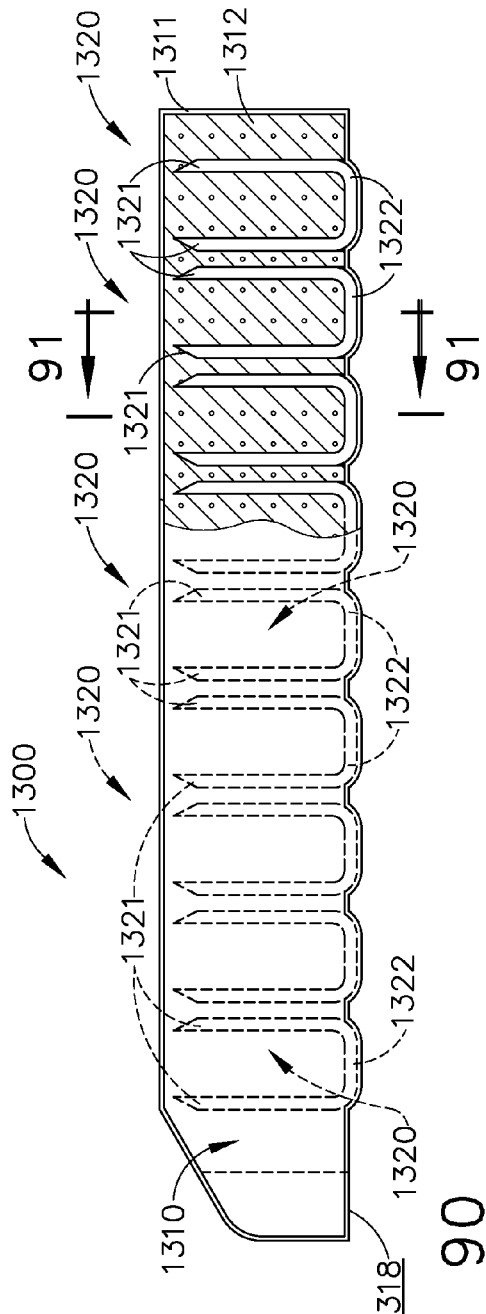
FIG. 90 is an elevational view of a staple cartridge in accordance with at least one embodiment comprising a protective layer surrounding staples positioned within a collapsible staple cartridge body.
Figure 91:
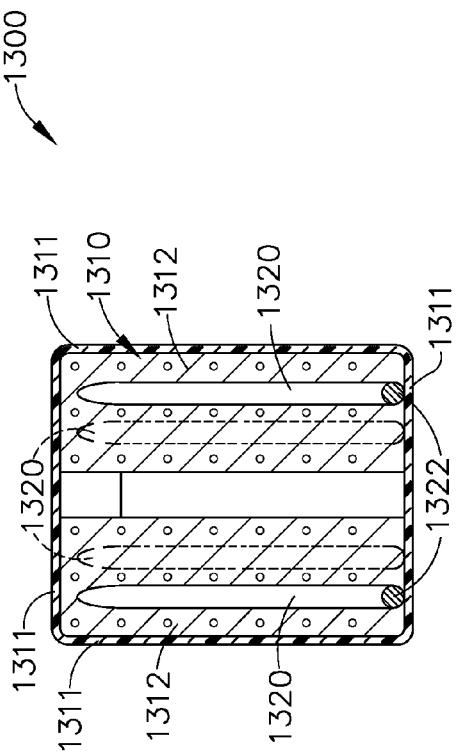
FIG. 91 is a cross-sectional view of the staple cartridge of FIG. 90 taken along line 91-91 in FIG. 90.

In various embodiments, referring now to FIGS. 90 and 91, a staple cartridge, such as staple cartridge 1300, for example, can comprise a compressible, implantable cartridge body 1310 including an outer layer 1311 and an inner layer 1312. Similar to the above, the staple cartridge 1300 can further comprise staples 1320 positioned within the cartridge body 1310 wherein each staple 1320 can comprise a base 1322 and one or more legs 1321 extending therefrom. Similar to staple cartridge 1200, the bases 1322 of staples 1320 can extend below the bottom surface 1318 of the inner layer 1312 and the outer layer 1311 can surround the bases 1322. In at least one such embodiment, the outer layer 1311 can be sufficiently flexible so as to envelop each staple base 1322 such that the outer layer 1311 conforms to the contour of the bases 1322. In at least one alternative embodiment, referring again to FIG. 89, the outer layer 1211 can be sufficiently rigid such that it extends around the bases 1222 without conforming to each base 1222. In any event, in various embodiments, the outer layer 1311 can be positioned intermediate the bases 1322 of staples 1320 and a staple cartridge support surface, such as support surfaces 1031 or 1131, for example, supporting the staple cartridge 1300. In at least one such embodiment, the outer layer 1311 can be positioned intermediate the bases 1322 and support slots, such as slots 1032 or 1132, for example, defined in the staple cartridge support surface. In at least one such embodiment, further to the above, the outer layer 1311 can be configured to limit the movement of the bases 1322 and/or increase the coefficient of friction between the bases 1322 and the staple cartridge support surface and/or support slots in order to reduce relative movement therebetween. In various alternative embodiments, referring now to FIGS. 92 and 93, the outer layer of a staple cartridge, such as staple cartridge 1400, for example, may not entirely surround the staples positioned therein. In at least one such embodiment, an outer layer 1411 of a compressible, implantable cartridge body 1410 may be assembled to the inner layer 1412 before the staple legs 1421 of staples 1420 are inserted into the cartridge body 1410. As a result of the above, the bases 1422 of staples 1420 may extend outside of the outer layer 1411 and, in at least one such embodiment, the bases 1422 may be positioned directly into the support slots 1032 or 1132 within the staple cartridge support surfaces 1031 or 1131, for example. In various embodiments, the staple legs 1421 may incise the outer layer 1411 when they are inserted therethrough. In various circumstances, the holes created by the staple legs 1421 may closely surround the staple legs 1421 such that very little, if any, fluid can leak between the staple legs 1421 and the outer layer 1411 which can reduce the possibility of, or prevent, the medicament contained within the staple cartridge body 1410 from being activated and/or leaking out of the cartridge body 1410 prematurely.

As discussed above, referring again to FIGS. 88 and 89, the legs 1221 of the staples 1220 can be embedded within the cartridge body 1210 and the bases 1222 of staples 1220 may extend outwardly from the bottom surface 1218 of the inner layer 1212. In various embodiments, further to the above, the inner layer 1212 may not comprise staple cavities configured to receive the staples 1220. In various other embodiments, referring now to FIGS. 94 and 95, a staple cartridge, such as staple cartridge 1500, for example, may comprise a compressible, implantable cartridge body 1510 comprising staple cavities 1515 which can be configured to receive at least a portion of the staples 1520 therein. In at least one such embodiment, a top portion of the staple legs 1521 of the staples 1520 may be embedded in the inner layer 1512 while a bottom portion of the staple legs 1521, and the bases 1522, may be positioned within the staple cavities 1515. In certain embodiments, the bases 1522 may be entirely positioned in the staple cavities 1515 while, in some embodiments, the bases 1522 may at least partially extend below the bottom surface 1518 of the inner layer 1512. Similar to the above, the outer layer 1511 may enclose the inner layer 1512 and the staples 1520 positioned therein. In certain other embodiments, referring now to FIG. 96, a staple cartridge 1600 may comprise staples 1620 positioned within staple cavities 1615 in a compressible, implantable cartridge body 1610 wherein at least a portion of the staples 1620 are not enclosed by the outer layer 1611. In at least one such embodiment, each staple 1620 can comprise staple legs 1621 which are at least partially embedded in the inner layer 1612 and, in addition, bases 1622 which extend outwardly around the outer layer 1611.

In various embodiments, referring now to FIGS. 97 and 98, a staple cartridge, such as staple cartridge 1700, for example, can comprise a compressible, implantable cartridge body 1710 and a plurality of staples 1720 at least partially positioned within the cartridge body 1710. The cartridge body 1710 can comprise an outer layer 1711, an inner layer 1712, and, in addition, an alignment matrix 1740 which can be configured to align and/or retain the staples 1720 in position within the cartridge body 1710. In at least one embodiment, the inner layer 1712 can comprise a recess 1741 which can be configured to receive the alignment matrix 1740 therein. In various embodiments, the alignment matrix 1140 can be press-fit within the recess 1741 and/or otherwise suitably secured to the inner layer 1712 utilizing at least one adhesive, such as fibrin and/or protein hydrogel, for example. In at least one embodiment, the recess 1741 can be configured such that the bottom surface 1742 of alignment matrix 1740 is aligned, or at least substantially aligned, with the bottom surface 1718 of the inner layer 1712. In certain embodiments, the bottom surface 1742 of the alignment matrix can be recessed with respect to and/or extend from the bottom surface 1718 of the second layer 1712. In various embodiments, each staple 1720 can comprise a base 1722 and one or more legs 1721 extending from the base 1722, wherein at least a portion of the staple legs 1721 can extend through the alignment matrix 1740. The alignment matrix 1740 can further comprise a plurality of apertures and/or slots, for example, extending therethrough which can be configured to receive the staple legs 1721 therein. In at least one such embodiment, each aperture can be configured to closely receive a staple leg 1721 such that there is little, if any, relative movement between the staple leg 1721 and the sidewalls of the aperture. In certain embodiments, the alignment matrix apertures may not extend entirely through the alignment matrix 1740 and the staple legs 1721 may be required to incise the alignment matrix 1740 as the staple legs 1721 are pushed therethrough.

In various embodiments, the alignment matrix 1740 can be comprised of a molded plastic body which, in at least one embodiment, can be stiffer or less compressible than the inner layer 1712 and/or the outer layer 1711. In at least one such embodiment, the alignment matrix 1740 can be comprised of a plastic material and/or any other suitable material, such as polydioxanone (PDS) and/or polyglycolic acid (PGA), for example. In certain embodiments, the alignment matrix 1740 can be assembled to the inner layer 1712 and the staple legs 1721 can thereafter be inserted through the alignment matrix 1740 and embedded into the inner layer 1712. In various embodiments, the bottom surface 1742 of the alignment matrix 1740 can comprise one or more grooves, slots, or troughs, for example, which can be configured to at least partially receive the bases 1722 of the staples 1720. Similar to the above, the outer layer 1711 can then be placed around the subassembly comprising the inner layer 1712, the alignment matrix 1740, and the staples 1720. Alternatively, the outer layer 1711 can be placed around a subassembly comprising the inner layer 1712 and the alignment matrix 1740 wherein the staples 1720 can be thereafter inserted through the outer layer 1711, the alignment matrix 1740, and the inner layer

1712. In any event, as a result of the above, the inner layer 1712, the alignment matrix 1740, and/or the outer layer 1711 can be configured to retain the staples 1720 in position until and/or after they are deformed by an anvil as described above. In at least one such embodiment, the alignment matrix 1740 can serve to hold the staples 1720 in place before the staple cartridge 1700 is implanted within a patient and, in addition, secure the tissue along the staple line after the staple cartridge 1700 has been implanted. In at least one embodiment, the staples 1720 may be secured within the alignment matrix 1740 without being embedded in the inner layer 1712 and/or the outer layer 1711, for example.

Figure 99:
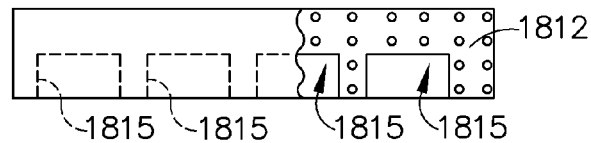
FIG. 99 is partial cut-away view of an inner layer of a compressible staple cartridge body.
Figure 100:
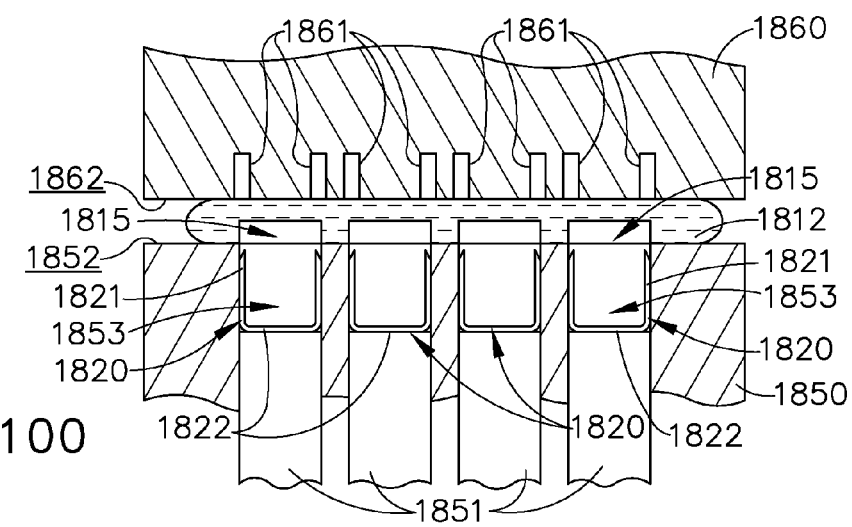
FIG. 100 is a diagram illustrating the inner layer of FIG. 99 compressed between a transfer plate and a support plate.
Figure 101:
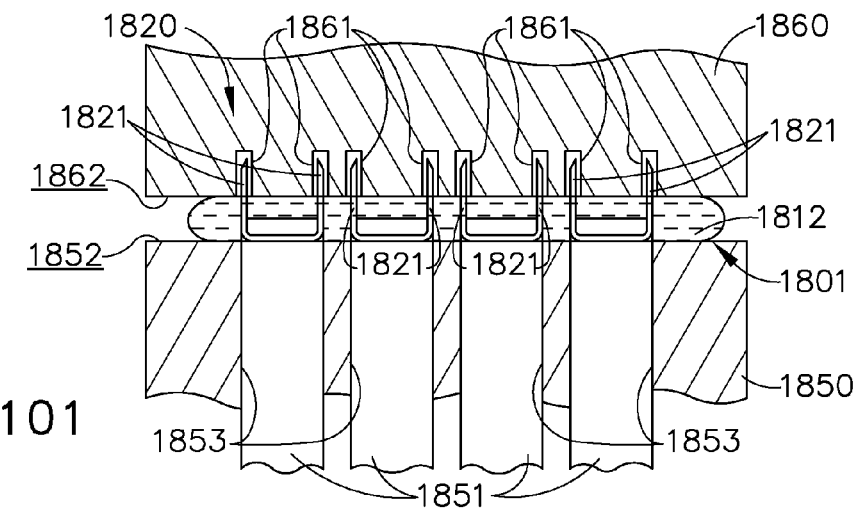
FIG. 101 is a diagram illustrating staples being inserted into the compressed inner layer of FIG. 100.

In various embodiments, referring now to FIGS. 99-105, a staple cartridge, such as staple cartridge 1800, for example, can be assembled by compressing an inner layer 1812, inserting staples, such as staples 1820, for example, into the inner layer 1812, and wrapping the inner layer 1812 with an outer layer 1811. Referring primarily to FIG. 99, a compressible inner layer 1812 is illustrated as comprising a plurality of staple cavities 1815 defined therein, although other embodiments are envisioned in which the inner layer 1812 does not comprise staple cavities, as described above. Referring now to FIG. 100, the compressible inner layer 1812 can be positioned intermediate a transfer plate 1850 and a support plate 1860 and compressed between the compression surfaces 1852 and 1862 thereof, respectively. As illustrated in FIG. 100, the top and bottom surfaces of the inner layer 1812 can be compressed toward one another and, in response thereto, the inner layer 1812 can bulge outwardly in the lateral directions. In certain embodiments, the inner layer 1812 can be compressed to a height which is approximately one-third of its original height, for example, and can have a height or thickness between approximately 0.06" and approximately 0.08" in its compressed state, for example. As also illustrated in FIG. 100, the transfer plate 1850 can further comprise a plurality of staples, such as staples 1820, for example, positioned within a plurality of staple wells 1853. In addition, the transfer plate 1850 can further comprise a plurality of drivers 1851 which can be configured to push the staples 1820 upwardly and out of the staple wells 1853. Referring now to FIG. 101, the drivers 1851 can be utilized to push the staple legs 1821 of the staples 1820 into and through the compressed inner layer 1812. In various embodiments, the drivers 1851 can be configured such that the top surfaces thereof are positioned flush, or at least nearly flush, with the compression surface 1852 of the transfer plate 1850 when the staples 1820 have been fully deployed from the staple wells 1853 of transfer plate 1850. In certain embodiments, as also illustrated in FIG. 101, the support plate 1860 can comprise a plurality of receiving apertures 1861 which can be configured to receive the staple legs 1821, or at least the tips of the staple legs 1821, after they are pushed through the inner layer 1812. The receiving apertures 1861, or the like, may be necessitated in embodiments where the inner layer 1812 has been compressed to a height which is shorter than the height of the staples 1820 and, thus, when the staples 1820 have been fully ejected from the staple wells 1853, the staple legs 1821 may protrude from the top surface of the compressed inner layer 1812. In certain other embodiments, the inner layer 1812 may be compressed to a height which is taller than the height of the staples 1820 and, as a result, the receiving apertures 1861 in support plate 1860 may be unnecessary.

Figure 102:
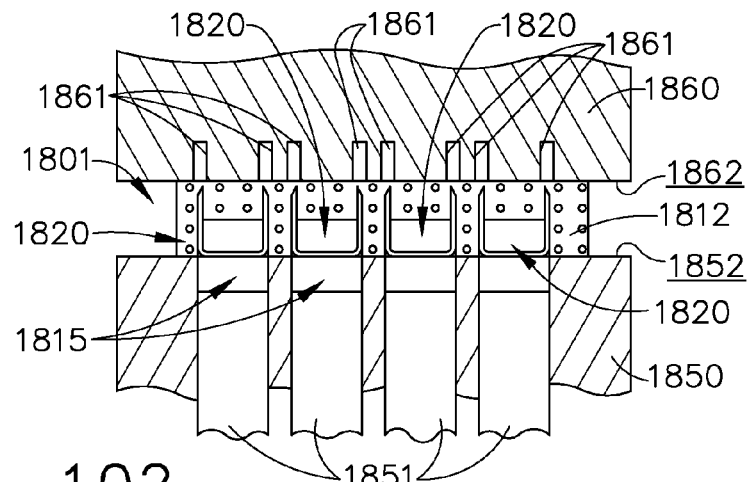
Figure 103:
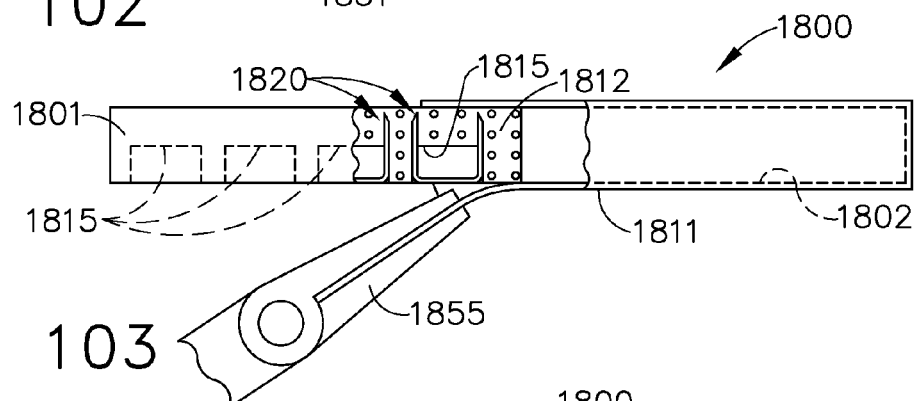
Figure 104:
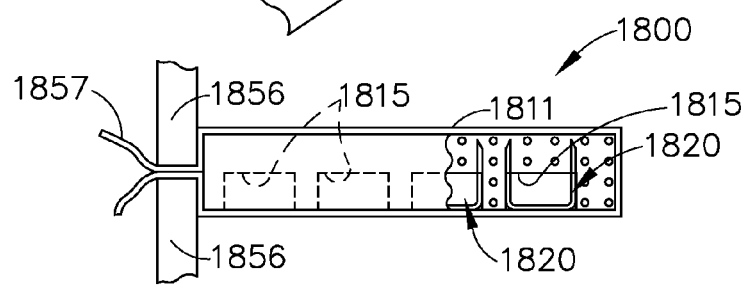
Figure 105:
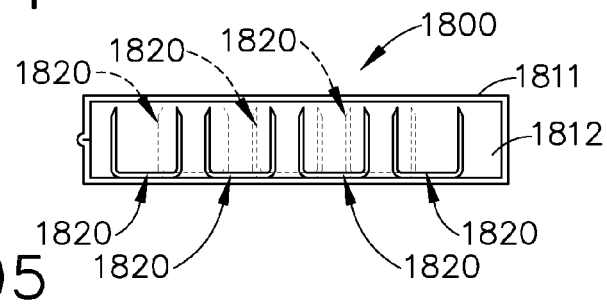

After the staples 1820 have been inserted into the inner layer 1812, referring now to FIG. 102, the support plate 1860 can be moved away from the transfer plate 1850 in order to allow the inner layer 1812 to decompress. In such circumstances, the inner layer 1812 can resiliently re-expand to its original, or at least near-original, uncompressed height. As the inner layer 1812 re-expands, the height of the inner layer 1812 can increase such that it exceeds the height of the staples 1820 and such that the staple legs 1821 of the staples 1820 no longer protrude from the top surface of the inner layer 1812. In various circumstances, the receiving apertures 1861 can be configured to hold the staple legs 1821 in position at least until the support plate 1860 has been sufficiently moved away such that the legs 1821 are no longer positioned within the receiving apertures 1861. In such circumstances, the receiving apertures 1861 can assist in maintaining the relative alignment of the staples 1820 within the inner layer 1812 as it re-expands. In various circumstances, the inner layer 1812 and the staples 1820 positioned therein can comprise a subassembly 1801 which, referring now to FIG. 103, can be inserted into an outer layer 1811, for example. In at least one such embodiment, the outer layer 1811 can comprise a cavity 1802 defined therein which can be configured to receive the subassembly 1801 therein. In various circumstances, a tool, such as pliers 1855, for example, can be utilized to pull the outer layer 1811 onto the subassembly 1801. Once the subassembly 1801 has been sufficiently positioned within the outer layer 1811, referring now to FIG. 104, the outer layer 1811 can be sealed. In various embodiments, the outer layer 1811 can be sealed utilizing the application of heat energy to a portion thereof. More particularly, in at least one embodiment, the outer layer 1811 can be comprised of a plastic material wherein the open end of the outer layer 1811 can be heat-staked by one or more heated elements, or irons, 1856 in order to bond and/or seal the perimeter of the open end of the outer layer 1811 together. In at least one such embodiment, referring now to FIG. 105, an excess portion 1857 of the outer layer 1811 can be removed and the staple cartridge 1800 can then be used as described herein.

Figure 106:
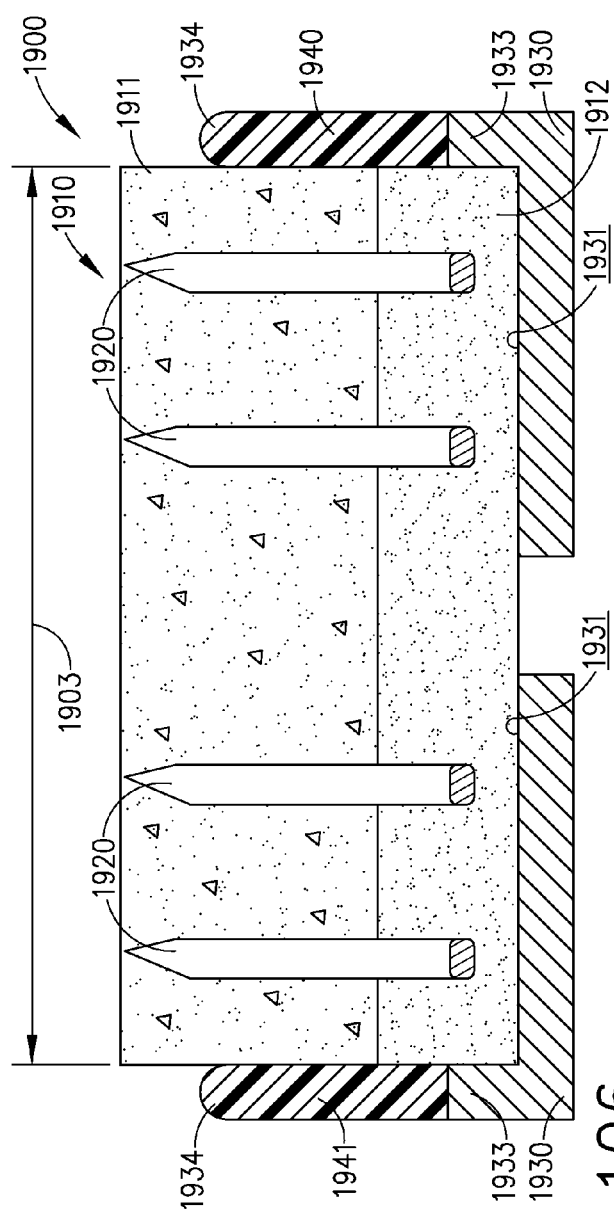
Figure 107:
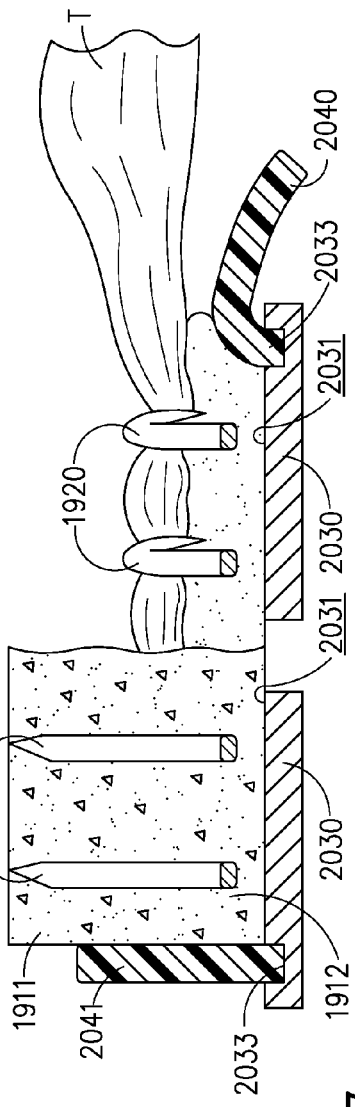

As described above, a staple cartridge can be positioned within and/or secured to a staple cartridge attachment portion. In various embodiments, referring now to FIGS. 106 and 107, a staple cartridge attachment portion can comprise a staple cartridge channel, such as staple cartridge channel 1930, for example, which can be configured to receive at least a portion of a staple cartridge, such as staple cartridge 1900, for example, therein. In at least one embodiment, the staple cartridge channel 1930 can comprise a bottom support surface 1931, a first lateral support wall 1940, and a second lateral support wall 1941. In use, the staple cartridge 1900 can be positioned within the staple cartridge channel 1930 such that the staple cartridge 1900 is positioned against and/or adjacent to the bottom support surface 1931 and positioned intermediate the first lateral support wall 1940 and the second lateral support wall 1941. In certain embodiments, the first lateral support wall 1940 and the second lateral support wall 1941 can define a lateral gap therebetween. In at least one such embodiment, the staple cartridge 1900 can comprise a lateral width 1903 which is the same as and/or wider than the lateral gap defined between the support walls 1940 and 1941 such that a compressible, implantable cartridge body 1910 of the staple cartridge 1900 can fit securely between the walls 1940 and 1941. In certain other embodiments, the lateral width 1903 of the staple cartridge 1900 can be shorter than the gap defined between the first and second side walls 1940 and 1941. In various embodiments, at least a portion of the walls 1940 and 1941 and the bottom support surface 1931 can be defined by a stamped metal channel while, in at least one embodiment, at least a portion of the lateral support wall 1940 and/or lateral support wall 1941 can be comprised of a flexible material, such as an elastomeric material, for example. Referring primarily to FIG. 106, the first side wall 1940 and the second side wall 1941 of the staple cartridge channel 1930 can each be comprised of a rigid portion 1933 extending upwardly from the bottom support surface 1931 and a flexible portion 1934 extending upwardly from the rigid portions 1933.

In various embodiments, further to the above, the cartridge body 1910 of staple cartridge 1900 can be comprised of one or more compressible layers, such as first layer 1911 and second layer 1912, for example. When the cartridge body 1910 is compressed against the bottom support surface 1931 by an anvil, as described above, the side portions of the cartridge body 1910 can expand laterally. In embodiments where the staple cartridge 1930 is comprised of rigid side walls, the lateral expansion of the cartridge body 1910 can be prevented, or at least limited, by the rigid side walls and, as a result, a significant amount of internal pressure, or stress, can be developed within the cartridge body 1910. In embodiments where at least a portion of the staple cartridge 1930 is comprised of flexible side walls, the flexible side walls can be configured to flex laterally and permit the side portions of the cartridge body 1910 to expand laterally, thereby reducing the internal pressure, or stress, generated within the cartridge body 1910. In embodiments where the cartridge channel does not comprise lateral side walls, or comprises lateral sidewalls which are relatively shorter than the staple cartridge, the side portions of the staple cartridge may expand laterally uninhibited, or at least substantially uninhibited. In any event, referring now to FIG. 107, a staple cartridge channel 2030 can comprise lateral sidewalls 2040 and 2041 which can be entirely comprised of a flexible material, such as an elastomeric material, for example. The staple cartridge channel 2030 can further comprise lateral slots 2033 extending along the sides of the bottom support surface 2031 of the staple cartridge channel 2030 which can be configured to receive and secure at least a portion of the lateral sidewalls 2040 and 2041 therein. In certain embodiments, the lateral side walls 2040 and 2041 can be secured in the slots 2033 via a snap-fit and/or press-fit arrangement while, in at least some embodiments, the lateral side walls 2040 and 2041 can be secured in the slots 2033 by one or more adhesives. In at least one embodiment, the sidewalls 2040 and 2041 may be detachable from the bottom support surface 2031 during use. In any event, a compressible, implantable cartridge body 2010 can be detached and/or disengaged from the lateral side walls 2040 and 2041 when the cartridge body 2010 is implanted with the staples 2020.

In various embodiments, referring now to FIG. 108, a surgical instrument can comprise a shaft 2150 and an end effector extending from the distal end of the shaft 2150. The end effector can comprise, similar to the above, a staple cartridge channel 2130, an anvil 2140 movable between an open position and a closed position, and a staple cartridge 2100 positioned intermediate the staple cartridge channel 2130 and the anvil 2140. Also similar to the above, the staple cartridge 2100 can comprise a compressible, implantable cartridge body 2110 and a plurality of staples 2120 positioned in the cartridge body 2110. In various embodiments, the staple cartridge channel 2130 can comprise, one, a bottom support surface 2131 against which the staple cartridge 2100 can be positioned, two, a distal end 2135 and, three, a proximal end 2136. In at least one embodiment, as illustrated in FIG. 108, the staple cartridge 2100 can comprise a first end 2105 which can be positionable in the distal end 2135 of the staple cartridge channel 2130 and a second end 2106 which can be positionable in the proximal end 2136 of the staple cartridge channel 2130. In various embodiments, the distal end 2135 of the staple cartridge channel 2130 can comprise at least one distal retention feature, such as a retention wall 2137, for example, and, similarly, the proximal end 2136 can comprise at least one proximal retention feature, such as a retention wall 2138, for example. In at least one such embodiment, the distal retention wall 2137 and the proximal retention wall 2138 can define a gap therebetween which can be equal to or less than the length of the staple cartridge 2100 such that the staple cartridge 2100 can fit securely within the staple cartridge channel 2130 when the staple cartridge 2100 is inserted therein.

In various embodiments, referring again to FIGS. 88 and 89, a staple cartridge, such as staple cartridge 1200, for example, can comprise a flat, or at least substantially flat, tissue-contacting surface 1219. In at least one such embodiment, the staple cartridge body 1210 of staple cartridge 1200 can comprise a first end 1205 which can be defined by a first height, or thickness, 1207 and a second end 1206 which can be defined by a second height, or thickness, 1208, wherein the first height 1207 can be equal to, or at least substantially equal to, the second height 1208. In certain embodiments, the cartridge body 1210 can comprise a constant, or at least substantially constant, height, or thickness, between the first end 1205 and the second end 1206. In at least one such embodiment, the tissue-contacting surface 1219 can be parallel, or at least substantially parallel, to the bottom surface 1218 of the cartridge body 1210. In various embodiments, referring once again to FIG. 108, the first end 2105 of the cartridge body 2110 of staple cartridge 2100 can be defined by a first height 2107 which is different than a second height 2108 of the second end 2106. In the illustrated embodiment, the first height 2107 is larger than the second height 2108, although the second height 2108 could be larger than the first height 2107 in alternative embodiments. In various embodiments, the height of the cartridge body 2110 can decrease linearly and/or geometrically between the first end 2105 and the second end 2106. In at least one such embodiment, the tissue-contacting surface 2119, which extends between the first end 2105 and the second end 2106, can be oriented along an angle defined therebetween. In at least one such embodiment, the tissue-contacting surface 2119 may not be parallel to the bottom surface 2118 of the cartridge body 2110 and/or parallel to the support surface 2131 of the staple cartridge channel 2130.

In various embodiments, referring again to FIGS. 108 and 109, the anvil 2140 can comprise a tissue-contacting surface 2141 which can be parallel, or at least substantially parallel, to the support surface 2131 of the staple cartridge channel 2130 when the anvil 2140 is in a closed position, as illustrated in FIG. 109. When the anvil 2140 is in a closed position, the anvil 2140 can be configured to compress the first end 2105 of the staple cartridge 2100 more than the second end 2106 owing to the taller height of the first end 2105 and the shorter height of the second end 2106. In some circumstances, including circumstances where the tissue T positioned intermediate the tissue contacting surfaces 2119 and 2141 has a constant, or at least substantially constant, thickness, the pressure generated within the tissue T and the cartridge 2100 can be greater at the distal end of the end effector than the proximal end of the end effector. More particularly, when the tissue T between the anvil 2140 and the staple cartridge 2100 has a substantially constant thickness, the tissue T positioned intermediate the distal end 2145 of the anvil 2140 and the first end 2105 of the staple cartridge 2100 can be more compressed than the tissue T positioned intermediate the proximal end 2146 of the anvil 2140 and the second end 2106 of the staple cartridge 2100. In various embodiments, a pressure gradient can be generated within the tissue T between the proximal end and the distal end of the end effector. More particularly, in at least one embodiment, when the tissue T between the anvil 2140 and the staple cartridge 2100 has a substantially constant thickness and the height of the staple cartridge 2100 decreases linearly from the distal end to the proximal end of the end effector, the pressure within the tissue T can decrease linearly from the distal end of the end effector to the proximal end of the end effector. Similarly, in at least one embodiment, when the tissue T between the anvil 2140 and the staple cartridge 2100 has a substantially constant thickness and the height of the staple cartridge 2100 decreases geometrically from the distal end to the proximal end of the end effector, the pressure within the tissue T can decrease geometrically from the distal end of the end effector to the proximal end of the end effector.

In various embodiments, referring again to FIG. 108, the tissue T positioned intermediate the staple cartridge 2100 and the anvil 2140 may not have a constant thickness throughout. In at least one such circumstance, the tissue T positioned between the proximal end 2146 of the anvil 2140 and the second end 2106 of the staple cartridge 2100 may be thicker than the tissue T positioned between the distal end 2145 of the anvil 2140 and the first end 2105 of the staple cartridge 2100. In such circumstances, as a result, the thicker tissue T may be generally positioned above the shorter proximal end 2106 of the staple cartridge 2100 and the thinner tissue T may be generally positioned above the taller distal end 2105. In use, the firing collar 2152 of the shaft 2150 can be advanced distally along the shaft spine 2151 such that the firing collar 2152 engages the cam portion 2143 of the anvil 2140 and rotates the anvil 2140 toward the staple cartridge 2100 as illustrated in FIG. 109. Once the anvil 2140 has been rotated into a fully-closed position, the tissue T may be compressed between the tissue-contacting surfaces 2119 and 2141 and, even though the height of the staple cartridge 2100 may not be constant between the proximal and distal ends of the end effector, the pressure or compressive forces applied to the tissue T may be constant, or at least substantially constant, thereacross. More particularly, as the thinner tissue T may be associated with the taller height of the staple cartridge 2100 and the thicker tissue T may be associated with the shorter height of the staple cartridge 2100, the cumulative, or summed, height of the tissue T and the staple cartridge 2100 may be constant, or at least substantially constant, between the proximal and distal ends of the end effector and, as a result, the compression of this cumulative height by the anvil 2140 may be constant, or at least substantially constant, thereacross.

Figure 110:
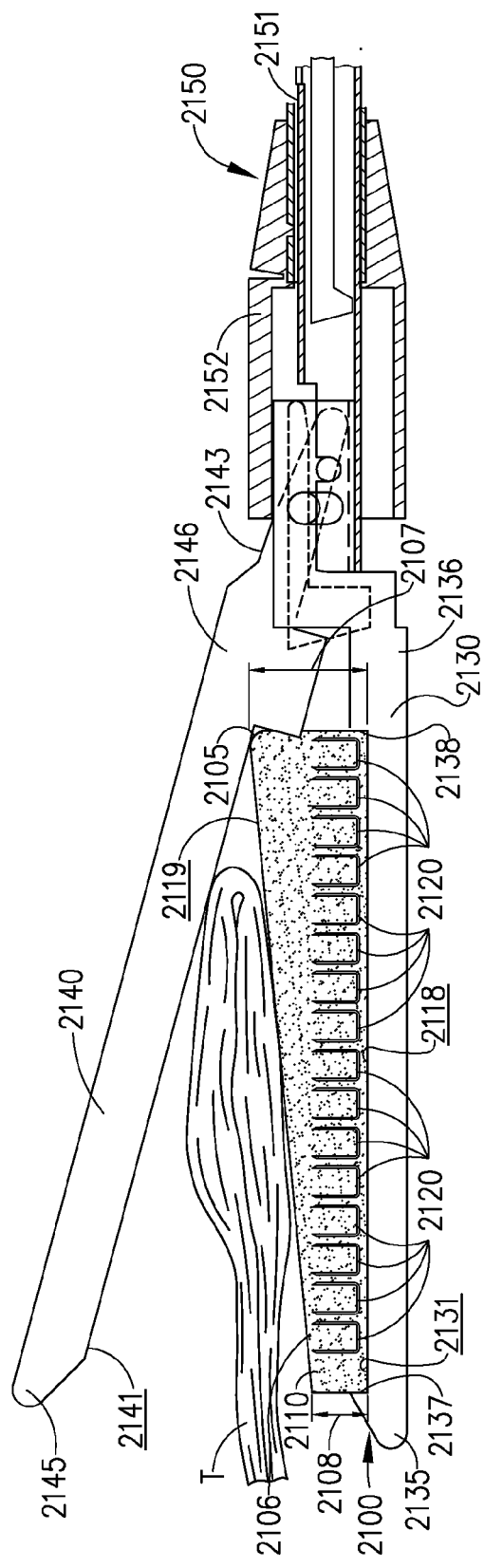

In various embodiments, referring again to FIGS. 108 and 109, the staple cartridge 2100 can comprise an asymmetrical configuration. In at least one such embodiment, for example, the height of the staple cartridge 2100 at the first end 2105 thereof may be higher than the height of the staple cartridge 2100 at the second end 2106 thereof. In certain embodiments, the staple cartridge 2100 and/or the staple cartridge channel 2130 can comprise one or more alignment and/or retention features which can be configured to assure that the staple cartridge 2100 can only be positioned within the staple cartridge channel 2130 in one orientation, i.e., an orientation in which the first end 2105 is positioned in the distal end 2135 of the staple cartridge channel 2130 and the second end 2106 is positioned in the proximal end 2136. In various alternative embodiments, the staple cartridge 2100 and/or the staple cartridge channel 2130 can comprise one or more alignment and/or retention features which can be configured to permit the staple cartridge 2100 to be positioned within the staple cartridge channel 2130 in more than one orientation. Referring now to FIG. 110, for example, the staple cartridge 2100 can be positioned within the staple cartridge channel 2130 such that the first end 2105 of the staple cartridge 2100 can be positioned in the proximal end 2136 of the staple cartridge channel 2130 and the second end 2106 can be positioned in the distal end 2135. In various embodiments, as a result, the shorter height of the staple cartridge 2100 can be positioned proximate the distal retention wall 2137 and the taller height of the staple cartridge 2100 can be positioned proximate to the proximal retention wall 2138. In at least one such embodiment, the staple cartridge 2100 can be suitably arranged to apply a constant, or at least substantially constant, clamping pressure to tissue T having a thicker portion within the distal end of the end effector and a thinner portion within the proximal end of the end effector. In various embodiments, the staple cartridge 2100, for example, can be selectively oriented within the staple cartridge channel 2130. In at least one such embodiment, the alignment and/or retention features of the staple cartridge 2100 can be symmetrical and a surgeon can selectively orient the staple cartridge 2100 within the staple cartridge channel 2130 in the orientations depicted in FIG. 108 and FIG. 110, for example.

Further to the above, the implantable cartridge body 2110 can comprise a longitudinal axis 2109 which, when the staple cartridge 2100 is positioned in the staple cartridge channel 2130, can extend between the proximal and distal ends of the end effector. In various embodiments, the thickness of the cartridge body 2110 can generally decrease and/or generally increase between the first end 2105 and the second end 2106 along the longitudinal axis 2109. In at least one such embodiment, the distance, or height, between the bottom surface 2118 and the tissue-contacting surface 2119 can generally decrease and/or generally increase between the first end 2105 and the second end 2106. In certain embodiments, the thickness of the cartridge body 2110 can both increase and decrease along the longitudinal axis 2109. In at least one such embodiment, the thickness of the cartridge body 2110 can comprise one or more portions which increase in thickness and one or more portions which can decrease in thickness. In various embodiments, referring again to FIG. Z, the staple cartridge 2100 can comprise a plurality of staples 2120 positioned therein. In use, as described above, the staples 2120 can be deformed when the anvil 2140 is moved into a closed position. In certain embodiments, each staple 2120 can have the same, or at least substantially the same, height. In at least one such embodiment, the height of a staple can be measured from the bottom of the base of the staple to the top, or tip, of the tallest leg of the staple, for example.

In various embodiments, the staples within a staple cartridge can have different staple heights. In at least one such embodiment, a staple cartridge can comprise a first group of staples having a first staple height which are positioned in a first portion of a compressible cartridge body and a second group of staples having a second staple height which are positioned in a second portion of the compressible cartridge body. In at least one embodiment, the first staple height can be taller than the second staple height and the first group of staples can be positioned in the first end 2105 of the staple cartridge 2100 while the second group of staples can be positioned in the second end 2106. Alternatively, the taller first group of staples can be positioned in the second end 2106 of the staple cartridge 2100 while the shorter second group of staples can be positioned in the first end 2105. In certain embodiments, a plurality of staple groups, each group having a different staple height, can be utilized. In at least one such embodiment, a third group having an intermediate staple height can be positioned in the cartridge body 2110 intermediate the first group of staples and the second group of staples. In various embodiments, each staple within a staple row in the staple cartridge can comprise a different staple height. In at least one embodiment, the tallest staple within a staple row can be positioned on a first end of a staple row and the shortest staple can be positioned on an opposite end of the staple row. In at least one such embodiment, the staples positioned intermediate the tallest staple and the shortest staple can be arranged such that the staple heights descend between the tallest staple and the shortest staple, for example.

In various embodiments, referring now to FIG. 111, an end effector of a surgical stapler can comprise an anvil 2240, a staple cartridge channel 2230, and a staple cartridge 2200 supported by the staple cartridge channel 2230. The staple cartridge 2200 can comprise a compressible, implantable cartridge body 2210 and a plurality of staples, such as staples 2220a and staples 2220b, for example, positioned therein. In various embodiments, the staple cartridge channel 2230 can comprise a cartridge support surface 2231 and a plurality of staple support slots, such as support slots 2232a and 2232b, for example, defined therein. In at least one such embodiment, the staple cartridge 2200 can comprise two outer rows of staples 2220a and two inner rows of staples 2220b, wherein the support slots 2232a can be configured to support the staples 2220a and the support slots 2232b can be configured to support the staples 2220b. Referring to FIGS. 111 and 112, the anvil 2240 can comprise a plurality of staple forming pockets 2242 defined therein which can be configured to receive and deform the staples 2220a and 2220b when the anvil 2240 is moved toward the staple cartridge 2200. In at least one such embodiment, the bottom surfaces of the support slots 2232a can be a first distance 2201a away from the top surfaces of the staple forming pockets 2242 while the bottom surfaces of the support slots 2232b can be a second distance 2201b away from the top surfaces of the staple forming pockets 2242. In at least one such embodiment, the support slots 2232b are positioned closer to the anvil 2240 owing to the raised step in the support surface 2231 in which they are defined. Owing to the different distances 2201a and 2201b, in various embodiments, the outer rows of staples 2220a and the inner rows of staples 2220b can be deformed to different formed heights. In various circumstances, staples deformed to different formed heights can apply different clamping pressures or forces to the tissue T being stapled. In addition to the above, the staples can begin with different unformed staple heights. In at least one such embodiment, referring again to FIG. 111, the outer staples 2220a can have an initial, unformed height which is greater than the initial, unformed height of the inner staples 2220b. As illustrated in FIGS. 111 and 112, the inner staples 2220b, which have a shorter unformed height than the outer staples 2220a, can also have a shorter formed height than the outer staples 2220b. In various alternative embodiments, the inner staples 2220b may have a taller unformed height than the outer staples 2220a yet have a shorter deformed staple height than the outer staples 2220a.

In various embodiments, further to the above, the anvil 2240 can be moved into a closed position, as illustrated in FIG. 112, in order to compress the cartridge body 2210 and deform the staples 2220a and 2220b. In certain embodiments, a surgical stapler comprising the end effector depicted in FIGS. 111 and 112, for example, can further comprise a cutting member which can be configured to transect the tissue T positioned intermediate the anvil 2240 and the staple cartridge 2200. In at least one such embodiment, the anvil 2240, the staple cartridge channel 2230 and/or the staple cartridge 2200 can define a slot configured to slidably receive a cutting member therein. More particularly, the anvil 2240 can comprise a slot portion 2249, the staple cartridge channel 2230 can comprise a slot portion 2239, and the staple cartridge 2200 can comprise a slot portion 2203 which can be aligned, or at least substantially aligned, with one another when the anvil 2240 is in a closed, or at least substantially closed, position. In various embodiments, the cutting member can be moved from the proximal end of the end effector toward the distal end of the end effector after the anvil 2240 has been closed and the staples 2220a, 2220b have been deformed. In at least one embodiment, the cutting member can be moved independently of the staple deformation process. In certain embodiments, the cutting member can be advanced at the same time that the staples are being deformed. In any event, in at least one embodiment, the cutting member can be configured to incise the tissue along a path positioned intermediate the inner rows of staples 2220b.

In various embodiments, as illustrated in FIG. 112, the inner staples 2220b can be formed to a shorter height than the outer staples 2220a wherein the inner staples 2220b can apply a larger clamping pressure or force to the tissue adjacent to the cut line created by the cutting member. In at least one such embodiment, the larger clamping pressure or force created by the inner staples 2220b can provide various therapeutic benefits such as reducing bleeding from the incised tissue T while the smaller clamping pressure created by the outer staples 2220a can provide flexibility within the stapled tissue. In various embodiments, referring again to FIGS. 111 and 112, the anvil 2240 can further comprise at least one piece of buttress material, such as buttress material 2260, for example, attached thereto. In at least one such embodiment, the legs of the staples 2220a, 2220b can be configured to incise the buttress material 2260 and/or pass through apertures in the buttress material 2260 when the staple cartridge 2200 is compressed by the anvil 2240 and thereafter contact the staple forming pockets 2242 in the anvil 2240. As the legs of the staples 2220a, 2220b are being deformed, the legs can contact and/or incise the buttress material 2260 once again. In various embodiments, the buttress material 2260 can improve the hemostasis of and/or provide strength to the tissue being stapled.

In various embodiments, referring again to FIGS. 111 and 112, the bottom surface of the cartridge body 2210 can comprise a stepped contour which matches, or at least substantially matches, the stepped contour of the cartridge support surface 2231. In certain embodiments, the bottom surface of the cartridge body 2210 can deform to match, or at least substantially match, the contour of the cartridge support surface 2231. In various embodiments, referring now to FIG. 113, an end effector, similar to the end effector depicted in FIG. 111, for example, can comprise a staple cartridge 2300 positioned therein. The staple cartridge 2300 can comprise a compressible, implantable body 2310 comprising an inner layer 2312 and an outer layer 2311 wherein, further to the above, the outer layer 2311 can be comprised of a water impermeable material in at least one embodiment. In various embodiments, the outer layer 2311 can extend around the staples 2220a, 2220b and can be positioned intermediate the staples 2220a, 2220b and the support slots 2232a, 2232b, respectively. In various embodiments, referring now to FIG. 114, an end effector, similar to the end effector depicted in FIG. 111, for example, can comprise a staple cartridge 2400 positioned therein. Similar to the staple cartridge 2300, the compressible, implantable cartridge body 2410 of staple cartridge 2400 can comprise an inner layer 2412 and an outer layer 2411; however; in at least one embodiment, the cartridge body 2410 may not comprise a cutting member slot therein. In at least one such embodiment, the cutting member may be required to incise the inner layer 2412 and/or the outer layer 2411, for example, as it is advanced through the staple cartridge.

In various embodiments, referring now to FIG. 115, an end effector of a surgical stapler can comprise an anvil 2540, a staple cartridge channel 2530, and a staple cartridge 2500 positioned in the staple cartridge channel 2530. Similar to the above, the staple cartridge 2500 can comprise a compressible, implantable cartridge body 2510, outer rows of staples 2220a, and inner rows of staples 2220b. The staple cartridge channel 2530 can comprise a flat, or an at least substantially flat, cartridge support surface 2531 and staple support slots 2532 defined therein. The anvil 2540 can comprise a stepped surface 2541 and a plurality of staple forming pockets, such as forming pockets 2542a and 2542b, for example, defined therein. Similar to the above, the forming pockets 2542a and the support slots 2532 can define a distance therebetween which is greater than the distance between the forming pockets 2452b and the support slots 2532. In various embodiments, the anvil 2540 can further comprise a piece of buttress material 2560 attached to the stepped surface 2541 of the anvil 2540. In at least one such embodiment, the buttress material 2560 can conform, or at least substantially conform, to the stepped surface 2541. In various embodiments, the buttress material 2560 can be removably attached to the surface 2541 by at least one adhesive, such as fibrin and/or protein hydrogel, for example. In certain embodiments, the cartridge body 2510 can also comprise a stepped profile which, in at least one embodiment, parallels, or at least substantially parallels, the stepped surface 2541 of the anvil 2540. More particularly, in at least one embodiment, the anvil 2540 can comprise steps 2548 extending toward the staple cartridge 2500 wherein the steps 2548 can comprise a step height which equals, or at least substantially equals, the step height of the steps 2508 extending from the cartridge body 2510. In at least one such embodiment, as a result of the above, the amount of the compressible cartridge body 2510 that can be captured in the first staples 2220a can be different than the amount of the compressible cartridge body 2510 that can be captured in the second staples 2220b, for example.

In various embodiments, referring now to FIG. 116, an end effector can comprise an anvil 2640, a staple cartridge channel 2530, and a staple cartridge 2600 positioned therebetween. The staple cartridge 2600 can comprise a compressible, implantable cartridge body 2610 including an inner layer 2612, an outer layer 2611, and a plurality of staples, such as staples 2220a and 2200b, for example, positioned therein. In various embodiments, the anvil 2640 can comprise a plurality of staple forming pockets 2642 in surface 2641 and the staple cartridge channel 2530 can comprise a plurality of staple forming slots 2532 defined in the support surface 2531. As illustrated in FIG. 116, the anvil surface 2641 can be parallel, or at least substantially parallel, to the cartridge support surface 2531 wherein each forming pocket 2642 can be positioned an equal, or at least substantially equal, distance away from an opposing and corresponding staple support slot 2532. In various embodiments, the staple cartridge 2600 can comprise staples having the same, or at least substantially the same, initial, unformed staple height and, in addition, the same, or at least substantially the same, formed staple height. In certain other embodiments, the outer rows of staples can comprise staples 2220a and the inner rows of staples can comprise staples 2220b wherein, as discussed above, the staples 2220a and 2220b can have different unformed staple heights. When the anvil 2640 is moved toward the staple cartridge 2600 into a closed position, the staples 2220a and 2220b can be formed such that they have the same, or at least substantially the same, formed staple height. In at least one such embodiment, as a result of the above, the formed outer staples 2220a and the inner staples 2220b may have the same, or at least substantially the same, amount of compressible cartridge body 2610 contained therein; however, as the outer staples 2220a have a taller unformed staple height than the inner staples 2220b and may have the same formed staple height nonetheless, a greater clamping pressure can be generated in the outer staples 2220a than the inner staples 2220b, for example.

In various embodiments, referring now to FIG. 117, an end effector of a surgical stapler can comprise an anvil 2740, a staple cartridge channel 2530, and a staple cartridge 2700 positioned within the staple cartridge channel 2530. Similar to the above, the staple cartridge 2700 can comprise a compressible, implantable cartridge body 2710 comprising an inner layer 2712, an outer layer 2711, and a plurality of staples, such as staples 2220a and 2220b, for example, positioned therein. In at least one embodiment, the thickness of the cartridge body 2710 can vary across its width. In at least one such embodiment, the cartridge body 2710 can comprise a center portion 2708 and side portions 2709, wherein the center portion 2708 can comprise a thickness which is greater than the thickness of the side portions 2709. In various embodiments, the thickest portion of the cartridge body 2710 can be located at the center portion 2708 while the thinnest portion of the cartridge body 2710 can be located at the side portions 2709. In at least one such embodiment, the thickness of the cartridge body 2710 can decrease gradually between the center portion 2708 and the side portions 2709. In certain embodiments, the thickness of the cartridge body 2710 can decrease linearly and/or geometrically between the center portion 2708 and the side portions 2709. In at least one such embodiment, the tissue-contacting surface 2719 of cartridge body 2710 can comprise two inclined, or angled, surfaces which slope downwardly from the center portion 2708 toward the side portions 2709. In various embodiments, the anvil 2740 can comprise two inclined, or angled, surfaces which parallel, or at least substantially parallel, the inclined tissue-contacting surfaces 2719. In at least one embodiment, the anvil 2740 can further comprise at least one piece of buttress material 2760 attached to the inclined surfaces of the anvil 2740.

In various embodiments, further to the above, the inner rows of staples in the staple cartridge 2700 can comprise the taller staples 2220a and the outer rows of staples can comprise the shorter staples 2220b. In at least one embodiment, the taller staples 2220a can be positioned within and/or adjacent to the thicker center portion 2708 while the staples 2220b can be positioned within and/or adjacent to the side portions 2709. In at least one such embodiment, as a result of the above, the taller staples 2220a can capture more material of the implantable cartridge body 2710 than the shorter staples 2220b. Such circumstances could result in the staples 2220a applying a greater clamping pressure to the tissue T than the staples 2220b. In certain embodiments, even though the taller staples 2220a may capture more material of the cartridge body 2710 therein than the shorter staples 2220b, the taller staples 2220a may have a taller formed staple height than the shorter staples 2220b owing to the inclined arrangement of the staple forming pockets 2742a and 2742b. Such considerations can be utilized to achieve a desired clamping pressure within the tissue captured by the staples 2220a and 2220b wherein, as a result, the clamping pressure in the staples 2220a can be greater than, less than, or equal to the clamping pressure applied to the tissue by the staples 2220b, for example. In various alternative embodiments to the end effector illustrated in FIG. 117, the shorter staples 2220b can be positioned within and/or adjacent to the thicker center portion 2708 of the cartridge body 2710 and the taller staples 2220a can be positioned within and/or adjacent to the thinner side portions 2709. Furthermore, although the staple cartridge 2700 is depicted as comprising inner and outer rows of staples, the staple cartridge 2700 may comprise additional rows of staples, such as staple rows positioned intermediate the inner and outer rows of staples, for example. In at least one such embodiment, the intermediate staple rows can comprise staples having an unformed staple height which is intermediate the unformed staple heights of the staples 2220a and 2220b and a formed staple height which is intermediate the formed staple heights of the staples 2220a and 2220b, for example.

In various embodiments, referring now to FIG. 118, an end effector of a surgical stapler can comprise an anvil 2840, a staple cartridge channel 2530, and a staple cartridge 2800 positioned within the staple cartridge channel 2530. Similar to the above, the staple cartridge 2800 can comprise a compressible, implantable cartridge body 2810 comprising an inner layer 2812, an outer layer 2811, and a plurality of staples, such as staples 2220a and 2220b, for example, positioned therein. In at least one embodiment, the thickness of the cartridge body 2810 can vary across its width. In at least one such embodiment, the cartridge body 2810 can comprise a center portion 2808 and side portions 2809, wherein the center portion 2808 can comprise a thickness which is less than the thickness of the side portions 2809. In various embodiments, the thinnest portion of the cartridge body 2810 can be located at the center portion 2808 while the thickest portion of the cartridge body 2810 can be located at the side portions 2809. In at least one such embodiment, the thickness of the cartridge body 2810 can increase gradually between the center portion 2808 and the side portions 2809. In certain embodiments, the thickness of the cartridge body 2810 can increase linearly and/or geometrically between the center portion 2808 and the side portions 2809. In at least one such embodiment, the tissue-contacting surface 2819 of cartridge body 2810 can comprise two inclined, or angled, surfaces which slope upwardly from the center portion 2808 toward the side portions 2809. In various embodiments, the anvil 2840 can comprise two inclined, or angled, surfaces which parallel, or at least substantially parallel, the inclined tissue-contacting surfaces 2819. In at least one embodiment, the anvil 2840 can further comprise at least one piece of buttress material 2860 attached to the inclined surfaces of the anvil 2840. In various embodiments, further to the above, the outer rows of staples in the staple cartridge 2800 can comprise the taller staples 2220a and the inner rows of staples can comprise the shorter staples 2220b. In at least one embodiment, the taller staples 2220a can be positioned within and/or adjacent to the thicker side portions 2809 while the staples 2220b can be positioned within and/or adjacent to the center portion 2808. In at least one such embodiment, as a result of the above, the taller staples 2220a can capture more material of the implantable cartridge body 2810 than the shorter staples 2220b.

As described above with regard to the embodiment of FIG. 111, for example, the staple cartridge channel 2230 can comprise a stepped support surface 2231 which can be configured to support the staples 2220a and 2220b at different heights with respect the anvil 2240. In various embodiments, the staple cartridge channel 2230 can be comprised of metal and the steps in the support surface 2231 may be formed in the support surface 2231 by a grinding operation, for example. In various embodiments, referring now to FIG. 119, an end effector of a surgical instrument can comprise a staple cartridge channel 2930 comprising a support insert 2935 positioned therein. More particularly, in at least one embodiment, the staple cartridge channel 2930 can be formed such that it has a flat, or at least substantially flat, support surface 2931, for example, which can be configured to support the insert 2935 which comprises the stepped surfaces for supporting the staples 2220a and 2220b of the staple cartridge 2200 at different heights. In at least one such embodiment, the insert 2935 can comprise a flat, or at least substantially flat, bottom surface which can be positioned against the support surface 2931. The insert 2935 can further comprise support slots, grooves, or troughs 2932a and 2932b which can be configured to support the staples 2220a and 2220b, respectively, at different heights. Similar to the above, the insert 2935 can comprise a knife slot 2939 defined therein which can be configured to permit a cutting member to pass therethrough. In various embodiments, the staple cartridge channel 2930 can be comprised of the same material as or a different material than the support insert 2935. In at least one embodiment, the staple cartridge channel 2930 and the support insert 2935 can both be comprised of metal, for example, while, in other embodiments, the staple cartridge channel 2930 can be comprised of metal, for example, and the support insert 2935 can be comprised of plastic, for example. In various embodiments, the support insert 2935 can be fastened and/or welded into the staple cartridge channel 2930. In certain embodiments, the support insert 2935 can be snap-fit and/or press-fit into the staple cartridge channel 2930. In at least one embodiment the support insert 2935 can be secured in the staple cartridge channel 2930 using an adhesive.

In various embodiments, referring now to FIG. 120, an end effector of a surgical stapler can comprise an anvil 3040, a staple cartridge channel 3030, and a compressible, implantable staple cartridge 3000 positioned in the staple cartridge channel 3030. Similar to the above, the anvil 3040 can comprise a plurality of staple-forming pockets 3042 defined therein and a knife slot 3049 which can be configured to slidably receive a cutting member therein. Also similar to the above, the staple cartridge channel 3030 can comprise a plurality of staple support slots 3032 defined therein and a knife slot 3039 which can also be configured to slidably receive a cutting member therein. In various embodiments, the staple cartridge 3000 can comprise a first layer 3011, a second layer 3012, and a plurality of staples, such as staples 3020a and 3020b, for example, positioned therein. In at least one embodiment, the staples 3020a can comprise an unformed staple height which is taller than the unformed staple height of the staples 3020b. In various embodiments, the first layer 3011 can be comprised of a first compressible material and the second layer 3012 can be comprised of a second compressible material. In certain embodiments, the first compressible material can be compressed at a rate which is higher than the second compressible material while, in certain other embodiments, the first compressible material can be compressed at a rate which is lower than the second compressible material. In at least one embodiment, the first compressible material can be comprised of a resilient material which can comprise a first spring rate and the second compressible material can be comprised of a resilient material which can comprise a second spring rate which is different than the first spring rate. In various embodiments, the first compressible material can comprise a spring rate which is greater than the spring rate of the second compressible material. In certain other embodiments, the first compressible material can comprise a spring rate which is less than the spring rate of the second compressible material. In various embodiments, the first compressible layer can comprise a first stiffness and the second compressible layer can comprise a second stiffness, wherein the first stiffness is different than the second stiffness. In various embodiments, the first compressible layer can comprise a stiffness which is greater than the stiffness of the second compressible layer. In certain other embodiments, the first compressible layer can comprise a stiffness which is less than the stiffness of the second compressible layer.

In various embodiments, referring again to FIG. 120, the second layer 3012 of the staple cartridge 3000 can comprise a constant, or at least substantially constant, thickness across the width thereof. In at least one embodiment, the first layer 3011 can comprise a thickness which varies across the width thereof. In at least one such embodiment, the first layer 3011 can comprise one or more steps 3008 which can increase the thickness of the cartridge body 3010 in certain portions of the cartridge body 3010, such as the center portion, for example. Referring again to FIG. 120, the shorter staples 3020b can be positioned in or aligned with the steps 3008, i.e., the thicker portions of the cartridge body 3010, and the taller staples 3020a can be positioned in or aligned with the thinner portions of the cartridge body 3010. In various embodiments, as a result of the thicker and thinner portions of the cartridge body 3010, the stiffness of the cartridge body 3010 can be greater along the inner rows of staples 3020b than the outer rows of staples 3020a. In various embodiments, the first layer 3011 can be connected to the second layer 3012. In at least one such embodiment, the first layer 3011 and the second layer 3012 can comprise interlocking features which can retain the layers 3011 and 3012 together. In certain embodiments, the first layer 3011 can comprise a first laminate and the second layer 3012 can comprise a second laminate, wherein the first laminate can be adhered to the second laminate by one or more adhesives. In various embodiments, the staple cartridge 3000 can comprise a knife slot 3003 which can be configured to slidably receive a cutting member therein.

In various embodiments, referring now to FIG. 121, a staple cartridge 3100 can comprise a compressible, implantable cartridge body 3110 comprising a single layer of compressible material and, in addition, a plurality of staples, such as staples 3020b, for example, positioned therein. In at least one embodiment, the thickness of the cartridge body 3110 can vary across the width thereof. In at least one such embodiment, the cartridge body 3110 can comprise steps 3108 extending along the side portions thereof. In various embodiments, referring now to FIG. 122, a staple cartridge 3200 can comprise a compressible, implantable cartridge body 3210 comprising a single layer of compressible material and, in addition, a plurality of staples, such as staples 3020b, for example, positioned therein. In at least one embodiment, the thickness of the cartridge body 3210 can vary across the width thereof. In at least one such embodiment, the cartridge body 3210 can comprise steps 3208 extending along the center portion thereof. In various embodiments, referring now to FIG. 123, a staple cartridge 3300 can comprise a compressible, implantable cartridge body 3310 wherein, similar to the above, the thickness of the cartridge body 3310 can vary across the width thereof. In at least one embodiment, the thickness of the cartridge body 3310 can increase geometrically between the side portions and the center portion of the cartridge body 3310. In at least one such embodiment, the thickness of the cartridge body 3310 can be defined by an arcuate or curved profile and can comprise an arcuate or curved tissue-contacting surface 3319. In certain embodiments, the thickness of the cartridge body 3310, and the contour of the tissue-contacting surface 3319, can be defined by one radius of curvature or, alternatively, by several radiuses of curvature, for example. In various embodiments, referring now to FIG. 124, a staple cartridge 3400 can comprise a compressible, implantable cartridge body 3410 wherein the thickness of the cartridge body 3410 can increase linearly, or at least substantially linearly, between the side portions and the center portion of the cartridge body 3410.

In various embodiments, referring now to FIG. 125, a staple cartridge 3500 can comprise a compressible, implantable cartridge body 3510 and a plurality of staples 3520 positioned therein. The implantable cartridge body 3510 can comprise a first inner layer 3512, a second inner layer 3513, and an outer layer 3511. In at least one embodiment, the first inner layer 3512 can comprise a first thickness and the second inner layer 3513 can comprise a second thickness wherein the second inner layer 3513 can be thicker than the first inner layer 3512. In at least one alternative embodiment, the first inner layer 3512 can be thicker than the second inner layer 3513. In another alternative embodiment, the first inner layer 3512 can have the same, or at least substantially the same, thickness as the second inner layer 3513. In certain embodiments, each staple 3520 can comprise a base 3522 and one or more deformable legs 3521 extending from the base 3522. In various embodiments, each leg 3521 can comprise a tip 3523 which is embedded in the first inner layer 3511 and, in addition, each base 3522 of the staples 3520 can be embedded in the second inner layer 3512. In at least one embodiment, the first inner layer 3512 and/or the second inner layer 3513 can comprise at least one medicament stored therein and, in various embodiments, the outer layer 3511 can encapsulate and seal the first inner layer 3512 and the second inner layer 3513 such that the medicament does not flow out of the staple cartridge body 3510 until after the outer layer 3511 has been punctured by the staples 3520. More particularly, further to the above, an anvil can be pushed downwardly against tissue positioned against the tissue-contacting surface 3519 of staple cartridge 3500 such that the cartridge body 3510 is compressed and the surface 3519 is moved downwardly toward, and at least partially below, the staple tips 3523 such that the tips 3523 rupture or puncture the outer layer 3511. After the outer layer 3511 has been breached by the staple legs 3521, the at least one medicament M can flow out of the cartridge body 3510 around the staple legs 3521. In various circumstances, additional compression of the cartridge body 3510 can squeeze additional medicament M out of the cartridge body 3510 as illustrated in FIG. 126.

In various embodiments, referring again to FIG. 125, the outer layer 3511 can comprise a water impermeable, or at least substantially impermeable, wrap which can configured to, one, keep the medicament from prematurely flowing out of the staple cartridge 3500 and, two, prevent fluids within a surgical site, for example, from prematurely entering into the staple cartridge 3500. In certain embodiments, the first inner layer 3512 can comprise a first medicament stored, or absorbed, therein and the second inner layer 3513 can comprise a second medicament stored, or absorbed, therein, wherein the second medicament can be different than the first medicament. In at least one embodiment, an initial compression of the cartridge body 3510, which causes the rupture of the outer layer 3511, can generally express the first medicament out of the first inner layer 3512 and a subsequent compression of the cartridge body 3510 can generally express the second medicament out of the second inner layer 3513. In such embodiments, however, portions of the first medicament and the second medicament may be expressed simultaneously although a majority of the medicament that is initially expressed can be comprised of the first medicament and a majority of the medicament subsequently expressed thereafter can be comprised of the second medicament. In certain embodiments, further to the above, the first inner layer 3512 can be comprised of a more compressible material than the second inner layer 3513 such that the initial compression forces or pressure, which can be lower than the subsequent compression forces or pressure, can cause a larger initial deflection within the first inner layer 3512 than the second inner layer 3513. This larger initial deflection within the first inner layer 3512 can cause a larger portion of the first medicament to be expressed from the first inner layer 3512 than the second medicament from the second inner layer 3513. In at least one embodiment, the first inner layer 3512 can be more porous and/or more flexible than the second inner layer 3513. In at least one such embodiment, the first inner layer 3512 can comprise a plurality of pores, or voids, 3508 defined therein and the second inner layer 3513 can comprise a plurality of pores, or voids, 3509 defined therein wherein, in various embodiments, the pores 3508 can be configured to store the first medicament in the first inner layer 3512 and the pores 3509 can be configured to store the second medicament in the second inner layer 3513. In certain embodiments, the size and density of the pores 3508 within the first inner layer 3512 and the pores 3509 within the second inner layer 3513 can be selected so as to provide a desired result described herein.

In various embodiments, referring again to FIGS. 125 and 126, the outer layer 3511, the first inner layer 3512, and/or the second inner layer 3513 can be comprised of a bioabsorbable material. In at least one embodiment, the first inner layer 3512 can be comprised of a first bioabsorbable material, the second inner layer 3513 can be comprised of a second bioabsorbable material, and the outer layer 3511 can be comprised of a third bioabsorbable material, wherein the first bioabsorbable material, the second bioabsorbable material, and/or the third bioabsorbable material can be comprised of different materials. In certain embodiments, the first bioabsorbable material can be bioabsorbed at a first rate, the second bioabsorbable material can be bioabsorbed at a second rate, and the third bioabsorbable material can be bioabsorbed at a third rate, wherein the first rate, the second rate, and/or the third rate can be different. In at least one such embodiment, when a material is bioabsorbed at a particular rate, such a rate can be defined as the amount of material mass that is absorbed by a patient's body over a unit of time. As it is known, the bodies of different patients may absorb different materials at different rates and, thus, such rates may be expressed as average rates in order to account for such variability. In any event, a faster rate may be a rate in which more mass is bioabsorbed for a unit of time than a slower rate. In various embodiments, referring again to FIGS. 125 and 126, the first inner layer 3512 and/or the second inner layer 3513 can be comprised of a material which bioabsorbs faster than the material comprising the outer layer 3511. In at least one such embodiment, the first inner layer 3512 and/or the second inner layer 3513 can be comprised of a bioabsorbable foam, tissue sealant, and/or hemostatic material, such as oxidized regenerated cellulose (ORC), for example, and the outer layer 3511 can be comprised of a buttress material and/or plastic material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In such embodiments, the first inner layer 3512 and/or the second inner layer 3513 can immediately treat the tissue and can reduce bleeding from the tissue, for example, wherein the outer layer 3514 can provide longer-term structural support and can be bioabsorbed at a slower rate.

Owing to the slower rate of bioabsorbability of the outer layer 3511, further to the above, the outer layer 3511 can buttress or structurally reinforce the tissue within the staple line as it heals. In certain embodiments, one of the first inner layer 3512 and the second inner layer 3513 can be comprised of a material which can be bioabsorbed faster than the other such that, in at least one embodiment, one of the layers can provide an initial release of a therapeutic material and the other layer can provide a sustained release of the same therapeutic material and/or a different therapeutic material. In at least one such embodiment, the rate in which a therapeutic material can be released from a layer 3512, 3513 can be a function of the bioabsorbability of the substrate layer in which the medicament is absorbed or dispersed. For example, in at least one embodiment, the substrate comprising the first inner layer 3512 can be bioabsorbed faster than the substrate comprising the second inner layer 3513 and, as a result, a medicament can be release from the first inner layer 3512 faster than the second inner layer 3513, for example. In various embodiments, as described herein, one or more of the layers 3511, 3512, and 3513 of the cartridge body 3510 can be adhered to one another by at least one adhesive, such as fibrin and/or protein hydrogel, for example. In certain embodiments, the adhesive can be water soluble and can be configured to release the connection between the layers as the staple cartridge 3500 is being implanted and/or some time thereafter. In at least one such embodiment, the adhesive can be configured to bioabsorb faster than the outer layer 3511, the first inner layer 3512, and/or the second inner layer 3513.

In various embodiments, referring now to FIGS. 127 and 128, a staple cartridge, such as staple cartridge 3600, for example, can comprise a cartridge body 3610 including a compressible first layer 3611, a second layer 3612 attached to the first layer 3611, and a removable compressible layer 3613 attached to the second layer 3612. In at least one such embodiment, the first layer 3611 can be comprised of a compressible foam material, the second layer 3612 can comprise a laminate material adhered to the first layer 3611 utilizing one or more adhesives, and the third layer 3613 can comprise a compressible foam material removably adhered to the second layer 3612 utilizing one or more adhesives, for example. In various embodiments, the staple cartridge 3600 can further comprise a plurality of staples, such as staples 3620, for example, positioned in the cartridge body 3610. In at least one such embodiment, each staple 3620 can comprise a base 3622 positioned in the third layer 3613 and one or more deformable legs 3621 extending upwardly from the base 3622 through the second layer 3612 and into the first layer 3611, for example. In use, further to the above, the top surface 3619 of the staple cartridge body 3610 can be pushed downwardly by an anvil until the staple legs 3621 penetrate through the top surface 3619 and the targeted tissue and contact the anvil. After the staple legs 3621 have been sufficiently deformed, the anvil can be moved away from the staple cartridge 3600 such that the compressible layers thereof can at least partially re-expand. In various circumstances, the insertion of the staples through the tissue can cause the tissue to bleed. In at least one embodiment, the third layer 3613 can be comprised of an absorbent material, such as protein hydrogel, for example, which can draw blood away from the stapled tissue. In addition to or in lieu of the above, the third layer 3613 can be comprised of a hemostatic material and/or tissue sealant, such as freeze-dried thrombin and/or fibrin, for example, which can be configured to reduce the bleeding from the tissue. In certain embodiments, the third layer 3613 may provide a structural support to the first layer 3611 and the second layer 3612 wherein the third layer 3613 may be comprised of a bioabsorbable material and/or a non-bioabsorbable material. In any event, in various embodiments, the third layer 3613 can be detached from the second layer 3612 after the staple cartridge 3610 has been implanted. In embodiments where the third layer 3613 comprises an implantable-quality material, the surgeon can elect whether to remove the third layer 3613 of the cartridge body 3610. In at least one embodiment, the third layer 3613 can be configured to be removed from the second layer 3612 in one piece.

In various embodiments, the first layer 3611 can be comprised of a first foam material and the third layer 3613 can be comprised of a second foam material which can be different than the first foam material. In at least one embodiment, the first foam material can have a first density and the second foam material can have a second density wherein the first density can be different than the second density. In at least one such embodiment, the second density can be higher than the first density wherein, as a result, the third layer 3613 may be less compressible, or have a lower compression rate, than the first layer 3611. In at least one alternative embodiment, the first density can be higher than the second density wherein, as a result, the first layer 3611 may be less compressible, or have a lower compression rate, than the third layer 3613. In various embodiments, referring now to FIGS. 129 and 130, a staple cartridge 3700, similar to the staple cartridge 3600, can comprise a cartridge body 3710 comprising a first compressible foam layer 3711, a second layer 3712 attached to the first layer 3711, and a detachable third compressible foam layer 3713 removably attached to the second layer 3712. In at least one such embodiment, the third layer 3713 can comprise a plurality of staple receiving slots, or cut-outs, 3709 which can each be configured to receive at least a portion of a staple 3620, such as a staple base 3622, for example, therein. In certain embodiments, the staples 3620 can be configured to slide within the staple receiving slots 3709 or, stated another way, the third layer 3713 can be configured to slide relative to the staples 3620 when the staple cartridge 3700 is positioned against the targeted tissue and compressed by an anvil, for example. In at least one embodiment, the receiving slots 3709 can be configured such that there is clearance between the staples 3620 and the side walls of the receiving slots 3709. In at least one such embodiment, as a result of the above, the staples 3620 may not capture a portion of the third layer 3713 therein when the staples 3620 are deformed, as illustrated in FIGS. 129 and 130. In certain other embodiments, the ends of the staple receiving slots 3709 adjacent to the second layer 3712 can be closed by a portion of the third layer 3713 and, as a result, at least a portion of the third layer 3713 can be captured within the staples 3620 when they are deformed. In any event, the third layer 3713 can comprise one or more perforations and/or score marks 3708, for example, which can be configured to permit the third layer 3713 to be removed from the second layer 3712 in two or more pieces as illustrated in FIG. 129. In FIG. 129, one of the pieces of the third layer 3713 is illustrated as being removed by a tool 3755. In various embodiments, the perforations 3708 can be arranged along a line positioned intermediate a first row of staples and a second row of staples.

In various embodiments, referring again to FIGS. 129 and 130, the bases 3622 of the staples 3620 can be positioned within the receiving slots 3709 wherein, in at least one embodiment, the side walls of the receiving slots 3709 can be configured to contact and releasable retain the staple legs 3621 in position. In certain embodiments, although not illustrated, the third layer 3713 can comprise an elongated slot surrounding all of the staples within a staple line. In at least one such embodiment, a staple cartridge comprising four staple rows, for example, can comprise an elongate slot aligned with each staple row in the bottom layer of the staple cartridge. Further to the above, at least a portion of the staple cartridge 3600 and/or the staple cartridge 3700 can be implanted within a patient and at least a portion of the staple cartridge can be removable from the patient. In at least one embodiment, referring again to FIGS. 129 and 130, the first layer 3711 and the second layer 3712 can be captured within the staples 3620 and can be implanted with the staples 3620, whereas the third layer 3713 can be optionally removed or detached from the staple cartridge 3700. In various circumstances, the removal of a portion of the implanted staple cartridge can reduce the amount of material that the patient's body has to reabsorb which can provide various therapeutic benefits. In the event that a portion of a staple cartridge is detached and removed, such as by a laparoscopic tool 3755, for example, the detached staple cartridge portion can be removed from the surgical site through a trocar, such as a trocar having a 5 mm aperture, for example. In certain embodiments, a cartridge body can comprise more than one layer that can be removed. For example, the cartridge body 3710 can comprise a fourth layer wherein the third layer of 3713 of the cartridge body 3710 can be comprised of a hemostatic material and the fourth layer can be comprised of a support layer. In at least one such embodiment, a surgeon can remove the support layer and then elect whether to remove the hemostatic layer, for example.

In various embodiments, referring now to FIG. 131, a staple cartridge, such as staple cartridge 3800, for example, can comprise a cartridge body 3810 including an outer layer 3811 and an inner layer 3812. The inner layer 3812 can be comprised of a compressible foam material and the outer layer 3811 can be at leas partially wrapped around the inner layer 3812. In at least one embodiment, the outer layer 3811 can comprise a first portion 3811a configured to be positioned on a first side of the inner layer 3812 and a second portion 3811b configured to be positioned on a second side of the inner layer 3812 wherein the first portion 3811a and the second portion 3811b can be connected by a flexible hinge, such as hinge 3809, for example. In at least one such embodiment, at least one adhesive, such as fibrin and/or protein hydrogel, for example, can be applied to the first side and/or the second side of the inner layer 3812 in order to secure the portions of the outer layer 3811 thereto. In various embodiments, the outer layer 3811 can comprise one or more fastening members extending therefrom. In at least one such embodiment, the outer layer 3811 can comprise a plurality of deformable legs 3821 extending from one side of the outer layer 3811 which can be seated in the compressible inner layer 3812. In at least one such embodiment, the legs 3821 may not protrude from the second side of the inner layer 3812 while, in at least one alternative embodiment, the legs 3821 may at least partially protrude from the inner layer 3812. When the compressible cartridge body 3810 is compressed, in use, the legs 3821 can be configured to pierce the inner layer 3812 and the second portion 3811b of the outer layer 3811. In certain embodiments, the second portion 3811b of the outer layer 3811 can comprise apertures, such as apertures 3808, for example defined therein which can be configured to receive the staple legs 3821. In certain embodiments, at least portions of the staple cartridge 3800 can comprise a knife slot 3803 which can be configured to slidably receive a cutting member therein. In at least one such embodiment, the knife slot 3803 may not extend entirely through the thickness of the cartridge body 3810 and, as a result, the cutting member may incise the cartridge body 3810 as it is moved relative thereto.

In various embodiments, referring now to FIG. 132, a staple cartridge 3900 can comprise, similar to staple cartridge 3800, a cartridge body 3910 including an inner layer 3812 and an outer layer 3811, wherein the outer layer 3811 can comprise a first portion 3811a positioned adjacent to the first side of the inner layer 3812 and a second portion 3811b positioned adjacent to the second side of the inner layer 3812. In at least one embodiment, similar to the above, the outer layer 3811 can comprise one or more fastening members extending therefrom. In at least one such embodiment, the outer layer 3811 can comprise a plurality of deformable legs 3921 extending from one side of the outer layer 3811 which can be seated in the compressible inner layer 3812. In certain embodiments, each deformable leg 3921 can comprise at least one hook or barb 3923 protruding therefrom which can be configured to engage the second portion 3811b of the outer layer 3811 and, as a result, retain the outer layer 3811 to the inner layer 3812. In at least one such embodiment, the barbs 3923 can be configured to protrude from the second side of the inner layer 3812 and extend through the apertures 3808 in the second portion 3811b of the outer layer 3811 such that the barbs 3923 can engage the outside surface of the outer layer 3811 and lock the outer layer 3811 to the inner layer 3812. In order to construct the staple cartridge 3900, the inner layer 3812 may be at least partially compressed in order to cause the barbs to protrude therefrom and enter into the apertures 3808. In at least one such embodiment, the staple cartridge 3900 can be at least partially pre-compressed when it is inserted into a staple cartridge, for example. In certain embodiments, further to the above, at least a portion of the legs 3921 can be embedded within the first portion 3811a of the outer layer 3811 wherein, in at least one embodiment, the outer layer 3811 can be comprised of a plastic material, such as polydioxanone (PDS) and/or polyglycolic acid (PGA), for example, and the plastic material can be overmolded around at least a portion of the legs 3921.

In various embodiments, referring now to FIGS. 133-137, a staple cartridge, such as staple cartridge 4000, for example, can comprise a cartridge body 4010 including a compressible first layer 4011 and a second layer 4012 and, in addition, a plurality of staples 4020 positioned within the cartridge body 4010. In certain embodiments, referring to FIG. 135, each staple 4020 can comprise a base 4022 and at least one deformable leg 4023 extending from the base 4022. In at least one embodiment, referring to FIG. 133, the staple cartridge 4000 can be positioned between a staple cartridge channel 4030 and an anvil 4040 of an end effector of a surgical stapler wherein the second layer 4012 of the cartridge body 4010 and/or the bases 4022 of the staples 4020 can be positioned against the staple cartridge channel 4030. In various embodiments, referring now to FIG. 134, the second layer 4012 can comprise a layer of pledgets 4060 interconnected to one another by a pledget support frame 4061. In at least one such embodiment, the pledgets 4060 and the pledget support frame 4061 can be comprised of a molded plastic material, such as polyglycolic acid (PGA), for example. Each pledget 4060 can comprise one or more apertures or slots 4062 which can be configured to receive a staple leg 4021 extending therethrough as illustrated in FIGS. 135 and 136. Each pledget 4060 can further comprise a receiving slot 4063 defined therein which can be configured to receive a base 4022 of a staple 4020. In various embodiments, referring again to FIG. 134, the pledgets 4060 and/or pledget support frame 4061 can comprise a plurality of score marks, perforations, or the like which can be configured to allow the pledgets 4060 to become detached from the pledget support frame 4061 at a desired location. Similarly, referring to FIG. 136, one or more pledgets 4060 can be connected to one another along a line comprising perforations and/or score marks 4064, for example. In use, the compressible foam layer 4011 can be positioned against the targeted tissue T and the cartridge body 4010 can be compressed by the anvil 4040 such that the anvil 4040 can deform the staples 4020. When the staples 4020 are deformed, the staple legs 4021 of each staple 4020 can capture the tissue T, a portion of the first layer 4011, and a pledget 4060 within the deformed staple. When the staple cartridge channel 4030 is moved away from the implanted staple cartridge 4060, for example, the pledget support frame 4061 can be detached from the pledgets 4060 and/or the pledgets 4060 can be detached from one another. In certain circumstances, the pledgets 4060 can be detached from the frame 4061 and/or each other when the staples 4020 are being deformed by the anvil 4040 as described above.

In various embodiments described herein, the staples of a staple cartridge can be fully formed by an anvil when the anvil is moved into a closed position. In various other embodiments, referring now to FIGS. 138-141, the staples of a staple cartridge, such as staple cartridge 4100, for example, can be deformed by an anvil when the anvil is moved into a closed position and, in addition, by a staple driver system which moves the staples toward the closed anvil. The staple cartridge 4100 can comprise a compressible cartridge body 4110 which can be comprised of a foam material, for example, and a plurality of staples 4120 at least partially positioned within the compressible cartridge body 4110. In various embodiments, the staple driver system can comprise a driver holder 4160, a plurality of staple drivers 4162 positioned within the driver holder 4160, and a staple cartridge pan 4180 which can be configured to retain the staple drivers 4162 in the driver holder 4160. In at least one such embodiment, the staple drivers 4162 can be positioned within one or more slots 4163 in the driver holder 4160 wherein the sidewalls of the slots 4163 can assist in guiding the staple drivers 4162 upwardly toward the anvil. In various embodiments, the staples 4120 can be supported within the slots 4163 by the staple drivers 4162 wherein, in at least one embodiment, the staples 4120 can be entirely positioned in the slots 4163 when the staples 4120 and the staple drivers 4162 are in their unfired positions. In certain other embodiments, at least a portion of the staples 4120 can extend upwardly through the open ends 4161 of slots 4163 when the staples 4120 and staple drivers 4162 are in their unfired positions. In at least one such embodiment, referring primarily now to FIG. 139, the bases of the staples 4120 can be positioned within the driver holder 4160 and the tips of the staples 4120 can be embedded within the compressible cartridge body 4110. In certain embodiments, approximately one-third of the height of the staples 4120 can be positioned within the driver holder 4160 and approximately two-thirds of the height of the staples 4120 can be positioned within the cartridge body 4110. In at least one embodiment, referring to FIG. 138A, the staple cartridge 4100 can further comprise a water impermeable wrap or membrane 4111 surrounding the cartridge body 4110 and the driver holder 4160, for example.

In use, the staple cartridge 4100 can be positioned within a staple cartridge channel, for example, and the anvil can be moved toward the staple cartridge 4100 into a closed position. In various embodiments, the anvil can contact and compress the compressible cartridge body 4110 when the anvil is moved into its closed position. In certain embodiments, the anvil may not contact the staples 4120 when the anvil is in its closed position. In certain other embodiments, the anvil may contact the legs of the staples 4120 and at least partially deform the staples 4120 when the anvil is moved into its closed position. In either event, the staple cartridge 4100 can further comprise one or more sleds 4170 which can be advanced longitudinally within the staple cartridge 4100 such that the sleds 4170 can sequentially engage the staple drivers 4162 and move the staple drivers 4162 and the staples 4120 toward the anvil. In various embodiments, the sleds 4170 can slide between the staple cartridge pan 4180 and the staple drivers 4162. In embodiments where the closure of the anvil has started the forming process of the staples 4120, the upward movement of the staples 4120 toward the anvil can complete the forming process and deform the staples 4120 to their fully formed, or at least desired, height. In embodiments where the closure of the anvil has not deformed the staples 4120, the upward movement of the staples 4120 toward the anvil can initiate and complete the forming process and deform the staples 4120 to their fully formed, or at least desired, height. In various embodiments, the sleds 4170 can be advanced from a proximal end of the staple cartridge 4100 to a distal end of the staple cartridge 4100 such that the staples 4120 positioned in the proximal end of the staple cartridge 4100 are fully formed before the staples 4120 positioned in the distal end of the staple cartridge 4100 are fully formed. In at least one embodiment, referring to FIG. 140, the sleds 4170 can each comprise at least one angled or inclined surface 4711 which can be configured to slide underneath the staple drivers 4162 and lift the staple drivers 4162 as illustrated in FIG. 141.

In various embodiments, further to the above, the staples 4120 can be formed in order to capture at least a portion of the tissue T and at least a portion of the compressible cartridge body 4110 of the staple cartridge 4100 therein. After the staples 4120 have been formed, the anvil and the staple cartridge channel 4130 of the surgical stapler can be moved away from the implanted staple cartridge 4100. In various circumstances, the cartridge pan 4180 can be fixedly engaged with the staple cartridge channel 4130 wherein, as a result, the cartridge pan 4180 can become detached from the compressible cartridge body 4110 as the staple cartridge channel 4130 is pulled away from the implanted cartridge body 4110. In various embodiments, referring again to FIG. 138, the cartridge pan 4180 can comprise opposing side walls 4181 between which the cartridge body 4110 can be removably positioned. In at least one such embodiment, the compressible cartridge body 4110 can be compressed between the side walls 4181 such that the cartridge body 4110 can be removably retained therebetween during use and releasably disengaged from the cartridge pan 4180 as the cartridge pan 4180 is pulled away. In at least one such embodiment, the driver holder 4160 can be connected to the cartridge pan 4180 such that the driver holder 4160, the drivers 4162, and/or the sleds 4170 can remain in the cartridge pan 4180 when the cartridge pan 4180 is removed from the surgical site. In certain other embodiments, the drivers 4162 can be ejected from the driver holder 4160 and left within the surgical site. In at least one such embodiment, the drivers 4162 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the drivers 4162 can be attached to the staples 4120 such that the drivers 4162 are deployed with the staples 4120. In at least one such embodiment, each driver 4162 can comprise a trough configured to receive the bases of the staples 4120, for example, wherein, in at least one embodiment, the troughs can be configured to receive the staple bases in a press-fit and/or snap-fit manner.

In certain embodiments, further to the above, the driver holder 4160 and/or the sleds 4170 can be ejected from the cartridge pan 4180. In at least one such embodiment, the sleds 4170 can slide between the cartridge pan 4180 and the driver holder 4160 such that, as the sleds 4170 are advanced in order to drive the staple drivers 4162 and staples 4120 upwardly, the sleds 4170 can move the driver holder 4160 upwardly out of the cartridge pan 4180 as well. In at least one such embodiment, the driver holder 4160 and/or the sleds 4170 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the sleds 4170 can be integrally formed and/or attached to a drive bar, or cutting member, which pushes the sleds 4170 through the staple cartridge 4100. In such embodiments, the sleds 4170 may not be ejected from the cartridge pan 4180 and may remain with the surgical stapler while, in other embodiments in which the sleds 4170 are not attached to the drive bar, the sleds 4170 may be left in the surgical site. In any event, further to the above, the compressibility of the cartridge body 4110 can allow thicker staple cartridges to be used within an end effector of a surgical stapler as the cartridge body 4110 can compress, or shrink, when the anvil of the stapler is closed. In certain embodiments, as a result of the staples being at least partially deformed upon the closure of the anvil, taller staples, such as staples having an approximately 0.18" staple height, for example, could be used, wherein approximately 0.12" of the staple height can be positioned within the compressible layer 4110 and wherein the compressible layer 4110 can have an uncompressed height of approximately 0.14", for example.

In various embodiments, referring now to FIGS. 142-145, a staple cartridge, such as staple cartridge 4200, for example, can comprise a compressible cartridge body 4210, a plurality of staples 4220 positioned therein, and a plurality of flexible lateral support members 4234. In various embodiments, referring now to FIG. 143, the staple cartridge 4200 can be positioned intermediate an anvil 4240 and a staple cartridge channel 4230 wherein, in at least one embodiment, the lateral support members 4234 can be attached to the staple cartridge channel 4230. When the anvil 4240 is moved downwardly to compress the cartridge body 4210 and at least partially deform the staples 4220, as illustrated in FIG. 144, the side portions of the cartridge body 4210 can bulge laterally and push the lateral support members 4234 outwardly. In at least one such embodiment, the lateral support members 4234 can be attached to the cartridge body 4210 and, when the cartridge body 4210 bulges laterally as described above, the lateral support members 4234 can detach from the cartridge body 4210 as illustrated in FIG. 144. In at least one embodiment, the lateral support members 4234 can be adhered to the cartridge body 4210 utilizing at least one adhesive, such as fibrin and/or protein hydrogel, for example. Similar to the above, the closing of the anvil 4240 may only partially deform the staples 4220, wherein the formation of the staples 4220 can be completed by the advancement of one or more sleds 4270 through the staple cartridge 4200 as illustrated in FIG. 145. In various embodiments, referring now to FIGS. 147 and 148, the sleds 4270 can be advanced from a proximal end of the staple cartridge 4200 to a distal end of the staple cartridge

4200 by a cutting member 4280. In at least one such embodiment, the cutting member 4280 can comprise a cutting element, or knife, 4283, which can be advanced through the tissue T and/or the compressible cartridge body 4210. In certain embodiments, the cutting member 4280 can comprise camming members 4282 which can travel along the outside surfaces of the jaws 4230 and 4240 and move or hold the jaws in position. In various embodiments, as a result of the above, the staples 4220 can be formed into their final shapes at the same time, or at least substantially the same time, as the tissue T is incised. In at least one such embodiment, the sleds 4270 can be positioned distally with respect to the knife 4283 such that the tissue T is only incised when the proceeding portion of the tissue has been fully stapled, for example.

In various embodiments, referring again to FIGS. 147 and 148, the sleds 4270 can comprise separate slidable members which are advanced together by the cutting member 4280. In at least one such embodiment, the sleds 4270 can be contained within the staple cartridge 4200 and the cutting member 4280 can be advanced into the staple cartridge 4200 by a firing bar 4281 such that the cutting member 4280 engages the sleds 4270 and advances the sleds 4270 distally. In certain embodiments, the sleds 4270 can be connected to one another. In either event, each sled 4270 can comprise an angled surface, or cam, 4271 which can be configured to lift the staples 4220 aligned within a staple row. In certain embodiments, the angled surfaces 4271 can be integrally formed with the cutting member 4280. In at least one embodiment, referring again to FIGS. 147 and 148, each staple 4200 can comprise a base, at least one deformable member extending from the base, and a crown 4229 overmolded onto and/or positioned around at least a portion of the base and/or the deformable members of the staple 4200. In various embodiments, such crowns 4229 can be configured to be driven directly by a sled 4270, for example. More particularly, in at least one embodiment, the crowns 4229 of staples 4220 can be configured such that the angled surfaces 4271 of the sleds 4270 can slide underneath and directly contact the crowns 4229 without a staple driver positioned therebetween. In such embodiments, each crown 4229 can comprise at least one co-operating angled or inclined surface which can be engaged by an angled surface 4271 of the sleds 4270 such that the co-operating angled surfaces can drive the staples 4220 upwardly when the sleds 4270 are slid underneath the staples 4220.

In various embodiments, referring now to FIG. 146, a staple cartridge, such as staple cartridge 4300, for example, can comprise a compressible body 4310 and a plurality of staples 4320 positioned within the compressible body 4310. Similar to the above, the staple cartridge 4300 can comprise flexible lateral supports 4334 which can be attached to a staple cartridge channel and/or adhered to the compressible body 4310. In addition to the above, the flexible lateral supports 4334 can be connected together by one or more struts, or connection members, 4335 which can be configured to hold the lateral supports 4334 together. In use, the connection members 4335 can be configured to prevent, or at least inhibit, the lateral supports 4334 from becoming prematurely detached from the cartridge body 4310. In certain embodiments, the connection members 4335 can be configured to hold the lateral supports 4334 together after the staple cartridge 4300 has been compressed by an anvil. In such embodiments, the lateral supports 4334 can resist the lateral bulging, or displacement, of the lateral portions of the cartridge body 4310. In certain embodiments, a cutting member, such as cutting member 4280, for example, can be configured to transect the connection members 4335 as the cutting member 4280 is moved distally within the cartridge body 4310. In at least one such embodiment, the cutting member 4280 can be configured to push one or more sleds, such as sleds 4270, for example, distally in order to form the staples 4320 against an anvil. The sleds 4270 can lead the cutting edge 4283 such that the cutting member 4280 does not transect a connection member 4335 until the staples 4320 adjacent to that connection member 4335 have been fully formed, or at least formed to a desired height. In various circumstances, the connection members 4335, in co-operation with the lateral supports 4334, can prevent, or at least reduce, the lateral movement of the compressible cartridge body 4310 and, concurrently, prevent, or at least reduce, the lateral movement of the staples 4320 positioned within the cartridge body 4310. In such circumstances, the connection members 4335 can hold the staples 4320 in position until after they are deformed and the connection members 4335 can be thereafter cut to release the lateral portions of the cartridge body 4310. As mentioned above, the lateral supports 4334 can be connected to the staple cartridge channel and, as a result, can be removed from the surgical site with the staple cartridge channel after the staple cartridge 4300 has been implanted. In certain embodiments, the lateral supports 4334 can be comprised of an implantable material and can be left within a surgical site. In at least one embodiment, the connection members 4335 can be positioned intermediate the cartridge body 4310 and the tissue T and, after the connection members 4335 have been detached from the lateral supports 4334, the connections members 4335 can remain implanted in the patient. In at least one such embodiment, the connection members 4335 can be comprised of an implantable material and, in certain embodiments, the connection members 4335 can be comprised of the same material as the lateral supports 4334, for example. In various embodiments, the connection members 4335 and/or lateral supports 4334 can be comprised of a flexible bioabsorbable material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, a connection member can comprise a sheet of material connecting the lateral supports 4334. In certain embodiments, a staple cartridge can comprise connection members extending across the top surface of the cartridge body 4310 and, in addition, connection members extending around the bottom surface of the cartridge body 4310.

In various embodiments, referring now to FIG. 149, a staple cartridge can comprise staples, such as staples 4420, for example, which can comprise a wire portion inserted into a crown portion. In at least one embodiment, the wire portion can be comprised of metal, such as titanium and/or stainless steel, for example, and/or plastic, such as polydioxanone (PDS) and/or polyglycolic acid (PGA), for example. In at least one embodiment, the crown portion can be comprised of metal, such as titanium and/or stainless steel, for example, and/or plastic, such as polydioxanone (PDS) and/or polyglycolic acid (PGA), for example. In certain embodiments, the wire portion of each staple 4420 can comprise a base 4422 and deformable legs 4421 extending from the base 4422 wherein the crown portion of each staple 4420 can comprise a crown 4429 which can be configured to receive at least a portion of a base 4422 therein. In order to assemble the portions of each staple 4420, referring now to FIGS. 150A-150C, the legs 4421 of the wire portion can be inserted into an opening 4426 in a crown 4429 wherein the opening 4426 can be configured to guide the legs 4421 into a base chamber 4427. The wire portion can be further inserted into the crown 4429 such that the legs 4421 exit the base chamber 4427 and the base 4422 of the wire portion enters into the base chamber 4427. In at least one such embodiment, the base chamber 4427 can be configured such that the wire portion is rotated within the crown 4429 as the base 4422 enters into the base chamber 4427 such that the staple legs 4421 are pointed in an upward, or at least substantially upward, direction. In various embodiments, referring again to FIG. 149, the crown 4429 can comprise exit holes 4425 which can be configured to receive the staple legs 4421 therein.

In various embodiments, further to the above, a surgical stapler can comprise a sled 4470 configured to transverse the staple cartridge 4400 and staple cartridge channel 4430 and move the staples 4420 contained within the cartridge body 4410 toward an anvil. In various circumstances, the sled 4470 can be moved from a proximal end of the staple cartridge channel 4430 to a distal end of the cartridge channel 4430 in order to implant the cartridge body 4410 and the staples 4420. In certain circumstances, the sled 4470 can be retracted or returned to the proximal end of the cartridge channel 4430 and another staple cartridge 4400 can be inserted into the cartridge channel 4430. Once the new staple cartridge 4400 has been positioned within the cartridge channel 4430, the sled 4470 can be advanced distally once again. In various embodiments, the surgical stapler may comprise one or more lock-out features which can prevent the sled 4470 from being advanced distally once again without a new staple cartridge 4400 being positioned within the cartridge channel 4430. In at least one such embodiment, referring again to FIG. 149, the staple cartridge channel 4430 can comprise a lock-out shoulder 4439 which can be configured to prevent, or at least limit, the distal movement of the sled 4470. More particularly, the sled 4470 can be configured to abut the shoulder 4439 unless the sled 4470 is at least partially lifted upwardly over the shoulder 4439 by a lift feature 4428, for example, extending between the proximal-most staples 4420 within a staple cartridge 4400. Stated another way, absent the presence of the proximal-most staples 4420 in a new staple cartridge 4400, the sled 4470 cannot be advanced. Thus, when an expended staple cartridge 4400 is present within the cartridge channel 4430, or no staple cartridge 4400 is present in the cartridge channel 4430 at all, the sled 4470 cannot be advanced within the cartridge channel 4430.

Further to the above, referring now to FIG. 151, a staple cartridge, such as staple cartridge 4500, for example, can be positioned within a staple cartridge channel 4530 and can comprise a compressible cartridge body 4510, a plurality of staples 4520 positioned within the cartridge body 4510, and a cartridge pan, or retainer, 4580. In various embodiments, the compressible cartridge body 4510 can comprise an outer layer 4511 and an inner layer 4512 wherein, in at least one embodiment, the outer layer 4511 can sealingly enclose the inner layer 4512. In at least one such embodiment, the outer layer 4511 can extend between the inner layer 4512 and the cartridge pan 4580. In certain other embodiments, the outer layer 4511 may only partially surround the inner layer 4512 and, in at least one such embodiment, the outer layer 4511 and the cartridge pan 4580 can co-operate to encompass, or at least substantially encompass, the inner layer 4512. In various embodiments, further to the above, the staples 4520 can be supported by the cartridge pan 4580 wherein the cartridge pan 4580 can comprise one or more staple support channels configured to support the staples 4520. In certain embodiments, the cartridge pan 4580 can be attached to the cartridge body 4510 wherein, in at least one such embodiment, the cartridge body 4510 can be compressed laterally between opposing side walls of the cartridge pan 4580. In various embodiments, the side walls of the cartridge pan 4580 can support the cartridge body 4510 laterally and, in at least one such embodiment, the cartridge pan 4580 can comprise one or more walls, or fins, 4582 extending upwardly from the bottom support 4583 into the cartridge body 4510. In at least one such embodiment, the cartridge body 4510 can comprise one or more slots, or channels, therein which can be configured to receive and/or interlock with the walls 4582. In various embodiments, the walls 4582 can extend partially, or almost entirely, through the cartridge body 4510. In at least one such embodiment, the walls 4582 can extend longitudinally through the staple cartridge 4500 between a first row of staples 4520 and a second row of staples 4520.

In various embodiments, the cartridge body 4510 and/or the cartridge pan 4580 can comprise co-operating retention features which can provide a snap-fit between the cartridge pan 4580 and the cartridge body 4510. In certain embodiments, the staple cartridge 4500 can be positioned within the cartridge channel 4530 such that the cartridge pan 4580 is positioned against and/or attached to the cartridge channel 4530. In at least one embodiment, the cartridge pan 4580 can be detachably coupled to the cartridge channel 4530 such that, after the staple cartridge 4500 has been compressed by the anvil 4540 and the staples 4520 have been deformed, the cartridge pan 4580 can detach from the cartridge channel 4530 and can be implanted with the cartridge body 4510. In at least one such embodiment, the cartridge pan 4580 can be comprised of a bioabsorbable material such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, a surgical stapler can further comprise a firing mechanism and/or driver which can be slid intermediate the staple cartridge channel 4530 and a bottom drive surface on the cartridge pan 4580 which can be configured to lift or eject the cartridge pan 4580 from the cartridge channel 4530. In certain embodiments, the cartridge body 4510 can be detachably coupled to the cartridge pan 4580 such that, after the staple cartridge 4500 has been compressed by the anvil 4540 and the staples 4520 have been deformed, the cartridge body 4510 can detach from the cartridge pan 4580. In at least one such embodiment, the cartridge pan 4580 can remain fixedly engaged with the cartridge channel 4530 such that the cartridge pan 4580 is removed from the surgical site with the cartridge channel 4530. In certain embodiments, a surgical stapler can further comprise a firing mechanism and/or driver which can be slid intermediate the staple cartridge pan 4580 and a bottom drive surface on the cartridge body 4510 which can be configured to lift or eject the cartridge body 4510 from the cartridge pan 4580. In at least one such embodiment, the staple cartridge 4500 can further comprise staple drivers positioned intermediate the cartridge pan 4580 and the staples 4520 such that, as the firing mechanism is slid distally, the staple drivers and the staples 4520 can be driven upwardly toward the anvil. In at least one such embodiment, the staple drivers can be at least partially embedded within the compressible cartridge body 4510.

In various embodiments, similar to the above, the staple cartridge 4500 can comprise a lock-out feature which can be configured to prevent, or at least limit, the distal movement of a cutting member unless a unfired staple cartridge 4500 has been positioned within the staple cartridge channel 4530. In certain embodiments, the staple cartridge pan 4580 can comprise a surface which lifts the cutting member upwardly and over a locking surface within the staple cartridge channel 4530, for example. In the event that a staple cartridge 4500 comprising a cartridge pan 4580 is not present in the cartridge channel 4530, the cutting member cannot be advanced. In at least one embodiment, the proximal-most staples, and/or any other suitable staples, within a staple cartridge 4500 can comprise a lifting surface which can sufficiently lift the cutting member over the locking surface. In addition to or in lieu of the above, various portions of the staple cartridge 4500 can be comprised of materials having different colors. In such embodiments, a surgeon may be able to visually identify when an unfired and/or fired staple cartridge is present in the staple cartridge channel 4530. In at least one such embodiment, the outer layer 4511 of the cartridge body 4510 may have a first color, the cartridge pan 4580 may have a second color, and the staple cartridge channel 4530 may have a third color. In the event that the surgeon sees the first color, the surgeon may know that an unfired cartridge 4500 is present in the staple cartridge channel 4530; in the event that the surgeon sees the second color, the surgeon may know that a fired cartridge 4500 is present in the staple cartridge channel 4530 and that the remaining cartridge pan 4580 needs to be removed; and in the event that the surgeon sees the third color, the surgeon may know that no portion of a staple cartridge 4500 remains within the cartridge channel 4530.

In various embodiments, referring now to FIG. 152, a staple cartridge, such as staple cartridge 4600, for example, can comprise a compressible, implantable cartridge body 4610 and a plurality of staples 4620 positioned therein. The cartridge body 4610 can comprise an outer layer 4611 and an inner layer 4612. In certain embodiments, the inner layer 4612 can comprise a plurality of pockets, such as pockets, or cavities, 4615, for example, defined therein which can facilitate the collapse of the cartridge body 4610. In at least one such embodiment, the inner layer 4612 can comprise a corrugated, or honeycomb-configured, lattice which can be configured to withstand a compressive force, or pressure, as long as the compressive force, or pressure, does not exceed a certain threshold value. When the threshold value has not been exceeded, the inner layer 4612 can deform at a linear, or at least substantially linear, rate with respect to the compressive force, or pressure, being applied. After the compressive force, or pressure, has exceeded the threshold value, the inner layer 4612 can suddenly succumb to large deflections and collapse, or buckle, as a result of the compressive load. In various embodiments, the lattice of the inner layer 4612 can be comprised of a plurality of sub-layers 4612*a* which can be connected together. In at least one embodiment, each sub-layer 4612*a* can comprise a plurality of alternating furrows and ridges, or waves, which can be aligned with the alternating furrows and ridges of an adjacent sub-layer 4612*a*. In at least one such embodiment, the furrows of a first sub-layer 4612*a* can be positioned adjacent to the ridges of a second sub-layer 4612*a* and, similarly, the ridges of the first sub-layer 4612*a* can be positioned adjacent to the furrows of the second sub-layer 4612*a*. In various embodiments, the adjacent sub-layers 4612*a* can be adhered to one another and/or the outer layer 4611 by at least one adhesive, such as fibrin and/or protein hydrogel, for example. FIG. 153 illustrates the staple cartridge 4600 after the cartridge body 4610 has been collapsed and the staples 4620 have been deformed in order to capture and hold tissue T against the cartridge body 4610.

In various embodiments, referring now to FIGS. 154-156, a staple cartridge, such as staple cartridge 4700, for example, can comprise a compressible, implantable cartridge body 4710 and a plurality of staples 4720 positioned within the cartridge body 4710. Similar to the above, the cartridge body 4710 can comprise an outer layer 4711 and an inner layer 4712, wherein the inner layer 4712 can comprise a plurality of sub-layers 4712*a*. Also similar to the above, each sub-layer 4712*a* can comprise alternating furrows 4717 and ridges 4718 which can be aligned with one another to define pockets, or cavities, 4715 therebetween. In at least one such embodiment, the furrows 4717 and/or the ridges 4718 can extend along axes which are parallel to one another and/or parallel to a longitudinal axis 4709. In various embodiments, the staples 4720 can be aligned in a plurality of staple rows which can extend along axes which are parallel to one another and/or parallel to the longitudinal axis 4709. In various alternative embodiments, referring again to FIGS. 152 and 153, the staples 4620 contained in the cartridge body 4600 can extend along axes which are traverse or perpendicular with respect to the axes defined by the furrows and ridges of the sub-layers 4612*a*. Referring again to FIGS. 154-156, the staples 4720 can extend through the furrows 4717 and the ridges 4718 wherein friction forces between the staples 4720 and the sub-layers 4712*a* can hold the staples 4720 within the cartridge body 4710. In certain embodiments, the plurality of sub-layers 4712*a* can be comprised of a buttress material and/or plastic material, such as polydioxanone (PDS) and/or polyglycolic acid (PGA), for example, which can be configured to hold the staples 4720 in an upright orientation, for example, and/or hold the staples 4720 in alignment with respect to each other as illustrated in FIGS. 154 and 155. FIG. 156 illustrates the staple cartridge 4700 after the cartridge body 4710 has been collapsed and the staples 4720 have been deformed in order to capture and hold tissue T against the cartridge body 4710.

In various embodiments, referring again to FIGS. 154-156, the cartridge body 4710 can resiliently or elastically collapse when it is compressed. In at least one such embodiment, the waves formed within each sub-layer 4712*a* by the furrows 4717 and the ridges 4718 can be flattened, or at least substantially flattened, when the cartridge body 4710 is compressed which can collapse, or at least substantially collapse, the cavities 4715 defined therebetween. In various circumstances, the cartridge body 4710, or at least portions of the cartridge body 4710, can resiliently or elastically re-expand after the compressive force, or pressure, has been removed from the cartridge body 4710. In at least one such embodiment, the connections between the furrows 4717 and the ridges 4718 of adjacent sub-layers 4712*a* can remain intact, or at least substantially intact, when the cartridge body 4710 is compressed such that, after the compression force has been removed from the cartridge body 4710, the sub-layers 4712*a* can bias themselves away from each other and, as a result, at least partially re-expand the cartridge body 4710. In certain embodiments, the cartridge body 4710 can be plastically deformed, or crushed, when it is compressed and, as a result, the cartridge body 4710 may not re-expand after the compressive force, or pressure, has been removed from the cartridge body 4710. In certain embodiments, referring now to FIG. 157, a staple cartridge, such as staple cartridge 4800, for example, can comprise a crushable cartridge body 4810 comprising an outer layer 4811 and an inner layer 4812, wherein the inner layer 4812 can comprise a corrugated, honeycomb-configured, lattice having a plurality of pockets, or cavities, 4815 defined therein. In various embodiments, the walls defining the lattice of inner layer 4812 can comprise one or more weakened, or thin, cross-sections 4819 which can be configured to allow the walls defining the lattice to break when the cartridge body 4810 is compressed. In such circumstances, the cartridge body 4810 can be crushed when the staple cartridge 4800 is implanted.

In various embodiments, referring now to FIGS. 158-160, a staple cartridge, such as staple cartridge 4900, for example, can comprise a cartridge body 4910 comprising an outer layer 4911 and a plurality of collapsible elements 4912 positioned intermediate top and bottom portions of the outer layer 4911, for example. Referring primarily to FIGS. 158 and 159, the staple cartridge 4900 can further comprise a plurality of staples 4920, wherein each staple 4920 can be positioned in a collapsible element 4912. More particularly, each collapsible element 4912 can comprise a first portion 4912a, a second portion 4012b, and a third portion 4012c which can co-operate to define a cavity 4915 therein which is configured to receive a staple 4920. In use, further to the above, the staple cartridge 4900 can be positioned within a staple cartridge channel and a compressive force can be applied to the tissue contacting surface 4919 in order to compress the cartridge body 4910. As the tissue contacting surface 4919 is moved downwardly, the collapsible elements 4912 can collapse. In such circumstances, the second portion 4912b of each collapsible element 4912 can collapse into a corresponding first portion 4912a and, similarly, the third portion 4912c of each collapsible element 4912 can collapse into a corresponding second portion 4912b. As the cartridge body 4910 is compressed and the collapsible elements 4912 are collapsed, the staples 4920 positioned within the collapsible elements 4912 can be deformed, as illustrated in FIG. 160. In various embodiments, the second portion 4912b of each collapsible element 4912 can be frictionally engaged and/or press-fit within a corresponding first portion 4912a such that, once the compressive force applied to the collapsible element 4912 exceeds the retention force retaining the first portion 4912a and the second portion 4912b in their extended position (FIG. 159), the first portion 4912a and the second portion 4912b can begin to slide relative to one another. Similarly, the third portion 4912c of each collapsible element 4912 can be frictionally engaged and/or press-fit within a corresponding second portion 4912b such that, once the compressive force applied to the collapsible element 4912 exceeds the retention force retaining the second portion 4912b and the third portion 4912c in their extended position (FIG. 159), the second portion 4912b and the third portion 4912c can begin to slide relative to one another.

In many embodiments described herein, a staple cartridge can comprise a plurality of staples therein. In various embodiments, such staples can be comprised of a metal wire deformed into a substantially U-shaped configuration having two staple legs. Other embodiments are envisioned in which staples can comprise different configurations such as two or more wires that have been joined together having three or more staple legs. In various embodiments, the wire, or wires, used to form the staples can comprise a round, or at least substantially round, cross-section. In at least one embodiment, the staple wires can comprise any other suitable cross-section, such as square and/or rectangular cross-sections, for example. In certain embodiments, the staples can be comprised of plastic wires. In at least one embodiment, the staples can be comprised of plastic-coated metal wires. In various embodiments, a cartridge can comprise any suitable type of fastener in addition to or in lieu of staples. In at least one such embodiment, such a fastener can comprise pivotable arms which are folded when engaged by an anvil. In certain embodiments, two-part fasteners could be utilized. In at least one such embodiment, a staple cartridge can comprise a plurality of first fastener portions and an anvil can comprise a plurality of second fastener portions which are connected to the first fastener portions when the anvil is compressed against the staple cartridge. In certain embodiments, as described above, a sled or driver can be advanced within a staple cartridge in order to complete the forming process of the staples. In certain embodiments, a sled or driver can be advanced within an anvil in order to move one or more forming members downwardly into engagement with the opposing staple cartridge and the staples, or fasteners, positioned therein.

In various embodiments described herein, a staple cartridge can comprise four rows of staples stored therein. In at least one embodiment, the four staple rows can be arranged in two inner staple rows and two outer staple rows. In at least one such embodiment, an inner staple row and an outer staple row can be positioned on a first side of a cutting member, or knife, slot within the staple cartridge and, similarly, an inner staple row and an outer staple row can be positioned on a second side of the cutting member, or knife, slot. In certain embodiments, a staple cartridge may not comprise a cutting member slot; however, such a staple cartridge may comprise a designated portion configured to be incised by a cutting member in lieu of a staple cartridge slot. In various embodiments, the inner staple rows can be arranged within the staple cartridge such that they are equally, or at least substantially equally, spaced from the cutting member slot. Similarly, the outer staple rows can be arranged within the staple cartridge such that they are equally, or at least substantially equally, spaced from the cutting member slot. In various embodiments, a staple cartridge can comprise more than or less than four rows of staples stored within a staple cartridge. In at least one embodiment, a staple cartridge can comprise six rows of staples. In at least one such embodiment, the staple cartridge can comprise three rows of staples on a first side of a cutting member slot and three rows of staples on a second side of the cutting member slot. In certain embodiments, a staple cartridge may comprise an odd number of staple rows. For example, a staple cartridge may comprise two rows of staples on a first side of a cutting member slot and three rows of staples on a second side of the cutting member slot. In various embodiments, the staple rows can comprise staples having the same, or at least substantially the same, unformed staple height. In certain other embodiments, one or more of the staple rows can comprise staples having a different unformed staple height than the other staples. In at least one such embodiment, the staples on a first side of a cutting member slot may have a first unformed height and the staples on a second side of a cutting member slot may have a second unformed height which is different than the first height, for example.

In various embodiments, referring now to FIGS. 161A-161D, an end effector of a surgical stapler can comprise a cartridge attachment portion, such as staple cartridge channel 5030, for example, a fastener cartridge removably positioned in the staple cartridge channel 5030, such as staple cartridge 5000, for example, and a jaw 5040 positioned opposite the staple cartridge 5000 and the staple cartridge channel 5030. The staple cartridge 5000 can comprise a compressible body 5010 and a plurality of staples 5020, and/or any other suitable fasteners, at least partially positioned in the compressible body 5010. In at least one such embodiment, each staple 5020 can comprise a base 5022 and, in addition, legs 5021 extending upwardly from the base 5022, wherein at least a portion of the legs 5021 can be embedded in the cartridge body 5010. In various embodiments, the compressible body 5010 can comprise a top, or tissue-contacting, surface 5019 and a bottom surface 5018, wherein the bottom surface 5018 can be positioned against and supported by a support surface 5031 of the staple cartridge channel 5030. Similar to the above, the support surface 5031 can comprise a plurality of support slots 5032 (FIG. 161D), for example, defined therein which can be configured to receive and support the bases 5022 of the staples 5020. In various embodiments, the end effector of the surgical stapler can further comprise a retention matrix, such as retention matrix 5050, for example, which can be configured to engage the staples 5020 and capture tissue therebetween. In at least one such embodiment, the retention matrix 5050 can be removably mounted to the jaw 5040. In use, once the staple cartridge 5000 has been positioned within the staple cartridge channel 5030, the jaw 5040, and the retention matrix 5050 attached thereto, can be moved toward the staple cartridge 5000 and the staple cartridge channel 5030. In at least one embodiment, the jaw 5040 can be moved downwardly along an axis 5099 such that the jaw 5040 and the staple cartridge channel 5030 remain parallel, or at least substantially parallel, to one another as the jaw 5040 is closed. More particularly, in at least one such embodiment, the jaw 5040 can be closed in a manner such that a tissue-contacting surface 5051 of the retention matrix 5050 is parallel, or at least substantially parallel, to the tissue-contacting surface 5019 of the staple cartridge 5000 as the jaw 5040 is moved toward the staple cartridge 5000.

In various embodiments, referring now to FIG. 161A, the retention matrix 5050 can be detachably secured to the jaw 5040 such that there is little, if any, relative movement between the retention matrix 5050 and the jaw 5040 when the retention matrix 5050 is attached to the jaw 5040. In at least one embodiment, the jaw 5040 can comprise one or more retention features which can be configured to hold the retention matrix 5050 in position. In at least one such embodiment, the retention matrix 5050 can be snap-fit and/or press-fit into the jaw 5040. In certain embodiments, the retention matrix 5050 can be adhered to the jaw 5040 utilizing at least one adhesive. In any event, the jaw 5040 can be moved into a position in which the retention matrix 5050 is in contact with the tissue T and the tissue T is positioned against the tissue-contacting surface 5019 of the staple cartridge 5000. When the tissue T is positioned against the staple cartridge 5000 by the jaw 5040, the compressible body 5010 of the staple cartridge 5000 may or may not be compressed by the jaw 5040. In either circumstance, in various embodiments, the legs 5021 of the staples 5200 may not protrude through the tissue-contacting surface 5019 of the staple cartridge 5000 as illustrated in FIG. 161A. Furthermore, as also illustrated in FIG. 161A, the jaw 5040 can hold the tissue T against the compressible body 5010 without engaging the retention matrix 5050 with the staples 5020. Such embodiments can permit a surgeon to open and close the jaw 5040 multiple times in order to obtain a desired positioning of the end effector within a surgical site, for example, without damaging the tissue T. Other embodiments are envisioned, however, where the staple tips 5023 can protrude from the tissue-contacting surface 5019 prior to the cartridge body 5010 being compressed by the anvil 5040. Once the end effector has been suitably positioned, referring now to FIG. 161B, the jaw 5040 can be moved downwardly toward the staple cartridge channel 5030 such that the compressible body 5010 is compressed by the anvil 5040 and such that the tissue-contacting surface 5019 is pushed downwardly relative to the staples 5020. As the tissue-contacting surface 5019 is pushed downwardly, the tips 5023 of the staple legs 5021 can pierce the tissue-contacting surface 5019 and pierce at least a portion of the tissue T. In such circumstances, the retention matrix 5050 may be positioned above the staples 5020 such that the retention apertures 5052 of retention matrix 5050 are aligned, or at least substantially aligned, with the tips 5023 of the staple legs 5021.

As the retention matrix 5050 is pushed downwardly along the axis 5099, referring now to FIG. 161C, the staple legs 5021 of staples 5020 can enter into the retention apertures 5052. In various embodiments, the staple legs 5021 can engage the side walls of the retention apertures 5052. In certain embodiments, as described in greater detail below, the retention matrix 5050 can comprise one or more retention members extending into and/or around the retention apertures 5052 which can engage the staple legs 5021. In either event, the staple legs 5021 can be retained in the retention apertures 5052. In various circumstances, the tips 5023 of the staple legs 5021 can enter into the retention apertures 5052 and can frictionally engage the retention members and/or the side walls of the apertures 5052. As the retention matrix 5050 is pushed toward the bases 5022 of the staples 5020, the staple legs 5021 can slide relative to the side walls and/or the retention members. As a result of the above, sliding friction forces can be created between the staple legs 5021 and the retention matrix 5050 wherein such sliding friction forces can resist the insertion of the retention matrix 5050 onto the staples 5020. In various embodiments, the sliding friction forces between the retention matrix 5050 and the staples 5020 can be constant, or at least substantially constant, as the retention matrix 5050 is slid downwardly along the staple legs 5021 of the staples 5020. In certain embodiments, the sliding friction forces may increase and/or decrease as the retention matrix 5050 is slid downwardly along the staple legs 5021 owing to variations in geometry of the staple legs 5021, the retention apertures 5052, and/or the retention members extending into and/or around the retention apertures 5052, for example. In various embodiments, the insertion of the retention matrix 5050 onto the staples 5020 can also be resisted by the compressible body 5010 of the staple cartridge 5000. More particularly, the compressible body 5010 can be comprised of an elastic material, for example, which can apply a resistive force to the retention matrix 5050 which increases as the distance in which the compressible body 5010 is compressed increases. In at least one such embodiment, the increase in the resistive force generated by the cartridge body 5010 can be linearly proportional, or at least substantially linearly proportional, with respect to the distance in which the cartridge body 5010 is compressed. In certain embodiments, the increase in the resistive force generated by the cartridge body 5010 can be geometrically proportional with respect to the distance in which the cartridge body 5010 is compressed.

In various embodiments, further to the above, a sufficient firing force can be applied to the jaw 5040 and the retention matrix 5050 in order to overcome the resistive and friction forces described above. In use, the retention matrix 5050 can be seated to any suitable depth with respect to the staples 5020. In at least one embodiment, the retention matrix 5050 can be seated to a depth with respect to the bases 5022 of the staples 5020 in order to secure two or more layers of tissue together and generate compressive forces, or pressure, within the tissue. In various circumstances, the system comprising the retention matrix 5050 and the staples 5020 can allow a surgeon to select the amount of compressive forces, or pressure, that is applied the tissue by selecting the depth in which the retention matrix 5050 is seated. For example, the retention matrix 5050 can be pushed downwardly toward the staple bases 5022 of the staples 5020 until the retention matrix 5050 is seated a certain depth 5011 away from the bottom of the support slots 5032, wherein a shorter depth 5011 can result in higher compressive forces, or pressure, being applied to the tissue T than a taller depth 5011 which can result in lower compressive forces, or pressure, being applied to the tissue T. In various embodiments, the compressive forces, or pressures, applied to the tissue T can be linearly proportional, or at least substantially linearly proportional, to the depth 5011 in which the retention matrix 5050 is seated. In various circumstances, the compressive forces, or pressure, applied to the tissue T can depend on the thickness of the tissue T positioned between the retention matrix 5050 and the staple cartridge 5020. More particularly, for a given distance 5011, the presence of thicker tissue T can result in higher compression forces, or pressure, than the presence of thinner tissue T.

In various circumstances, further to the above, a surgeon can adjust the depth in which the retention matrix 5050 is seated in order to account for thicker and/or thinner tissue positioned within the end effector and to apply a certain or predetermined pressure to the tissue T regardless of the tissue thickness. For example, the surgeon can seat the retention matrix 5050 to a shorter depth 5011 when fastening thinner tissue T or a taller depth 5011 when fastening thicker tissue T in order to arrive at the same, or at least substantially the same, compression pressure within the tissue. In certain embodiments, further to the above, a surgeon can selectively determine the amount of compressive pressure to apply to the tissue T positioned between the retention matrix 5050 and the staple cartridge 5010. In various circumstances, a surgeon can engage the retention matrix 5050 with the staples 5020 and position the retention matrix 5050 a first distance away from the bases 5022 of the staples 5020 in order to apply a first compressive pressure to the tissue. The surgeon can alternatively position the retention matrix 5050 a second distance away from the bases 5022, which is shorter than the first distance, in order to apply a second compressive pressure to the tissue which is greater than the first pressure. The surgeon can alternatively position the retention matrix 5050 a third distance away from the bases 5022, which is shorter than the second distance, in order to apply a third compressive pressure to the tissue which is greater than the second pressure. In various embodiments, the fastening system comprising the retention matrix 5050 and the staples 5020 can be configured to permit a surgeon to apply a wide range of compressive pressures to the targeted tissue.

In various embodiments, referring now to FIG. 161D, the staple legs 5021 can be inserted through the retention matrix 5050 such that the staple leg tips 5023 extend above the top surface of the retention matrix 5050. In at least one embodiment, referring again to FIG. 161C, the jaw 5040 can further comprise clearance apertures 5042 defined therein which can be configured to receive the staple leg tips 5023 as they pass through the retention apertures 5052 in the retention matrix 5050. In at least one such embodiment, the clearance apertures 5042 can be aligned with the retention apertures 5052 such that the legs 5021 do not contact the jaw 5040. In various embodiments, the clearance apertures 5042 can have a sufficient depth such that the staple legs 5021 do not contact the jaw 5040 regardless of the distance in which the retention matrix 5050 is seated. After the retention matrix 5050 has been engaged with the staples 5020 and seated to a desired position, referring now to FIG. 161D, the staple cartridge channel 5030 and the jaw 5040 can be moved away from the tissue T. More particularly, the staple cartridge channel 5030 can be detached from the implanted staple cartridge 5000 and the anvil 5040 can be detached from the implanted retention matrix 5050. As the jaw 5040 is moved away from the retention matrix 5050 and the staple supports 5032 are moved away from the staple bases 5022, the distance 5011 between the retention matrix 5050 and the bottom of the bases 5022 can be maintained eventhough the jaw 5040 and the staple cartridge channel 5030 are no longer providing support thereto. In various embodiments, the static friction forces between the staple legs 5021 and the retention matrix 5050 can be sufficient to maintain the retention matrix 5050 in position despite a biasing force being applied to the retention matrix 5050 by the compressed cartridge body 5010 and/or the compressed tissue T. In at least one such embodiment, the cartridge body 5010 can be comprised of a resilient material which, when compressed, can apply an elastic biasing force to the retention matrix 5050 and the staples 5020 in a manner which tends to push the retention matrix 5050 and the staples 5020 apart, although such movement is opposed by the frictional engagement between the staple legs 5021 and the retention matrix 5050.

In various embodiments, as described above, a retention matrix can comprise a plurality of retention apertures, wherein each retention aperture can be configured to receive a leg of a fastener therein. In at least one embodiment, referring now to FIG. 162, a portion of a retention matrix 5150 is illustrated therein which can comprise a retention aperture 5152 defined by a perimeter 5156. In various embodiments, the perimeter 5156 of the aperture 5152 can comprise a circular, or at least substantially circular, profile and/or any other suitable profile. In certain embodiments, the retention matrix 5150 can comprise one or more retention members, such as retention members 5153, for example, which extend into the aperture 5152 and can be configured to engage a fastener leg when the fastener leg is inserted therethrough. In at least one such embodiment, each retention member 5153 can comprise a cantilever which extends inwardly toward a center axis 5159, i.e., toward the center of the aperture 5152. In various embodiments, each cantilever can comprise a first end which is attached to the retention matrix body 5158 and a second end which forms the perimeter 5156 of the retention aperture 5152. In certain embodiments, the perimeter 5156 of a retention aperture 5152 can be defined by a first diameter, or width, and a fastener leg can be defined by a second diameter, or width, wherein the second diameter can be larger than the first diameter. In at least one such embodiment, the fastener leg can be configured to contact and deflect one or more of the retention members 5153 in order to increase the diameter of the retention aperture 5152 as the fastener leg is being inserted therethrough. In certain embodiments, further to the above, the fastener leg can define a perimeter which is larger than the perimeter 5156 of the retention aperture 5152 such that the fastener leg can expand the perimeter 5156 when the fastener leg is inserted therein.

In various embodiments, referring again to FIG. 162, the aperture 5152 can be defined by the deformable members 5153, wherein each deformable member 5153 can be configured to deflect relative to, or independently of, the other deformable members 5153. In at least one such embodiment, adjacent deformable members 5153 can be separated by slots 5154 which can be configured to permit each deformable member 5153 to flex relative to the others. In certain embodiments, each slot 5154 can comprise a first end 5155 in the retention matrix body 5158, a second end opening into the retention aperture 5152, and a constant, or at least substantially constant, width extending between the first end 5155 and the second end. In various other embodiments, the width of each slot 5154 may not be constant and each slot 5154 may increase and/or decrease in width between the first and second ends thereof. In certain embodiments, the first ends 5155 of the slots 5154 can comprise an enlarged portion, such as a circular portion, which can provide, one, strain relief to the bases of the deformable members 5153 attached to the retention matrix body 5158 and, two, means for increasing the flexibility of the deformable members 5153. In various embodiments, the geometry of the deformable members 5153, and/or slots 5154, can be selected so as to provide the deformable members 5153 with a desired flexibility. In certain embodiments, for example, the slots 5154 can be lengthened in order to create longer deformable members 5153 which can be more flexible than deformable members 5153 having a shorter length. In at least one embodiment, the width of each deformable member 5153 can be selected so as to provide a desired flexibility thereof. More particularly, deformable members having a thinner width can be more flexible than deformable members having a thicker width. In certain embodiments, referring again to FIG. 162, the first ends of the cantilevers of deformable members 5153 attached to the retention matrix body 5158 can be wider than the second ends of the cantilevers. In at least one such embodiment, the cantilevers can be tapered in a linear, or at least substantially linear, manner between the first and second ends thereof.

In various embodiments, referring again to FIG. 162, the retention matrix body 5158 can comprise a flat, or at least substantially flat, sheet of material having a tissue-contacting surface 5151 and a top surface 5157. In at least one such embodiment, the tissue-contacting surface 5151 and the top surface 5157 can be parallel, or at least substantially parallel, to one another. In various embodiments, each deformable member 5153 can comprise a first portion 5153a and a second portion 5153b, wherein the first portion 5153a can extend in a first direction and the second portion 5153b can extend in a different, or second, direction. In at least one such embodiment, the retention matrix body 5158 can define a plane and the first portions 5153a of the deformable members 5153 can lie within such a plane. In various embodiments, the second portions 5153b of the deformable members 5153 can extend at an angle relative to the first portions 5153a. In at least one such embodiment, the second portions 5153b can extend in directions which are pointed away from the top surface 5157 of the retention matrix body 5158 and, in certain embodiments, the second portions 5153b can converge toward the central axis 5159 of the retention aperture 5152. In any event, in various embodiments, the second portions 5153b can be configured to deflect away from the central axis 5159 when the fastener leg is inserted therethrough. In embodiments where a staple leg 5021 of a staple 5020 is inserted into a retention aperture 5152, the deformable members 5153 can deform in a direction which is generally away from the bases 5122 of the staples 5120. In certain embodiments, as a result, the deformable members 5153 can deflect in a general direction which is the same as, or at least substantially the same as, the direction in which the staple legs 5021 are being inserted.

In various embodiments, referring again to FIG. BD, the second portions 5153b of the deformable members 5153 can each comprise a sharp tip, for example, which can be configured to slide against a staple leg 5021 as the staple leg 5021 is inserted therein. The sharp tips of the second portions 5153b can also be configured to bite into the staple leg 5021 in the event that the staple leg 5021 were to be pulled in the opposite direction, i.e., in a direction which would remove the staple leg 5021 from the retention aperture 5052. In certain circumstances, the second portions 5153b can be inclined at an angle relative to the side of the staple leg 5021 which is greater than 90 degrees and, as a result, the second portions 5153b may dig, or burrow, into the side of the staple leg 5021 when the staple leg 5021 experiences a force which tends to withdraw the staple leg 5021 from the retention aperture 5052. In certain embodiments, the staple legs 5021 can comprise indentations and/or concavities, such as microindentations, for example, in the surfaces thereof which can be configured to receive the tips of the deformable members 5053, for example, therein. In at least one such embodiment, the tips of the deformable members 5053 can catch in and burrow into the indentations in the staple legs 5021 when a withdrawing force is applied to the staple legs 5021. In various embodiments, as a result of the burrowing of the second portions 5153b into the staple legs 5021, forces acting to remove the staple legs 5021 from the retention apertures 5022 may only seat the second portions 5153b deeper into the staple legs 5021 and increase the force required to remove the staple legs 5021. Furthermore, owing to the upward inclination of the second portions 5153b, in at least one embodiment, the second portions 5153b can be more permissive to the insertion of a staple leg 5021 within a retention aperture 5152 and more resistive to withdrawal of the staple leg 5021. In at least one embodiment, as a result, the force required to insert a staple leg 5021 into a retention aperture 5022 may be less than the force required to remove the staple leg 5021 from the retention aperture 5022. In various embodiments, the force needed to remove the staple leg 5021 from the retention aperture 5022 can be approximately 50 percent greater than the force needed to insert the staple leg 5021 into the retention aperture 5022, for example. In various other embodiments, the force needed to remove the staple leg 5021 may between approximately 10 percent and approximately 100 percent greater than the force needed to insert the staple leg 5021, for example. In certain embodiments, the force needed to remove the staple leg 5021 may be approximately 100 percent, approximately 150 percent, approximately 200 percent, and/or greater than approximately 200 percent larger than the force needed to insert the staple leg 5021, for example.

In certain embodiments, referring again to FIG. 162, the second portions 5153b can be arranged circumferentially around the aperture 5152 and can define a pocket therebetween. More particularly, the second portions 5153b can define a pocket 5160 which can be configured to receive the tip of the fastener leg when it is inserted into the retention aperture 5152. In various embodiments, the second portions 5153b of the deformable members 5153 can comprise an annular, or an at least substantially annular, contour which can co-operatively define an annular, or at least substantially annular, profile of the pocket 1560, for example. In at least one such embodiment, the second portions 5153b can define a conical or frustoconical pocket. In various embodiments, the pocket can be defined by a suitable number of deformable members, such as four deformable members 5153 (FIG. 162), six deformable members 5153 (FIG. 163), or eight deformable members 5153 (FIG. 164), for example. In certain embodiments, referring now to FIG. 165, the deformable members of a retention matrix, such as retention matrix 5250, for example, can form a pyramidal shape, or an at least substantially pyramidal shape, for example. In various embodiments, a retention matrix 5250 can comprise a plurality of retention apertures, such as retention aperture 5252, for example, which can be defined by a perimeter 5256. In various embodiments, the perimeter 5256 can comprise a polygonal, or at least substantially polygonal, profile and/or any other suitable profile. In certain embodiments, the retention matrix 5250 can comprise one or more retention members, such as retention members 5253, for example, which extend into the aperture 5252 and can be configured to engage a fastener leg when the fastener leg is inserted therethrough. In at least one such embodiment, each retention member 5253 can comprise a cantilever which extends inwardly toward a center axis 5259, i.e., toward the center of the aperture 5252. In various embodiments, each cantilever can comprise a first end which is attached to the retention matrix body 5258 and a second end which forms the perimeter 5256 of the retention aperture 5252. In certain embodiments, the perimeter 5256 of a retention aperture 5252 can be defined by a first diameter, or width, and a fastener leg can be defined by a second diameter, or width, wherein the second diameter can be larger than the first diameter. In at least one such embodiment, the fastener leg can be configured to contact and deflect one or more of the retention members 5253 in order to increase the diameter of the retention aperture 5252 as the fastener leg is being inserted therethrough. In certain embodiments, further to the above, the fastener leg can define a perimeter which is larger than the perimeter 5256 of the retention aperture 5252 such that the fastener leg can expand the perimeter 5256 when the fastener leg is inserted therein.

In various embodiments, referring again to FIG. 165, the aperture 5252 can be defined by the deformable members 5253, wherein each deformable member 5253 can be configured to deflect relative to, or independently of, the other deformable members 5253. In at least one such embodiment, adjacent deformable members 5253 can be separated by slots 5254 which can be configured to permit each deformable member 5253 to flex relative to the others. In various embodiments, the retention matrix body 5258 can comprise a flat, or at least substantially flat, sheet of material having a tissue-contacting surface 5251 and a top surface 5257. In at least one such embodiment, the tissue-contacting surface 5251 and the top surface 5257 can be parallel, or at least substantially parallel, to one another. In various embodiments, each deformable member 5253 can comprise a first portion 5253*a* and a second portion 5253*b*, wherein the first portion 5253*a* can extend in a first direction and the second portion 5253*b* can extend in a different, or second, direction. In at least one such embodiment, the retention matrix body 5258 can define a plane and the first portions 5253*a* of the deformable members 5253 can lie within such a plane. In various embodiments, the second portions 5253*b* of the deformable members 5253 can extend at an angle relative to the first portions 5253*a*. In at least one such embodiment, the second portions 5253*b* can extend in directions which are pointed away from the top surface 5257 of the retention matrix body 5258 and, in certain embodiments, the second portions 5253*b* can converge toward the central axis 5259 of the retention aperture 5252. In any event, in various embodiments, the second portions 5253*b* can be configured to deflect away from the central axis 5259 when the fastener leg is inserted therethrough. In certain embodiments, referring again to FIG. 165, the second portions 5253*b* can be arranged circumferentially around the aperture 5252 and can define a pocket therebetween. More particularly, the second portions 5253*b* can define a pocket which can be configured to receive the tip of the fastener leg when it is inserted into the retention aperture 5252. In various embodiments, the second portions 5253*b* of the deformable members 5253 can define a polygonal, or an at least substantially polygonal, pocket, for example. In various embodiments, the pocket can be defined by a suitable number of deformable members, such as four deformable members 5253 (FIG. 165) which can define a square, six deformable members 5253 (FIG. 166) which can define a hexagon, or eight deformable members 5253 (FIG. 167) which can define an octagon, for example.

In various embodiments, referring now to FIG. 168, a retention matrix, such as retention matrix 5350, for example, can be formed from a flat, or an at least substantially flat, sheet of material such as titanium and/or stainless steel, for example. In at least one such embodiment, a plurality of apertures 5352 can be formed in the body 5358 of the retention matrix 5350 by one or more stamping processes. The sheet of material can be positioned in a stamping die which, when actuated, can punch out certain portions of the material in order to form slots 5354, apertures 5355 of slots 5354, and/or the perimeter 5356 of the retention aperture 5352, for example. The stamping die can also be configured to bend the deformable members 5353 in a suitable configuration. In at least one such embodiment, the stamping die can deform the second portions 5353*b* upwardly relative to the first portions 5353*a* along a crease line 5353*c*. In various embodiments, referring now to FIG. 169, a retention matrix, such as retention matrix 5450, for example, can comprise a plurality of retention apertures 5452. Similar to the above, the perimeter 5456 of each retention aperture 5452 can be defined by a plurality of deformable members 5453 separated by slots, or slits, 5454. In at least one such embodiment, the entirety of each deformable member 5453 can be bent upwardly wherein the free ends of the cantilevers comprising the deformable members 5453 can define the perimeter 5456. In various embodiments, the retention matrix 5450 can comprise a plurality of apertures 5455 surrounding, or at least substantially surrounding, the retention aperture 5452. In at least one such embodiment, the apertures 5455 can be arranged in a circular array surrounding or enclosing a perimeter defined by the fixed ends of the cantilevers of the deformable members 5453. In certain embodiments, each aperture 5455 can comprise a circular, or at least substantially circular, perimeter and/or any other suitable perimeter. In use, the apertures 5455 can provide, one, strain relief to the bases of the deformable members 5453 attached to the retention matrix body 5458 and, two, means for increasing the flexibility of the deformable members 5453. In various embodiments, larger apertures 5455 can provide more flexibility to the deformable members 5453 as compared to smaller apertures 5455. Furthermore, apertures 5455 which are closer to the deformable members 5453 can provide more flexibility as compared to apertures 5455 which are further away.

In various embodiments, referring now to FIG. 170, a retention matrix, such as retention matrix 5550, for example, can comprise a plurality of retention apertures 5552. Each retention aperture 5552 can comprise an elongate slot 5554 having enlarged circular, or at least substantially circular, ends 5555. In at least one such embodiment, the ends 5555 can be defined by a diameter which is wider than the slot 5554. In certain embodiments, the elongate slot 5554 and the ends 5555 can positioned along, and/or centered along, a longitudinal axis 5559. In various embodiments, the slot 5554 and the ends 5555 can define two opposing tabs 5553 which can be configured to engage a leg of a fastener and deflect as the fastener leg is inserted therethrough. In at least one embodiment, ends 5555 having a larger perimeter, or diameter, can define longer tabs 5553 which can be more flexible than tabs 5553 defined by ends 5555 having a smaller perimeter, or diameter. In various embodiments, the ends 5555 can have the same perimeter and diameter and, in at least one such embodiment, each tab 5553 can be symmetrical about an axis which is perpendicular, or at least substantially perpendicular, to the longitudinal axis 5559. Alternatively, the ends 5555 can have different perimeters and/or diameters wherein, in at least one embodiment, each tab 5553 may not be symmetrical about its axis. In at least one such alternative embodiment, the tabs 5553 may twist about their axes as the fastener leg is inserted through the retention aperture 5552. In various embodiments, referring now to FIG. 171, a retention matrix, such as retention matrix 5650, for example, can comprise a plurality of retention apertures 5652. Each retention aperture 5652 can comprise an elongate slot 5654 comprising circular, or at least substantially circular, ends 5655. In at least one such embodiment, the elongate slot 5654 and the ends 5655 can be positioned along, and/or centered along, a longitudinal axis 5659. In various embodiments, each end 5655 can be defined by a diameter which is the same as, or at least substantially the same as, the width of the slot 5654.

In various embodiments, referring now to FIG. 172, a retention matrix, such as retention matrix 5750, for example, can comprise a plurality of retention apertures 5752. Each retention aperture 5752 can comprise a plurality of slots, such as slots 5754, for example, having enlarged ends 5755. In at least one such embodiment, the slots 5754 and the ends 5755 can be positioned along and/or centered along longitudinal axes 5759. In various embodiments, the axes 5759 can extend in directions which are perpendicular or transverse to one another. In certain embodiments, the slots 5754 and the ends 5755 can define four tabs 5753, for example, which can be configured to engage a fastener leg and deflect when the fastener leg is inserted through the retention aperture 5752. In at least one embodiment, each tab 5753 can comprise a triangular, or at least substantially triangular, configuration, such as an equilateral triangle, for example. In various other embodiments, referring now to FIG. 173, a retention matrix, such as retention matrix 5850, for example, can comprise a plurality of retention apertures 5852. Each retention aperture 5852 can comprise a plurality of slots, such as slots 5854, for example, having ends 5855, wherein the slots 5854 and the ends 5855 can be positioned along and/or centered along longitudinal axes 5859. In various embodiments, the axes 5859 can extend in directions which are perpendicular or transverse to one another. In certain embodiments, the slots 5854 and the ends 5855 can define tabs 5853 which can be configured to engage a fastener leg and deflect when the fastener leg is inserted through the retention aperture 5852. In at least one embodiment, each tab 5853 can comprise an arcuate profile. More particularly, each tab 5853 can comprise a curved end, as opposed to a pointed end depicted in FIG. 170, which can be configured to contact the fastener leg.

In various embodiments, referring now to FIG. 174, a retention matrix, such as retention matrix 5950, for example, can comprise a plurality of retention apertures 5952. Each retention aperture 5952 can comprise a plurality of slots, such as slots 5954, for example, wherein each slot 5954 can extend along, and/or can be centered along, an axis 5959. In various embodiments, the axes 5959 can be transverse to each other and, in at least one such embodiment, the axes 5959 can be arranged such that all of the axes 5959 extend through a center of the retention aperture 5952 and are spaced equidistantly, or at least substantially equidistantly, from each other. In at least one embodiment, each slot 5954 can comprise an open end facing the center of the retention aperture 5952 and a second, or closed, end 5955 at the opposite end of the slot 5954. Similar to the above, the slots 5954 and the ends 5955 can define three tabs 5953, for example, which can be configured to engage a fastener leg and deflect when the fastener leg is inserted into the retention aperture 5952. In various embodiments, each tab 5953 can comprise an arcuate configuration extending between adjacent ends 5955 of the slots 5954. In various embodiments, referring now to FIG. 175, a retention matrix, such as retention matrix 6050, for example, can comprise a plurality of retention apertures 6052. Each retention aperture 6052 can comprise a tab 6053 which can be configured to engage a fastener leg and to deflect when the fastener leg is inserted into the retention aperture 6052. In at least one such embodiment, the tab 6053 can comprise a base fixed to the retention matrix body 6058 and a free end comprising an arcuate or curved profile 6056 which can be configured to contact the fastener leg. In certain embodiments, the fastener leg can be a staple leg comprised of a round wire wherein the curved profile 6056 can be configured to match, or at least substantially match, a curved outer surface of the round wire.

In various embodiments, referring again to FIG. 175, the retention matrix body 6058 can comprise a plurality of slots 6054 and apertures 6055 which can be configured to define the tab 6053 and various portions of the retention aperture 6052. In at least one embodiment, the tab 6053 can comprise a rectangular configuration comprising parallel, or at least substantially parallel, sides. In certain embodiments, referring now to FIG. 176, a retention matrix, such as retention matrix 6150, for example, can comprise a plurality of retention apertures 6152. Each retention aperture 6152 can comprise a tab 6153 which can be configured to engage a fastener leg and to deflect when the fastener leg is inserted into the retention aperture 6152. In at least one such embodiment, the tab 6153 can comprise a base fixed to the retention matrix body 6158 and a free end comprising an arcuate or curved profile 6156 which can be configured to contact the fastener leg. In various embodiments, the retention matrix body 6158 can comprise a plurality of slots 6154 and apertures 6155 which can be configured to define the tab 6153 and various portions of the retention aperture 6152. In at least one embodiment, the tab 6153 can comprise a tapered configuration comprising arcuate sides. In at least one such embodiment, the tab 6153 can taper geometrically with the base being wider than the free end, for example.

In various embodiments, as described above, a fastening system can comprise a plurality of staples comprising staple legs which are inserted through a plurality of retention apertures in a retention matrix. In certain embodiments, as described in greater detail below, the staples can be held in a first jaw and the retention matrix can be held in a second jaw, wherein at least one of the first jaw and the second jaw can be moved toward the other. In various circumstances, the staples positioned within the first jaw can be secured therein such that the staple legs are aligned with the retention apertures when the retention matrix is engaged with the staple legs. In certain embodiments, referring to FIGS. 177 and 178, a fastener system can comprise a staple cartridge 6200, for example, positioned in a first jaw of a surgical stapler and a retention matrix 6250, for example, positioned in a second jaw of the surgical stapler. Referring now to FIGS. 184 and 185, further to the above, the retention matrix 6250 can comprise a plurality of retention apertures 6252, wherein each retention aperture 6252 can comprise a perimeter 6256 defined by one or more deflectable members 6253. In at least one such embodiment, further to the above, the deflectable members 6253 defining each aperture 6252 can define a pocket 6201. In various embodiments, each pocket 6201 can comprise a curved and/or concave surface, for example, which can be configured to guide a tip of a staple leg into the aperture 6252 in the event that the staple leg is misaligned with the retention aperture 6252 and initially contacts the deflectable members 6253 and/or the tissue-contacting surface 6251, for example.

In various embodiments, further to the above, the fastening system can further comprise a plurality of staples 6220 comprising staple legs 6221 which can be inserted through the retention apertures 6252 in the retention matrix 6250. In at least one such embodiment, each staple 6220 can comprise a substantially U-shaped configuration, for example, comprising a base 6222 from which the staple legs 6221 can extend upwardly. In various embodiments, referring now to FIGS. 180 and 181, the retention apertures 6252 in the retention matrix 6250 can be arranged in two parallel, or at least substantially parallel, longitudinal rows, for example, which can extend along, or parallel to, a longitudinal axis of the retention matrix. In certain embodiments, the retention apertures 6252 in a first row can be offset, or staggered, with respect to the retention apertures 6252 in a second row. In at least one such embodiment, each staple 6220 can comprise a first staple leg 6221 positioned in a retention aperture 6252 in the first row of and a second staple leg 6221 positioned in a retention aperture 6252 in the second row wherein, as a result, the bases 6222 can extend in a direction which is transverse to the longitudinal axis of the retention matrix 6250. In at least one such embodiment, the staples 6220 can be parallel, or at least substantially parallel, to one another. More particularly, a base 6222a of a staple 6220a be parallel to, or at least substantially parallel to, a base 6222b of a staple 6220b which can be parallel to, or at least substantially parallel to, a base 6222c of a staple 6220c, for example. In at least one embodiment, the staple legs 6221a of staple 6220a can define a plane which is parallel to, or at least substantially parallel to, a plane defined by the staple legs 6221b of staple 6220b which can be parallel to, or at least substantially parallel to, a plane defined by the staple legs 6221 of staple 6220c, for example.

In various embodiments, referring now to FIGS. 177 and 179, the staple cartridge 6200 can comprise a plurality of staples 6220 and, in addition, an alignment matrix 6260 comprising a plurality of alignment guides, such as slots, grooves, and/or apertures, for example, which can be configured to align the staples 6220. In various circumstances, the alignment matrix 6260 can be configured such that the staple legs 6221 of the staples 6220 are aligned with the retention apertures 6252 in the retention matrix 6250 before the retention matrix 6250 is engaged with the staple legs 6221. In various embodiments, referring now to FIGS. 182 and 183, the alignment matrix 6260 can comprise a plurality of alignment apertures 6262 which can be configured to closely receive the staple legs 6221 of the staples 6220. In at least one such embodiment, each staple 6220 can comprise a base 6222 and two staple legs 6221 extending from the base 6222 wherein the bases 6222 of the staples 6220 can extend around a bottom surface 6264 of the retention matrix 6260 and the staple legs 6221 can extend upwardly through the alignment apertures 6262. In certain embodiments, each alignment aperture 6262 can be circular, or at least substantially circular, and can be defined by a diameter which is equal to or slightly larger than the diameter of the staple leg 6221 extending therethrough. In various embodiments, the alignment matrix 6260 can further comprise a plurality of raised members 6263 which can extend upwardly from the top surface 6261 of the alignment matrix 6260 and surround, or at least partially surround, the alignment apertures 6262. In certain embodiments, the raised members 6263 can provide for longer alignment apertures 6262 wherein, in various circumstances, longer apertures 6262 can provide more control over the alignment of the staple legs 6221 than shorter apertures 6262.

In use, in various embodiments, a first jaw supporting the staple cartridge 6200 can be positioned on one side of the tissue that is to be stapled and a second jaw supporting the retention matrix 6250 can be positioned on the other side of the tissue. Once the jaws have been suitably positioned relative to the tissue, in certain embodiments, the second jaw and the retention matrix 6250 can be moved toward the staple cartridge 6200. As the staple legs 6221 are being inserted through the retention apertures 6252 of the retention matrix 6250, in various embodiments, a tissue-contacting, or bottom, surface 6251 of the retention matrix 6250 can contact the tissue and press the tissue against the tissue-contacting, or top, surface 6261 of the alignment matrix 6260. In various other embodiments, as described in greater detail further below, the staple cartridge 6200 can further comprise a compressible cartridge body positioned above the top surface 6261 of the alignment matrix 6260, for example, which can contact the tissue. In certain embodiments, referring again to FIGS. 179 and 183, the alignment matrix 6260 can further comprise one or more apertures 6203 defined therein which, when the alignment matrix 6260 is positioned against tissue, can be configured to receive a portion of the tissue therein. In embodiments where a compressible cartridge body is positioned above and/or against the alignment matrix 6260, a portion of the compressible cartridge body can enter into the apertures 6203 when the cartridge body is compressed. Similarly, the retention matrix 6250 can comprise a plurality of apertures 6202 which can be configured to receive at least a portion of the tissue therein when the retention matrix 6250 is positioned against the tissue.

As the staple legs 6221 of the staples 6220 are inserted through the retention apertures 6252 of the retention matrix 6250, further to the above, the tips of the staple legs 6221 may protrude upwardly from the top surface 6257 of the retention matrix 6250. In various circumstances, as described above, the tips of the staple legs 6221 may remain unbent after they have been inserted through the retention apertures 6252. In certain embodiments, referring now to FIGS. 186-189, a fastening system comprising the staple cartridge 6200 and the retention matrix 6250 may further comprise a plurality of protective caps or covers, such as caps 6270, for example, which can be assembled to the staple legs 6221 protruding above the retention matrix 6250. In various embodiments, each cap 6270 can entirely, or at least partially, cover the sharp end of a staple leg 6221 such that the sharp end does not contact tissue positioned adjacent thereto. In at least one embodiment, referring now to FIG. 189, each cap 6270 can comprise an aperture 6271 defined therein which can be configured to closely receive a tip of a staple leg 6221 therein. In various embodiments, the caps 6270 can be comprised of an elastomeric material, such as silicone, polyisoprene, sanoprene, and/or natural rubber, for example. In at least one embodiment, the aperture 6271 can comprise a perimeter or diameter which is smaller than the perimeter or diameter of the staple leg 6221 inserted therein. In at least one such embodiment, the aperture 6271 in the protective cap 6270 can expand in order to receive the staple leg 6221 therein. In various alternative embodiments, the caps 6270 may not comprise apertures and the tips of the staple legs 6221 can be configured to incise the caps 6270 as the legs 6221 are inserted therein. In any event, in various embodiments, each cap 6270 can be seated onto a staple leg 6221 until the base 6272 of the cap 6270 abuts, or is positioned adjacent to, the top surface 6257 of the retention matrix 6250. In various circumstances, the caps 6270 can be configured such that they are seated snugly onto the tips of the staple legs 6221 such that they are not easily removed therefrom. In certain embodiments, each cap 6270 can comprise a conical, or at least substantially conical, outer surface, for example. In various embodiments, the caps 6270 can comprise any suitable shape, such as shapes comprising a parabolic, or at least substantially parabolic, outer surface, for example.

In various embodiments, the fastener system described above, for example, could be deployed using the surgical stapler depicted in FIGS. 190-192, for example. In various embodiments, the end effector can comprise a first jaw, or staple cartridge channel, 6230 which can be configured to support the staple cartridge 6200 therein and a second jaw 6240 which can be configured to support the retention matrix 6250 and the plurality of protective caps 6270. Referring primarily to FIG. 190, which illustrates the second jaw 6240 in an open configuration, the jaws 6230 and 6240 can be positioned relative to tissue T such that the tissue T is positioned intermediate the retention matrix 6250 and the staple cartridge 6200. In various embodiments, as discussed above, the staple cartridge 6200 can further comprise a compressible cartridge body, such as cartridge body 6210, for example, in which the staples 6220 and the alignment matrix 6260 can be positioned. In at least one such embodiment, the tissue T can be positioned against a top surface of the cartridge body 6210. In certain embodiments, the second jaw 6240 can comprise a plurality of recesses, or apertures, 6245 configured to receive the plurality of protective caps 6270 and, in addition, one or more retention features, or retainers, which can be configured to hold the retention matrix 6250 in position over the caps 6270. In at least one such embodiment, the retention matrix 6250 can be configured to retain the caps 6270 in the apertures 6245. In various embodiments, referring now to FIG. 202, each aperture 6245 can be configured to receive a portion of, or the entirety of, a cap 6270 therein. In certain embodiments, the apertures 6245 can be sufficiently sized and configured such that the caps 6270 can be secured therein by at least one of a press-fit and/or snap fit arrangement, for example. In some embodiments, at least one adhesive could be utilized to secure the caps 6270 in the apertures 6245. In at least one such embodiment, such an adhesive could be selected such that caps 6270 can detach from the second jaw 6240 after the caps 6270 have been engaged with the staple legs 6221 and the second jaw 6240 is moved away from the implanted fastener assembly. In certain embodiments, referring now to FIG. 203, the second jaw 6240 can further comprise at least one cover sheet 6246 which can be assembled to the second jaw 6240 and can extend over and retain the caps 6270 in the apertures 6245. In at least one such embodiment, at least a portion of the cover sheet 6246 can be secured to the jaw 6240 utilizing at least one adhesive, for example. In use, in at least one embodiment, the cover sheet 6246 can be at least partially detached from the jaw 6240 before the end effector is inserted into a surgical site. In certain embodiments, the cover sheet 6246 can be comprised of an implantable material, such as PDS and/or PGA, for example, which can be incised by the staple legs 6221 as the staple legs 6221 emerge from the retention matrix 6250. In at least one such embodiment, the cover sheet 6246 can be secured in the fastening system intermediate the covers 6270 and the retention matrix 6250.

Further to the above, referring now to FIG. 191, the jaw 6240 can be moved from an open position to a closed position in which the tissue T is positioned against the retention matrix 6250 and the cartridge body 6210. In such a position, the retention matrix 6250 may not yet be engaged with the staples 6220. In various embodiments, the jaw 6240 can be moved between its open position and its closed position by an actuator 6235. In at least one such embodiment, the jaw 6240 can comprise a distal pin 6243 and a proximal pin 6244 extending therefrom, wherein the distal pin 6243 can slide vertically, or at least substantially vertically, within a distal slot 6233 defined in the cartridge channel 6230, and wherein the proximal pin 6244 can slide vertically, or at least substantially vertically, within a proximal slot 6234 which is also defined in the staple cartridge channel 6230. In use, the actuator 6235 can be retracted proximally in order to drive the pins 6243 and 6244 into the upper ends of their respective slots 6233 and 6234 as illustrated in FIG. 191. In at least one such embodiment, the actuator 6235 can comprise a distal drive slot 6236 and a proximal drive slot 6237, wherein the sidewalls of the drive slots 6236 and 6237 can be configured to contact the distal pin 6243 and the proximal pin 6244, respectively, and drive the pins 6243 and 6244 upwardly as the actuator 6235 is moved proximally. More particularly, as the actuator 6235 is moved proximally, the distal pin 6243 can slide up an inclined first portion 6236*a* of the distal drive slot 6236 into an intermediate, or second, portion 6236*b* and, similarly, the proximal pin 6244 can slide up an inclined first portion 6237*a* of the distal drive slot 6237 into an intermediate, or second, portion 6237*b*. As the pins 6243 and 6244 are both moved upwardly, the jaw 6240 can be rotated downwardly toward the tissue T into a closed position.

Further to the above, referring now to FIG. 192, the actuator 6235 can be pulled further proximally in order to push the second jaw 6240 downwardly toward the first jaw 6230, compress the cartridge body 6210, and engage the retention matrix 6250 and the plurality of protective caps 6270 with the staple legs of the staples 6220. In at least one such embodiment, the additional proximal movement of the actuator 6235 can cause the sidewalls of the drive slots 6236 and 6237 to contact the pins 6243 and 6244, respectively, and drive the pins 6243 and 6244 downwardly toward the bottom ends of the slots 6233 and 6234, respectively. In such circumstances, the actuator 6235 can be pulled proximally such that, one, the distal pin 6243 exits the second portion 6236*b* of the drive slot 6236 and enters into an inclined third portion 6236*c* and, similarly, the proximal pin 6244 exits the second portion 6237*b* of the drive slot 6237 and enters into an inclined third portion 6237*c*. As the pins 6243 and 6244 are both moved downwardly, the second jaw 6240 can move downwardly toward the first jaw 6230 into a fired position. In at least one such embodiment, the second jaw 6240 can be moved downwardly such that the retention matrix 6250 remains parallel, or at least substantially parallel, to the top surface of the cartridge body 6210 and/or parallel, or at least substantially parallel, to the alignment matrix 6260. In any event, once the retention matrix 6250 and the protective caps 6270 have been engaged with the staple legs 6221 of the staples 6220, as illustrated in FIG. 194, the second jaw 6240 can be returned to an open, or an at least substantially open, position. In at least one such embodiment, the actuator 6235 can be pushed distally in order to drive the pins 6243 and 6244 to the top ends of the slots 6233 and 6234, respectively, and then driven downwardly toward the bottom ends of the slots 6233 and 6234 once the pins have passed through the intermediate portions 6236*b* and 6237*b* of the respective drive slots 6236 and 6237. Once the second jaw 6240 has been opened, the first jaw 6230 can be detached from the implanted staple cartridge 6200 and the first and second jaws 6230, 6240 can be removed away from the implanted fastener assembly, as illustrated in FIG. 193.

Referring to FIG. 192 once again, the reader will note that the pins 6243 and 6244 are not illustrated as being seated in the very bottoms of their respective slots 6233 and 6234 eventhough the retention matrix 6250 and the caps 6270 have been engaged with the staple legs 6221. Such circumstances can arise when thick tissue T is positioned between the retention matrix 6250 and the cartridge body 6210. In circumstances where thinner tissue T is positioned between the retention matrix 6250 and the cartridge body 6210, referring now to FIG. 195, the pins 6243 and 6244 can be drive further downwardly into their respective slots 6233 and 6234 as illustrated in FIG. 197. In general, in at least one such embodiment, the actuator 6235 can be pulled proximally in order to drive the pins 6243 and 6244 upwardly and downwardly through the progressions described above and illustrated in FIGS. 195-197 and, owing to the thinner tissue T, the retention matrix 6250 and the protective caps 6270 can be driven further onto the staple legs 6221 of the staples 6220, as illustrated in FIGS. 198 and 199. In various embodiments, as a result of the adjustability afforded by the retention matrix 6250, the same, or at least substantially the same, compressive pressure can be obtained in the fastened tissue regardless of whether the tissue captured within the end effector is thick or thin. In certain embodiments, the adjustability afforded by the retention matrix 6250 can allow a surgeon can select whether to apply a larger compressive pressure or a smaller compressive pressure to the tissue by selecting the depth to which the retention matrix 6250 is seated. In at least one such embodiment, the range in which the retention matrix 6250 can be seated onto the staple legs 6221 can be determined by the lengths, or ranges, of the slots 6233 and 6234, for example.

In various embodiments, as described above, the protective caps 6270 can be comprised of a soft or flexible material, for example, which can be configured to grip the ends of the staple legs 6221. In certain embodiments, the protective caps 6270 can be comprised of a bioabsorbable plastic, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and/or a biocompatible metal, such as titanium and/or stainless steel, for example. As illustrated in FIG. 189, in at least one embodiment, each cap 6270 can be unconnected to the other caps 6270. In certain other embodiments, one or more caps 6270 can be mounted to the retention matrix 6250. In at least one such embodiment, the caps 6270 can be connected to the retention matrix 6250 by at least one adhesive, for example, wherein the apertures 6271 in the caps 6270 can be aligned, or at least substantially aligned, with the retention apertures 6252 in the retention matrix 6270. In various embodiments, referring now to FIG. 200, a protective cap, such as a cap 6370, for example, can define an inner cavity, or dome, 6374 which can be configured to receive a tip of a staple leg 6221, for example, therein. In at least one such embodiment, the cap 6370 can comprise a bottom 6372 and an aperture 6371 extending through the bottom 6372. In various embodiments, the aperture 6371 can be defined by one or more deflectable members 6373 which can be configured to deflect when the staple leg 6221 is inserted therethrough. In certain embodiments, two or more caps 6370, for example, can be connected together to form an array of caps 6370. In at least one such embodiment, referring now to FIG. 201, a plurality of caps 6370 can be connected together by a sheet of material 6375. In certain embodiments, the sheet 6375 can be sufficiently rigid in order to maintain a desired arrangement and/or alignment of the caps 6370. In at least one embodiment, the caps 6370 can be comprised of a biocompatible metal, such as titanium and/or stainless steel, for example, and the sheet 6375 can be comprised of a bioabsorbable plastic, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, a sheet 6375 can be comprised of a bioabsorbable material including an anti-microbial agent, such as colloidal silver and/or triclosan, for example, stored and/or dispersed therein which can be released as the sheet 6375 is bioabsorbed, for example.

In various embodiments, further to the above, the sheet 6375 can be injection molded around the caps 6370 utilizing an injection molding process, for example, such that the caps 6370 are embedded in the sheet 6375. In certain other embodiments, the sheet 6375 can be molded utilizing an injection molding process, for example, wherein apertures 6376 can be formed in the sheet 6375 during the injection molding process and/or after the injection molding process utilizing a stamping process, for example. In either event, the caps 6370 can be inserted into and secured in the apertures 6376 utilizing a press-fit and/or snap-fit interconnection and/or at least one adhesive. In certain embodiments, each cap 6370 can comprise an annular groove surrounding, or at least partially surrounding, the perimeter of the cap 6370 which can be configured to receive the perimeter of an aperture 6376 therein. In certain embodiments, the sheet 6375 can be comprised of a flexible and/or pliable material which can permit relative movement between the caps 6370. In at least one such embodiment, the flexible sheet 6375 can be comprised of a rubber, plastic, and/or silicone material, for example, and the caps 6370 can be comprised of a rigid material, such as metal, for example. In at least one such embodiment, similar to the above, the flexible material can be molded around the caps 6370. In certain embodiments, the caps 6370 can be pressed into a pre-molded sheet 6375, for example. In various embodiments, the durometer of the flexible material can be selected to provide a desired stiffness of the sheet 6375. In certain embodiments, the sheet 6375 can be configured such that it comprises a flexible band. In any event, the sheet 6375 can facilitate the assembly of the caps 6370 into an end effector as a plurality of the caps 6370 can be positioned and/or aligned simultaneously within the end effector. Furthermore, the sheet 6375 connecting the caps 6370, once implanted, can strengthen or bolster the tissue along the staple line, for example. In addition to or in lieu of a sheet connecting the caps 6370, the caps 6370 can be connected together by a plurality of links. In at least one such embodiment, such links can be flexible and can permit relative movement between the caps 6370.

In various embodiments, referring now to FIGS. 204 and 205, a protective cap, such as cap 6470, for example, can comprise a forming surface which can be configured to deform a tip of a staple leg. In at least one such embodiment, the cap 6470 can comprise a base 6472 which can include an aperture 6471 extending therethrough. In various embodiments, the aperture 6471 can be configured to closely receive a staple leg, such as a staple leg 6221, for example, therein. In at least one embodiment, the aperture 6471 can be defined by a diameter or perimeter which can be equal to or larger than the diameter or perimeter of the staple leg 6221. In various embodiments, the cap 6470 can further comprise a cavity, or dome, 6474 which can be configured to receive the tip of the staple leg 6221 as it is inserted into the cap 6470. Referring primarily to FIG. 205, the cap 6470 can further comprise an anvil, or forming surface, 6473 which can be configured to deflect and deform the staple leg 6221. In various circumstances, the forming surface 6473 can be curved and/or concave, for example, and can be configured to curl the staple leg 6221 as it is inserted into the cap 6470. In certain embodiments, the staple leg 6221 can be sufficiently deformed such that it cannot be withdrawn through the aperture 6471 and, as a result, the cap 6470 can become locked to the staple leg 6221. In at least one such embodiment, the base 6472 of the cap 6470 can define a lip extending around the aperture 6471 which can prevent the deformed staple leg 6221 from being removed from the cavity 6474. In various circumstances, as a result of the above, one or more caps 6470 can prevent, or inhibit, a retention matrix, such as retention matrix 6250, for example, from backing up or being disengaged from the staples 6220. In various embodiments, although not illustrated, the cap 6470 can be symmetrically, or at least substantially symmetrically, formed, and the aperture 6471 can be located along a central axis 6479 extending through the cap 6470. In various alternative embodiments, referring again to FIG. 204, the aperture 6471 can be offset with respect to the central axis 6479. In at least one such embodiment, the offset aperture 6471 can allow the staple leg 6221 to contact a side of the forming surface 6473 and curl over to the other side of the forming surface 6473 instead of contacting the center of the forming surface 6473, as may occur in embodiments comprising a centered aperture 6471 mentioned above.

In various embodiments, as discussed above, a retention matrix, such as retention matrix 6250, for example, can be comprised of a sheet of material and a plurality of retention apertures 6252 extending therethrough. In at least some embodiments, the sheet of material comprising the retention matrix 6250 can be rigid or substantially inflexible. In certain other embodiments, a retention matrix can be comprised of an array of retention matrix elements and a plurality of flexible connectors, or links, connecting the retention matrix elements. In various embodiments, referring now to FIG. 206, a retention matrix, or a portion of retention matrix, 6550 can comprise a plurality of element bodies 6505 which can be connected together by one or more connecting links 6507. In at least one embodiment, each element body 6505 can comprise a plurality of deformable members 6553 which define a retention aperture 6552 therein. In certain embodiments, the element bodies 6505 and the connecting links 6507 of a retention matrix 6550 can be integrally formed and can comprise a unitary piece of material. In various embodiments, the retention matrix 6550 can be stamped or cast, for example, from a metal material, such as titanium and/or stainless steel, for example. In at least one embodiment, the retention matrix 6550 can be comprised of plastic, such as polyetheretherketone (PEEK), polypropylene which is marketed under the trade name Prolene, polyester, polyethylene terephthalate which is marketed under the trade names Ethibond and Mersilene, polyvinylidene fluoride, polyvinylidene fluoride-co-hexafluoropropylene, poly hexafluoropropylene-VDF which is marketed under the trade name Pronova, and/or long-chain aliphatic polymers Nylon 6 and Nylon 6,6 which are marketed under the trade names Ethilon & Nurolon, for example, and can be formed by an injection molding process, for example. In certain embodiments, the element bodies 6505 may not be integrally formed with the connecting links 6507. In various embodiments, a plurality of singular element bodies 6505 can be produced which are subsequently connected together and embedded in a retention matrix. In at least one such embodiment, the element bodies 6505 can be stamped from a metal material, such as titanium and/or stainless steel, for example, and placed in a plastic injection mold wherein a plastic material can be injected into the mold to form, one, a rim 6506 of material surrounding, or at least partially surrounding, the element bodies 6505 and, two, connecting links 6507 extending from the rims 6506. In certain other embodiments, one or more connector lattices can be formed comprising apertures defined within a plurality of rims 6506 wherein each such aperture can be configured to receive an element body 6505 therein. In at least one embodiment, each element body 6505 can comprise a circular, or at least substantially circular, outer perimeter and, similarly, each rim 6506 can define a circular, or at least substantially circular, aperture therein, wherein the diameter of the aperture can be equal to or smaller than the diameter of the element body 6505. In at least one such embodiment, the element bodies 6505 can be press-fit or embedded into the apertures in the rims 6505. In certain embodiments, the element bodies 6505 can be secured in the apertures utilizing at least one adhesive.

In various embodiments, further to the above, a retention matrix can comprise a plurality of element bodies 6505 and a plurality of connecting links 6507 which can connect the element bodies 6505 in any suitable array, such as those illustrated in FIGS. 207-210, for example. Regardless of the pattern of the array, in various embodiments, the connecting links 6507 can be configured to allow the element bodies 6505 and the retention apertures 6552 to move relative to one another. In at least one such embodiment, the lattice of element bodies 6505 and connecting links 6507 comprising the retention matrix 6550, once engaged with tissue, can be configured to stretch, twist, contract, and/or otherwise flex in order to permit at least some movement within the tissue yet, at the same time, resist larger movements thereof. In various embodiments, each connecting link 6507 can comprise a flexible member configured to stretch, twist, and/or contract in order to permit the retention matrix 6550 to flex intermediate the matrix retention elements 6505, for example. Referring again to FIG. 206, each link 6507 extending from a rim 6506 can be defined by a width which is narrower than the width of the element body 6505 and/or the rim 6506. In certain embodiments, referring to FIGS. 207-210, one or more links 6507 can comprise straight portions which extend along a line between adjacent element bodies 6506, for example. In at least one such embodiment, each link 6507 can comprise a first end attached to a first rim 6506 and a second end attached to a second rim 6506. In certain embodiments, referring once again to FIG. 206, two or more links 6507 can be connected to one another. In at least one such embodiment, two or more links 6507 can be connected at an intermediate hinge 6509, for example. In various embodiments, the hinge 6509 can comprise a reduction in cross-sectional thickness in one or more directions as compared to the cross-sectional thickness of the links 6507 which can permit the connected links 6507 to move relative to each other, for example. In certain embodiments, the retention matrix 6550 can further comprise hinges 6508 which can connect the links 6507 to the rims 6506 and permit relative movement between the links 6507 and the rims 6506. Similar to hinges 6509, hinges 6508 can comprise a reduction in cross-sectional thickness in one or more directions as compared to the cross-sectional thickness of the links 6507, for example.

In various embodiments, further to the above, the connected links 6507 can extend in different directions. In at least one such embodiment, a first link 6507 can extend in a first direction and a second link 6507 can extend in a second direction, wherein the first direction can be different than the second direction. In certain embodiments, the first link 6507 can extend along a first line and the second link 6507 can extend along a second line, wherein the first line and the second line can intersect each other at an angle, such as approximately 30 degrees, approximately 45 degrees, approximately 60 degrees, and/or approximately 90 degrees, for example. In various embodiments, the hinges 6508 and/or hinges 6509 can comprise living hinges which can permit the links 6507 to move relative to each other a number of times without breaking. In certain embodiments, the hinges 6508 and/or hinges 6509 can comprise frangible, or easily-breakable, portions which can break when flexed too far and/or flexed too many times. In at least one such embodiment, such frangible portions can permit one or more portions of the retention matrix 6550 to break away from another portion of the retention matrix 6550. In various embodiments, the hinges 6508 and/or hinges 6509, for example, can comprise sections of the retention matrix 6550 which are easier to incise than the other portions of the retention matrix 6550. More particularly, an implanted retention matrix, and the tissue fastened by the implanted retention matrix, may oftentimes by incised by a cutting member for various reasons and, in order to facilitate such cross-cutting, the hinges 6508 and/or hinges 6509 can provide avenues, or thin sections, through which a cutting member can more easily pass through the retention matrix 6550, for example. In various embodiments, further to the above, the connecting links 6507 can comprise one or more coined features or material upsets, for example, defined therein which can facilitate the bending, breakage, and/or incision of the connecting links 6507.

In various embodiments, a retention matrix can comprise a plurality of retention matrix elements, such as matrix element bodies 6505, for example, which can be embedded in a flexible sheet, or band, of material. In at least one embodiment, a flexible sheet of material can be formed from a bioabsorbable, elastomeric material, such as silicone, for example, wherein the flexible sheet can be produced with a plurality of apertures defined therein. In at least one such embodiment, a solid flexible sheet can be molded and a plurality of apertures can be punched out of the flexible sheet. In various alternative embodiments, the flexible sheet can be molded and the apertures defined therein can be formed during the molding process. In either event, the retention matrix elements 6505, for example, can be inserted into and retained within the flexible sheet. In certain other embodiments, similar to the above, the flexible sheet can be formed around the matrix elements 6505. In at least one embodiment, the flexible sheet can be comprised of a woven mesh, for example, and/or any other suitable material. Such a woven mesh, further to the above, may be easy to cross-cut.

In various embodiments, referring now to FIGS. 211 and 212, a fastener system comprising a retention matrix, such as retention matrix 6250, for example, can further comprise a cover, such as cover 6670, for example, which can cover the tips of the staple legs 6221 when they extend above the top surface 6257 of the retention matrix 6250. In various embodiments, the cover 6670 can be attached to the retention matrix 6250. In certain embodiments, the cover 6670 and/or the retention matrix 6250 can comprise retention features which can be configured to retain the cover 6670 to the retention matrix 6250. In at least one embodiment, at least one adhesive can be utilized to adhere the cover 6670 to the retention matrix 6250. In at least one embodiment, the cover 6670 can be comprised of a single layer, although the cover 6670 is illustrated as comprising two layers as described in greater detail further below. In various embodiments, referring primarily to FIG. 212, the tips of the staple legs 6221 can extend through a bottom surface 6673 of the cover 6670; however, the cover 6670 can comprise a sufficient thickness such that the staple tips do not extend through the top surface 6675 of the cover 6670. In at least one such embodiment, as a result, the tips of the staple legs 6221 may not protrude from the cover 6670. In various embodiments, the cover 6670 can comprise a plurality of layers. In at least one such embodiment, the cover 6670 can comprise a first layer 6671 and a second layer 6672. In at least one embodiment, the first layer 6671 and the second layer 6672 can be attached to one another wherein, in at least one embodiment, the second layer 6672 can comprise a bottom surface 6676 which is adhered to the first layer 6671. In various embodiments, the first layer 6671 and the second layer 6672 can comprise different thicknesses while, in certain embodiments, they can comprise the same thickness. In at least one embodiment, the first layer 6671 and the second layer 6672 can comprise substantially the same width and/or length. In alternative embodiments, the layers 6671 and 6672 can comprise different widths and/or lengths.

In various embodiments, further to the above, the first layer 6671 can be comprised of a compressible foam, mesh material, and/or hydrogel, for example, which can be incised by the staple legs 6211. In at least one embodiment, the second layer 6672 can be comprise of a tougher material, or skin, such as PGA and/or PDS, for example, and/or any suitable buttress material. In at least one such embodiment, the staple legs 6221 can be configured to penetrate the first layer 6671; however, in various embodiments, the staple legs 6221 may be unable to penetrate the second layer 6672. In certain embodiments, the second layer 6672 can be comprised of a material having a sufficient resiliency and/or toughness which can permit the second layer 6672 to be contacted and displaced by the staple leg 6221 but not be incised, or only marginally incised, by the staple tip of the staple leg 6221. Although not illustrated, a cover can comprise more than two layers wherein one or more of such layers may be penetration-resistant. In use, in at least one such embodiment, the retention matrix 6250 can be positioned against the tissue to be fastened and pushed downwardly such that the staple legs 6221 of the staples 6220 are pushed through the tissue T and the retention apertures 6252 in the retention matrix 6250 and enter into the first layer 6271 of the cover 6270. In various embodiments, the tips of the staple legs 6221 may not enter, or at least substantially enter, into the second layer 6272 of the cover 6270. After the retention matrix 6250 has been suitably positioned, the jaw 6240 can be opened and the cover 6670 and the retention matrix 6250 can detach from the jaw 6240 as illustrated in FIG. 211. As illustrated in FIG. 211, a jaw 6640 can be configured to hold more than one retention matrix 6250 and cover 6670. In at least one such embodiment, the jaw 6640 can comprise two channels 6679 which each can be configured to receive a cover 6670 therein and a retention matrix 6250 positioned thereover such that the tissue-contacting surface 6251 of each retention matrix 6250 depends downwardly from the bottom of the jaw 6240. In at least one such embodiment, a retention matrix 6250 and a cover 6270 can be housed in the jaw 6640 on each side of a knife slot 6678. In use, both retention matrices 6250 and covers 6670 can be deployed simultaneously and/or to the same depth with respect to opposing staple cartridges, such as cartridges 6200, for example, positioned thereacross. Thereafter, in various embodiments, the fastened tissue can be incised along a cutting line by a cutting member that traverses the knife slot 6678 wherein the jaw 6640 can then be re-opened. In certain embodiments, the covers 6670 may not be attached to the retention matrix 6250. In at least one such embodiment, the covers 6670 can be positioned in the channels 6679 and can be retained in the channels 6679 by the retention matrices 6250 which can be secured to the jaw 6640. In various embodiments, the each retention matrix 6250 can be wider and/or longer than their respective covers 6670 such that the retention matrices 6250 can retain the entirety of their covers 6670 in position. In certain embodiments, each retention matrix 6250 can comprise the same width and/or length as their respective cover 6670, for example.

In various embodiments, as described above, a fastener system can comprise a layer of material which can be attached to a retention matrix, such as retention matrix 6250, for example. In at least one embodiment, referring now to FIG. 215, a layer of material 6870 can be attached to the bottom surface 6251 of the retention matrix 6250. In certain embodiments, the layer 6870 and/or the retention matrix 6250 can comprise retention features which can be configured to retain the layer 6870 to the retention matrix 6250. In at least one embodiment, at least one adhesive can be utilized to adhere the layer 6870 to the retention matrix 6250. In any event, the layer 6870 can comprise a bottom, or tissue-contacting, surface 6873 which can be configured to contact the tissue T when the retention matrix 6250 is moved downwardly toward the staples 6220 to engage the retention apertures 6252 with the staple legs 6221. In at least one such embodiment, the layer 6870 can be comprised of a compressible material, such as a bioabsorbable foam, for example, which can be compressed between the bottom surface 6251 of the retention matrix 6250 and the tissue T. In various embodiments, the layer 6870 can further comprise at least one medicament stored and/or absorbed therein which can be expressed from the layer 6870 as the layer 6870 is compressed. In at least one embodiment, the medicament can comprise at least one tissue sealant, hemostatic agent, and/or anti-microbial material, such as ionized silver and/or triclosan, for example. In various embodiments, the compression of the layer 6870 can squeeze the medicament from the layer 6870 such that the entirety of, or at least a significant portion of, the surface of the tissue T is covered with the medicament. Furthermore, as the layer 6870 is compressed and the staple legs 6221 penetrate the tissue T and the layer 6870, the medicament can flow down the staple legs 6221 and treat the tissue that has just been incised by the staple legs 6221, for example. In various embodiments, the body of the retention matrix 6250 can comprise a first layer which is comprised of a biocompatible material, such as titanium and/or stainless steel, for example, and the bottom layer 6870 can comprise a second layer comprised of a bioabsorbable material, such as oxidized regenerated cellulose (ORC), biologically active agents like fibrin and/or thrombin (either in their liquid state or freeze dried), glycerin, absorbable porcine gelatin in either flue or foam configurations, and/or anti-microbials, such as ionized silver and/or triclosan, for example. Additional bioabsorbable materials can comprise Surgicel Nu-Knit, Surgicel Fibrillar, collagen/ORC which is a hybrid with a built in collagen matrix and is marketed under the trade name Promogran, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. Although only one layer 6870 is illustrated in FIG. 215, any suitable number of layers could be used. In at least one embodiment, a first layer comprising a first medicament could be attached to the retention matrix 6250 and a second layer comprising a second, or different, medicament could be attached to the first layer. In at least one such embodiment, a plurality of layers could be used wherein each layer can comprise a different medicament and/or a different combination of medicaments contained therein.

In various embodiments, referring now to FIG. 213, a fastener system can comprise a layer of material 6770 attached to the bottom surface 6251 of the retention matrix 6250. In certain embodiments, the layer 6770 and/or the retention matrix 6250 can comprise retention features which can be configured to retain the layer 6770 to the retention matrix 6250. In at least one embodiment, at least one adhesive can be utilized to adhere the layer 6770 to the retention matrix 6250. In any event, the layer 6770 can comprise a bottom, or tissue-contacting, surface 6773 which can be configured to contact the tissue T when the retention matrix 6250 is moved downwardly toward the staples 6220 to engage the retention apertures 6252 with the staple legs 6221. In at least one such embodiment, the layer 6770 can be comprised of a compressible material, such as a bioabsorbable foam, for example, which can be compressed between the surface 6251 of the retention matrix 6250 and the tissue T. In various embodiments, the layer 6770 can further comprise one or more encapsulations, or cells, 6774 which can be configured to store at least one medicament therein. In certain embodiments, referring to FIG. 214, the encapsulations 6774 can be aligned, or at least substantially aligned, with the retention apertures 6252 such that, when the staple legs 6221 are pushed through the tissue T and the layer 6770, the staple legs 6221 can puncture and/or otherwise rupture the encapsulations 6774. After the encapsulations 6774 have been ruptured, the at least one medicament M stored in the encapsulations 6774 can flow out onto the tissue T. In at least one such embodiment, the medicament M can comprise a fluid which can flow or wick down the staple legs 6221 and treat the tissue T that was just incised by the staple legs. As a result of the above, the medicament stored within the encapsulations 6774 can provide a localized treatment to the tissue. In certain embodiments, the encapsulations 6774 in the sheet 6770 can comprise different medicaments stored therein. For example, a first group of encapsulations 6774 can comprise a first medicament, or a first combination of medicaments, stored therein and a second group of encapsulations can comprise a different medicament, or a different combination of medicaments, stored therein. In various embodiments, the layer 6770 can be comprised of a flexible silicone sheet and the encapsulations 6774 can represent voids in the silicone sheet. In at least one such embodiment, the silicone sheet can comprise two layers that can be attached to one another wherein the encapsulations 6774 can be defined between the two layers. In various embodiments, the layer 6770 can comprise one or more thin sections or weakened portions, such as partial perforations, for example, which can facilitate the incision of the layer 6770 and the rupture of the encapsulations 6774 by the legs 6221. In certain embodiments, at least a portion of the encapsulations 6774 can be positioned within domes 6777, wherein the domes 6777 can extend upwardly from the sheet 6770. In at least one such embodiment, the domes 6777 and/or at least a portion of the encapsulations 6774 can be positioned within the pockets 6201 formed within the retention matrix 6250. In certain embodiments, the encapsulations 6774 may comprise discrete cells which are unconnected to each other. In certain other embodiments, one or more of the encapsulations 6774 can be in fluid communication with each other via one or more passageways, conduits, and/or channels, for example, extending through the layer 6770. The disclosure of U.S. Pat. No. 7,780,685, entitled ADHESIVE AND MECHANICAL FASTENER, which issued on Aug. 24, 2010, is hereby incorporated by reference in its entirety.

In various embodiments, further to the above, a staple cartridge comprising a cartridge body, staples, and/or an alignment matrix therein can be loaded into a first jaw of an end effector and, similarly, a retention matrix and/or one or more covers can be loaded into a second jaw of the end effector. In certain embodiments, referring now to FIG. 216, an instrument, such as cartridge loader 6990, for example, can be used to insert two or more fastener cartridges into an end effector at the same. In at least one embodiment, the cartridge loader 6990 can comprise a handle 6991 and a cartridge carrier 6992, wherein the cartridge carrier 6992 can comprise a first retention portion configured to retain the cartridge body 6210 of the staple cartridge 6200 thereto and, in addition, a second retention portion configured to retain a cartridge body 6980 which supports, one, a plurality of protective caps 6270 therein and, two, a retention matrix 6250 along the bottom surface thereof, for example. In various embodiments, the first and second retention portions can each comprise one or more retention members configured to releasably engage the cartridge bodies 6210 and 6980. In use, referring now to FIGS. 217 and 218, an end effector can comprise a first, or bottom, jaw 6230 and a second, or top, jaw 6940, wherein the staple cartridge 6200 can be loaded into the first jaw 6230 and the cartridge body 6980 can be loaded into the second jaw 6940. In various circumstances, the top jaw 6940 can be rotated from an open position (FIG. 217) to a closed position (FIG. 218) by an actuator 6235, wherein the operation of the actuator 6235 is described above and is not repeated herein for the sake of brevity. Once the top jaw 6940 is in its closed position, referring now to FIG. 218, the distal end 6993 of the cartridge carrier 6992 can be inserted into the end effector such that the staple cartridge 6200 is slid through the distal end 6938 of the first jaw 6930 and into a first attachment portion, or channel, 6939 in the first jaw 6230. Similarly, the distal end 6993 of the cartridge carrier 6992 can be inserted into the end effector such that the cartridge body 6980 is slid through the distal end 6948 of the second jaw 6940 and into a second attachment portion, or channel, 6949 in the second jaw 6940. A surgeon, or other clinician, holding the handle 6991 of the cartridge loader 6990 can push the staple cartridge 6200 and the cartridge body 6980 through the channels 6939 and 6949, respectively, until the staple cartridge 6200 and the cartridge body 6980 are fully seated therein.

As the staple cartridge 6200 and the cartridge body 6980 are being seated, the staple cartridge 6200 and the cartridge body 6980 can each engage one or more retention portions in their respective jaws 6230 and 6940, as described in greater detail further below. In any event, once the staple cartridge 6200 and the cartridge body 6980 have been seated, referring now to FIG. 219, the cartridge loader 6990 can be detached from the staple cartridge 6200 and the cartridge body 6980 and removed from the end effector. In at least one such embodiment, the retention force holding the staple cartridge 6200 in the first jaw 6230 can be greater than the retention force holding the staple cartridge 6200 to the cartridge carrier 6992 such that, as the cartridge carrier 6992 is pulled distally out of the end effector, the staple cartridge 6200 can remain behind in the first jaw 6230. Similarly, the retention force holding the cartridge body 6980 in the second jaw 6940 can be greater than the retention force holding the cartridge body 6940 to the cartridge carrier 6992 such that, as the cartridge carrier 6992 is pulled distally out of the end effector, the cartridge body 6940 can remain behind in the second jaw 6940. Once the cartridge loader 6990 has been removed from the end effector, the loaded first jaw 6230 and the loaded second jaw 6940 can be positioned relative to the tissue T that is to be stapled. Referring now to FIG. 220, the second jaw 6940 can be moved from an open position (FIG. 219) to a fired position (FIG. 220) in order to engage the retention matrix 6250 and the plurality of protective caps 6270 carried by the cartridge body 6980 with the staples 6220 positioned within the staple cartridge 6200.

Referring now to FIGS. 221 and 222, the second jaw 6940 can be re-opened and the plurality of protective caps 6270 and the retention matrix 6250 can detach from the cartridge body 6980 such that the caps 6270 and the retention matrix 6250 can remain engaged with the tissue T and the staple cartridge 6200. In at least one embodiment, the cartridge body 6980 can comprise a plurality of pockets in which the plurality of caps 6270 can be removably positioned and one or more retention slots configured to removably retain the retention matrix 6250 thereto. In various embodiments, the retention members of the second jaw 6940 engaged with the cartridge body 6980 can retain the cartridge body 6980 in the second jaw 6940 after the second jaw 6940 has been opened. In certain embodiments, the cartridge body 6980 can be configured to tear as the second jaw 6940 is opened such that a portion of the cartridge body 6980 is implanted with the caps 6270 and the retention matrix 6250 and a portion of the cartridge body 6980 remains in the second jaw 6940. Similarly, referring again to FIGS. 221 and 222, the retention members of the first jaw 6230 engaged with the cartridge body 6210 can retain the cartridge body 6210 in the first jaw 6230 after the second jaw 6940 has been opened. In certain embodiments, the cartridge body 6210 can be configured to tear as the first jaw 6230 is pulled away from the implanted cartridge 6200 such that a portion of the cartridge body 6210 is implanted with the staples 6220 and alignment matrix 6260 and a portion of the cartridge body 6210 remains in the first jaw 6230. In various embodiments, referring now to FIGS. 223-225, a staple cartridge, such as staple cartridge 6900, for example, can comprise one or more longitudinal retention slots 6913 extending along the length of the cartridge body 6910 which, when the staple cartridge 6900 is inserted into a jaw 6930, for example, can be configured to receive one or more longitudinal retention rails 6916 extending from the jaw 6930 therein. In use, in at least one embodiment, an end of the retention slots 6913 can be aligned with the distal ends of the retention rails 6916 before the staple cartridge 6900 is slid through the distal end 6938 of the retention channel 6939, for example.

In various embodiments, referring again to FIG. 225, the jaw 6940 can comprise two retention channels 6949, wherein each retention channel 6949 can be configured to receive a cartridge body 6980 comprising a plurality of caps 6270 and a retention matrix 6250 therein. In certain embodiments, each cartridge body 6980 can comprise one or more longitudinal retention shoulders 6917 which can be configured to be slid along one or more longitudinal retention rails 6918 of the second jaw 6940 as the cartridge bodies 6980 are inserted into their respective retention channels 6949 in jaw 6940. In various embodiments, the retention rails 6918 and the retention shoulders 6917 can co-operate to retain the cartridge body 6980 in the second jaw 6940 as the cartridge bodies 6980 are detached from the caps 6270 and the retention matrix 6250 stored therein. In various embodiments, referring now to FIG. 224, the second jaw 6940 can further comprise one or more distal bumps, or retention members, 6915 extending therefrom which can be configured to removably lock the cartridge bodies 6980 in their respective retention channels. In at least one such embodiment, the second jaw 6940 can comprise a distal bump 6915 configured and positioned relative to each retention channel 6949 such that each cartridge body 6980 can flex around the bumps 6915 as the cartridge bodies 6980 are being inserted into the channels 6949 wherein, just as the cartridge bodies 6915 are being fully seated in the channels 6949, the distal ends of the cartridge bodies 6980 can clear and snap over the bumps 6915. In order to remove the cartridge bodies 6980 after they have been expended, as described above, the cartridge bodies 6980 can be pulled back over the bumps 6915 and removed from the retention channels 6949. Similar to the above, the first jaw 6930 can comprise one or more distal retention bumps 6914 extending therefrom which can be configured to be received in one or more retention grooves, or slots, 6912 (FIG. 223) in the cartridge body 6910 when the staple cartridge 6900 has been fully seated.

In various embodiments, further to the above, a first fastener cartridge comprising a plurality of first fasteners positioned therein can be positioned in a first jaw of a surgical fastening device and a second fastener cartridge comprising a plurality of second fasteners positioned therein can be positioned in a second jaw of the surgical fastening device. In use, the first jaw and/or the second jaw can be moved toward the other in order to engage the first fasteners with the second fasteners and secure tissue therebetween. In certain embodiments, the first fastener cartridge and the second fastener cartridge can be engaged with each other as the first fasteners are engaged with the second fasteners. In at least one embodiment, the body of the first fastener cartridge can be comprised of a first compressible material and the body of the second fastener cartridge can be comprised of a second compressible material, wherein the first body and/or the second body can be compressed against the tissue being fastened. After the tissue has been fastened, the first jaw can be moved away from the implanted first fastener cartridge and the second jaw can be moved away from the implanted second fastener cartridge. Thereafter, the first jaw can be reloaded with another first fastener cartridge, or the like, and the second jaw can be reloaded with another second fastener cartridge, or the like, and the surgical fastening instrument can be reused. While staples can be used in some embodiments, other embodiments are envisioned comprising other types of fasteners, such as two-part fasteners which are locked together when they are engaged with one another, for example. In at least one such embodiment, the first fastener cartridge can comprise a first storage portion for storing the first fastener portions and the second fastener cartridge can comprise a second storage portion for storing the second fastener portions. In various embodiments, the fastening systems described herein can utilize fasteners comprising any suitable type of material and/or form. In certain embodiments, the fasteners can comprise penetrating members. Such penetrating members could be comprised of a polymer, a composite, and/or a multi-layered substrate, for example. An example of a multi-layered substrate could be a wire or a sheet substrate with an elastomeric or polymeric coating. It could be a thin sheet formed such that penetrating members are oriented perpendicular, or at least substantially perpendicular, to the connecting member. The penetrating members could comprise a rectangular profile, semi-circular profile, and/or any beam profile. In various embodiments, the fasteners described herein can be manufactured utilizing any suitable process, such as a wire extruding process, for example. Another possibility is the use of microfabrication to create hollow penetrating members. These penetrating members could be fabricated from a process which is different than a wire extruded process and could use a combination of materials.

As described above, the tips of staple legs protruding through a retention matrix can be covered by one or more caps and/or covers. In certain embodiments, the tips of the staple legs can be deformed after they have been inserted through the retention matrix. In at least one embodiment, a jaw holding the retention matrix can further comprise anvil pockets positioned above and/or aligned with the retention apertures which can be configured to deform the staple legs as they protrude above the retention matrix. In various embodiments, the staple legs of each staple can be curled inwardly toward each other and/or toward the center of the staple, for example. In certain other embodiments, one or more of the staple legs of a staple can be curled outwardly away from the other staple legs and/or away from the center of the staple. In various embodiments, regardless of the direction in which the staple legs are curled, the tips of the staple legs can contact the body of the retention matrix and may not re-enter the tissue that has been fastened by the staples. In at least one embodiment, the deformation of the staple legs after they have passed through the retention matrix can lock the retention matrix in position.

In various embodiments, referring now to FIGS. 226 and 227, a surgical stapling instrument, such as surgical stapler 7000, for example, can comprise a first jaw 7030 and a second jaw 7040, wherein the second jaw 7040 can be moved toward and away from the first jaw 7030 by the movement of actuator 6235. The operation of actuator 6235 is described above and is not repeated herein for the sake of brevity. In various embodiments, the first jaw 7030 can comprise a distal end 7031 and a proximal end 7032, wherein the first jaw 7030 can define a channel extending between the distal end 7031 and the proximal end 7032 which is configured to receive a staple cartridge. For the purposes of illustration, the cartridge body of such a staple cartridge is not depicted in FIG. 226, although such a staple cartridge can comprise a cartridge body, staples 6220 positioned within the cartridge body, and staple drivers 7012 positioned underneath the staples 6220. In certain embodiments, although not illustrated in FIG. 226 for the sake of clarity, the second jaw 7040 can be configured to hold a retention matrix, such as retention matrix 6250, for example, over the staples 6220 and/or move the retention matrix into engagement with the legs of the staples 6220 as described above. In at least one embodiment, the surgical stapler 7000 can further comprise a sled 7010 positioned in the first jaw 7030 which can be slid from the distal end 7031 of the first jaw 7030 toward the proximal end 7032, for example, and lift the staple drivers 7012, and the staple 6220 supported thereon, toward the retention matrix and the second jaw 7040. In various other embodiments, the sled 7010 can be moved from the proximal end 7032 toward the distal end 7031 in order to deploy the staples 6020, for example. In at least one embodiment, the sled 7010 can comprise one or more inclined ramps, or cams, 7011 which can be configured to slide underneath the staple drivers 7012 and lift the staple drivers 7012 upwardly. In various embodiments, the surgical stapler 7000 can further comprise a pull, or push, rod operably coupled to the sled 7010 which can be moved proximally and/or distally by an actuator located on a handle and/or shaft of the surgical stapler 7000, for example.

In various embodiments, referring again to FIG. 226, the second jaw 7040 of the surgical stapler 7000 can comprise a frame 7041, a distal end 7048, and a proximal end 7049 positioned opposite the distal end 7048. In certain embodiments, the second jaw 7040 can further comprise a guide system comprising one or more guide rails, such as guide rails 7045 and 7046, for example, extending along the longitudinal axis of the frame 7041 which, as described in greater detail further below, can be configured to guide one or more anvils, or cams, which can engage and deform the staple legs of the staples 6220 after the staple legs 6221 of the staples 6220 have passed through the retention matrix. In at least one such embodiment, the guide rails 7045 and 7046 can comprise a guide wire or cable which extends along a top portion or surface of the frame 7041, around a distal post 7047, and back along the top portion or surface of the frame 7041, for example. In various embodiments, as mentioned above and referring primarily now to FIGS. 228 and 230, the second jaw 7040 can further comprise one or more anvils, or cams, such as first anvil 7050 and second anvil 7060, for example, which can be moved longitudinally along the second jaw 7040 in order to deform the legs of the staples 6220 after they have passed through the retention matrix. In at least one embodiment, the surgical stapler 7000 can further comprise a first anvil driver, or actuator, 7051 connected to and/or operably coupled to the first anvil 7050 which can be configured to pull the first anvil 7050 proximally and/or push the first anvil 7050 distally. Similarly, in at least one embodiment, the surgical stapler 7000 can further comprise a second anvil driver, or actuator, connected to and/or operably coupled to the second anvil 7060 which can be configured to push the second anvil 7060 distally and/or pull the second anvil 7060 proximally. In various embodiments, the first anvil 7050 can comprise guide slots 7052 and the second anvil 7060 can comprise guide slots 7062 which can each be configured to slidably receive guide rail 7045 or guide rail 7046 therein. In at least one such embodiment, the guide rails 7045 and 7046 can be closely received within the guide slots 7052 and 7062 such that relative lateral, or side-to-side, movement therebetween can be prevented, or at least limited.

In certain embodiments, further to the above, the first anvil 7050 can be pulled proximally and the second anvil 7060 can be pulled distally. In at least one embodiment, referring to FIG. 226, the guide rails 7045 and 7046 and the distal post 7047 can comprise a pulley system configured to pull the second anvil 7060 distally and/or pull the second anvil 7060 proximally. In at least one such embodiment, the guide rail 7045 and the guide rail 7046 can comprise a continuous wire or cable extending around the distal post 7047, wherein a portion of the continuous wire can be pulled in order to cycle the wire around the distal post 7047. In various embodiments, the guide rail 7046, for example, can be mounted to the second anvil 7060 such that, when the continuous cable is cycled in a first direction, the second anvil 7060 can be pulled distally toward the distal end 7048 of the jaw 7040 and, when the continuous cable is cycled in a second, or opposite, direction, the second anvil 7060 can be pulled proximally toward the proximal end 7049. In at least one embodiment, referring now to FIG. 228, the guide rail 7046 can be secured within a guide slot 7062 such that a pulling force can be transmitted therebetween. In at least one such embodiment, the guide rail 7045 can be configured to slide within the other guide slot 7062. In various embodiments, the first anvil 7050 may operate independently of the second anvil 7060 and the pulley system and the guide slots 7052 defined in the first anvil 7050 may be configured to slidably receive the guide rails 7045 and 7046 such that relative movement is permitted therebetween. In various embodiments, the continuous cable comprising guide rails 7045 and 7046 can be sufficiently flexible in order to accommodate the opening and closing of the top jaw 7040. The continuous cable can also be sufficiently flexible in order to accommodate the vertical movement of the second anvil 7060 toward and away from the bottom jaw 7030, which is described in greater detail further below.

In various embodiments, referring again to FIGS. 228 and 230, the first anvil 7050 can comprise cam followers 7055 extending therefrom which can be configured to ride in one or more cam slots, or guide slots, such as cam slot 7070 (FIG. 231), for example, defined in the frame 7041 of the second jaw 7040. More particularly, in at least one embodiment, the frame 7041 can comprise a first cam slot 7070 extending longitudinally along a first side of the frame 7041 and a second cam 7070 extending longitudinally along a second, or opposite, side of the frame 7041, wherein the cam followers 7055 extending from a first side of the first anvil 7050 can ride in the first cam slot 7070 and the cam followers 7055 extending from a second side of the first anvil 7050 can ride in the second cam slot 7070. In at least one such embodiment, the contours of each cam slot 7070 can be identical, or at least substantially identical, and can be aligned, or at least substantially aligned, with one another. Similarly, in various embodiments, the second anvil 7060 can comprise cam followers 7065 extending therefrom which can be configured to ride in the cam slots 7070 (FIG. 231) defined in the frame 7041 of the second jaw 7040. More particularly, in at least one embodiment, the cam followers 7065 extending from a first side of the second anvil 7060 can ride in the first cam slot 7070 and the cam followers 7065 extending from a second side of the second anvil 7060 can ride in the second cam slot 7070. In use, the cam followers 7055 of the first anvil 7050 and the cam followers 7065 of the second anvil 7060 can slide within the cam slots 7070 such that first anvil 7050 and the second anvil 7060 follow the contours of the cam slots 7070 as the first anvil 7050 and the second anvil 7060 are pulled proximally and/or pushed distally. In various embodiments, each cam slot 7070 can comprise a plurality of dwell, or upper, portions 7071 and a plurality of driver, or lower, portions 7072 which can be configured to move the anvils 7050 and 7060 vertically, i.e., toward and away from the bottom jaw 7030, at the same time that the anvils 7050 and 7060 are being moved longitudinally, i.e., between the distal end 7048 and the proximal end 7049 of the frame 7041, as described in greater detail further below.

When the surgical stapler 7000 is in an unfired condition, referring to FIG. 231, the first anvil 7050 can be positioned at the distal end 7048 of the frame 7041 and the second anvil 7060 can be positioned at the proximal end 7049 of the frame 7041; furthermore, referring now to FIG. 232, the staples 6220 positioned in the first jaw 7030 may not yet be inserted into the tissue T and/or the retention matrix positioned thereabove when the surgical stapler 7000 is in an unfired condition. In use, referring now to FIG. 233, the staples 6220 can be driven upwardly within the staple cavities 7033 of a staple cartridge by the staple drivers 7012 and, in addition, the first anvil 7050 can be moved proximally from the distal end 7048 of the frame 7041 toward the distal end 7049 in order to engage the staple legs 6221 of the staples 6220. In at least one embodiment, the staples 6220 can be driven upwardly before the first anvil 7050 is engaged with the staple legs 6221 thereof. In various embodiments, all of the staples 6220 may be deployed upwardly by the sled 7010 before the first anvil 7050 is advanced into contact with the staple legs 6221 or, alternatively, the sled 7010 may be moved proximally at the same time that the first anvil 7050 is moved proximally, although the sled 7010 may sufficiently lead the first anvil 7050 in order to deploy the staples 6220 ahead of the first anvil 7050. In various embodiments, as illustrated in FIG. 233, the cam slots 7070 can be configured and arranged such that the forming surfaces, such as forming, or camming, surfaces 7053 and 7054, for example, of the first cam 7050 can contact at least some of the staple legs 6221 when the first cam 7050 is passing through a dwell, or upper, position. In various circumstances, the cam followers 7055 of the first anvil 7050 can each be positioned in a dwell portion 7071 of the cam slots 7070 such that the forming surfaces 7053 and 7054 are in a raised position and such that the staple legs 6221 are only partially deformed when the anvil 7050 passes thereby in the dwell position. As the first cam 7050 is moved further along the cam slots 7070, as illustrated in FIG. 234, the cam followers 7055 of the first anvil 7050 can be driven into driven, or lower, portions 7072 of the cam slots 7070 such that the forming surfaces 7053 and 7054 are moved vertically downwardly toward the staple legs 6021 in order to drive the staple legs 6021 into their finally formed configurations. Thereafter, as the first anvil 7050 is progressed further along the cam slots 7070, the first anvil 7050 can be driven vertically upwardly into another set of dwell portions 7071 of the cam slots 7070. As illustrated in FIGS. 233 and 234, the reader will note that the first anvil 7050 may only engage some of the staple legs and not others. In at least one such embodiment, the first anvil 7050 can be configured to only deform a group of staple legs comprising the distal staple legs 6221 of the staples 6220, for example. In at least one such embodiment, the first anvil 7050 can be configured to deform the distal staple legs 6221 toward the center of the staples 6220. In various embodiments, each proximal staple leg 6221 can be contacted twice by the first anvil 7050, i.e., by a first forming surface 7053 and by a second forming surface 7054 aligned with the first forming surface 7053. In at least one such embodiment, the first forming surfaces 7053 can deform the distal staple legs 6221 into a partially-deformed configuration when the first anvil 7050 is in a dwell, or upper, position and the second forming surfaces 7054 can deform the distal staple legs 6221 into a fully-formed configuration when the first anvil 7050 is moved into a driven, or lower, position. In various embodiments, referring now to FIGS. 228 and 229, the first anvil 7050 can comprise a plurality of first forming surfaces 7053 and a plurality of second forming surfaces 7054 in order to deform the distal staple legs 6221 of staples 6220 when the staple legs 6221 are arranged in more than one row or line. In various embodiments, as described in greater detail further below, the proximal staple legs 6221 of the staples 6020 can be deformed by the second anvil 7060, for example.

In various embodiments, further to the above, the first anvil 7050 can be moved from the distal end 7048 of the frame 7041 to the proximal end 7049 in order to deform all of the distal staple legs 6221 of the staples 6220. As the reader will note, the first anvil 7050 can be moved up and down relative to the undeformed proximal staple legs 6221 and, in order to accommodate such relative movement, in various embodiments, the first anvil 7050 can comprise one or more clearance slots 7057 (FIG. 230) which can be configured to receive the unbent proximal staple legs 6221 as the first anvil 7050 bends the distal staple legs 6221. Similarly, referring again to FIG. 228, the second anvil 7060 can comprise a clearance slot 7067 which can be configured to accommodate the vertical movement of the first cam actuator 7051 which moves up and down as the first anvil 7050 is moved between its dwell and driven positions as described above. After all of the distal staple legs 6221 have been bent, in at least one embodiment, the second anvil 7060 can be moved from the proximal end 7049 of the frame 7041 to the distal end 7048 by the anvil actuator 7061. Similar to the above, referring now to FIG. 235, the cam followers 7065 of the second anvil 7060 can slide within the cam slots 7070 such that the second anvil 7060 is moved between dwell, or upper, positions and driven, or lower, positions in order to deform the proximal staple legs 6221 inwardly toward the centers of the staples 6220, for example. Similar to the above, the second anvil 7060 can comprise a plurality of first forming, or camming, surfaces 7063 and a plurality of second forming, or camming, surfaces 7064 which can each be configured to at least partially deform and/or completely deform one or more of the proximal staple legs 6021. Referring again to FIG. 229, the second anvil 7060 can comprise a plurality of first forming surface 7063 and a plurality of second forming surfaces 7064 which can be configured to deform the proximal staple legs 6221 of staples 6220 arranged in a plurality of rows, or lines, for example. As also illustrated in FIG. 229, the first forming surfaces 7063 and the second forming surfaces 7064 of the second anvil 7060 may not be aligned with the first forming surfaces 7053 and the second forming surfaces 7054 of the first anvil 7050 wherein, as a result, the proximal legs 6221 of the staples 6220 may be positioned in different rows, or lines, than the distal legs 6221 of the staples 6220. As the reader will also note, the second anvil 7060 can push the first anvil 7050 as the second anvil 7060 is moved distally. In at least one such embodiment, the second anvil 7060 can push the first anvil 7050 back into the distal end 7048 of the frame 7041 such that the first anvil 7050 can be returned to its initial, or unfired, position. After all of the proximal staple legs 6221 of the staples 6220 have been deformed, the second anvil 7060 can be retracted proximally and returned to its initial, or unfired, position. In this way, the surgical stapler 7000 can be reset such that a new staple cartridge can be positioned in the first jaw 7030 and a new retention matrix can be positioned in the second jaw 7040 in order to use the surgical stapler 7000 once again.

In various embodiments, as described above, a surgical stapler can comprise two or more anvils which can travel longitudinally in order to engage the legs of a plurality of staples in a transverse direction. In certain embodiments, a surgical stapler can comprise an anvil which is moved proximally, for example, in order to deform a first group of staple legs and distally, for example, in order to deform a second group of staple legs. In at least one such embodiment, such an anvil can comprise forming surfaces facing proximally and forming surfaces facing distally, for example.

In various embodiments, referring now to FIG. 236, an anvil, such as anvil 7140, for example, can comprise a bottom, or tissue-contacting, surface 7141 and a plurality of forming pockets 7142 defined therein. In at least one embodiment, the anvil 7140 can comprise more than one plate, such as pocket plates 7143, for example, which can be welded into a frame 7144. In at least one such embodiment, each pocket plate 7143 can be positioned in a plate channel 7145 in the frame 7144 and welded to the frame 7144 through a weld slot 7146 extending through the frame 7144 in order to form a longitudinal weld 7147. In various circumstances, the longitudinal weld 7147 can comprise a continuous weld extending along the entire length of the weld slot 7146 or a series of spaced-apart spot welds extending along the length thereof, for example. In various embodiments, each pocket plate 7143 can comprise two or more plate portions that have been welded together. In at least one such embodiment, each pocket plate 7143 can comprise a first plate portion 7143a and a second plate portion 7143b which can be welded together along a seam 7148. In various embodiments, the first plate portion 7143a and the second plate portion 7143b of each plate 7143 can be welded together before the plates 7143 are welded into the plate channels 7145 in the frame 7144. In at least one such embodiment, the first plate portion 7143a and the second plate portion 7143b can comprise co-operating profiles, such as the toothed profiles illustrated in FIG. 236, for example, which can be fitted together to form a tight seam 7148. In at least one embodiment, each plate 7143 can comprise a height of approximately 0.02", for example, which can be taller than the depth of the plate channels 7145 such that the tissue-contacting surfaces 7141 thereof extend from the frame 7044 of the anvil 7040. In certain embodiments, referring now to FIG. 237, the plates 7143 can be connected together by at least one weld 7149 at the distal ends of the plates 7143, for example.

As illustrated in FIGS. 236 and 237, each pocket plate 7143 can comprise a plurality of forming pockets 7142 defined therein. In various embodiments, the forming pockets 7142 can be formed in the plates 7143 by any suitable manufacturing process, such as a grinding process and/or electrode-burning process, for example. In at least one such embodiment, referring now to FIGS. 238 and 239, each forming pocket 7142 can be manufactured by first forming a deep well 7150, then forming an arcuate or curved surface 7151 surrounding the deep well 7150, and then forming a staple leg guide groove 7152 in the curved surface 7151, for example. In various other embodiments, these steps can be performed in any suitable order. In various embodiments, referring now to FIG. 240, the staple forming pockets 7142 can be formed such that the inner edges 7153 of the forming pockets are separated by a consistent, or at least substantially consistent, gap 7154. In at least one such embodiment, the gap 7154 can be approximately 0.008", for example. Furthermore, in at least one such embodiment, the forming pockets 7142 can be positioned along two or more rows, or lines, the centerlines of which can be separated by a consistent, or at least substantially consistent, spacing 7155. In at least one such embodiment, the spacing 7155 between the centerlines can be approximately 0.035", for example. In various embodiments, referring again to FIG. 240, each forming pocket 7142 can taper between a narrow width 7156 and a wide width 7157. In at least one such embodiment, the narrow width 7156 can be approximately 0.045" and the wide width 7157 can be approximately 0.075", for example. In various embodiments, the plates 7143 can be comprised of the same material as the frame 7144. In at least one such embodiment, the plates 7143 and the frame 7144 can both be comprised of stainless steel, such as a 300 series or a 400 series stainless steel, for example, and/or titanium, for example. In various other embodiments, the plates 7143 and the frame 7144 can be comprised of different materials. In at least one such embodiment, the plates 7143 can be comprised of a ceramic material, for example, and the frame 7144 can be comprised of a stainless steel and/or titanium, for example. In various circumstances, depending on the materials used, at least one brazing process could be used to secure the plates 7143 in the frame 7144 in addition to or in lieu of the welding processes described above, for example.

In various embodiments, referring now to FIGS. 241-243, an anvil 7240 can comprise a frame 7244 and a plurality of pocket plates 7243 which can be inserted into the frame 7244. Similar to the above, each pocket plate 7243 can comprise a plurality of forming pockets 7242 defined therein. In at least one embodiment, the anvil frame 7244 can comprise retention slots 7246 defined therein which can each be configured to receive a retention rail 7247 extending from a pocket plate 7243. In order to assemble the pocket plates 7243 to the anvil frame 7244, the side walls 7245 of the anvil frame 7244 can be flexed or splayed outwardly, as illustrated in FIG. 242, in order to widen the retention slots 7246 such that each retention slot 7246 can receive a retention rail 7247 of a pocket plate 7243 therein. Once the retention rails 7247 have been positioned in the retention slots 7246, the side walls 7245 can be released, as illustrated in FIG. 243, thereby allowing the frame 7244 to resiliently contract and/or return to its unflexed state. In such circumstances, the retention slots 7246 can contract and thereby capture the retention rails 7247 therein. In certain embodiments, the retention rails 7247 and/or the retention slots 7246 can comprise one or more co-operating tapered surfaces which, after the flexed retention slots 7246 have been released, can form a taper-lock engagement which can retain the retention rails 7247 in the retention slots 7246. Similar to the above, the pocket plates 7243 can be comprised of the same material as or a different material than the frame 7244. In at least one such embodiment, the plates 7243 can be comprised of a ceramic material, for example, and the frame 7244 can be comprised of a stainless steel and/or titanium, for example. In various circumstances, depending on the materials used, at least one brazing process and/or at least one welding process, for example, could be used to secure the plates 7243 in the frame 7244.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:
1. A surgical stapling system, comprising:
    a first staple comprised of a wire, wherein said first staple comprises:
        a first base; and
        a first leg extending from said first base;
    a second staple comprised of a wire, wherein said second staple comprises:
        a second base; and
        a second leg extending from said second base;
    a retention matrix, comprising:
        a first matrix element, comprising:
            first receiving means for receiving said first leg;
            first alignment means for aligning said first leg with said first receiving means; and
            first retention means for engaging said first leg;
        a second matrix element, comprising:
            second receiving means for receiving said second leg;
            second alignment means for aligning said second leg with said second receiving means; and
            second retention means for engaging said second leg; and
        flexible connecting means for connecting said first matrix element and said second matrix element.

2. A surgical stapling system, comprising:
a first fastener comprising a first base and a first leg extending from said first base;
a second fastener comprising a second base and a second leg extending from said second base;
a retention matrix, comprising:
a first matrix element, comprising:
a first aperture configured to receive said first leg;
a first pocket surrounding said first aperture; and
a first retention tab configured to engage said first leg;
a second matrix element, comprising:
a second aperture configured to receive said second leg;
a second pocket surrounding said second aperture; and
a second retention tab configured to engage said second leg;
a flexible connector attached to said first matrix element and said second matrix element; and
an alignment matrix comprising a first alignment guide operably engaged with said first leg and a second alignment guide operably engaged with said second leg, wherein said alignment matrix is configured to align said first leg with said second leg.

3. A surgical stapling system, comprising:
a first staple comprising a first leg;
a second staple comprising a second leg;
a retention matrix, comprising:
a first matrix element, comprising:
a first aperture configured to receive said first leg;
a first alignment pocket at least partially surrounding said first aperture, wherein said first alignment pocket is configured to guide said first leg into said first aperture; and
a first retention portion configured to engage said first leg;
a second matrix element, comprising:
a second aperture configured to receive said second leg;
a second alignment pocket at least partially surrounding said second aperture, wherein said second alignment pocket is configured to guide said second leg into said second aperture; and
a second retention portion configured to engage said second leg; and
a connecting link connecting said first matrix element and said second matrix element; and
an alignment matrix comprising a first alignment guide operably engaged with said first leg and a second alignment guide operably engaged with said second leg, wherein said alignment matrix is configured to align said first leg with said second leg.

4. A surgical stapling system, comprising:
a first fastener comprising a first leg;
a second fastener comprising a second leg;
a retention matrix, comprising:
a first matrix element, comprising:
a first aperture configured to receive said first leg; and
a first retention portion configured to engage said first leg;
a second matrix element, comprising:
a second aperture configured to receive said second leg; and
a second retention portion configured to engage said second leg;
a flexible connector attached to said first matrix element and said second matrix element; and
an alignment matrix comprising a first alignment guide operably engaged with said first leg and a second alignment guide operably engaged with said second leg, wherein said alignment matrix is configured to align said first leg with said second leg.

5. A surgical stapling system, comprising:
a first staple comprising a first leg;
a second staple comprising a second leg;
a retention matrix, comprising:
a first matrix element, comprising:
first receiving means for receiving said first leg;
first alignment means for aligning said first leg with said first receiving means; and
first retention means for engaging said first leg;
a second matrix element, comprising:
second receiving means for receiving said second leg;
second alignment means for aligning said second leg with said second receiving means; and
second retention means for engaging said second leg; and
flexible connecting means for connecting said first matrix element and said second matrix element.

6. A surgical stapling system, comprising:
a first staple comprised of a wire, wherein said first staple comprises:
a first base; and
a first leg extending from said first base;
a second staple comprised of a wire, wherein said second staple comprises:
a second base; and
a second leg extending from said second base;
a retention matrix, comprising:
a first matrix element, comprising:
a first aperture configured to receive said first leg;
a first alignment pocket at least partially surrounding said first aperture, wherein said first alignment pocket is configured to guide said first leg into said first aperture; and
a first retention member configured to engage said first leg;
a second matrix element, comprising:
a second aperture configured to receive said second leg;
a second alignment pocket at least partially surrounding said second aperture, wherein said second alignment pocket is configured to guide said second leg into said second aperture; and
a second retention member configured to engage said second leg; and
a connecting link connecting said first matrix element and said second matrix element; and
an alignment matrix comprising a first alignment guide operably engaged with said first leg and a second alignment guide operably engaged with said second leg, wherein said alignment matrix is configured to align said first leg with said second leg.

7. The surgical stapling system of claim 6, wherein said first matrix element, said second matrix element, and said connecting link are comprised of a unitary piece of material.

8. The surgical stapling system of claim 7, wherein said first matrix element, said second matrix element, and said connecting link are formed from a sheet of metal.

9. The surgical stapling system of claim 8, wherein said connecting link comprises a sheet thickness and at least one thickness which is thinner than said sheet thickness.

10. The surgical stapling system of claim 6, wherein said first matrix element and said second matrix element are comprised of a metal material, and wherein said connecting link is comprised of a plastic material.

11. The surgical stapling system of claim 10, wherein said plastic material of said connecting link at least partially surrounds said first matrix element and said second matrix element.

12. The surgical stapling system of claim 10, wherein said connecting link comprises a first aperture and a second aperture, wherein said first matrix element is positioned within said first aperture of said connecting link, and wherein said second matrix element is positioned within said second aperture of said connecting link.

13. The surgical stapling system of claim 12, wherein said connecting link is molded around said first matrix element and said second matrix element.

14. The surgical stapling system of claim 6, wherein said first matrix element comprises a first width, wherein said second matrix element comprises a second width, and wherein said connecting link comprises a width which is narrower than said first width and said second width.

15. The surgical stapling system of claim 6, wherein said connecting link comprises a first link portion and a second link portion, wherein said first link portion extends from said first matrix element in a first direction, wherein said second link portion extends from said second matrix element in a second direction, and wherein said first direction is different than said second direction.

16. The surgical stapling system of claim 15, wherein said connecting link further comprises a first hinge connecting said first link portion to said first matrix element and a second hinge connecting said second link portion to said second matrix element.

17. The surgical stapling system of claim 16, wherein said connecting link further comprises an intermediate hinge connecting said first link portion and said link second portion.

18. The surgical stapling system of claim 6, wherein said first alignment pocket comprises a first frustoconical configuration, and wherein said second alignment pocket comprises a second frustoconical configuration.

19. The surgical stapling system of claim 6, wherein said first alignment pocket comprises a first angled surface and said second alignment pocket comprises a second angled surface.

20. The surgical stapling system of claim 6, further comprising:
a third staple comprised of a wire, wherein said third staple comprises:
a third base; and
a third leg extending from said third base, wherein said retention matrix further comprises a third matrix element, comprising:
a third aperture configured to receive said third leg;
a third pocket surrounding said third aperture;
a third retention member configured to engage said third leg; and
a second connecting link connecting said second matrix element and said third matrix element.

21. The surgical stapling system of claim 6, wherein said retention matrix further comprises a flexible sheet, and wherein said first matrix element and said second matrix element are embedded within said flexible sheet.

22. The surgical stapling system of claim 21, wherein said flexible sheet is comprised of a woven mesh material.

23. The surgical stapling system of claim 21, wherein said flexible sheet is comprised of an elastomeric material.

24. The surgical stapling system of claim 6, wherein said retention matrix comprises a first tissue-contacting surface, and wherein said alignment matrix comprises a second tissue-contacting surface.

* * * * *